(12) United States Patent
Movassaghi et al.

(10) Patent No.: US 10,640,508 B2
(45) Date of Patent: May 5, 2020

(54) DIAZENE DIRECTED MODULAR SYNTHESIS OF COMPOUNDS WITH QUATERNARY CARBON CENTERS

(71) Applicant: Massachusetts Institute of Technology, Cambridge, MA (US)

(72) Inventors: Mohammad Movassaghi, Arlington, MA (US); Petra Lindovska, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/161,036

(22) Filed: Oct. 15, 2018

(65) Prior Publication Data

US 2019/0119286 A1   Apr. 25, 2019

Related U.S. Application Data

(60) Provisional application No. 62/572,189, filed on Oct. 13, 2017.

(51) Int. Cl.
C07D 487/04 (2006.01)

(52) U.S. Cl.
CPC .................. C07D 487/04 (2013.01)

(58) Field of Classification Search
CPC .................................................. C07D 487/04
See application file for complete search history.

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 4,906,562 A | 3/1990 | Hellström et al. |
| 4,935,495 A | 6/1990 | Hellström et al. |
| 4,940,726 A | 7/1990 | Pettit et al. |
| 4,946,778 A | 8/1990 | Ladner et al. |
| 4,996,237 A | 2/1991 | Pettit et al. |
| 5,225,539 A | 7/1993 | Winter et al. |
| 5,242,824 A | 9/1993 | Hellström et al. |
| 5,338,845 A | 8/1994 | Barrow et al. |
| 5,409,953 A | 4/1995 | Pettit et al. |
| 5,423,753 A | 6/1995 | Fowles et al. |
| 5,430,062 A | 7/1995 | Cushman et al. |
| 5,475,092 A | 12/1995 | Chari et al. |
| 5,504,074 A | 4/1996 | D'Amato et al. |
| 5,525,632 A | 6/1996 | Obsumi et al. |
| 5,545,806 A | 8/1996 | Lonberg et al. |
| 5,561,122 A | 10/1996 | Pettit |
| 5,569,786 A | 10/1996 | Pettit et al. |
| 5,569,825 A | 10/1996 | Lonberg et al. |
| 5,585,089 A | 12/1996 | Queen |
| 5,625,126 A | 4/1997 | Lonberg et al. |
| 5,633,425 A | 5/1997 | Lonberg et al. |
| 5,646,176 A | 7/1997 | Golik et al. |
| 5,661,016 A | 8/1997 | Lonberg et al. |
| 5,661,143 A | 8/1997 | D'Amato et al. |
| 5,674,906 A | 10/1997 | Hatanaka et al. |
| 5,731,353 A | 3/1998 | Ohsumi et al. |
| 5,821,337 A | 10/1998 | Carter et al. |
| 5,877,158 A | 3/1999 | Bosslet et al. |
| 5,886,025 A | 3/1999 | Pinney |
| 5,892,069 A | 4/1999 | D'Amato et al. |
| 5,929,211 A | 7/1999 | Ashkenazi et al. |
| 5,985,837 A | 11/1999 | Ritter et al. |
| 6,054,297 A | 4/2000 | Carter et al. |
| 6,103,236 A | 8/2000 | Suzawa et al. |
| 6,147,076 A | 11/2000 | Danishefsky et al. |

(Continued)

FOREIGN PATENT DOCUMENTS

| | | |
|---|---|---|
| CN | 105198885 A | 12/2015 |
| EP | 0105360 A | 4/1984 |

(Continued)

OTHER PUBLICATIONS

Accolla et al., "Monoclonal antibodies specific for carcinoembryonic antigen an produced by two hybrid cell lines." Proc Natl. Acad. Sci. USA 77:563-566.

(Continued)

*Primary Examiner* — Golam M Shameem
(74) *Attorney, Agent, or Firm* — Wolf, Greenfield & Sacks, P.C.

(57) ABSTRACT

Diazene-directed modular synthesis is described for the preparation Csp2-Csp3 and Csp3-Csp3 linkages where one or more stereogenic quaternary carbon centers are formed. The disclosed methods are directed to the preparation of compounds of Formula (I), or a pharmaceutically acceptable salt, tautomer or stereoisomer thereof, from compounds of Formula (II):

Formula (I)

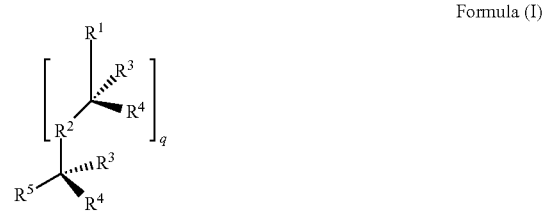

Formula (II)

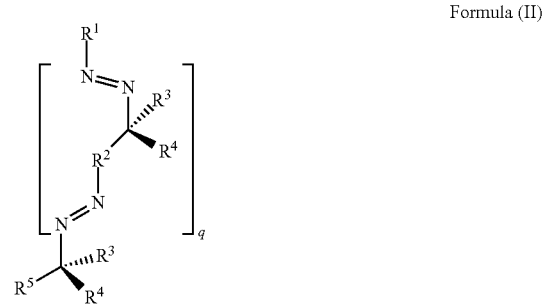

wherein $R^1$-$R^5$ and q are as defined independently for each occurrence herein. A wide variety of compounds can be accessed in this manner, including oligocyclotryptamines, where the stereochemistry of each subunit is beneficially secured before fragment coupling.

20 Claims, 8 Drawing Sheets

(56) References Cited

U.S. PATENT DOCUMENTS

| | | |
|---|---|---|
| 6,150,407 A | 11/2000 | Tusé et al. |
| 6,162,810 A | 12/2000 | Carson et al. |
| 6,162,930 A | 12/2000 | Pinney et al. |
| 6,169,104 B1 | 1/2001 | Tusé et al. |
| 6,201,001 B1 | 3/2001 | Wang et al. |
| 6,214,345 B1 | 4/2001 | Firestone et al. |
| 6,232,327 B1 | 5/2001 | Nickel et al. |
| 6,262,094 B1 | 7/2001 | Hoefle et al. |
| 6,268,488 B1 | 7/2001 | Barbas, III et al. |
| 6,271,220 B1 | 8/2001 | Garst |
| 6,329,420 B1 | 12/2001 | Uckun et al. |
| 6,335,364 B1 | 1/2002 | Uckun et al. |
| 6,350,777 B2 | 2/2002 | Pinney et al. |
| 6,358,957 B1 | 3/2002 | Fukumoto et al. |
| 6,407,213 B1 | 6/2002 | Carter et al. |
| 6,423,753 B1 | 7/2002 | Dougherty |
| 6,433,012 B1 | 8/2002 | Tusé et al. |
| 6,528,676 B1 | 3/2003 | D'Amato et al. |
| 6,582,928 B1 | 6/2003 | Ashkenazi et al. |
| 6,620,976 B2 | 9/2003 | Sakanoue et al. |
| 6,639,055 B1 | 10/2003 | Carter et al. |
| 6,677,435 B2 | 1/2004 | Barbas, III et al. |
| 6,759,509 B1 | 7/2004 | King et al. |
| 6,815,530 B2 | 11/2004 | Ekwuribe et al. |
| 6,835,802 B2 | 12/2004 | Ekwuribe et al. |
| 6,855,689 B2 | 2/2005 | Firestone et al. |
| 6,858,580 B2 | 2/2005 | Ekwuribe et al. |
| 6,870,033 B1 | 3/2005 | Hsei et al. |
| 6,897,034 B2 | 5/2005 | Bebbington et al. |
| 7,018,809 B1 | 3/2006 | Carter |
| 7,030,082 B2 | 4/2006 | Soltero et al. |
| 7,087,840 B2 | 8/2006 | Herring et al. |
| 7,091,186 B2 | 8/2006 | Senter et al. |
| 7,115,573 B2 | 10/2006 | Pickford et al. |
| 7,119,162 B2 | 10/2006 | Ekwuribe et al. |
| 7,122,636 B1 | 10/2006 | Hsei et al. |
| 7,183,076 B2 | 2/2007 | Arathoon et al. |
| 7,214,663 B2 | 5/2007 | Bebbington et al. |
| 7,214,776 B2 | 5/2007 | Hsei et al. |
| 7,223,837 B2 | 5/2007 | de Groot et al. |
| 7,256,257 B2 | 8/2007 | Doronina et al. |
| 7,304,032 B2 | 12/2007 | Bebbington et al. |
| 7,319,139 B2 | 1/2008 | Brasalawsky et al. |
| 7,375,078 B2 | 5/2008 | Feng |
| 7,427,399 B2 | 9/2008 | Jakobovits et al. |
| 7,479,544 B2 | 1/2009 | Clark et al. |
| 7,494,646 B2 | 2/2009 | Jakobovits et al. |
| 7,507,405 B2 | 3/2009 | Hsei et al. |
| 7,521,541 B2 | 4/2009 | Eigenbrot et al. |
| 7,541,442 B2 | 6/2009 | Gudas et al. |
| 7,547,768 B2 | 6/2009 | Dowd et al. |
| 7,553,816 B2 | 6/2009 | Senter et al. |
| 7,585,834 B2 | 9/2009 | Wender et al. |
| 7,595,379 B2 | 9/2009 | Gudas et al. |
| 7,659,241 B2 | 2/2010 | Senter et al. |
| 7,662,936 B2 | 2/2010 | Kadkhodayan et al. |
| 7,691,962 B2 | 4/2010 | Boyd et al. |
| 7,696,313 B2 | 4/2010 | Pickford et al. |
| 7,705,045 B2 | 4/2010 | de Groot et al. |
| 7,714,016 B2 | 5/2010 | Gangwar et al. |
| 7,723,485 B2 | 5/2010 | Junutula et al. |
| 7,745,394 B2 | 6/2010 | Doronina et al. |
| 7,749,504 B2 | 7/2010 | Cairns et al. |
| 7,750,116 B1 | 7/2010 | Doronina et al. |
| 7,754,441 B2 | 7/2010 | de Sauvage et al. |
| 7,754,681 B2 | 7/2010 | Feng |
| 7,803,915 B2 | 9/2010 | Cairns et al. |
| 7,811,565 B2 | 10/2010 | Jakobovits et al. |
| 7,816,317 B2 | 10/2010 | Bebbington et al. |
| 7,829,531 B2 | 11/2010 | Senter et al. |
| 7,834,154 B2 | 11/2010 | Koch et al. |
| 7,842,789 B2 | 11/2010 | Hsei et al. |
| 7,846,893 B2 | 12/2010 | Sinko et al. |
| 7,851,437 B2 | 12/2010 | Senter et al. |
| 7,855,275 B2 | 12/2010 | Eigenbrot et al. |
| 7,858,759 B2 | 12/2010 | Brandt et al. |
| 7,888,536 B2 | 2/2011 | Davis et al. |
| 7,893,023 B2 | 2/2011 | Trouet et al. |
| 7,964,566 B2 | 6/2011 | Doronina et al. |
| 7,964,567 B2 | 6/2011 | Doronina et al. |
| 7,968,090 B2 | 6/2011 | Raitano et al. |
| 7,989,434 B2 | 8/2011 | Feng |
| 7,989,595 B2 | 8/2011 | Dennis et al. |
| 8,012,978 B2 | 9/2011 | Zhao et al. |
| 8,158,590 B2 | 4/2012 | Beusker et al. |
| 8,337,856 B2 | 12/2012 | Blättler et al. |
| 9,353,150 B2 | 5/2016 | Movassaghi et al. |
| 9,434,736 B2 | 9/2016 | Movassaghi et al. |
| 9,464,093 B2 | 10/2016 | Tun et al. |
| 9,962,383 B2 | 5/2018 | Movassaghi et al. |
| 2003/0096743 A1 | 5/2003 | Senter et al. |
| 2003/0130189 A1 | 7/2003 | Senter et al. |
| 2003/0149003 A1 | 8/2003 | Chaplin et al. |
| 2005/0143429 A1 | 6/2005 | Danishefsky et al. |
| 2008/0050310 A1 | 2/2008 | Ebens et al. |
| 2008/0267981 A1 | 10/2008 | Janda et al. |
| 2009/0068202 A1 | 3/2009 | Chen et al. |
| 2009/0203584 A1 | 8/2009 | Cuthbertson et al. |
| 2009/0280056 A1 | 11/2009 | Dennis et al. |
| 2010/0125065 A1 | 5/2010 | Moon et al. |
| 2010/0210543 A1 | 8/2010 | Rabuka et al. |
| 2010/0215669 A1 | 8/2010 | Chen et al. |
| 2011/0118480 A1 | 5/2011 | Vijayaraghavan et al. |
| 2011/0124844 A1 | 5/2011 | Davis et al. |
| 2011/0135667 A1 | 6/2011 | Chen et al. |
| 2011/0137017 A1 | 6/2011 | Eigenbrot et al. |
| 2011/0142859 A1 | 6/2011 | Ebens, Jr. et al. |
| 2011/0195021 A1 | 8/2011 | Deckert et al. |
| 2011/0195022 A1 | 8/2011 | Deckert et al. |
| 2011/0269972 A1 | 11/2011 | Loh et al. |
| 2012/0183566 A1 | 7/2012 | Barfield et al. |
| 2014/0187500 A1 | 7/2014 | Movassaghi et al. |
| 2015/0080405 A1 | 3/2015 | Movassaghi et al. |
| 2015/0274742 A1 | 10/2015 | Tun et al. |
| 2016/0354483 A1 | 12/2016 | Movassaghi et al. |
| 2017/0333405 A1 | 11/2017 | Movassaghi et al. |
| 2017/0342077 A1 | 11/2017 | Movassaghi et al. |
| 2018/0360830 A1 | 12/2018 | Movassaghi et al. |

FOREIGN PATENT DOCUMENTS

| | | |
|---|---|---|
| EP | 0171496 A2 | 2/1986 |
| EP | 0173494 A2 | 3/1986 |
| EP | 0184187 A2 | 6/1986 |
| EP | 0217577 A | 4/1987 |
| EP | 0375562 A | 6/1990 |
| WO | WO 83/03679 A1 | 10/1983 |
| WO | WO 86/01533 A1 | 3/1986 |
| WO | WO 87/02671 A1 | 5/1987 |
| WO | WO 88/03145 A2 | 5/1988 |
| WO | WO 91/00295 A1 | 1/1991 |
| WO | WO 92/016486 A1 | 10/1992 |
| WO | WO 93/08829 A1 | 5/1993 |
| WO | WO 94/04690 A1 | 3/1994 |
| WO | WO 94/14787 A1 | 7/1994 |
| WO | WO 95/04535 A1 | 2/1995 |
| WO | WO 97/34631 A1 | 9/1997 |
| WO | WO 98/039323 A1 | 9/1998 |
| WO | WO 99/02166 A1 | 1/1999 |
| WO | WO 99/02514 A2 | 1/1999 |
| WO | WO 99/034788 A1 | 7/1999 |
| WO | WO 99/035150 A1 | 7/1999 |
| WO | WO 99/035164 A1 | 7/1999 |
| WO | WO 99/048495 A1 | 9/1999 |
| WO | WO 99/051224 A1 | 10/1999 |
| WO | WO 99/051246 A1 | 10/1999 |
| WO | WO 00/00514 A2 | 1/2000 |
| WO | WO 00/41669 A2 | 1/2000 |
| WO | WO 2000/006556 A1 | 2/2000 |
| WO | WO 00/26229 A1 | 5/2000 |
| WO | WO 2000/035865 A2 | 6/2000 |
| WO | WO 00/40529 A1 | 7/2000 |
| WO | WO 2000/048590 A1 | 8/2000 |
| WO | WO 2000/048591 A1 | 8/2000 |

(56) References Cited

FOREIGN PATENT DOCUMENTS

| | | |
|---|---|---|
| WO | WO 2000/073264 A1 | 12/2000 |
| WO | WO 2001/009103 A2 | 2/2001 |
| WO | WO 2001/012579 A2 | 2/2001 |
| WO | WO 2001/019794 A2 | 3/2001 |
| WO | WO 2001/022954 A2 | 4/2001 |
| WO | WO 2001/024763 A2 | 4/2001 |
| WO | WO 01/30803 A1 | 5/2001 |
| WO | WO 01/40268 A2 | 6/2001 |
| WO | WO 01/40309 A2 | 6/2001 |
| WO | WO 2001/068654 A2 | 9/2001 |
| WO | WO 2001/081288 A1 | 11/2001 |
| WO | WO 2001/081355 A1 | 11/2001 |
| WO | WO 2001/082909 A2 | 11/2001 |
| WO | WO 2001/084929 A1 | 11/2001 |
| WO | WO 2001/092224 A2 | 12/2001 |
| WO | WO 02/04434 A1 | 1/2002 |
| WO | WO 02/06267 A2 | 1/2002 |
| WO | WO 02/08213 A1 | 1/2002 |
| WO | WO 02/016429 A2 | 2/2002 |
| WO | WO 02/16581 A2 | 2/2002 |
| WO | WO 2002/012228 A1 | 2/2002 |
| WO | WO 2002/014329 A1 | 2/2002 |
| WO | WO 2002/022576 A2 | 3/2002 |
| WO | WO 2002/022626 A1 | 3/2002 |
| WO | WO 02/42319 A2 | 5/2002 |
| WO | WO 02/47604 A2 | 6/2002 |
| WO | WO 2002/043661 A2 | 6/2002 |
| WO | WO 2002/050007 A2 | 6/2002 |
| WO | WO 2002/060872 A1 | 8/2002 |
| WO | WO 02/088172 A2 | 11/2002 |
| WO | WO 2002/098883 A1 | 12/2002 |
| WO | WO 03/000113 A2 | 1/2003 |
| WO | WO 03/024392 A2 | 3/2003 |
| WO | WO 03/026577 A2 | 4/2003 |
| WO | WO 03/043583 A2 | 5/2003 |
| WO | WO 2003/068144 A2 | 8/2003 |
| WO | WO 2003/106621 A2 | 12/2003 |
| WO | WO 2004/005470 A2 | 1/2004 |
| WO | WO 04/016225 A2 | 2/2004 |
| WO | WO 2004/010957 A2 | 2/2004 |
| WO | WO 2004/013093 A2 | 2/2004 |
| WO | WO 2004/016801 A2 | 2/2004 |
| WO | WO 04/032828 A2 | 4/2004 |
| WO | WO 2004/032828 A2 | 4/2004 |
| WO | WO 2004/043344 A2 | 5/2004 |
| WO | WO 2004/043493 A1 | 5/2004 |
| WO | WO 04/045516 A2 | 6/2004 |
| WO | WO 2004/050867 A1 | 6/2004 |
| WO | WO 2004/090113 A2 | 10/2004 |
| WO | WO 2004/106343 A2 | 12/2004 |
| WO | WO 2004/110498 A2 | 12/2004 |
| WO | WO 2005/001038 A2 | 1/2005 |
| WO | WO 2005/009369 A2 | 2/2005 |
| WO | WO 2005/037992 A2 | 4/2005 |
| WO | WO 2005/070026 A2 | 8/2005 |
| WO | WO 2005/077090 A2 | 8/2005 |
| WO | WO 2005/081711 A2 | 9/2005 |
| WO | WO 2005/082023 A2 | 9/2005 |
| WO | WO 2005/084390 A2 | 9/2005 |
| WO | WO 2006/044643 A2 | 4/2006 |
| WO | WO 2006/055578 A2 | 5/2006 |
| WO | WO 2006/065533 A2 | 6/2006 |
| WO | WO 2006/086733 A2 | 8/2006 |
| WO | WO 2006/113909 A2 | 10/2006 |
| WO | WO 2006/128103 A2 | 11/2006 |
| WO | WO 2006/132670 A2 | 12/2006 |
| WO | WO 2007/008603 A1 | 1/2007 |
| WO | WO 2007/008848 A1 | 1/2007 |
| WO | WO 2007/011968 A2 | 1/2007 |
| WO | WO 2007/019232 A2 | 2/2007 |
| WO | WO 2007/024222 A1 | 3/2007 |
| WO | WO 2007/024536 A2 | 3/2007 |
| WO | WO 2007/030642 A2 | 3/2007 |
| WO | WO 2007/062138 A2 | 5/2007 |
| WO | WO 2007/075326 A2 | 7/2007 |
| WO | WO 2007/089149 A2 | 8/2007 |
| WO | WO 2007/103288 A2 | 9/2007 |
| WO | WO 2007/137170 A2 | 11/2007 |
| WO | WO 2008/025020 A2 | 2/2008 |
| WO | WO 2008/070593 A2 | 6/2008 |
| WO | WO 2008/078109 A2 | 7/2008 |
| WO | WO 2009/017394 A2 | 2/2009 |
| WO | WO 2009/048967 A1 | 4/2009 |
| WO | WO 2009/052431 A2 | 4/2009 |
| WO | WO 2009/080830 A1 | 7/2009 |
| WO | WO 2009/080831 A1 | 7/2009 |
| WO | WO 2009/080832 A1 | 7/2009 |
| WO | WO 2009/117531 A1 | 9/2009 |
| WO | WO 2009/134870 A1 | 11/2009 |
| WO | WO 2009/134952 A2 | 11/2009 |
| WO | WO 2009/134976 A1 | 11/2009 |
| WO | WO 2009/134977 A1 | 11/2009 |
| WO | WO 2009/135181 A2 | 11/2009 |
| WO | WO 2010/008726 A1 | 1/2010 |
| WO | WO 2010/025272 A1 | 3/2010 |
| WO | WO 2010/128087 A2 | 5/2010 |
| WO | WO 2010/062171 A2 | 6/2010 |
| WO | WO 2010/081004 A1 | 7/2010 |
| WO | WO 2010/111018 A1 | 9/2010 |
| WO | WO 2011/038159 A2 | 9/2010 |
| WO | WO 2010/126551 A1 | 11/2010 |
| WO | WO 2010/126552 A1 | 11/2010 |
| WO | WO 2010/141566 A1 | 12/2010 |
| WO | WO 2011/100403 A1 | 2/2011 |
| WO | WO 2011/106528 A1 | 2/2011 |
| WO | WO 2011/112978 A1 | 3/2011 |
| WO | WO 2011/050180 A1 | 4/2011 |
| WO | WO 2011/130613 A1 | 4/2011 |
| WO | WO 2011/091286 A1 | 7/2011 |
| WO | WO 2011/100398 A1 | 8/2011 |
| WO | WO 2011/133039 A2 | 10/2011 |
| WO | WO 2011/162933 A1 | 12/2011 |
| WO | WO 2012/019024 A2 | 2/2012 |
| WO | WO 2012/047724 A2 | 4/2012 |
| WO | WO 2012/054748 A2 | 4/2012 |
| WO | WO 2012/149412 A2 | 4/2012 |
| WO | WO 2012/058592 A2 | 5/2012 |
| WO | WO 2012/061590 A1 | 5/2012 |
| WO | WO 2012/078688 A2 | 6/2012 |
| WO | WO 2012/112687 A1 | 8/2012 |
| WO | WO 2012/112708 A1 | 8/2012 |
| WO | WO 2012/128868 A2 | 9/2012 |
| WO | WO 2012/135517 A2 | 10/2012 |
| WO | WO 2012/135522 A2 | 10/2012 |
| WO | WO 2012/135675 A2 | 10/2012 |
| WO | WO 2012/135740 A2 | 10/2012 |
| WO | WO 2012/138537 A2 | 10/2012 |
| WO | WO 2012/138749 A2 | 10/2012 |
| WO | WO 2012/145112 A2 | 10/2012 |
| WO | WO 2012/177837 A2 | 12/2012 |
| WO | WO 2013/049410 A1 | 4/2013 |
| WO | WO 2013/055990 A1 | 4/2013 |
| WO | WO 2013/055993 A1 | 4/2013 |
| WO | WO 2014/059314 A1 | 4/2014 |

OTHER PUBLICATIONS

Adam, W. et al., "Photochemistry of the Azoalkanes 2,3-Diazabicyclo[2.2.1]hept-2-ene and Spiro[cyclopropane-1, 7-[2,3]diazabicyclo[2.2.1]hept-2-ene]: On the Questions of One-Bond vs. Two-Bond Cleavage during the Denitrogenation, Cyclization vs. Rearrangement of the 1,3-Diradicals, and Double Inversion," J. Org. Chem. 1985, 50, pp. 3303-3312.

Adams et al., Concise Total Synthesis of (+)-Luteoalbusins A and B. Organic Letters Aug. 2015;17(17):4268-4271. DOI: 10.1021/acs.orglett.5b02059.

Adj I Bade, Y. et al., "In Vitro Cytotoxicity of Polyindolenine Alkaloids on Rat Hepatoma Cell Lines. Structure Activity Relationships," Journal of Ethnopharmacology 1990, 29, pp. 127-136.

Aleksandrzak et al., "Antimitotic activity of diaryl compounds with structural features resembling combretastatin A-4." Anticancer Drugs. Jul. 1998; 9(6):545-50.

(56) References Cited

OTHER PUBLICATIONS

Aliev et al., "A concise approach to the epidithiodiketopiperazine (ETP) core." Tetrahedron Lett. 2006; 47(14):2387-2390.
Amador, T. A. et al., "Antinociceptive Profile of Hodgkinsine," Planta Med 2000, 66, pp. 770-772.
Amir et al., "Self-immolative dendrimers." Angew Chem Int Ed Engl. Sep. 29, 2003; 42(37):4494-9.
Amsberry et al., "The lactonization of 2'-hydroxyhydrocinnamic acid amides: a potential prodrug for amines." J. Org. Chem. 1990; 55(23):5867-5877.
Andersen et al., Penicillium expansum: consistent production of patulin, chaetoglobosins, and other secondary metabolites in culture and their natural occurrence in fruit products. J Agric Food Chem. Apr. 21, 2004;52(8):2421-8.
Anderson et al., "Studies on Total Synthesis of the Cytotoxic Marine Alkaloid Agelastatin A," J. Org. Chem., 63:7594-7595 (1998).
Andres et al., ""Combretatropones"—hybrids of combretastatin and colchicine. Synthesis and biochemical evaluation" Bioorganic. Med. Chem. Lett. 1993; 3(4):571-576.
Anet, E. F. L. J. et al., "Hodgkinsine, the Alkaloid of Hodgkinsonia Frutescens F. Muell," J. Chem. 1961, 14, pp. 173-174.
Anthon I, U. et al., "Naturally Occurring Cyclotryptophans and Cyclotryptamines," Alkaloids: Chemical and Biological Perspectives, Pelletier, S. W., Ed.; Pergamon: London, 1999; vol. 13, pp. 163-236.
Bacher et al., "D-24851, a novel synthetic microtubule inhibitor, exerts curative antitumoral activity in vivo, shows efficacy toward multidrug-resistant tumor cells, and lacks neurotoxicity." Cancer Res. Jan. 1, 2001; 61(1):392-9.
Bai et al., "Interaction of dolastatin 10 with tubulin: induction of aggregation and binding and dissociation reactions." Molecular Pharmacology May 1995; 47(5):965-976.
Baldwin, J. E. et al., "Azo Anions in Synthesis. Use of Trityl- and Diphenyl-4-Pyridylmenthylhydrazones for Reductive C—C Bond Formation," Tetrahedron 1986, vol. 42, No. 15, pp. 4235-4246.
Banwell et al., "Synthesis, X-Ray Crystal Structure and Tubulin-Binding Properties of a Benzofuran Analogue of the Potent Cytotoxic Agent Combretastatin A4." Australian Journal of Chemistry 1999; 52(8):767-774.
Barrow et al., "WIN 64821, a new competitive antagonist to substance P, isolated from an *Aspergillus* species: structure determination and solution conformation." J. Org. Chem. 1993; 58(22):6016-6021.
Baselga et al., "Phase II study of weekly intravenous recombinant humanized anti-p185HER2 monoclonal antibody in patients with HER2/neu-overexpressing metastatic breast cancer." J Clin Oncol. Mar. 1996; 14(3):737-44.
Bast et al., "Reactivity of a monoclonal antibody with human ovarian carcinoma." J Clin Invest. Nov. 1981; 68(5):1331-7.
Beck et al., "Mild Aerobic Oxidative Palladium (II) Catalyzed C—H Bond Functionalization: Regioselective and Switchable C—H Alkenylation and Annulation of Pyrroles." J. Am. Chem. Soc. 2006; 128(8):2528-2529.
Bedford et al., "Synthesis of water-soluble prodrugs of the cytotoxic agent Combretastatin A4." Bioorganic. Med. Chem. Lett. 1996; 6(2):157-160.
Behenna et al., Confirmation of the absolute configuration of (−)-aurantioclavine. Tetrahedron Letters Apr. 2011;52(17):2152-2154.
Beidler et al., "Cloning and high level expression of a chimeric antibody with specificity for human carcinoembryonic antigen." J Immunol Dec. 1, 1988; 141(11):4053-4060.
Belmar et al., Total Synthesis of (±)-Communesin F via a Cycloaddition with Indol-2-one. J. Am. Chem. Soc., 2012;134(41):16941-16943. DOI: 10.1021/ja307277w.
Belmar et al., Total Synthesis of (±)-isophellibiline and (±)-communesin F, and Design, Synthesis and Pharmacological Evaluation of Dihydro-β-erythroidine (DHβE) Analogs. Pennsylvania State University Dissertation 2012.

Benkovics et al., Oxaziridine-mediated oxyamination of indoles: an approach to 3-aminoindoles and enantiomerically enriched 3-aminopyrroloindolines. Angew Chem Int Ed Engl. Nov. 22, 2010;49(48):9153-7. doi: 10.1002/anie.201004635.
Beretz, A. et al., "Polyindolinic Alkaloids from Psychotria forsteriana. Potent Inhibitors of the Aggregation of Human Platelets," Planta Med. 1985, 51, pp. 300-303.
Bernardo et al., "A Novel Redox Mechanism for the Glutathione-dependent Reversible Uptake of a Fungal Toxin in Cells." J Biol. Chem. 2003; 278(47):46549-46555.
Bertling et al., "Candida albicans and its metabolite gliotoxin inhibit platelet function via interaction with thiols." Thromb Haemost. Aug. 2010;104(2):270-8.
Better et al., "*Escherichia coli* secretion of an active chimeric antibody fragment." Science May 20, 1988; 240(4855):1041-1043.
Bird et al., "Single-chain antigen-binding proteins." Science Apr. 28, 1989;244(4903):409.
Blokhin et al., "Characterization of the interaction of the marine cyanobacterial natural product curacin A with the colchicine site of tubulin and initial structure-activity studies with analogues." Molecular Pharmacology Sep. 1995; 48(3):523-531.
Boger et al., "Synthesis of the lower subunit of rhizoxin." J. Org. Chem.1992; 57(8):2235-2244.
Bowen et al., "Functional effects of CD30 on a large granular lymphoma cell line, YT. Inhibition of cytotoxicity, regulation of CD28 and IL-2R, and induction of homotypic aggregation." J Immunol Dec. 1, 1993; 151(11):5896-5906.
Boyer et al. Synthesis and Anticancer Activity of Epipolythiodiketopiperazine Alkaloids. Chem Sci. 2013;4(4):1646-1657. doi:10.1039/C35C50174D.
Boyer et al., Concise Total Synthesis of (+)-Gliocladins B and C. Chem Sci. Jan. 1, 2012;3(6):1798-1803. Epub Mar. 30, 2012.
Brak et al., Total Synthesis of (−)-Aurantioclavine. Org. Lett., 2010;12(9):2004-2007. DOI: 10.1021/ol100470g.
Brown et al., "Investigation of various N-heterocyclic substituted piperazine versions of 5/7-{[2-(4-aryl-piperazin-1-yl)-ethyl]-propyl-amino }-5,6,7,8-tetrahydro-naphthalen-2-ol: effect on affinity and selectivity for dopamine D3 receptor." Bioorg Med Chem. Jun. 1, 2009;17(11):3923-33.
Bumol et al., "Unique glycoprotein-proteoglycan complex defined by monoclonal antibody on human melanoma cells." Proc Natl Acad Sci U S A. Feb. 1982; 79(4):1245-9.
Bundgaard, H., "(C) Means to enhance penetration: (1) Prodrugs as a means to improve the delivery of peptide drugs." Advanced Drug Delivery Revieivs. 1992; 8(1):1-38.
Canham, S. M. et al., "Stereocontrolled enantioselective total synthesis of the [2+2] quadrigeminealkaloids," Tetrahedron 2015, 71, pp. 6424-6436.
Carter et al., "High Level *Escherichia coli* Expression and Production of a Bivalent Humanized Antibody Fragment." Bio/Technology 10, 163-167 (1992).
Chaib et al., "Anti-leukemia activity of chaetocin via death receptor-dependent apoptosis and dual modulation of the histone methyltransferase SUV39H1." Leukemia. Apr. 2012;26(4):662-74.
Chang, H.-H. et al., "Heterocyclic Compounds. Part 15. NN'-Di-t-Butylthiadiaziridine 1, 1-Dioxide:Synthesis and Reactions," J. Chem. Soc., Perkin Trans. 1, 1977, pp. 1601-1605.
Chen et al., "Ecology-based screen identifies new metabolites from a Cordyceps-colonizing fungus as cancer cell proliferation inhibitors and apoptosis inducers." Cell Prolif. Dec. 2009;42(6):838-47.
Cherblanc et al., "On the Determination of the Stereochemistry of Semisynthetic Natural Product Analogues using Chiroptical Spectroscopy: Desulfurization of Epidithiodioxopiperazine Fungal Metabolites." Chem.-Eur. J. 2011; 17(42):11868-11875.
Choi et al., "Agelastatin A (AgA), a Marine Sponge Derived Alkaloid, Inhibits Wnt/Beta-Catenin Signaling and Selectively Induces Apoptosis in Chronic Lymphocytic Leukemia Independently of p53," Blood (ASH Annual Meeting Abstracts), 118:Abstract1786, 2 pages (2011).
Chou et al., "Therapeutic Cure against Human Tumor Xenografts inNude Mice by a Microtubule Stabilization Agent,Fludelone, via Parenteral or Oral Route." Cancer Res. 2005; 65(20):9445-9454.

(56) References Cited

OTHER PUBLICATIONS

Codelli et al., "Enantioselective Total Synthesis of (−)-Acetylaranotin, a Dihydrooxepine Epidithiodiketopiperazine." J. Am. Chem. Soc. 2012; 134(4):1930-1933.
Coffen et al., "A short synthesis of aromatic analogues of the aranotins." J. Org. Chem. Mar. 18, 1977;42(6):948-52.
Cogan et al., Asymmetric synthesis of chiral amines by highly diastereoselective 1,2-additions of organometallic reagents to N-tert-butanesulfinyl imines. Tetrahedron Jul. 1999;55(29):8883-8904.
Coleman et al., "Antifungal activity of microbial secondary metabolites." PLoS One. 2011;6(9):e25321.
Collet, F. et al., "Catalytic C—H amination: recent progress and future directions," Chem. Commun. 2009, pp. 5061-5074.
Combeau et al., "RPR112378 and RPR115781: Two Representatives of a New Family of Microtubule Assembly Inhibitors." Molecular Pharmacology Mar. 2000; 57(3):553-563.
Cook et al., "Epidithiodiketopiperazines Block the Interaction between Hypoxia-inducible Factor-1α (HIF-1 α) and p300 by a Zinc Ejection Mechanism." J Biol. Chem. 2009; 284:26831-26838.
Cordell, G. A. et al., Bisindole Alkaloids,"The Alkaloids: Chemistry and Physiology," Manske R. H. F., Rodrigo, R. G. A., Ed.; Academic Press: New York, 1981; vol. 20, pp. 3-295.
Coretese et al., "Podophyllotoxin as a probe for the colchicine binding site of tubulin." J Biol Chem. Feb. 25, 1997;252(4):1134-40.
Corey, E. J. et al., "Enantioselective Total Synthesis of Ecteinascidin 743," J. Am. Chem. Soc. 1996, 118, pp. 9202-9203.
Coste et al., Concise Total Synthesis of (+)-Bionectins A and C. Chem Sci. 2013;4(8):3191-3197. doi:10.1039/C3SC51150B.
Coussens et al., "Tyrosine kinase receptor with extensive homology to EGF receptor shares chromosomal location with neu oncogene." Science Dec. 6, 1985; 230(4730):1132-1139.
Crawley et al., A Synthetic Approach to Nomofungin/Communesin B. Org. Lett., 2003, 5 (18), pp. 3169-3171. DOI: 10.1021/o1034407v.
Crich et al., "Expedient Synthesis of threo-β-Hydroxy-α-amino Acid Derivatives: Phenylalanine, Tyrosine, Histidine, and Tryptophan." J. Org. Chem. 2006; 71(18):7106-7109.
Crich, D. et al., "Chemistry of the Hexahydropyrrolo[2,3-b]indoles: Configuration, Conformation, Reactivity, and Applications in Synthesis," Acc. Chem. Res. 2007, 40, pp. 151-161.
Cushman et al., "Synthesis and evaluation of stilbene and dihydrostilbene derivatives as potential anticancer agents that inhibit tubulin polymerization." J. Med. Chem. 1991; 34(8):2579-2588.
Cushman et al., "Synthesis of Analogs of 2-Methoxyestradiol with Enhanced Inhibitory Effects on Tubulin Polymerization and Cancer Cell Growth." J. Med. Chem.1997; 40(15):2323-2334.
Dalsgaard, P. W. et al., "Communesins G and H, New Alkaloids from the Psychrotolerant Fungus *Penicillium rivulum*," J. Nat. Prod. 2005, 68, pp. 258-261.
D'Ambrosia et al., "Agelastatin A, a New Skeleton Cytotoxic Alkaloid of the Oroidin Family. Isolation from the Axinellid Sponge Agelas dendromorpha of the Coral Sea," J. Chem. Soc., Chem. Commun., pp. 1305-1306 (1993).
D'Ambrosio et al., "The Active Centres of Agelastatin A, a Strongly Cytotoxic Alkaloid of the Coral Sea Axinellid Sponge Agelas dendromorpha, as Determined by Comparative Bioassays with Semisynthetic Derivatives," Helv. Chem. Acta, 79:727-735(1996).
Davis, F. A. et al., "Adventures in Sulfur-Nitrogen Chemistry," J. Org. Chem. 2006, 71, pp. 8993-9003.
Davis, F. A. et al., "Asymmetric synthesis of amino acids using sulfinimines (thiooxime S-oxides)," Chem. Soc. Rev. 1998, 27, pp. 13-18.
De Groot et al., ""Cascade-release dendrimers" liberate all end groups upon a single triggering event in the dendritic core." Angew Chem Int Ed Engl. Sep. 29, 2003; 42(37):4490-4.
De Groot et al., "Design, Synthesis, and Biological Evaluation of a Dual Tumor-specific Motive Containing Integrin-targeted Plasmin-cleavable Doxorubicin Prodrug." Molecular Cancer Therapeutics 2002; 1(11):901-911.

De Groot et al., "Synthesis and Biological Evaluation of Novel Prodrugs of Anthracyclines for Selective Activation by the Tumor-Associated Protease Plasmin." J. Med. Chem. 1999; 42(25):5277-5283.
De Loera, D. et al., "Efficient Aziridine Synthesis in Metastable Crystalline Phases by Photoinduced Denitrogenation of Crystalline Triazolines," Org. Lett. 2012, vol. 14, No. 15, pp. 3874-3877.
De Loera, D. et al., "Photoinduced and Thermal Denitrogenation of Bulky Triazoline Crystals: Insights into Solid-to-Solid Transformation," J. Am. Chem. Soc. 2013, 135, pp. 6626-6632.
DeLorbe et al., "General Approach for Preparing Epidithiodioxopiperazines from Trioxopiperazine Precursors: Enantioselective Total Syntheses of (+)- and (−)-Gliocladine C, (+)-Leptosin D, (+)-T988C, (+)-Bionectin A, and (+)-Gliocladin A." J. Am. Chem. Soc. 2013; 135(10):4117-4128.
Delorbe et al., Enantioselective Total Synthesis of (+)-Gliocladine C: Convergent Construction of Cyclotryptamine-Fused Polyoxopiperazines and a General Approach for Preparing Epidithiodioxopiperazines from Trioxopiperazine Precursors. J Am Chem Soc. Apr. 7, 2011;133(17):6549-52.
Denmark et al., "Palladium-Catalyzed Cross-Coupling Reactions of 2-Indolyldimethylsilanols with Substituted Aryl Halides." Org. Lett. 2004; 6(20):3649-3652.
Depew et al., "Total Synthesis of 5-N-Acetylardeemin and Amauromine: Practical Routes to Potential MDR Reversal Agents." J. Am. Chem. Soc.1999; 121(51):11953-11963.
DePorter, S. M. et al., "N-Nosyl oxaziridines as terminal oxidants in copper(ll)-catalyzed olefinoxyaminations," Tetrahedron 2010, 51, pp. 5223-5225.
Dippold et al., "Cell surface antigens of human malignant melanoma: definition of six antigenic systems with mouse monoclonal antibodies." Proc Natl Acad Sci U S A. Oct. 1980; 77(10): 6114-6118.
Dong et al., "Nematicidal epipolysulfanyldioxopiperazines from Gliocladium roseum." J Nat Prod. Oct. 2005;68(10):1510-3.
Dorr et al., "Antitumor activity of combretastatin-A4 phosphate, a natural product tubulin inhibitor." Invest. New Drugs Jun. 1996; 14(2):131-137.
Du Bois, J., "Rhodium-Catalyzed C—H Amination. An Enabling Method for Chemical Synthesis," Org. Process Res. Dev. 2011, 15, pp. 758-762.
Dubey et al., Direct organocatalytic coupling of carboxylated piperazine-2,5-diones with indoles through conjugate addition of carbon nucleophiles to indolenine intermediates. Tetrahedron Lett. 2010;51(4):609-612. doi:10.1016/j.tetlet.2009.11.068.
Dubowchik et al., "Monomethoxytrityl (MMT) as a versatile amino protecting group for complex prodrugs of anticancer compounds sensitive to strong acids, bases and nucleophiles." Tetrahedron Letters 1997; 38(30):5257-60.
Dubs et al., "Eine neue Methode zur Herstellung gemischter Disulfide. Vorläufige Mitteilung" Helv. Chim. Acta 1976; 59(4):1307-1311.
Ducki et al., "Potent antimitotic and cell growth inhibitory properties of substituted chalcones." Bioorg Med Chem Lett. May 5, 1998; 8(9):1051-6.
Engel, P. S. et al., "Thermolysis of Free-Radical Initiators: tert-Butylazocumene and Its 1,3- and 1,4-Bisazo and 1,3,5-Trisazo Analogues," J. Am. Chem. Soc. 2001, 123, pp. 3706-3715.
Engel, P. S., "Mechanism of the Thermal and Photochemical Decomposition of Azoalkanes," Chemical Reviews Apr. 1980, vol. 80, No. 2, 52 pages.
Engel, P. S., "Photochemistry of Aliphatic Azo Compounds in Solution," Accounts of Chemical Research 1973, vol. 6, pp. 275-281.
Espino, C. G. et al., "A Rh-Catalyzed C—H Insertion Reaction for the Oxidative Conversion of Carbamates to Oxazolidinones," Angew. Chem. Int. Ed. 2001, 40:3, pp. 598-600.
Espino, C. G. et al., "Expanding the Scope of C—H Amination through Catalyst Design," J. Am. Chem. Soc. 2004, 126, pp. 15378-15379.
Eto et al., Conformation of aromatic rings in isolable atropisomers of 2-arylindoline derivatives and kinetic evidences for π-π interaction. Tetrahedron Lett. Jan. 23, 2010;66(4):898-903.

(56) References Cited

OTHER PUBLICATIONS

Fan, Y.-Q. et al., "Alkaloids with Cardiovascular Effects from the Marine-Derived Fungus Penicilliumexpansum Y32," Mar. Drugs 2015, 13, pp. 6489-6504.
Fang, C.-L. et al., "Dimerization of a 3-Substituted Oxindole at C-3 and Its Application to the Synthesis of (±)-Folicanthine," J. Am. Chem. Soc. 1994, 116, pp. 9480-9486.
Fink et al., "Mercaptoacyl Dipeptides as Orally Active Dual Inhibitors of Angiotensin-Converting Enzyme and Neutral Endopeptidase." J. Med. Chem.1996; 39(16):3158-3168.
Fiori, K. W. et al., "A mechanistic analysis of the Rh-catalyzed intramolecular C—H amination reaction," Tetrahedron 2009, 65, pp. 3042-3051.
Fiori, K. W. et al., "Catalytic Intermolecular Amination of C—H Bonds: Method Development and Mechanistic Insights," J. Am. Chem. Soc. 2007, 129, pp. 562-568.
Firouzabadi et al., "Bispyridinesilver permanganate[Ag(C5H5N)2]MnO4: an efficient oxidizing reagent for organic substrates." Tetrahedron Lett. 1982; 23(17): 1847-1850.
Flynn et al., "The synthesis and tubulin binding activity of thiophene-based analogues of combretastatin A-4." Bioorg Med Chem Lett. Sep. 3, 2001; 11(17):2341-3.
Foo, K. et al., "Total Synthesis-Guided Structure Elucidation of (+)-Psychotetramine," Angew. Chem. Int. Ed. Engl. 2011, 50(12), pp. 2716-2719.
Fotsis et al., "The endogenous oestrogen metabolite 2-methoxyoestradiol inhibits angiogenesis and suppresses tumour growth." Nature. Mar. 17, 1994; 368(6468):237-9.
Francisco et al., "Agonistic properties and in vivo antitumor activity of the anti-CD-40 antibody, SGN-14" Cancer Res. 2000; 60:3225-3231.
Frisch et al., "Synthesis of Short Polyoxyethylene-Based Heterobifunctional Cross-Linking Reagents. Application to the Coupling of Peptides to Liposomes." Bioconjugate Chem., 1996, 7 (2), pp. 180-186.
Fuchs, J. R. et al., "Total Synthesis of (±)-Perophoramidine," J. Am. Chem. Soc. 2004, 126, pp. 5068-5069.
Fukuyama et al., "A total synthesis of gliotoxin." J. Am. Chem. Soc. 1976; 98(21):6723-6724.
Furst, L. et al., "Total Synthesis of (+)-Gliocladin C Enabled by Visible-Light Photoredox Catalysis," Angew. Chem. Int. Ed. 2011, 50, pp. 9655-9659.
Gardiner et al., "The epipolythiodioxopiperazine (ETP) class of fungal toxins: distribution, mode of action, functions and biosynthesis." Microbiology. Apr. 2005; 151(Pt 4):1021-32.
Gardner et al., "Understanding C—H bond oxidations: H. and H− transfer in the oxidation of toluene by permanganate." Science. Sep. 29, 1995; 269(5232):1849-51.
Gastpar et al., "Methoxy-Substituted 3-Formyl-2-phenylindoles Inhibit Tubulin Polymerization." J. Med. Chem.1998; 41(25):4965-4972.
Gerwick et al., "Structure of Curacin A, a Novel Antimitotic, Antiproliferative and Brine Shrimp Toxic Natural Product from the Marine Cyanobacterium Lyngbya majuscula." J. Org. Chem.1994; 59(6):1243-1245.
Getahun et al., "Synthesis of alkoxy-substituted diaryl compounds and correlation of ring separation with inhibition of tubulin polymerization: differential enhancement of inhibitory effects under suboptimal polymerization reaction conditions." J. Med. Chem. 1992; 35(6):1058-1067.
Gilow et al., "Sulfenylation of some pyrroles and indoles." J Heterocyclic Chem. 1991, 28(4):1025-1034.
Goldman et al., "Immunolocalization of neuroblastoma using radiolabeled monoclonal antibody UJ13A." J. Pediatr. 1984; 105:252-256.
Goldstraw et al., Non-small-cell lung cancer. Lancet 2011;378:1727-40.
Golitz, P. et al., "A New Method for the Introduction of Trifluoromethyl Groups," Angew. Chem. Int. Ed. Engl. 1977, 16, No. 12, pp. 854-855.

Govek, S. P. et al., "Total Synthesis of (+)-asperazine," Tetrahedron 2007, 63, pp. 8499-8513.
Greene, T. W. et al., "Greene's Protective Groups in Organic Synthesis," Fifth Edition, Wiley, New York, NY 2014, Chapter 7, "Protection for the Amino Group," 299 pages (Parts 1 & 2).
Greiner et al., "Identification of a specific inhibitor of the histone methyltransferase SU(VAR)3-9." Nat Chem Biol. Aug. 2005;1(3):143-5.
Gueritte-Voegelein, F. et al., "Alkaloids From Psychotria Oleoides with Activity on Growth Hormone Release," J. Nat. Prod. 1992, 55, pp. 923-930.
Gwaltney et al., "Novel sulfonate derivatives: potent antimitotic agents." Bioorg Med Chem Lett. Jul. 9, 2001; 11(13):1671-3.
Hadimani et al., "Synthesis, in vitro, and in vivo evaluation of phosphate ester derivatives of combretastatin A-4." Bioorg. Med. Chem. Lett. 2003; 13(9):1505-1508.
Hale et al., "Enantiospecific Formal Total Synthesis of the Tumor and GSK-3b Inhibiting Alkaloid, (−)-Agelastatin A," Org. Lett., 5(16):2927-2930 (2003).
Hall, E. S. et al., "Biogenetic-Type Synthesis of the Calycanthaceous Alkaloids," Tetrahedron 1967, 23, pp. 4131-4141.
Hamada et al., "Selective removal of electron-accepting p-toluene- and naphthalenesulfonyl protecting groups for amino function via photoinduced donor acceptor ion pairs with electron-donating aromatics." J. Am. Chem. Soc. 1986; 108(1):140-145.
Hammonds et al., "Studies to show that with podophyllotoxin the early replicative stages of herpes simplex virus type 1 depend upon functional cytoplasmic microtubules." J Med Microbiol. Sep. 1996; 45(3):167-72.
Han et al., "Synthesis and Anticancer Activity of All Known (−)-Agelastatin Alkaloids," The Journal of Organic Chemistry, 78, p. 11970-11984 (2013).
Han, S.-J. et al., "A Diastereodivergent Synthetic Strategy for the Syntheses of Communesin F andPerophoramidine," Org. Lett. 2014, 16, pp. 3316-3319.
Han, S.-J. et al., "Evolution of a Unified, Sterodivergent Approach to the Synthesis of Communesin F and Perophoramidine," J. Org. Chem. 2015, 80, pp. 528-547.
Hansen et al., "A stereoselective synthetic approach to (2S,3R)-N-(1',1'-dimethy1-2',3'-epoxypropyl)-3-hydroxytryptophan, a component of cyclomarin A." Tetrahedron: Asymmetry 2006; 17(1):15-21.
Hatanaka et al., "Novel B-ring modified combretastatin analogues: syntheses and antineoplastic activity." Bioorg Med Chem Lett. Dec. 1, 1998; 8(23):3371-4.
Hay et al., "A 2-nitroimidazole carbate prodrug of 5-amino-1-(chloromethyl)-3-[(5,6,7-trimethoxyindol-2-yl)carbonyl]-1,2-dihydro-3H-benz[e]indole (amino-seco-CBI-TMI) for use with ADEPT and GDEPT. " Bioorg. Med. Chem. Lett. 1999; 9:2237-2242.
Hayashi, H. et al., "New Insecticidal Compounds, Communesins C, D and E, from Penicillium expansum Link MK-57," Biosci. Biotechnol. Biochem. 2004, 68, pp. 753-756.
He et al., Total Syntheses of (−)-Asperlicin and (−)-Asperlicin C. J Am Chem Soc. Jun. 11, 1998;120(25):6417-8.
Hegedus, L. S. et al., "Palladium-Catalyzed Reactions in the Synthesis of 3- and 4-Substituted Indoles. 3. Total Synthesis of(±)-Aurantioclavine," J. Org. Chem. 1987, 52, pp. 3319-3322.
Hellström et al., "Antitumor effects of L6, an IgG2a antibody that reacts with most human carcinomas." Proc Natl Acad Sci U S A. Sep. 1986; 83(18): 7059-7063.
Hendrickson, J. B. et al., "Total Synthesis of the Calycanthaceous Alkaloids. Chimonanthine," R. Proc. Chem. Soc. 1962, pp. 383-384.
Hendrickson, J.B. et al., "Total Synthesis of the Calycanthaceous Alkaloids," Tetrahedron 1964, vol. 20, pp. 565-579.
Herscheid et al., "Biosynthesis of gliotoxin. Synthesis of sulfur-bridged dioxopiperazines from N-hydroxyamino acids." J. Org. Chem. 1980; 45(10):1885-1888.
Herzon, S. B. et al., "Enantioselective Synthesis of Stephacidin B," J. Am. Chem. Soc. 2005, 127, pp. 5342-5344.
Higuchi et al., First Total Synthesis of Hinckdentine A. Org Lett. 2009;11(1):197-9.

(56) References Cited

OTHER PUBLICATIONS

Higuchi et al., Preparation of 2,2-disubstituted 1,2-dihydro-3H-indol-3-ones via oxidation of 2-substituted indoles and Mannich-type reaction. Tetrahedron Lett. Feb. 6, 2010;66(6):1236-43.
Hino et al., "Synthesis of 3,6-diethoxycarbonyl-3,6-epipolythia-2,5-piperazinedione derivatives." Tetrahedron Lett. 1971; 12(33):3127-3129.
Hino, T. et al., "Chemistry and Reactions of Cyclic Tautomers of Tryptamines and Tryptophans," The Alkaloids: Chemistry and Pharmacology, Brossi, A., Ed.; Academic Press: New York, 1989; vol. 34, pp. 1-75.
Hino, T. et al., "Oxidative Dimerization of Nb-Methoxycarbonyltryptamines by Dye-Sensitized Photooxygenation in Formic Acid. Synthesis of (±)-Folicanthine and (±)-Chimonanthine," Tetrahedron Letters 1978, 49, pp. 4913-4916.
Hino, T. et al., "Total Synthesis of (±)-Folicanthine," Tetrahedron Letters 1963, 25, pp. 1757-1760.
Hoffmann, S. et al., "A Powerful Br0nsted Acid Catalyst for the Organocatalytic Asymmetric Transfer Hydrogenation of Imines," Angew. Chem. Int. Ed. 2005, 44, pp. 7424-7427.
Hoijemberg, P. A. et al., "Photolysis of an asymmetrically substituted diazene in solution and in the crystalline state," Photochem. Photobiol. Sci. 2009, 8, pp. 961-969.
Holwell et al., "Anti-vascular effects of vinflunine in the MAC 15A transplantable adenocarcinoma model." Br. J. Cancer., 2001; 84:290-295.
Hoogenboom et al., "By-passing immunisation. Human antibodies from synthetic repertoires of germline VH gene segments rearranged in vitro." J Mol Biol. Sep. 20, 1992; 227(2):381-8.
Hossain, T. Md. et al., "Synthesis of Bisbicyclo[1.1.1]pentyldiazene. The Smallest Brigehead Diazene," J. Org. Chem. 2001, 66, pp. 6282-6285.
Hsieh et al., "Structure-activity and crystallographic analysis of benzophenone derivatives—the potential anticancer agents." Bioorg Med Chem Lett. 2002; 13(1):101-105.
Huang et al., "Diketopiperazines from Marine Organisms." Chem. Biodiv. 2010; 7(12):2809-2829.
Huard, K. et al., "N-Tosyloxycarbamates as Reagents in Rhodium-Catalyzed C—H Amination Reactions," Chem. Eur. J. 2008, 14, pp. 6222-6230.
Huston et al., "Protein engineering of antibody binding sites: recovery of specific activity in an anti-digoxin single-chain Fv analogue produced in *Escherichia coli*." Proc Natl Acad Sci U S A. Aug. 1988; 85(16):5879-5883.
Ikeda, H. et al., "Evidence for Significant Through-Space and Through-Bond Electronic Coupling in the 1,4-Diphenylcyclohexane-1,4-diyl Radical Cation Gained by Absorption Spectroscopy and OFT Calculations," Chem. Eur. J. 2007, 13, DD. 9207-9215.
Isham et al., "Chaetocin: a promising new antimyeloma agent with in vitro and in vivo activity mediated via imposition of oxidative stress." Blood. Mar. 15, 2007;109(6):2579-88.
Isham et al., "The anticancer effects of chaetocin are independent of programmed cell death and hypoxia, and are associated with inhibition of endothelial cell proliferation." Br J Cancer. Jan. 17, 2012;106(2):314-23.
Ishikawa, H. et al., "Dimerization of indole derivatives with hypervalent iodines(lll): a new entry for the concise total synthesis of rac- and meso-chimonanthines," Tetrahedron Lett. 2002, 43, pp. 5637-5639.
Iwasa et al., "Total Synthesis of (+)-Chaetocin and its Analogues: Their Histone Methyltransferase G9a Inhibitory Activity." J. Am. Chem. Soc. 2010; 132(12):4078-4079.
Iwasa, et al., "Epipolythiodiketopiperazine Alkaloids: Total Syntheses and Biological Activities." Isr. J Chem. 2011; 51(3-4):420-433.
Jadulco, R. C., "Isolation and Structure Elucidation of Bioactive Secondary Metabolites from Marine Sponges and Sponge-derived Fungi," 2002, 88 pages.
Jadulco, R. et al., "New Communesin Derivatives from the Fungus *Penicillium* sp. Derived from theMediterranean Sponge *Axinella verrucosa*," J. Nat. Prod. 2004, 67, pp. 78-81.
Jamison, C. R. et al., "Enantioselective Synthesis of Polypyrroloindolines by Controlled Oligomerization," Nat. Chem. 2017, doi: 10.1038/nchem.2825, 1 page.
Janik et al., "Synthesis and antimicrobtubule activity of combretatropone derivatives." Bioorg. Med. Chem. Lett. 2002; 10:1895-1903.
Jannic, V. et al., Pyrrolidinoindoline alkaloids from Psychotria oleoides and Psychotria lyciiflora. J Nat Prod. Jun. 1999;62(6):838-43.
Jespers et al., "Guiding the selection of human antibodies from phage display repertoires to a single epitope of an antigen." Biotechnology (N Y). Sep. 1994; 12(9):899-903.
Jiang et al., "Disulfide- and Multisulfide-Containing Metabolites from Marine Organisms." Chem. Rev. 2012; 112(4):2179-2207.
Jiang et al., "Epipolythiodioxopiperazines from fungi: chemistry and bioactivities." Mini Rev Med Chem. Aug. 2011;11(9):728-45.
Jiang et al., "Synthesis and biological evaluation of 2-styrylquinazolin-4(3H)-ones, a new class of antimitotic anticancer agents which inhibit tubulin polymerization." J. Med. Chem.1990; 33(6):1721-1728.
Jones et al., "Replacing the complementarity-determining regions in a human antibody with those from a mouse." Nature. May 29-Jun. 4, 1986;321(6069):522-5.
Jordan et al., "Fungal epipolythiodioxopiperazine toxins have therapeutic potential and roles in disease." Trends Pharmacol. Sci. 8, 144-149.
Jouanneau et al., "Derivatization of agelastatin A leading to bioactive analogs and a trifunctional probe," Bioorganic & Medicinal Chemistry Letters, 26, p. 2092-2097 (2016).
Kabat et al., "Origins of antibody complementarity and specificity—hypervariable regions and minigene hypothesis." J Immunol Sep. 1, 1980; 125(3):961-969.
Kakeya, et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid." Chem. Pharm. Bull. 1984 32(2):692-698.
Kaneko et al., "New hydrazone derivatives of Adriamycin and their immunoconjugates—a correlation between acid stability and cytotoxicity." Bioconjugate Chem.1991; 2(3):133-141.
Kanoh et al., "(−)-Phenylahistin arrests cells in mitosis by inhibiting tubulin polymerization." J Antibiot (Tokyo). Feb. 1999; 52(2):134-41.
Kapoor, "Inhibition of osteopontin dependent carcinogenesis," J. Cancer Res. Clin. Oncol., 134, p. 927-928 (2008).
Karaman et al., "Preparation and properties of quaternary ammonium and phosphonium permanganates." J. Org. Chem.1984; 49(23):4509-4516.
Kennett et al., "Hybrid myelomas producing antibodies against a human neuroblastoma antigen present on fetal brain." Science Mar. 16, 1979: 203(4385):1120-1121.
Kieffer, M. E. et al., "Copper-Catalyzed Diastereoselective Arylation of Tryptophan Derivatives: Total Synthesis of (+)-Naseseazines A and B," J. Am. Chem. Soc. 2013, 135(15), pp. 5557-5560.
Kim et al., "Alkylthiolation of allylic sulfides. [2,3] Sigmatropic rearrangement of thiosulfonium ions." J. Org. Chem. 1979; 44(12):1897-1904.
Kim et al., "Concise Total Synthesis and Stereochemical Revision of (+)-Naseseazines A and B: Regioselective Arylative Dimerization of Diketopiperazine Alkaloids." J. Am. Chem. Soc. 2011; 133(38):14940-14943.
Kim et al., "General Approach to Epipolythiodiketopiperazine Alkaloids: Total Synthesis of (+)-Chaetocins A and C and (+)-12,12'-Dideoxychetracin A." J. Am. Chem. Soc. 2010:132 (41):14376-14378.
Kim et al., "Total synthesis of (+)-11,11'-dideoxyverticillin A." Science. Apr. 10, 2009;324(5924):238-41.
Kim et al., Biogenetically inspired syntheses of alkaloid natural products. Chem Soc Rev. Nov. 2009;38(11):3035-50. doi: 10.1039/b819925f. Epub Sep. 23, 2009.
Kim et al., General approach to epipolythiodiketopiperazine alkaloids: total synthesis of (+)-chaetocins A and C and (+)-12,12'-dideoxychetracin A. J Am Chem Soc. Oct. 20, 2010;132(41):14376-8. doi: 10.1021/ja106869s.

(56) References Cited

OTHER PUBLICATIONS

Kim et al., Total synthesis of (+)-11, 11'-dideoxyverticillin A, Science. 2009;324(5924):238-41.
Kim, H. et al., "Transition-Metal-Mediated Direct C—H Amination of Hydrocarbons with Amine Reactants: The Most Desirable but Challenging C—N Bond-Formation Approach," ACS Catal. 2016, 6, pp. 2341-2351.
Kim, J. et al., "Biogenetically-Inspired Total Synthesis of Epidithiodiketopiperazines," Acc. Chem. Res. 2015, 48, pp. 1159-1171.
King et al., "Facile synthesis of maleimide bifuntional linkers," Tetrahedron Lett. 2002; 43:1987-1990.
Kingsbury et al., "A novel peptide delivery system involving peptidase activated prodrugs as antimicrobial agents. Synthesis and biological activity of peptidyl derivatives of 5-fluorouracil." J. Med. Chem. 1984; 27:1447-1451.
Kingston et al., "The Chemistry of Taxol, a Clinically Useful Anticancer Agent." J. Nat. Prod. 1990; 53(1):1-12.
Kishi et al., "Total synthesis of dehydrogliotoxin." J. Am. Chem. Soc. 1973; 95(19):6492-6493.
Kishi et al., "Total synthesis of sporidesmin A." J. Am. Chem. Soc. 1973; 95(19):6493-6495.
Kitir, B. et al., "Total synthesis and structural validation of cyclodepsipeptides solonamide A and B," Tetrahedron 2014, 70, pp. 7721-7732.
Kobayashi et al., "Synthetic study on an antitumor antibiotic rhizoxin by using an enzymatic process on prochiral β-substituted glutarates." Pure Appl. Chem. 1992; 64(8):1121-1124.
Kodanko, J. J. et al., "Enantioselective Total Syntheses of the Cyclotryptamine Alkaloids Hodgkinsine and Hodgkinsine B," Angew. Chem. Int. Ed. 2003, 42, pp. 2528-2531.
Kodanko, J. J. et al., "Synthesis of All Low-energy Stereoisomers of the Tris(pyrrolidinoindoline) Alkaloid Hodgkinsine and Preliminary Assessment of Their Antinociceptive Activity," J. Org. Chem. 2007, 72, pp. 7909-7914.
Köhler et al., "Continuous cultures of fused cells secreting antibody of predefined specificity." Nature 256, 495-497 (1975).
Kosower, E. M., "Monosubstituted Diazenes (Diimides). Suprising Intermediates," Accounts of Chemical Research 1971, vol. 1, No. 6, pp. 193-198.
Kozbor, Immunology Today, vol. 4, 1983, pp. 72-79.
Kricheldorf, H.R. "Synthese von Isothiocyanatocarbonsäurechloriden aus Lactamen." Angew. Chem. 1975; 87(14):517.
Krishnan, S. et al., "Pd-Catalyzed Enantioselective Aerobic Oxidation of Secondary Alcohols:Applications to the Total Synthesis of Alkaloids," J. Am. Chem. Soc. 2008, 130, pp. 137 45-13754.
Kroutil et al., "First preparative biocatalytic hydrolysis and S-methylation of cyclic trithiocarbonates." Tetrahedron 2002; 58(13):2589-2592.
Ksander et al., Chemie der α-Aminonitrile 1. Mitteilung Einleitung und Wege zu Uroporphyrinogen-octanitrilen. Helv Chim Acta. Jul. 8, 1987;70(4):1115-72.
Kung et al., "Small molecule blockade of transcriptional coactivation of the hypoxia-inducible factor pathway." Cancer Cell. Jul. 2004;6(1):33-43.
Kurokawa, T. et al., "Synthesis of 1,3-Diamines Through Rhodium-Catalyzed C—H Insertion," Angew. Chem. Int. Ed. 2009, 48, pp. 2777-2779.
Kyoizumi et al., "Monoclonal antibodies to human squamous cell carcinoma of the lung and their application to tumor diagnosis." Cancer Res. Jul. 1985; 45(7):3274-81.
Laguzza et al., "New antitumor monoclonal antibody-vinca conjugates LY203725 and related compounds: design, preparation, and representative in vivo activity." J. Med. Chem. 1989; 32(3):548-555.
Langer, R., "New methods of drug delivery," Science Sep. 28, 1990: vol. 249, Issue 4976, pp. 1527-1533.
Lathrop et al., Radical-mediated dimerization and oxidation reactions for the synthesis of complex alkaloids. Chimia (Aarau). 2012;66(6):389-93. doi: 10.2533/chimia.2012.389.
Lathrop, S. P. et al., "Application of diazene-directed fragment assembly to the total synthesis and stereochemical assignment of ( +)-desmethyl-meso-chimonanthine and related heterodimeric alkaloids," Chem. Sci. 2014, 5, DD. 333-340.
Lavielle et al., "New .alpha.-amino phosphonic acid derivatives of vinblastine: chemistry and antitumor activity." J. Med. Chem.1991; 34(7):1998-2003.
Lawrence et al., "The interaction of chalcones with tubulin." Anticancer Drug Des. Apr. 2000; 15(2):135-41.
Lebsack, A. D. et al., "Enantioselective Total Synthesis of Quadrigemine C and Psycholeine," J. Am. Chem. Soc. 2002, 124, pp. 9008-9009.
Lee et al., "Antihepatoma activity of chaetocin due to deregulated splicing of hypoxia-inducible factor 1α pre-mRNA in mice and in vitro." Hepatology. Jan. 2011;53(1):171-80.
Leoni et al., "Indanocine, a microtubule-binding indanone and a selective inducer of apoptosis in multidrug-resistant cancer cells." J Natl Cancer Inst. Feb. 2, 2000;92(3):217-24.
Li et al., "An integrated approach to the discovery of potent agelastatin A analogues for brain tumors: chemical synthesis and biological, physicochemical and CNS pharmacokinetic analyses," Med. Chem. Commun., 4, p. 1093-1098 (2013).
Li et al., "Pharmacokinetics of Agelastatin A in the central nervous system," Med. Chem. Commun., 3, p. 233-237, (2012).
Li et al., Cytotoxic metabolites from the antarctic psychrophilic fungus *Oidiodendron truncatum*. J Nat Prod. May 25, 2012;75(5):920-7. doi: 10.1021/np3000443. Epub May 14, 2012.
Li et al., General Approach for the Synthesis of Ajmaline/Sarpagine Indole Alkaloids: Enantiospecific Total Synthesis of (+)-Ajmaline, Alkaloid G, and Norsuaveoline via the Asymmetric Pictet-Spengler Reaction. J Am Chem Soc. Jul. 16, 1999;121(30):6998-7010.
Li et al., Ligand-based targeted therapy: a novel strategy for hepatocellular carcinoma. Int J Nanomedicine. Oct. 31, 2016;11:5645-5669. eCollection 2016.
Liang et al., Organocatalytic stereoselective conjugate addition of 3-substituted oxindoles with in situ generated ortho-quinone methides. Tetrahedron Lett. May 2, 2018;59(18):1742-7.
Libot, F. et al., "Biomimetic Transformation of Hodgkinsine, a Pyrrolidinoindoline Alkaloids," Heterocycles 1988, 27, pp. 2381-2386.
Libot, F. et al., "Rubiacees D'Oceanie: Alcalo'Ides de Psychotria Oleoides de Nouvelle-Caledonie et de Calycodendron Milnei du Vanuatu (Nouvelles-Hebrides)," Journal of Natural Products 1987, vol. 50, No. 3, pp. 468-473.
Lim, Y.-K. et al., "Novel Route to Azobenzenes via Pd-Catalyzed Coupling Reactions of Aryl Hydrazides with Aryl Halides, Followed by Direct Oxidations," Org. Lett. 2003, vol. 5, No. 7, pp. 979-982.
Lin et al., "Antimitotic natural products combretastatin A-4 and combretastatin A-2: studies on the mechanism of their inhibition of the binding of colchicine to tubulin." Biochemistry 1989; 28(17):6984-6991.
Lin, H.-C. et al., "Elucidation of the Concise Biosynthetic Pathway of the Communesin lndole Alkaloids," Angew. Chem. Int. Ed. 2015, 54, pp. 3004-3007.
Lin, H.-C. et al., "P450-Mediated Coupling of lndole Fragments to Forge Communesin and Unnatural Isomers," J. Am. Chem. Soc. 2016, 138, pp. 4002-4005.
Lindovska, P. et al., "Concise Synthesis of (−)-Hodgkinsine, (−)-Calycosidine, (−)-Hodgkinsine B, (−)-Quadrigemine C, and (−)-Psycholeine via Convergent and Directed Modular Assembly of Cyclotryptamines," https://www.ncbi.nlm.nih.qov/m/pubmed/29058431, 2017, 7 paqes.
Link, J. T. et al., "Stereocontrolled Total Syntheses of meso-Chimonanthine and meso-Calycanthine via a Novel Samarium Mediated Reductive Dialkylation," J. Am. Chem. Soc. 1996, 118, pp. 8166-8167.
Little, R. D. et al., "Total Synthesis of the Marine Natural Product i19(121-Capnellene. Reversal of Regiochemistry in the lntramolecular 1,3-Diyl Trapping Reaction," J. Am. Chem. Soc. 1983, 105, pp. 928-932.
Little, R. D., "Diyl Trapping and Electroreductive Cyclization Reactions," Chem. Rev. 1996, 96, pp. 93-114.

(56) References Cited

OTHER PUBLICATIONS

Liu et al., "Chimeric Mouse-Human IgG1 Antibody That Can Mediate Lysis of Cancer Cells." Proc. Natl. Acad. Sci., USA May 1987; 84:3439-3443.
Liu et al., "Production of a Mouse-Human Chimeric Monoclonal Antibody to CD20 with Potent Fc-Dependent Biologic Activity." J. Immunol. Nov. 1987; 139:3521-3526.
Liu et al., "Verticillin A overcomes apoptosis resistance in human colon carcinoma through DNA methylation-dependent upregulation of BNIP3." Cancer Res. Nov. 1, 2011;71(21):6807-16.
Liu, P. et al., "Total Synthesis of the Polycyclic Fungal Metabolite (±)-Communesin F," Angew. Chem. Int. Ed. 2010, 49, pp. 2000-2003.
Loach, R. P. et al., "Concise Total Synthesis of (+)-Asperazine, (+)-Pestalazine A, and (+)-iso-Pestalazine A. Structure Revision of ( +)-Pestalazine A," J. Am. Chem. Soc. 2016, 138(3), pp. 1057-1064.
Mahboobi et al., "Synthetic 2-Aroylindole Derivatives as a New Class of Potent Tubulin-Inhibitory, Antimitotic Agents." J. Med. Chem. 2001; 44(26):4535-4553.
Mannila et al., "Combretastatin Analogs via Hydration of Stilbene Derivatives." Liebigs. Ann. Chem. 1993; 1993(9):1037-1039.
March, "Advanced Organic Chemistry," Third Edition: John Wiley & Sons, inc. New York, NY, Chapter 1, "Localized Chemical Bonding" n pp. 16-18.
Marks et al., "By-passing immunization. Human antibodies from V-gene libraries displayed on phage." J Mol Biol. Dec. 5, 1991; 222(3):581-97.
Mascitti, V. et al., "Total Synthesis of (±)-Pentacycloanammoxic Acid," J. Am. Chem. Soc. 2004, 126, pp. 15664-15665.
Mason et al., "Agelastatin A: a novel inhibitor of osteopontin-mediated adhesion, invasion, and colony formation," Mol. Cancer Ther., 7:548-558 (2008).
Matano et al., "Synthesis and Charge-Carrier Transport Properties of Poly(phosphole P-alkanesulfonylimide)s," Org. Lett., 2013, 15 (4), pp. 932-935.
Matsuda, Y. et al., "Total Synthesis and Structure Reinvestigation of So-Called Isochimonanthine," Heterocycles 2005, 65, pp. 1031-1033.
May, J. A. et al., "Biomimetic approach to communesin B (a.k.a. nomofungin)," Tetrahedron Letters 2003, 44, pp. 1203-1205.
May, J. A. et al., "The structural and synthetic implications of the biosynthesis of the calycanthaceous alkaloids, the communesins, and nomofungin," Tetrahedron 2006, 62, pp. 5262-5271.
Medarde et al., "Synthesis and antineoplastic activity of combretastatin analogues: Heterocombretastatins." Eur. J. Med. Chem., 1998; 33(1)71-77.
Medarde et al., "Synthesis and pharmacological activity of combretastatin analogues. Naphthylcombretastatins and related compounds." Bioorganic. Med. Chem. Lett. 1995; 5(3):229-232.
Medarde et al., "Synthesis and pharmacological activity of diarylindole derivatives. Cytotoxic agents based on combretastatins." Bioorg Med Chem Lett. Aug. 1, 1999; 9(16):2303-2308.
Medina et al., "Novel antineoplastic agents with efficacy against multidrug resistant tumor cells." Bioorg Med Chem Lett. Oct. 6, 1998; 8(19):2653-6.
Merchant et al., "An efficient route to human bispecific IgG." Nat Biotechnol. Jul. 1998;16(7):677-81.
Michaelis, D. J. et al., "Oxaziridine-mediated enantioselective aminohydroxylation of styrenes catalyzed by copper(ll) bis(oxazoline) complexes," Tetrahedron 2009, 65, pp. 5118-5124.
Miknis et al., "Total synthesis of (.+-.)-aspirochlorine." J. Am. Chem. Soc. 1993; 115(2):536-547.
Miller et al., "Specific Inhibition of Viral Ribonucleic Acid Replication by Gliotoxin." Science Jan. 26, 1968; 159(3813):431-432.
Miller et al., "Treatment of B-Cell Lymphoma with Monoclonal Anti-Idiotype Antibody." N Engl J Med 1982; 306:517-522.
Milstein et al., "Hybrid hybridomas and their use in immunohistochemistry." Nature. Oct. 6-12, 1983;305(5934):537-40.
Moody et al., "Dirhodium(II) tetraacetate catalysed reactions of diazo thioamides: isolation and cycloaddition of anhydro-4-hydroxy-1,3-thiazolium hydroxides (thioisomünchnones), an approach to analogues of dehydrogliotoxin." Org. Biomol. Chem. 2003;1(15):2716-2722.
Morrison, S.L, "Transfectomas provide novel chimeric antibodies." Science Sep. 20, 1985; 229(4719):1202-1207.
Morton, D. et al., "Chiral non-racemic sulfinimines: versatile reagents for asymmetric synthesis,"Tetrahedron 2006, 62, pp. 8869-8905.
Movassaghi et al., Total Synthesis of All (−)-Agelastatin Alkaloids Asymmetric Synthesis Ii: More Methods and Applications. 2013;391-396. DOI: 10.1002/9783527652235.ch49.
Movassaghi et al., Total synthesis of all (−)-agelastatin alkaloids. Chem. Sci. 2010;1:561-66.
Movassaghi, M. et al., "Concise Total Synthesis of (−)-Calycanthine, (+)-Chimonanthine, and(+)-Folicanthine,"Angew. Chem. Int. Ed. 2007, 46, pp. 3725-3728.
Movassaghi, M. et al., "Concise Total Synthesis of (+)-WIN 64821 and (−)-Ditryptophenaline," Angew. Chem. Int. Ed. 2008, 47, pp. 1485-1487.
Movassaghi, M. et al., "Directed Heterodimerization: Stereocontrolled Assembly via Solvent-Caged Unsymmetrical Diazene Fragmentation," J. Am. Chem. Soc. 2011, 133, pp. 13002-13005.
Mu et al, "Synthesis, anticancer activity, and inhibition of tubulin polymerization by conformationally restricted analogues of lavendustin A." J Med Chem. Apr. 24, 2003; 46(9):1670-82.
Müllbacher et al., "Structural relationship of epipolythiodioxopiperazines and their immunomodulating activity." Molec. Immunol. Feb. 1986; 23(2):231-235.
Myers et al., A Concise, Stereocontrolled Synthesis of (−)-Saframycin A by the Directed Condensation of α-Amino Aldehyde Precursors. J Am Chem Soc. Nov. 5, 1999;121(46):10828-29.
Nakada et al., "The first total synthesis of the antitumor macrolide, rhizoxin." Tetrahedron Lett., 1993; 34(6):1039-1042.
Nakagawa, M. et al., "Oxidative Dimerization of Nb-Acyltryptophans Total Synthesis and Absolute Configuration of Ditryptophenaline," Tetrahedron Letters 1981, vol. 22, No. 52, pp. 5323-5326.
Nam et al., "Combretastatin A-4 analogues as antimitotic antitumor agents." Curr Med Chem. Sep. 2003; 10(17):1697-722.
Nam et al., "Synthesis and anti-tumor activity of novel combretastatins: combretocyclopentenones and related analogues." Bioorg Med Chem Lett. 2002; 12(15):1955-1958.
Nascimento, R. R. G. et al., "New Alkaloids from *Margaritopsis carrascoana* (Rubiaceae)," J. Braz. Chem. Soc. 2015, vol. 26, No. 6, pp. 1152-1159.
Nelsen, S. F. et al., "Azocumene. I. Preparation and Decomposition of Azocumene. Unsymmetrical Coupling Products of the Cumyl Radical," Journal of the American Chemical Society, Jan. 5, 1966, 88:1, pp. 137-143.
Nelson, H. M. et al., "Chiral Anion Phase Transfer of Aryldiazonium Cations: An EnantioselectiveSynthesis of C3-Diazenated Pyrroloindolines," Angew. Chem. Int. Ed. 2014, 53, pp. 5600-5603.
Neuman, R. C. et al., "cis-Diazenes. Viscosity Effects, One-Bond Scission, and Cis-Trans Isomerization," J. Org. Chem. 1990, 55, pp. 2682-2688.
Nguyen-Hai et al., "Combretoxazolones: synthesis, cytotoxicity and antitumor activity." Bioorg. Med. Chem. Lett. 2001; 11(23):3073-3076.
Nicolaou et al., "A Practical Sulfenylation of 2,5-Diketopiperazines." Angem. Chem. Int. Ed. 2012; 51(3):728-732.
Nicolaou et al., "Synthesis of epothilones A and B in solid and solution phase." Nature. May 15, 1997;387(6630):268-72.
Nicolaou et al., "Total Synthesis of Epicoccin G." J. Am. Chem. Soc. 2011; 133(21):8150-8153.
Nielsenw et al., "Glycolamide Esters as Biolabile Prodrugs of Carboxylic Acid Agents: Synthesis, Stability, Bioconversion, and Physicochemical Properties." J. Pharma. Sciences. 1988; 77(4):285-298.
Nishida et al., "Fungal metabolite gliotoxin targets flavocytochrome b558 in the activation of the human neutrophil NADPH oxidase." Infect Immun Jan. 2005;73(1):235-44.

(56) References Cited

OTHER PUBLICATIONS

Nishimura et al., "Recombinant human-mouse chimeric monoclonal antibody specific for common acute lymphocytic leukemia antigen." Cancer Res. Feb. 15, 1987;47(4):999-1005.
Numata, A. et al., "Communesins, Cytotoxic Metabolites of a Fungus Isolated from a Marine Alga," Tetrahedron Lett. 1993, 34, pp. 2355-2358.
Oguri et al., "Amino Acids and Peptides. XXIX. A New Efficient Asymmetric Synthesis of α-Amino Acid Derivatives with Recycle of a Chiral Reagent-Asymmetric Alkylation of a Chiral Schiff Base from Glycine." Chem. Pharm. Bull. 1978; 26(3):803-808.
Ohme, R. et al., "Preparation of Azo Compounds from N,N'-Dialkylsulfamides," Angew. Chem. Internat. Edit. 1965, vol. 4, No. 5, p. 433.
Okabe et al., "Elimination of Small Cell Lung Cancer Cells in Vitro from Human Bone Marrow by a Monoclonal Antibody." Cancer Res. May 1985; 45:1930-1933.
Okoth et al., "End-labeled amino terminated monotelechelic glycopolymers generated by ROMP and Cu(I)-catalyzed azide—alkyne cycloaddition," Beilstein J. Org. Chem. 2013, 9, 608-612.
Oshumi et al., "Novel Combretastatin Analogues Effective against Murine Solid Tumors: Design and Structure—Activity Relationships." J. Med. Chem.1998; 41(16):3022-3032.
Oshumi et al., "Syntheses and antitumor activity of cis-restricted combretastatins: 5-membered heterocyclic analogues." Bioorg Med Chem Lett. Nov. 17, 1998; 8(22):3153-8.
Ottenheijm et al., "Approaches to analogs of dehydrogliotoxin. 6. An efficient synthesis of a gliotoxin analog with anti-reverse transcriptase activity." J. Org. Chem. 1976: 41(21):3433-3438.
Overman et al., "Construction of Epidithiodioxopiperazines by Directed Oxidation of Hydroxyproline-Derived Dioxopiperazines." Org. Lett. 2007; 9(25):5267-5270.
Overman et al., The cyanomethyl group for nitrogen protection and iminium ion generation in ring-enlarging pyrrolidine annulation. A short synthesis of the amaryllidaceae alkaloid d,1-crinin. Tetrahedron Lett. 1982;23(27):2741-4.
Overman, L. E. et al., "Direct Stereo- and Enantiocontrolled Synthesis of Vicinal Stereogenic Quaternary Carbon Centers. Total Synthesis of meso- and (−)-Chimonanthine and (+)-Calycanthine," J. Am. Chem. Soc. 1999, 121, pp. 7702-7703.
Overman, L. E. et al., "Enantioselective Construction of Vicinal Stereogenic Quaternary Centers by Dialkylation: Practical Total Syntheses of(+)- and meso-Chimonanthine," Angew. Chem. Int. Ed. 2000, vol. 39, No. 1, pp. 213-215.
Overman, L. E. et al., "Enantioselective synthesis of (−)-idiospermuline," Tetrahedron 2003, 59, pp. 6905-6919.
Overman, L. E. et al., "Enantioselective Total Synthesis of (+)-Gliocladin C," Org. Lett. 2007, 9(2), pp. 339-341.
Overman, L. E. et al., "Enantioselective Total Synthesis of the Cyclotryptamine Alkaloid ldiospermuline," Angew. Chem. Int. Ed. 2003, 42, pp. 2525-2528.
Owellen et al., "Inhibition of tubulin-microtubule polymerization by drugs of the Vinca alkaloid class." Cancer Res. Apr. 1976; 36(4):1499-502.
Pahl et al., "The immunosuppressive fungal metabolite gliotoxin specifically inhibits transcription factor NF-kappaB." J Exp Med. Apr. 1, 1996; 183(4): 1829-1840.
Pangborn et al., "Safe and Convenient Procedure for Solvent Purification," Organometallics, 1996, 15 (5), pp. 1518-1520.
Patel et al., "Straightforward access to protected syn alpha-amino-beta-hydroxy acid derivatives." Angew Chem Int Ed Engl. 2008; 47(22):4224-7.
Patron et al., "Origin and distribution of epipolythiodioxopiperazine (ETP) gene clusters in filamentous ascomycetes." BMC Evolutionary Biology 2007; 7:174.
Perez-Balado, C. et al., "Expedient Total Synthesis of WIN 64745 and WIN 64821," Org. Lett. 2008, vol. 10, No. 17, pp. 3701-3704.

Perez-Balado, C. et al., "Stereocontrolled and Versatile Total Synthesis of Bispyrrolidinoindoline Diketopiperazine Alkaloids: Structural Revision of the Fungal Isolate (+)-Asperdimin," Chem. Eur. J. 2009, 15, pp. 9928-9937.
Pettit et al., "Antineoplastic agents 365. Dolastatin 10 SAR probes." Anticancer Drug Des. Jun. 1998; 13(4):243-77.
Pettit et al., "Antineoplastic Agents, 122. Constituents of Combretum caffrum." J. Nat. Prod. 1987; 50(3):386-391.
Pettit et al., "Antineoplastic agents. 113. Synthesis of natural (−)-combretastatin." J. Org. Chem. 1985; 50(18):3404-3406.
Pettit et al., "Antineoplastic agents. 257. Isolation and structure of spongistatin 1." J. Org. Chem.1993; 58(6):1302-1304.
Pettit et al., "Antineoplastic Agents. 291. Isolation and Synthesis of Combretastatins A-4, A-5, and A-6." J. Med. Chem. 1995; 38(10):1666-1672.
Pettit et al., "Antineoplastic Agents. 443. Synthesis of the Cancer Cell Growth Inhibitor Hydroxyphenstatin and Its Sodium Diphosphate Prodrug." J. Med. Chem. 2000; 43(14):2731-2737.
Pettit et al., "Antineoplastic agents. 487. Synthesis and biological evaluation of the antineoplastic agent 3,4-methylenedioxy-5,4'-dimethoxy-3'-amino-Z-stilbene and derived amino acid amides." J Med Chem. Feb. 13, 2003; 46(4):525-31.
Pettit et al., "cation salts, combretastatin A-3, diphosphate, prodrugs." Anti-Cancer Drug Design 2000: 15(6):397-403.
Pettit et al., "Isolation and structure of combretastatin." Canadian Journal of Chemistry, 1982, 60(11): 1374-137.
Pettit et al., "The isolation and structure of a remarkable marine animal antineoplastic constituent: dolastatin 10." J. Am. Chem. Soc.1987; 109(22):6883-6885.
Pinney et al., "A new anti-tubulin agent containing the benzo[b]thiophene ring system." Bioorg Med Chem Lett. Apr. 19, 1999; 9(8):1081-6.
Pinney et al., "Synthesis and biological evaluation of aryl azide derivatives of combretastatin A-4 as molecular probes for tubulin." Bioorg Med Chem. Oct. 2000; 8(10):2417-25.
Poisel et al., "Syntheseversuche in der Reihe der 3.6-Epidithio-2.5-dioxo-piperazin-Antibiotika Gliotoxin, Sporidesmin, Aranotin and Chaetocin, II." Chem. Ber., 1971; 104(6):17141721.
Polaske et al., "Enantioselective organocatalytic α-sulfenylation of substituted diketopiperazines." Tetrahedron: Asym. 2009; 20(23):2742-2750.
Porter, N. A. et al., "Diazenyl Radicals: A 15N CIDNP and Radical Trapping Study of Unsymmetric Diazenes," Journal of the American Chemical Society Feb. 1, 1978, 100:3, pp. 920-925.
Porter, N. A. et al., "Photolysis of Unsymmetric Azo Compounds. Cis Azo Compound Intermediates," Journal of the American Chemical Society Jun. 27, 1973, 95:13, pp. 4361-4367.
Pubchem CID 161244 deposited on Mar. 27, 2005, pp. 1-15.
Pubchem CID 18624123 deposited on Dec. 4, 2007, pp. 1-12.
Pubchem Cid 69829071 deposited on Dec. 1, 2012, pp. 1-12.
Rao et al., "Radical mediated enantioselective construction of C-1 to C-9 segment of rhizoxin." Tetrahedron Lett. 1992; 33(27):3907-3910.
Rao et al., "Studies directed towards the total synthesis of rhizoxin: Stereoselective synthesis of C-12 to C-18 segment." Tetrahedron Lett. 1993; 34(4):707-710.
Rasolonjanahary, R. et al., "Psycholeine, a natural alkaloid extracted from Psychotria oleoides, acts as a weak antagonist of somatostatin," European Journal of Pharmacology 1995, 285, pp. 19-23.
Rautio et al., "Prodrugs: design and clinical applications." Nat Rev Drug Discov. Mar. 2008; 7(3):255-70.
Rautio, J. (Ed), Prodrugs and Targeted Delivery, Wiley, 2011.
Rezanka et al., "Pharmacologically Active Sulfur-Containing Compounds." Anti-Infect. Agents Med. Chem., 2006; 5(2):187-224.
Rightsel et al., "Antiviral Activity of Gliotoxin and Gliotoxin Acetate." Nature. Dec. 26, 1964;204:1333-4.
Robak, M. T. et al., "Synthesis and Applications of tert-Butanesulfinamide," Chem. Rev. 2010, 110, pp. 3600-3637 40 (Parts 1 & 2).
Robinson, R. et al., "Calcycanthine and Calycanthidine," Chem. Ind. 1954, 27, pp. 783-784.
Rodrigues et al., "Engineering Fab' fragments for efficient F(ab)2 formation in *Escherichia coli* and for improved in vivo stability." J Immunol. Dec. 15, 1993. 151(12):6954-6961.

(56) References Cited

OTHER PUBLICATIONS

Rodrigues et al., "Synthesis and beta-lactamase-mediated activation of a cephalosporin-taxol prodrug." Chem Biol. Apr. 1995; 2(4):223-7.
Roizen, J. L. et al., "Metal Catalyzed Nitrogen-Atom Transfer methods for the Oxidation of Aliphatic C—H Bonds," Accounts of Chemical Research, Jan. 10, 2012, vol. 45, No. 6, pp. 911-922.
Roizen, J. L. et al., "Selective Intermolecular Amination of C—H Bonds at Tertiary Carbon Centers," Angew. Chem. Int. Ed. 2013, 52, pp. 11343-11346.
Ross et al., "The Chemistry of Methyl Vinyl Ketone. II. Reactions with Esters, β-Keto Esters, Malonic Ester, Amines, Tar Bases, and Inorganic Salts." J. Org. Chem. 1964; 29(8):2346-2350.
Rowland et al., "Antitumor properties of vindesine-monoclonal antibody conjugates." Cancer Immunol. Immunother. Feb. 1985; 19(1):1-7.
Ruff et al., "Thiolation of symmetrical and unsymmetrical diketopiperazines." Org. Biomol. Chem. 2012; 10(5):935-940.
Saad, H.-E. A. et al., "Biological Activities of Pyrrolidinoindoline Alkaloids from Calycodendron milnei," Planta Med. 1995, 61, pp. 313-316.
Sala et al., "Tetrabutylammonium permanganate: an efficient oxidant for organic substrates." J. Chem. Soc., Chem. Commun. 1978; 253-254.
Salayova et al., Stereoselective synthesis of 1-methoxyspiroindoline phytoalexins and their amino analogues. Tetrahedron: Asymmetry. Sep. 15, 2014;24(16-17):1221-33.
Schammel, A. W. et al., "Exploration of the interrupted Fischer indolization reaction," Tetrahedron 2010, 66, pp. 4687-4695.
Schiff et al., "Promotion of microtubule assembly in vitro by taxol." Nature 1979; 277:665-667.
Schmidt. M.A. et al., "New Strategies for the Synthesis of Hexahydropyrroloindole Alkaloids Inspired by Biosynthetic Hypotheses," Synlett 2008, 3, pp. 0313-0324.
Schumacher et al., "Potent Antitumor Activity of 2-Methoxyestradiol in Human Pancreatic Cancer Cell Lines." Clin. Cancer Res. 1999; 5(3):493-499.
Scott, A. I. et al., "Reaction Pathways in the Photochemical Conversion of Diphenylamines toCarbazoles," J. Am. Chem. Soc. 1964, 86, pp. 302-303.
Senanayake, C.H. et al., "Enantiopure Sulfoxides and Sulfinamides: Recent Developments in Their Stereoselective Synthesis and Applications to Asymmetric Synthesis," Aldrichim. Acta 2005, 38, pp. 93-104.
Seo, J. H. et al., "Synthetic Studies on Perophoramidine and the Communesins: Construction of the Vicinal Quaternary Stereocenters," J. Org. Chem. 2006, 71, pp. 8891-8900.
Sevier et al., "Formation and transfer of disulphide bonds in living cells." Nat Rev Mol Cell Biol. Nov. 2002;3(11):836-47.
Shamis et al., "Bioactivation of Self-Immolative Dendritic Prodrugs by Catalytic Antibody 38C2," J. Am. Chem. Soc. 2004; 126 (6):1726-1731.
Shan et al., "Selective, covalent modification of β-tubulin residue Cys-239 by T138067, an antitumor agent with in vivo efficacy against multidrug-resistant tumors." Proc. Nat. Acad. Sci. USA May 11, 1999; 96(10):5686-5691.
Shaw et al., "Mouse/Human Chimeric Antibodies to a Tumor-Associated Antigen: Biologic Activity of the Four Human IgG Subclasses." J. Natl. Cancer Inst. Dec. 7, 1988; 80(19):1553-1559.
Shi et al., "Distinct reactivity differences of metal oxo and its corresponding hydroxo moieties in oxidations: implications from a manganese(IV) complex having dihydroxide ligand." Angew Chem Int Ed Engl. Aug. 1, 2011; 50(32):7321-4.
Shin, K. et al., "Transition-Metal-Catalyzed C—N Bond Forming Reactions Using Organic Azides as the Nitrogen Source: a Journey for the Mild and Versatile C—H Amination," Acc. Chem. Res. 2015, 48, pp. 1040-1052.
Shirai et al., "Asymmetric synthesis of antimitotic combretadioxolane with potent antitumor activity against multi-drug resistant cells." Bioorg Med Chem Lett. Aug. 4, 1998; 8(15):1997-2000.
Shirai et al., "Synthesis and nti-tubulin activity of aza-combretastatins." Bioorganic. Med. Chem. Lett. 1994; 4(5):699-704.
Shiraki, S. et al., "Solid-state photochemistry of crystalline pyrazolines: reliable generation and reactivity control of 1,3-biradicals and their potential for the green chemistry sysnthesis of substitutedcyclopropanes," Photochem. Photobiol. Sci. 2012, 11, pp. 1929-1937.
Shiraki, S. et al., "The synthesis and stereospecific solid-state photodecarbonylation of hexasubstituted mesa- and d,/-ketones," Photochem. Photobiol. Sci. 2011, 10, pp. 1480-1487.
Singh et al., "Antineoplastic agents. 166. Isolation, structure, and synthesis of combretastatin C-1." J. Org. Chem. 1989; 54(17):4105-4114.
Singh et al., Recent trends in targeted anticancer prodrug and conjugate design. Curr Med Chem. 2008;15(18):1802-26.
Slamon et al., "Studies of the HER-2/neu proto-oncogene in human breast and ovarian cancer." Science May 12, 1989; 244(4905):707-712.
Snell, R. H. et al., "Catalytic Enantioselective Total Synthesis of Hodgkinsine B," Angew. Chem. Int. Ed. 2011, 50, pp. 9116-9119.
Soledade et al., "Minor phytotoxins from the blackleg fungus Phoma lingam." Phytochem. 1990; 29(3):777-782.
Solladie-Cavallo et al., "A Four-Step Diastereoselective Synthesis of D-erythro-Sphingosine by an Enantioselective Aldol Reaction Using a Titanium Enolate Derived from a Chiral Iminoglycinate." J. Org. Chem. 1994; 59(11):3240-3242.
Solladie-Cavallo et al., "A four-step synthesis of erythro-m-chloro-3-hydroxytyrosine ethyl ester enantiomerically pure." Tetrahedron Lett., 1998; 39(15):2191-2194.
Solladie-Cavallo et al., "Diastereoselective monoalkylation of lithium and potassium enolates of a chiral imine of ethyl glycinate: the role of added salts." Organometallics1993; 12(9):3743-3747.
Solladie-Cavallo et al., "Enantioselective synthesis of optically pure natural S(+) or unnatural R(-) DABA." Tetrahedron Lett. 1989;30(44):6011-6014.
Somei, M. et al., "A novel reductive amino-cyclization method and its application for the total syntheses of (±)-aurantio-clavine and (±)-lophocerine," Heterocycles 2007, 7 4, pp. 943-950.
Somei, M. et al., "Preparations of melatonin and 1-hydroxymelatonin, and its novel nucleophilicdimerization to (±)-3a,3a'-bispyrrolo[2,3-b]indoles," Heterocycles 1999, 51 (6), pp. 1237-1242.
Speth et al., "Gliotoxin as putative virulence factor and immunotherapeutic target in a cell culture model of cerebral aspergillosis." Mol Immunol. Sep. 2011;48(15-16):2122-9.
Springer et al., "The structure of ditryptophenaline—a new metabolite of aspergillusflavus." Tetrahedron Lett. 1977: 18(28):2403-2406.
Steininger, E., "Synthesis of 5-Chloromethyl-2,dinitrotetrahydrofuran," Angew. Chem. Internat. Edit.1965, vol. 4, No. 5, p. 433.
Stephens, D. E. et al., "Straightforward Access to Hexahydropyrrolo[2,3-b]indole Core by aRegioselective C3-Azo Coupling Reaction of Arenediazonium Compounds with Tryptamines," Eur. J. Org. Chem. 2014, pp. 3662-3670.
Steplewski et al., "Release of Monoclonal Antibody-defined Antigens by Colorectal Carcinoma and Melanoma Cells." Cancer Res. Jul. 1981; 41:2723-2727.
Steven, A. et al., "Total Synthesis of Complex Cyclotryptamine Alkaloids: Stereocontrolled Construction of Quaternary Carbon Stereocenters," Angew. Chem. Int. Ed. 2007, 46, pp. 5488-5508.
Still et al., "Rapid chromatographic technique for preparative separations with moderate resolution" J. Org. Chem. 1978, 43, 2923.
Stork, The stereospecific synthesis of reserpine. Pure Appl Chem. 1989;61(3):439-42.
Storm et al., "Effect of small changes in orientation on reaction rate." J. Am. Chem. Soc. 1972; 94(16):5815-5825.
Stout et al., "Potent Fluorinated Agelastatin Analogues for Chronic Lymphocytic Leukemia: Design, Synthesis, and Pharmacokinetic Studies," J. Med. Chem., 57, p. 5085-5093 (2014).
Strassner et al., "Mechanism of Permanganate Oxidation of Alkanes: Hydrogen Abstraction and Oxygen Rebound" J. Am. Chem. Soc. 2000; 122(32):7821-7822.

(56) References Cited

OTHER PUBLICATIONS

Stueber et al, "Carbonates, Thiocarbonates, and the Corresponding Monoalkyl Derivatives. 1. Their Preparation and Isotropic 13C NMR Chemical Shifts." Inorg. Chem. 2001; 40(8):1902-1911.
Suetsugu, S. et al., "Asymmetric Synthesis of (−)-Aurantioclavine via Palladium-CatalyzedIntramolecular Allylic Amination," Org. Lett. 2014, 16, pp. 996-999.
Sugiyama et al., "Syntheses of four unusual amino acids, constituents of cyclomarin A." Tetrahedron Lett. 2002: 43(19):3489-2492.
Sumiyoshi, T. et al., "Laser Flash Photolysis of Azocumenes. Direct Observation of StepwiseDecomposition," Bull. Chem. Soc. Jpn. 1987, 60, pp. 77-81.
Sun et al., "Chimeric Antibody with Human Constant Regions and Mouse Variable Regions Directed Against Carcinoma-Associated Antigen 17-1A." Proc. Natl. Acad. Sci., USA Jan. 1987; 84:214-218.
Sun et al., "Enabling ScFvs as multi-drug carriers: A dendritic approach," Bioorganic & Medicinal Chemistry Letters 2003; 11:1761-1768.
Sun et al., "Syntheses of Dendritic Linkers Containing Chlorambucil Residues for the Preparation of Antibody-Multidrug Immunoconjugates," Bioorganic & Medicinal Chemistry Letters 2002; 12:2213-2215.
Sun et al., Construction of 3-oxyindoles via hypervalent iodine mediated tandem cyclization-acctoxylation of o-acyl anilines. Chem Commun. 2010;46(36):6834-6.
Suresh et al., "Bispecific monoclonal antibodies from hybrid hybridomas." Methods Enzymol. 1986;121:210-28.
Szalai et al., "Geometric disassembly of dendrimers: dendritic amplification." J Am Chem Soc. Dec. 24, 2003;125(51):15688-9.
Tadano, S. et al., "Bio-Inspired Dimerization Reaction of Tryptophan Derivatives in Aqueous AcidicMedia: Three-Step Syntheses of (+)-WIN 64821, (−)-Ditryptophenaline, and (+)-Naseseazine B," Angew. Chem. Int. Ed. 2013, 52, pp. 7990-7994.
Tahir et al., "Secreted Caveolin-1 Stimulates Cell Survival/Clonal Growth and Contributes to Metastasis in Androgen-insensitive Prostate Cancer." Cancer Res. 2001; 61(10):3882-3885.
Takahashi et al., "Inhibition of histone H3K9 methyltransferases by gliotoxin and related epipolythiodioxopiperazines." J Antibiot (Tokyo). May 2012;65(5):263-5.
Teng et al., "Construction and testing of mouse—human heteromyelomas for human monoclonal antibody production." Proc Natl Acad Sci U S A. Dec. 1983; 80(23): 7308-7312.
Teng et al., "Unnatural enantiomer of chaetocin shows strong apoptosis-inducing activity through caspase-8/caspase-3 activation." Bioorg. Med. Chem. Lett. 2010; 20(17):5085-5088.
Teniou et al., "(+)(1R,2R,5R) 2-Hydroxy-3-pinanone as Chiral Auxiliary in Erythro-selective Aldol Reactions." Asian J Chem. 2006; 18:2487-2490.
Tibodeau et al., "The anticancer agent chaetocin is a competitive substrate and inhibitor of thioredoxin reductase." Antioxid Redox Signal. May 2009; 11(5):1097-106.
Tilvi et al., "Agelastatin E, Agelastatin F, and Benzosceptrin C from the Marine Sponge Agelas dendromorpha," J. Nat. Prod., 73, p. 720-723 (2010).
Timberlake, J. W. et al., "Thiadiaziridine 1, 1-Dioxides: Synthesis and Chemistry," J. Org. Chem. 1981, 46, pp. 2082-2089.
Toki et al., "Protease-Mediated Fragmentation of p-Amidobenzyl Ethers: A New Strategy for the Activation of Anticancer Prodrugs." J. Org. Chem. 2002; 67(6):1866-1872.
Trail et al., "Cure of xenografted human carcinomas by BR96-doxorubicin immunoconjugates." Science Jul. 9, 1993; 261(5118):212-215.
Trail et al., "Effect of Linker Variation on the Stability, Potency, and Efficacy of Carcinoma-reactive BR64-Doxorubicin Immunoconjugates." Cancer Research 1997; 57:100-105.
Traunecker et al., "Bispecific single chain molecules (Janusins) target cytotoxic lymphocytes on HIV infected cells." EMBO J. Dec. 1991; 10(12): 3655-3659.

Trost, B. M. et al., "Recent Advances on the Total Syntheses of Communesin Alkaloids andPerophoramidine," Chem. Eur. J. 2015, 21, pp. 16318-16343.
Trown, P.W, "Antiviral activity of N, N'-dimethyl-epidithiapiperazinedione, a synthetic compound related to the gliotoxins, LL-S88alpha and beta, chetomin and the sporidesmins." Biochem Biophys Res Commun. Nov. 8, 1968;33(3):402-7.
Tsuji, T. et al., "Diazenes. VI. Alkyldizenes," Journal of the American Chemical Society 1971, 93(8), pp. 1992-1999.
Uckun et al., "Structure-based design of a novel synthetic spiroketal pyran as a pharmacophore for the marine natural product spongistatin 1." Bioorg Med Chem Lett. Mar. 20, 2000; 10(6):541-5.
Uraguchi, D. et al., "Catalytic Asymmetric Oxidation of N-Sulfonyl I mines with HydrogenPeroxide-Trichloroacetonitrile System," J. Am. Chem. Soc. 2013, 135, pp. 8161-8164.
Usami et al., "Gliocladins A—C and Glioperazine ; Cytotoxic Dioxo- or Trioxopiperazine Metabolites from a Gliocladium Sp. Separated from a Sea Hare." Heterocycles 2004; 63(5):2004:1123-1129.
Varki et al., "Antigens associated with a human lung adenocarcinoma defined by monoclonal antibodies." Cancer Res. Feb. 1984;44(2):681-7.
Verbitski, S. M. et al., "Isolation, Structure Determination, and Biological Activity of a Novel Alkaloid, Perophoramidine, from the Philippine Ascidian Perophora namei," J. Org. Chem. 2002, 67, pp. 7124-7126.
Verdier-Pinard et al., "A Steroid Derivative with Paclitaxel-Like Effects on Tubulin Polymerization." Molecular Pharmacology Mar. 2000: 57(3):568-575.
Verdier-Pinard et al., "Biosynthesis of radiolabeled curacin A and its rapid and apparently irreversible binding to the colchicine site of tubulin." Arch Biochem Biophys. Oct. 1, 1999; 370(1):51-8.
Verhoeyan et al., "Reshaping human antibodies: grafting an antilysozyme activity." Science Mar. 25, 1988; 239(4847):1534-1536.
Verott A, L. et al., "Pyrrolidinoindoline Alkaloids from Psychotria colorata," J. Nat. Prod. 1998, 61, pp. 392-396.
Verott A, L. et al., "Synthesis and Antinociceptive Activity of Chimonanthines and Pyrrolidinoindoline-Type Alkaloids," Bioorganic & Medicinal Chemistry 2002, 10, pp. 2133-2142.
Vichai et al., "Sulforhodamine B colorimetric assay for cytotoxicity screening." Nat Protoc. 2006; 1(3):1112-6.
Vingushin et al., "Gliotoxin is a dual inhibitor of farnesyltransferase and geranylgeranyltransferase I with antitumor activity against breast cancer in vivo." Med Oncol. 2004;21(1):21-30.
Wahl et al., "The anti-CD30 monoclonal antibody SGN-30 promotes growth arrest and DNA fragmentation in vitro and affects antitumor activity in models of Hodgkin's disease." Cancer Res. Jul. 1, 2002; 62(13):3736-42.
Walker et al., "A High Yielding Synthesis of N-Alkyl Maleimides Using a Novel Modification of the Mitsunobu Reaction." J. Org. Chem., 1995; 60(16):5352-5355.
Wang et al., "Potent, Orally Active Heterocycle-Based Combretastatin A-4 Analogues: Synthesis, Structure-Activity Relationship, Pharmacokinetics, and In Vivo Antitumor Activity Evaluation." J. Med. Chem. 2002; 45(8):1697-1711.
Wang et al., "Synthesis of B-ring homologated estradiol analogues that modulate tubulin polymerization and microtubule stability." J Med Chem. Jun. 15, 2000; 43(12):2419-29.
Wantanabe et al., Reaction of 1-Acyl and Aroyl-2-hydroxy-3,3-dimethylindolines with Arylamines Catalyzed by BF3•Etherate. Formation of Dihydroindolo[1,2-c]quinazoline. Heterocycles. 2007;71(2):343-59.
Ward et al., "Binding activities of a repertoire of single immunoglobulin variable domains secreted from *Escherichia coli*." Nature. Oct. 12, 1989;341(6242):544-6.
Waring et al., "Gliotoxin and related epipolythiodioxopiperazines." Gen Pharmacol. Dec. 1996;27(8):1311-6.
Waring et al., "The chemistry and biology of the immunomodulating agent gliotoxin and related epipolythiodioxopiperazines." Med Res Rev. Oct.-Dec. 1988;8(4):499-524.
Wen et al., "Synthesis of a fully protected (2S,3R)-N-(1',1'-dimethyl-2'-propenyl)-3-hydroxytryptophan from tryptophan." Tetrahedron Lett. 2002: 43(30):5291-5294.

(56) References Cited

OTHER PUBLICATIONS

Wen et al., "Total Synthesis of Cyclomarin C." Org. Lett. 2004; 6(16):2721-2724.
Wender, P. A. et al., "Practical Synthesis of Prostratin, OPP, and Their Analogs, Adjuvant Leads Against Latent HIV," Science May 8, 2008, 320(5876), pp. 649-652.
Wenkert et al., "Five-membered aromatic heterocycles as dienophiles in Diels-Alder reactions. Furan, pyrrole, and indole." J. Am. Chem. Soc. 1988; 110(21):7188-7194.
White, K. L. et al., "Concise Total Syntheses of (+)-Haplocidine and (+)-Haplocine Via Late-StageOxidation of (+)-Fendleridine Derivatives," J. Am. Chem. Soc. 2016, 138(35), pp. 11383-11389.
Wigley, L. J. et al., "Natural and directed biosynthesis of communesin alkaloids," Phytochemistry 2006, 67, pp. 561-569.
Williams et al., "Divergent, generalized synthesis of unsymmetrically substituted 2,5-piperazinediones." J. Am. Chem. Soc. 1985; 107(11):3246-3253.
Williams et al., "Syntheses of the fungal metabolites (.+-.)-gliovictin and (.+-.)-hyalodendrin." J. Org. Chem. 1980; 45(13):2625-2631.
Williamson, K. S. et al., "Iron Catalyzed Asymmetric Oxyamination of Olefins," J. Am. Chem. Soc. 2012, 134, pp. 12370-12373.
Williamson, K. S. et al., "Iron-Catalyzed Aminohydroxylation of Olefins," J. Am. Chem. Soc. 2010, 132, pp. 4570-4571.
Wood et al., "The interaction with tubulin of a series of stilbenes based on combretastatin A-4." Br J Cancer. Apr. 1995; 71(4):705-11.
Wood et al., "The synthesis and in vivo assembly of functional antibodies in yeast." Nature 1985; 314:446-449.
Woodward, R. B. et al., "Calycanthine: The Structure of the Alkaloid and its Degradation Product, Calycanine," Proc. Chem. Soc. 1960, pp. 76-78.
Wu-Wong et al., "Identification and Characterization of A-105972, an Antineoplastic Agent." Cancer Res. 2001; 61:1486-1492.
Xie, W. et al., "Highly Enantioselective Bromocyclization of Tryptamines and Its Application in theSynthesis of(−)-Chimonanthine," Angew. Chem. Int. Ed. 2013, 52, pp. 12924-12927.
Xu, J.-B. et al., "Studies on the Alkaloids of the Calycanthaceae and Their Syntheses," Molecules 2015, 20, pp. 6715-6738.
Xu, L. et al., "Iridium(111)-Catalyzed Regioselective C7-Amination of N-Pivaloylindoles with Sulfonoazides," J. Org. Chem. 2016, 81, pp. 10476-10483.
Xu, Z. et al., "Total Synthesis of Clavicipitic Acid and Aurantioclavine: Stereochemistry of Clavicipitic Acid Revisited," J. Org. Chem. 2010, 75, pp. 7626-7635.
Yamada, F. et al., "A Total and Practical Synthesis of Ergot Alkaloid, (±)-Aurantioclavine," Chem. Pharm. Bull. 1985, 33, pp. 2162-2163.
Yamada, K. et al., "Concise Synthesis of (±)-Aurantioclavine through a Base-Promoted Pictet-Spengler Reaction," Eur. J. Org. Chem. 2009, pp. 5752-5759.
Yanagihara et al., "Leptosins isolated from marine fungus *Leptoshaeria* species inhibit DNA topoisomerases I and/or II and induce apoptosis by inactivation of Akt/protein kinase B." Cancer Sci. Nov. 2005;96(11):816-24.
Yang, J. et al., "Total Synthesis of (±)-Communesin F," J. Am. Chem. Soc. 2007, 129, pp. 13794-13795.
Yano et al., "Chetomin induces degradation of XIAP and enhances TRAIL sensitivity in urogenital cancer cells." Int J Oncol. Feb. 2011;38(2):365-74.
Yu et al., A General Strategy for the Synthesis of Vincamajine-Related Indole Alkaloids: Stereocontrolled Total Synthesis of (+)-Dehydrovoachalotine, (−)-Vincamajinine, and (−)-11-Methoxy-17-epivincamajine as Well as the Related Quebrachidine Diol, Vincamajine Diol, and Vincarinoll. J Org Chem. Apr. 19, 2005;70(10):3963-79.
Yu et al., Stereocontrolled Total Synthesis of (−)-Vincamajinine and (−)-11-Methoxy-17-epivincamajine. J Am Chem Soc. Jan. 21, 2004;126(5):1358-9.
Zalatan, D. N. et al., "Metal-Catalyzed Oxidations of C—H to C—N Bonds," Top. Curr. Chem. 2010, 292, pp. 347-378.
Zalatan, D. N. et al., "Understanding the Differential Performance of Rh2(esp)2 as a Catalyst for C—H Amination," J. Am. Chem. Soc. 2009, 131, pp. 7558-7559.
Zhang et al., "Microtubule effects of welwistatin, a cyanobacterial indolinone that circumvents multiple drug resistance." Molecular Pharmacology Feb. 1996; 49(2):288-294.
Zhang et al., "PARP and RIP 1 are required for autophagy induced by 11'-deoxyverticillin A, which precedes caspase-dependent apoptosis." Autophagy. Jun. 2011;7(6):598-612.
Zheng et al., "Bionectins A—C, Epidithiodioxopiperazines with Anti-MRSA Activity, from Bionectra byssicola F120," J. Nat. Prod., 2006, 69 (12), pp. 1816-1819.
Zhou, P. et al., "Recent advances in asymmetric reactions using sulfinimines (N-sulfinyl imines)," Tetrahedron 2004, 60, pp. 8003-8030.
Zhu et al., Aptamer-Drug Conjugates. Bioconjug Chem. Nov. 18, 2015;26(11):2186-97. doi: 10.1021/acs.bioconjchem.5b00291. Epub Jul. 14, 2015.
Zuo, Z. et al., "Enantioselective Total Syntheses of Communesins A and B," Angew. Chem. Int. Ed. 2011, 50, pp. 12008-12011.
Zuo, Z. et al., "Total Synthesis and Absolute Stereochemical Assignment of (−)-Communesin F," J. Am. Chem. Soc. 2010, 132, pp. 13226-13228.
PCT/US2018/032327, Jul. 23, 2018, Invitation to Pay Additional Fees.
PCT/US2018/032327, Sep. 21, 2018, International Search Report and Written Opinion.
Invitation to Pay Additional Fees for pct/2018/032327, dated Jul. 23, 2018.
International Search Report and Written Opinion for PCT/US2018/032327, dated Sep. 21, 2018.

*meso*-chimonanthine (1)

(−)-calycanthidine (2)

(−)-hodgkinsine B (3)

(−)-hodgkinsine (4)

(−)-calycosidine (5)

(+)-quadrigemine I (6)

(−)-quadrigemine C (7)

(−)-psycholeine (8)

DIAZENE DIRECTED MODULAR SYNTHESIS OF COMPOUNDS WITH QUATERNARY CARBON CENTERS

RELATED APPLICATIONS

This application claims priority under 35 U.S.C. 119(e) to U.S. provisional application, U.S. Ser. No. 62/572,189, filed Oct. 13, 2017, which is incorporated by reference in its entirety.

GOVERNMENT SUPPORT

This invention was made with government support under Grant No. R01 GM089732 awarded by the National Institutes of Health. The government has certain rights in the invention.

BACKGROUND

The establishment of quaternary centers, particularly with defined stereochemistry, remains a challenge in the field of organic synthesis. As a variety of natural products, bioactive molecules, and other analogs possess such a feature, novel methods and approaches are necessary that improve access to these compounds.

BRIEF SUMMARY

Various inventive embodiments disclosed herein are generally directed to formation of quaternary centers as shown below using novel diazene-directed synthesis methodologies and processes, wherein X, R, R', R", and EWG (electron withdrawing group) are each as defined and discussed herein.

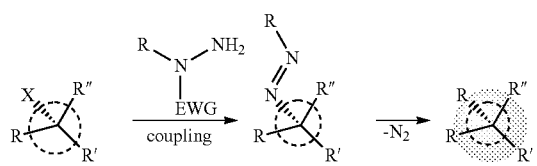

The implementation of the new diazene synthesis has resulted in the convergent and enantioselective total syntheses of (−)-hodgkinsine B, (−)-hodgkinsine, (−)-calycosidine, (−)-quadrigemine C, and (−)-psycholeine (8) via completely stereocontrolled assembly of cyclotryptamines, and can be applied to other natural products as well (FIG. 1B)

In one embodiment, the present disclosure provides a method of preparing compounds of Formula (I), or a pharmaceutically acceptable salt, tautomer or stereoisomer thereof comprising reacting a compound of Formula (II) and thereby extruding dinitrogen to provide a compound of Formula (I):

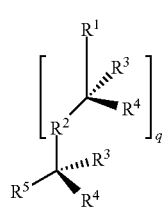

Formula (I)

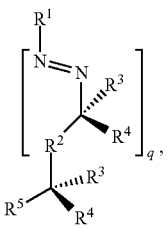

Formula (II)

$R^1$ is tertiary alkyl, alkenyl, aryl, heteroaryl, carbocyclyl, or heterocyclyl or at least one moiety of structure:

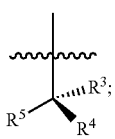

and
$R^2$, $R^3$, $R^4$, and $R^5$ are each occurrence, each independently selected from alkyl, aryl, heteroaryl, carbocyclyl, or heterocyclic, wherein any two of $R^3$, $R^4$, and $R^5$ taken together with the carbon atoms to which they are attached form a $C_{5-14}$ membered saturated, unsaturated, or aromatic carbocyclic ring or a $C_{5-14}$ membered saturated, unsaturated, or aromatic heterocyclic ring; and wherein any tertiary alkyl, aryl, heteroaryl, carbocyclyl, or heterocyclyl, $C_{5-14}$ membered saturated, unsaturated, or aromatic carbocyclic ring or a $C_{5-14}$ membered saturated, unsaturated, or aromatic heterocyclic ring can be further substituted with one or more halogen, alkyl, heteroaryl, carbocyclyl, heterocyclyl, $C_{3-14}$ membered saturated, unsaturated, or aromatic carbocyclic, or $C_{3-14}$ membered saturated, unsaturated, or aromatic heterocyclic rings; and
q is an integer of from 0-8.

In another embodiment, the method as disclosed herein is useful for the preparation of compounds of Formula (I):

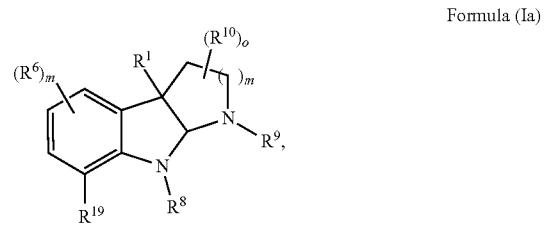

Formula (Ia)

wherein
$R^1$ is tertiary alkyl, alkenyl, aryl, heteroaryl, carbocyclyl, heterocyclyl,

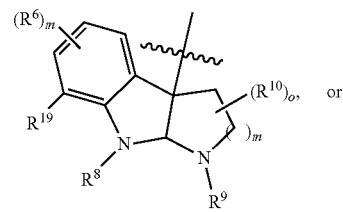

or

-continued

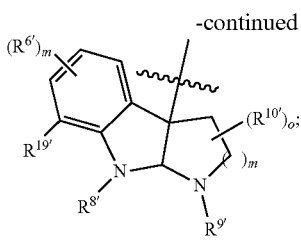

$R^6$ and $R^{6'}$ are each independently selected from halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl; wherein two $R^6$ groups taken together with the carbon atoms to which they are attached form an aryl, heteroaryl, carbocyclic, or heterocyclic ring; $R^8$, $R^9$, $R^{8'}$ and $R^{9'}$ are each independently selected from H, $C_1$-$C_{12}$ alkyl, $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —SR$^{11}$, —S(=O)$_p$R$^{13}$, —S(=O)$_2$NR$^{11}$R$^{12}$, —C(=O)O(CH$_2$)$_o$R$^{11}$, aryl, heteroaryl, carbocyclyl, or heterocyclyl; $R^{10}$ and $R^{10'}$ are each independently selected from H, $C_1$-$C_{12}$ alkyl; $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —S(=O)$_p$R$^{13}$, —OH, —OR$^{11}$, —OC(=O)R$^{11}$, —NR$^{11}$R$^{12}$, aryl, heteroaryl, carbocyclyl, or heterocyclyl, wherein two $R^{10}$ groups taken together with the carbon atoms to which they are attached form an aryl, heteroaryl, carbocyclic, or heterocyclic ring; $R^{11}$ and $R^{12}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring; $R^{13}$ and $R^{14}$ are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —OR$^{11}$, —(CH$_2$)$_r$SiMe$_3$, or —(CH$_2$)$_r$R$^{11}$;
$R^{15}$ is —S(=O)$_p$R$^{13}$, —S(=O)$_2$NR$^{11}$R$^{12}$, —C(=O)R$^{13}$, —C(=O)R$^{20}$, —C(=O)O(CH$_2$)$_r$R$^{20}$, —C(=O)CF$_3$, —C(=O)OR$^{20}$, —P(=O)R$^{13}$R$^{14}$, or, —P(=O)NR$^{11}$R$^{12}$;
$R^{19}$ and $R^{19'}$ are each independently selected from H, tertiary alkyl, alkenyl, aryl, heteroaryl, carbocyclyl, heterocyclyl,

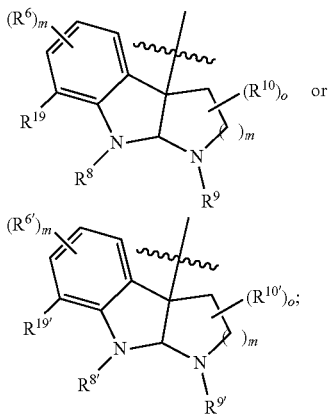

$R^{20}$ is —Si(alkyl)$_3$, —Si(alkyl)$_2$aryl, or Si(aryl)$_2$alkyl; and
m is an integer from 0 to 3;
n and o are each independently an integer from 0 to 4;
p is 1 or 2; and
r is an integer from 1 to 4.

In specific embodiments, the compounds of Formula (I) prepared by the disclosed methods are:

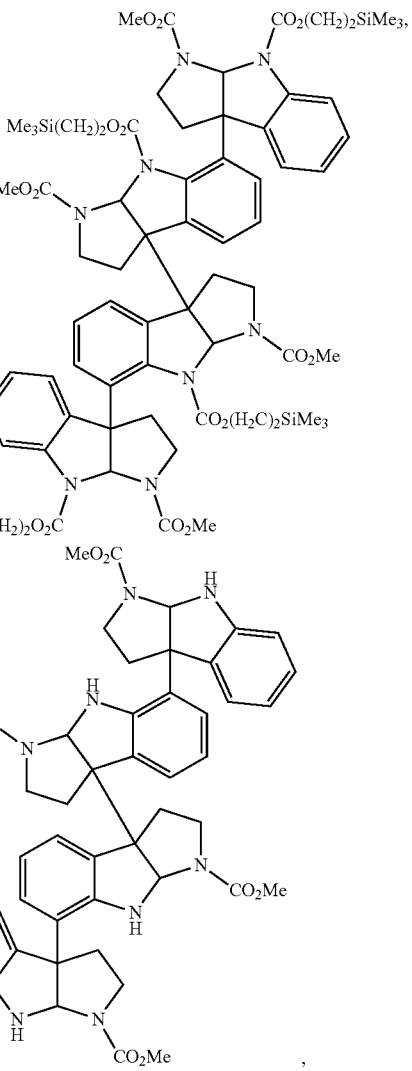

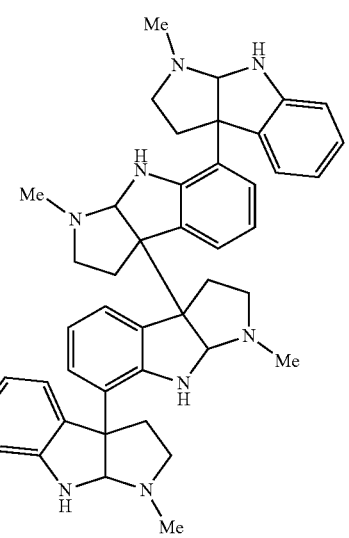

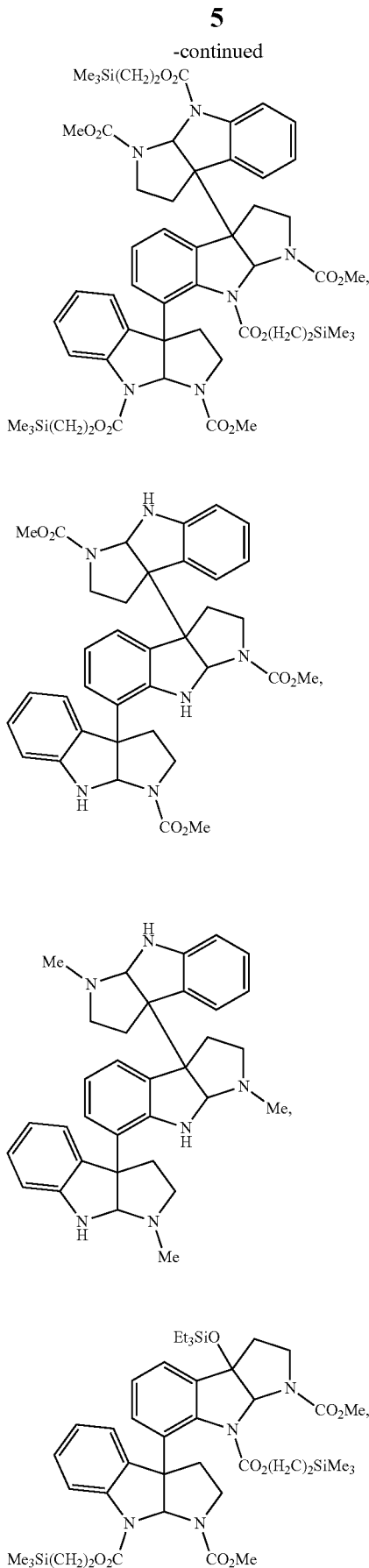

BRIEF DESCRIPTION OF THE FIGURES

The skilled artisan will understand that the drawings are primarily for illustrative purposes and are not intended to limit the scope of the inventive subject matter described herein.

DETAILED DESCRIPTION

Figure 1:
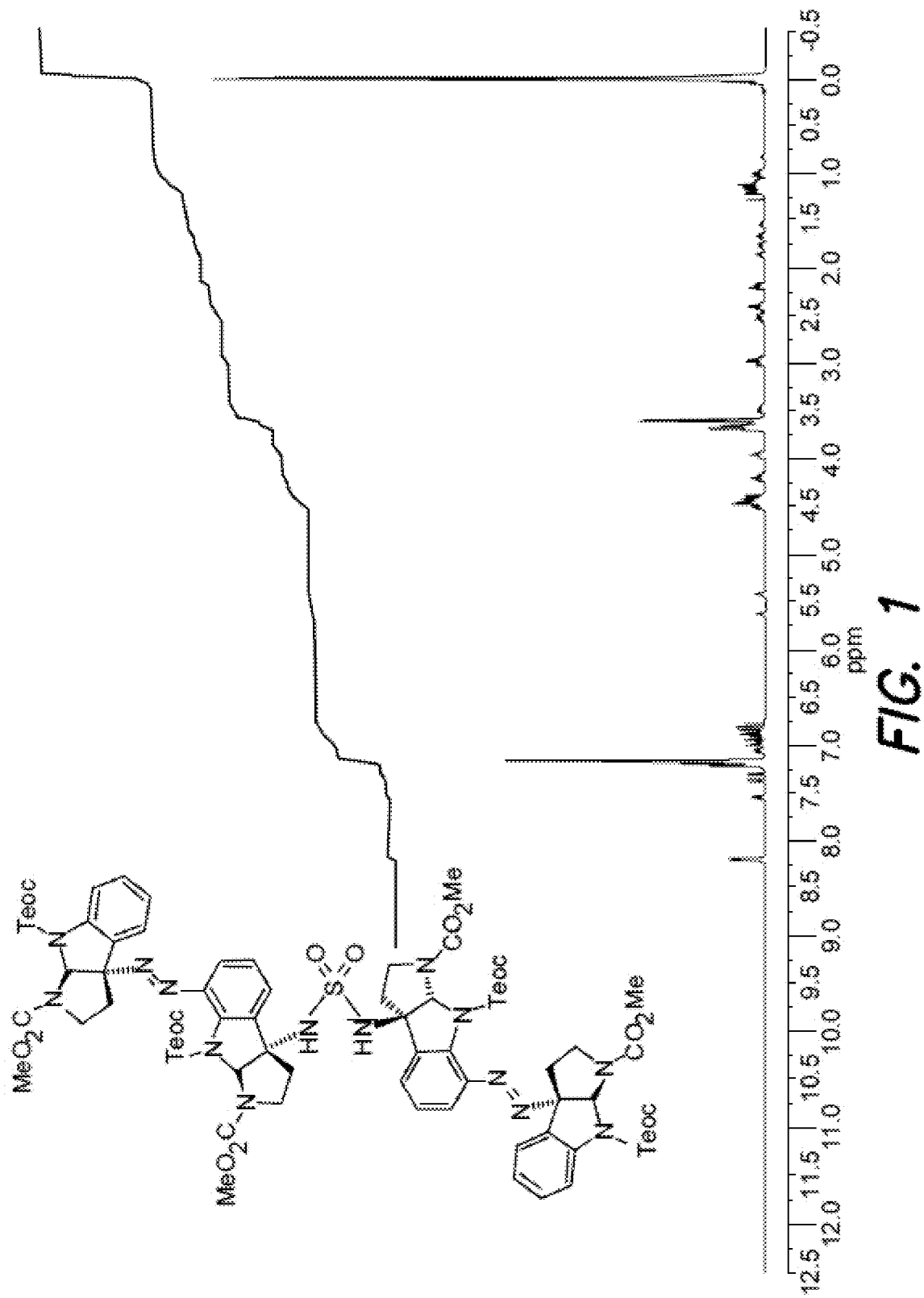
FIG. 1 shows the $^1$H NMR spectrum of the sulfamide-diazene intermediate of (−)-quadrigemine C.

In the following description, certain specific details are set forth in order to provide a thorough understanding of various embodiments. However, one skilled in the art will understand that the invention can be practiced without these details. In other instances, well-known structures have not been shown or described in detail to avoid unnecessarily obscuring descriptions of the embodiments.

All definitions, as defined and used herein, should be understood to control over dictionary definitions, definitions in documents incorporated by reference, and/or ordinary meanings of the defined terms. Use of flow diagrams is not meant to be limiting with respect to the order of operations performed for all embodiments. The indefinite articles "a" and "an," as used herein in the specification and in the claims, unless clearly indicated to the contrary, should be understood to mean "at least one."

Reference throughout this specification to "one embodiment" or "an embodiment," etc. means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It is to be understood that the phrase "each occurrence" and "each independently selected from" as used in the specification, and in the claims means, for example, that two or more $R^x$ groups can be non-equivalent selections when appearing together in one compound or formula. Where the phrase "$R^x$ and $R^y$ are each independently selected from" is used interchangeably, it is intended to have the same meaning as "$R^x$ and $R^y$ are each occurrence, each independently selected from."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

"Alkyl" or "alkyl group" refers to a fully saturated, straight or branched hydrocarbon chain radical, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical. Alkylenes comprising any number of carbon atoms from 1 to 12 are included. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Examples of $C_1$-$C_3$ alkyl includes methyl, ethyl, n-propyl, and i-propyl. Examples of $C_1$-$C_4$ alkyl includes methyl, ethyl, n-propyl, i-propyl, n-butyl, i-butyl, and sec-butyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl groups comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —$OR_a$ where $R_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula —$NHR_a$ or —$NR_aR_a$ where each $R_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —C(=O)$R_a$ moiety, wherein $R_a$ is an alkyl, alkenyl or alkynyl radical as defined above. A non-limiting example of an alkyl carbonyl is the methyl carbonyl ("acetyl") moiety. Alkylcarbonyl groups can also be referred to as "Cw-Cz acyl" where w and z depicts the range of the number of carbon in $R_a$, as defined above. For example, "$C_1$-$C_{10}$ acyl" refers to alkylcarbonyl group as defined above, where $R_a$ is $C_1$-$C_{10}$ alkyl, $C_1$-$C_{10}$ alkenyl, or $C_1$-$C_{10}$ alkynyl radical as defined above. Unless stated otherwise specifically in the specification, an alkyl carbonyl group can be optionally substituted.

"Aryl" or "aryl ring" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" refers to a radical of the formula —$R_b$-$R_c$ where $R_b$ is an alkylene, alkenylene or alkynylene group as defined above and $R_c$ is one or more aryl radicals as defined above, for example, benzyl, diphenylmethyl and the like. Unless stated otherwise specifically in the specification, an aralkyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls, cycloalkyl, cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula —$R_b$-$R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above that is substituted by one or more halo radicals, as defined above, e.g., 1-fluoropropynyl, 1-fluorobutynyl, and the like. Unless stated otherwise specifically in the specification, a haloalkenyl group can be optionally substituted.

"Heterocyclyl," "heterocyclic ring" or "heterocycle" refers to a stable 3- to 20-membered non-aromatic ring radical which consists of two to twelve carbon atoms and from one to six heteroatoms selected from the group consisting of nitrogen, oxygen and sulfur. Heterocyclyl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heterocyclylalkyl" refers to a radical of the formula —$R_b$-$R_e$ where $R_b$ is an alkylene, alkenylene, or alkynylene chain as defined above and $R_e$ is a heterocyclyl radical as defined above, and if the heterocyclyl is a nitrogen-containing heterocyclyl, the heterocyclyl can be attached to the alkyl, alkenyl, alkynyl radical at the nitrogen atom. Unless stated otherwise specifically in the specification, a heterocyclylalkyl group can be optionally substituted.

"Heteroaryl" or "heteroaryl ring" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in this disclosure, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula —$R_b$—$R_f$ where $R_b$ is an alkylene, alkenylene, or alkynylene chain as defined above and $R_f$ is a heteroaryl radical as defined above. Unless stated otherwise specifically in the specification, a heteroarylalkyl group can be optionally substituted.

"Thioalkyl" refers to a radical of the formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (i.e., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, enamines, and diazenyl; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —N=N-aryl, —N=N-heteroaryl, —N=N-carbocyclyl, or —N=N-heterocyclyl, —$NR_g$C(=O)$OR_h$, —$NR_g$SO$_2R_h$, —OC(=O)

$NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

Exemplary carbon atom substituents include halogen, $-CN$, $-NO_2$, $-N_3$, $-SO_2H$, $-SO_3H$, $-OH$, $-OR^{aa}$, $-ON(R^{bb})_2$, $-N(R^{bb})_2$, $-N(R^{bb})_3{}^+X^-$, $-N(OR^{cc})R^{bb}$, $-SH$, $-SR^{aa}$, $-SSR^{cc}$, $-C(=O)R^{aa}$, $-CO_2H$, $-CHO$, $-C(OR^{cc})_2$, $-CO_2R^{aa}$, $-OC(=O)R^{aa}$, $-OCO_2R^{aa}$, $-C(=O)N(R^{bb})_2$, $-OC(=O)N(R^{bb})_2$, $-NR^{bb}C(=O)R^{aa}$, $-NR^{bb}CO_2R^{aa}$, $-NR^{bb}C(=O)N(R^{bb})_2$, $-C(=NR^{bb})R^{aa}$, $-C(=NR^{bb})OR^{aa}$, $-OC(=NR^{bb})R^{aa}$, $-OC(=NR^{bb})OR^{aa}$, $-C(=NR^{bb})N(R^{bb})_2$, $-OC(=NR^{bb})N(R^{bb})_2$, $-NR^{bb}C(=NR^{bb})N(R^{bb})_2$, $-C(=O)NR^{bb}SO_2R^{aa}$, $-NR^{bb}SO_2R^{aa}$, $-SO_2N(R^{bb})_2$, $-SO_2R^{aa}$, $-SO_2OR^{aa}$, $-OSO_2R^{aa}$, $-S(=O)R^{aa}$, $-OS(=O)R^{aa}$, $-Si(R^{aa})_3$, $-OSi(R^{aa})_3$ $-C(=S)N(R^{bb})_2$, $-C(=O)SR^{aa}$, $-C(=S)SR^{aa}$, $-SC(=S)SR^{aa}$, $-SC(=O)SR^{aa}$, $-OC(=O)SR^{aa}$, $-SC(=O)OR^{aa}$, $-SC(=O)R^{aa}$, $-P(=O)(R^{aa})_2$, $-P(=O)(OR^{cc})_2$, $-OP(=O)(R^{aa})_2$, $-OP(=O)(OR^{cc})_2$, $-P(=O)(N(R^{bb})_2)_2$, $-OP(=O)(N(R^{bb})_2)_2$, $-NR^{bb}P(=O)(R^{aa})_2$, $-NR^{bb}P(=O)(OR^{cc})_2$, $-NR^{bb}P(=O)(N(R^{bb})_2)_2$, $-P(R^{cc})_2$, $-P(OR^{cc})_2$, $-P(R^{cc})_3{}^+X^-$, $-P(OR^{cc})_3{}^+X^-$, $-P(R^{cc})_4$, $-P(OR^{cc})_4$, $-OP(R^{cc})_2$, $-OP(R^{cc})_3{}^+X^-$, $-OP(OR^{cc})_2$, $-OP(OR^{cc})_3{}^+X^-$, $-OP(R^{cc})_4$, $-OP(OR^{cc})_4$, $-B(R^{aa})_2$, $-B(OR^{cc})_2$, $-BR^{aa}(OR^{cc})$, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein X$^-$ is a counterion;

or two geminal hydrogens on a carbon atom are replaced with the group $=O$, $=S$, $=NN(R^{bb})_2$, $=NNR^{bb}C(=O)R^{aa}$, $=NNR^{bb}C(=O)OR^{aa}$, $=NNR^{bb}S(=O)_2R^{aa}$, $=NR^{bb}$, or $=NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, $-OH$, $-OR^{aa}$, $-N(R^{cc})_2$, $-CN$, $-C(=O)R^{aa}$, $-C(=O)N(R^{cc})_2$, $-CO_2R^{aa}$, $-SO_2R^{aa}$, $-C(=NR^{cc})OR^{aa}$, $-C(=NR^{cc})N(R_c)_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)(R^{aa})_2$, $-P(=O)(OR^{cc})_2$, $-P(=O)(N(R^{cc})_2)_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein X$^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, $-CN$, $-NO_2$, $-N_3$, $-SO_2H$, $-SO_3H$, $-OH$, $-OR^{ee}$, $-ON(R^{ff})_2$, $-N(R^{ff})_2$, $-N(R^{ff})_3{}^+X^-$, $-N(OR^{ee})R^{ff}$, $-SH$, $-SR^{ee}$, $-SSR^{ee}$, $-C(=O)R^{ee}$, $-CO_2H$, $-CO_2R^{ee}$, $-OC(=O)R^{ee}$, $-OCO_2R^{ee}$, $-C(=O)N(R^{ff})_2$, $-OC(=O)N(R^{ff})_2$, $-NR^{ff}C(=O)R^{ee}$, $-NR^{ff}CO_2R^{ee}$, $-NR^{ff}C(=O)N(R^{ff})_2$, $-C(=NR^{ff})OR^{ee}$, $-OC(=NR^{ff})R^{ee}$, $-OC(=NR^{ff})OR^{ee}$, $-C(=NR^{ff})N(R^{ff})_2$, $-OC(=NR^{ff})N(R^{ff})_2$, $-NR^{ff}C(=NR^{ff})N(R^{ff})_2$, $-NR^{ff}SO_2R^{ee}$, $-SO_2N(R^{ff})_2$, $-SO_2R^{ee}$, $-SO_2OR^{ee}$, $-OSO_2R^{ee}$, $-S(=O)R^{ee}$, $-Si(R^{ee})_3$, $-OSi(R^{ee})_3$, $-C(=S)N(R^{ff})_2$, $-C(=O)SR^{ee}$, $-C(=S)SR^{ee}$, $-SC(=S)SR^{ee}$, $-P(=O)(OR^{ee})_2$, $-P(=O)(R^{ee})_2$, $-OP(=O)(R^{ee})_2$, $-OP(=O)(OR^{ee})_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$carbocyclyl, 3-10 membered heterocyclyl, $C_{6-10}$aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form $=O$ or $=S$; wherein X$^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, $-CN$, $-NO_2$, $-N_3$, $-SO_2H$, $-SO_3H$, $-OH$, $-OC_{1-6}$ alkyl, $-ON(C_{1-6}$ alkyl$)_2$, $-N(C_{1-6}$ alkyl$)_2$, $-N(C_{1-6}$ alkyl$)_3{}^+X^-$, —NH($C_{1-6}$ alkyl)$_2^+$X$^-$, —NH$_2$($C_{1-6}$ alkyl)$^+$X$^-$, —NH$_3^+$X$^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

In certain embodiments, the carbon atom substituents are independently halogen, substituted (e.g., substituted with one or more halogen) or unsubstituted $C_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$. In certain embodiments, the carbon atom substituents are independently halogen, substituted (e.g., substituted with one or more halogen) or unsubstituted $C_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$, wherein R$^{aa}$ is hydrogen, substituted (e.g., substituted with one or more halogen) or unsubstituted $C_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted $C_{1-6}$ alkyl, or a nitrogen protecting group. In certain embodiments, the carbon atom substituents are independently halogen, substituted (e.g., substituted with one or more halogen) or unsubstituted $C_{1-6}$ alkyl, —OR$^{aa}$, —SR$^{aa}$, —N(R$^{bb}$)$_2$, —CN, —SCN, or —NO$_2$. In certain embodiments, the carbon atom substituents are independently halogen, substituted (e.g., substituted with one or more halogen moieties) or unsubstituted $C_{1-6}$ alkyl, —OR$^{aa}$, —SR$^{aa}$, —N(R$^{bb}$)$_2$, —CN, —SCN, or —NO$_2$, wherein R$^{aa}$ is hydrogen, substituted (e.g., substituted with one or more halogen) or unsubstituted $C_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted $C_{1-6}$ alkyl, or a nitrogen protecting group. In certain embodiments, a carbon atom substituent is —N=N-aryl, —N=N-heteroaryl, —N=N-carbocyclyl, or —N=N-heterocyclyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

Nitrogen atoms can be substituted or unsubstituted as valency permits, and include primary, secondary, tertiary, and quaternary nitrogen atoms. Exemplary nitrogen atom substituents include hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the nitrogen atom substituents are independently substituted (e.g., substituted with one or more halogen) or unsubstituted $C_{1-6}$ alkyl, —C(=O)R$^{aa}$, —CO$_2$R$^{aa}$, —C(=O)N(R$^{bb}$)$_2$, or a nitrogen protecting group. In certain embodiments, the nitrogen atom substituents are independently substituted (e.g., substituted with one or more halogen) or unsubstituted $C_{1-6}$ alkyl, —C(=O)R$^{aa}$, —CO$_2$R$^{aa}$, —C(=O)N(R$^{bb}$)$_2$, or a nitrogen protecting group, wherein R$^{aa}$ is hydrogen, substituted (e.g., substituted with one or more halogen) or unsubstituted $C_{1-6}$ alkyl, or an oxygen protecting group when attached to an oxygen atom; and each R$^{bb}$ is independently hydrogen, substituted (e.g., substituted with one or more halogen) or unsubstituted $C_{1-6}$ alkyl, or a nitrogen protecting group. In certain embodiments, the nitrogen atom substituents are independently substituted (e.g., substituted with one or more halogen) or unsubstituted $C_{1-6}$ alkyl or a nitrogen protecting group.

In certain embodiments, the substituent present on a nitrogen atom is a nitrogen protecting group (also referred to as an amino protecting group). Nitrogen protecting groups include —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —C(=O)R$^{aa}$) include formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O)OR$^{aa}$) include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), Teoc, 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., —S(=O)$_2$R$^{aa}$) include p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, a nitrogen protecting group is Bn, Boc, Cbz, Fmoc, trifluoroacetyl, triphenylmethyl, acetyl, or Ts. In certain embodiments, a nitrogen protecting group is Teoc.

In certain embodiments, the oxygen atom substituents are independently substituted (e.g., substituted with one or more halogen) or unsubstituted $C_{1-6}$ alkyl, —C(=O)$R^{aa}$, —CO$_2R^{aa}$, —C(=O)N($R^{bb}$)$_2$, or an oxygen protecting group. In certain embodiments, the oxygen atom substituents are independently substituted (e.g., substituted with one or more halogen) or unsubstituted $C_{1-6}$ alkyl, —C(=O)$R^{aa}$, —CO$_2R^{aa}$, —C(=O)N($R^{bb}$)$_2$, or an oxygen protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the oxygen atom substituents are independently substituted (e.g., substituted with one or more halogen) or unsubstituted $C_{1-6}$ alkyl or an oxygen protecting group.

In certain embodiments, the substituent present on an oxygen atom is an oxygen protecting group (also referred to herein as an "hydroxyl protecting group"). Oxygen protecting groups include —$R^{aa}$, —N($R^{bb}$)$_2$, —C(=O)S$R^{aa}$, —C(=O)$R^{aa}$, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P($R^{cc}$)$_3^+$X$^-$, —P(O$R^{cc}$)$_2$, —P(O$R^{cc}$)$_3^+$X$^-$, —P(=O)($R^{aa}$)$_2$, —P(=O)(OR)$_2$, and —P(=O)(N($R^{bb}$)$_2$)$_2$, wherein X$^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a, 4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, an oxygen protecting group is silyl, TBDPS, TBDMS, TIPS, TES, TMS, MOM, THP, t-Bu, Bn, allyl, acetyl, pivaloyl, or benzoyl.

In certain embodiments, the sulfur atom substituents are independently substituted (e.g., substituted with one or more halogen) or unsubstituted $C_{1-6}$ alkyl, —C(=O)$R^{aa}$, —CO$_2R^{aa}$, —C(=O)N($R^{bb}$)$_2$, or a sulfur protecting group. In certain embodiments, the sulfur atom substituents are independently substituted (e.g., substituted with one or more halogen) or unsubstituted $C_{1-6}$ alkyl, —C(=O)$R^{aa}$, —CO$_2R^{aa}$, —C(=O)N($R^{bb}$)$_2$, or a sulfur protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the sulfur atom substituents are independently substituted (e.g., substituted with one or more halogen) or unsubstituted $C_{1-6}$ alkyl or a sulfur protecting group.

In certain embodiments, the substituent present on a sulfur atom is a sulfur protecting group (also referred to as a "thiol protecting group"). Sulfur protecting groups include —$R^{aa}$, —N($R^{bb}$)$_2$, —C(=O)S$R^{aa}$, —C(=O)$R^{aa}$, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P($R_{cc}$)$_3^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein R$^{aa}$, R$^{bb}$, and R$^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

The "molecular weight" of —R, wherein —R is any monovalent moiety, is calculated by substracting the atomic weight of a hydrogen atom from the molecular weight of the molecule R—H. The "molecular weight" of -L-, wherein -L- is any divalent moiety, is calculated by substracting the combined atomic weight of two hydrogen atoms from the molecular weight of the molecule H-L-H.

In certain embodiments, the molecular weight of a substituent is lower than 200, lower than 150, lower than 100, lower than 50, or lower than 25 g/mol. In certain embodiments, a substituent consists of carbon, hydrogen, fluorine, chlorine, bromine, iodine, oxygen, sulfur, nitrogen, and/or silicon atoms. In certain embodiments, a substituent consists of carbon, hydrogen, fluorine, chlorine, bromine, and/or iodine atoms. In certain embodiments, a substituent consists of carbon, hydrogen, and/or fluorine atoms. In certain embodiments, a substituent does not comprise one or more, two or more, or three or more hydrogen bond donors. In certain embodiments, a substituent does not comprise one or more, two or more, or three or more hydrogen bond acceptors.

As used herein, the symbol

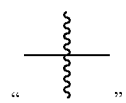

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

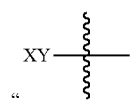

indicates that the chemical entity "XY" is bonded to another chemical entity via the point of attachment bond. Furthermore, the specific point of attachment to the non-depicted chemical entity can be specified by inference. For example, the compound CH$_3$—R$^3$, wherein R$^3$ is H or

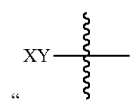

infers that when R$^3$ is "XY", the point of attachment bond is the same bond as the bond by which R$^3$ is depicted as being bonded to CH$_3$.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring can be replaced with a nitrogen atom.

"Optional" or "optionally" means that the subsequently described event of circumstances can or cannot occur, and that the description includes instances where said event or circumstance occurs and instances in which it does not. For example, "optionally substituted aryl" means that the aryl radical can or cannot be substituted and that the description includes both substituted aryl radicals and aryl radicals having no substitution.

Total synthesis refers to the complete chemical synthesis of a complex molecule, typically a natural product or a structurally similar analog or derivative thereof, starting from commercially available precursor compounds. It is often desirable to perform total syntheses in a "convergent" manner, where efficiency and overall chemical yield are improved by synthesizing several complex individual components in stage one, followed by combination of the components in a subsequent stage to yield a more advanced compound or final product. While convergent synthetic methods are sometimes desirable, for complex molecular frameworks such as cyclotryptamines and oligocyclotryptamines, there can be many different possible linear or convergent approaches. The success of any particular approach is highly unpredictable.

The compounds of the invention, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present invention is meant to include all such possible isomers, as well as their racemic and optically pure forms whether or not they are specifically depicted herein. Optically active (+) and (−), (R)- and (S)-, or (D)- and (L)-isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Crystallization is a method commonly used to isolate a reaction product, for example one of the compounds disclosed herein, in purified form. Often, crystallization produces a solvate of the compound of the invention. As used herein, the term "solvate" refers to an aggregate that comprises one or more molecules of a compound of the invention with one or more molecules of solvent, typically in co-crystallized form. The solvent can be water, in which case the solvate can be a hydrate. Alternatively, the solvent can be an organic solvent. Thus, the compounds of the present invention can exist as a hydrate, including a monohydrate, dihydrate, hemihydrate, sesquihydrate, trihydrate, tetrahydrate and the like, as well as the corresponding solvated forms. The compound of the invention can be true solvates, while in other cases, the compound of the invention can merely retain adventitious water or be a mixture of water plus some adventitious solvent.

The chemical naming protocol and structure diagrams used herein are a modified form of the I.U.P.A.C. nomenclature system, using the ACD/Name Version 9.07 software program, ChemDraw Ultra Version 11.0.1 and/or ChemDraw Ultra Version 14.0 and/or ChemDraw Professional 16.0.0.82 software naming program (CambridgeSoft), or the like. For complex chemical names employed herein, a substituent group is named before the group to which it attaches. For example, cyclopropylethyl comprises an ethyl backbone with cyclopropyl substituent. Except as described below, all bonds are identified in the chemical structure diagrams herein, except for some carbon atoms, which are assumed to be bonded to sufficient hydrogen atoms to complete the valency.

Following below are more detailed descriptions of various concepts related to, and embodiments of, inventive methods for Diazene Directed Modular Synthesis of Compounds with Quaternary Carbon Centers. It should be appreciated that various concepts introduced above and discussed in greater detail below can be implemented in any of numerous ways, as the disclosed concepts are not limited to any particular manner of implementation. Examples of specific implementations and applications are provided primarily for illustrative purposes.

Hexahydropyrroloindole alkaloids constitute a structurally and biologically fascinating class of natural products. A subset of these natural products, alkaloids comprised of multiple cyclotryptamine units, presents a considerable synthetic challenge due to the presence of multiple quaternary stereocenters as well as numerous basic nitrogen atoms. To date, no method exists for the multiple and directed assembly of whole cyclotryptamine fragments with complete absolute and relative stereochemical control. Herein is disclosed the development of a new and efficient strategy for the synthesis of aryl-alkyl diazenes as prelude for formation of the $C_{sp2}$-$C_{sp3}$ bonds in complex polycyclotryptamine alkaloids. The implementation of this new diazene synthesis has resulted in the convergent and enantioselective total syntheses of (−)-hodgkinsine B (3), (−)-hodgkinsine (4), (−)-calycosidine (5), (−)-quadrigemine C (7), and (−)-psycholeine (8) via completely stereocontrolled assembly of cyclotryptamines.

In one embodiment, the present disclosure provides method of preparing compounds of Formula (I), or a pharmaceutically acceptable salt, tautomer or stereoisomer thereof, comprising reacting a compound of Formula (II), and thereby extruding dinitrogen to provide a compound of Formula (I):

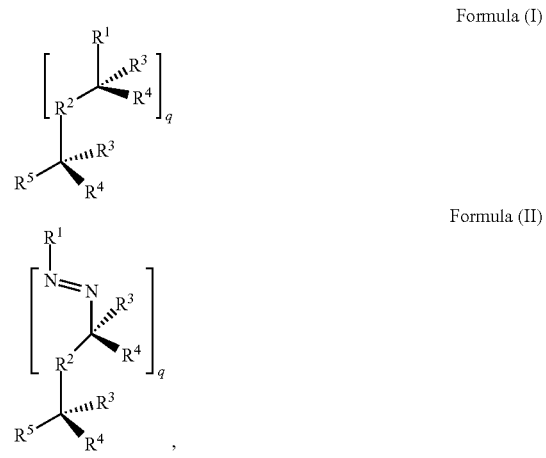

wherein $R^1$ is tertiary alkyl, alkenyl, aryl, heteroaryl, carbocyclyl, or heterocyclyl or at least one moiety of structure:

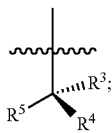

and
$R^2$, $R^3$, $R^4$, and $R^5$ are each occurrence, each independently selected from tertiary alkyl, aryl, heteroaryl, carbocyclyl, or heterocyclic, wherein any two of $R^3$, $R^4$, and $R^5$ taken together with the carbon atoms to which they are attached form a $C_{5-14}$ membered saturated, unsaturated, or aromatic carbocyclic ring or a $C_{5-14}$ membered saturated, unsaturated, or aromatic heterocyclic ring; and wherein any tertiary alkyl, aryl, heteroaryl, carbocyclyl, or heterocyclyl, $C_{5-14}$ membered saturated, unsaturated, or aromatic carbocyclic ring or a $C_{5-14}$ membered saturated, unsaturated, or aromatic heterocyclic ring can be further substituted with one or more halogen, alkyl, heteroaryl, carbocyclyl, heterocyclyl, $C_{3-14}$ membered saturated, unsaturated, or aromatic carbocyclic, or $C_{3-14}$ membered saturated, unsaturated, or aromatic heterocyclic rings; and q is an integer from 0-8.

In some embodiments, q is 1, 2, 3, 4, 5, 6, 7, or 8. In other embodiments, q is an integer from 0 to 1, 0 to 2, 0 to 3, 0 to 4, 0 to 5, 0 to 6, or 0 to 7.

In various embodiments, the formation of the compound of Formula (I) from the compound of Formula (II) occurs via a radical recombination reaction. In another embodiment, the stereochemical configuration of the compound of Formula (II) is retained in the compound of Formula (I) following the reaction. In other embodiments, the radical recombination reaction results in a Csp3-Csp3 bond or a Csp3-Csp2-bond. In a specific embodiment, the bond formed is a Csp3-Csp2 bond. In another specific embodiment, the bond formed is a Csp3-Csp2 bond. The radical recombination reaction can be initiated under photolysis conditions by irradiating the compounds of Formula (II). In some embodiments, the irradiation is carried out in a photoreactor. In other embodiments, the photoreactor is equipped with 1 to about 20 lamps operating at a wavelength λ from about 250 nm to about 400 nm. Various wavelengths of light may be suitable including 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm, continuing up to about 400 nm, inclusive of all values therebetween. In more specific embodiments, the wavelength λ is 300 nm or 380 nm.

In other embodiments, the radical recombination reaction can be initiated under thermal conditions, such as described in Nelsen, S. F.; Bartlett, P. D. *JACS* 1966, 88, 137-143 and 143-149, and Engel, P. S.; Pan, L.; Ying, Y.; Alemany, L. B. *JACS* 2001, 123, 3706-3715, each of which is herein expressly incorporated by reference. In some embodiments, the thermal reaction is carried out from about 60° C. to about 250° C. In other embodiments, the thermal reaction is carried out from 100° C. to about 150° C. In a specific embodiment, the thermal reaction is carried out at 120° C. In another embodiment, the radical recombination reaction can be initiated under flash vacuum pyrolysis conditions.

In another embodiment, the present method as disclosed herein is useful in preparing compound of Formula (I), wherein compounds of Formula (I) are:

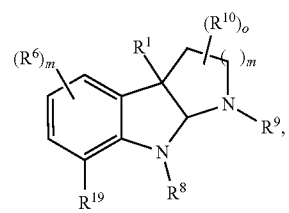

Formula (Ia)

and
wherein $R^1$ is tertiary alkyl, alkenyl, aryl, heteroaryl, carbocyclyl, heterocyclyl,

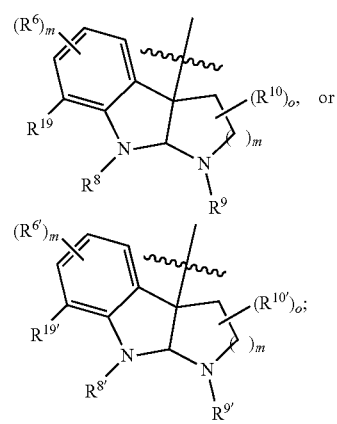

$R^6$ and $R^{6'}$ are each independently selected from halogen, —OH, —$OR^{11}$, —$OC(=O)R^{11}$, —$NR^{11}R^{12}$, —$S(=O)_pR^{13}$, —$C(=O)R^{11}$, —$C(=O)OR^{11}$, —$C(=O)NR^{11}NR^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl; wherein two $R^6$ or two $R^{6'}$ groups taken together with the carbon atoms to which they are attached form an aryl, heteroaryl, carbocyclic, or heterocyclic ring;
$R^8$, $R^9$, $R^{8'}$, and $R^{9'}$ are each independently selected from H, $C_1$-$C_{12}$ alkyl, $C_2$-$C_{12}$ alkenyl, $C_2$-$C_{12}$ alkynyl, —$C(=O)R^{11}$, —$C(=O)OR^{11}$, —$C(=O)NR^{11}R^{12}$, —$SR^{11}$, —$S(=O)_pR^{13}$, —$S(=O)_2NR^{11}R^{12}$, —$C(=O)O(CH_2)_oR^{11}$, aryl, heteroaryl, carbocyclyl, or heterocyclyl;
$R^{10}$ and $R^{10'}$ are each independently selected from H, $C_1$-$C_{12}$ alkyl; $C_2$-$C_{12}$ alkenyl, $C_2$-$C_{12}$ alkynyl, —$C(=O)R^{11}$, —$C(=O)OR^{11}$, —$C(=O)NR^{11}R^{12}$, —$S(=O)_pR^{13}$, —OH, —$OR^{11}$, —$OC(=O)R^{11}$, —$NR^{11}R^{12}$, aryl, heteroaryl, carbocyclyl, or heterocyclyl, wherein two $R^{10}$ or two $R^{10'}$ groups taken together with the carbon atoms to which they are attached form an aryl, heteroaryl, carbocyclic, or heterocyclic ring;
$R^{11}$ and $R^{12}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;
$R^{13}$ and $R^{14}$ are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —$OR^{11}$, —$(CH_2)_rSiMe_3$, or —$(CH_2)_rR^{11}$;

$R^{15}$ is $-S(=O)_pR^{13}$, $-S(=O)_2NR^{11}R^{12}$, $-C(=O)R^{13}$, $-C(=O)R^{20}$, $-C(=O)O(CH_2)_rR^{20}$, $-C(=O)CF_3$, $-C(=O)OR^{20}$, $-P(=O)R^{13}R^{14}$, or, $-P(=O)NR^{11}R^{12}$; $R^{19}$ and $R^{19'}$ are each independently selected from H, tertiary alkyl, alkenyl, aryl, heteroaryl, carbocyclyl, heterocyclyl,

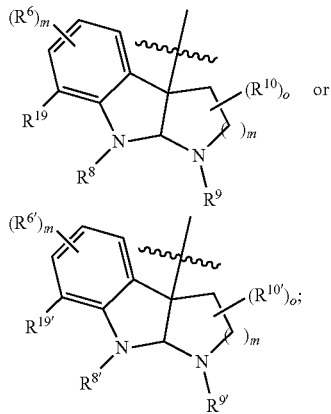

$R^{20}$ is $-Si(alkyl)_3$, $-Si(alkyl)_2aryl$, or $Si(aryl)_2alkyl$; and
m is an integer from 0 to 3;
n and o are each independently an integer from 0 to 4;
p is 1 or 2; and
r is an integer from 1 to 4.

In another embodiment, the present method as disclosed herein is useful in preparing compounds of Formula (Ia):

Formula (Ia)

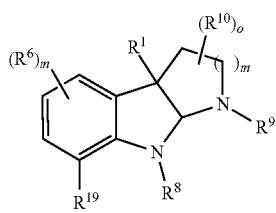

wherein $R^1$ is further defined as

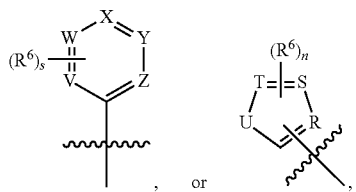

and
wherein V, W, X, Y, and Z are each independently selected from $-CH$ or N;
R, S, and T are each independently selected from $-CH$ or N; and
U is O, S, or $NR^{11}$; wherein $R^{11}$ is independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl; and
n is an integer from 0-4; and
s is an integer from 0-5.

In a more specific embodiment, the present method as disclosed herein is useful in preparing compounds of Formula (I), wherein compounds of Formula (I) are:

Formula (Ib)

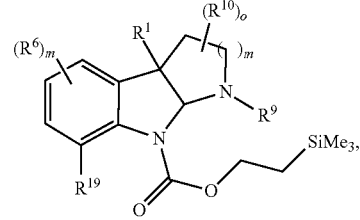

and
wherein $R^{19}$ is H, tertiary alkyl, alkenyl, aryl, heteroaryl, carbocyclyl, heterocyclyl,

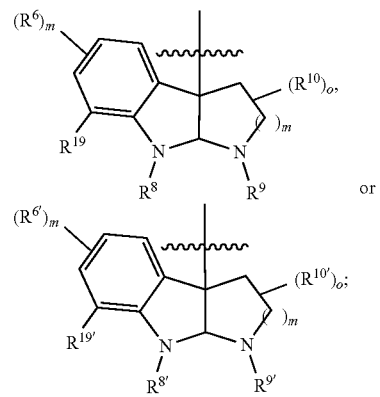

and
$R^8$ and $R^{8'}$ are $-C(=O)O(CH_2)_2SiMe_3$; and
$R^6$, $R^{6'}$, $R^9$, $R^{9'}$, $R^{10}$, $R^{10'}$, and $R^{19'}$ are defined as above for Formula (Ia).

In another embodiment, the method as presently disclosed herein is useful in preparing compounds of Formula (IIa):

Formula (IIa)

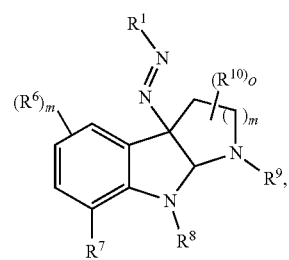

wherein $R^1$ is tertiary alkyl, alkenyl, aryl, heteroaryl, carbocyclyl, heterocyclyl,

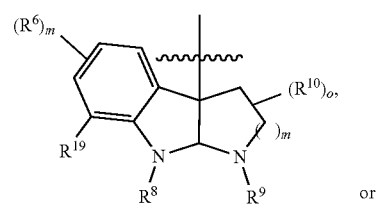

or

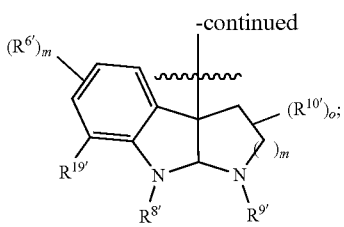

$R^6$ and $R^{6'}$ are each independently selected from halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl; wherein two $R^6$ or two $R^{6'}$ groups taken together with the carbon atoms to which they are attached form an aryl, heteroaryl, carbocyclic, or heterocyclic ring;

$R^7$ and $R^{7'}$ are each independently selected from H, —N$_3$, —N(R$^{15}$)NH$_2$, —NHR$^{15}$,

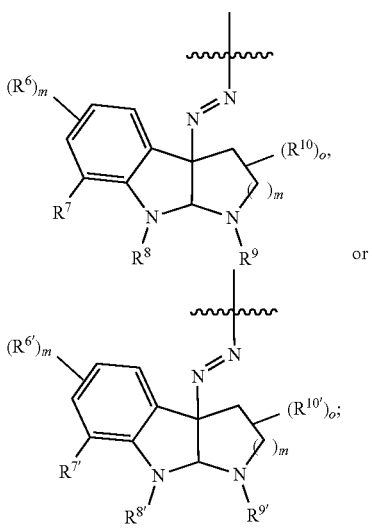

$R^8$, $R^{8'}$, $R^9$, and $R^{9'}$ are each independently selected from H, $C_1$-$C_{12}$ alkyl, $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —SR$^{11}$, —S(=O)$_p$R$^{13}$, —S(=O)$_2$NR$^{11}$R$^{12}$, —C(=O)O(CH$_2$)$_o$R$^{11}$, aryl, heteroaryl, carbocyclyl, or heterocyclyl;

$R^{10}$ and $R^{10'}$ are each independently selected from H, $C_1$-$C_{12}$ alkyl; $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —S(=O)$_p$R$^{13}$, —OH, —OR$^{11}$, —OC(=O)R$^{11}$, —NR$^{11}$R$^{12}$, aryl, heteroaryl, carbocyclyl, or heterocyclyl, wherein two $R^{10}$ or two $R^{10'}$ groups taken together with the carbon atoms to which they are attached form an aryl, heteroaryl, carbocyclic, or heterocyclic ring;

$R^{11}$ and $R^{12}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;

$R^{13}$ and $R^{14}$ are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —OR$^{11}$, —(CH$_2$)$_r$SiMe$_3$, or —(CH$_2$)$_r$R$^{11}$;

$R^{15}$ is —S(=O)$_p$R$^{13}$, —S(=O)$_2$NR$^{11}$R$^{12}$, —C(=O)R$^{13}$, —C(=O)R$^{20}$, —C(=O)O(CH$_2$)$_r$R$^{20}$, —C(=O)CF$_3$, —C(=O)OR$^{20}$, —P(=O)R$^{13}$R$^{14}$, or, —P(=O)NR$^{11}$R$^{12}$;

$R^{19}$ and $R^{19'}$ are each independently H;

$R^{20}$ is —Si(alkyl)$_3$, —Si(alkyl)$_2$aryl, or Si(aryl)$_2$alkyl; and m is an integer from 0 to 3;

n and o are each independently an integer from 0 to 4;

p is 1 or 2; and r is an integer from 1 to 4.

In another embodiment, the method as presently disclosed herein is useful in preparing compounds of Formula (IIa): wherein $R^1$ is,

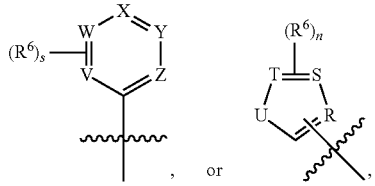

and wherein V, W, X, Y, and Z are each independently selected from —CH or N;

R, S, and T are each independently selected from —CH or N;

U is O, S, or NR$^{11}$; wherein $R^{11}$ is independently selected from H, $C_1$-$C_{12}$ alkyl, $C_2$-$C_{12}$ alkenyl, $C_2$-$C_{12}$ alkynyl, —Si(alkyl)$_3$, —Si(alkyl)$_2$aryl, Si(aryl)$_2$alkyl, aryl, heteroaryl, carbocyclyl, or heterocyclyl, and wherein $R^{11}$ and $R^{12}$ taken together with the carbon atoms to which they are attached form an aryl, heteroaryl, carbocyclic, or heterocyclic ring; and n is an integer from 0-4; and s is an integer from 0-5; and wherein $R^6$, $R^7$, $R^8$, $R^9$, and $R^{10}$ are defined as above for Formula (IIa).

In another embodiment, the present disclosure provides a method of preparing compounds of Formula (II) by reacting compounds of Formula (III) and compounds of Formula (IV):

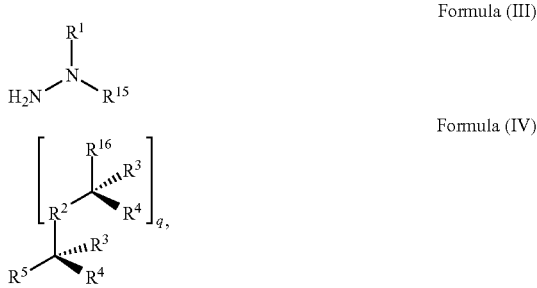

wherein $R^1$ is alkenyl, aryl, or heteroaryl; and $R^2$, $R^3$, $R^4$, and $R^5$ are each occurrence, each independently selected from alkyl, aryl, heteroaryl, carbocyclyl, or heterocyclic, wherein any two of $R^3$, $R^4$ and $R^5$ taken together with the carbon atoms to which they are attached form a $C_{5-14}$ membered saturated, unsaturated, or aromatic carbocyclic ring or a $C_{5-14}$ membered saturated, unsaturated, or aromatic heterocyclic ring; and wherein any tertiary alkyl, aryl, heteroaryl, carbocyclyl, or heterocyclyl, $C_{5-14}$ membered saturated, unsaturated, or aromatic carbocyclic ring or a $C_{5-14}$ membered saturated, unsaturated, or aromatic heterocyclic ring can be further substituted with one or more halogen, alkyl, heteroaryl, carbocyclyl, heterocyclyl, $C_{3-14}$ membered saturated, unsaturated, or aromatic carbocyclic, or $C_{3-14}$ membered saturated, unsaturated, or aromatic heterocyclic rings;

$R^{11}$ and $R^{12}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;

$R^{13}$ and $R^{14}$ are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —$OR^{11}$, —$(CH_2)_rSiMe_3$, or —$(CH_2)_rR^{11}$;

$R^{15}$ is —$S(=O)_pR^{13}$, —$S(=O)_2NR^{11}R^{12}$, —$C(=O)R^{13}$, —$C(=O)R^{20}$, —$C(=O)O(CH_2)_rR^{20}$, —$C(=O)CF_3$, —$C(=O)OR^{20}$, —$P(=O)R^{13}R^{14}$, or, —$P(=O)NR^{11}R^{12}$;

$R^{16}$ is I, Br, Cl, —OH, —$OSO_2CF_3$, —$OS(O)_2R^{13}$, —OP($=O)R^{13}R^{14}$, —$OC(=NR^{11})R^{12}$, —$OC(=NR^{11})CCl_3$, —$OR^{11}$, or —$N_2^+X^-$, wherein $X^-$ is halogen;

$R^{20}$ is —$Si(alkyl)_3$, —$Si(alkyl)_2aryl$, or $Si(aryl)_2alkyl$; and m is an integer from 0 to 3;
n and o are each independently an integer from 0 to 4;
p is 1 or 2;
q is an integer of from 0-8; and
r is an integer from 1 to 4.

In one embodiment the method comprises an electrophilic activation of a compound of Formula (IV). In another embodiment, the electrophilic activation comprises reaction of the compound of Formula (IV) with a silver (I) salt and a base. In various embodiments, the silver (I) salt can be $AgOSO_2CF_3$, $AgSbF_6$, $Ag(OSO_2CF_2CF_2CF_3)$, $AgBF_4$, or $AgN(SO_2CF_3)_2$. In specific embodiments, the silver (I) salt is $AgOSO_2CF_3$ or $AgSbF_6$. In other embodiments, the compound of Formula (III) is resistant to oxidation by the silver (I) salt. In other embodiments, the compound of Formula (III) is less prone to oxidation. The presence of an electron withdrawing group renders compounds of Formula (III) resistant to oxidization under the reaction conditions for at least 45 minutes, and typically for a period of up to 6 hours or more. In contrast, a compound such as phenylhydrazine with no electron withdrawing group affords no desired products, as it is decomposed immediately in the presence of the silver (I) salts. In a specific embodiment of a compound of Formula (III), $R^{15}$ is —$S(=O)_pR^{13}$, wherein p is 2 and $R^{13}$ is $C_1$-$C_{12}$ alkyl. Accordingly, when $R^{15}$ is —$S(=O)_pR^{13}$, wherein p is 2 and $R^{13}$ is $C_1$-$C_{12}$ alkyl, the compound of Formula (II) is formed in one synthetic step.

The new diazene synthesis strategy is facilitated through placement of an electron withdrawing group on the hydrazine that makes the nucleophilic hydrazine compatible with conditions needed for activation of the electrophile. The highlighted examples allow the union of the nucleophile and the electrophile followed by spontaneous loss of the electron withdrawing group to give the diazene.

Other examples of electron withdrawing groups demonstrated in data provided herein include but are not limited to the use of BOC and trifluoroacetyl group. These groups lead to efficient formation of the nucleophile-electrophile adduct as the hydrazine intermediate. In an embodiment using trifluoroacetyl, a mild deacylation and oxidation leads to the desired diazene.

The methanesulfonyl group shown above does not require a separate step, but this characteristic can be applicable to other variations, embodiments, and implementations:

important: other sulfonyl groups

R = alkyl, amide, alkoxy
other sulfoxides based nucleophiles

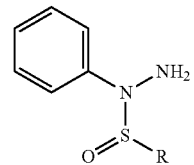

R = alkyl, aryl, amide, alkoxy
other phosphrous based nucleophiles

R = alkyl, aryl, amide, alkoxy other acyl groups        other carbamates

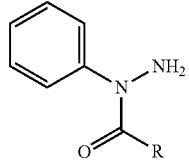 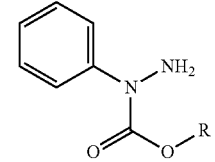

R = alkyl, aryl, silyl        R = alkyl, aryl, silyl

In addition to the methane sulfonamide, this strategy can be applied to arene sulfonamides (e.g., toluenesulfonyl, benzenesulfonyl), and alkyl sulfonyl derivatives along with sulfonamide ($RSO_2$ vs. $R_2NSO_2$) or sulfamate ($RSO_2$ vs. $ROSO_2$) variations. Use of sulfoxide variations (SO vs. $SO_2$) is also possible. Additionally, phosphorous based systems can be utilized as well ($RSO_2$ vs. $R_2PO$). Such embodiments provide benefits similar to the exemplary reagent class discussed herein.

Other hydrazines including simple amides and carbamates can be utilized, and in some implementations, can be as equally effective as the Boc-carbamate and the TFA-amide that have been demonstrated herein.

Use of these reagent classes can be extended to conditions not necessary involving silver activation. These nucleophiles are excellent substitutes for direct synthesis of diazene through N-alkylation (under a variety of conditions).

These reagent classes stand in contrast to simple hydrazine ($ArNHNH_2$) since exposure of $ArNHNH_2$ to promoters such as silver may not be possible due to rapid oxidation of the hydrazine. These hydrazines may be used for simple electrophiles (primary and secondary electrophiles), but for complex and sterically crowded electrophiles (tertiary carbon), technology and methods as disclosed herein is needed.

In yet another embodiment, the method as presently disclosed herein is useful in preparing compounds of Formula (II) from compounds of Formula (III), wherein the compound of Formula (III) is:

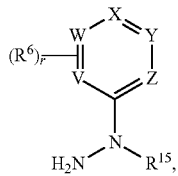

Formula (IIIa)

wherein V, W, X, Y, and Z are each independently selected from —CH or N; and r is an integer from 0 to 5.

In other embodiments, the method as presently disclosed herein is useful in preparing compounds of Formula (II) from compounds of Formula (III), wherein the compound of Formula (III) is:

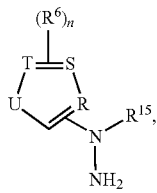

Formula (IIIb)

wherein R, S, and T are each independently selected from —CH or N; and

U is O, S, or $NR^{11}$, wherein $R^{11}$ is independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl; and n is an integer from 0 to 4.

In still other various embodiments, the compound of Formula (III) is:

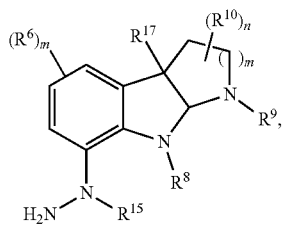

Formula (IIIc)

wherein $R^6$ and $R^{6'}$ are each independently selected from halogen, —OH, —$OR^{11}$, —$OC(=O)R^{11}$, —$NR^{11}R^{12}$, —$S(=O)_pR^{13}$, —$C(=O)R^{11}$, —$C(=O)OR^{11}$, —$C(=O)NR^{11}NR^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl; wherein two $R^6$ or two $R^{6'}$ groups taken together with the carbon atoms to which they are attached form an aryl, heteroaryl, carbocyclic, or heterocyclic ring;

$R^{17}$ is H, —OH, —$OR^{11}$, —$NR^{11}R^{12}$, aryl, heteroaryl, carbocyclyl, heterocyclyl,

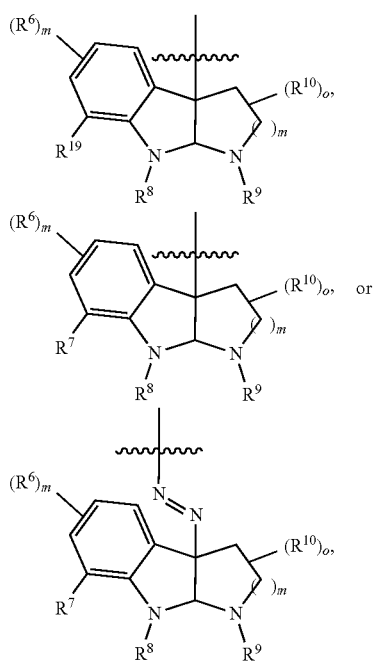

wherein
$R^7$ and $R^{7'}$ are each independently selected from H, —$N_3$, —$N(R^{15})NH_2$, —$NHR^{15}$,

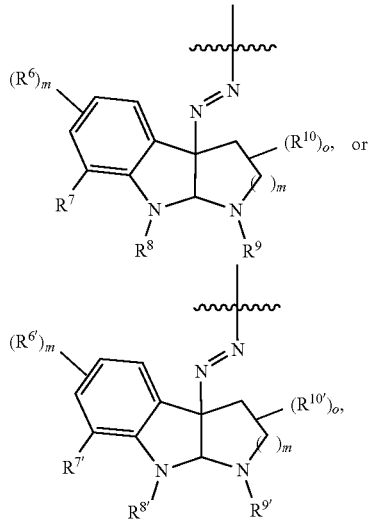

and wherein
$R^{19}$ and $R^{19'}$ are each independently selected from H, tertiary alkyl, alkenyl, aryl, heteroaryl, carbocyclyl, heterocyclyl,

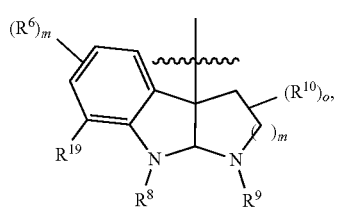

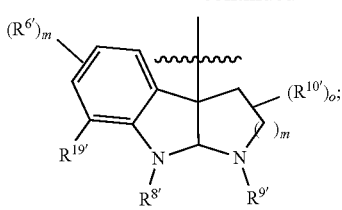

$R^8$, $R^{8'}$, $R^9$, and, $R^{9'}$ are each independently selected from H, $C_1$-$C_{12}$ alkyl, $C_2$-$C_{12}$ alkenyl, $C_2$-$C_{12}$ alkynyl, —C(=O)$R^{11}$, —C(=O)O$R^{11}$, —C(=O)N$R^{11}R^{12}$, —S$R^{11}$, —S(=O)$_p R^{13}$, —S(=O)$_2$N$R^{11}R^{12}$, —C(=O)O(CH$_2$)$_o R^{11}$, aryl, heteroaryl, carbocyclyl, or heterocyclyl;

$R^{10}$ and $R^{10'}$ are each independently selected from H, $C_1$-$C_{12}$ alkyl; $C_2$-$C_{12}$ alkenyl, $C_2$-$C_{12}$ alkynyl, —C(=O)$R^{11}$, —C(=O)O$R^{11}$, —C(=O)N$R^{11}R^{12}$, —S(=O)$_p R^{13}$, —OH, —O$R^{11}$, —OC(=O)$R^{11}$, —N$R^{11}R^{12}$, aryl, heteroaryl, carbocyclyl, or heterocyclyl, wherein two $R^{10}$ or two $R^{10'}$ groups taken together with the carbon atoms to which they are attached form an aryl, heteroaryl, carbocyclic, or heterocyclic ring;

$R^{11}$ and $R^{12}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;

$R^{13}$ and $R^{14}$ are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —O$R^{11}$, —(CH$_2$)$_r$SiMe$_3$, or —(CH$_2$)$_r R^{11}$;

$R^{15}$ is —S(=O)$_p R^{13}$, —S(=O)$_2$N$R^{11}R^{12}$, —C(=O)$R^{13}$, —C(=O)$R^{20}$, —C(=O)O(CH$_2$)$_r R^{20}$, —C(=O)CF$_3$, —C(=O)O$R^{20}$, —P(=O)$R^{13}R^{14}$, or, —P(=O)N$R^{11}R^{12}$;

$R^{20}$ is —Si(alkyl)$_3$, —Si(alkyl)$_2$aryl, or Si(aryl)$_2$alkyl; and m is an integer from 0 to 3;

n and o are each independently an integer from 0 to 4;

p is 1 or 2; and r is an integer from 1 to 4.

In another embodiment, the present disclosure provides a method of preparing the compound of Formula (II) by reacting compounds of Formula (III) and compounds of Formula (IV), wherein the compound of Formula (IV) is:

Formula (IVa)

wherein $R^{16}$ is I, Br, Cl, —OH, —OSO$_2$CF$_3$, —OS(O)$_2 R^{13}$, —OP(=O)$R^{13}R^{14}$, —OC(=N$R^{11}$)$R^{12}$, —OC(=N$R^{11}$)CCl$_3$, —O$R^{11}$, or —N$_2^+$X$^-$, wherein X$^-$ is halogen;

$R^{21}$ is H, halogen, alkyl, alkenyl, alkynyl, aryl, heteroaryl, carbocyclyl, heterocyclyl, —N$_3$,

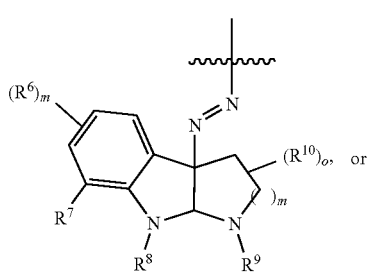

wherein $R^7$ and $R^{7'}$ are each independently selected from H, —N$_3$, —N($R^{15}$)NH$_2$, —NH$R^{15}$, -continued

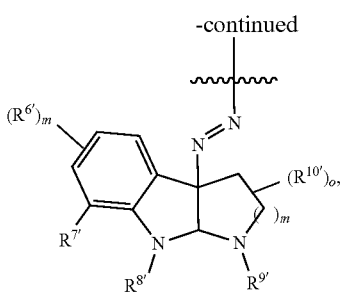

and
wherein $R^{19}$ and $R^{19'}$ are each independently selected from H, tertiary alkyl, alkenyl, aryl, heteroaryl, carbocyclyl, heterocyclyl,

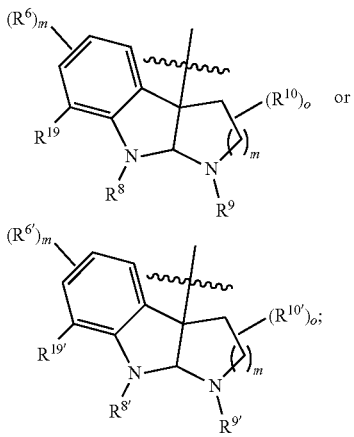

$R^6$ and $R^{6'}$ are each independently selected from halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl; wherein two $R^6$ or two $R^{6'}$ groups taken together with the carbon atoms to which they are attached form an aryl, heteroaryl, carbocyclic, or heterocyclic ring;

$R^8$, $R^{8'}$, $R^9$, and, $R^{9'}$ are each independently selected from H, $C_1$-$C_{12}$ alkyl, $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —SR$^{11}$, —S(=O)$_p$R$^{13}$, —S(=O)$_2$NR$^{11}$R$^{12}$, —C(=O)O(CH$_2$)$_o$R$^{11}$, aryl, heteroaryl, carbocyclyl, or heterocyclyl;

$R^{10}$ and $R^{10'}$ are each independently selected from H, $C_1$-$C_{12}$ alkyl; $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —S(=O)$_p$R$^{13}$, —OH, —OR$^{11}$, —OC(=O)R$^{11}$, —NR$^{11}$R$^{12}$, aryl, heteroaryl, carbocyclyl, or heterocyclyl, wherein two $R^{10}$ or two $R^{10'}$ groups taken together with the carbon atoms to which they are attached form an aryl, heteroaryl, carbocyclic, or heterocyclic ring;

$R^{11}$ and $R^{12}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;

$R^{13}$ and $R^{14}$ are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —OR$^{11}$, —(CH$_2$)$_r$SiMe$_3$, or —(CH$_2$)$_r$R$^{11}$;

$R^{15}$ is —S(=O)$_p$R$^{13}$, —S(=O)$_2$NR$^{11}$R$^{12}$, —C(=O)R$^{13}$, —C(=O)R$^{20}$, —C(=O)O(CH$_2$)$_r$R$^{20}$, —C(=O)CF$_3$, —C(=O)OR$^{20}$, —P(=O)R$^{13}$R$^{14}$, or, —P(=O)NR$^{11}$R$^{12}$;

$R^{20}$ is —Si(alkyl)$_3$, —Si(alkyl)$_2$aryl, or Si(aryl)$_2$alkyl; and m is an integer from 0 to 3;

n and o are each independently an integer from 0 to 4;

p is 1 or 2; and r is an integer from 1 to 4.

In another embodiment, the present disclosure provides a method of preparing the compound of Formula (II) from the compound of Formula (IIIc) and the compound of Formula (IVa):

Formula (IVa)

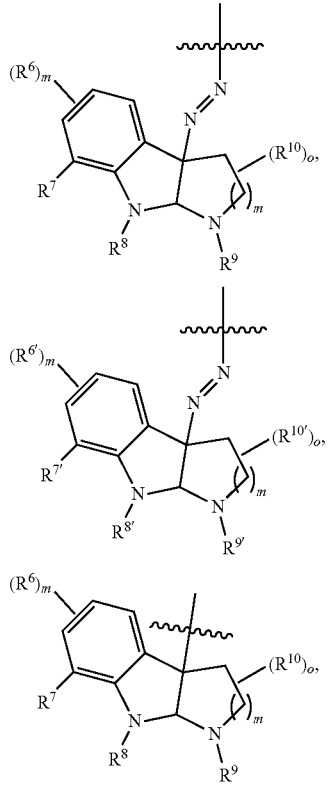

wherein $R^{16}$ is I, Br, Cl, —OH, —OSO$_2$CF$_3$, —OS(O)$_2$R$^{13}$, —OP(=O)R$^{13}$R$^{14}$, —OC(=NR$^{11}$)R$^{12}$, —OC(=NR$^{11}$)CCl$_3$, —OR$^{11}$, or —N$_2^+$X$^-$, wherein X$^-$ is halogen;

$R^{21}$ is H, halogen, alkyl, alkenyl, alkynyl, aryl, heteroaryl, carbocyclyl, heterocyclyl, —N$_3$, -continued

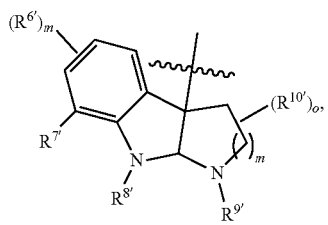

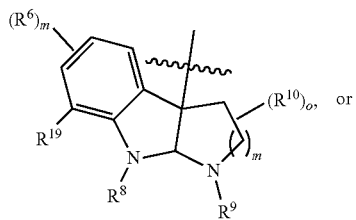

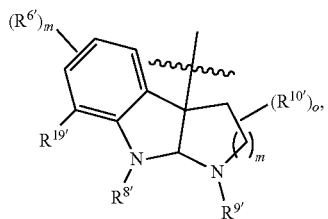

wherein
$R^7$ and $R^{7'}$ are each independently selected from H, $-N_3$, $-N(R^{15})NH_2$, $-NHR^{15}$,

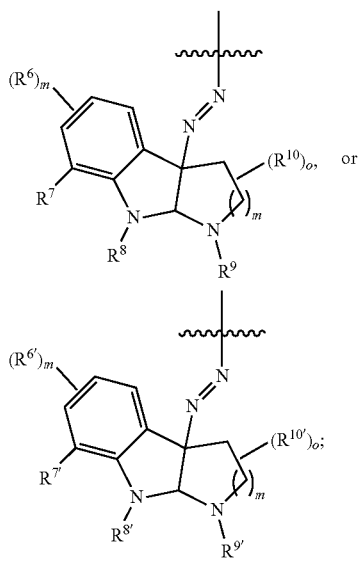

and wherein
$R^{19}$ and $R^{19'}$ are each independently selected from H, tertiary alkyl, alkenyl, aryl, heteroaryl, carbocyclyl, heterocyclyl,

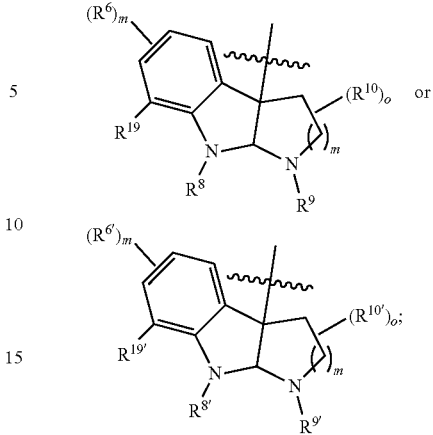

$R^6$ and $R^{6'}$ are each independently selected from halogen, $-OH$, $-OR^{11}$, $-OC(=O)R^{11}$, $-NR^{11}R^{12}$, $-S(=O)_pR^{13}$, $-C(=O)R^{11}$, $-C(=O)OR^{11}$, $-C(=O)NR^{11}NR^{12}$, $C_1-C_{12}$ alkyl, $C_2-C_{12}$ alkenyl, $C_2-C_{12}$ alkynyl, aryl, heteroaryl, carbocyclyl, or heterocyclyl; wherein two $R^6$ or two $R^{6'}$ groups taken together with the carbon atoms to which they are attached form an aryl, heteroaryl, carbocyclic, or heterocyclic ring;

$R^8$, $R^{8'}$, $R^9$, and, $R^{9'}$ are each independently selected from H, $C_1-C_{12}$ alkyl, $C_2-C_{12}$ alkenyl, $C_2-C_{12}$ alkynyl, $-C(=O)R^{11}$, $-C(=O)OR^{11}$, $-C(=O)NR^{11}R^{12}$, $-SR^{11}$, $-S(=O)_pR^{13}$, $-S(=O)_2NR^{11}R^{12}$, $-C(=O)O(CH_2)_oR^{11}$, aryl, heteroaryl, carbocyclyl, or heterocyclyl;

$R^{10}$ and $R^{10'}$ are each independently selected from H, $C_1-C_{12}$ alkyl; $C_2-C_{12}$ alkenyl, $C_2-C_{12}$ alkynyl, $-C(=O)R^{11}$, $-C(=O)OR^{11}$, $-C(=O)NR^{11}R^{12}$, $-S(=O)_pR^{13}$, $-OH$, $-OR^{11}$, $-OC(=O)R^{11}$, $-NR^{11}R^{12}$, aryl, heteroaryl, carbocyclyl, or heterocyclyl, wherein two $R^{10}$ or two $R^{10'}$ groups taken together with the carbon atoms to which they are attached form an aryl, heteroaryl, carbocyclic, or heterocyclic ring;

$R^{11}$ and $R^{12}$ are each independently selected from H, $C_1-C_{12}$ alkyl, $C_2-C_{12}$ alkenyl, $C_2-C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;

$R^{13}$ and $R^{14}$ are each independently selected from $C_1-C_{12}$ alkyl, $C_2-C_{12}$ alkenyl, $C_2-C_{12}$ alkynyl, aryl, heteroaryl, carbocyclyl, heterocyclyl, $-OR^{11}$, $-(CH_2)_rSiMe_3$, or $-(CH_2)_rR^{11}$;

$R^{15}$ is $-S(=O)_pR^{13}$, $-S(=O)_2NR^{11}R^{12}$, $-C(=O)R^{13}$, $-C(=O)R^{20}$, $-C(=O)O(CH_2)_rR^{20}$, $-C(=O)CF_3$, $-C(=O)OR^{20}$, $-P(=O)R^{13}R^{14}$, or, $-P(=O)NR^{11}R^{12}$;

$R^{20}$ is $-Si(alkyl)_3$, $-Si(alkyl)_2aryl$, or $Si(aryl)_2alkyl$; and m is an integer from 0 to 3;

n and o are each independently an integer from 0 to 4;

p is 1 or 2; and r is an integer from 1 to 4.

In various embodiments, the present disclosure provides a method of preparing the compound of Formula (II) by the extrusion of sulfur dioxide from compounds of Formula (V):

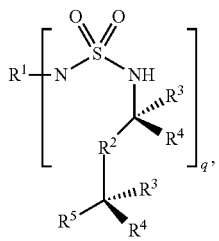

wherein $R^1$ is tertiary alkyl, alkenyl, aryl, heteroaryl, carbocyclyl, or heterocyclyl or at least one moiety of structure:

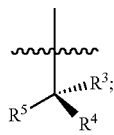

and $R^2$, $R^3$, $R^4$, and $R^5$ are each occurrence, each independently selected from alkyl, aryl, heteroaryl, carbocyclyl, or heterocyclic, wherein any two of $R^3$, $R^4$, and $R^5$ taken together with the carbon atoms to which they are attached form a $C_{5-14}$ membered saturated, unsaturated, or aromatic carbocyclic ring or a $C_{5-14}$ membered saturated, unsaturated, or aromatic heterocyclic ring; and wherein any tertiary alkyl, aryl, heteroaryl, carbocyclyl, or heterocyclyl, $C_{5-14}$ membered saturated, unsaturated, or aromatic carbocyclic ring or a $C_{5-14}$ membered saturated, unsaturated, or aromatic heterocyclic ring can be further substituted with one or more halogen, alkyl, heteroaryl, carbocyclyl, heterocyclyl, $C_{3-14}$ membered saturated, unsaturated, or aromatic carbocyclic, or $C_{3-14}$ membered saturated, unsaturated, or aromatic heterocyclic rings; and q is an integer of from 0-8. In some embodiments, q is 1, 2, 3, 4, 5, 6, 7, or 8. In other embodiments, q is an integer from 0 to 1, 0 to 2, 0 to 3, 0 to 4, 0 to 5, 0 to 6, or 0 to 7.

In some embodiments the extrusion of sulfur dioxide is carried out in the presence of an oxidizing reagent. In some embodiments, the oxidizing reagent is N-chlorosuccinimide, N-chloro-N-methyl benzamide, 1,3-dichloro-5,5-dimethylhydantoin, trichloroisocyanuric acid, N-bromosuccinimide, 1,3-dichloro-5,5-dimethylhydantoin, iodosobenzene, PhI(OAc)$_2$, or PhI(OCOCF$_3$)$_2$. In one specific embodiment, the oxidizing reagent used to carry out the extrusion of sulfur dioxide is 1,3-dichloro-5,5-dimethylhydantoin.

In another embodiment, the method as disclosed herein is useful for the preparation of the compound of Formula (II), wherein the compound of Formula (V) is:

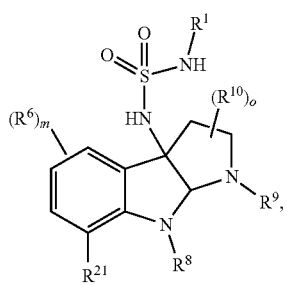

Formula (Va)

wherein $R^1$ is tertiary alkyl, alkenyl, aryl, heteroaryl, carbocyclyl, heterocyclyl,

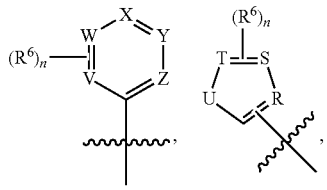

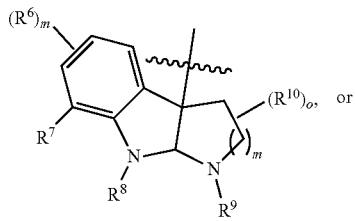

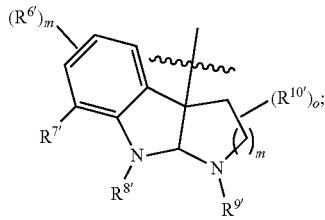

V, W, X, Y, and Z are each independently selected from —CH or N;

R, S, and T are each independently selected from —CH or N;

U is O, S, or NR$^{11}$;

$R^{21}$ is H, halogen, alkyl, alkenyl, alkynyl, aryl, heteroaryl, carbocyclyl, heterocyclyl, —N$_3$,

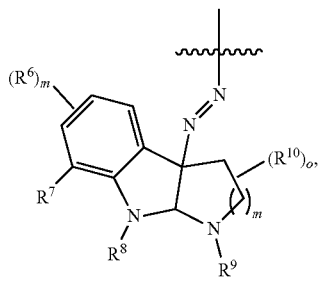

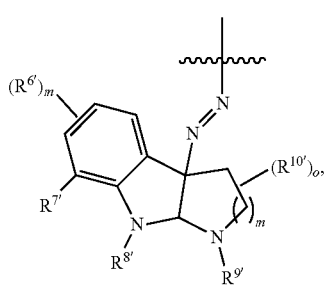

-continued

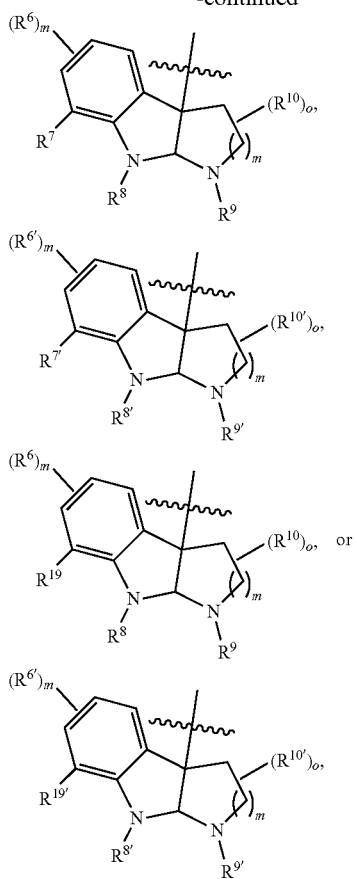

wherein $R^7$ and $R^{7'}$ are each independently selected from H, —$N_3$, —$N(R^{15})NH_2$, —$NHR^{15}$,

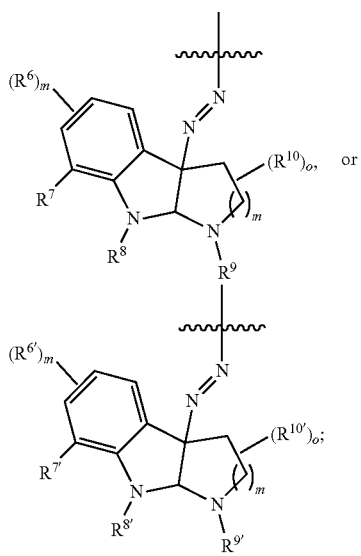

and wherein $R^{19}$ and $R^{19'}$ are each independently selected from H, tertiary alkyl, alkenyl, aryl, heteroaryl, carbocyclyl, heterocyclyl,

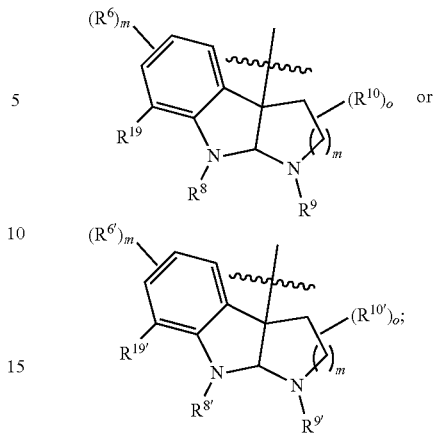

$R^6$ and $R^{6'}$ are each independently selected from halogen, —OH, —$OR^{11}$, —$OC(\!=\!O)R^{11}$, —$NR^{11}R^{12}$, —$S(\!=\!O)_pR^{13}$, —$C(\!=\!O)R^{11}$, —$C(\!=\!O)OR^{11}$, —$C(\!=\!O)NR^{11}NR^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl; wherein two $R^6$ or two $R^{6'}$ groups taken together with the carbon atoms to which they are attached form an aryl, heteroaryl, carbocyclic, or heterocyclic ring;

$R^8$, $R^{8'}$, $R^9$, and, $R^{9'}$ are each independently selected from H, $C_1$-$C_{12}$ alkyl, $C_2$-$C_{12}$ alkenyl, $C_2$-$C_{12}$ alkynyl, —$C(\!=\!O)R^{11}$, —$C(\!=\!O)OR^{11}$, —$C(\!=\!O)NR^{11}R^{12}$, —$SR^{11}$, —$S(\!=\!O)_pR^{13}$, —$S(\!=\!O)_2NR^{11}R^{12}$, —$C(\!=\!O)O(CH_2)_oR^{11}$, aryl, heteroaryl, carbocyclyl, or heterocyclyl;

$R^{10}$ and $R^{10'}$ are each independently selected from H, $C_1$-$C_{12}$ alkyl; $C_2$-$C_{12}$ alkenyl, $C_2$-$C_{12}$ alkynyl, —$C(\!=\!O)R^{11}$, —$C(\!=\!O)OR^{11}$, —$C(\!=\!O)NR^{11}R^{12}$, —$S(\!=\!O)_pR^{13}$, —OH, —$OR^{11}$, —$OC(\!=\!O)R^{11}$, —$NR^{11}R^{12}$, aryl, heteroaryl, carbocyclyl, or heterocyclyl, wherein two $R^{10}$ or two $R^{10'}$ groups taken together with the carbon atoms to which they are attached form an aryl, heteroaryl, carbocyclic, or heterocyclic ring;

$R^{11}$ and $R^{12}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;

$R^{13}$ and $R^{14}$ are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —$OR^{11}$, —$(CH_2)_rSiMe_3$, or —$(CH_2)_rR^{11}$;

$R^{15}$ is —$S(\!=\!O)_pR^{13}$, —$S(\!=\!O)_2NR^{11}R^{12}$, —$C(\!=\!O)R^{13}$, —$C(\!=\!O)R^{20}$, —$C(\!=\!O)O(CH_2)_rR^{20}$, —$C(\!=\!O)CF_3$, —$C(\!=\!O)OR^{20}$, —$P(\!=\!O)R^{13}R^{14}$, or, —$P(\!=\!O)NR^{11}R^{12}$;

$R^{20}$ is —Si(alkyl)$_3$, —Si(alkyl)$_2$aryl, or Si(aryl)$_2$alkyl; and m is an integer from 0 to 3;

n and o are each independently an integer from 0 to 4;

p is 1 or 2; and r is an integer from 1 to 4.

In other various embodiments, the present disclosure provides a method of preparing compounds of Formula (V) according to the following steps:

a. reacting a compound of Formula (VI) and a compound of Formula (IV) to give a compound of Formula (VII):

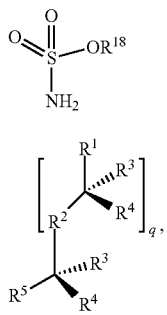

Formula (VI)

Formula (IV)

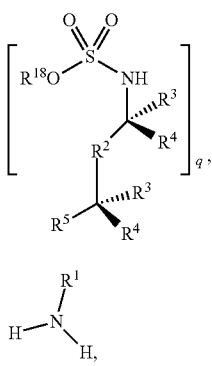

wherein $R^{16}$ is I, Br, Cl, —OH, —OSO$_2$CF$_3$, —OS(O)$_2$R$^{13}$, —OP(=O)R$^{13}$R$^{14}$, —OC(=NR$^{11}$)R$^{12}$, —OC(=NR$^{11}$)CCl$_3$, —OR$^{11}$, or —N$_2^+$X$^-$, wherein X$^-$ is halogen; and $R^{18}$ is aryl, or heteroaryl; and $R^2$, $R^3$, $R^4$, and $R^5$ are defined as above for Formula (I).

b. reacting a compound of Formula (VII) and a compound of Formula (VIII) to provide the compound of Formula (VI):

Formula (VII)

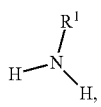

Formula (VIII)

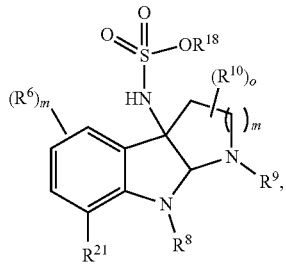

wherein $R^1$ is tertiary alkyl, alkenyl, aryl, heteroaryl, carbocyclyl, or heterocyclyl.

In another embodiment, the method as disclosed herein is useful for the preparation of the compound of Formula (V) from the compound of Formula (VIII) and the compound of Formula (VII), wherein the compound of Formula (VII) is:

Formula (VIIa)

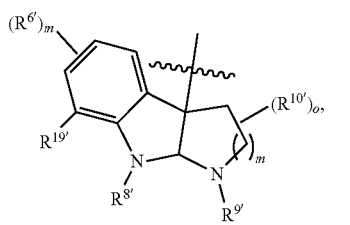

wherein $R^{21}$ is H, halogen, alkyl, alkenyl, alkynyl, aryl, heteroaryl, carbocyclyl, heterocyclyl, —N$_3$,

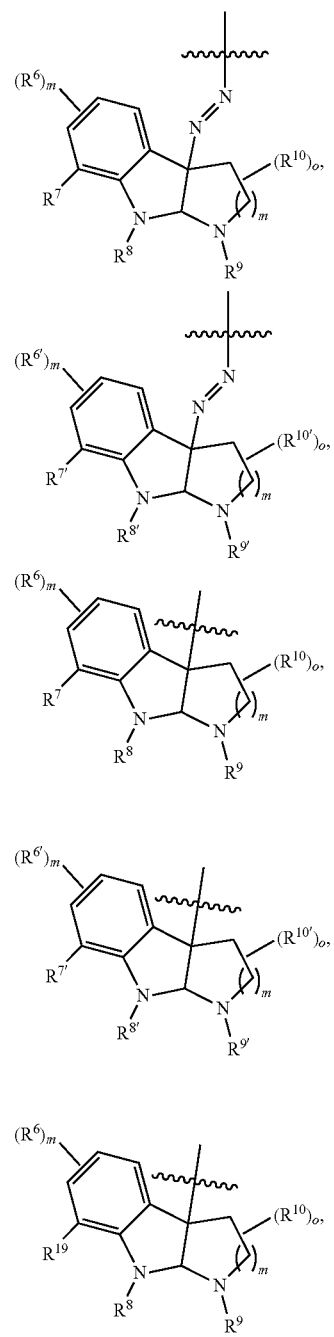

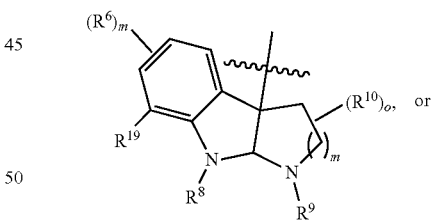

wherein $R^7$ and $R^{7'}$ are each independently selected from H, —N$_3$, —N(R$^{15}$)NH$_2$, —NHR$^{15}$,

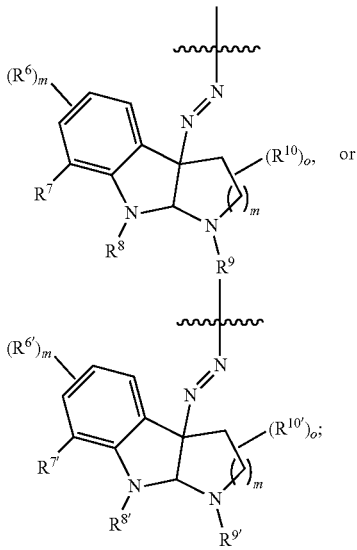

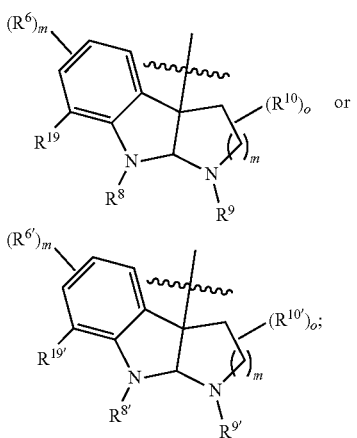

and
wherein $R^{19}$ and $R^{19'}$ are each independently selected from H, tertiary alkyl, alkenyl, aryl, heteroaryl, carbocyclyl, heterocyclyl,

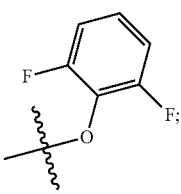 [SMILES: *Oc1c(F)cccc1F]

$R^6$ and $R^{6'}$ are each independently selected from halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl; wherein two $R^6$ or two $R^{6'}$ groups taken together with the carbon atoms to which they are attached form an aryl, heteroaryl, carbocyclic, or heterocyclic ring;

$R^8$, $R^{8'}$, $R^9$, and, $R^{9'}$ are each independently selected from H, $C_1$-$C_{12}$ alkyl, $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —SR$^{11}$, —S(=O)$_p$R$^{13}$, —S(=O)$_2$NR$^{11}$R$^{12}$, —C(=O)O(CH$_2$)$_o$R$^{11}$, aryl, heteroaryl, carbocyclyl, or heterocyclyl;

$R^{10}$ and $R^{10'}$ are each independently selected from H, $C_1$-$C_{12}$ alkyl, $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —S(=O)$_p$R$^{13}$, —OH, —OR$^{11}$, —OC(=O)R$^{11}$, —NR$^{11}$R$^{12}$, aryl, heteroaryl, carbocyclyl, or heterocyclyl, wherein two $R^{10}$ or two $R^{10'}$ groups taken together with the carbon atoms to which they are attached form an aryl, heteroaryl, carbocyclic, or heterocyclic ring;

$R^{11}$ and $R^{12}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;

$R^{13}$ and $R^{14}$ are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —OR$^{11}$, —(CH$_2$)$_r$SiMe$_3$, or —(CH$_2$)$_r$R$^{11}$;

$R^{15}$ is —S(=O)$_p$R$^{13}$, —S(=O)$_2$NR$^{11}$R$^{12}$, —C(=O)R$^{13}$, —C(=O)R$^{20}$, —C(=O)O(CH$_2$)$_r$R$^{20}$, —C(=O)CF$_3$, —C(=O)OR$^{20}$, —P(=O)R$^{13}$R$^{14}$, or, —P(=O)NR$^{11}$R$^{12}$;

$R^{18}$ is

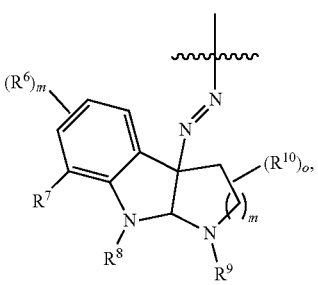

$R^{20}$ is —Si(alkyl)$_3$, —Si(alkyl)$_2$aryl, or Si(aryl)$_2$alkyl; and m is an integer from 0 to 3;

n and o are each independently an integer from 0 to 4;

p is 1 or 2; and r is an integer from 1 to 4.

In other various embodiments, the method as disclosed herein is useful for preparing the compound of Formula (V) from the compound of Formula (VII), and the compound of Formula (VIII), wherein the compound Formula (VIII) is:

Formula (VIIIa)

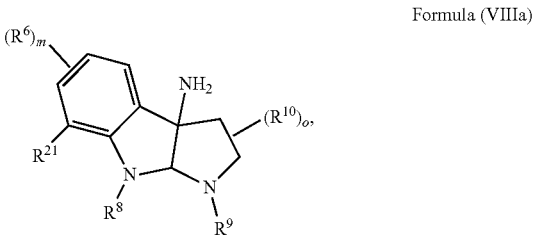

wherein $R^{21}$ is H, halogen, alkyl, alkenyl, alkynyl, aryl, heteroaryl, carbocyclyl, heterocyclyl, —N$_3$,

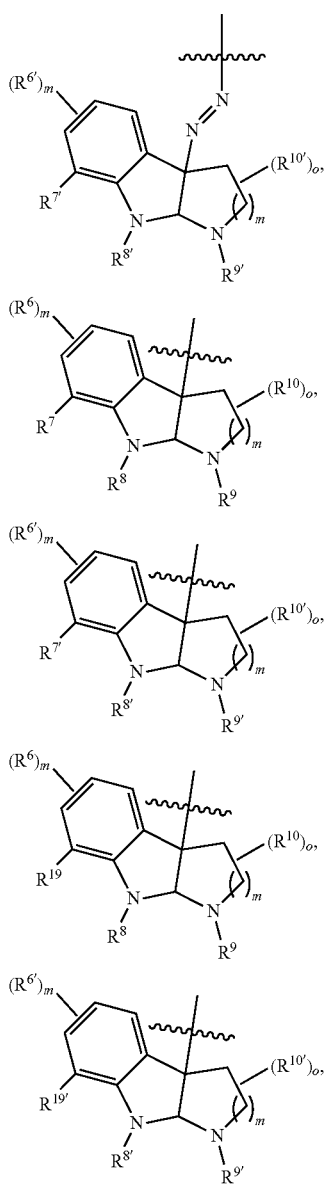

wherein R⁷ and R⁷' are each independently selected from H, —N₃, —N(R¹⁵)NH₂, —NHR¹⁵,

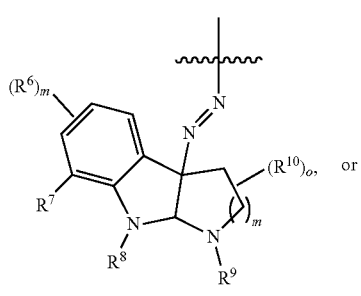

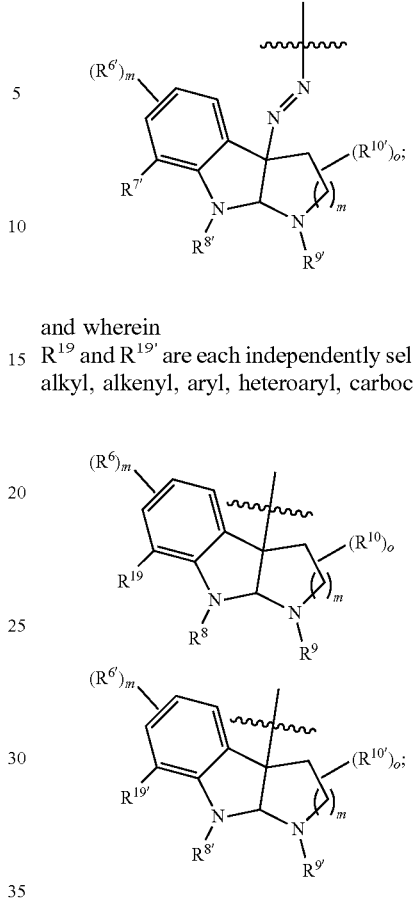

and wherein
R¹⁹ and R¹⁹' are each independently selected from H, tertiary alkyl, alkenyl, aryl, heteroaryl, carbocyclyl, heterocyclyl, R⁶ and R⁶' are each independently selected from halogen, —OH, —OR¹¹, —OC(=O)R¹¹, —NR¹¹R¹², —S(=O)ₚR¹³, —C(=O)R¹¹, —C(=O)OR¹¹, —C(=O)NR¹¹R¹², C₁-C₁₂ alkyl, C₂-C₁₂ alkenyl, C₂-C₁₂ alkynyl, aryl, heteroaryl, carbocyclyl, or heterocyclyl; wherein two R⁶ or two R⁶' groups taken together with the carbon atoms to which they are attached form an aryl, heteroaryl, carbocyclic, or heterocyclic ring;
R⁸, R⁸', R⁹, and, R⁹' are each independently selected from H, C₁-C₁₂ alkyl, C₂-C₁₂ alkenyl, C₂-C₁₂ alkynyl, —C(=O)R¹¹, —C(=O)OR¹¹, —C(=O)NR¹¹R¹², —SR¹¹, —S(=O)ₚR¹³, —S(=O)₂NR¹¹R¹², —C(=O)O(CH₂)ₒR¹¹, aryl, heteroaryl, carbocyclyl, or heterocyclyl;
R¹⁰ and R¹⁰' are each independently selected from H, C₁-C₁₂ alkyl; C₂-C₁₂ alkenyl, C₂-C₁₂ alkynyl, —C(=O)R¹¹, —C(=O)OR¹¹, —C(=O)NR¹¹R¹², —S(=O)ₚR¹³, —OH, —OR¹¹, —OC(=O)R¹¹, —NR¹¹R¹², aryl, heteroaryl, carbocyclyl, or heterocyclyl, wherein two R¹⁰ or two R¹⁰' groups taken together with the carbon atoms to which they are attached form an aryl, heteroaryl, carbocyclic, or heterocyclic ring;
R¹¹ and R¹² are each independently selected from H, C₁-C₁₂ alkyl, C₂-C₁₂ alkenyl, C₂-C₁₂ alkynyl, aryl, heteroaryl, carbocyclyl, or heterocyclyl, wherein R¹¹ and R¹² taken together with the carbon atoms to which they are attached form an aryl, heteroaryl, carbocyclic, or heterocyclic ring;
R¹³ and R¹⁴ are each independently selected from C₁-C₁₂ alkyl, C₂-C₁₂ alkenyl, C₂-C₁₂ alkynyl, aryl, heteroaryl, carbocyclyl, heterocyclyl, —OR¹¹, —(CH₂)ᵣSiMe₃, or —(CH₂)ᵣR¹¹;

$R^{15}$ is $-S(=O)_pR^{13}$, $-S(=O)_2NR^{11}R^{12}$, $-C(=O)R^{13}$, $-C(=O)R^{20}$, $-C(=O)O(CH_2)_rR^{20}$, $-C(=O)CF_3$, $-C(=O)OR^{20}$, $-P(=O)R^{13}R^{14}$, or, $-P(=O)NR^{11}R^{12}$;

$R^{20}$ is $-Si(alkyl)_3$, $-Si(alkyl)_2aryl$, or $Si(aryl)_2alkyl$; and m is an integer from 0 to 3;

n and o are each independently an integer from 0 to 4;

p is 1 or 2; and r is an integer from 1 to 4.

In other various embodiments, the method as disclosed herein is useful for preparing the compound of Formula (V) from the compound of Formula (VIIa), and the compound of Formula (VIIIa), as described above.

In other various embodiments, the method as described herein is useful for the preparation of the following compounds of Formula (I):

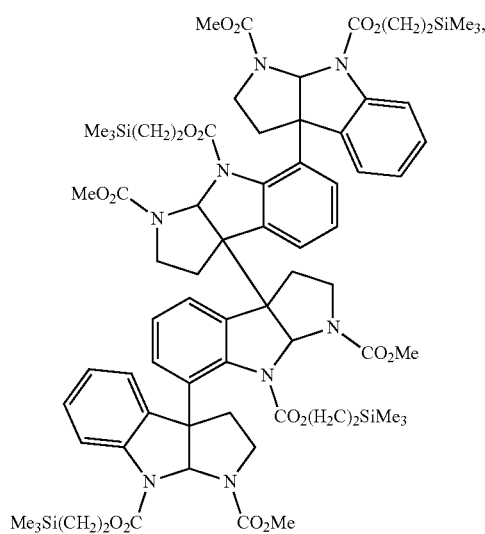

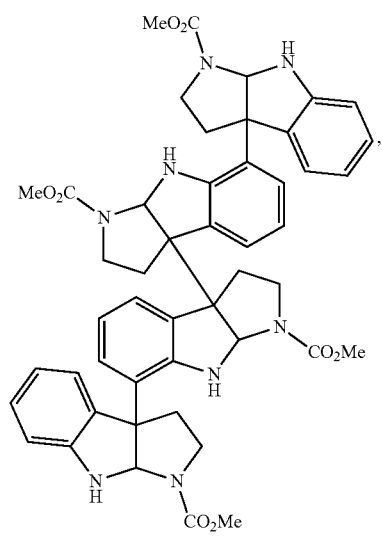

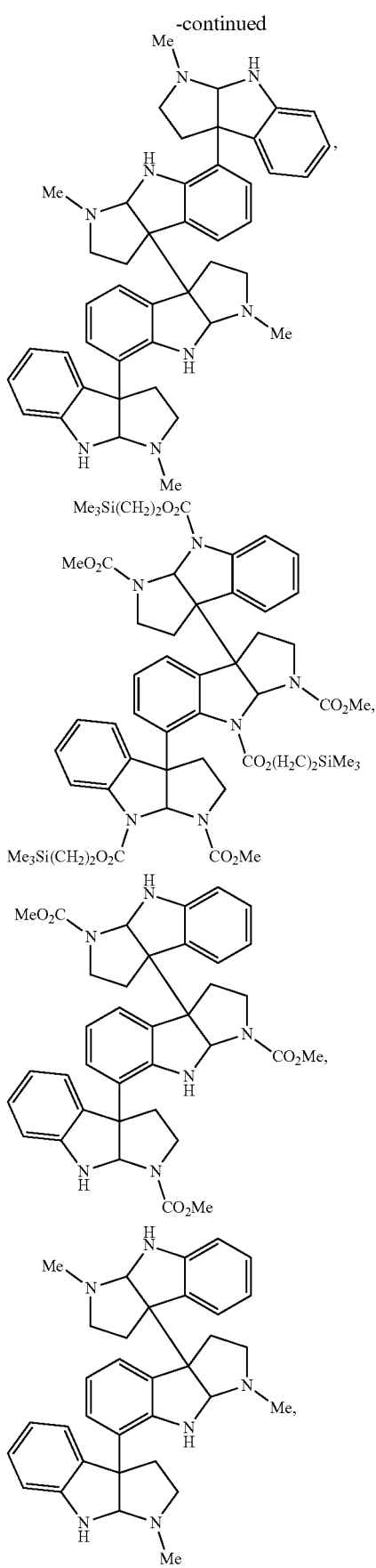

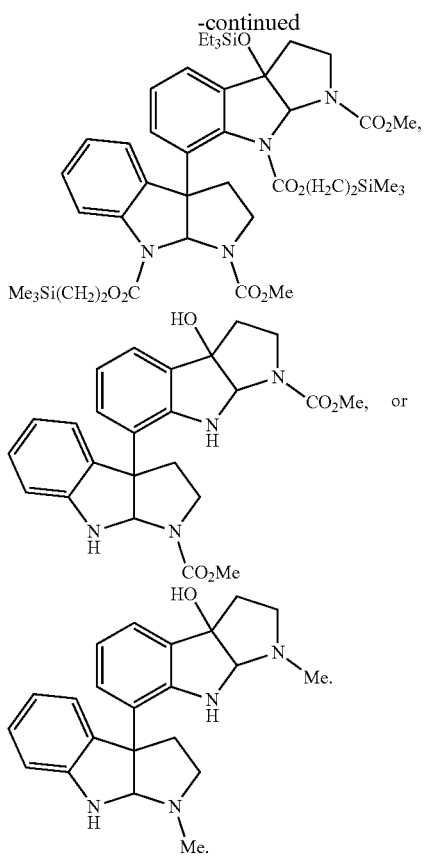

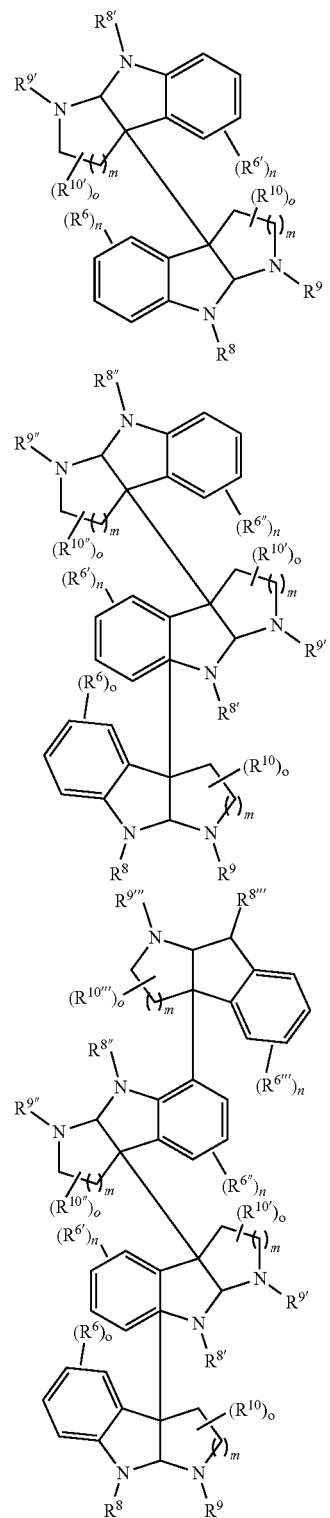

Formula (I)

The union of tertiary electrophiles with N1,N1-disubstituted hydrazines containing electron withdrawing groups (EWG) provides diazene intermediates that are further transformed to afford the quaternary stereocenters disclosed herein. It is to be understood that although reference is made to exemplary EWGs, the disclosure is not limited to the EWGs discussed, and additional EWGs are within the scope of the disclosure. The disclosure provides examples of arenes where it is understood that the disclosed syntheses are general in nature, and thus applicable to additional compounds, including but not limited to a variety of heteroarenes, heterocycles, aryl hydrazine components, diazene derivatives, and ultimately the quaternary carbon-containing products that result.

The disclosure also provides a modular synthesis, with examples of polycyclotryptamines and oligocyclotryptamines provided. Specifically, diazene-directed modular synthesis of (−)-quadrigemine C, (−)-hodgkinsine, and (−)-hodgkinsine B is described, and it is to be understood that the methods and approaches discussed herein can be generalized and applied to the synthesis of a variety of compounds, such as those represented by Formula (I). The disclosed methods and processes of diazene-directed modular synthesis provide for preparing a variety of compounds where the stereochemistry of each tricycle is secured before fragment coupling. It is to be understood that variations in the benzene substructure, amine alkyl groups, relative stereochemistry of subunits, the number of subunits, and the number of subunits on each tail (moving away from the Csp3-Csp3 center), are within the scope of the disclosure.

A summary of the advancements facilitating the implementation of new and inventive syntheses, including syntheses of oligocyclotryptamines and related compounds, is provided below. The methods disclosed describe the sole strategy available to access these compounds using a modular and iterative approach that secures the absolute and relative stereochemistry of each cyclotryptamine component. The advancements include:

(1) Development of a new class of hydrazide nucleophiles capable of generating diazenes intermediates directly. This new class avoids complications with oxidation conditions normally needed for diazene synthesis that are incompatible with structures of oligocyclotryptamines. This approach to diazene synthesis has revolutionized synthesis of diazenes intermediates, complex diazenes, and strategies for fragment assembly, and has numerous additional applications.

(2) Demonstration of the first example of C3-C7' coupled dimeric cyclotryptamines through expulsion of dinitrogen and "fusion of two cyclotryptamine fragments". This required the synthesis of diazene intermediate that were previously inaccessible and demonstrated their ability to lose dinitrogen and afford the desired C—C bond of interest.

(3) Development of strategies to carry out coupling of complex fragments and functionalization of sterically crowded substrates. This required development of strategies that rely on "spatial separation of functionalization chemistry from the sterically crowded positions in the substructures".

(4) Illustration of the synthesis of dimeric, trimeric, and tetrameric oligocyclotryptamines with applications in many other members of the family that have otherwise been inaccessible through chemical synthesis.

(5) Demonstration that this new technology allows controlled modular synthesis of oligocyclotryptamines and derivatives of these and related alkaloids. The chemistry provides the only sterochemically unambiguous solution to a unique class of alkaloids with known biological activity (with application in neurochemistry, neurodegenerative diseases, use as anticancer agents, use as analgesics, etc.) with impact in areas such as Alzheimer's disease, cancer, addiction, and pain treatment. It has been established that the bioactivity of these compounds is directly proportional to the length of the oligomeric chain. Thus, the controlled and modular synthesis of oligomers is a significant advancement with a wide range of applications.

(6) Clarification of the complex stereochemistry possessed by oligotryptamines and derivatives. Compounds such as these are typically very rare in nature and the small samples obtained from nature are plagued by stereochemical ambiguity and uncertainty due to the overlapping signals of the repeating units, hindered bond rotation leading to line broadening due to severe steric congestion, and instability of the compounds to heat and oxidation. Samples prepared by the disclosed methods are formed with predetermined and established stereochemistry in an iterative fashion, thus allowing ease of assignment of the final oligomeric product.

The methods described herein are exemplified with representative synthesis as follows. The demonstration begins with the establishment of an efficient and adaptable synthesis of key building blocks. For example, the following synthesis of versatile monomers is useful for application in the diazene directed modular synthesis of oligocyclotryptamines, as well as other differentially substituted derivatives. In certain embodiments, a method described herein is illustrated by a scheme described herein. In certain embodiments, a method described herein is a method illustrated by a scheme described herein without some or all the reaction conditions (e.g., reagents, solvents, concentration, temperature, atmosphere, pressure, time, irradiation, purification, isolation, yield, and enantiomeric excess, etc.) provided in the scheme described herein.

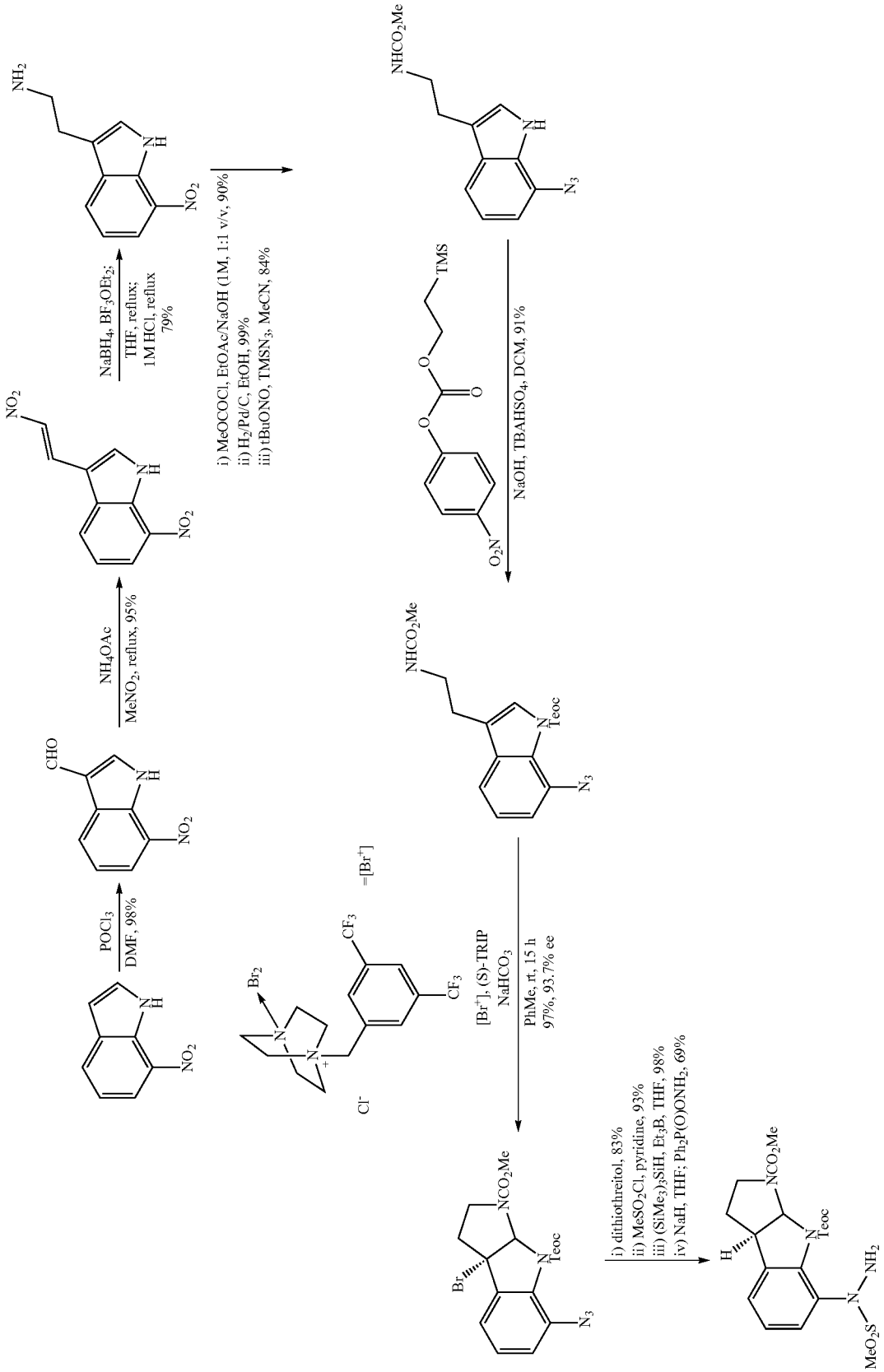

The cyclotryptamine building block provides the repeating tricyclic portion of oligocyclotryptamines, and is properly functionalized for further chemistry. Notably, it contains:

(i) a designed (1) N1-aryl N1-sulfonyl hydrazide portion developed for direct access to diazene upon trapping of carbocations;

(ii) a specific indoline nitrogen protecting group (Teoc, trimethylsilylethoxycarbonyl) capable of "remote" deprotection at the final stage of synthesis in a crowded environment of oligocyclotryptamines;

(iii) azide as the precursor for the key sulfonyl hydrazide to allow introduction of the requisite nucleophilic functional group useful in the enantioselective synthesis.

The above timing and order of events can be critical to the success of the synthesis of this building block, according to some embodiments. Although the building block has been experimentally demonstrated to have utility in the synthesis of dimeric, trimeric, and tetrameric cyclotryptamines herein, it can be applied in numerous other applications and to numerous other syntheses.

In addition, the necessary C7-sulfonyl hydrazine can be established by an alternative synthesis starting from readily available materials. The C3a-bromocyclotryptamine derivative can be reduced in high yield to the corresponding C3a-H cyclotryptamine using $(Me_3Si)_3SiH/Et_3B$. Subsequent treatment with methanesulfonyl azide in the presence of an Ir-catalyst and silver salt promoters leads to a carbamate directed C7-sulfonamidation of the cyclotryptamine structure. The sulfonamide is then converted to the desired sulfonylhydrazine via direct amination of the sulfonamide. One of the benefits of this method is the opportunity to utilize starting materials unsubstituted at the C7 position.

Electrophilic activation of the same C3a-bromocyclotryptamine used in the synthesis of the sulfonylhydrazine above was suitable for preparing (+)-28. Using silver trifluoromethanesulfonate in the presence of 2,6-difluorophenylsulfamate led to the desired sulfamate ester (+)-27 in 83% yield (a. 2,6-difluorophenyl sulfamate, AgOTf, DTBMP, $CH_2Cl_2$, 22° C., 1 h; alternatively, sulfamate ester (+)-27 could be obtained starting from the reduced C3a-H intermediate via Rh-catalyzed amination). Exposure of sulfamate ester (+)-27 to pyridine in an acetonitrile-water mixture at 70° C. afforded the amine (+)-28 in 81% yield (b. pyridine, $MeCN-H_2O$, 70° C., 23 h).

The building blocks described, as well as a range of other electron withdrawing group-substituted hydrazines, have demonstrated utility in the synthesis of diazene intermediates that serve as precursors to C—C bond formation. The following representative series show aspects of the development of the novel technology to access oligocyclotryptamines using a modular diazene-directed synthesis. In these cases, a Csp2-Csp3 bond is formed.

The Use of N1-Aryl N1-Boc Aryl Hydrazine:

A notable advance is the discovery of a hydrazine derivative that is compatible with conditions needed for electrophilic activation of the readily available cyclotryptamine-bromide starting material. The introduction of the electron-withdrawing group on the nitrogen of the hydrazine allows its exposure to silver (I) without undergoing undesired decompositions via redox chemistry. Another advance is that the necessary N—N bond of the projected diazene is already present when using a hydrazine precursor. This aspect of the disclosure has implications and applications for all other diazene related chemistry.

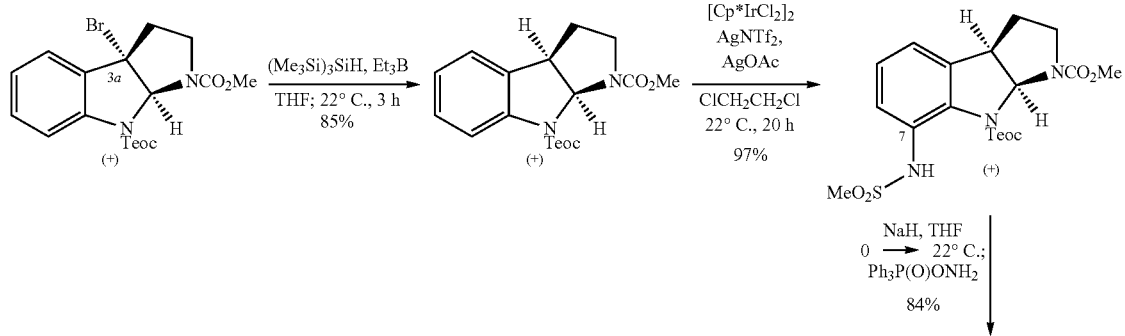

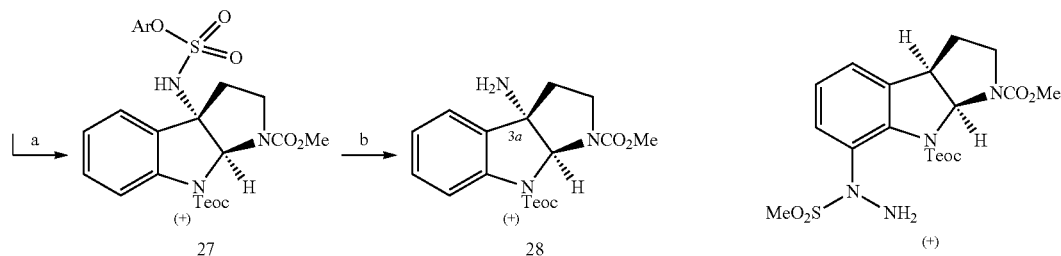

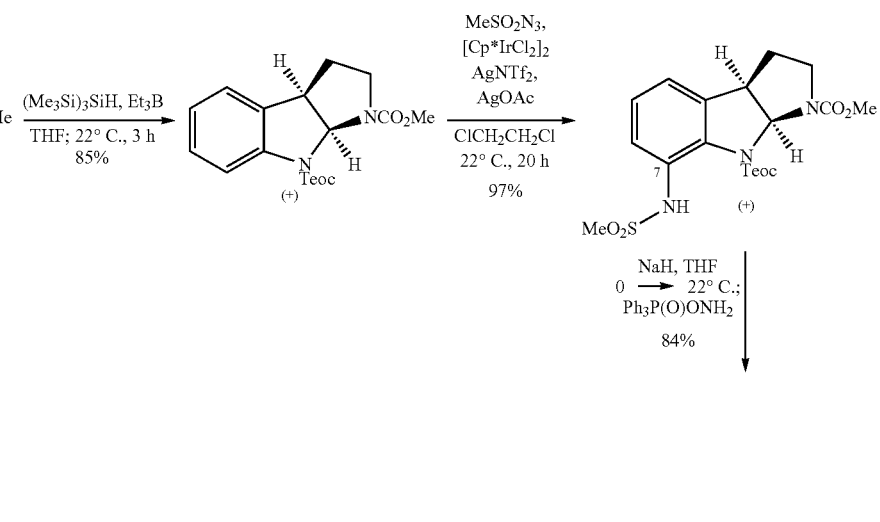

Successful Addition of Hydrazine Nucleophile:

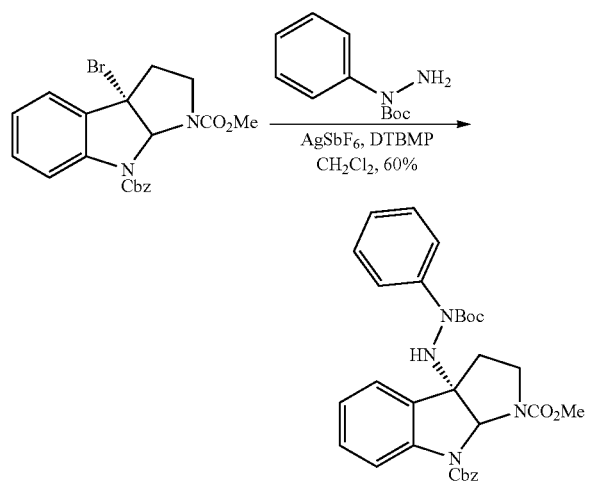

Use of Trifluoroacetylated Hydrazines as Nucleophiles:

The trifluoroacetyl is compatible with mild removal of the acetyl group and oxidation to the desired N-aryl N-cyclotryptaminyl diazene. This strategy allows the first synthesis of cyclotryptamine C3-aryldizene using nucleophilic hydrazine derivatives, retaining the preexisting C3-stereochemistry in the product.

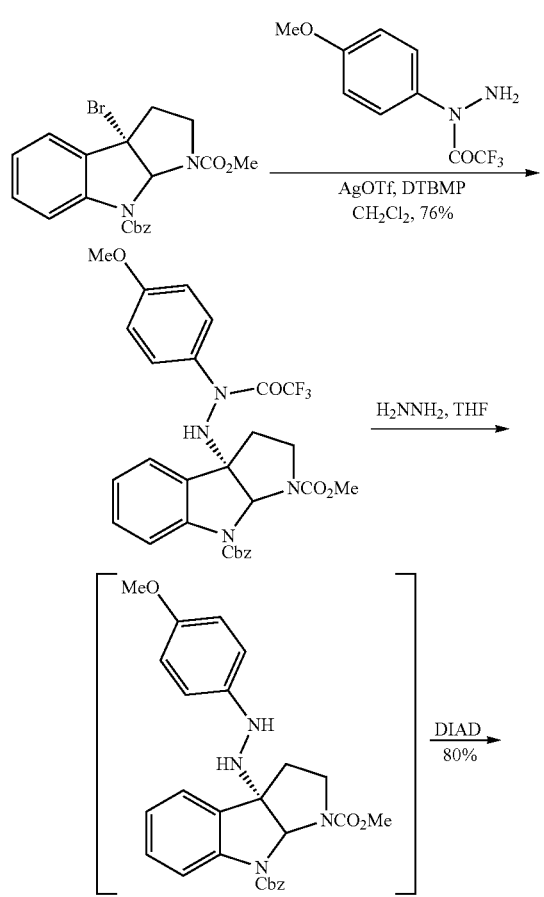

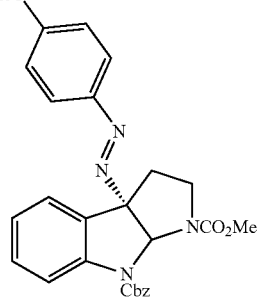

Use of Methanesulfonylated Hydrazines as Nucleophiles:

In addition to the efficient preparation of the C7-sulfonylhydrazine compounds disclosed above, the use of a methanesulfonyl electron-withdrawing on the hydrazine nucleophile has the additional benefit of reducing the overall three step sequence in the previous example to a single step, according to some embodiments. This has revolutionized synthesis of these and other alkyl diazenes. This approach has applications in many other areas, including but not limited to synthesis of heteroaryl derivatives, which are currently being pursued using an alternative, less efficient strategies.

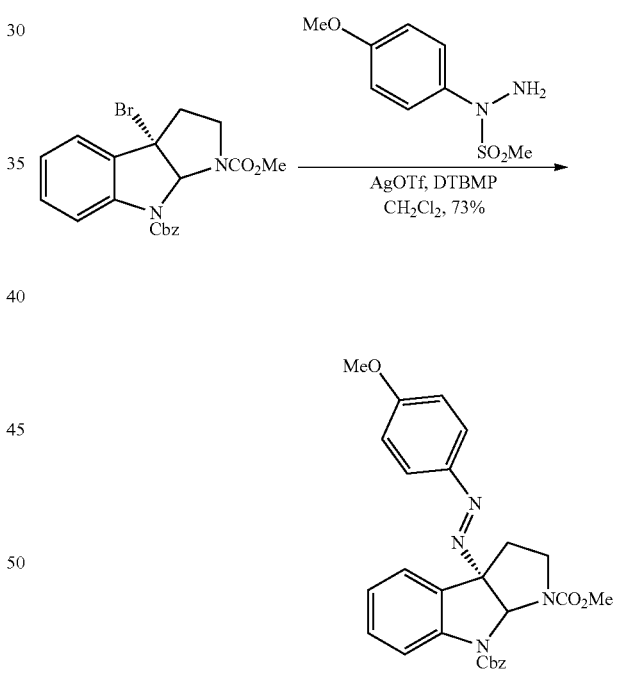

Successful Cyclotryptamine Diazene Synthesis:

The synthesis and use of such N-sulfonyl aryl hydrazine nucleophiles is applicable to challenging substrates and coupling, as shown below. The necessary cyclotryptamines hydrazines needed as repeating substructure of oligocyclotryptamines can be prepared. The example shown represents a successful synthesis of a dimeric cyclotryptamine diazene product.

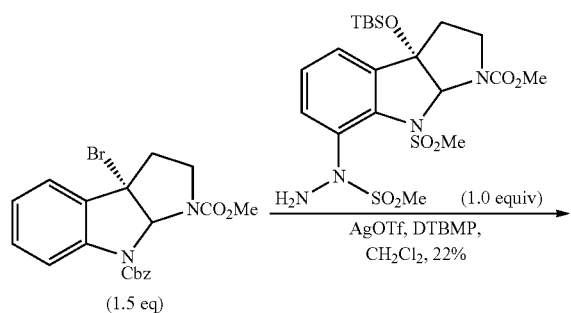
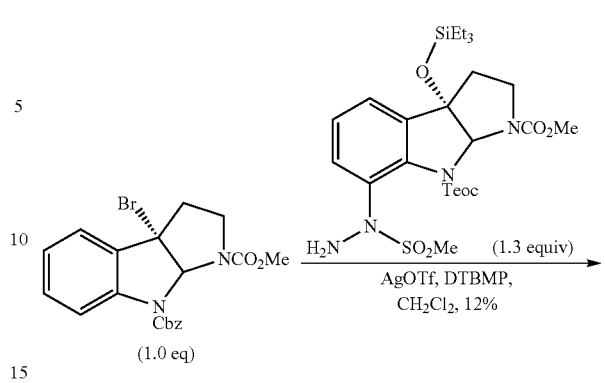

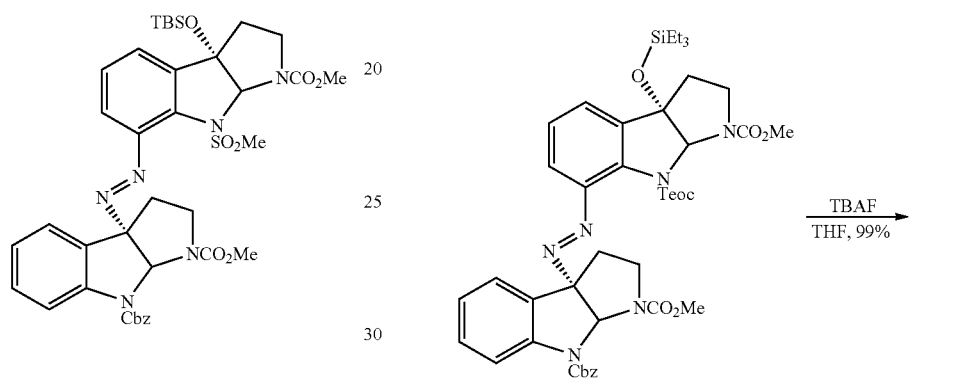

Use of Indoline Nitrogen Protecting Group Allowing Final Stage Removal:

Access to dimeric diazenes revealed the significant challenges in both introduction and removal of the internal indoline protective group once attachments are introduced at the C7-position. While it was discovered that the use of Teoc (trimethylsilylethoxycarbonyl) is useful since the deprotection is initiated "remote" (nucleophilic addition at the silicon of trimethylsilyl group) from the congested linkage area, the tight steric pressure at the juncture greatly complicates carrying out chemistry close to the linkage. Even a labile o-nitrobenzenesulfonyl group, typically an easily removable group, once introduced at the internal indoline nitrogen is not subject to deprotection under a variety of conditions due to severe steric pressures. In cases where a free internal nitrogen is deemed desirable, Teoc has proven to be a useful protecting group. However, it is the function, and not the particular group that is the relevant element. Other groups possessing the similar feature of carrying out the chemistry away from the steric congestion can alternatively be used. Furthermore, silyl group variants are also possible. In one embodiment, use of a triisopropylsilyl version instead of trimethylsilyl can provide a similar result, although Teoc is typically preferred.

The efficiency of Teoc deprotection in the case above can be compared with the challenges shown in the case where nosylate is used to protect the internal indoline nitrogen.

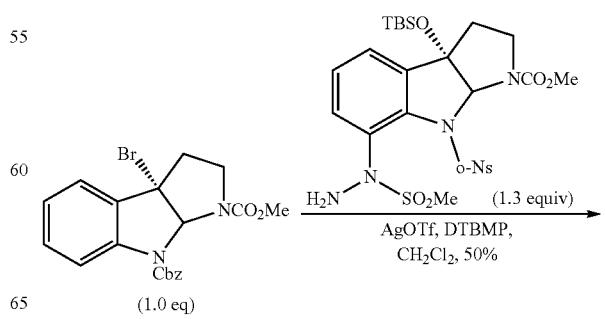

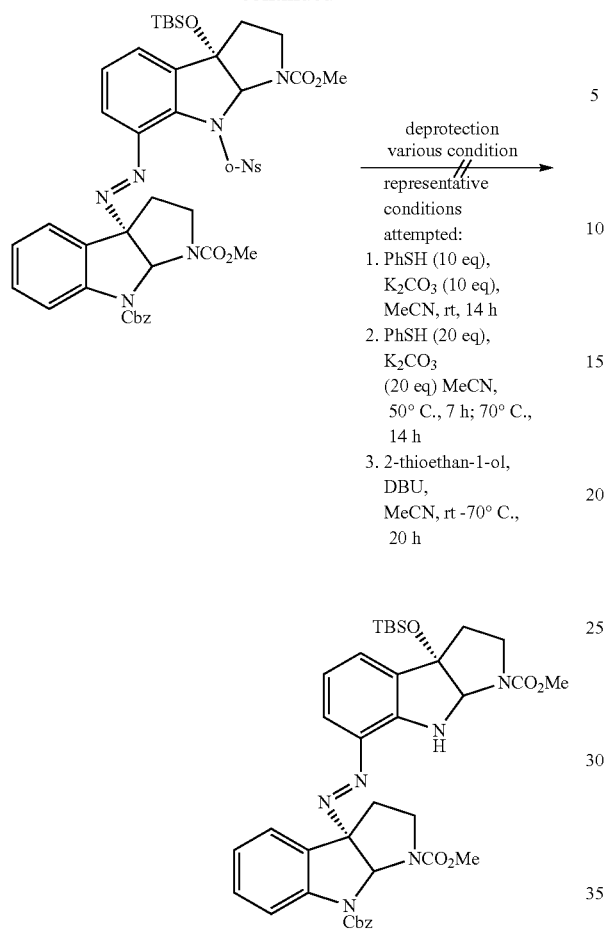

Successful Modular Synthesis of C3-C7 Dimeric Cyclotryptamine Synthesis:

The synthesis of the diazene linked dimer and its conversion to the C—C linked dimer is applicable on a range of substrates. Shown above is the repeating unit to highlight the prospects of a controlled chain growth in accessing oligo-cyclotryptamines. With synthesis of the first diazene linked dimeric cyclotryptamine the next step was to accomplish the first fusion of the two fragments as shown above constituting the first synthesis of a C3-C7 dimeric cyclotryptamine via this novel strategy.

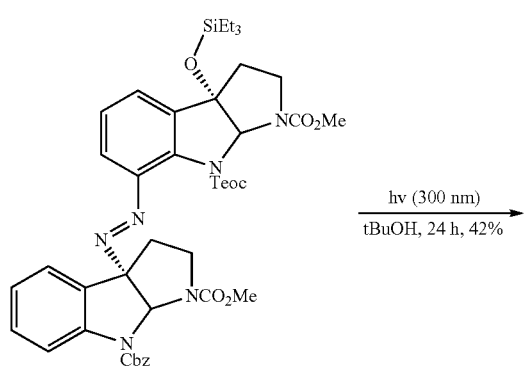

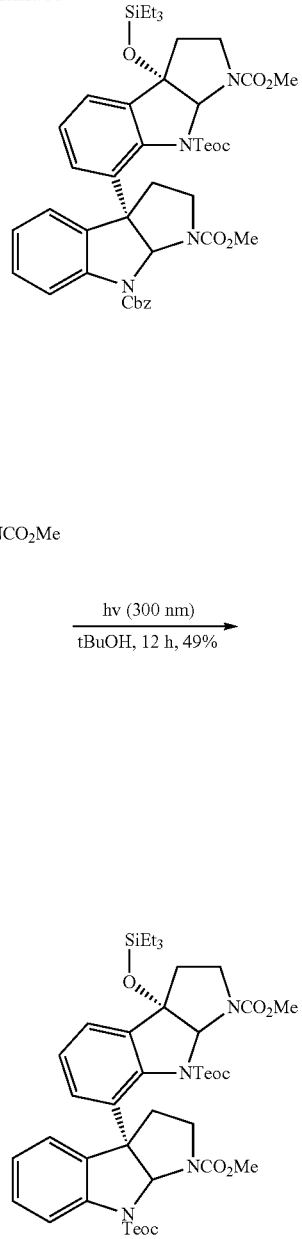

Strategy for "Chain Extension" Via CH-Amination of Dimeric Substrates:

The approach began with preparation of the aryl-alkyl dimeric diazene. Electrophilic activation of bromocyclotryptamine (+)-26 using silver trifluoromethanesulfonate in the presence of hydrazide (−)-31 directly afforded the aryl-alkyl dimeric diazene (+)-32 in 60% yield. Similarly, the use of enantiomeric hydrazide (+)-31 as nucleophile under identical conditions led to the formation of diastereomeric diazene dimer (−)-33 in 59% yield. Importantly, the formation of either dimeric diazene diastereomer proceeds with equal efficiency. Indeed, this approach allows for the synthesis of any desired diastereomer with complete control of relative and absolute stereochemistry independent of potential substrate bias.

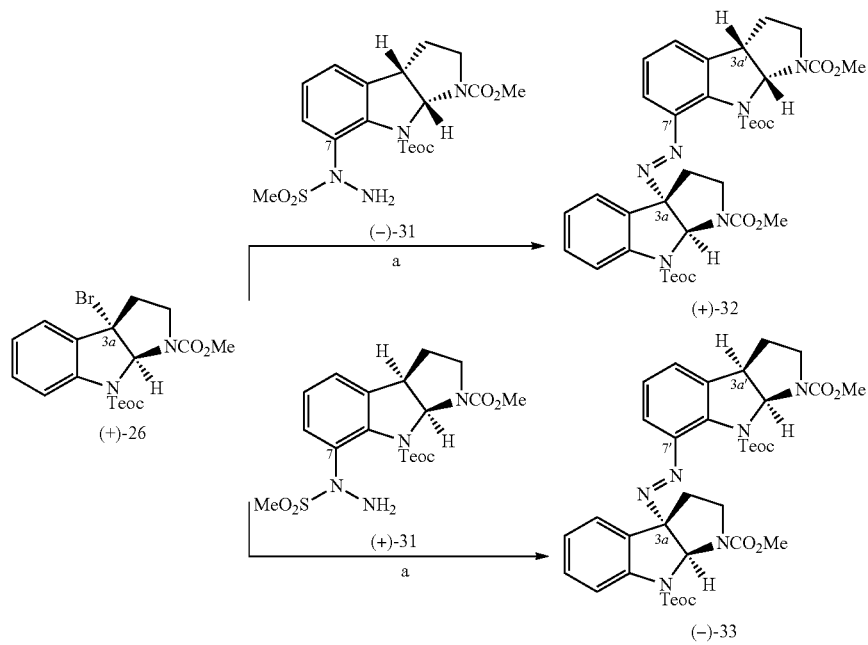

As an alternative to electrophilic activation at C3 to give coupling products, a strategy of this disclosure is based on CH-amination chemistry that alternatively affords the formation of a Csp3-Csp3 bond. This approach is applicable starting from either stereochemical combination (R or S) as shown in the following two examples. Furthermore, the CH-amination approach is also applicable to substrates possessing a pre-existing diazene moiety, or one where the C—C linkage is already established.

-continued

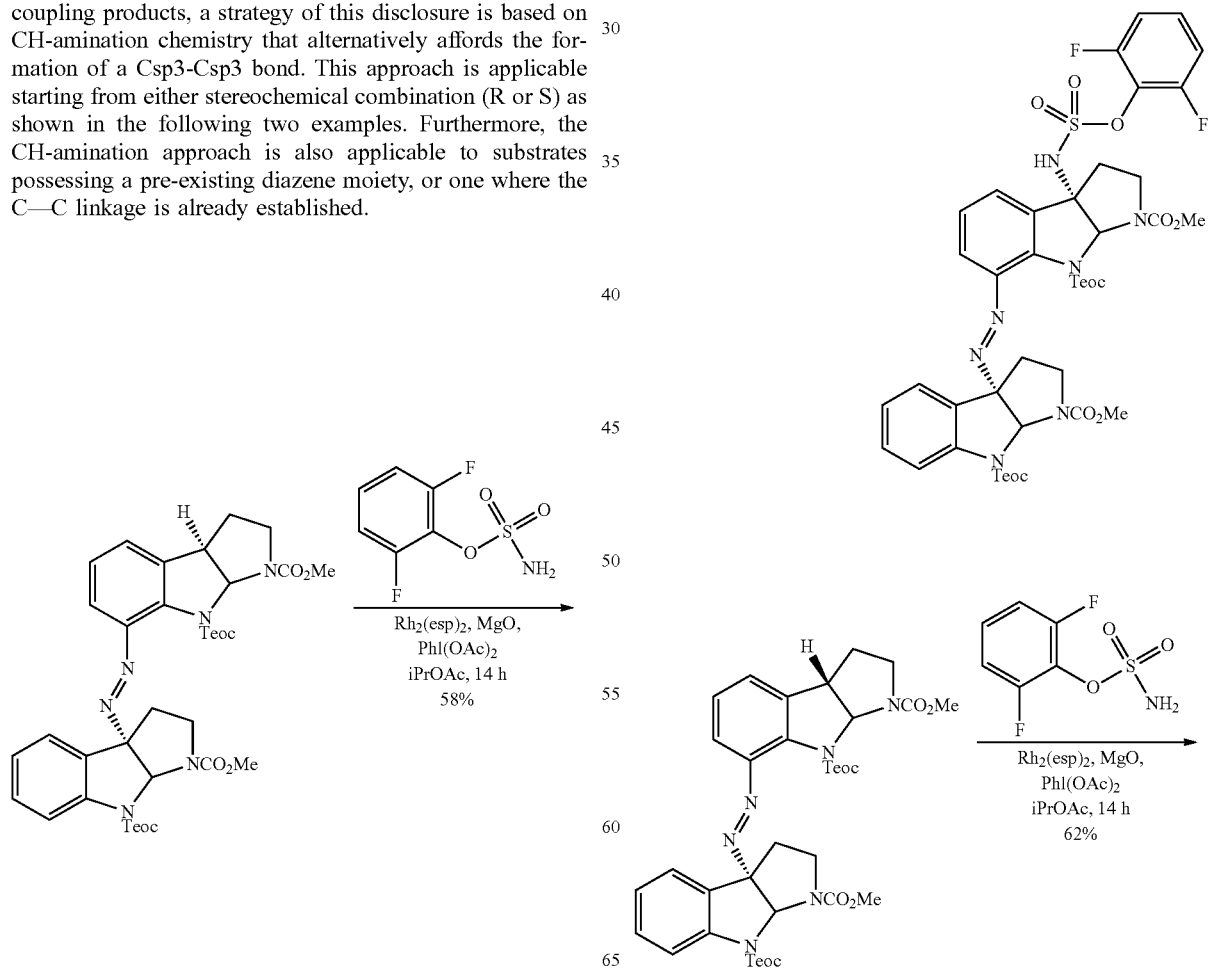

-continued

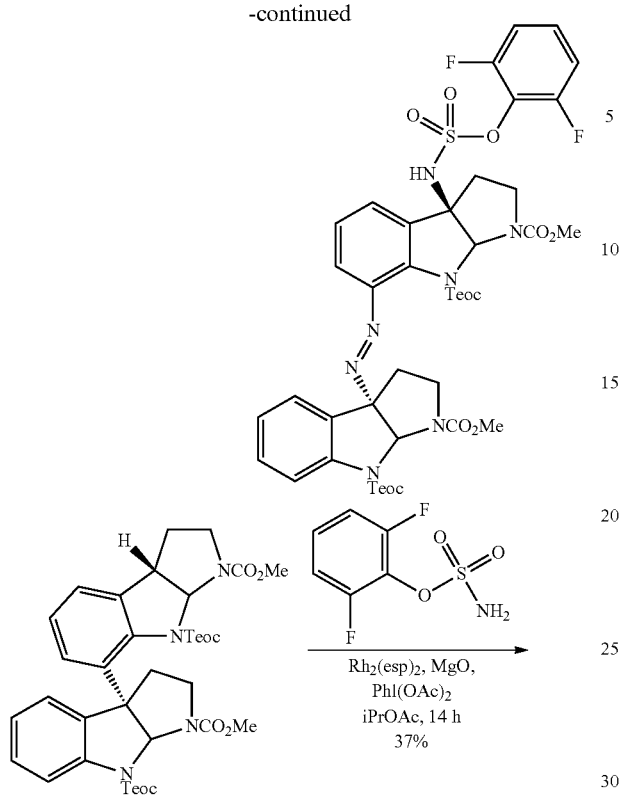

The added versatility of the CH-amination method increases the range of possible target molecules, as it too is demonstrated to be operable in complex molecular environments, as exemplified in the successful synthesis of (−)-quadrigemine C. Application of both the Csp2-Csp3 and Csp3-Csp3 bond forming reactions to the synthesis of trimeric and tetrameric cyclotryptamines serves to illustrate the robust nature of the chemistry developed.

The Retrosynthetic Analysis of (−)-Quadrigemine C, a Tetrameric Cyclotryptamine:

A modular synthesis employing simple cyclotryptamines as starting material that are fused together via diazene chemistry is provided. This requires unprecedented multiple diazene fragmentations between from Csp2-Csp3 centers and Csp3-Csp3 centers to assemble the structure. No prior example in complex synthesis exists using such complex diazenes or the iterative use of mono- or poly-diazene intermediates in assembly of multiple fragments. Here four pieces are coupled by loss of three dinitrogen molecules as highlighted by the retrosynthesis below.

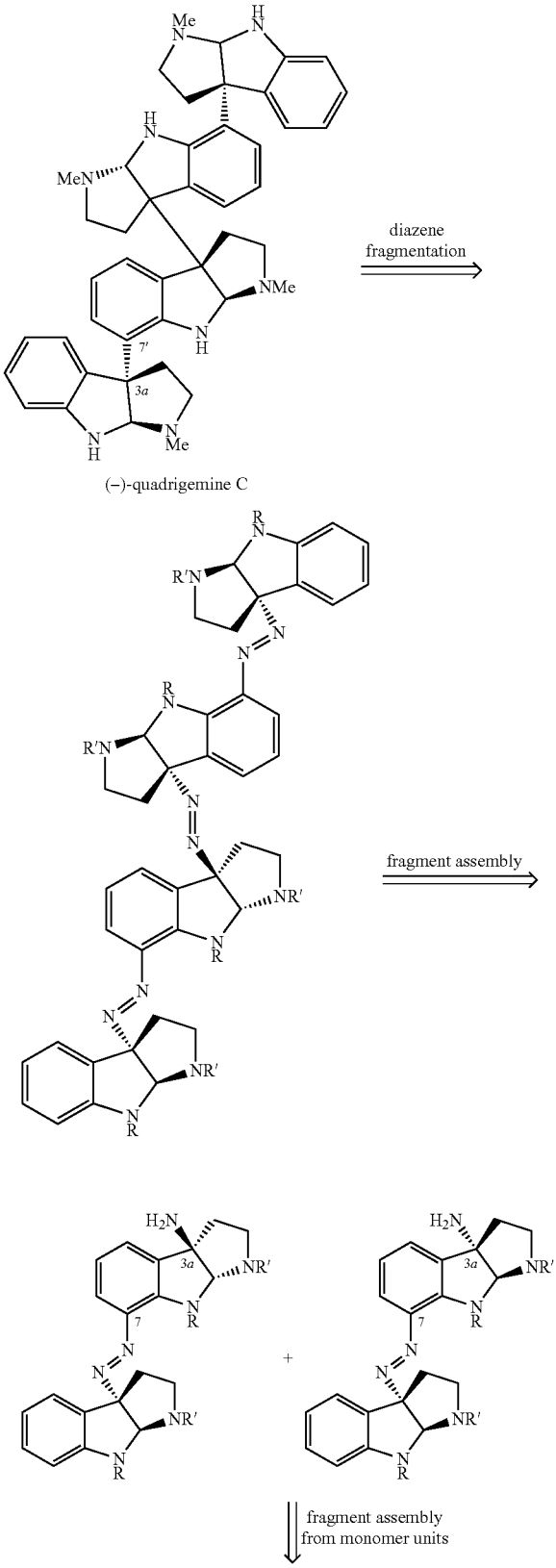

-continued

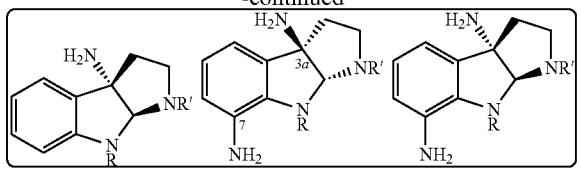

An objective of the synthetic approach to alkaloid (−)-7 was to establish a general strategy for the union of stereochemically defined cyclotryptamine units via diazene-directed fragment assembly, thus controlling the absolute stereochemistry of all eight stereogenic centers. Envisioned was securing all four quaternary stereocenters via completely stereoselective C—C bond formations following nitrogen extrusion from the tris-diazene tetramer 10. While the vicinal $C_{sp3}$-$C_{sp3}$ quaternary stereocenters could be secured via implementation of mixed sulfamide chemistry, the introduction of the remaining $C_{sp2}$-$C_{sp3}$ linked stereocenters using an analogous C7-C3a diazene via oxidation of the corresponding mixed sulfamide was expected to prove less efficient in these complex settings due to competitive arene-halogenation of electron-rich cyclotryptamine. The requirement for obviating multiple oxidative N—N bond formation steps in such complex settings as well as the desire to develop a more direct synthesis of diazenes prompted the investigation of a new aryl-alkyl diazene synthetic strategy using hydrazines. The development and implementation of a new aryl-alkyl diazene synthetic strategy in the total synthesis of tetramer (−)-7 as well as trimers (−)-3 and (−)-4 can serve as a foundation for further application to related complex natural products.

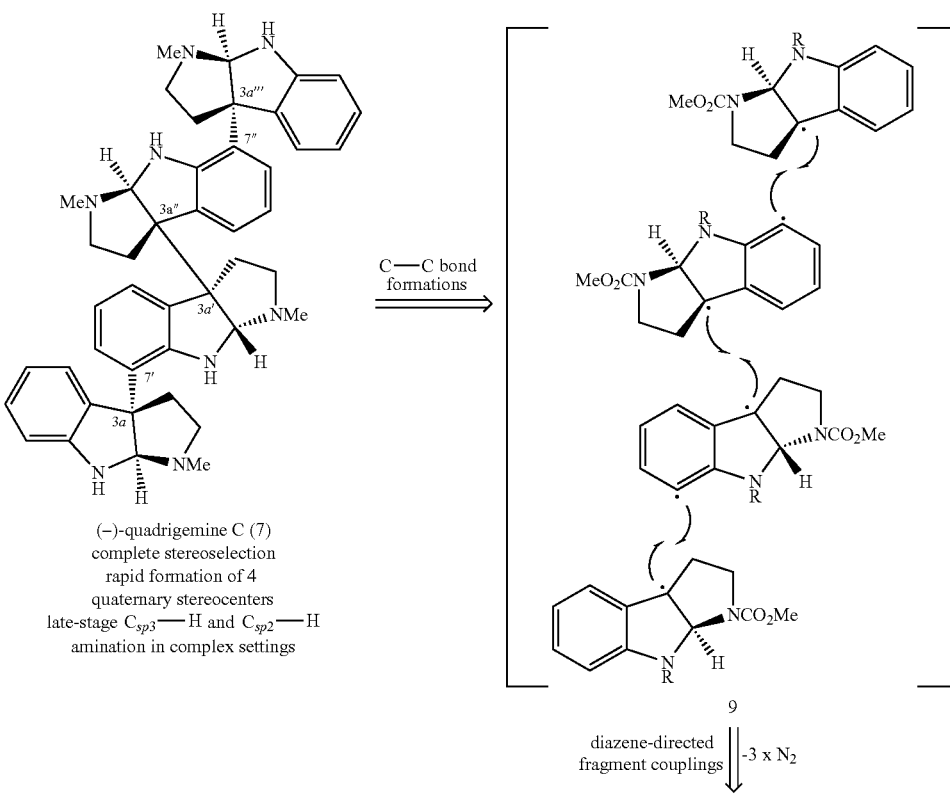

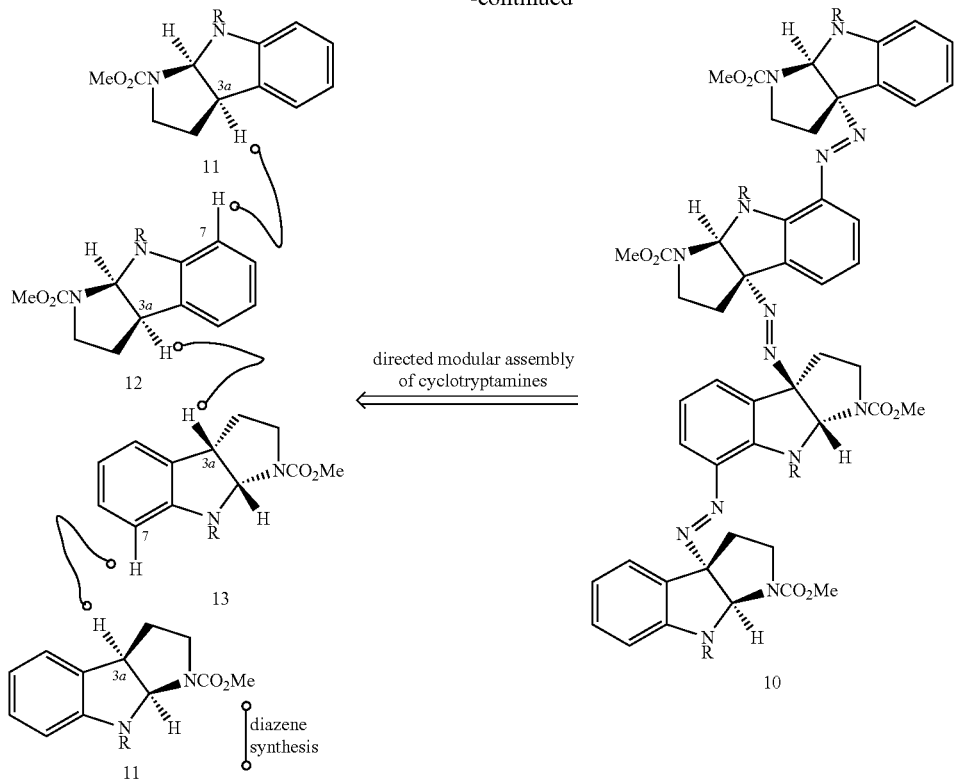

Iterative and Modular Cyclotryptamine-Chain Extension: The illustrative example below shows how the disclosed modular strategy for the synthesis of (−)-quadrigemine C is begun. Highly efficient sulfonyl hydrazine coupling with a bromocyclotryptamine promoted by AgOTf and base gives rise to the diazene linked dimer in 56%. The building blocks are constructed from either C3-H halogenation, from C3-OH derivatives, or from C3-H amination of the functionalized cyclotryptamines as disclosed above, and form the foundation for some embodiments of this modular and iterative synthesis of oligocyclotryptamines.

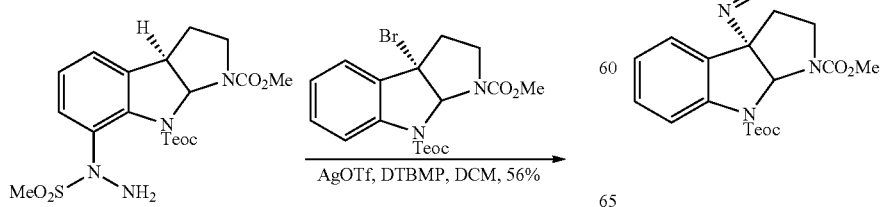

-continued

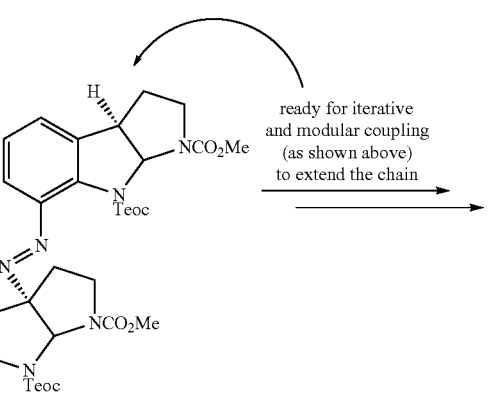

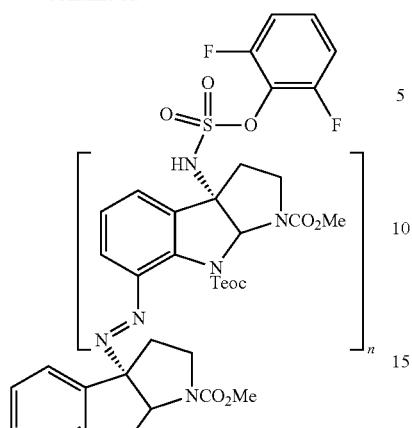

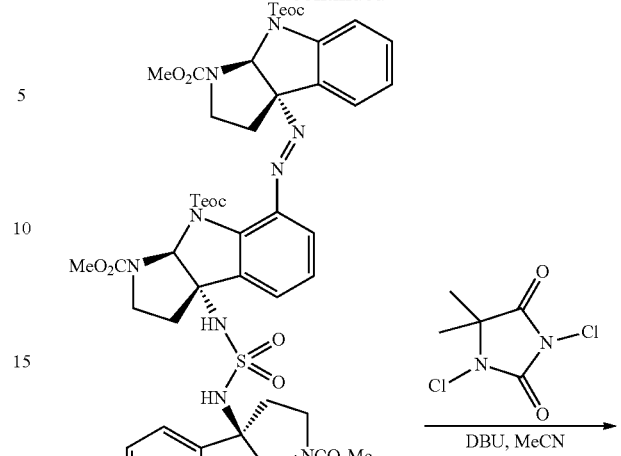

Successful Synthesis of the Proposed Precursor to (−)-Quadrigemine C:

Once the first diazene moiety is installed from Csp2-Csp3 coupling, the CH-amination method is initiated. Installation of the 2-6-difluorosulfamate occurs via CH-activation of the precursor to produce the electrophile ready for addition of a —NH$_2$-containing dimeric cyclotryptamine. DMAP promotes nucleophilic addition to obtain the tetrameric sulfamide product possessing Teoc groups at the internal indoline nitrogen positions, which undergoes extrusion of sulfur dioxide upon treatment with 1,3-dichloro-5,5-dimethylhydantoin (or other electrophilic chlorinating reagent) to provide the key diazene-containing tetrameric intermediate. Up to this point, the coupling of highly complex fragments where four cyclotryptamines are united via three diazene linkers has been surprisingly demonstrated. All components have predetermined absolute and relative stereochemistry, setting the stage from C—C bond formation to complete the framework of the natural product scaffold.

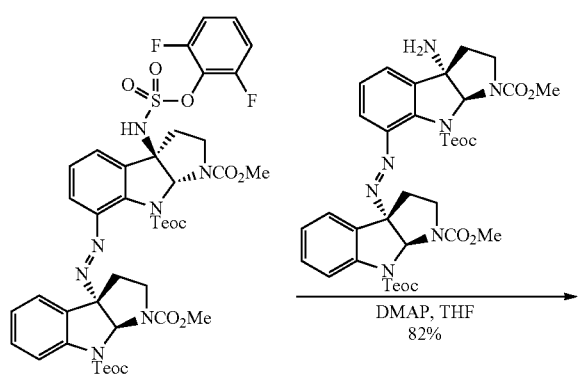

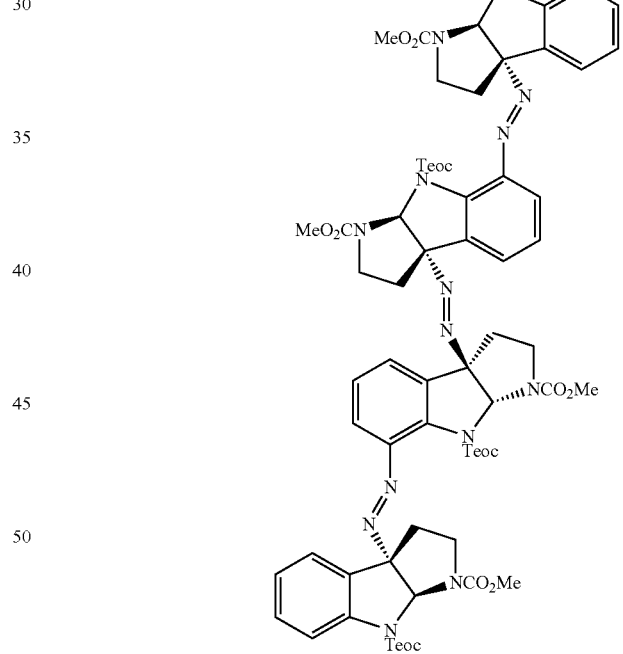

Successful Completion of the (−)-Quadrigemine C Synthesis Using the Modular Assembly Approach:

Photoexpulsion of the diazene linkers occurs in the next stage in stepwise fashion. As shown, the first irradiation at a higher wavelength (i.e., 380 nm) leads to expulsion of dinitrogen and formation of the Csp3-Csp3 bond uniting the C3 positions of the two internal cyclotryptamines. The second irradiation at a lower wavelength (i.e., 300 nm) results in formation of the two Csp2-Csp3 bonds between the external and internal cyclotryptamines to establish the requisite connectivity. Deprotection of TeOC and reduction then provides (−)-quadrigemine C.

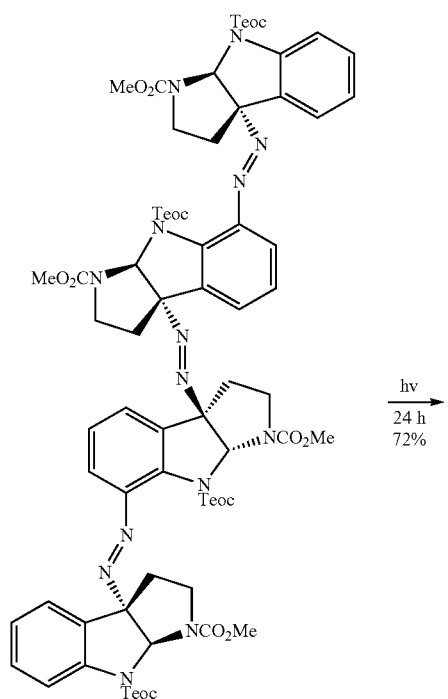

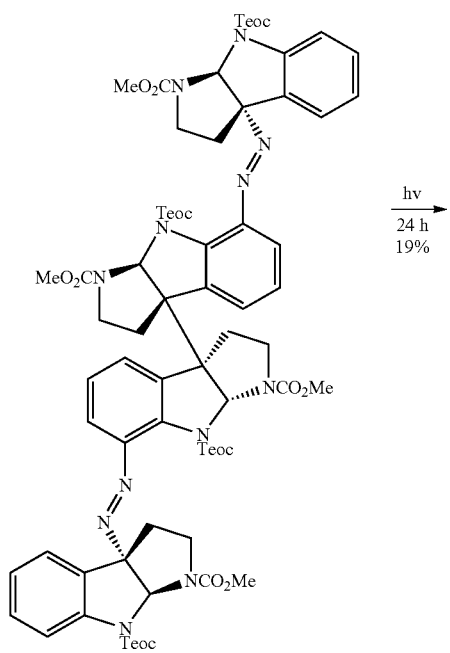

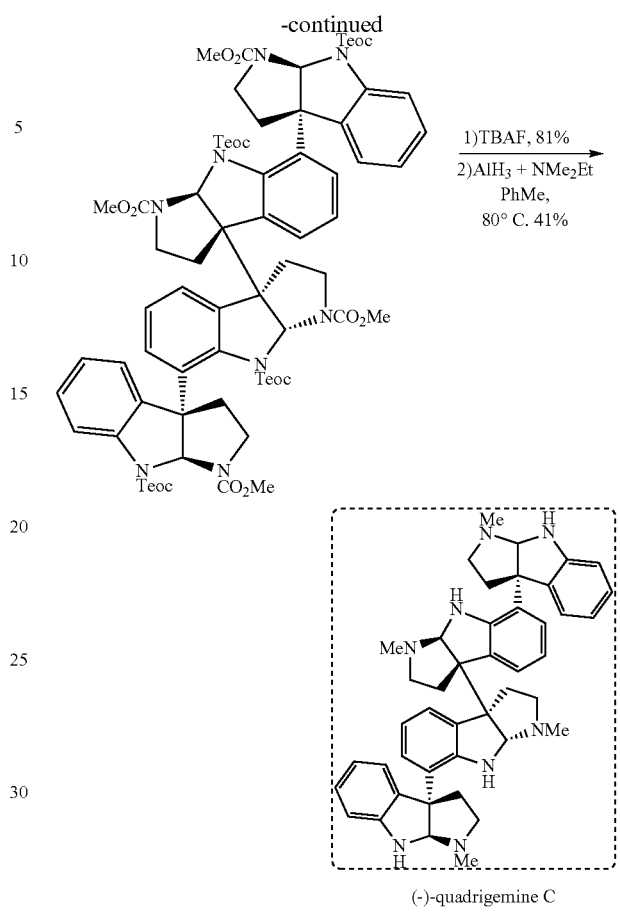

(−)-quadrigemine C

Of note in the above synthesis is that a complete control of stereochemistry and regioselectivity in fragment unions has been established in the total synthesis of (−)-quadrigemine C. Generation of four quaternary centers—very challenging structural features—is notable. The ability to distinguish between Csp3-Csp3 vs. Csp3-Csp2 linked diazenes in the fragmentation is also is a substantial achievement. In some embodiments, conditions can be specified to reduce the photoexpulsion of three molecules of dinitrogen from the starting material to a single step.

Successful Application to Synthesis (−)-Hodgkinsine and (−)-Hodgkinsine B Using the Modular Assembly Approach:

Similar to the tetrameric case above, complete control of stereochemistry and regioselectivity in fragment unions is achieved in the synthesis (−)-hodgkinsine and (−)-hodgkinsine B. For both natural products, an azide compound serves as a precursor to the electron withdrawing group-containing hydrazine, although methods are disclosed for alternative preparations of this key building block. Formation of the Csp2-Csp3 diazene occurs via silver (I) promoted electrophilic activation of a C3-bromide, followed by hydrazine addition. Next, the CH-amination reaction is carried out to install the sulfamate moiety. Nucleophilic addition of a C3-aminocyclotryptamine derived from the requisite C3-bromide intermediate, followed by subsequent $SO_2$ extrusion after treatment with an electrophilic chlorinating reagent affords the bis-diazene compound. Under irradiation conditions, dinitrogen is expelled and (−)-hodgkinsine and (−)-hodgkinsine B are each obtained after Teoc-deprotection and reduction of the methyl carbamate.

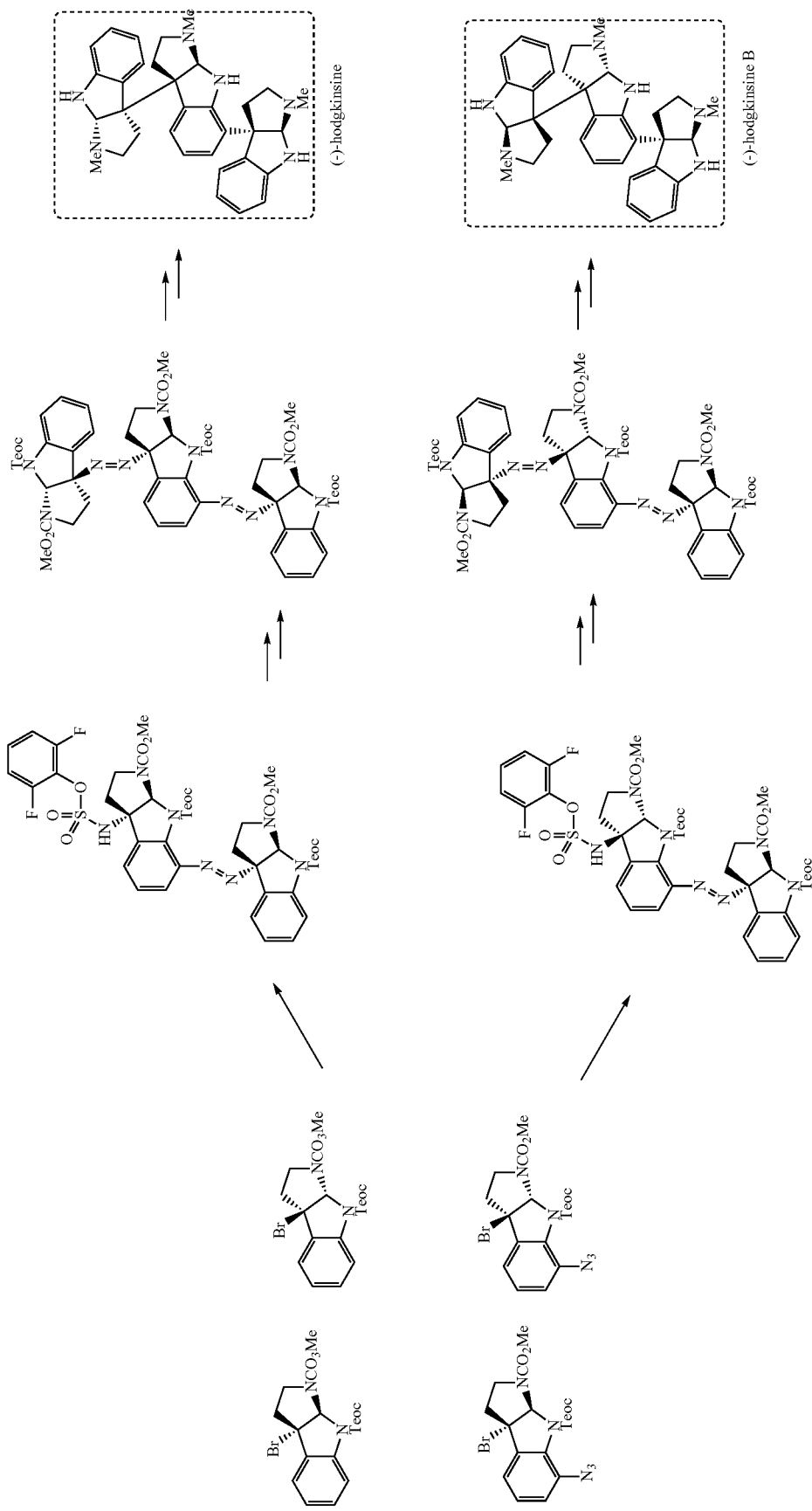

In summary, this technology and chemistry has application to many other areas beyond the examples provided, including but not limited to other arene hydrazines beyond those discussed herein. For ease of understanding, simple arenes and very complex arenes such as indolines are provided herein. However, many additional other compounds including many other heteroarenes (pyridines, pyrimidines, pyrroles, oxazoles, thiazoles, diazoles, etc.) can use a similar strategy for synthesis of the diazene intermediate and the desired product, and are within the scope of this disclosure.

The disclosed methods have application in a variety of fields, including pharmaceutical sciences, medicinal chemistry, and process chemistry, among others, as there are presently no other options for such regiospecific coupling. Transition metal chemistry does not work with such sterically crowded carbon centers for coupling, and other methods of coupling heteroarenes are plagued by competing regioisomer formation.

Although discussed with particular examples and compounds herein, the disclosure applies to many other electrophile classes. Herein is focused on tertiary electrophiles, but it is likely that secondary electrophiles will cause complications with the intermediate diazene (via tautomerization to a hydrazone). For example, some embodiments of the disclosure can utilize other cyclotryptamines, substituted on the arene-ring, the nitrogens, or the aminoethyl group. As another example, in some embodiments, other tertiary electrophiles can be utilized, including R, R', and R" as carbon or any derivative where one or two are heteroatoms.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

In addition, those of ordinary skill in the art recognize that some functional groups can be protected/deprotected using various protecting groups before a certain reaction takes place. Suitable conditions for protecting and/or deprotecting specific functional group, and the use of protecting groups are well-known in the art.

For example, various kinds of protecting groups are described in T.W. Greene and G.M. Wuts, Protecting Groups in Organic Synthesis, Second edition, Wiley, New York, 1991, and other references cited above.

All documents cited herein are herein incorporated by reference in their entirety for all purposes.

Generally, this disclosure includes a method for modular synthesis comprising:

(a) performing a coupling reaction between a tertiary electrophilic group (I) and a suitably protected N1,N1-disubstituted hydrazine (II) to provide a diazene (III);

(b) performing a photoexpulsion of a nitrogen molecule to obtain a coupled product with a quaternary stereocenter; and (c) deprotecting the coupled product to obtain a dimeric cyclotryptamine (IV) wherein the general reaction scheme is as follows:

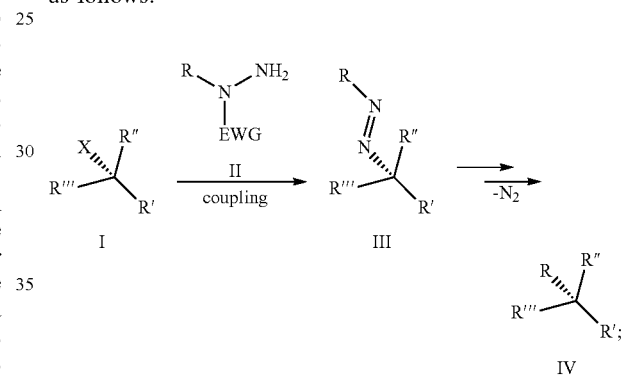

The method includes stereoselective synthesis strategies, and can further comprise additional steps/elements, including chain extension. As discussed herein, iterative and modular cyclotryptamine-chain extension is one such representative process:

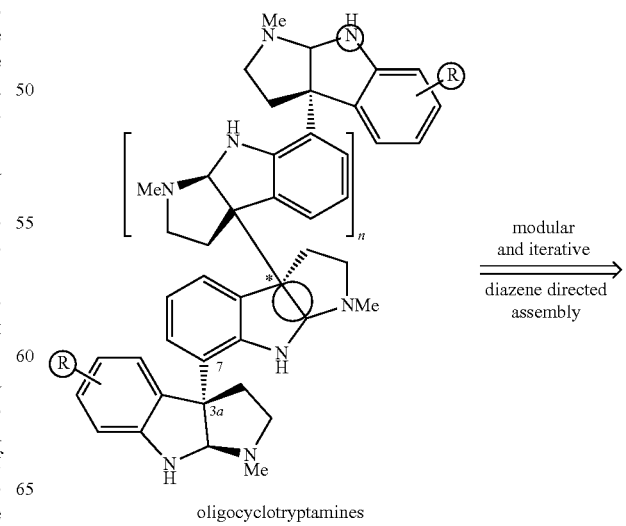

-continued

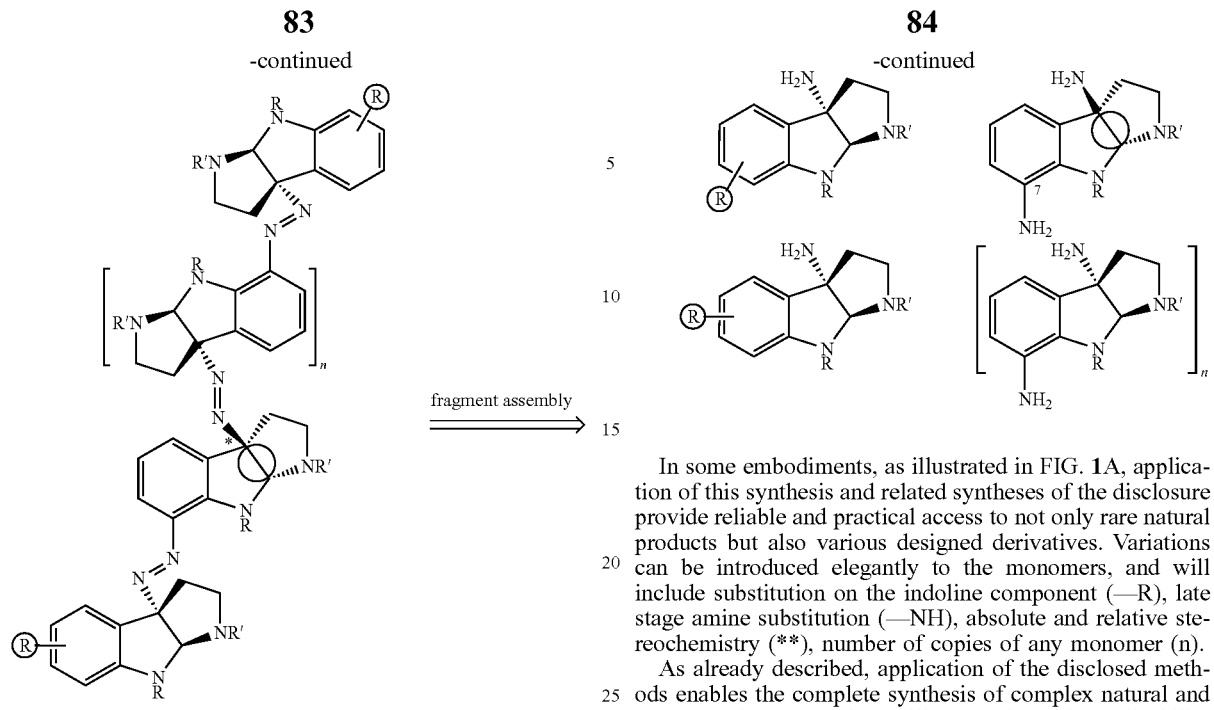

fragment assembly

Figure 1A:
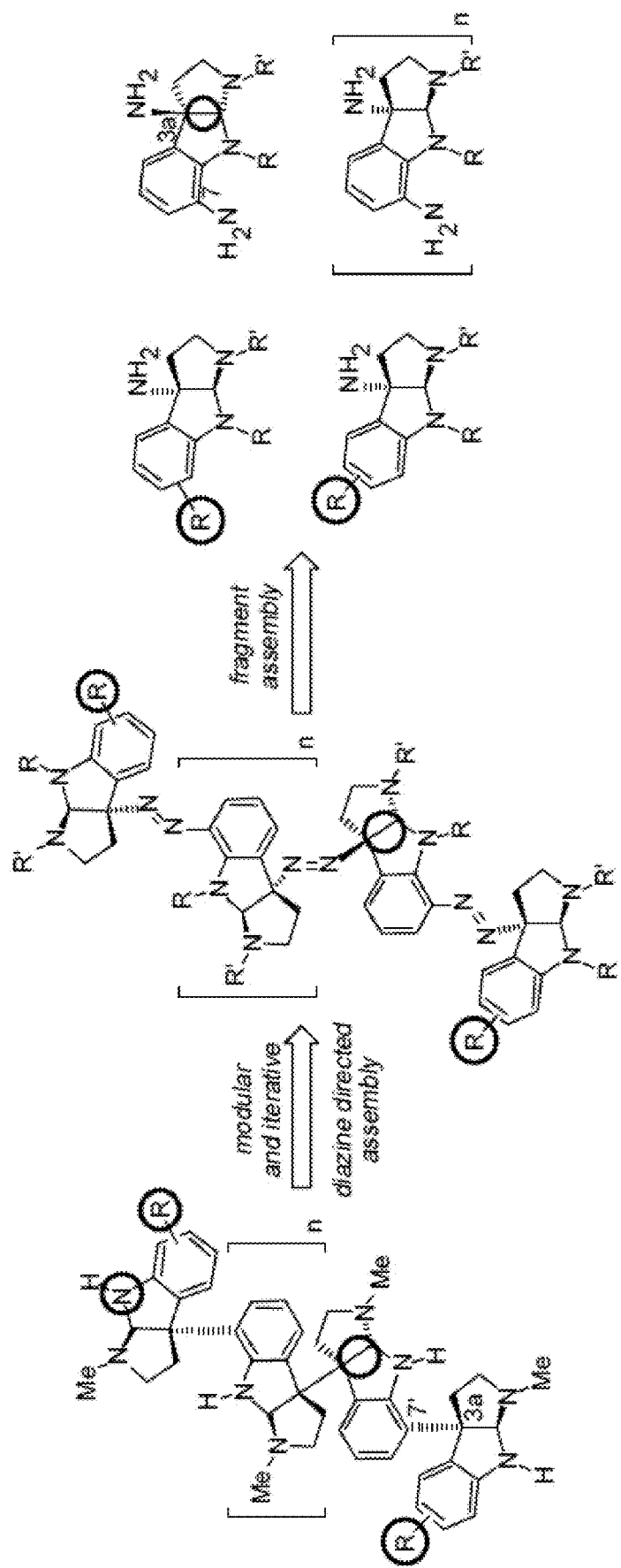
FIG. 1A shows the iterative and modular synthesis of oligocyclotryptamines from various building blocks, according to some embodiments of the disclosure.
Figure 1B:
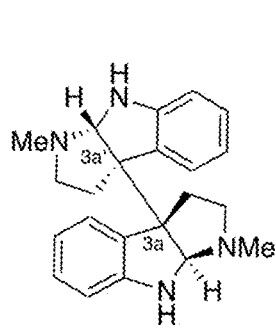
FIG. 1B exemplifies natural products accessible via the diazene-directed assembly of cyclotryptamine fragments.
Figure 1B:
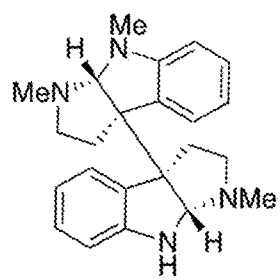
Figure 1B:
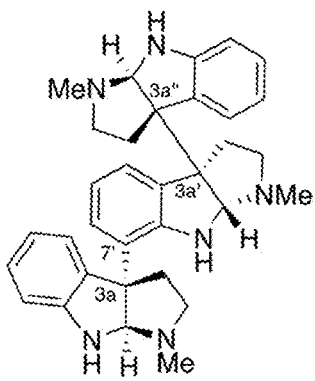
Figure 1B:
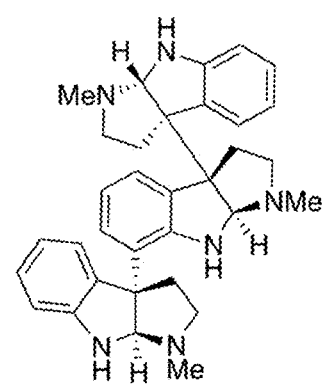
Figure 1B:
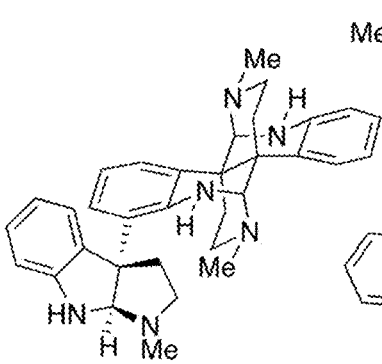
Figure 1B:
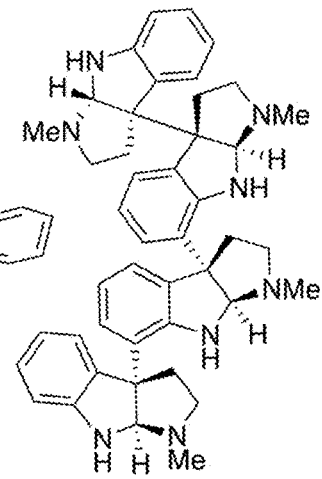
Figure 1B:
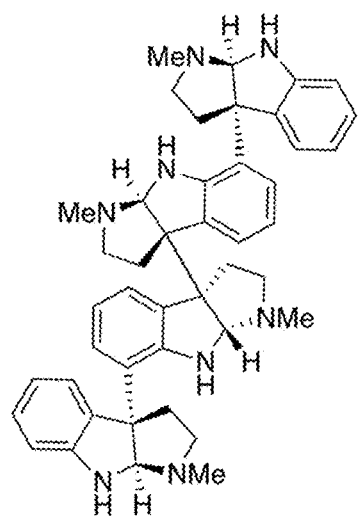
Figure 1B:
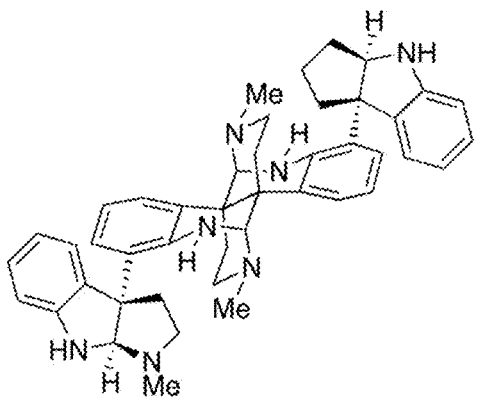

In some embodiments, as illustrated in FIG. 1A, application of this synthesis and related syntheses of the disclosure provide reliable and practical access to not only rare natural products but also various designed derivatives. Variations can be introduced elegantly to the monomers, and will include substitution on the indoline component (—R), late stage amine substitution (—NH), absolute and relative stereochemistry (**), number of copies of any monomer (n).

As already described, application of the disclosed methods enables the complete synthesis of complex natural and non-natural compounds. To illustrate the wide applicability of the disclosed technology, example syntheses utilizing the diazene-directed assembly of cyclotryptamine fragments are shown below, starting from their respective monomer building blocks.

Total Synthesis of (−)-Hodgkinsine B

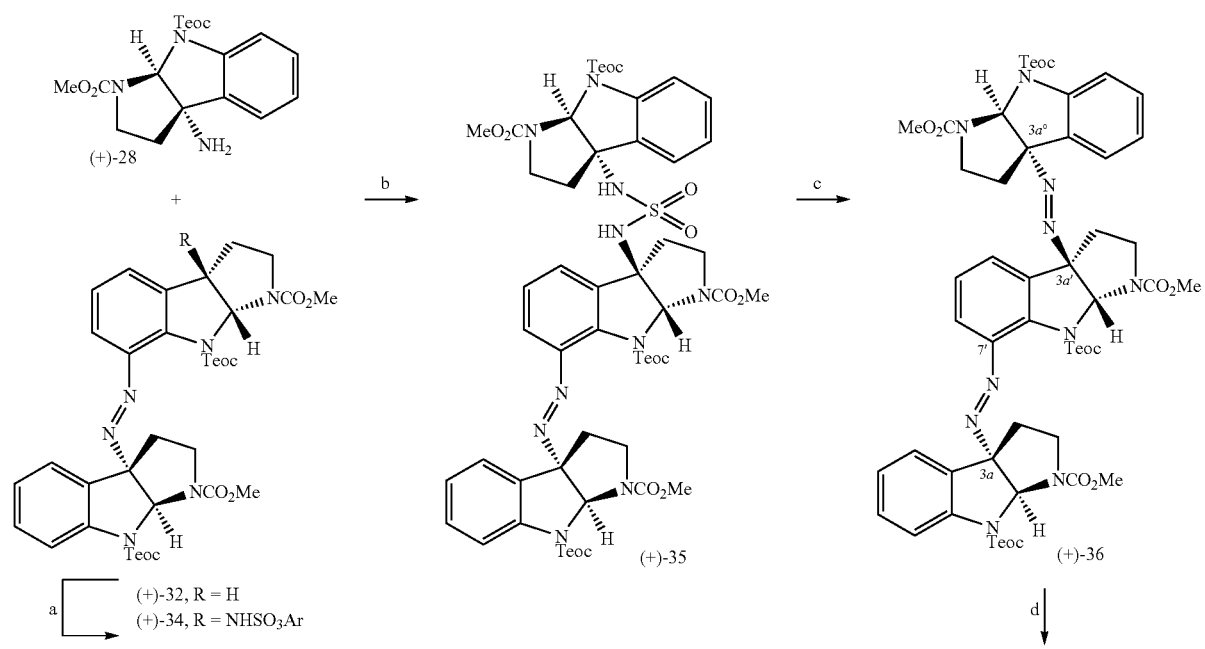

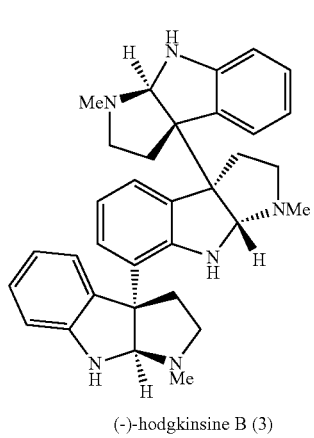

(−)-hodgkinsine B (3)

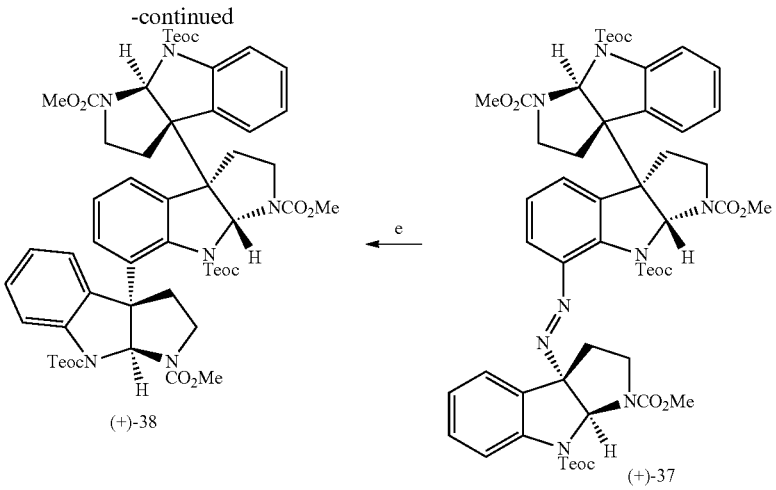

*Reagents and conditions: (a) 2,6-difluorophenyl sulfamate, $Rh_2(esp)_2$, $Ph(Me)_2CCO_2H$, $PhI(OAc)_2$, MgO, 5 Å MS, i-PrOAc, 22° C., 22 h, 58%. (b) DMAP, THF, 22° C., 24 h, 94%. (c) 1,3-dichloro-5,5'-dimethylhydantoin, 1,8-diazabicyclo[5.4.0]undec-7-ene, MeCN, 22° C., 1 h, 91%. (d) hv (380 nm), 25° C., 15 h, 73%. (e) hv (300 nm), 25° C., 30 h, 51%. (f) TBAF, THF, 22° C., 1 h, 98%. (g) Red-Al, PhMe, 70° C., 1 h, 68%. Ar=2,6-difluorobenzene In the approach to (−)-hodgkinsine B, The formation of trimeric cyclotryptamine (−)-3 was envisioned via sequential coupling of three distinct monomeric cyclotryptamines. Having secured the C3a-C7 dimeric diazene (+)-32 through the union of two cyclotryptamine monomers (+)-26 and (−)-31, the synthesis of a $C3a'_{sp3}$-$C3a''_{sp3}$ diazene linker was envisaged arising from the coupling of the corresponding dimeric sulfamate ester and the monomeric amine (+)-28. Synthesis of the diazene dimer sulfamate ester (+)-34 was accomplished using Rh-catalyzed intermolecular $C_{3a}$—H amination starting from dimeric (+)-32 in 58% yield. It is quite likely that this is the most complex substrate to which an intermolecular Rh-catalyzed C—H amination has been applied. Exposure of diazene dimer sulfamate ester (+)-34 to amine (+)-28 in the presence of 4-(N,N-dimethylamino) pyridine (DMAP) in tetrahydrofuran then yielded the desired diazene dimer mixed sulfamide (+)-35 in 94% yield. Remarkably, this reaction proceeded in high yield, using only a slight excess (1.1 equiv) of amine (+)-28, despite the tremendous steric requirements. Next, oxidation of diazene dimer mixed sulfamide (+)-35 using 1,3-dichloro-5,5-dimethylhydantoin (DCDMH) in the presence of 1,8-diazabicyclo[5.4.0]undec-7ene (DBU) provided the trimeric bis-diazene (+)-36 in 91% isolated yield. A thin film of bis-diazene trimer (+)-36 was then photolyzed using 380 nm light, selectively activating the more labile C3a'-C3a" diazene, and affording cleanly the desired mono-diazene trimer (+)-37. Notably, according to the design, the more robust C7'-C3a diazene linker remained intact during this process. Next, photolysis of the remaining C7'-C3a diazene trimer (+)-37 as a thin film was achieved using higher energy 300 nm light. Importantly, the application of diazene-based fragment assembly strategy has allowed the synthesis of a complex, functionalized cyclotryptamine trimer with complete control over the absolute as well as relative stereochemistry of all six stereocenters, three of which are quaternary. Treatment of trimer (+)-38 with tetra-n-butylammonium fluoride (TBAF) resulted in global deprotection of all (trimethylsilyl) ethyl carbamate moieties in high yield. The choice of this N1-protective group was important as the steric constraints of the C7'-C3a linkage rendered other groups difficult to remove. It was postulated that the removal of the (trimethylsilyl)ethyl carbamate may be facilitated by nucleophilic attack at the more accessible trimethylsilyl group. Exhaustive reduction of the methyl carbamates with Red-Al afforded (−)-hodgkinsine B (3) in 68% yield. Significantly, alkaloid (−)-3 was prepared in 11 steps in its longest linear sequence, starting from (+)-26.

Total Synthesis of (−)-hodgkinsine (4) and (−)-calycosidine (5)

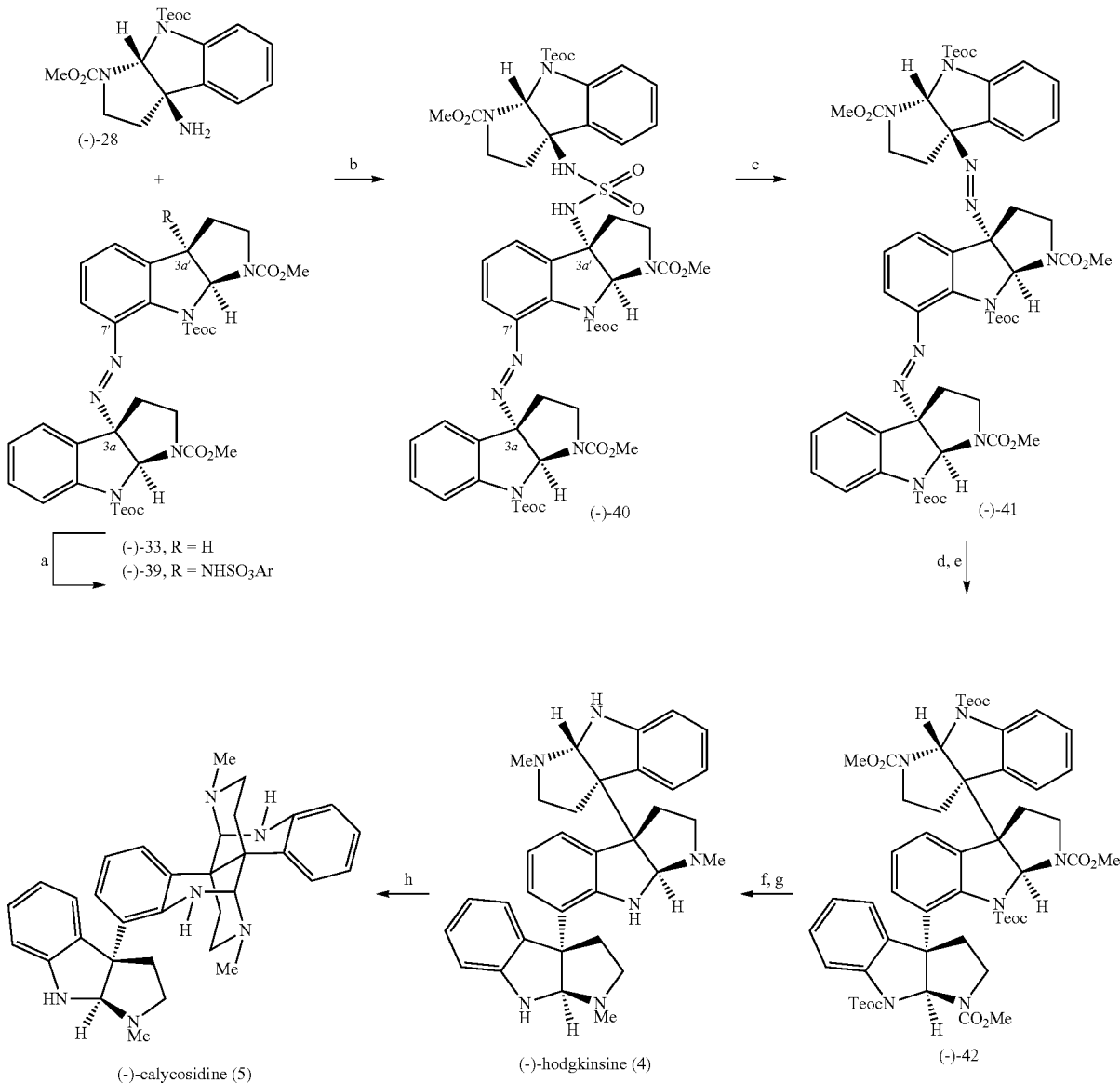

(−)-calycosidine (5)

(−)-hodgkinsine (4)

(−)-42

[a]Reagents and conditions: (a) 2,6-difluorophenyl sulfamate, $Rh_2(esp)_2$, $Ph(Me)_2CCO_2H$, $PhI(OAc)_2$, MgO, 5 Å MS, i-PrOAc, 22° C., 14 h, 60%. (b) DMAP, THF, (−)-28, 22° C., 24 h, 98%; (c) 1,3-dichloro-5,5'-dimethylhydantoin, 1,8-diazabicyclo[5.4.0]undec-7-ene, MeCN, 22° C., 1 h, 88%; (d) hv (380 nm), 25° C., 15 h, 73%. (e) hv (300 nm), 25° C., 15 h, 62%. (f) TBAF, THF, 22° C., 1 h, 96%. (g) Red-Al, PhMe, 70° C., 1 h, 73%. (h) $H_2O$, $CH_3COOH$, 95° C., 36 h, 42%. Ar=2,6-difluorobenzene.

The diazene-based coupling strategy of monomeric cyclotryptamines was then employed to prepare a more complex member of the *calycanthaceous* alkaloid family, (−)-calycosidine (5) via acid-catalyzed rearrangement of isomeric trimeric (−)-hodgkinsine (4). Similar to the approach to (−)-hodgkinsine B (3), the synthetic plan for accessing (−)-hodgkinsine (4) relied on the sequential coupling of the appropriate monomeric fragments bromocyclotryptamine (+)-26, hydrazide (+)-31 and amine (−)-28, via the formation of the C3a'-C3a" and C3a-C7' diazene linkers. Starting with dimeric diazene (−)-33, the Rh-catalyzed C—H amination afforded the diazene dimer sulfamate ester (−)-39 in 60% yield (Scheme 7). Notably, this challenging transformation proceeds with equal efficiency on both diazene dimer diastereomers (+)-32 and (−)-33 despite potential substrate bias. Treatment of diazene dimer sulfamate ester (−)-39 with DMAP in the presence of amine (−)-28, followed by a mild oxidation of the mixed sulfamide (−)-40 to diazene afforded the bis-diazene trimer (−)-41 in 86% yield over two steps. Stepwise photolysis of the two diazenes yielded the trimer (−)-42 in 45% yield over two steps. A global deprotection of all (trimethylsilyl)ethyl carbamates followed by an exhaustive reduction using Red-Al led to formation of (−)-hodgkinsine (4) in 70% yield over two steps.

Convergent and Completely Stereoselective Total Synthesis of (−)-Quadrigemine C (7) and (−)-Psycholeine (8)
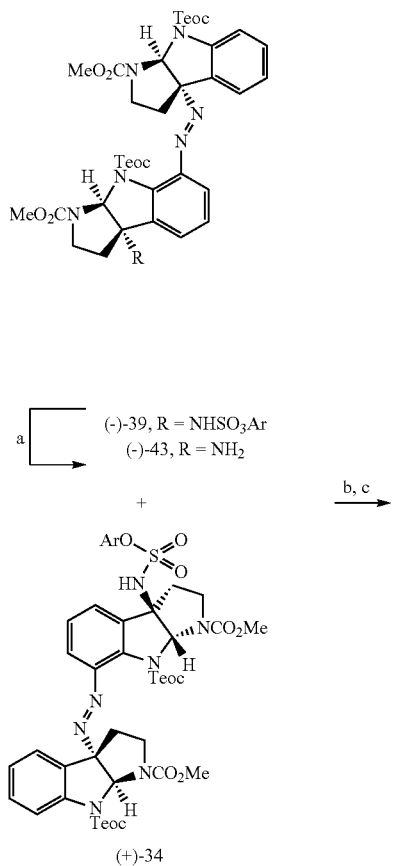
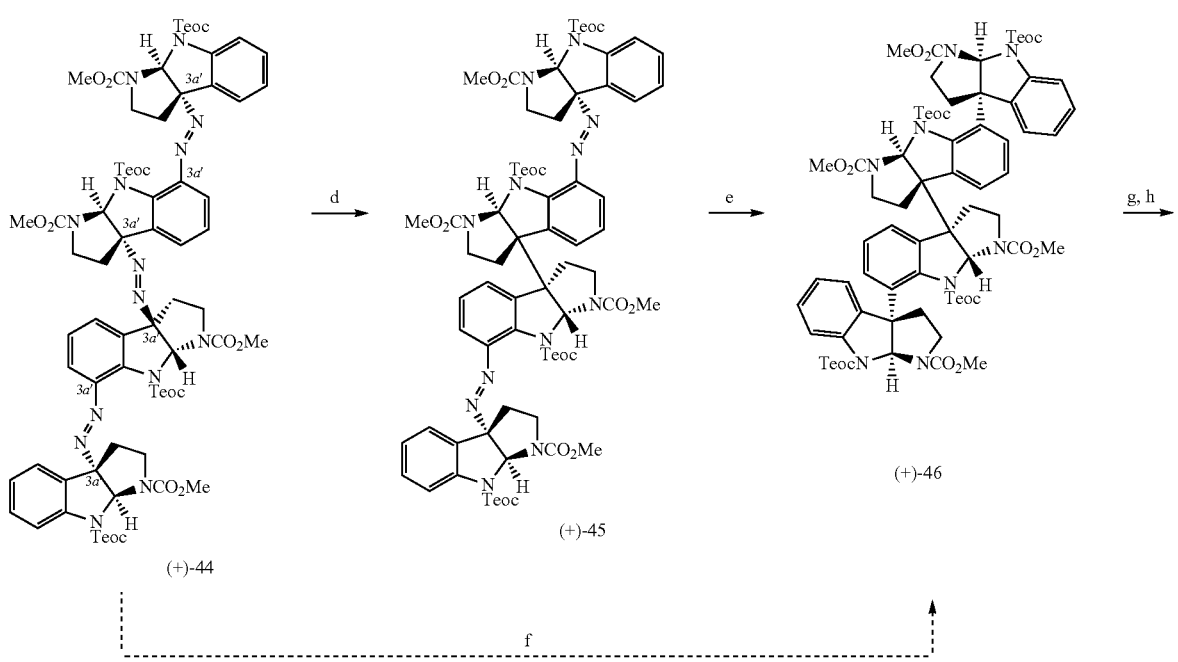

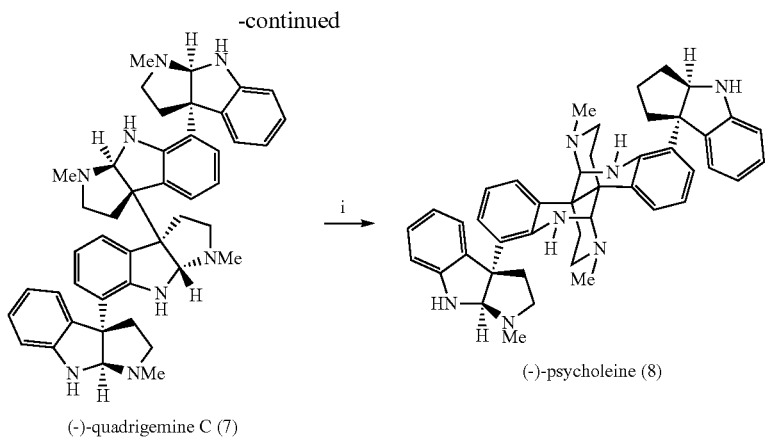

(-)-quadrigemine C (7) →i (-)-psycholeine (8)

<sup>a</sup>Reagents and conditions: (a) pyridine, MeCN—H₂O, 70° C., 24 h, 84%. (b) DMAP, THF, 22° C., 7 h, 94%. (c) 1,3-dichloro-5,5'-dimethylhydantoin, 1,8-diazabicyclo [5.4.0]undec-7-ene, MeCN, 22° C., 1 h, 74%. (d) hv (380 nm), 25° C., 24 h, 72%. (e) hv (300 nm), 25° C., 18 h, 44%. (f) hv (300 nm), 25° C., 19 h, 22%. (g) TBAF, THF, 22° C., 1 h, 87%. (h) EtN(Me)₂.AlH₃, PhMe, 60° C., 1 h, 62%. (i) H₂O, CH₃COOH, 95° C., 36 h, 36%. Ar=2,6-difluorobenzene In order to further demonstrate the versatility of the functional cyclotryptamine monomers in the highly convergent diazene-directed fragment assembly approach, the synthesis of a complex tetrameric alkaloid (−)-psycholeine (8) via the acid-catalyzed rearrangement of isomeric (−)-quadrigemine C (7) was envisioned. To synthesize alkaloid (−)-7 from the tetrameric tris-diazene intermediate (+)-44, the coupling of the corresponding diazene dimers (+)-34 and (−)-43 was sought. The diazene dimer amine (−)-43 was accessed in 84% yield via hydrolysis of the corresponding sulfamate ester (−)-39. The coupling of amine (−)-43 and sulfamate ester (+)-34 followed by oxidation of the mixed sulfamide proceeded in a 70% overall yield to give tris-diazene tetramer (+)-44. Notably, the modular design of the synthetic strategy allows for the highly convergent assembly of cyclotryptamine monomers into any desired diastereomer of tris-diazene tetramer (+)-44 while exerting complete control over any particular stereocenter present. Selective photolysis of the C3a'-C3a" diazene led to bis-diazene tetramer (+)-45 in 72% yield. Next, photolysis of both C7'-C3a and C7"-C3a''' diazene linkers using 300 nm light afforded tetramer (+)-46 in 44% yield. Notably, starting with tris-diazene tetramer (+)-44, photolysis using 300 nm light afforded tetramer (+)-46 in 22% yield, offering an example where three molecules of dinitrogen are photoextruded from a single intermediate to adjoin four monomers via three carbon-carbon bonds. Importantly, this transformation secured all four quaternary stereocenters with complete stereocontrol in a single step. Global deprotection of (trimethylsilyl)ethyl carbamates followed by an exhaustive reduction of all methyl carbamates gave (−)-quadrigemine C (7) in 54% yield over two steps.

The disclosure provides versatile strategies for the modular synthesis of higher order cyclotryptamine alkaloids via the convergent and directed modular assembly of whole cyclotryptamine subunits, enabled by the new methodology for synthesis of aryl-alkyl diazenes through the coupling of electronically-deactivated aryl hydrazines with bromocyclotryptamines. The diazene-guided stereoselective assembly of cyclotryptamine fragments at both the C3a-C3a' and C3a-C7 linkages was used to secure all stereocenters present with complete relative and absolute stereochemical control. The synthesis of the C3a- and C7-functional cyclotryptamine monomers was realized through the systematic application of Rh- and Ir-catalyzed C—H amination chemistry, respectively, in complex settings. The combination of advanced C—H amination chemistry, the new aryl-alkyl diazene synthesis chemistry, and the diazene-directed fragment coupling enables highly convergent and systematic assembly of cyclotryptamine monomers. Successful implementation of this chemistry is demonstrated by the total synthesis of (−)-hodgkinsine (4), (−)-hodgkinsine B (3) and (−)-quadrigemine C (7), through the modular and directed coupling of cyclotryptamine precursors with complete stereoselection for all the quaternary stereocenters.

In certain embodiments, the present disclosure provides embodiments 1 to 34, shown below.

Embodiment 1

A method of preparing compounds of Formula (I), or a pharmaceutically acceptable salt, tautomer or stereoisomer thereof, comprising reacting a compound of Formula (II), and thereby extruding dinitrogen to provide a compound of Formula (I):

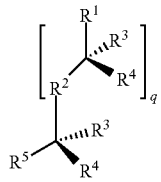

Formula (I)

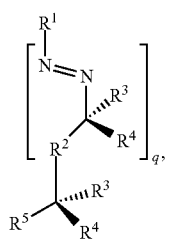

Formula (II)

wherein $R^1$ is tertiary alkyl, alkenyl, aryl, heteroaryl, carbocyclyl, or heterocyclyl or at least one moiety of structure:

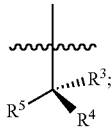

and $R^2$, $R^3$, $R^4$, and $R^5$ are each occurrence, each independently selected from tertiary alkyl, aryl, heteroaryl, carbocyclyl, or heterocyclic, wherein any two of $R^3$, $R^4$, and $R^5$ taken together with the carbon atoms to which they are attached form a $C_{5-14}$ membered saturated, unsaturated, or aromatic carbocyclic ring or a $C_{5-14}$ membered saturated, unsaturated, or aromatic heterocyclic ring; and wherein any tertiary alkyl, aryl, heteroaryl, carbocyclyl, or heterocyclyl, $C_{5-14}$ membered saturated, unsaturated, or aromatic carbocyclic ring or a $C_{5-14}$ membered saturated, unsaturated, or aromatic heterocyclic ring can be further substituted with one or more halogen, alkyl, heteroaryl, carbocyclyl, heterocyclyl, $C_{3-14}$ membered saturated, unsaturated, or aromatic carbocyclic, or $C_{3-14}$ membered saturated, unsaturated, or aromatic heterocyclic rings; and q is an integer from 0-8.

Embodiment 2

The method of embodiment 1, wherein the compound of Formula (I) is:

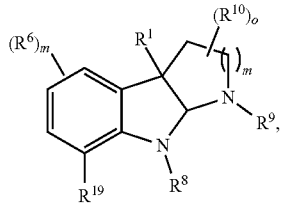

Formula (Ia)

wherein $R^1$ is tertiary alkyl, alkenyl, aryl, heteroaryl, carbocyclyl, heterocyclyl,

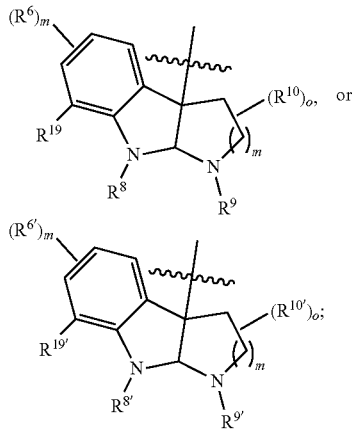

$R^6$ and $R^{6'}$ are each independently selected from halogen, —OH, —$OR^{11}$, —$OC(=O)R^{11}$, —$NR^{11}R^{12}$, —$S(=O)_pR^{13}$, —$C(=O)R^{11}$, —$C(=O)OR^{11}$, —$C(=O)NR^{11}NR^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl; wherein two $R^6$ or two $R^{6'}$ groups taken together with the carbon atoms to which they are attached form an aryl, heteroaryl, carbocyclic, or heterocyclic ring;

$R^8$, $R^9$, $R^{8'}$, and $R^{9'}$ are each independently selected from H, $C_1$-$C_{12}$ alkyl, $C_2$-$C_{12}$ alkenyl, $C_2$-$C_{12}$ alkynyl, —$C(=O)R^{11}$, —$C(=O)OR^{11}$, —$C(=O)NR^{11}R^{12}$, —$SR^{11}$, —$S(=O)_pR^{13}$, —$S(=O)_2NR^{11}R^{12}$, —$C(=O)O(CH_2)_oR^{11}$, aryl, heteroaryl, carbocyclyl, or heterocyclyl;

$R^{10}$ and $R^{10'}$ are each independently selected from H, $C_1$-$C_{12}$ alkyl; $C_2$-$C_{12}$ alkenyl, $C_2$-$C_{12}$ alkynyl, —$C(=O)R^{11}$, —$C(=O)OR^{11}$, —$C(=O)NR^{11}R^{12}$, —$S(=O)_pR^{13}$, —OH, —$OR^{11}$, —$OC(=O)R^{11}$, —$NR^{11}R^{12}$, aryl, heteroaryl, carbocyclyl, or heterocyclyl, wherein two $R^{10}$ or two $R^{10'}$ groups taken together with the carbon atoms to which they are attached form an aryl, heteroaryl, carbocyclic, or heterocyclic ring;

$R^{11}$ and $R^{12}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;

$R^{13}$ and $R^{14}$ are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —$OR^{11}$, —$(CH_2)_rSiMe_3$, or —$(CH_2)_rR^{11}$;

$R^{15}$ is —$S(=O)_pR^{13}$, —$S(=O)_2NR^{11}R^{12}$, —$C(=O)R^{13}$, —$C(=O)R^{20}$, —$C(=O)O(CH_2)_rR^{20}$, —$C(=O)CF_3$, —$C(=O)OR^{20}$, —$P(=O)R^{13}R^{14}$, or, —$P(=O)NR^{11}R^{12}$;

$R^{19}$ and $R^{19'}$ are each independently selected from H, tertiary alkyl, alkenyl, aryl, heteroaryl, carbocyclyl, heterocyclyl,

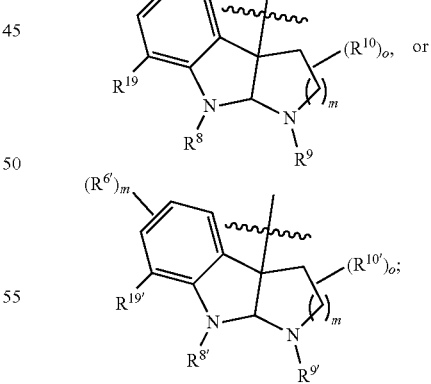

$R^{20}$ is —$Si(alkyl)_3$, —$Si(alkyl)_2aryl$, or $Si(aryl)_2alkyl$; and m is an integer from 0 to 3;

n and o are each independently an integer from 0 to 4;

p is 1 or 2; and r is an integer from 1 to 4.

Embodiment 3

The method of embodiment 2, wherein $R^1$ is comprised of

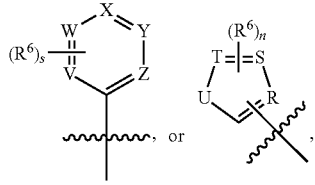

wherein

V, W, X, Y, and Z are each independently selected from —CH or N;

R, S, and T are each independently selected from —CH or N; and

U is O, S, or $NR^{11}$; wherein $R^{11}$ is independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl; and n is an integer from 0-4; and s is an integer from 0-5.

Embodiment 4

The method of embodiment 2, wherein the compound of Formula (I) is:

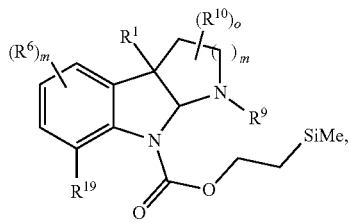

Formula (Ib)

wherein $R^{19}$ is H, tertiary alkyl, alkenyl, aryl, heteroaryl, carbocyclyl, heterocyclyl,

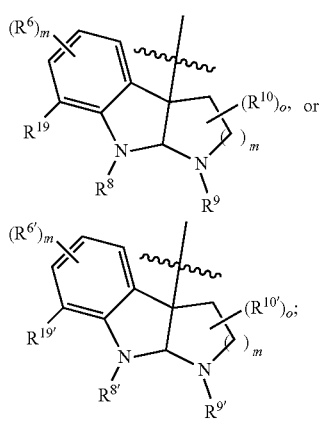

and $R^8$ and $R^{8'}$ is —C(=O)O(CH$_2$)$_2$SiMe$_3$.

Embodiment 5

The method of embodiment 1, wherein the compound of Formula (II) is:

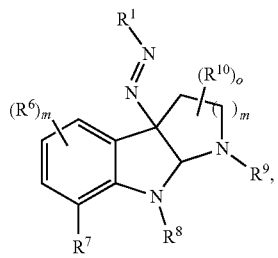

Formula (IIa)

wherein $R^1$ is tertiary alkyl, alkenyl, aryl, heteroaryl, carbocyclyl, heterocyclyl,

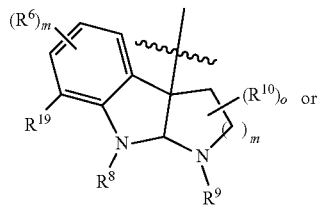

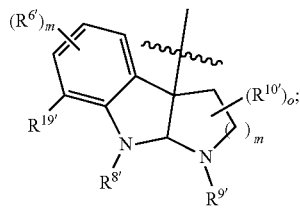

$R^6$ and $R^{6'}$ are each independently selected from halogen, —OH, —$OR^{11}$, —OC(=O)$R^{11}$, —$NR^{11}R^{12}$, —S(=O)$_p R^{13}$, —C(=O)$R^{11}$, —C(=O)O$R^{11}$, —C(=O)NR$^{11}$NR$^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl; wherein two $R^6$ or two $R^{6'}$ groups taken together with the carbon atoms to which they are attached form an aryl, heteroaryl, carbocyclic, or heterocyclic ring;

$R^7$ and $R^{7'}$ are each independently selected from H, —$N_3$, —N($R^{15}$)NH$_2$, —NHR$^{15}$,

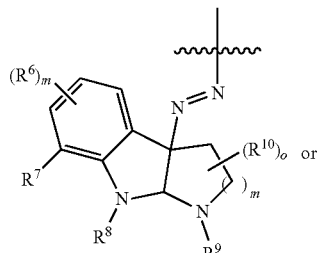

-continued

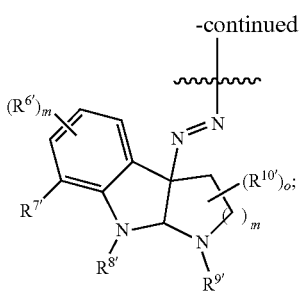

$R^8$, $R^{8'}$, $R^9$, and, $R^{9'}$ are each independently selected from H, $C_1$-$C_{12}$ alkyl, $C_2$-$C_{12}$ alkenyl, $C_2$-$C_{12}$ alkynyl, —C(=O)$R^{11}$, —C(=O)O$R^{11}$, —C(=O)N$R^{11}R^{12}$, —S$R^{11}$, —S(=O)$_p$$R^{13}$, —S(=O)$_2$N$R^{11}R^{12}$, —C(=O)O(CH$_2$)$_o$$R^{11}$, aryl, heteroaryl, carbocyclyl, or heterocyclyl;

$R^{10}$ and $R^{10'}$ are each independently selected from H, $C_1$-$C_{12}$ alkyl; $C_2$-$C_{12}$ alkenyl, $C_2$-$C_{12}$ alkynyl, —C(=O)$R^{11}$, —C(=O)O$R^{11}$, —C(=O)N$R^{11}R^{12}$, —S(=O)$_p$$R^{13}$, —OH, —O$R^{11}$, —OC(=O)$R^{11}$, —N$R^{11}R^{12}$, aryl, heteroaryl, carbocyclyl, or heterocyclyl, wherein two $R^{10}$ groups taken together with the carbon atoms to which they are attached form an aryl, heteroaryl, carbocyclic, or heterocyclic ring;

$R^{11}$ and $R^{12}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;

$R^{13}$ and $R^{14}$ are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —O$R^{11}$, —(CH$_2$)$_r$SiMe$_3$, or —(CH$_2$)$_r$$R^{11}$;

$R^{15}$ is —S(=O)$_p$$R^{13}$, —S(=O)$_2$N$R^{11}R^{12}$, —C(=O)$R^{13}$, —C(=O)$R^{20}$, —C(=O)O(CH$_2$)$_r$$R^{20}$, —C(=O)CF$_3$, —C(=O)O$R^{20}$, —P(=O)$R^{13}R^{14}$, or, —P(=O)N$R^{11}R^{12}$;

$R^{19}$ and $R^{19'}$ are each independently H;

$R^{20}$ is —Si(alkyl)$_3$, —Si(alkyl)$_2$aryl, or Si(aryl)$_2$alkyl; and m is an integer from 0 to 3;

n and o are each independently an integer from 0 to 4;

p is 1 or 2; and r is an integer from 1 to 4.

Embodiment 6

The method of embodiment 5, wherein $R^1$ is,

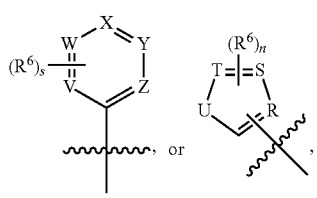

wherein

V, W, X, Y, and Z are each independently selected from —CH or N;

R, S, and T are each independently selected from —CH or N;

U is O, S, or N$R^{11}$; wherein $R^{11}$ is independently selected from H, $C_1$-$C_{12}$ alkyl, $C_2$-$C_{12}$ alkenyl, $C_2$-$C_{12}$ alkynyl, —Si(alkyl)$_3$, —Si(alkyl)$_2$aryl, Si(aryl)$_2$alkyl, aryl, heteroaryl, carbocyclyl, or heterocyclyl, and wherein $R^{11}$ and $R^{12}$ taken together with the carbon atoms to which they are attached form an aryl, heteroaryl, carbocyclic, or heterocyclic ring; and n is an integer from 0-4; and s is an integer from 0-5.

Embodiment 7

The method of embodiment 1, wherein the compound of Formula (II) is prepared by reacting a compound of Formula (III), and a compound of Formula (IV):

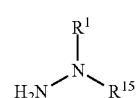

Formula (III)

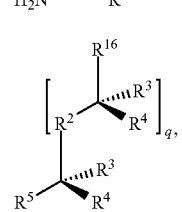

Formula (IV)

wherein $R^1$ is alkenyl, aryl, or heteroaryl; and $R^2$, $R^3$, $R^4$, and $R^5$ are each occurrence, each independently selected from alkyl, aryl, heteroaryl, carbocyclyl, or heterocyclic, wherein any two of $R^3$, $R^4$, and $R^5$ taken together with the carbon atoms to which they are attached form a $C_{5-14}$ membered saturated, unsaturated, or aromatic carbocyclic ring or a $C_{5-14}$ membered saturated, unsaturated, or aromatic heterocyclic ring; and wherein any tertiary alkyl, aryl, heteroaryl, carbocyclyl, or heterocyclyl, $C_{5-14}$ membered saturated, unsaturated, or aromatic carbocyclic ring or a $C_{5-14}$ membered saturated, unsaturated, or aromatic heterocyclic ring can be further substituted with one or more halogen, alkyl, heteroaryl, carbocyclyl, heterocyclyl, $C_{3-14}$ membered saturated, unsaturated, or aromatic carbocyclic, or $C_{3-14}$ membered saturated, unsaturated, or aromatic heterocyclic rings;

$R^{11}$ and $R^{12}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;

$R^{13}$ and $R^{14}$ are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —O$R^{11}$, —(CH$_2$)$_r$SiMe$_3$, or —(CH$_2$)$_r$$R^{11}$;

$R^{15}$ is —S(=O)$_p$$R^{13}$, —S(=O)$_2$N$R^{11}R^{12}$, —C(=O)$R^{13}$, —C(=O)$R^{20}$, —C(=O)O(CH$_2$)$_r$$R^{20}$, —C(=O)CF$_3$, —C(=O)O$R^{20}$, —P(=O)$R^{13}R^{14}$, or, —P(=O)N$R^{11}R^{12}$;

$R^{16}$ is I, Br, Cl, —OH, —OSO$_2$CF$_3$, —OS(O)$_2$$R^{13}$, —OP(=O)$R^{13}R^{14}$, —OC(=N$R^{11}$)$R^{12}$, —OC(=N$R^{11}$)CCl$_3$, —O$R^{11}$, or —N$_2$$^+$X$^-$, wherein X$^-$ is halogen;

$R^{20}$ is —Si(alkyl)$_3$, —Si(alkyl)$_2$aryl, or Si(aryl)$_2$alkyl; and m is an integer from 0 to 3;

n and o are each independently an integer from 0 to 4;

p is 1 or 2;
q is an integer of from 0-8; and
r is an integer from 1 to 4.

Embodiment 8

The method of embodiment 7, wherein the compound of Formula (III) is:

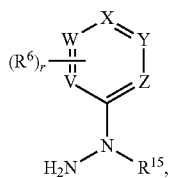

Formula (IIIa)

wherein
V, W, X, Y, and Z are each independently selected from —CH or N; and
r is an integer from 0 to 5.

Embodiment 9

The method of embodiment 7, wherein the compound of Formula (III) is:

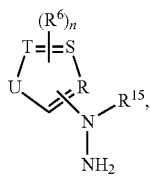

Formula (IIIb)

wherein
R, S, and T are each independently selected from —CH or N; and
U is O, S, or $NR^{11}$, wherein $R^{11}$ is independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl; and
n is an integer from 0 to 4.

Embodiment 10

The method of embodiment 7, wherein the compound of Formula (III) is:

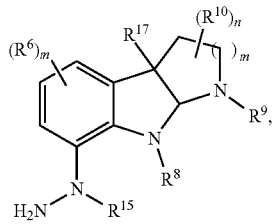

Formula (IIIc)

wherein
$R^6$ and $R^{6'}$ are each independently selected from halogen, —OH, —$OR^{11}$, —$OC(=O)R^{11}$, —$NR^{11}R^{12}$, —$S(=O)_pR^{13}$, —$C(=O)R^{11}$, —$C(=O)OR^{11}$, —$C(=O)$ $NR^{11}NR^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl; wherein two $R^6$ or two $R^{6'}$ groups taken together with the carbon atoms to which they are attached form an aryl, heteroaryl, carbocyclic, or heterocyclic ring;
$R^{17}$ is H, —OH, —$OR^{11}$, —$NR^{11}R^{12}$, aryl, heteroaryl, carbocyclyl, heterocyclyl,

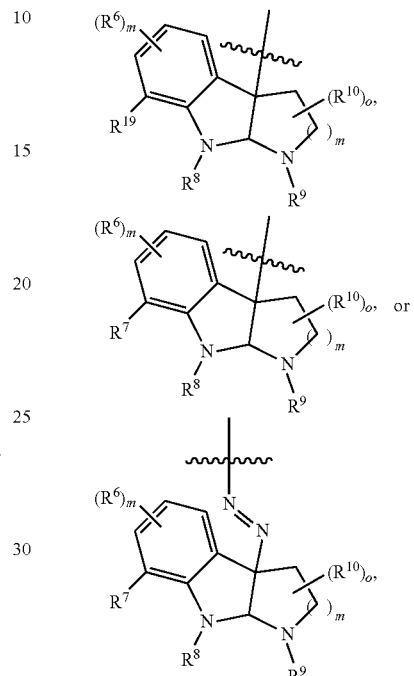

wherein
$R^7$ and $R^{7'}$ are each independently selected from H, —$N_3$, —$N(R^{15})NH_2$, —$NHR^{15}$,

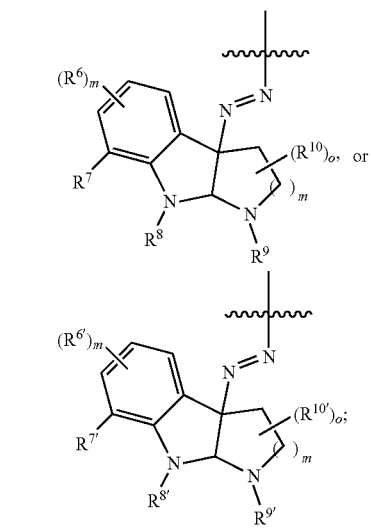

and wherein
$R^{19}$ and $R^{19'}$ are each independently selected from H, tertiary alkyl, alkenyl, aryl, heteroaryl, carbocyclyl, heterocyclyl,

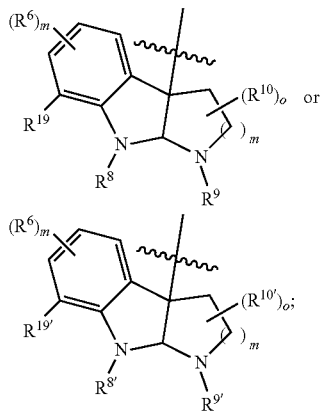

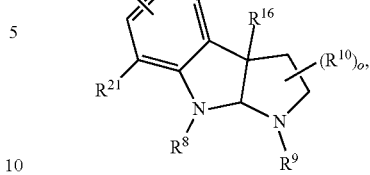

$R^8$, $R^{8'}$, $R^9$, and, $R^{9'}$ are each independently selected from H, $C_1$-$C_{12}$ alkyl, $C_2$-$C_{12}$ alkenyl, $C_2$-$C_{12}$ alkynyl, —C(=O)$R^{11}$, —C(=O)O$R^{11}$, —C(=O)N$R^{11}R^{12}$, —S$R^{11}$, —S(=O)$_p R^{13}$, —S(=O)$_2$N$R^{11}R^{12}$, —C(=O)O(CH$_2$)$_o R^{11}$, aryl, heteroaryl, carbocyclyl, or heterocyclyl;

$R^{10}$ and $R^{10'}$ are each independently selected from H, $C_1$-$C_{12}$ alkyl; $C_2$-$C_{12}$ alkenyl, $C_2$-$C_{12}$ alkynyl, —C(=O)$R^{11}$, —C(=O)O$R^{11}$, —C(=O)N$R^{11}R^{12}$, —S(=O)$_p R^{13}$, —OH, —OR$^{11}$, —OC(=O)$R^{11}$, —NR$^{11}R^{12}$, aryl, heteroaryl, carbocyclyl, or heterocyclyl, wherein two $R^{10}$ or two $R^{10'}$ groups taken together with the carbon atoms to which they are attached form an aryl, heteroaryl, carbocyclic, or heterocyclic ring;

$R^{11}$ and $R^{12}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;

$R^{13}$ and $R^{14}$ are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —OR$^{11}$, —(CH$_2$)$_r$SiMe$_3$, or —(CH$_2$)$_r R^{11}$;

$R^{15}$ is —S(=O)$_p R^{13}$, —S(=O)$_2$NR$^{11}R^{12}$, —C(=O)$R^{13}$, —C(=O)$R^{20}$, —C(=O)O(CH$_2$)$_r R^{20}$, —C(=O)CF$_3$, —C(=O)O$R^{20}$, —P(=O)$R^{13}R^{14}$, or, —P(=O)NR$^{11}R^{12}$;

$R^{20}$ is —Si(alkyl)$_3$, —Si(alkyl)$_2$aryl, or Si(aryl)$_2$alkyl; and m is an integer from 0 to 3;

n and o are each independently an integer from 0 to 4;

p is 1 or 2; and r is an integer from 1 to 4.

Embodiment 11

The method of embodiment 7, wherein $R^{15}$ is —S(=O)$_p R^{13}$, wherein p is 2, and $R^{13}$ is $C_1$-$C_{12}$ alkyl.

Embodiment 12

The method of embodiment 11, wherein the compound of Formula (II) is formed in one synthetic step.

Embodiment 13

The method of embodiment 7, wherein the compound of Formula (IV) is:

Formula (IVa)

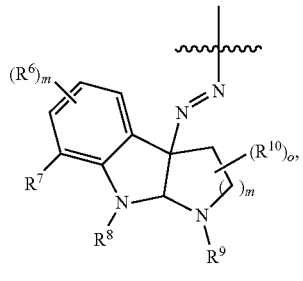

wherein $R^{16}$ is I, Br, Cl, —OH, —OSO$_2$CF$_3$, —OS(O)$_2R^{13}$, —OP(=O)$R^{13}R^{14}$, —OC(=NR$^{11}$)$R^{12}$, —OC(=NR$^{11}$)CCl$_3$, —OR$^{11}$, or —N$_2^+$X$^-$, wherein X$^-$ is halogen;

$R^{21}$ is H, halogen, alkyl, alkenyl, alkynyl, aryl, heteroaryl, carbocyclyl, heterocyclyl, —N$_3$,

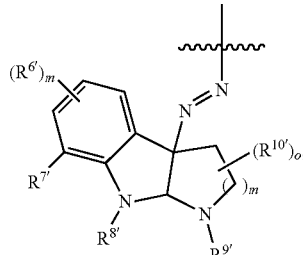

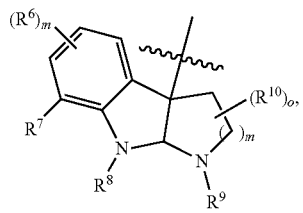

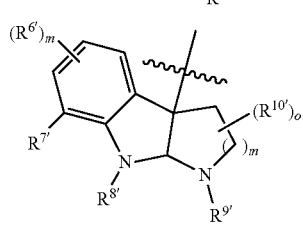

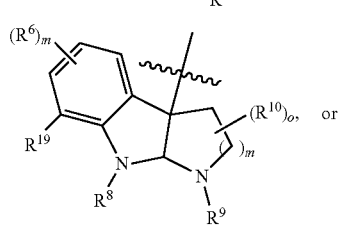

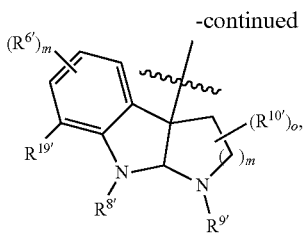

wherein $R^7$ and $R^{7'}$ are each independently selected from H, —$N_3$, —$N(R^{15})NH_2$, —$NHR^{15}$,

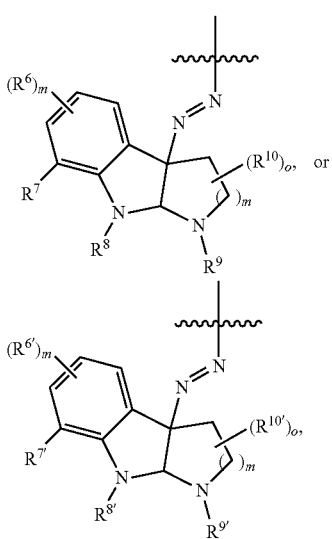

and wherein $R^{19}$ and $R^{19'}$ are each independently selected from H, tertiary alkyl, alkenyl, aryl, heteroaryl, carbocyclyl, heterocyclyl,

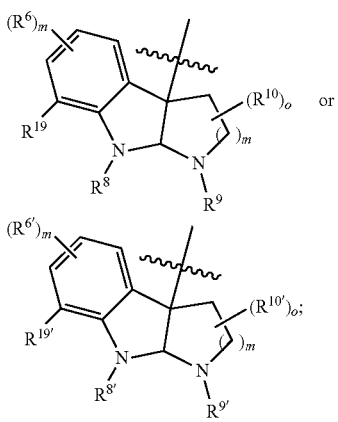

$R^6$ and $R^{6'}$ are each independently selected from halogen, —OH, —$OR^{11}$, —$OC(=O)R^{11}$, —$NR^{11}R^{12}$, —$S(=O)_pR^{13}$, —$C(=O)R^{11}$, —$C(=O)OR^{11}$, —$C(=O)NR^{11}NR^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl; wherein two $R^6$ or two $R^{6'}$ groups taken together with the carbon atoms to which they are attached form an aryl, heteroaryl, carbocyclic, or heterocyclic ring;

$R^8$, $R^{8'}$, $R^9$, and $R^{9'}$ are each independently selected from H, $C_1$-$C_{12}$ alkyl, $C_2$-$C_{12}$ alkenyl, $C_2$-$C_{12}$ alkynyl, —$C(=O)R^{11}$, —$C(=O)OR^{11}$, —$C(=O)NR^{11}R^{12}$, —$SR^{11}$, —$S(=O)_pR^{13}$, —$S(=O)_2NR^{11}R^{12}$, —$C(=O)O(CH_2)_oR^{11}$, aryl, heteroaryl, carbocyclyl, or heterocyclyl;

$R^{10}$ and $R^{10'}$ are each independently selected from H, $C_1$-$C_{12}$ alkyl; $C_2$-$C_{12}$ alkenyl, $C_2$-$C_{12}$ alkynyl, —$C(=O)R^{11}$, —$C(=O)OR^{11}$, —$C(=O)NR^{11}R^{12}$, —$S(=O)_pR^{13}$, —OH, —$OR^{11}$, —$OC(=O)R^{11}$, —$NR^{11}R^{12}$, aryl, heteroaryl, carbocyclyl, or heterocyclyl, wherein two $R^{10}$ or two $R^{10'}$ groups taken together with the carbon atoms to which they are attached form an aryl, heteroaryl, carbocyclic, or heterocyclic ring;

$R^{11}$ and $R^{12}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;

$R^{13}$ and $R^{14}$ are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —$OR^{11}$, —$(CH_2)_rSiMe_3$, or —$(CH_2)_rR^{11}$;

$R^{15}$ is —$S(=O)_pR^{13}$, —$S(=O)_2NR^{11}R^{12}$, —$C(=O)R^{13}$, —$C(=O)R^{20}$, —$C(=O)O(CH_2)_rR^{20}$, —$C(=O)CF_3$, —$C(=O)OR^{20}$, —$P(=O)R^{13}R^{14}$, or, —$P(=O)NR^{11}R^{12}$;

$R^{20}$ is —$Si(alkyl)_3$, —$Si(alkyl)_2aryl$, or $Si(aryl)_2alkyl$; and m is an integer from 0 to 3;

n and o are each independently an integer from 0 to 4;

p is 1 or 2; and r is an integer from 1 to 4.

Embodiment 14

The method of embodiment 10, wherein the compound of Formula (IV) is:

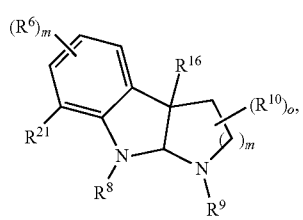

Formula (IVa)

wherein $R^{16}$ is I, Br, Cl, —OH, —$OSO_2CF_3$, —$OS(O)_2R^{13}$, —OP(=O)$R^{13}R^{14}$, —$OC(=NR^{11})R^{12}$, —$OC(=NR^{11})CCl_3$, —$OR^{11}$, or —$N_2^+X^-$, wherein $X^-$ is halogen;

$R^{21}$ is H, halogen, alkyl, alkenyl, alkynyl, aryl, heteroaryl, carbocyclyl, heterocyclyl, —$N_3$,

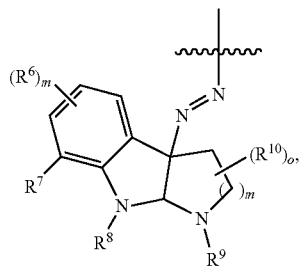

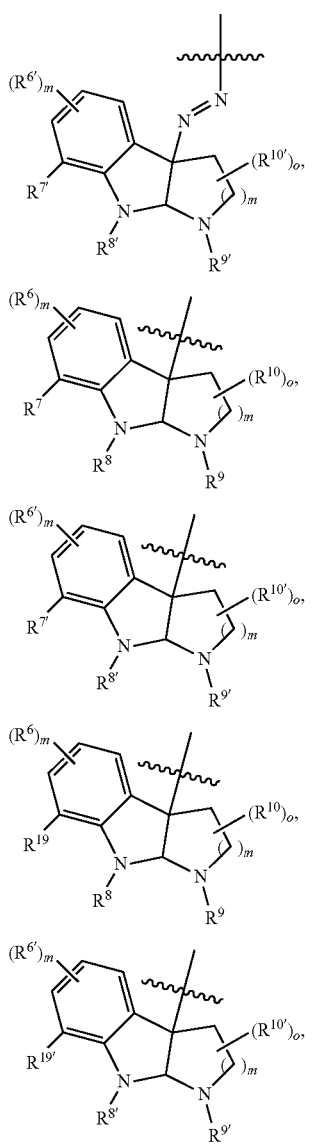

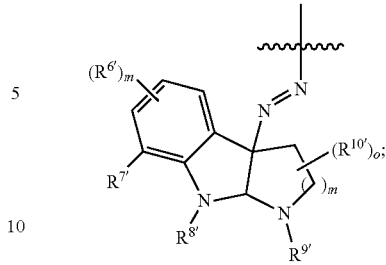

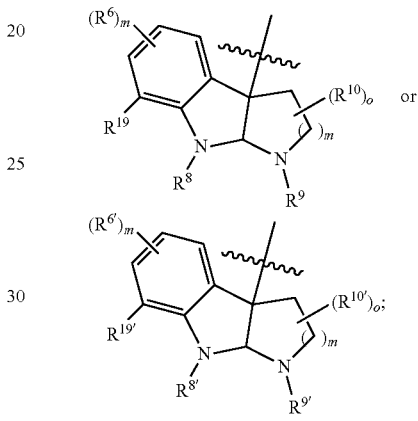

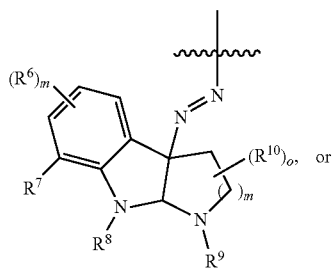

wherein
R$^7$ and R$^{7'}$ are each independently selected from H, —N$_3$, —N(R$^{15}$)NH$_2$, —NHR$^{15}$, and wherein
R$^{19}$ and R$^{19'}$ are each independently selected from H, tertiary alkyl, alkenyl, aryl, heteroaryl, carbocyclyl, heterocyclyl, R$^6$ and R$^{6'}$ are each independently selected from halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O) NR$^{11}$NR$^{12}$, C$_1$-C$_{12}$ alkyl, C$_2$-C$_{12}$ alkenyl, C$_2$-C$_{12}$ alkynyl, aryl, heteroaryl, carbocyclyl, or heterocyclyl; wherein two R$^6$ or two R$^{6'}$ groups taken together with the carbon atoms to which they are attached form an aryl, heteroaryl, carbocyclic, or heterocyclic ring;

R$^8$, R$^{8'}$, R$^9$, and, R$^{9'}$ are each independently selected from H, C$_1$-C$_{12}$ alkyl, C$_2$-C$_{12}$ alkenyl, C$_2$-C$_{12}$ alkynyl, —C(=O) R$^{11}$, —C(=O)OR$^{11}$, —C(=O)NR$^{11}$R$^{12}$, —SR$^{11}$, —S(=O)$_p$R$^{13}$, —S(=O)$_2$NR$^{11}$R$^{12}$, —C(=O)O(CH$_2$)$_o$R$^{11}$, aryl, heteroaryl, carbocyclyl, or heterocyclyl;

R$^{10}$ and R$^{10'}$ are each independently selected from H, C$_1$-C$_{12}$ alkyl; C$_2$-C$_{12}$ alkenyl, C$_2$-C$_{12}$ alkynyl, —C(=O) R$^{11}$, —C(=O)OR$^{11}$, —C(=O)NR$^{11}$R$^{12}$, —S(=O)$_p$R$^{13}$, —OH, —OR$^{11}$, —OC(=O)R$^{11}$, —NR$^{11}$R$^{12}$, aryl, heteroaryl, carbocyclyl, or heterocyclyl, wherein two R$^{10}$ or two R$^{10'}$ groups taken together with the carbon atoms to which they are attached form an aryl, heteroaryl, carbocyclic, or heterocyclic ring;

R$^{11}$ and R$^{12}$ are each independently selected from H, C$_1$-C$_{12}$ alkyl, C$_2$-C$_{12}$ alkenyl, C$_2$-C$_{12}$ alkynyl, aryl, heteroaryl, carbocyclyl, or heterocyclyl, wherein R$^{11}$ and R$^{12}$ taken together with the carbon atoms to which they are attached form an aryl, heteroaryl, carbocyclic, or heterocyclic ring;

R$^{13}$ and R$^{14}$ are each independently selected from C$_1$-C$_{12}$ alkyl, C$_2$-C$_{12}$ alkenyl, C$_2$-C$_{12}$ alkynyl, aryl, heteroaryl, carbocyclyl, heterocyclyl, —OR$^{11}$, —(CH$_2$)$_r$SiMe$_3$, or —(CH$_2$)$_r$R$^{11}$;

$R^{15}$ is $-S(=O)_pR^{13}$, $-S(=O)_2NR^{11}R^{12}$, $-C(=O)R^{13}$, $-C(=O)R^{20}$, $-C(=O)O(CH_2)_rR^{20}$, $-C(=O)CF_3$, $-C(=O)OR^{20}$, $-P(=O)R^{13}R^{14}$, or, $-P(=O)NR^{11}R^{12}$;

$R^{20}$ is $-Si(alkyl)_3$, $-Si(alkyl)_2aryl$, or $Si(aryl)_2alkyl$; and m is an integer from 0 to 3;

n and o are each independently an integer from 0 to 4;

p is 1 or 2; and r is an integer from 1 to 4.

Embodiment 15

The method of embodiment 1, wherein the compound of Formula (II) is prepared by the extrusion of sulfur dioxide from a compound of Formula (V):

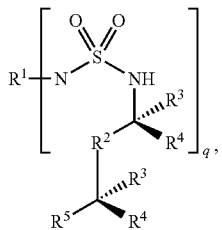

Formula (V)

wherein $R^1$ is tertiary alkyl, alkenyl, aryl, heteroaryl, carbocyclyl, or heterocyclyl or at least one moiety of structure:

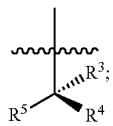

and $R^2$, $R^3$, $R^4$, and $R^5$ are each occurrence, each independently selected from alkyl, aryl, heteroaryl, carbocyclyl, or heterocyclic, wherein any two of $R^3$, $R^4$, and $R^5$ taken together with the carbon atoms to which they are attached form a $C_{5-14}$ membered saturated, unsaturated, or aromatic carbocyclic ring or a $C_{5-14}$ membered saturated, unsaturated, or aromatic heterocyclic ring; and wherein any tertiary alkyl, aryl, heteroaryl, carbocyclyl, or heterocyclyl, $C_{5-14}$ membered saturated, unsaturated, or aromatic carbocyclic ring or a $C_{5-14}$ membered saturated, unsaturated, or aromatic heterocyclic ring can be further substituted with one or more halogen, alkyl, heteroaryl, carbocyclyl, heterocyclyl, $C_{3-14}$ membered saturated, unsaturated, or aromatic carbocyclic, or $C_{3-14}$ membered saturated, unsaturated, or aromatic heterocyclic rings; and q is an integer of from 0-8.

Embodiment 16

The method of embodiment 15, wherein the compound of Formula (V) is:

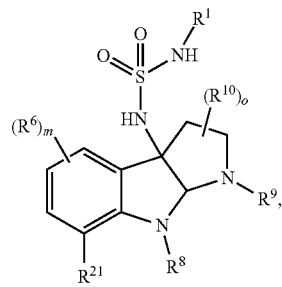

Formula (Va)

wherein $R^1$ is tertiary alkyl, alkenyl, aryl, heteroaryl, carbocyclyl, heterocyclyl,

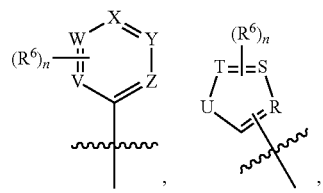

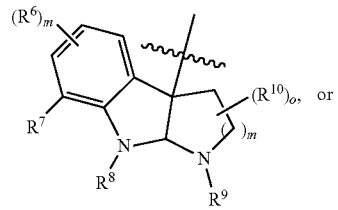

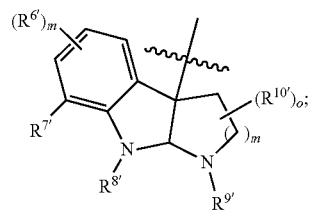

V, W, X, Y, and Z are each independently selected from —CH or N;

R, S, and T are each independently selected from —CH or N;

U is O, S, or $NR^{11}$;

$R^{21}$ is H, halogen, alkyl, alkenyl, alkynyl, aryl, heteroaryl, carbocyclyl, heterocyclyl, $-N_3$,

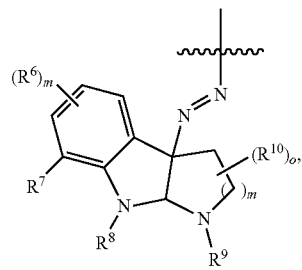

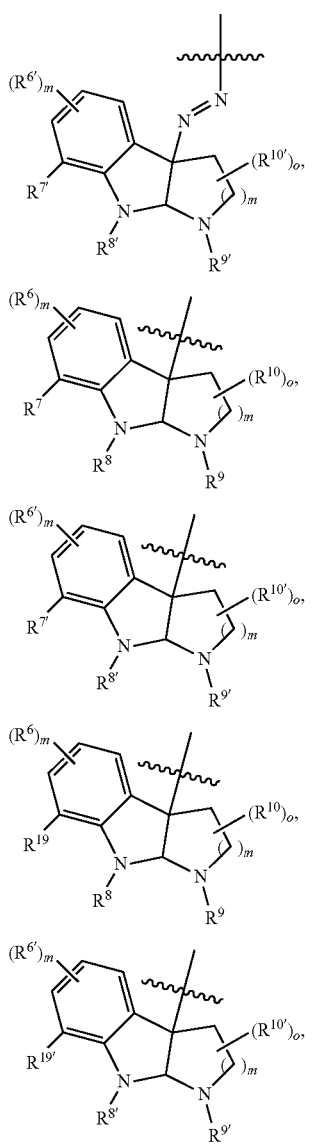

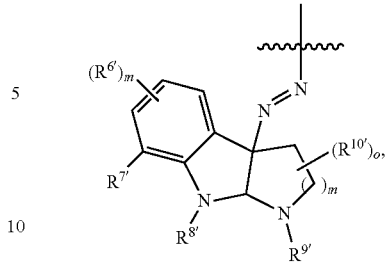

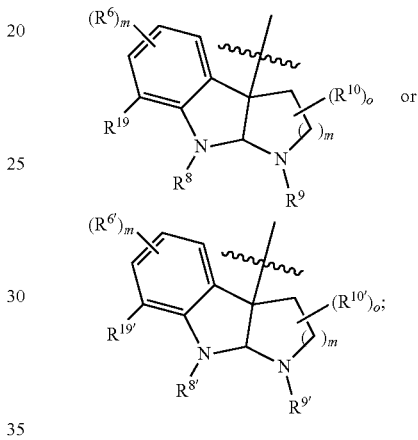

and wherein
R$^{19}$ and R$^{19'}$ are each independently selected from H, tertiary alkyl, alkenyl, aryl, heteroaryl, carbocyclyl, heterocyclyl, wherein
R$^{7}$ and R$^{7'}$ are each independently selected from H, —N$_3$, —N(R$^{15}$)NH$_2$, —NHR$^{15}$,

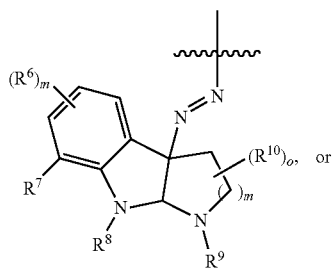

R$^{6}$ and R$^{6'}$ are each independently selected from halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, C$_1$-C$_{12}$ alkyl, C$_2$-C$_{12}$ alkenyl, C$_2$-C$_{12}$ alkynyl, aryl, heteroaryl, carbocyclyl, or heterocyclyl; wherein two R$^{6}$ or two R$^{6'}$ groups taken together with the carbon atoms to which they are attached form an aryl, heteroaryl, carbocyclic, or heterocyclic ring;

R$^{8}$, R$^{8'}$, R$^{9}$, and R$^{9'}$ are each independently selected from H, C$_1$-C$_{12}$ alkyl, C$_2$-C$_{12}$ alkenyl, C$_2$-C$_{12}$ alkynyl, —C(=O)R$^{11}$, —C(=O)OR$^{11}$, —C(=O)NR$^{11}$R$^{12}$, —SR$^{11}$, —S(=O)$_p$R$^{13}$, —S(=O)$_2$NR$^{11}$R$^{12}$, —C(=O)O(CH$_2$)$_o$R$^{11}$, aryl, heteroaryl, carbocyclyl, or heterocyclyl;

R$^{10}$ and R$^{10'}$ are each independently selected from H, C$_1$-C$_{12}$ alkyl, C$_2$-C$_{12}$ alkenyl, C$_2$-C$_{12}$ alkynyl, —C(=O)R$^{11}$, —C(=O)OR$^{11}$, —C(=O)NR$^{11}$R$^{12}$, —S(=O)$_p$R$^{13}$, —OH, —OR$^{11}$, —OC(=O)R$^{11}$, —NR$^{11}$R$^{12}$, aryl, heteroaryl, carbocyclyl, or heterocyclyl, wherein two R$^{10}$ or two R$^{10'}$ groups taken together with the carbon atoms to which they are attached form an aryl, heteroaryl, carbocyclic, or heterocyclic ring;

R$^{11}$ and R$^{12}$ are each independently selected from H, C$_1$-C$_{12}$ alkyl, C$_2$-C$_{12}$ alkenyl, C$_2$-C$_{12}$ alkynyl, aryl, heteroaryl, carbocyclyl, or heterocyclyl, wherein R$^{11}$ and R$^{12}$ taken together with the carbon atoms to which they are attached form an aryl, heteroaryl, carbocyclic, or heterocyclic ring;

R$^{13}$ and R$^{14}$ are each independently selected from C$_1$-C$_{12}$ alkyl, C$_2$-C$_{12}$ alkenyl, C$_2$-C$_{12}$ alkynyl, aryl, heteroaryl, carbocyclyl, heterocyclyl, —OR$^{11}$, —(CH$_2$)$_r$SiMe$_3$, or —(CH$_2$)$_r$R$^{11}$;

$R^{15}$ is $-S(=O)_pR^{13}$, $-S(=O)_2NR^{11}R^{12}$, $-C(=O)R^{13}$, $-C(=O)R^{20}$, $-C(=O)O(CH_2)_rR^{20}$, $-C(=O)CF_3$, $-C(=O)OR^{20}$, $-P(=O)R^{13}R^{14}$, or, $-P(=O)NR^{11}R^{12}$;

$R^{20}$ is $-Si(alkyl)_3$, $-Si(alkyl)_2aryl$, or $Si(aryl)_2alkyl$; and m is an integer from 0 to 3;
n and o are each independently an integer from 0 to 4;
p is 1 or 2; and
r is an integer from 1 to 4.

Embodiment 17

The method of embodiment 15, wherein the compound of Formula (V) is prepared by the following steps:

a. reacting a compound of Formula (VI), and a compound of Formula (IV) to give a compound of Formula (VII):

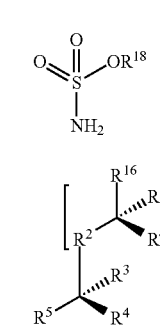

Formula (VI)

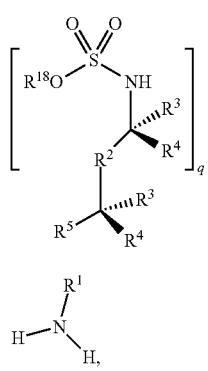

Formula (IV)

wherein
$R^{16}$ is I, Br, Cl, $-OH$, $-OSO_2CF_3$, $-OS(O)_2R^{13}$, $-OP(=O)R^{13}R^{14}$, $-OC(=NR^{11})R^{12}$, $-OC(=NR^{11})CCl_3$, $-OR^{11}$, or $-N_2^+X^-$, wherein $X^-$ is halogen; and
$R^{18}$ is aryl, or heteroaryl; and b. reacting a compound of Formula (VII), and a compound of Formula (VIII) to provide the compound of Formula (VI):

Formula (VII)

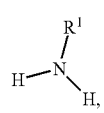

Formula (VIII)

wherein
$R^1$ is tertiary alkyl, alkenyl, aryl, heteroaryl, carbocyclyl, or heterocyclyl.

Embodiment 18

The method of embodiment 17, wherein the compound of Formula (VII) is:

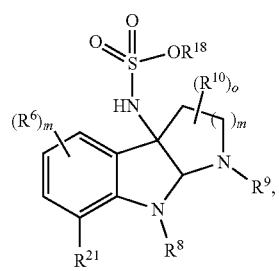

Formula (VIIa)

wherein
$R^{21}$ is H, halogen, alkyl, alkenyl, alkynyl, aryl, heteroaryl, carbocyclyl, heterocyclyl, $-N_3$,

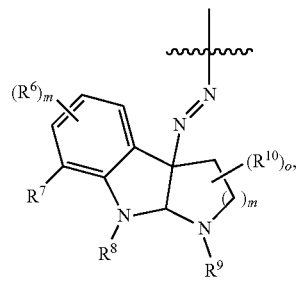

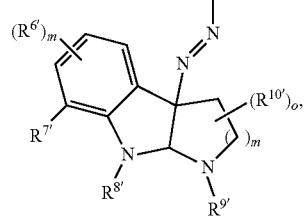

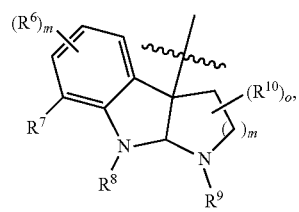

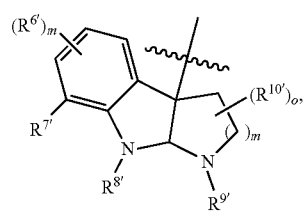

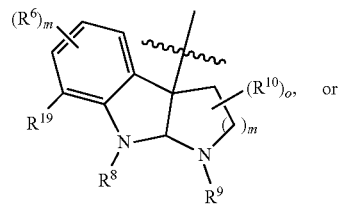 or

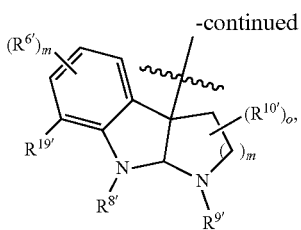

wherein $R^7$ and $R^{7'}$ are each independently selected from H, $-N_3$, $-N(R^{15})NH_2$, $-NHR^{15}$,

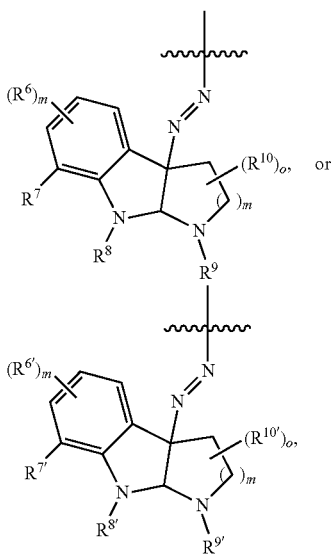

and wherein $R^{19}$ and $R^{19'}$ are each independently selected from H, tertiary alkyl, alkenyl, aryl, heteroaryl, carbocyclyl, heterocyclyl,

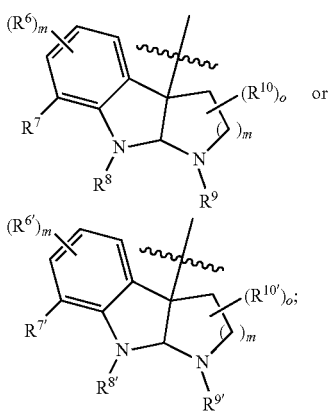

$R^6$ and $R^{6'}$ are each independently selected from halogen, $-OH$, $-OR^{11}$, $-OC(=O)R^{11}$, $-NR^{11}R^{12}$, $-S(=O)_pR^{13}$, $-C(=O)R^{11}$, $-C(=O)OR^{11}$, $-C(=O)NR^{11}NR^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl; wherein two $R^6$ or two $R^{6'}$ groups taken together with the carbon atoms to which they are attached form an aryl, heteroaryl, carbocyclic, or heterocyclic ring;

$R^8$, $R^{8'}$, $R^9$, and $R^{9'}$ are each independently selected from H, $C_1$-$C_{12}$ alkyl, $C_2$-$C_{12}$ alkenyl, $C_2$-$C_2$ alkynyl, $-C(=O)R^{11}$, $-C(=O)OR^{11}$, $-C(=O)NR^{11}R^{12}$, $-SR^{11}$, $-S(=O)_pR^{13}$, $-S(=O)_2NR^{11}R^{12}$, $-C(=O)O(CH_2)_oR^{11}$, aryl, heteroaryl, carbocyclyl, or heterocyclyl;

$R^{10}$ and $R^{10'}$ are each independently selected from H, $C_1$-$C_{12}$ alkyl; $C_2$-$C_{12}$ alkenyl, $C_2$-$C_{12}$ alkynyl, $-C(=O)R^{11}$, $-C(=O)OR^{11}$, $-C(=O)NR^{11}R^{12}$, $-S(=O)_pR^{13}$, $-OH$, $-OR^{11}$, $-OC(=O)R^{11}$, $-NR^{11}R^{12}$, aryl, heteroaryl, carbocyclyl, or heterocyclyl, wherein two $R^{10}$ or two $R^{10'}$ groups taken together with the carbon atoms to which they are attached form an aryl, heteroaryl, carbocyclic, or heterocyclic ring;

$R^{11}$ and $R^{12}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;

$R^{13}$ and $R^{14}$ are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, $-OR^{11}$, $-(CH_2)_rSiMe_3$, or $-(CH_2)_rR^{11}$;

$R^{15}$ is $-S(=O)_pR^{13}$, $-S(=O)_2NR^{11}R^{12}$, $-C(=O)R^{13}$, $-C(=O)R^{20}$, $-C(=O)O(CH_2)_rR^{20}$, $-C(=O)CF_3$, $-C(=O)OR^{20}$, $-P(=O)R^{13}R^{14}$, or, $-P(=O)NR^{11}R^{12}$;

$R^{18}$ is

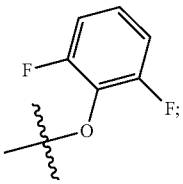 [SMILES: *Oc1c(F)cccc1F]

$R^{20}$ is $-Si(alkyl)_3$, $-Si(alkyl)_2aryl$, or $Si(aryl)_2alkyl$; and m is an integer from 0 to 3;
n and o are each independently an integer from 0 to 4;
p is 1 or 2; and
r is an integer from 1 to 4.

Embodiment 19

The method of embodiment 17, wherein the compound of Formula (VIII) is:

Formula (VIIIa)

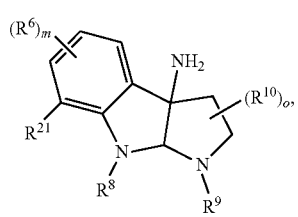

wherein $R^{21}$ is H, halogen, alkyl, alkenyl, alkynyl, aryl, heteroaryl, carbocyclyl, heterocyclyl, $-N_3$,

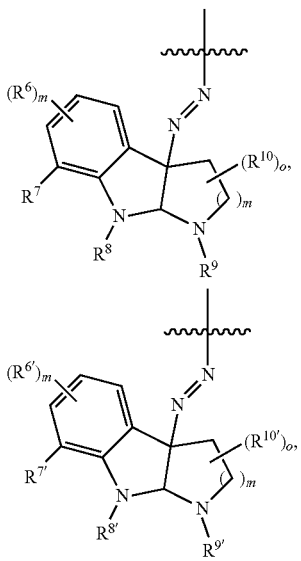

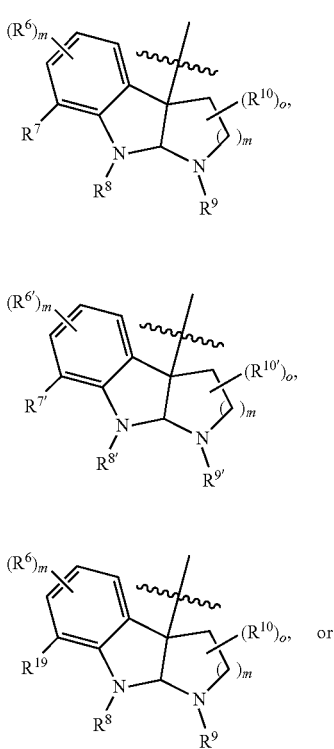

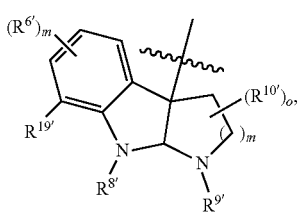

wherein $R^7$ and $R^{7'}$ are each independently selected from H, —$N_3$, —$N(R^{15})NH_2$, —$NHR^{15}$,

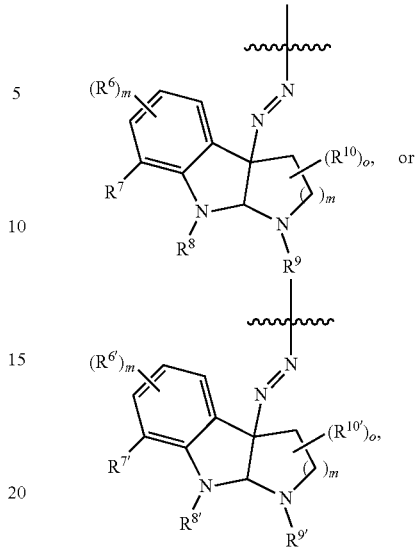

and wherein $R^{19}$ and $R^{19'}$ are each independently selected from H, tertiary alkyl, alkenyl, aryl, heteroaryl, carbocyclyl, heterocyclyl,

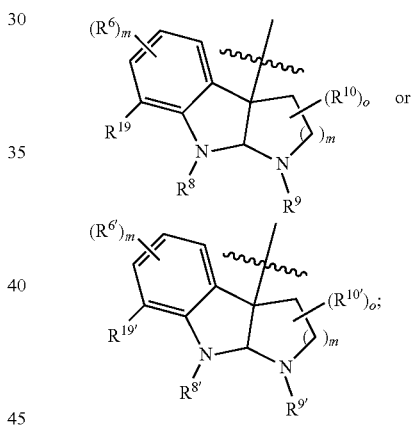

$R^6$ and $R^{6'}$ are each independently selected from halogen, —OH, —$OR^{11}$, —$OC(=O)R^{11}$, —$NR^{11}R^{12}$, —$S(=O)_pR^{13}$, —$C(=O)R^{11}$, —$C(=O)OR^{11}$, —$C(=O)NR^{11}NR^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl; wherein two $R^6$ or two $R^{6'}$ groups taken together with the carbon atoms to which they are attached form an aryl, heteroaryl, carbocyclic, or heterocyclic ring;

$R^8$, $R^{8'}$, $R^9$, and $R^{9'}$ are each independently selected from H, $C_1$-$C_{12}$ alkyl, $C_2$-$C_{12}$ alkenyl, $C_2$-$C_{12}$ alkynyl, —$C(=O)R^{11}$, —$C(=O)OR^{11}$, —$C(=O)NR^{11}R^{12}$, —$SR^{11}$, —$S(=O)_pR^{13}$, —$S(=O)_2NR^{11}R^{12}$, —$C(=O)O(CH_2)_oR_{11}$, aryl, heteroaryl, carbocyclyl, or heterocyclyl;

$R^{10}$ and $R^{10'}$ are each independently selected from H, $C_1$-$C_{12}$ alkyl; $C_2$-$C_{12}$ alkenyl, $C_2$-$C_{12}$ alkynyl, —$C(=O)R^{11}$, —$C(=O)OR^{11}$, —$C(=O)NR^{11}R^{12}$, —$S(=O)_pR^{13}$, —OH, —$OR^{11}$, —$OC(=O)R^{11}$, —$NR^{11}R^{12}$, aryl, heteroaryl, carbocyclyl, or heterocyclyl, wherein two $R^{10}$ or two $R^{10'}$ groups taken together with the carbon atoms to which they are attached form an aryl, heteroaryl, carbocyclic, or heterocyclic ring;

$R^{11}$ and $R^{12}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;

$R^{13}$ and $R^{14}$ are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —$OR^{11}$, —$(CH_2)_rSiMe_3$, or —$(CH_2)_rR^{11}$;

$R^{15}$ is —$S(=O)_pR^{13}$, —$S(=O)_2NR^{11}R^{12}$, —$C(=O)R^{13}$, —$C(=O)R^{20}$, —$C(=O)O(CH_2)_rR^{20}$, —$C(=O)CF_3$, —$C(=O)OR^{20}$, —$P(=O)R^{13}R^{14}$, or, —$P(=O)NR^{11}R^{12}$;

$R^{20}$ is —$Si(alkyl)_3$, —$Si(alkyl)_2aryl$, or $Si(aryl)_2alkyl$; and m is an integer from 0 to 3;

n and o are each independently an integer from 0 to 4;

p is 1 or 2; and r is an integer from 1 to 4.

Embodiment 20

The method of embodiment 18, wherein the compound of Formula (VIII) is:

Formula (VIIIa)

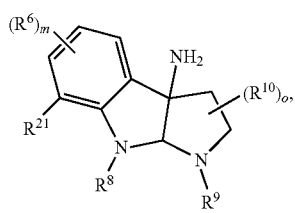

wherein $R^{21}$ is H, halogen, alkyl, alkenyl, alkynyl, aryl, heteroaryl, carbocyclyl, heterocyclyl, —$N_3$,

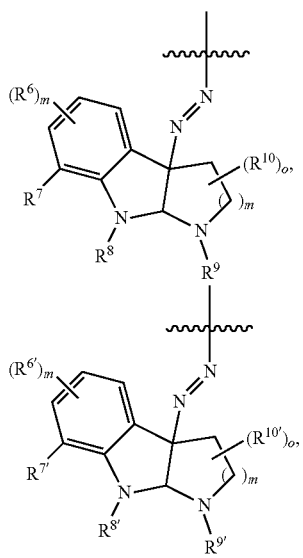

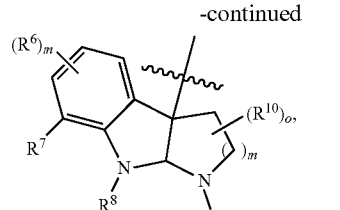

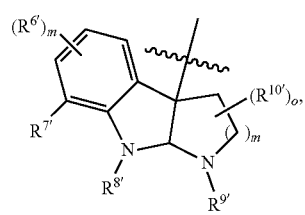

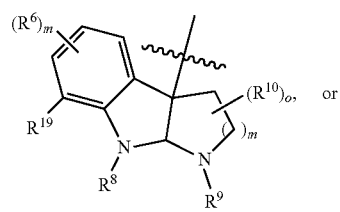

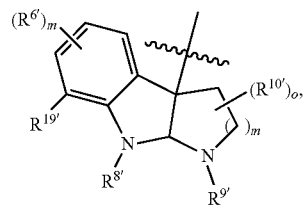

wherein $R^7$ and $R^{7'}$ are each independently selected from H, —$N_3$, —$N(R^{15})NH_2$, —$NHR^{15}$,

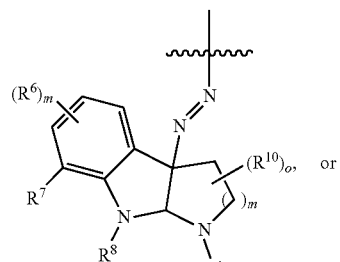

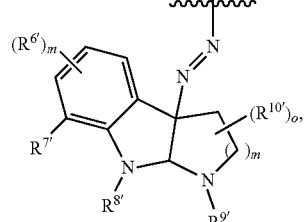

and wherein $R^{19}$ and $R^{19'}$ are each independently selected from H, tertiary alkyl, alkenyl, aryl, heteroaryl, carbocyclyl, heterocyclyl,

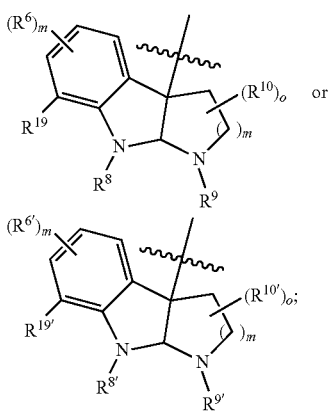

R[6] and R[6'] are each independently selected from halogen, —OH, —OR[11], —OC(=O)R[11], —NR[11]R[12], —S(=O)$_p$R[13], —C(=O)R[11], —C(=O)OR[11], —C(=O)NR[11]NR[12], $C_1$-$C_{12}$ alkyl, $C_2$-$C_{12}$ alkenyl, $C_2$-$C_{12}$ alkynyl, aryl, heteroaryl, carbocyclyl, or heterocyclyl; wherein two R[6] or two R[6'] groups taken together with the carbon atoms to which they are attached form an aryl, heteroaryl, carbocyclic, or heterocyclic ring;

R[8], R[8'], R[9], and R[9'] are each independently selected from H, $C_1$-$C_{12}$ alkyl, $C_2$-$C_{12}$ alkenyl, $C_2$-$C_{12}$ alkynyl, —C(=O)R[11], —C(=O)OR[11], —C(=O)NR[11]R[12], —SR[11], —S(=O)$_p$R[13], —S(=O)$_2$NR[11]R[12], —C(=O)O(CH$_2$)$_o$R[11], aryl, heteroaryl, carbocyclyl, or heterocyclyl;

R[10] and R[10'] are each independently selected from H, $C_1$-$C_{12}$ alkyl; $C_2$-$C_{12}$ alkenyl, $C_2$-$C_{12}$ alkynyl, —C(=O)R[11], —C(=O)OR[11], —C(=O)NR[11]R[12], —S(=O)$_p$R[13], —OH, —OR[11], —OC(=O)R[11], —NR[11]R[12], aryl, heteroaryl, carbocyclyl, or heterocyclyl, wherein two R[10] or two R[10'] groups taken together with the carbon atoms to which they are attached form an aryl, heteroaryl, carbocyclic, or heterocyclic ring;

R[11] and R[12] are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein R[11] and R[12] taken together with the carbon atoms to which they are attached form an aryl, heteroaryl, carbocyclic, or heterocyclic ring;

R[13] and R[14] are each independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —OR[11], —(CH$_2$)$_r$SiMe$_3$, or —(CH$_2$)$_r$R[11];

R[15] is —S(=O)$_p$R[13], —S(=O)$_2$NR[11]R[12], —C(=O)R[13], —C(=O)R[20], —C(=O)O(CH$_2$)$_r$R[20], —C(=O)CF$_3$, —C(=O)OR[20], —P(=O)R[13]R[14], or, —P(=O)NR[11]R[12];

R[20] is —Si(alkyl)$_3$, —Si(alkyl)$_2$aryl, or Si(aryl)$_2$alkyl; and m is an integer from 0 to 3;
n and o are each independently an integer from 0 to 4;
p is 1 or 2; and
r is an integer from 1 to 4.

Embodiment 21

The method of embodiment 1, wherein the reaction is a radical recombination reaction.

Embodiment 22

The method of embodiment 21, wherein the reaction is carried out by irradiation.

Embodiment 23

The method of embodiment 22, wherein the irradiation occurs in a photoreactor.

Embodiment 24

The method of embodiment 23, wherein the photoreactor is equipped with 1 to about 20 lamps operating at a wavelength λ from about 250 nm to about 400 nm.

Embodiment 25

The method of embodiment 24 wherein the wavelength λ is 300 nm or 380 nm.

Embodiment 26

The method of embodiment 21, wherein the radical recombination reaction results in the formation of a Csp3-Csp3 bond or a Csp3-Csp2 bond.

Embodiment 27

The method of embodiment 1, wherein the stereochemical configuration of the compound of Formula (II) is retained in the compound of Formula (I) following the reaction.

Embodiment 28

The method of embodiment 7, wherein the reaction comprises an electrophilic activation of a compound of Formula (IV).

Embodiment 29

The method of embodiment 28, wherein the electrophilic activation comprises reaction of the compound of Formula (IV) with a silver (I) salt, and a base.

Embodiment 30

The method of embodiment 29, wherein the silver (I) salt is AgOSO$_2$CF$_3$ or AgSF$_6$.

Embodiment 31

The method of embodiment 29, wherein the compound of Formula (III) is resistant to oxidation by the silver (I) salt.

Embodiment 32

The method of embodiment 15, wherein the sulfur dioxide extrusion is carried out in the presence of an oxidizing agent.

Embodiment 33

The method of embodiment 32, wherein the oxidizing agent is an electrophilic halogenating reagent.

Embodiment 34

The method of embodiment 1, wherein the compounds of Formula (I) are:

121
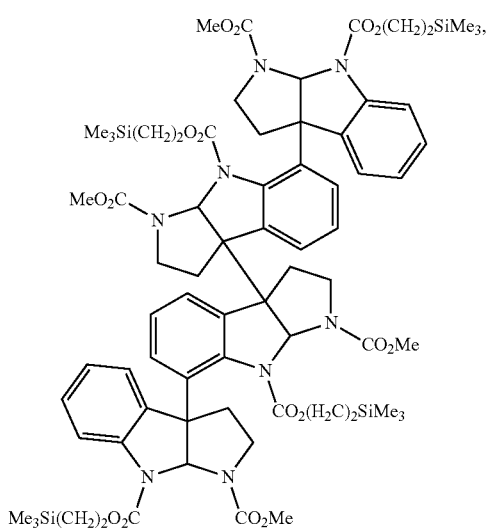
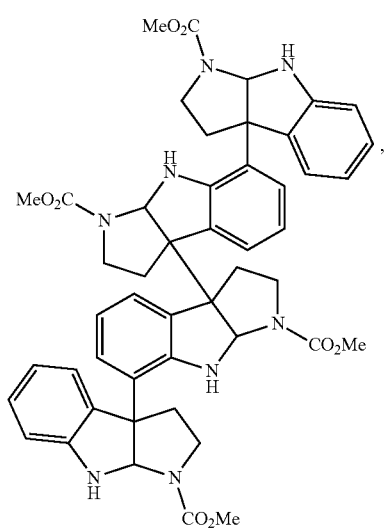
,
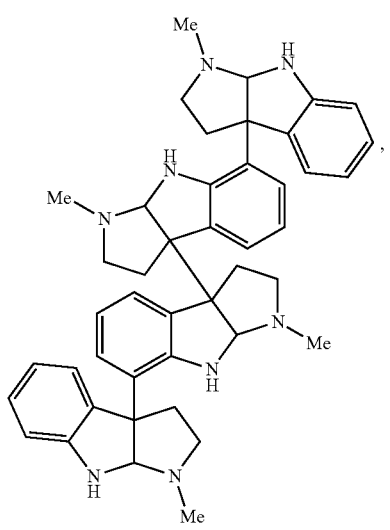
,
122
-continued
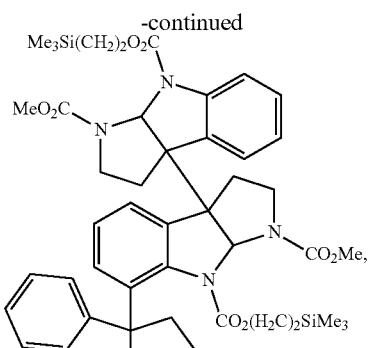
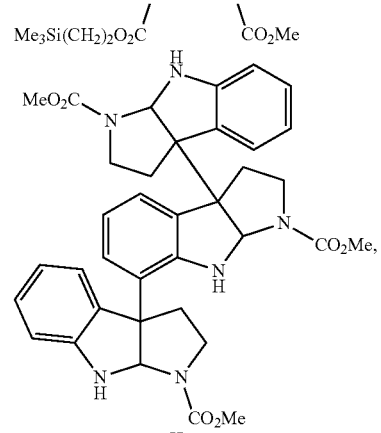
,
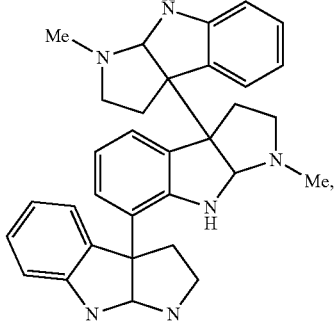
,
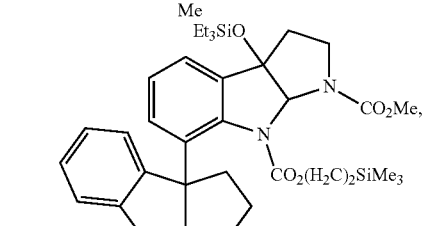
,
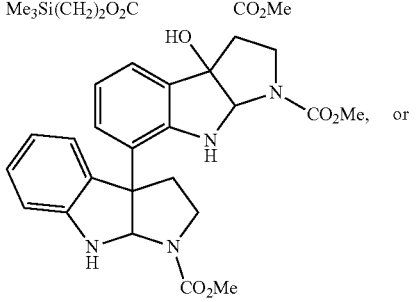
or -continued

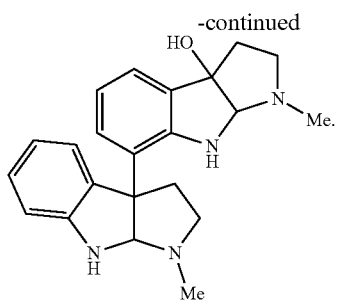

In another aspect, the present disclosure provides a method of preparing a compound of Formula (II'):

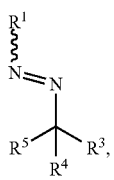

Formula (II')

or a salt, tautomer, or stereoisomer thereof, comprising reacting a compound of Formula (III'), or a salt, tautomer, or stereoisomer thereof, and a compound of Formula (IV'), or a salt, tautomer, or stereoisomer thereof:

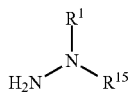

Formula (III')

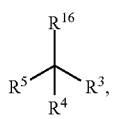

Formula (IV')

wherein:

$R^1$ is alkenyl, aryl, or heteroaryl;

zero, one, two, or three of (i) $R^3$ and $R^4$, (ii) $R^3$ and $R^5$, and (iii) $R^4$ and $R^5$ taken together with the carbon atoms to which they are attached independently form a substituted or unsubstituted, 5-14 membered ring, and the remaining $R^3$, $R^4$, and/or $R^5$ are independently absent, alkyl, aryl, heteroaryl, carbocyclyl, or heterocyclyl, provided that each of $R^4$ and $R^5$ is not absent;

each instance of $R^{11}$ and $R^{12}$ is independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^{11}$ and $R^{12}$ taken together with the carbon atoms to which they are attached form an aryl, heteroaryl, carbocyclic, or heterocyclic ring;

each instance of $R^{13}$ and $R^{14}$ is independently selected from $C_1$-$C_{12}$ alkyl, $C_2$-$C_{12}$ alkenyl, $C_2$-$C_{12}$ alkynyl, aryl, heteroaryl, carbocyclyl, heterocyclyl, —$OR^{11}$, —$(CH_2)_rSiMe_3$, or —$(CH_2)_rR^{11}$;

each instance of $R^{15}$ is independently —$S(=O)_pR^{13}$, —$S(=O)_2NR^{11}R^{12}$, —$C(=O)R^{13}$, —$C(=O)R^{20}$, —$C(=O)O(CH_2)_rR^{20}$, —$C(=O)CF_3$, —$C(=O)OR^{20}$, —$P(=O)R^{13}R^{14}$, or, —$P(=O)NR^{11}R^{12}$;

each instance of $R^{16}$ is independently I, Br, Cl, —OH, —$OSO_2CF_3$, —$OS(O)_2R^{13}$, —$OP(=O)R^{13}R^{14}$, —$OC(=NR^{11})R^{12}$, —$OC(=NR^{11})CCl_3$, —$OR^{11}$, or —$N_2^+X^-$, wherein $X^-$ is halogen;

each instance of $R^{20}$ is independently —$Si(alkyl)_3$, —$Si(alkyl)_2aryl$, or $Si(aryl)_2alkyl$;

each instance of p is independently 1 or 2; and each instance of r is independently an integer from 1 to 4.

In certain embodiments, a compound of Formula (II'), or a salt, tautomer, or stereoisomer thereof, is of the formula:

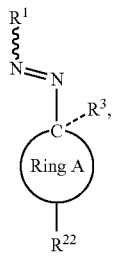

Formula (II'-A)

or a salt, tautomer, or stereoisomer thereof, and a compound of Formula (IV'), or a salt, tautomer, or stereoisomer thereof, is of the formula:

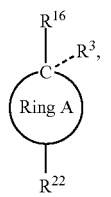

Formula (IV'-A)

or a salt, tautomer, or stereoisomer thereof, wherein:

Ring A is a substituted or unsubstituted, 5-14 membered ring;

------ is a single bond or absent;

$R^3$ is absent, alkyl, aryl, heteroaryl, carbocyclyl, or heterocyclyl, or $R^3$ is fused to Ring A to additionally form a substituted or unsubstituted, 5-14 membered ring;

$R^{22}$ is absent, hydrogen, alkyl, aryl, heteroaryl, carbocyclyl, heterocyclyl, —N=N-aryl, —N=N-heteroaryl, —N=N-carbocyclyl, or —N=N-heterocyclyl.

In certain embodiments, Ring A is a substituted or unsubstituted, 5-14 membered ring, saturated, unsaturated, or aromatic, carbocyclic ring or a substituted or unsubstituted, 5-14 membered, saturated, unsaturated, or aromatic, heterocyclic ring;

$R^3$ is absent, alkyl, aryl, heteroaryl, carbocyclyl, or heterocyclyl, or $R^3$ is fused to Ring A to additionally form a substituted or unsubstituted, 5-14 membered, saturated, unsaturated, or aromatic, carbocyclic ring or a substituted or unsubstituted, 5-14 membered, saturated, unsaturated, or aromatic, heterocyclic ring.

Ring A comprises one or more carbon atoms in the ring system. In certain embodiments, Ring A is substituted or unsubstituted, 5-14 membered, monocyclic ring. In certain embodiments, Ring A is substituted or unsubstituted, 5-14 membered, bicyclic ring. In certain embodiments, Ring A is substituted or unsubstituted, 5-14 membered, tricyclic ring.

In certain embodiments, $R^3$ is fused to Ring A to additionally form a substituted or unsubstituted, 5-14 membered, monocyclic ring. In certain embodiments, $R^3$ is fused to Ring A to additionally form a substituted or unsubstituted, 5-7 membered, monocyclic ring.

In certain embodiments, a ring is a carbocyclic ring. In certain embodiments, a ring is a heterocyclic ring. In certain embodiments, a ring is an aryl ring. In certain embodiments, a ring is a heteroaryl ring.

In certain embodiments, a compound of Formula (IV'-A), or a salt, tautomer, or stereoisomer thereof, is of the formula:

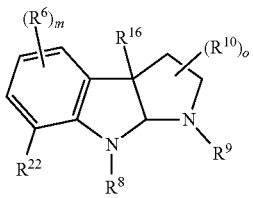

Formula (IV'-B) or a salt, tautomer, or stereoisomer thereof, wherein:

each instance of $R^6$ is independently halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl, or two $R^6$ groups taken together with the carbon atoms to which they are attached form an aryl, heteroaryl, carbocyclic, or heterocyclic ring;

each instance of $R^8$ and $R^9$ is independently H, $C_1$-$C_{12}$ alkyl, $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —SR$^{11}$, —S(=O)$_p$R$^{13}$, —S(=O)$_2$NR$^{11}$R$^{12}$, —C(=O)O(CH$_2$)$_o$R$^{11}$, aryl, heteroaryl, carbocyclyl, heterocyclyl, —C(=O)OCH$_2$CH$_2$Si(CH$_3$)$_3$, or nitrogen protecting group;

each instance of $R^{10}$ is independently selected from H, $C_1$-$C_{12}$ alkyl; $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —S(=O)$_p$R$^{13}$, —OH, —OR$^{11}$, —OC(=O)R$^{11}$, —NR$^{11}$R$^{12}$, aryl, heteroaryl, carbocyclyl, or heterocyclyl, or two $R^{10}$ groups taken together with the carbon atoms to which they are attached form an aryl, heteroaryl, carbocyclic, or heterocyclic ring;

each instance of o is independently an integer from 0 to 4; and each instance of m is an integer from 0 to 3.

In certain embodiments, $R^{22}$ is

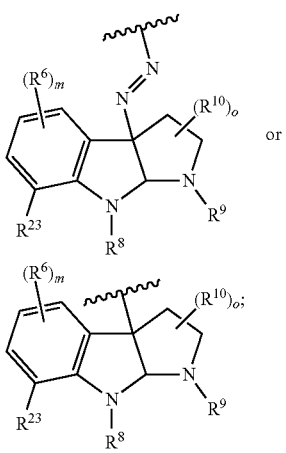

and $R^{23}$ is absent, hydrogen, alkyl, aryl, heteroaryl, carbocyclyl, heterocyclyl, —N=N-aryl, —N=N-heteroaryl, —N=N-carbocyclyl, or —N=N-heterocyclyl.

In certain embodiments, the compound of Formula (III'), or a salt, tautomer, or stereoisomer thereof, is of the formula:

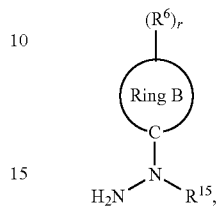

or a salt, tautomer, or stereoisomer thereof, wherein:

Ring B is a substituted or unsubstituted, 5-14 membered ring;

each instance of $R^6$ is independently halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl, or two $R^6$ groups taken together with the carbon atoms to which they are attached form an aryl, heteroaryl, carbocyclic, or heterocyclic ring; and r is an integer from 0 to 5.

Ring B comprises one or more carbon atoms in the ring system. In certain embodiments, Ring B is substituted or unsubstituted, 5-14 membered, monocyclic ring. In certain embodiments, Ring B is substituted or unsubstituted, 5-14 membered, bicyclic ring. In certain embodiments, Ring B is substituted or unsubstituted, 5-14 membered, tricyclic ring.

In certain embodiments, the compound of Formula (III'), or a salt, tautomer, or stereoisomer thereof, is of the formula:

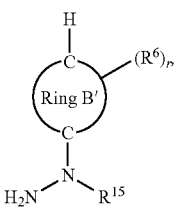

or a salt, tautomer, or stereoisomer thereof, wherein Ring B' is a substituted or unsubstituted, 5-14 membered ring comprising two or more carbon atoms in the ring system.

In certain embodiments, the compound of Formula (III') or a salt, tautomer, or stereoisomer thereof, is of the formula:

Formula (III'-A)

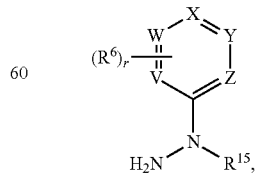

or a salt, tautomer, or stereoisomer thereof, wherein V, W, X, Y, and Z are each independently —CH or N.

In certain embodiments, the compound of Formula (III'), or a salt, tautomer, or stereoisomer thereof, is of the formula:

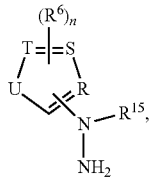

Formula (III'-B)

or a salt, tautomer, or stereoisomer thereof, wherein
R, S, and T are each independently —CH or N; and
U is O, S, or NR$^{11}$, wherein R$^{11}$ is independently H, $C_1$-$C_{12}$ alkyl, $C_2$-$C_{12}$ alkenyl, $C_2$-$C_{12}$ alkynyl, aryl, heteroaryl, carbocyclyl, or heterocyclyl; and
n is an integer from 0 to 4.

In certain embodiments, the compound of Formula (III'), or a salt, tautomer, or stereoisomer thereof, is of the formula:

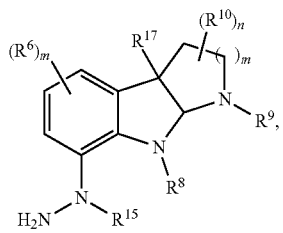

Formula (III'-C)

or a salt, tautomer, or stereoisomer thereof, wherein:
each instance of R$^6$ is independently halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl, or two R$^6$ groups taken together with the carbon atoms to which they are attached form an aryl, heteroaryl, carbocyclic, or heterocyclic ring;
each instance of R$^8$ and R$^9$ is independently H, $C_1$-$C_{12}$ alkyl, $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —SR$^{11}$, —S(=O)$_p$R$^{13}$, —S(=O)$_2$NR$^{11}$R$^{12}$, —C(=O)O(CH$_2$)$_o$R$^{11}$, aryl, heteroaryl, carbocyclyl, heterocyclyl, —C(=O) OCH$_2$CH$_2$Si(CH$_3$)$_3$, or nitrogen protecting group;
each instance of R$^{10}$ is independently H, $C_1$-$C_{12}$ alkyl, $C_2$-$C_{12}$ alkenyl, $C_2$-$C_{12}$ alkynyl, —C(=O)R$^{11}$, —C(=O) OR$^{11}$, —C(=O)NR$^{11}$R$^{12}$, —S(=O)$_p$R$^{13}$, —OH, —OR$^{11}$, —OC(=O)R$^{11}$, —NR$^{11}$R$^{12}$, aryl, heteroaryl, carbocyclyl, or heterocyclyl, or two R$^{10}$ groups taken together with the carbon atoms to which they are attached form an aryl, heteroaryl, carbocyclic, or heterocyclic ring;
R$^{17}$ is H, —OH, —OR$^{11}$, —NR$^{11}$R$^{12}$, aryl, heteroaryl, carbocyclyl, heterocyclyl,

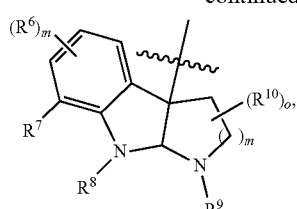

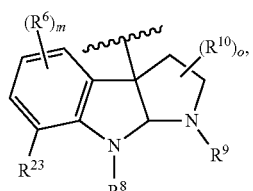

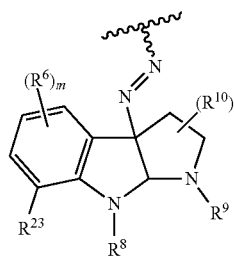 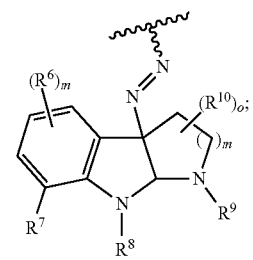

R$^{19}$ is selected from H, alkyl, alkenyl, aryl, heteroaryl, carbocyclyl, heterocyclyl, and

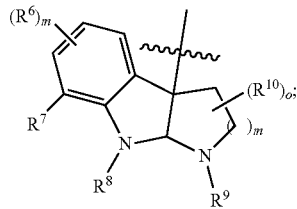

R$^7$ is H, —N$_3$, —N(R$^{15}$)NH$_2$, —NHR$^{15}$, hydrogen, alkyl, aryl, heteroaryl, carbocyclyl, heterocyclyl, —N=N-aryl, —N=N-heteroaryl, —N=N-carbocyclyl, or —N=N-heterocyclyl;

R$^{23}$ is absent, hydrogen, alkyl, aryl, heteroaryl, carbocyclyl, heterocyclyl, —N=N-aryl, —N=N-heteroaryl, —N=N-carbocyclyl, or —N=N-heterocyclyl;

m is an integer from 0 to 3; and n and o are each independently an integer from 0 to 4.

In certain embodiments, a method described herein further comprises reacting a compound of Formula (VI'):

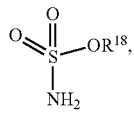

or a salt, tautomer, or stereoisomer thereof, and a compound of Formula (II'), or a salt, tautomer, or stereoisomer thereof, to provide a compound of Formula (VII'):

Formula (VII')

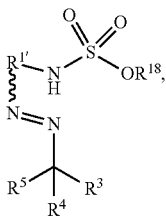

or a salt, tautomer, or stereoisomer thereof, wherein:
R[1'] is alkenylene, arylene, or heteroarylene; and
R[18] is aryl or heteroaryl.

In certain embodiments, $R^1$ is $R^{1'}$—H.

In certain embodiments, a method described herein further comprises reacting a compound of Formula (VII'):

Formula (VII')

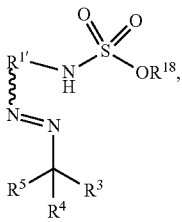

or a salt, tautomer, or stereoisomer thereof, and a compound of Formula (VIII'):

Formula (VIII')

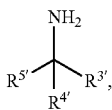

or a salt, tautomer, or stereoisomer thereof, to provide the compound of Formula (IX'):

Formula (IX')

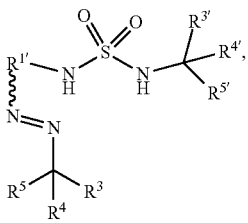

or a salt, tautomer, or stereoisomer thereof, wherein:
zero, one, two, or three of (i) $R^{3'}$ and $R^{4'}$, (ii) $R^{3'}$ and $R^{5'}$, and (iii) $R^{4'}$ and $R^{5'}$ taken together with the carbon atoms to which they are attached independently form a substituted or unsubstituted, 5-14 membered ring, and the remaining $R^{3'}$, $R^{4'}$, and/or $R^{5'}$ are independently absent, alkyl, aryl, heteroaryl, carbocyclyl, or heterocyclyl, provided that each of $R^{4'}$ and $R^{5'}$ is not absent.

In certain embodiments, the compound of Formula (VIII'), or a salt, tautomer, or stereoisomer thereof, is of the formula:

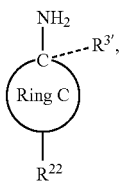

or a salt, tautomer, or stereoisomer thereof, wherein:
Ring C is a substituted or unsubstituted, 5-14 membered ring;
------ is a single bond or absent;
$R^{3'}$ is absent, alkyl, aryl, heteroaryl, carbocyclyl, or heterocyclyl, or $R^{3'}$ is fused to Ring C to additionally form a substituted or unsubstituted, 5-14 membered ring; and
$R^{22}$ is absent, hydrogen, alkyl, aryl, heteroaryl, carbocyclyl, heterocyclyl, —N=N-aryl, —N=N-heteroaryl, —N=N-carbocyclyl, or —N=N-heterocyclyl.

Ring C comprises one or more carbon atoms in the ring system. In certain embodiments, Ring C is substituted or unsubstituted, 5-14 membered, monocyclic ring. In certain embodiments, Ring C is substituted or unsubstituted, 5-14 membered, bicyclic ring. In certain embodiments, Ring C is substituted or unsubstituted, 5-14 membered, tricyclic ring.

In certain embodiments, $R^{3'}$ is fused to Ring C to additionally form a substituted or unsubstituted, 5-14 membered, monocyclic ring. In certain embodiments, $R^{3'}$ is fused to Ring C to additionally form a substituted or unsubstituted, 5-7 membered, monocyclic ring.

In certain embodiments, the compound of Formula (VIII'), or a salt, tautomer, or stereoisomer thereof, is of the formula:

Formula (VIII'-A)

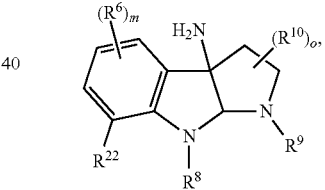

or a salt, tautomer, or stereoisomer thereof, wherein:
each instance of $R^6$ is independently halogen, —OH, —OR[11], —OC(=O)R[11], —NR[11]R[12], —S(=O)$_p$R[13], —C(=O)R[11], —C(=O)OR[11], —C(=O)NR[11]NR[12], $C_1$-$C_{12}$ alkyl, $C_2$-$C_{12}$ alkenyl, $C_2$-$C_{12}$ alkynyl, aryl, heteroaryl, carbocyclyl, or heterocyclyl, or two $R^6$ groups taken together with the carbon atoms to which they are attached form an aryl, heteroaryl, carbocyclic, or heterocyclic ring;
each instance of $R^8$ and $R^9$ is independently H, $C_1$-$C_{12}$ alkyl, $C_2$-$C_{12}$ alkenyl, $C_2$-$C_{12}$ alkynyl, —C(=O)R[11], —C(=O)OR[11], —C(=O)NR[11]R[12], —SR[11], —S(=O)$_p$R[13], —S(=O)$_2$NR[11]R[12], —C(=O)O(CH$_2$)$_o$R[11], aryl, heteroaryl, carbocyclyl, heterocyclyl, —C(=O)OCH$_2$CH$_2$Si(CH$_3$)$_3$, or nitrogen protecting group;
each instance of $R^{10}$ is independently H, $C_1$-$C_{12}$ alkyl; $C_2$-$C_{12}$ alkenyl, $C_2$-$C_{12}$ alkynyl, —C(=O)R[11], —C(=O)OR[11], —C(=O)NR[11]R[12], —S(=O)$_p$R[13], —OH, —OR[11], —OC(=O)R[11], —NR[11]R[12], aryl, heteroaryl, carbocyclyl, or heterocyclyl, or two $R^{10}$ groups taken together with the carbon atoms to which they are attached form an aryl, heteroaryl, carbocyclic, or heterocyclic ring;

$R^{11}$ and $R^{12}$ are each independently H, alkyl, alkenyl, alkynyl, aryl, heteroaryl, carbocyclyl, or heterocyclyl, or $R^{11}$ and $R^{12}$ taken together with the nitrogen atom to which they are attached form a heteroaryl or heterocyclic ring;

$R^{13}$ and $R^{14}$ are each independently alkyl, alkenyl, alkynyl, aryl, heteroaryl, carbocyclyl, heterocyclyl, $-OR^{11}$, $-(CH_2)_oSiMe_3$, or $-(CH_2)_rR^{11}$;

each instance of o is independently an integer from 0 to 4;

p is 1 or 2;

r is an integer from 1 to 4; and each instance of m is an integer from 0 to 3.

In certain embodiments, a method described herein further comprises reacting a compound of Formula (IX'):

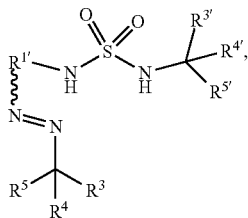

Formula (IX')

or a salt, tautomer, or stereoisomer thereof, by extruding sulfur dioxide to form a compound of Formula (X'):

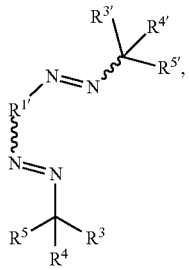

Formula (X')

or a salt, tautomer, or stereoisomer thereof.

In certain embodiments, a method described herein further comprises reacting a compound of Formula (X'):

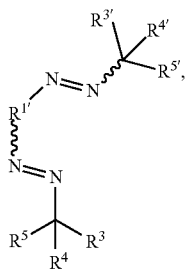

Formula (X')

or a salt, tautomer, or stereoisomer thereof, by extruding one or more equivalents of dinitrogen.

In certain embodiments, a product of reacting a compound of Formula (X'), or a salt, tautomer, or stereoisomer thereof, is a compound of the formula:

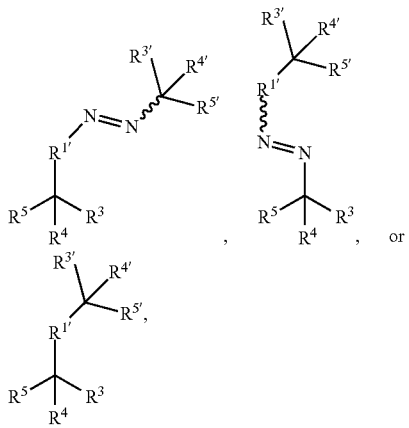

or a salt, tautomer, or stereoisomer thereof.

In certain embodiments, a product of reacting a compound of Formula (X'), or a salt, tautomer, or stereoisomer thereof, is a compound of the formula:

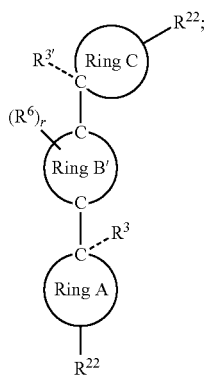

or a salt, tautomer, or stereoisomer thereof, wherein:

each instance of Ring A and Ring C is independently a substituted or unsubstituted, 5-14 membered ring;

Ring B' is a substituted or unsubstituted, 5-14 membered ring comprising two or more carbon atoms in the ring system;

$R^3$ is absent, alkyl, aryl, heteroaryl, carbocyclyl, or heterocyclyl, or $R^3$ attached to Ring A is fused to Ring A to additionally form a substituted or unsubstituted, 5-14 membered ring;

$R^{3'}$ is absent, alkyl, aryl, heteroaryl, carbocyclyl, or heterocyclyl, or $R^{3'}$ attached to Ring C is fused to Ring C to additionally form a substituted or unsubstituted, 5-14 membered ring;

each instance of $R^6$ is independently halogen, $-OH$, $-OR^{11}$, $-OC(=O)R^{11}$, $-NR^{11}R^{12}$, $-S(=O)_pR^{13}$, $-C(=O)R^{11}$, $-C(=O)OR^{11}$, $-C(=O)NR^{11}NR^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl, or two $R^6$ groups taken together with the carbon atoms to which they are attached form an aryl, heteroaryl, carbocyclic, or heterocyclic ring;

r is an integer from 0 to 5; and each instance of $R^{22}$ is independently absent, hydrogen, alkyl, aryl, heteroaryl, carbocyclyl, heterocyclyl, $-N=N-$aryl, $-N=N-$heteroaryl, $-N=N-$carbocyclyl, or $-N=N-$heterocyclyl.

In certain embodiments, a product of reacting a compound of Formula (X'), or a salt, tautomer, or stereoisomer thereof, is of the formula:

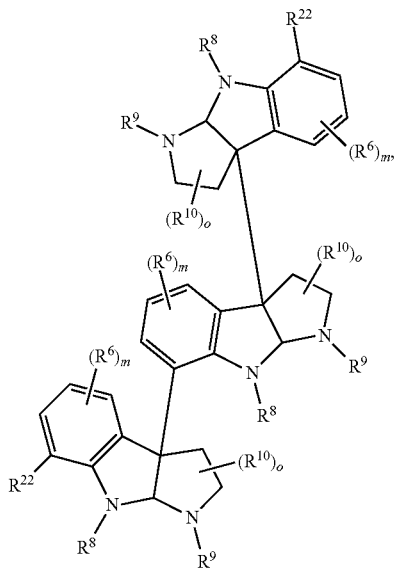

or a salt, tautomer, or stereoisomer thereof, wherein:

each instance of $R^6$ is independently halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl, or two $R^6$ groups taken together with the carbon atoms to which they are attached form an aryl, heteroaryl, carbocyclic, or heterocyclic ring;

each instance of $R^8$ and $R^9$ is independently H, $C_1$-$C_{12}$ alkyl, $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —SR$^{11}$, —S(=O)$_p$R$^{13}$, —S(=O)$_2$NR$^{11}$R$^{12}$, —C(=O)O(CH$_2$)$_o$R$^{11}$, aryl, heteroaryl, carbocyclyl, heterocyclyl, —C(=O)OCH$_2$CH$_2$Si(CH$_3$)$_3$, or nitrogen protecting group;

each instance of $R^{10}$ is independently selected from H, $C_1$-$C_{12}$ alkyl; $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —S(=O)$_p$R$^{13}$, —OH, —OR$^{11}$, —OC(=O)R$^{11}$, —NR$^{11}$R$^{12}$, aryl, heteroaryl, carbocyclyl, or heterocyclyl, or two $R^{10}$ groups taken together with the carbon atoms to which they are attached form an aryl, heteroaryl, carbocyclic, or heterocyclic ring;

each instance of o is independently an integer from 0 to 4;

each instance of m is an integer from 0 to 3; and each instance of $R^{22}$ is independently absent, hydrogen, alkyl, aryl, heteroaryl, carbocyclyl, heterocyclyl, —N=N-aryl, —N=N-heteroaryl, —N=N-carbocyclyl, or —N=N-heterocyclyl.

In certain embodiments, a method described herein further comprises reacting a compound of Formula (II'):

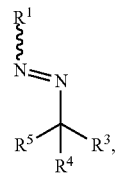

Formula (II')

or a salt, tautomer, or stereoisomer thereof, by extruding one or more equivalents of dinitrogen.

In certain embodiments, a product of reacting a compound of Formula (II'), or a salt, tautomer, or stereoisomer thereof, is a compound of Formula (I'):

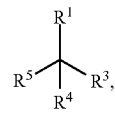

Formula (I')

or a salt, tautomer, or stereoisomer thereof.

In certain embodiments, the compound of Formula (I'), or a salt, tautomer, or stereoisomer thereof, is of the formula:

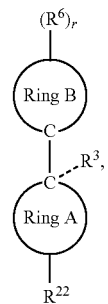

or a salt, tautomer, or stereoisomer thereof, wherein:

$R^{22}$ is absent, hydrogen, alkyl, aryl, heteroaryl, carbocyclyl, heterocyclyl, —N=N-aryl, —N=N-heteroaryl, —N=N-carbocyclyl, or —N=N-heterocyclyl;

Ring A is a substituted or unsubstituted, 5-14 membered ring;

------ is a single bond or absent;

$R^3$ is absent, alkyl, aryl, heteroaryl, carbocyclyl, or heterocyclyl, or $R^3$ is fused to Ring A to additionally form a substituted or unsubstituted, 5-14 membered ring;

Ring B is a substituted or unsubstituted, 5-14 membered ring;

each instance of $R^6$ is independently halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl, or two $R^6$ groups taken together with the carbon atoms to which they are attached form an aryl, heteroaryl, carbocyclic, or heterocyclic ring; and r is an integer from 0 to 5.

In certain embodiments, the compound of Formula (I'), or a salt, tautomer, or stereoisomer thereof, is:

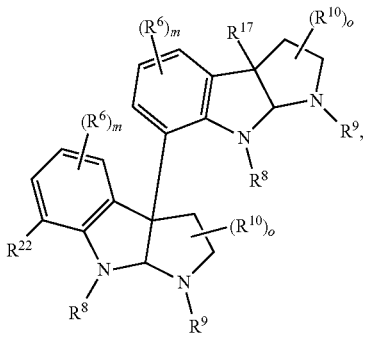

or a salt, tautomer, or stereoisomer thereof, wherein:

each instance of $R^6$ is independently halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl, or two $R^6$ groups taken together with the carbon atoms to which they are attached form an aryl, heteroaryl, carbocyclic, or heterocyclic ring;

each instance of $R^8$ and $R^9$ is independently H, $C_1$-$C_{12}$ alkyl, $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —SR$^{11}$, —S(=O)$_p$R$^{13}$, —S(=O)$_2$NR$^{11}$R$^{12}$, —C(=O)O(CH$_2$)$_o$R$^{11}$, aryl, heteroaryl, carbocyclyl, heterocyclyl, —C(=O)OCH$_2$CH$_2$Si(CH$_3$)$_3$, or nitrogen protecting group;

each instance of $R^{10}$ is independently selected from H, $C_1$-$C_{12}$ alkyl; $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —S(=O)$_p$R$^{13}$, —OH, —OR$^{11}$, —OC(=O)R$^{11}$, —NR$^{11}$R$^{12}$, aryl, heteroaryl, carbocyclyl, or heterocyclyl, or two $R^{10}$ groups taken together with the carbon atoms to which they are attached form an aryl, heteroaryl, carbocyclic, or heterocyclic ring;

each instance of o is independently an integer from 0 to 4;

each instance of m is an integer from 0 to 3;

each instance of $R^{22}$ is independently absent, hydrogen, alkyl, aryl, heteroaryl, carbocyclyl, heterocyclyl, —N=N-aryl, —N=N-heteroaryl, —N=N-carbocyclyl, or —N=N-heterocyclyl;

$R^{17}$ is H, —OH, —OR$^{11}$, —NR$^{11}$R$^{12}$, aryl, heteroaryl, carbocyclyl, heterocyclyl,

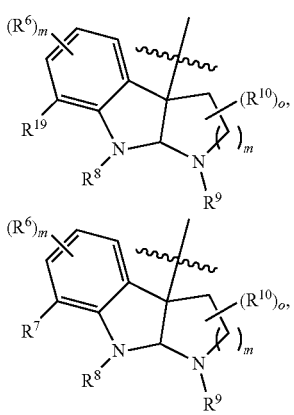

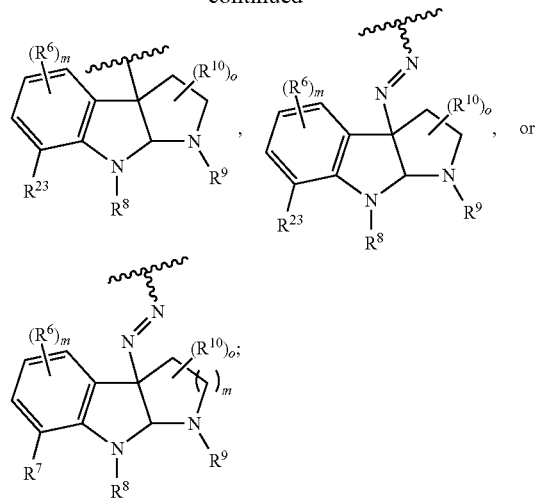

$R^{19}$ is selected from H, alkyl, alkenyl, aryl, heteroaryl, carbocyclyl, heterocyclyl, and

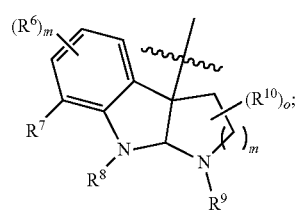

$R^7$ is H, —N$_3$, —N(R$^{15}$)NH$_2$, —NHR$^{15}$, hydrogen, alkyl, aryl, heteroaryl, carbocyclyl, heterocyclyl, —N=N-aryl, —N=N-heteroaryl, —N=N-carbocyclyl, or —N=N-heterocyclyl; and $R^{23}$ is absent, hydrogen, alkyl, aryl, heteroaryl, carbocyclyl, heterocyclyl, —N=N-aryl, —N=N-heteroaryl, —N=N-carbocyclyl, or —N=N-heterocyclyl.

In certain embodiments, the reaction by extruding one or more equivalents of dinitrogen is a radical recombination reaction. In certain embodiments, the reaction by extruding one or more equivalents of dinitrogen is carried out by irradiation. In certain embodiments, the irradiation occurs in a photoreactor. In certain embodiments, the photoreactor is equipped with 1 to about 20 lamps operating at a wavelength λ from about 250 nm to about 400 nm. In certain embodiments, the wavelength λ is about 300 nm or about 380 nm. In certain embodiments, the radical recombination reaction results in the formation of a Csp3-Csp3 bond or a Csp3-Csp2 bond.

In certain embodiments, the reaction of a compound of Formula (III'), or a salt, tautomer, or stereoisomer thereof, and a compound of Formula (IV'), or a salt, tautomer, or stereoisomer thereof, comprises an electrophilic activation of a compound of Formula (IV'), or a salt, tautomer, or stereoisomer thereof. In certain embodiments, the electrophilic activation comprises reaction of the compound of Formula (IV'), or a salt, tautomer, or stereoisomer thereof, with a silver (I) salt, and a base. In certain embodiments, the silver (I) salt is AgOSO$_2$CF$_3$ or AgSF$_6$.

In certain embodiments, the compound of Formula (III'), or a salt, tautomer, or stereoisomer thereof, is resistant to oxidation by the silver (I) salt.

In certain embodiments, the reaction by extruding sulfur dioxide is carried out in the presence of an oxidizing agent. In certain embodiments, the oxidizing agent is an electrophilic halogenating reagent.
In certain embodiments, a product of reacting a compound of Formula (X') or (II'), or a salt, tautomer, or stereoisomer thereof, is of the formula:
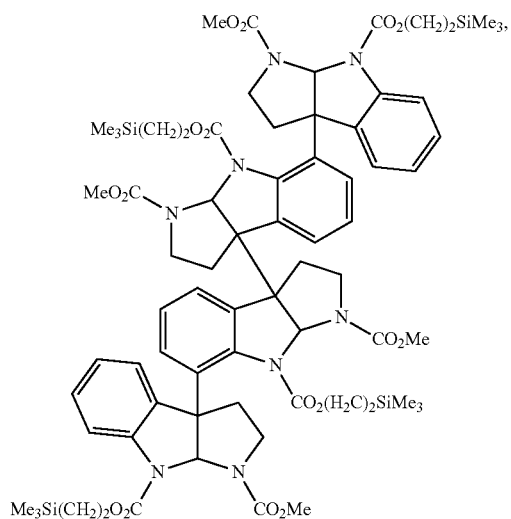
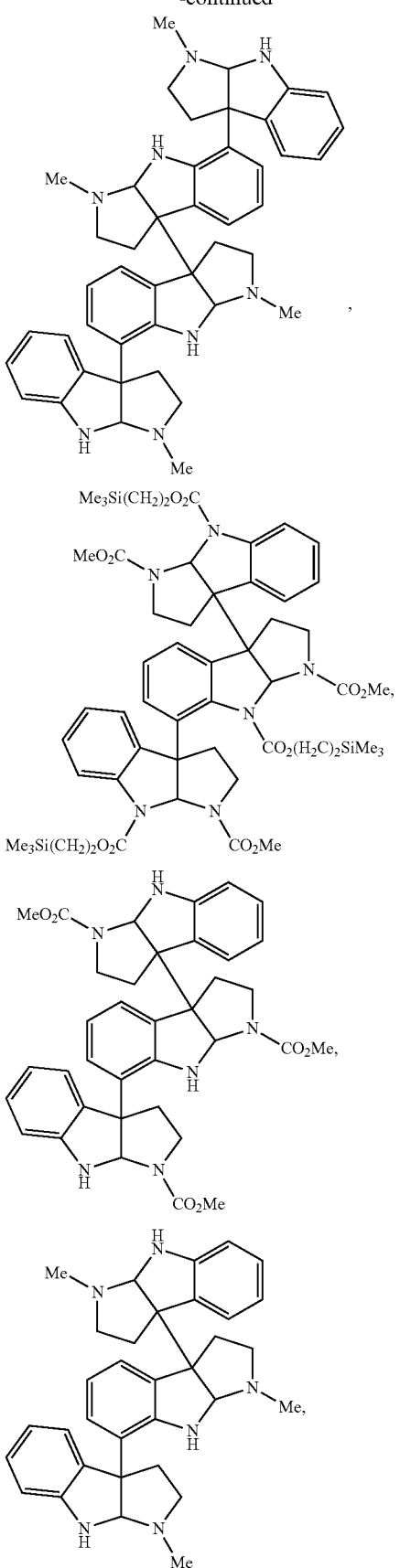

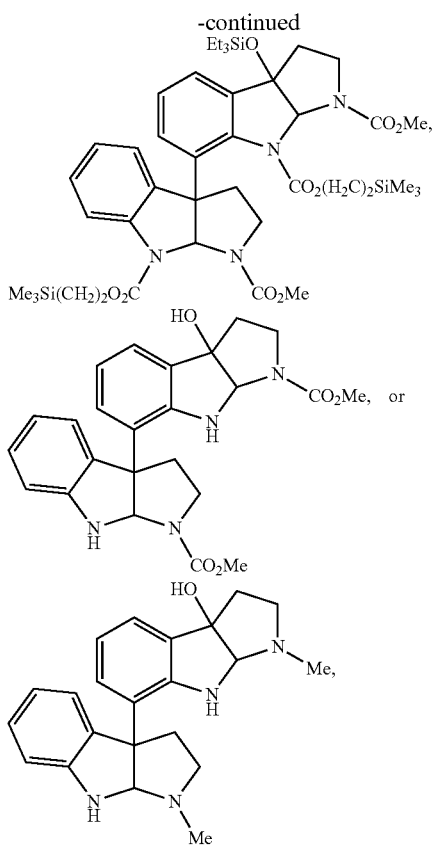

or a salt, tautomer, or stereoisomer thereof.

Using the methods described herein, various stereogenic quaternary carbon-containing compounds, including oligocyclotryptamines, can be prepared from the appropriate starting materials and intermediates, as shown below with more experimental detail in the following representative schemes.

EXAMPLES

General Procedures.

All reactions were performed in oven-dried or flame-dried round-bottom flasks, unless noted otherwise. The flasks were fitted with rubber septa, and reactions were conducted under a positive pressure of argon. Cannulae or gas-tight syringes with stainless steel needles were used to transfer air- or moisture-sensitive liquids. Where necessary (so noted), solutions were deoxygenated by sparging with nitrogen for a minimum of 5 min. Flash column chromatography was performed as described by Still et al (W. C. Still, M. Kahn, and A. Mitra. *J. Org. Chem.* 1978, 43, 2923) using granular silica gel (60-Å pore size, 40-63 μm, 4-6% $H_2O$ content, Zeochem) or non-activated alumina (80-325 mesh, chromatographic grade). Analytical thin layer chromatography (TLC) was performed using glass plates pre-coated with 0.25 mm 230-400 mesh silica gel impregnated with a fluorescent indicator (254 nm) or basic alumina impregnated with a fluorescent indicator (254 nm). TLC plates were visualized by exposure to short wave ultraviolet light (254 nm) and irreversibly stained by treatment with an aqueous solution of ceric ammonium molybdate (CAM) followed by heating (~1 min) on a hot plate (~250° C.). Organic solutions were concentrated at 29-35° C. on rotary evaporators capable of achieving a minimum pressure of ~2 torr. The diazene photolysis was accomplished by irradiation in a Rayonet RMR-200 photochemical reactor (Southern New England Ultraviolet Company, Branford, Conn., USA) equipped with 16 lamps.

Materials.

Commercial reagents and solvents were used as received with the following exceptions: dichloromethane, acetonitrile, tetrahydrofuran, methanol, pyridine, toluene, and triethylamine were purchased from J. T. Baker (Cycletainer™) and were purified by the method of Grubbs et al. under positive argon pressure (A. B. Pangborn, M. A. Giardello, R. H. Grubbs, R. K. Rosen, and F. J. Timmers. *Organometallics* 1996, 15, 1518). Benzene and 1,2-dichloroethane were dried by distillation over calcium hydride under an inert nitrogen atmosphere and used directly. Silver bis(trifluoromethanesulfonyl)imide, palladium on carbon, and dichloro(pentamethylcyclo-pentadienyl) iridium (III) dimer were purchased from Strem Chemicals; 2,6-di-tert-butyl-4-methylpyridine was purchased from Matrix Scientific and was further purified by flash column chromatography on silica gel (eluent: hexanes); tetra-n-butylammonium hydrogen sulfate and 2-methyl-2-phenylpropionic acid were purchased from TCI America; tryptamine was purchased from AK Scientific, Inc. All other solvents and chemicals were purchased from Sigma-Aldrich, Alfa Aesar, Acros Organics, or Combi-Blocks Inc.

Instrumentation.

Proton nuclear magnetic resonance ($^1H$ NMR) spectra were recorded with a Varian inverse probe 500 INOVA spectrometer, or a Bruker AVANCE III 400 spectrometer. Chemical shifts are recorded in parts per million on the δ scale and are referenced from the residual protium in the NMR solvent ($CHCl_3$: δ 7.26, $CD_2HCN$: 1.94, $C_6D_5H$: 7.16, $CD_3SOCD_2H$: 2.50) (G. R. Fulmer, A. J. M. Miller, N. H. Sherden, H. E. Gottlieb, A. Nudelman, B. M. Stoltz, J. E. Bercaw, K. I. Goldberg. *Organometallics* 2010, 29, 2176). Data are reported as follows: chemical shift [multiplicity (s=singlet, d=doublet, t=triplet, q=quartet, m=multiplet), coupling constant(s) in Hertz, integration, assignment]. Carbon-13 nuclear magnetic resonance ($^{13}C$ NMR) spectra were recorded with a Varian 500 INOVA spectrometer, or a Bruker AVANCE III 400 spectrometer and are recorded in parts per million on the δ scale and are referenced from the carbon resonances of the solvent ($CDCl_3$: δ 77.16, $CD_3CN$: 118.26, $C_6D_6$: 128.06, DMSO-$d_6$: 39.52). Data are reported as follows: chemical shift [multiplicity (s=singlet, d=doublet, t=triplet, q=quartet, m=multiplet), coupling constant(s) in Hertz, assignment]. Fluorine-19 nuclear magnetic resonance spectra were recorded with a Varian 300 INOVA spectrometer and are recorded in parts per million on the δ scale and are referenced from the fluorine resonances of α,α,α-trifluorotoluene ($CF_3CO_2H$ δ −63.72). Data are reported as follows: chemical shift [multiplicity (s=singlet, d=doublet, t=triplet, q=quartet, m=multiplet), coupling constant(s) in Hertz, integration, assignment]. Infrared data were obtained with a Perkin-Elmer 2000 FTIR and are reported as follows: [frequency of absorption ($cm^{-1}$), intensity of absorption (s=strong, m=medium, w=weak, br=broad), assignment]. High resolution mass spectra (HRMS) were recorded on a Bruker Daltonics APEXIV 4.7 Tesla FT-ICR-MS using electrospray (ESI) (m/z) ionization source or direct analysis in real time (DART) ionization source.

Example 1. Synthesis of (−)-quadrigemine C

Sulfamide Formation

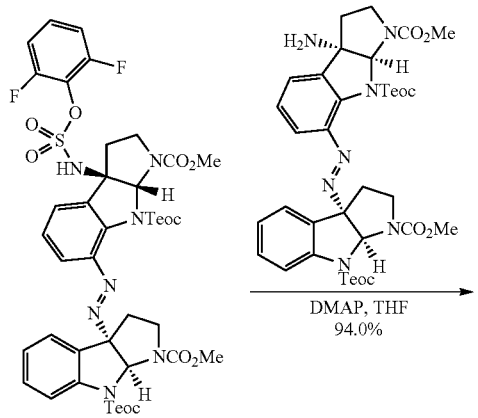

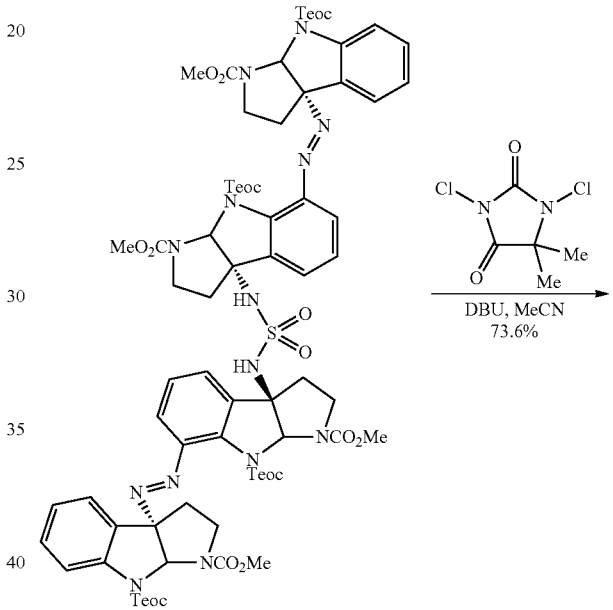

A sample of 4-(dimethylamino)pyridine (137 mg, 1.12 mmol, 2.20 equiv) was added to a solution of cyclotryptamine diazene sulfamate ester (490 mg, 511 μmol, 1 equiv) and cyclotryptamine diazene amine (430 mg, 562 μmol, 1.10 equiv) in tetrahydrofuran (5.10 mL) at 22° C. After 7 h, the bright yellow solution was concentrated under reduced pressure. The resulting residue was purified by flash column chromatography on silica gel (eluent: 30%→75% ethyl acetate in hexanes) to afford cyclotryptamine tetramer (766 mg, 94.0%) as a bright yellow amorphous gum.

As a result of the slow conformational equilibration at ambient temperature, NMR spectra were collected at elevated temperature. Structural assignments were made using additional information from gCOSY, HSQC, and HMBC experiments also collected at elevated temperature.

$^1$H NMR (400 MHz, C$_6$D$_6$, 70° C.): δ 8.19 (d, J=8.1 Hz, 2H), 7.53 (d, J=7.4 Hz, 1H), 7.36 (d, J=8.0 Hz, 1H), 7.30 (d, J=8.0 Hz, 1H), 7.22-7.14 (m, 6H), 7.05 (d, J=7.3 Hz, 1H), 6.99 (td, J=7.5, 0.7 Hz, 1H), 6.93 (t, J=7.8 Hz, 1H), 6.87 (td, J=7.5, 5.6 Hz, 2H), 6.83 (s, 1H), 6.80 (s, 1H), 5.62 (br-s, 1H), 5.42 (br-s, 1H), 4.53-4.35 (m, 6H), 4.19 (app-dtd, J=17.3, 10.9, 6.4 Hz, 2H), 4.00-3.90 (m, 2H), 3.68 (s, 3H), 3.65 (s, 3H), 3.62 (s, 3H), 3.59 (s, 3H), 3.55-3.40 (m, 2H), 2.96 (td, J=11.7, 5.3 Hz, 2H), 2.58-2.44 (m, 2H), 2.39 (ddd, J=15.5, 9.9, 6.1 Hz, 2H), 2.19 (ddd, J=12.3, 4.9, 2.4 Hz, 2H), 1.86 (dd, J=12.0, 4.9 Hz, 1H), 1.77 (dd, J=12.0, 5.1 Hz, 1H), 1.65 (td, J=11.9, 8.1 Hz, 1H), 1.54 (td, J=11.9, 8.5 Hz, 1H), 1.24-0.94 (m, 8), 0.00 (s, 9H), -0.01 (s, 9H), -0.02 (s, 9H), -0.04 (s, 9H). See FIG. 1 for $^1$H NMR spectrum.

$^{13}$C NMR (100 MHz, C$_6$D$_6$, 70° C.): δ 156.4, 156.2, 155.3 (2C), 154.9, 154.8 (2C), 153.7, 144.5, 144.4, 142.7, 142.6, 141.0, 140.8, 135.0, 134.8, 130.3, 130.2 (2C), 130.0, 126.2, 126.0 (2C), 125.8 (2C), 125.2, 123.6, 123.5, 119.5, 119.2, 116.8, 116.6, 89.9, 89.8, 81.8, 81.6, 79.8, 79.5, 71.1, 70.9, 65.7, 65.5, 64.4, 64.2, 52.4 (4C), 46.0 (2C), 44.6 (2C), 37.1, 36.7 (2C), 36.4, 18.2 (2C), 18.0, 17.9, −1.5 (4C).

FTIR (thin film) cm$^{-1}$: 3228 (w), 2954 (m), 1700 (s), 1457 (m), 838 (m).

HRMS (ESI) (m/z): calculated for C$_{72}$H$_{100}$N$_{14}$NaO$_{18}$SSi$_4$ [M+Na]$^+$: 1615.6030, found: 1615.6162.

$[\alpha]_D^{24}$: +130 (c=0.59, CH$_2$Cl$_2$).

TLC (70% ethyl acetate in hexanes), Rf: 0.21 (UV, CAM).

Sulfur Extrusion

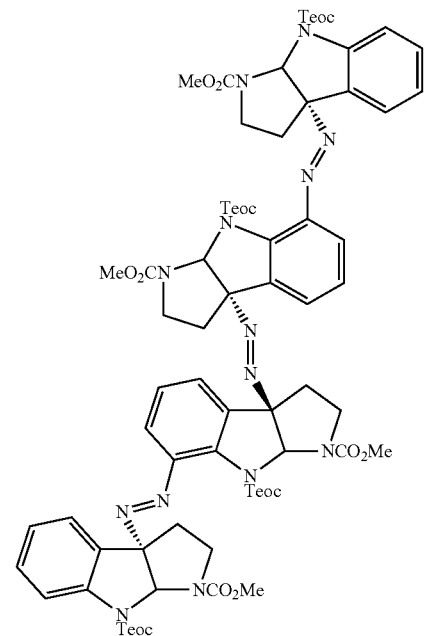

To a solution of mixed sulfamide (766 mg, 481 µmol, 1 equiv) in acetonitrile (24.1 mL) at 22° C. was added via syringe 1,8-diazabicyclo[5.4.0]undec-7-ene (DBU, 215 µL, 1.44 mmol, 3.00 equiv) followed immediately by 1,3-dichloro-5,5-dimethylhydantoin (236 mg, 1.20 mmol, 2.50 equiv) in a single portion. After 1 h, the mixture was diluted with dichloromethane (10 mL) and was washed with a saturated aqueous potassium carbonate-water solution (1:1, 30 mL). The aqueous layer was extracted with dichloromethane (3×30 mL). The combined organic extracts were dried over anhydrous sodium sulfate, were filtered, and were concentrated under reduced pressure. The resulting residue was purified by flash column chromatography on silica gel (eluent: 35→60% ethyl acetate in hexanes) to afford unsymmetrical cyclotryptamine tetramer diazene (541 mg, 73.6%) as a bright yellow amorphous gum.

As a result of the slow conformational equilibration at ambient temperature, NMR spectra were collected at elevated temperature. Structural assignments were made using additional information from gCOSY, HSQC, and HMBC experiments also collected at elevated temperature.

Figure 2:
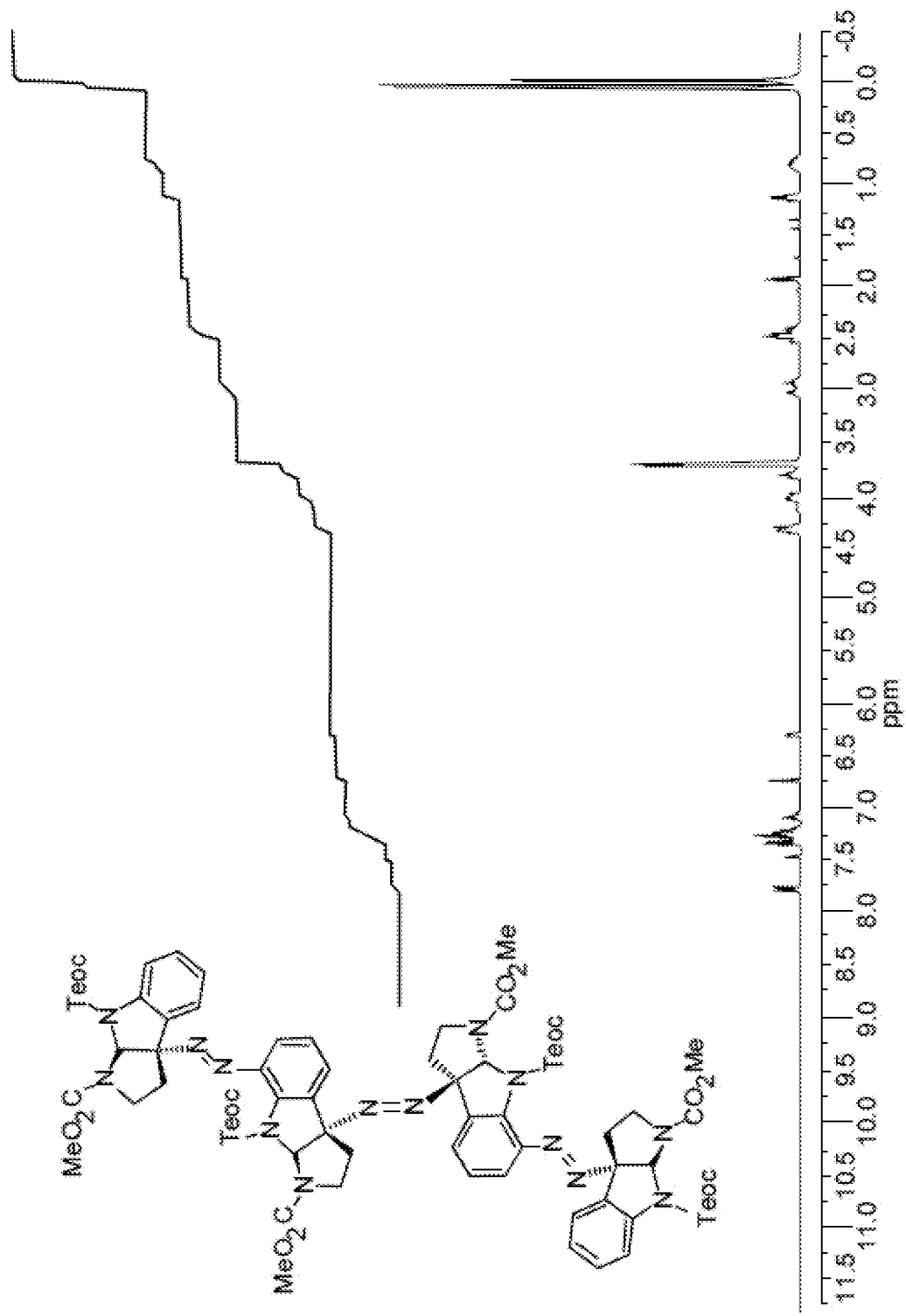
FIG. 2 shows the $^1$H NMR spectrum of the tri-diazene intermediate of (−)-quadrigemine C.

$^1$H NMR (400 MHz, CD$_3$CN, 50° C.): δ 7.77 (d, J=8.1 Hz, 2H), 7.48 (d, J=8.9 Hz, 1H), 7.38–7.18 (m, 9H), 7.09 (app-dtd, J=1.0, 7.5, 11.6 Hz, 2H), 6.74 (app-s, 2H), 6.32 (app-d, J=1.7 Hz, 1H), 6.30 (app-d, J=2.2 Hz, 1H), 4.40–4.26 (m, 4H), 4.19–3.94 (m, 4H), 3.89–3.73 (m, 4H), 3.70 (s, 6H), 3.69 (s, 3H), 3.68 (s, 3H), 3.08–2.98 (m, 2H), 2.93 (td, J=5.6, 11.4 Hz, 2H), 2.56–2.35 (m, 8H), 1.18–1.07 (m, 4H), 0.92–0.69 (m, 4H), 0.07 (s, 9H), 0.05 (s, 9H), 0.01 (s, 9H), −0.01 (s, 9H). See FIG. 2 for $^1$H NMR spectrum.

$^{13}$C NMR (100 MHz, CD$_3$CN, 50° C.): δ 156.3, 156.2, 156.0 (2C), 155.3, 155.2, 154.5 (2C), 144.7, 144.6, 143.4, 143.2, 141.4, 141.0, 134.7 (2C), 131.1 (3C), 130.7, 127.7, 127.6, 127.1 (2C), 126.8, 126.7, 124.6 (2C), 120.3, 119.9, 117.1, 116.9, 90.3, 90.1, 89.5 (2C), 81.8, 81.7, 79.8, 79.7, 65.8, 65.7, 65.2 (2C), 53.4 (2C), 53.3 (2C), 47.0, 46.9, 46.7 (2C), 37.4, 37.1, 33.7 (2C), 18.7 (4C), −1.1 (4C).

FTIR (thin film) cm$^{-1}$: 2954 (m), 1717 (s), 1448 (w), 1395 (m).

HRMS (ESI) (m/z): calculated for C$_{72}$H$_{98}$N$_{14}$NaO$_{16}$SSi$_4$ [M+Na]$^+$: 1549.6255, found: 1549.6665.

[α]$_D^{24}$: +145 (c=0.62, CH$_2$Cl$_2$).

TLC (60% ethyl acetate in hexanes), Rf: 0.33 (UV, CAM).

Csp3-Csp3 Bond Formation

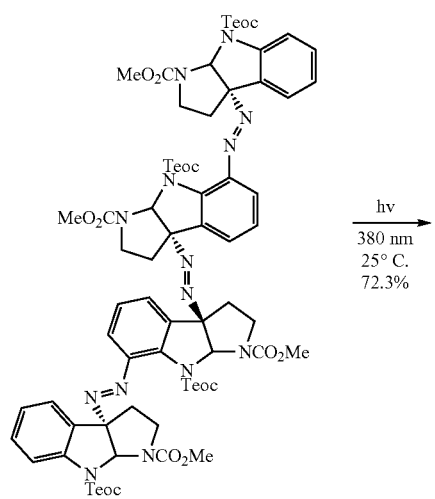

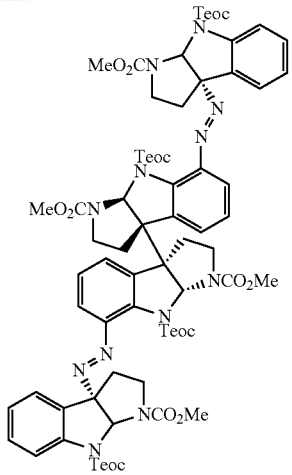

A solution of unsymmetrical tetramer diazene (541 mg, 354 µmol, 1 equiv) in dichloromethane (30 mL) was concentrated under reduced pressure in a 2 L round bottom flask to provide a thin film of diazene coating the flask. The flask was back filled with argon and irradiated in a Rayonet photoreactor equipped with 16 radially distributed (r=12.7 cm) 25 W lamps (λ=380 nm) at 25° C. After 24 h, the lamps were turned off and the resulting residue was purified by flash column chromatography on silica gel (eluent: 30→70% ethyl acetate in hexanes) to afford the cyclotryptamine tetramer (384 mg, 72.3%) as a bright yellow amorphous gum.

As a result of the slow conformational equilibration at ambient temperature, NMR spectra were collected at elevated temperature.

$^1$H NMR (400 MHz, CD$_3$CN, 70° C.): δ 7.78 (app-t, J=7.2 Hz, 2H), 7.49 (app-t, J=6.8 Hz, 1H), 7.37–7.26 (m, 3H), 7.21–7.14 (m, 2H), 7.14–7.01 (m, 4H), 6.94 (br-s, 2H), 6.75 (dd, J=6.5, 10.7 Hz, 2H), 6.22 (app-br-s, 2H), 4.41–4.26 (m, 4H), 4.13–3.93 (m, 4H), 3.93–3.78 (m, 2H), 3.78–3.65 (m, 14H), 3.09–2.94 (m, 2H), 2.80–2.66 (m, 2H), 2.57–2.34 (m, 4H), 2.26 (app-br-s, 4H), 1.20–1.06 (m, 4H), 1.01–0.79 (m, 4H), 0.13–0.01 (m, 36H).

$^{13}$C NMR (100 MHz, CD$_3$CN, 70° C.): δ 156.5, 156.4, 155.9, 155.8, 154.9 (2C), 154.8 (2C), 145.0, 144.9, 143.4, 143.3, 141.3, 140.8, 136.9 (2C), 131.4, 131.3, 131.2, 131.0, 127.4, 127.3, 127.0 (2C), 126.9, 124.8, 124.7, 119.8, 119.4, 117.2 (2C), 90.4 (2C), 82.0, 81.9, 80.5, 80.0, 66.2 (2C), 65.4, 65.3, 62.3 (2C), 53.5 (2C), 53.5 (2C), 47.2, 47.1, 46.7 (2C), 37.8, 37.6, 34.7, 34.6, 19.1 (3C), 19.0, −0.8 (2C), −0.9 (2C).

FTIR (thin film) cm$^{-1}$: 2954 (m), 1717 (s), 1457 (m), 1251 (w).

HRMS (ESI) (m/z): calculated for C$_{72}$H$_{98}$N$_{12}$NaO$_{16}$SSi$_4$ [M+Na]$^+$: 1521.6193, found: 1521.6283.

[α]$_D^{24}$: +155 (c=0.55, CH$_2$Cl$_2$).

TLC (50% ethyl acetate in hexanes), Rf: 0.13 (UV, CAM).

Csp2-Cs3 Bond Formation

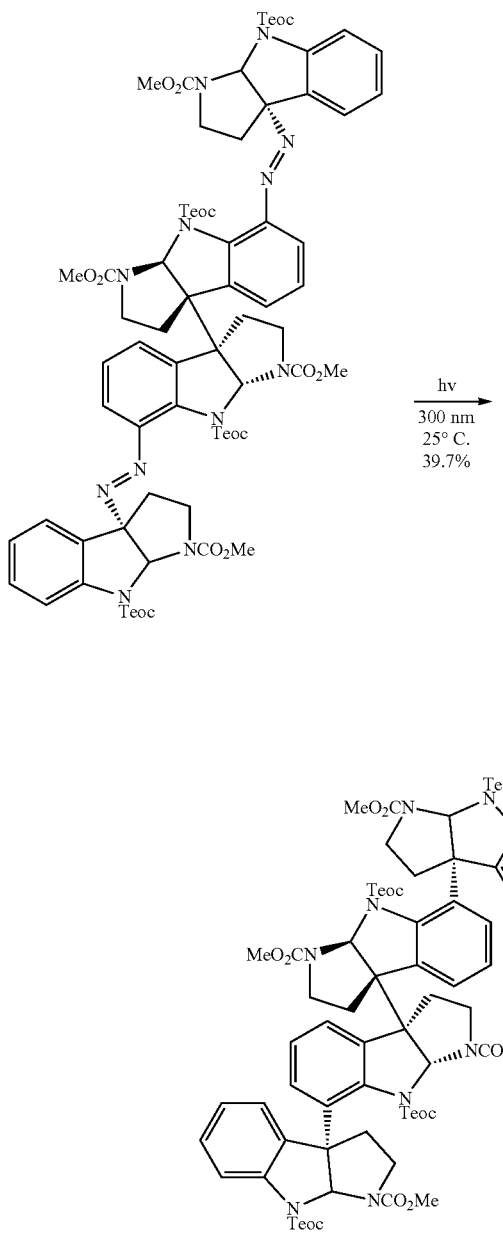

A solution of unsymmetrical tetramer diazene (17.3 mg, 11.5 μmol, 1 equiv) in dichloromethane (5 mL) was concentrated under reduced pressure in a 100 mL round bottom flask to provide a thin film of diazene coating the flask. The flask was back filled with argon and irradiated in a Rayonet photoreactor equipped with 16 radially distributed (r=12.7 cm) 25 W lamps (λ=300 nm) at 25° C. After 24 h, the lamps were turned off and the resulting residue was purified by flash column chromatography on silica gel (eluent: 25→50% ethyl acetate in hexanes) to afford the cyclotryptamine tetramer (6.60 mg, 39.7%) as an off-white amorphous gum.

As a result of the slow conformational equilibration at ambient temperature, NMR spectra were collected at elevated temperature.

Teoc Deprotection

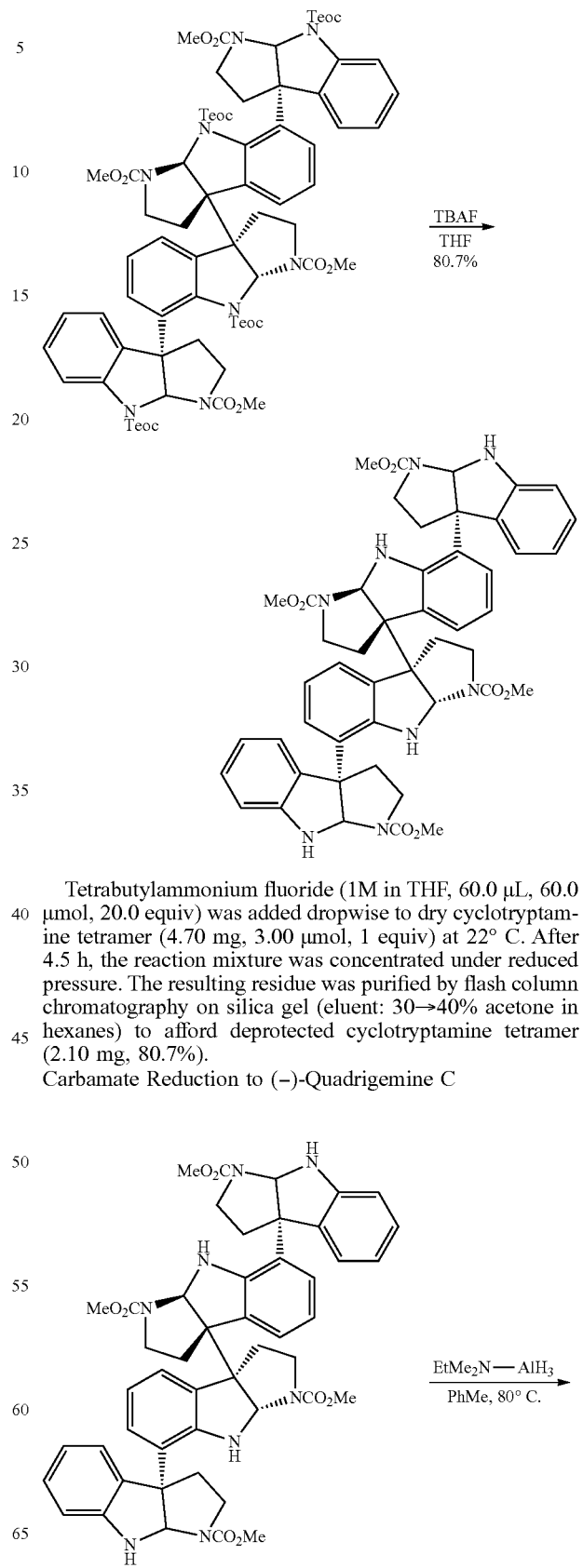

Tetrabutylammonium fluoride (1M in THF, 60.0 μL, 60.0 μmol, 20.0 equiv) was added dropwise to dry cyclotryptamine tetramer (4.70 mg, 3.00 μmol, 1 equiv) at 22° C. After 4.5 h, the reaction mixture was concentrated under reduced pressure. The resulting residue was purified by flash column chromatography on silica gel (eluent: 30→40% acetone in hexanes) to afford deprotected cyclotryptamine tetramer (2.10 mg, 80.7%).

Carbamate Reduction to (−)-Quadrigemine C

-continued

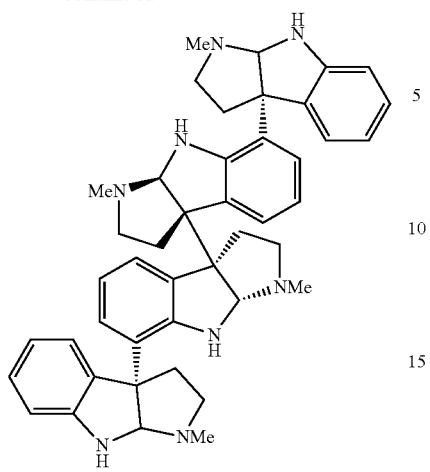

Figure 3:
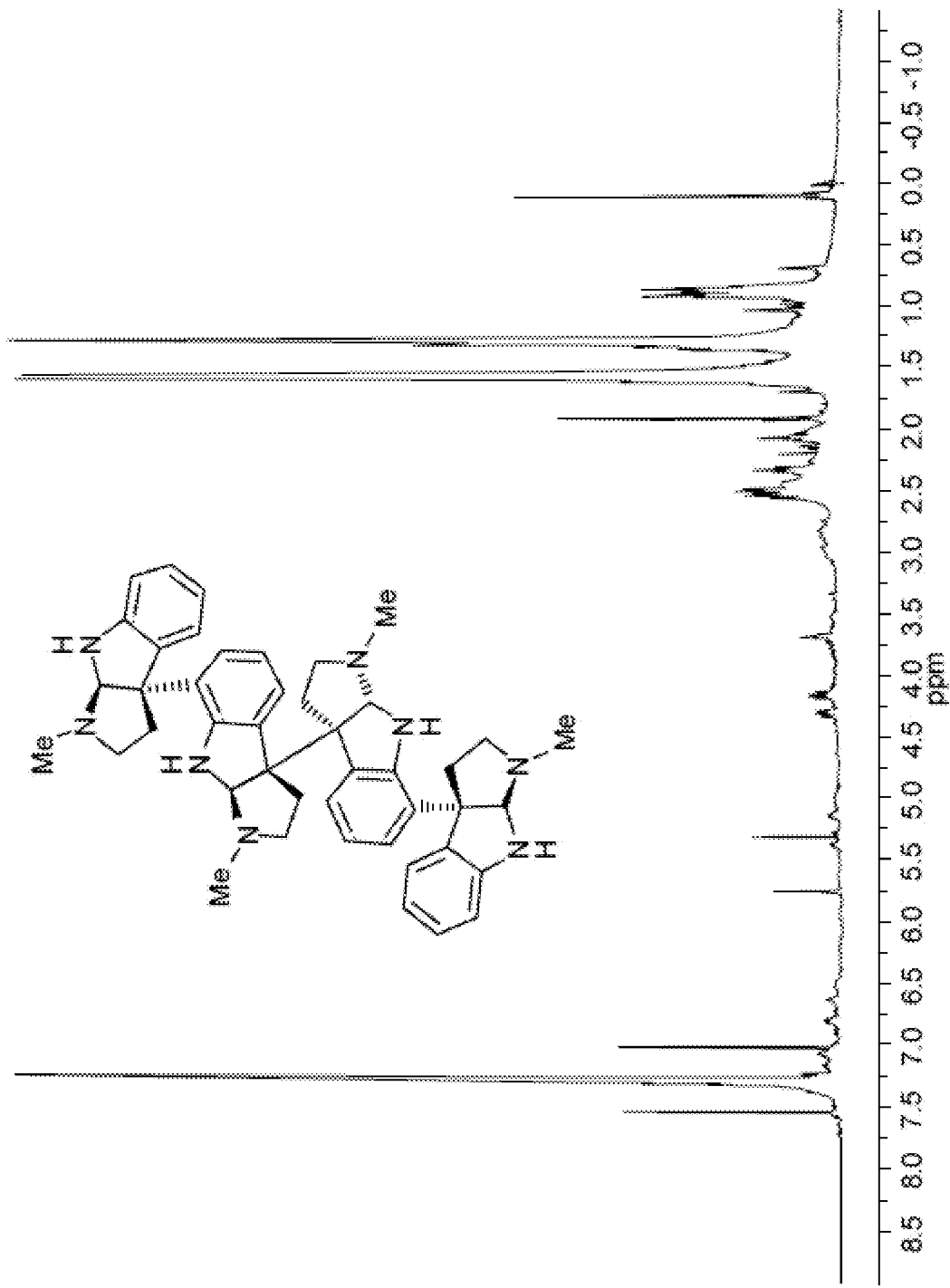
FIG. 3 shows the $^1$H NMR spectrum of (−)-quadrigemine C.
Figure 4:
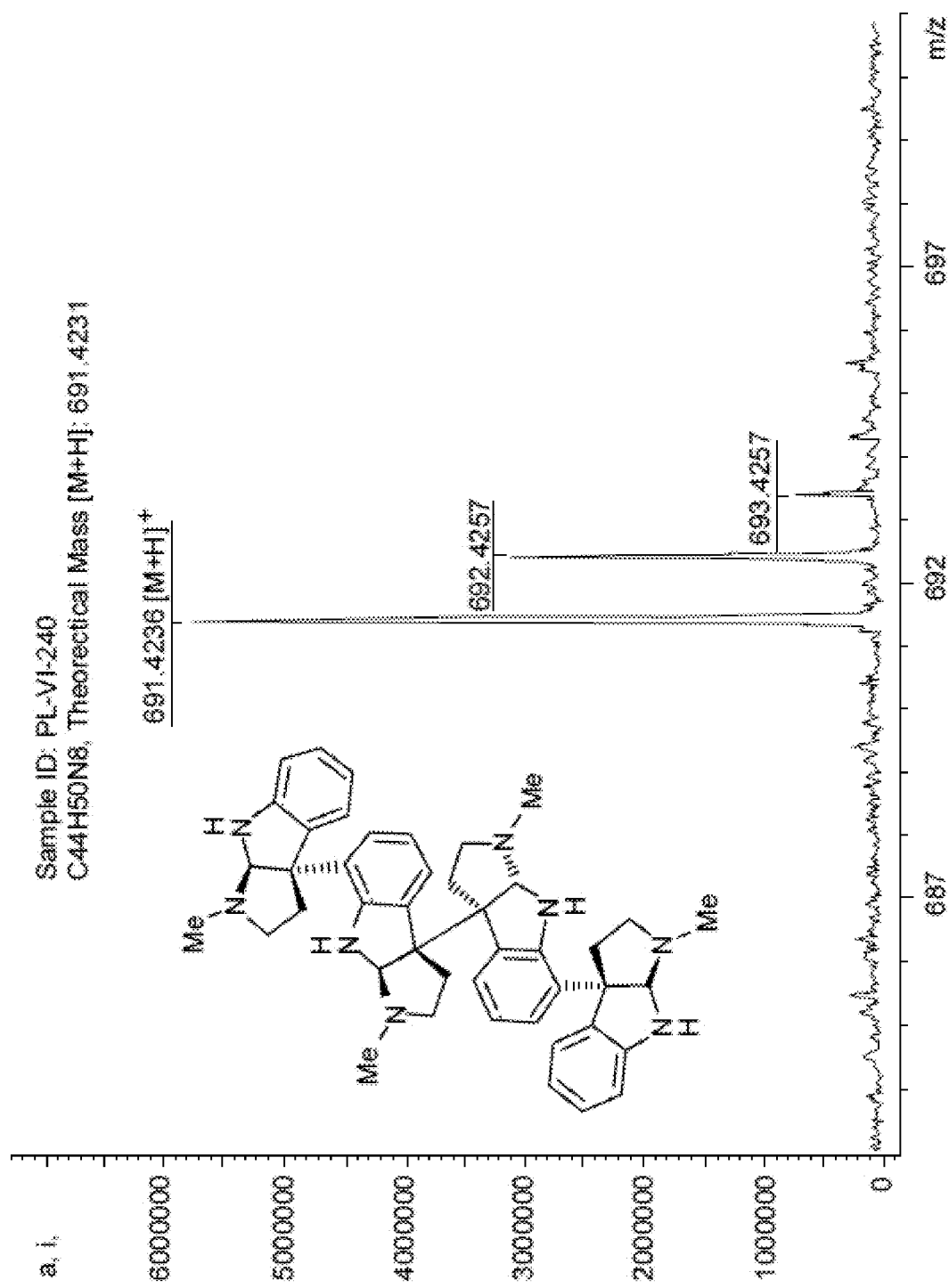
FIG. 4 is the mass spectral data confirming the formation of (−)-quadrigemine C.

Cyclotryptamine tetramer (0.70 mg, 10 μmol, 1 equiv) was azeotropically dried from anhydrous benzene (2×1 mL) and the residue was dissolved in toluene (50 μL). A solution of alane N,N-dimethylethylamine complex in toluene (0.5 M, 0.15 mL, 60 μmol, 60 equiv) was added via syringe at 23° C. The reaction flask was sealed and heated to 80° C. After 1 h, the reaction mixture was allowed to cool to 23° C. and excess reducing reagent was quenched by the addition of saturated aqueous sodium sulfate solution (0.10 mL). The resulting heterogeneous mixture was stirred for 10 min and then solid anhydrous sodium sulfate was added. The mixture was filtered through a plug of Celite and the filter cake was rinsed with ethyl acetate (5 mL). The filtrate was concentrated under reduced pressure. The resulting residue was purified by flash column chromatography on silica gel (eluent: 30%→100% CMA in chloroform) to afford quadrigemine C (0.28 mg, 40%). See FIG. 3 for $^1$H NMR spectrum and FIG. 4 for mass spectral data.

Example 2. Synthesis of (−)-hodgkinsine

Sulfamide Formation

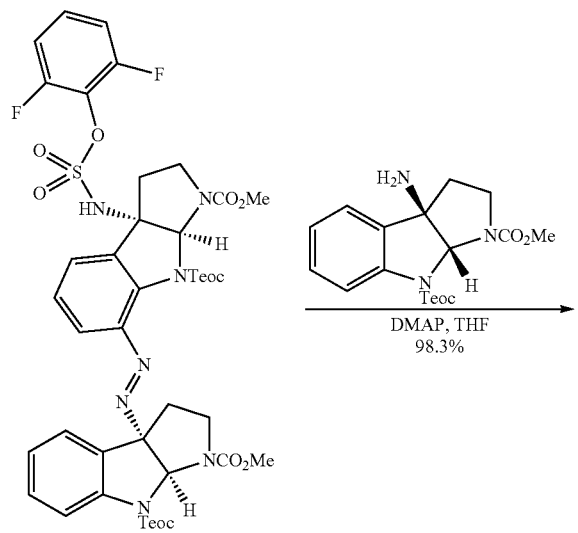

-continued

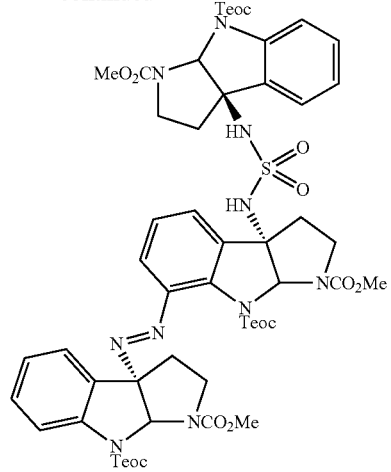

A sample of 4-(dimethylamino)pyridine (109 mg, 891 μmol, 2.20 equiv) was added to a solution of cyclotryptamine diazene sulfamate ester (388 mg, 405 μmol, 1 equiv) and cyclotryptamine amine (168 mg, 446 μmol, 1.10 equiv) in tetrahydrofuran (4.10 mL) at 22° C. After 24 h, the bright yellow solution was concentrated under reduced pressure. The resulting residue was purified by flash column chromatography on silica gel (eluent: 20%→70% ethyl acetate in hexanes) to afford cyclotryptamine trimer (480 mg, 98.3%) as a bright yellow amorphous gum.

As a result of the slow conformational equilibration at ambient temperature, NMR spectra were collected at elevated temperature. Structural assignments were made using additional information from gCOSY, HSQC, and HMBC experiments also collected at elevated temperature.

$^{13}$C NMR (100 MHz, C$_6$D$_6$, 70° C.): δ 156.0, 155.3, 155.2, 154.9, 154.4, 153.9, 144.6, 144.1, 142.8, 141.1, 134.6, 130.9, 130.5, 130.3, 126.1, 125.8, 125.3, 124.6, 123.9, 123.6, 119.4, 117.6, 116.8, 89.9, 82.2, 80.2 (2C), 71.4, 71.3, 65.5, 64.8, 64.3, 52.4 (3C), 46.1, 45.0, 44.7, 37.2, 36.7, 36.2, 18.2 (2C), 18.1, −1.5 (3C).

FTIR (thin film) cm$^{-1}$: 3228 (m), 2955 (m), 1715 (s), 1402 (m).

HRMS (ESI) (m/z): calculated for C$_{54}$H$_{76}$N$_{10}$NaO$_{14}$SSi$_3$ [M+Na]$^+$: 1227.4463, found: 1227.4462.

[α]$_D^{24}$: −83 (c=0.64, CH$_2$Cl$_2$).

TLC (60% ethyl acetate in hexanes), Rf: 0.28 (UV, CAM).

Sulfur Extrusion

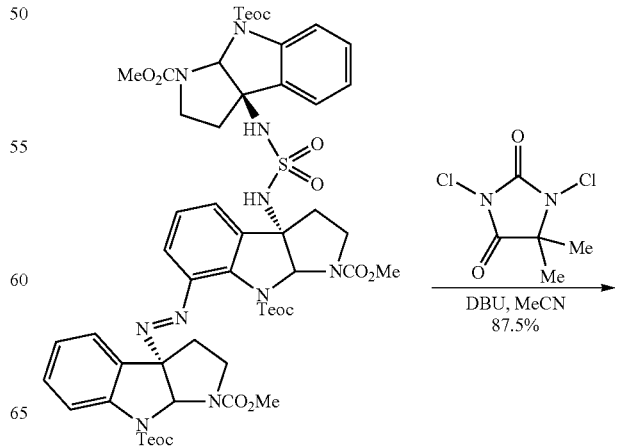

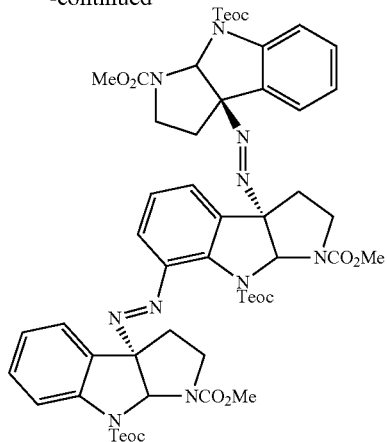

To a solution of mixed sulfamide (480 mg, 398 μmol, 1 equiv) in acetonitrile (20.0 mL) at 22° C. was added via syringe 1,8-diazabicyclo[5.4.0]undec-7-ene (DBU, 178 μL, 1.19 mmol, 3.00 equiv) followed immediately by 1,3-dichloro-5,5-dimethylhydantoin (196 mg, 995 μmol, 2.50 equiv) in a single portion. After 1 h, the mixture was diluted with dichloromethane (20 mL) and was washed with a saturated aqueous potassium carbonate-water solution (1:1, 30 mL). The aqueous layer was extracted with dichloromethane (3×30 mL). The combined organic extracts were dried over anhydrous sodium sulfate, were filtered, and were concentrated under reduced pressure. The resulting residue was purified by flash column chromatography on silica gel (eluent: 20→50% ethyl acetate in hexanes) to afford unsymmetrical cyclotryptamine trimer diazene (397 mg, 87.5%) as a bright yellow amorphous gum.

As a result of the slow conformational equilibration at ambient temperature, NMR spectra were collected at elevated temperature. Structural assignments were made using additional information from gCOSY, HSQC, and HMBC experiments also collected at elevated temperature.

$^1$H NMR (400 MHz, CD$_3$CN, 50° C.): δ 7.77 (d, J=8.0 Hz, 1H), 7.70 (d, J=8.0 Hz, 1H), 7.42–7.19 (m, 6H), 7.12 (app-t, J=6.4 Hz, 1H), 7.08 (app-t, J=7.5 Hz, 1H), 7.02 (app-t, J=7.4 Hz, 1H), 6.73 (s, 1H), 6.46 (s, 1H), 6.39 (s, 1H), 4.38–4.20 (m, 4H), 4.20–4.08 (m, 1H), 4.01 (br-dd, J=7.4, 10.3 Hz, 1H), 3.93–3.76 (m, 3H), 3.69 (app-s, 6H), 3.65 (s, 3H), 3.08–2.89 (m, 2H), 2.57 (dd, J=5.1, 12.5 Hz, 1H), 2.53–2.38 (m, 3H), 2.37–2.20 (m, 2H), 1.17–1.03 (m, 4H), 0.90–0.67 (m, 2H), 0.07 (app-s, 18H), −0.03 (s, 9H).

$^{13}$C NMR (100 MHz, CD$_3$CN, 50° C.): δ 156.2, 156.0 (2C), 155.3, 154.4, 154.3, 144.6, 144.5, 143.1, 141.3, 134.8, 131.2, 131.1, 130.6, 130.1, 127.7, 127.1, 126.6, 125.9, 124.6, 124.5, 119.8, 117.2, 117.0, 90.2, 89.6, 89.3, 81.8, 79.7, 79.6, 65.7, 65.2, 65.1, 53.3 (2C), 53.2, 46.9, 46.6 (2C), 36.9, 36.0, 33.6, 18.6 (3C), −1.2 (2C), −1.3.

FTIR (thin film) cm$^{-1}$: 2954 (m), 1713 (s), 1401 (m), 1552 (w).

HRMS (ESI) (m/z): calculated for C$_{54}$H$_{74}$N$_{10}$NaO$_{12}$Si$_3$ [M+Na]$^+$: 1161.4688, found: 1161.4673.

[α]$_D^{24}$: −86 (c=0.61, CH$_2$Cl$_2$).

TLC (50% ethyl acetate in hexanes), Rf: 0.23 (UV, CAM).

Csp3-Csp3 Bond Formation

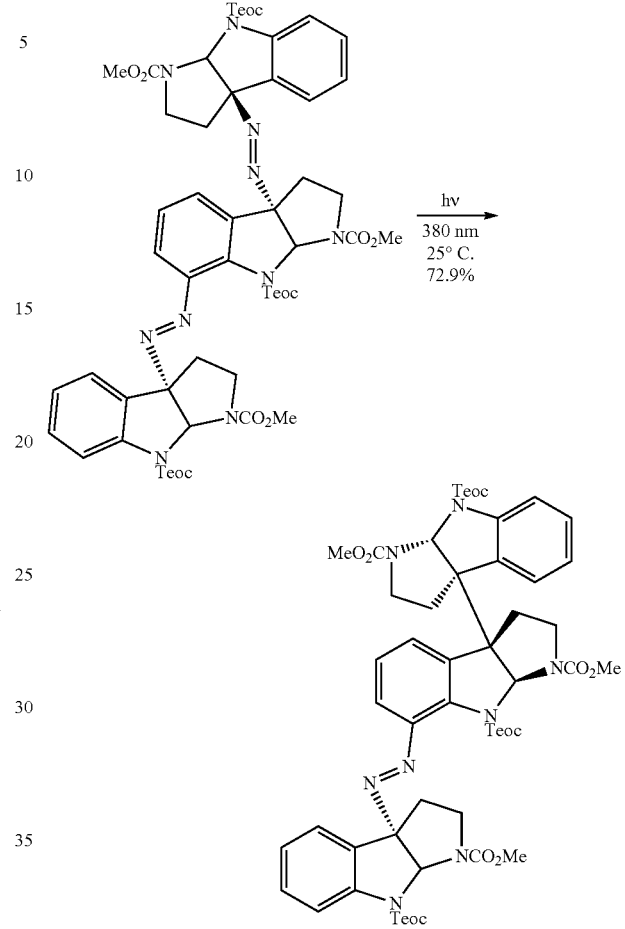

A solution of trimer diazene (397 mg, 348 μmol, 1 equiv) in dichloromethane (30 mL) was concentrated under reduced pressure in a 1 L round bottom flask to provide a thin film of diazene coating the flask. The flask was back filled with argon and irradiated in a Rayonet photoreactor equipped with 16 radially distributed (r=12.7 cm) 25 W lamps (λ=380 nm) at 25° C. After 15 h, the lamps were turned off and the resulting residue was purified by flash column chromatography on silica gel (eluent: 20→60% ethyl acetate in hexanes) to afford the cyclotryptamine trimer (282 mg, 72.9%) as a bright yellow amorphous gum.

As a result of the slow conformational equilibration at ambient temperature, NMR spectra were collected at elevated temperature.

$^1$H NMR (400 MHz, CD$_3$CN, 60° C.): δ 7.75 (d, J=8.0 Hz, 1H), 7.66 (d, J=8.0 Hz, 1H, 7.38–7.27 (m, 2H), 7.27–7.15 (m, 4H), 7.06 (app-t, J=7.5 Hz, 1H), 6.77 (app-t, J=7.8 Hz, 1H), 6.69 (s, 1H), 6.41 (br-d, J=5.8 Hz, 1H), 6.23 (s, 1H), 6.08 (s, 1H), 4.39–4.28 (m, 3H), 4.21 (td, J=7.0, 10.5 Hz, 1H), 3.99 (dd, J=7.8, 11.1 Hz, 1H), 3.94–3.85 (m, 1H), 3.82 (dd, J=7.7, 11.0 Hz, 1H), 3.75 (dd, J=7.9, 10.9 Hz, 1H), 3.72–3.62 (m, 10H), 3.01 (td, J=5.6, 11.6 Hz, 1H), 2.75 (app-dtd, J=5.5, 11.5, 14.1 Hz, 2H), 2.47 (td, J=7.8, 12.1 Hz, 1H), 2.35 (app-ddd, J=7.0, 12.2, 13.5 Hz, 3H), 2.28–2.16 (m, 2H), 1.18–1.04 (m, 4H), 0.94–0.81 (m, 2H), 0.10 (s, 9H), 0.07 (s, 9H), 0.06 (s, 9H).

$^{13}$C NMR (100 MHz, CD$_3$CN, 60° C.): δ 156.4, 155.9, 155.8, 154.6, 154.4, 154.3, 144.8, 144.5, 143.0, 141.2, 137.3, 132.2, 131.1, 130.8, 130.4, 127.0, 126.9, 125.3, 124.8, 124.6, 119.2, 117.3, 117.1, 90.2, 81.7, 80.3, 79.9, 65.8, 65.4, 65.3, 62.7, 61.8, 53.4 (2C), 53.3, 47.1, 46.9, 46.5, 37.2, 36.2, 34.2, 18.9, 18.8, 18.6, −1.1 (3C).

FTIR (thin film) cm$^{-1}$: 2954 (m), 1717 (s), 1448 (w), 1400 (w).

HRMS (ESI) (m/z): calculated for $C_{54}H_{74}N_8NaO_{12}Si_3$ [M+Na]$^+$: 1133.4626, found: 1133.4601.

[α]$_D^{24}$: 162 (c=0.54, CH$_2$Cl$_2$).

TLC (50% ethyl acetate in hexanes), Rf: 0.19 (UV, CAM).

Csp2-Csp3 Bond Formation

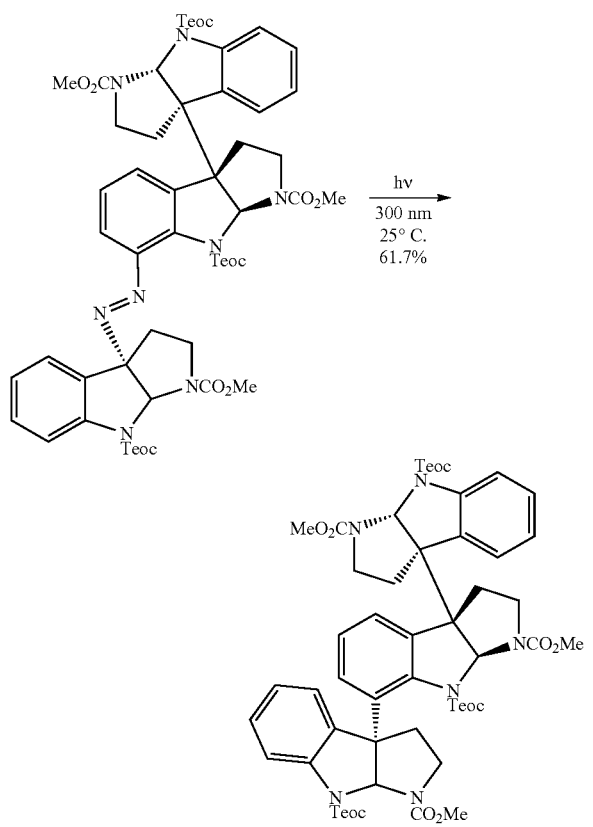

A solution of trimer diazene (141 mg, 127 μmol, 1 equiv) in dichloromethane (15 mL) was concentrated under reduced pressure in a 2 L round bottom flask to provide a thin film of diazene coating the flask. The flask was back filled with argon and irradiated in a Rayonet photoreactor equipped with 16 radially distributed (r=12.7 cm) 25 W lamps (λ=300 nm) at 25° C. After 15 h, the lamps were turned off and the resulting residue was purified by flash column chromatography on silica gel (eluent: 30→40% ethyl acetate in hexanes) to afford the cyclotryptamine trimer (84.9 mg, 61.7%) as an off-white solid.

As a result of the slow conformational equilibration at ambient temperature, NMR spectra were collected at elevated temperature.

$^1$H NMR (400 MHz, CD$_3$CN, 60° C.): δ 7.74 (d, J=8.0 Hz, 1H0, 7.70 (d, J=8.1 Hz, 1H), 7.29 (app-dd, J=7.2, 14.2 Hz, 2H), 7.22 (app-t, J=7.8 Hz, 1H), 7.137.00 (m, 2H), 6.91 (d, J=7.5 Hz, 1H), 6.78 (d, J=7.5 Hz, 1H), 6.69 (s, 1H), 6.48 (d, J=7.9 Hz, 1H), 6.40 (br-d, J=5.8 Hz, 1H), 6.36 (s, 1H), 6.04 (s, 1H), 4.504.34 (m, 2H), 4.334.22 (m, 2H), 3.94 (td, J=6.0, 11.4 Hz, 1H), 3.80 (dd, J=7.4, 11.1 Hz, 1H), 3.763.56 (m, 13H), 2.95 (td, J=8.3, 11.8 Hz, 1H), 2.792.36 (m, 3H), 2.352.15 (m, 3H), 2.09 (td, J=8.5, 11.9 Hz, 1H), 1.251.06 (m, 4H), 1.040.81 (m, 2H), 0.12 (s, 9H), 0.08 (s, 9H), 0.06 (s, 9H).

$^{13}$C NMR (100 MHz, CD$_3$CN, 60° C.): δ 156.2, 156.0, 155.8, 155.0 (2C), 154.4, 144.5, 144.4, 142.7, 139.5, 138.2, 134.8, 133.0, 132.3, 130.4, 129.8, 127.4, 125.5, 125.4, 125.3, 125.0, 124.3, 117.6, 117.2, 83.0, 80.7, 80.2, 66.1, 65.4, 65.0, 61.7 (2C), 61.5, 53.4, 53.2, 53.1, 46.9 (2C), 46.1, 35.7, 34.3, 33.4, 19.0 (2C), 18.7, −1.0 (2C), −1.1.

FTIR (thin film) cm$^{-1}$: 2954 (m), 1716 (s), 1447 (w), 1400 (m).

HRMS (ESI) (m/z): calculated for $C_{54}H_{74}N_6NaO_{12}Si_3$ [M+Na]$^+$: 1105.4565, found: 1105.4539.

[α]$_D^{24}$: −35 (c=0.57, CH$_2$Cl$_2$).

TLC (50% ethyl acetate in hexanes), Rf: 0.28 (UV, CAM).

M.p.: 108-110 (CH$_2$Cl$_2$).

Teoc Deprotection

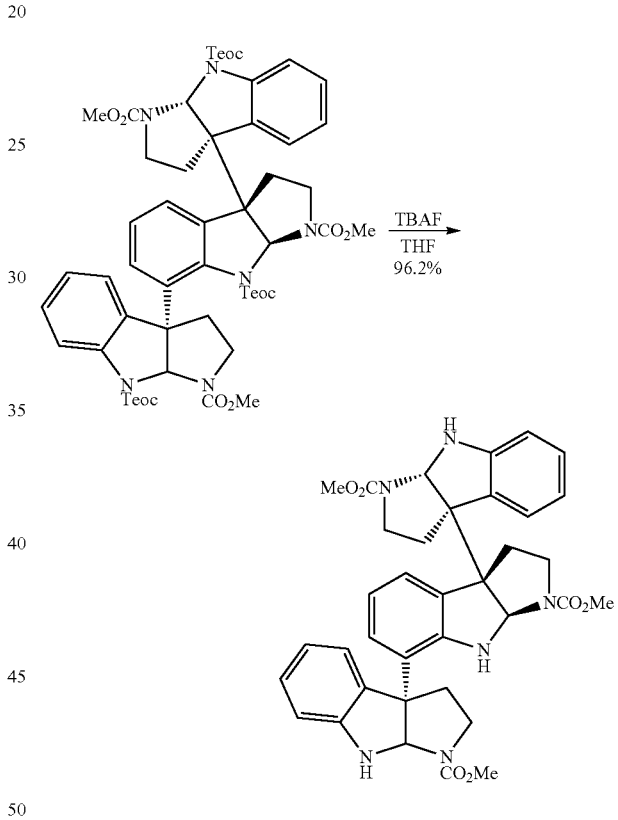

Tetrabutylammonium fluoride (1M in THF, 1.80 mL, 1.80 mmol, 15.0 equiv) was added dropwise to dry cyclotryptamine trimer (130 mg, 120 μmol, 1 equiv) at 22° C. After 2 h, the reaction mixture was concentrated under reduced pressure. The resulting residue was purified by flash column chromatography on silica gel (eluent: 20→40% acetone in hexanes) to afford deprotected cyclotryptamine trimer (75.1 mg, 96.2%).

FTIR (thin film) cm$^{-1}$: 3335 (m), 2955 (m), 1700 (s), 1608 (w), 1457 (s).

HRMS (ESI) (m/z): calculated for $C_{36}H_{39}N_6O_6$ [M+H]$^+$: 651.2926, found: 651.2916.

[α]$_D^{24}$: +187 (c=0.54, CH$_2$Cl$_2$).

TLC (70% ethyl acetate in hexanes), Rf: 0.10 (UV, CAM).

M.p.: 153-155 (CH$_2$Cl$_2$).

Carbamate Reduction to (−)-Hodgkinsine

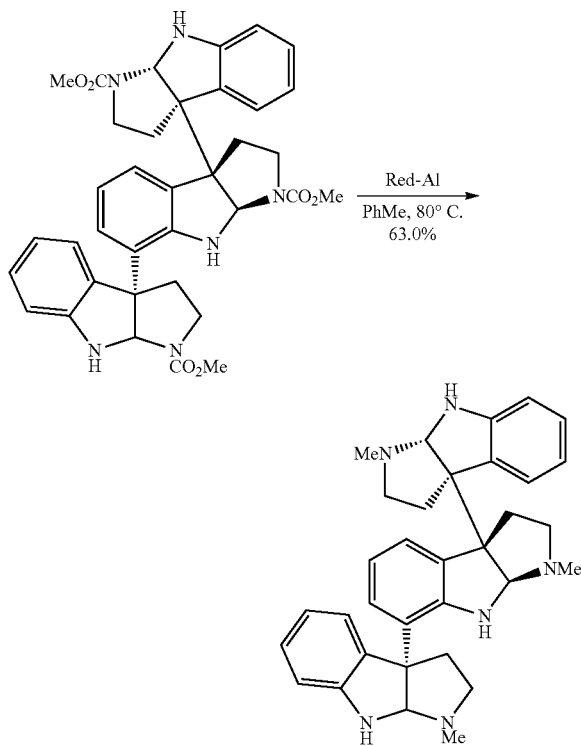

Figure 5:
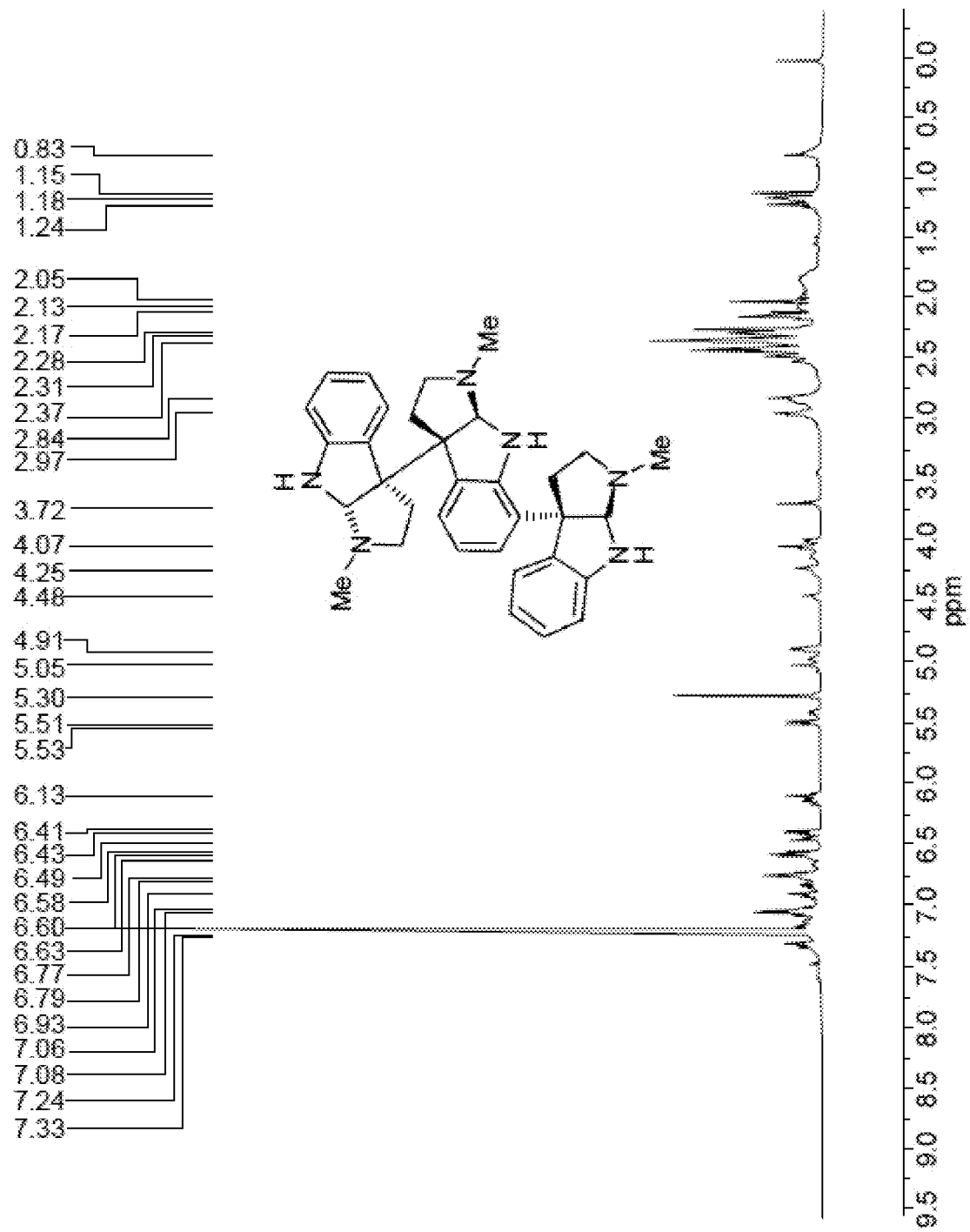
FIG. 5 shows the $^1$H NMR spectrum of (−)-hodgkinsine.

Cyclotryptamine trimer (4.90 mg, 8.00 μmol, 1 equiv) was azeotropically dried from anhydrous benzene (2×1 mL) and the residue was dissolved in toluene (80.0 μL). A solution of sodium bis(2-methoxyethoxy)aluminum hydride in toluene (Red-Al, 70% wt, 53.0 μL, 184 μmol, 23.0 equiv) was added via syringe at 22° C. The reaction flask was sealed and heated to 80° C. After 1 h, the reaction mixture was allowed to cool to 22° C. and excess reducing reagent was quenched by the addition of saturated aqueous sodium sulfate solution (100 μL). The resulting heterogeneous mixture was stirred for 10 min and then solid anhydrous sodium sulfate was added. The mixture was filtered through a plug of Celite and the filter cake was rinsed with ethyl acetate (5 mL). The filtrate was concentrated under reduced pressure. The resulting residue was purified by flash column chromatography on silica gel (eluent: 35%→50% CMA in chloroform) to afford hodgkinsine (2.60 mg, 63.0%). See FIG. 5 for $^1$H NMR spectrum.

Figure 6:
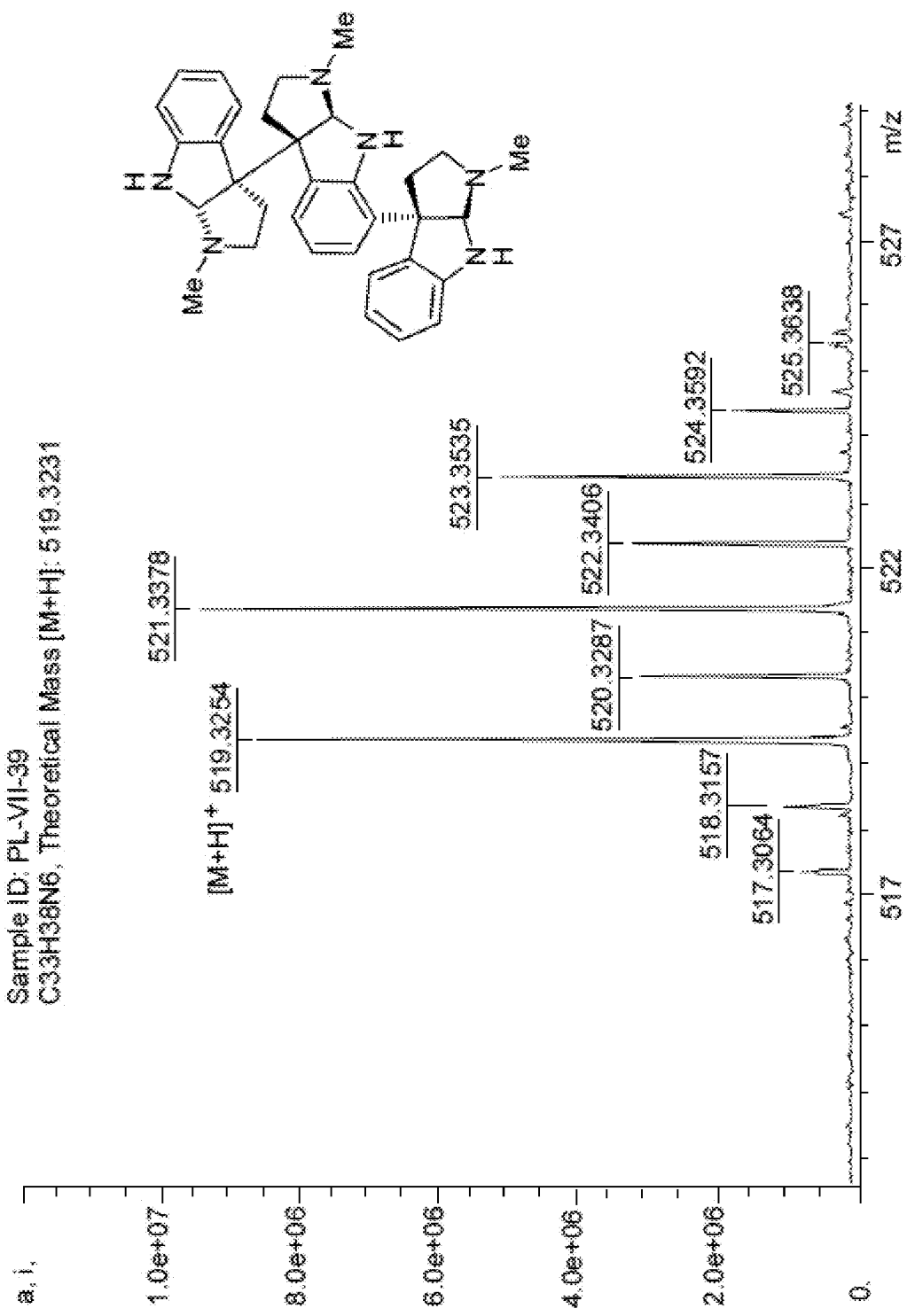
FIG. 6 is the mass spectral data confirming the formation of (−)-hodgkinsine.

HRMS (DART) (m/z): calculated for $C_{33}H_{39}N_6[M+H]^+$: 519.3231, found: 519.3254 (FIG. 6).

Example 3. Building Block Synthesis

Formation of Azide

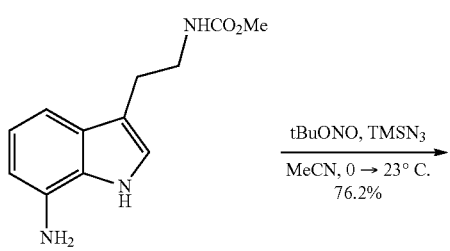

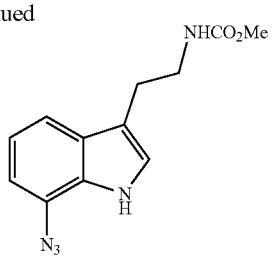

To a solution of methyl (2-(7-amino-1H-indol-3-yl)ethyl) carbamate (998 mg, 4.28 mmol, 1 equiv) in acetonitrile (54.0 mL) at 0° C. were sequentially added tert-butyl nitrite (825 μL, 6.24 mmol, 1.50 equiv) and azidotrimethylsilane (1.01 mL, 7.28 mmol, 1.70 equiv). The reaction mixture was allowed to warm to 22° C. After 24 h, the reaction mixture was concentrated under reduced pressure. The resulting residue was purified by flash column chromatography on silica gel (eluent: 30%→40% ethyl acetate in hexanes) to afford cyclotryptamine azide (846 mg, 76.2%).

$^1$H NMR (400 MHz, CDCl$_3$, 20° C.): δ 8.29 (s, 1H, NH), 7.39 (d, J=7.9 Hz, 1H, C$_4$H), 7.13 (app-t, J=7.8 Hz, 1H, C$_5$H), 7.02 (br-s, 1H, C$_{8a}$H), 6.98 (d, J=7.5 Hz, 1H, C$_6$H), 4.80 (s, 1H, NHCO$_2$CH$_3$), 3.67 (s, 3H, NHCO$_2$CH$_3$), 3.51 (dd, J=6.1, 12.4 Hz, 2H, C$_2$H$_2$), 2.95 (t, J=6.8 Hz, 2H, C$_3$H$_2$).

$^{13}$C NMR (100 MHz, CDCl$_3$, 20° C.): δ 157.2 (NHCO$_2$CH$_3$), 129.1 (C$_{4a}$), 128.6 (C$_{7a}$), 124.6 (C$_7$), 122.7 (C$_{8a}$), 120.3 (C$_5$), 115.5 (C$_4$), 113.6 (C$_{3a}$), 110.6 (C$_6$), 52.2 (NHCO$_2$CH$_3$), 41.4 (C$_2$), 25.9 (C$_3$).

FTIR (thin film) cm$^{-1}$: 3322 (s), 2946 (m), 2115 (s), 1700 (s), 1522 (m), 1282 (m).

HRMS (DART) (m/z): calculated for $C_{12}H_{14}N_5O_2$ [M+H]$^+$: 260.1142, found 260.1152.

TLC (50% ethyl acetate in hexanes), Rf: 0.43 (UV, CAM).

M.p.: 87-89 (CH$_2$Cl$_2$).

Nitrogen Protection with Teoc

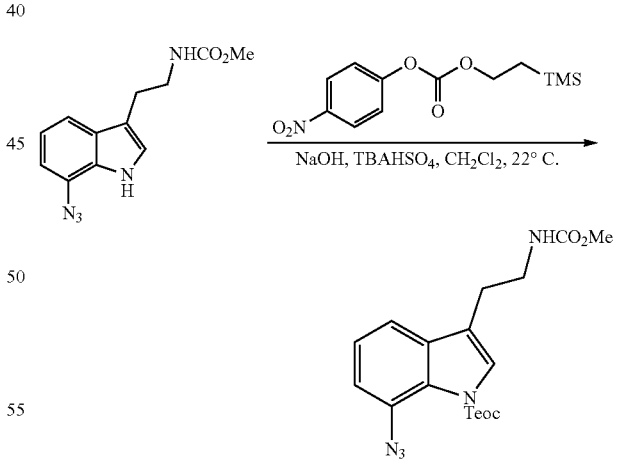

To a solution of methyl (2-(7-azido-1H-indol-3-yl)ethyl) carbamate (1.66 g, 6.40 mmol, 1 equiv), 4-nitrophenyl (2-(trimethylsilyl)ethyl) carbonate (2.72 g, 9.60 mmol, 1.50 equiv) and tetrabutylammonium hydrogensulfate (217 mg, 640 μmol, 10.0 mol %) in dichloromethane (64.0 mL) at 22° C. was added finely powdered sodium hydroxide (768 mg, 19.2 mmol, 3.00 equiv). After 15.5 h, the reaction mixture was washed with aqueous sodium hydroxide (1N, 100 mL) and the aqueous layer was extracted with dichloromethane (3×50 mL). The combined organic layers were dried over anhydrous sodium sulfate, were filtered and were concentrated under reduced pressure. The resulting residue was purified by flash column chromatography on silica gel (eluent: 5%→15% acetone in hexanes) to afford 2-(trimethylsilyl)ethyl-7-azido-3-(2-((methoxycarbonyl)amino)ethyl)-1H-indole-1-carboxylate (2.53 g, 98.0%) as an off-white amorphous gum. Structural assignments were made using additional information from gHSQC and gHMBC experiments.

$^1$H NMR (400 MHz, CDCl$_3$, 20° C.): δ 7.42 (s, 1H, C$_{8a}$H), 7.35 (d, J=7.7 Hz, 1H, C$_4$H), 7.28 (app-t, J=7.8 Hz, 1H, C$_5$H), 7.14 (d, J=8.4 Hz, 1H, C$_6$H), 4.78 (br-s, 1H, NHCO$_2$CH$_3$), 4.54-4.44 (m, 2H, NCO$_2$CH$_2$CH$_2$Si(CH$_3$)$_3$), 3.67 (s, 3H, NHCO$_2$CH$_3$), 3.49 (dd, J=6.4, 12.9 Hz, 2H, C$_2$H$_2$), 2.88 (t, J=6.8 Hz, 2H, C$_3$H$_2$), 1.26-1.17 (m, 2H, NCO$_2$CH$_2$CH$_2$Si(CH$_3$)$_3$), 0.09 (s, 9H, NCO$_2$CH$_2$CH$_2$Si(CH$_3$)$_3$).

$^{13}$C NMR (100 MHz, CDCl$_3$, 20° C.): δ 157.1 (NHCO$_2$CH$_3$), 150.4 (NCO$_2$CH$_2$CH$_2$Si(CH$_3$)$_3$), 133.9 (C$_{4a}$), 127.9 (C$_7$), 126.8 (C$_{7a}$), 126.1 (C$_{8a}$), 124.1 (C$_5$), 117.8 (C$_{3a}$), 116.0 (C$_6$), 115.9 (C$_4$), 66.4 (NCO$_2$CH$_2$CH$_2$Si(CH$_3$)$_3$), 52.2 (NCO$_2$CH$_3$), 40.6 (C$_2$), 25.6 (C$_3$), 17.7 (NCO$_2$CH$_2$CH$_2$Si(CH$_3$)$_3$), −1.4 (NCO$_2$CH$_2$CH$_2$Si(CH$_3$)$_3$).

FTIR (thin film) cm$^{-1}$: 3370 (m), 2954 (s), 2115 (s), 1728 (s), 1526 (w).

HRMS (DART) (m/z): calculated for C$_{18}$H$_{29}$N$_6$O$_4$Si [M+NH$_4$]$^+$: 421.2014, found 421.2005.

TLC (20% ethyl acetate in hexanes), Rf: 0.34 (UV, CAM).

Cyclization to Cyclotryptamine

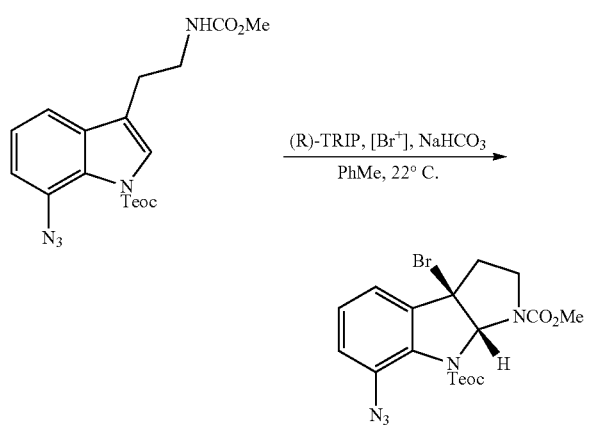

A sample of bromine salt S1 (Xie, W.; Jiang, G.; Liu, H.; Hu, J.; Pan, X.; Zhang, H.; Wan, X.; Lai, Y.; Ma, D. *Angew. Chem. Int. Ed.* 2013, 52, 12924 (the entirety is herein explicitly incorporate by reference)) (4.32 g, 8.09 mmol, 1.30 equiv) was added to a suspension of tryptamine (2.51 g, 6.22 mmol, 1 equiv), (R)-3,3'-Bis(2,4,6-triisopropyl-phenyl)-1,1'-binaphthyl-2,2'-diyl hydrogen phosphate ((R)-TRIP, 468 mg, 622 µmol, 10.0 mol %), and sodium hydrogen carbonate (2.09 g, 24.9 mmol, 4.00 equiv) in toluene (124 mL) at 22° C. After stirring for 22 h, the yellow suspension was diluted with a saturated aqueous sodium thiosulfate solution (50 mL) and was stirred vigorously for 10 min. The biphasic mixture was further diluted with deionized water (50 mL) and was then extracted with dichloromethane (3×50 mL). The combined organic extracts were dried over anhydrous sodium sulfate, were filtered, and were concentrated under reduced pressure. The resulting residue was purified by flash column chromatography on silica gel (eluent: 5→10% acetone in hexanes) to afford bromocyclotryptamine (2.69 g, 89.7%, 97:3 er) as a colorless amorphous gum (further elution with 60% ethyl acetate in hexanes allows for the recovery of the (S)-TRIP catalyst). The enantiomeric ratio was determined by chiral HPLC analysis (Chiralpak IA, 5% iPrOH/95% hexanes, 0.75 mL/min, 254 nm, t$_R$ (major)=8.69 min, t$_R$ (minor)=11.0 min). Structural assignments were made using additional information from gHSQC and gHMBC experiments.

$^1$H NMR (400 MHz, CDCl$_3$, 20° C.): δ 7.21 (app-t, J=7.6 Hz, 1H, C$_5$H), 7.16 (dd, J=1.4, 7.6 Hz, 1H, C$_4$H), 7.03 (d, J=7.5 Hz, 1H, C$_6$H), 6.31 (br-s, 1H, C$_{8a}$H), 4.48-4.29 (m, 2H, NCO$_2$CH$_2$CH$_2$Si(CH$_3$)$_3$) 3.74 (s, 3H, NCO$_2$CH$_3$), 3.67 (t, J=7.9 Hz, 1H, C$_3$H$_a$), 2.88-2.67 (m, 3H, C$_3$H$_b$, C$_2$H$_2$), 1.13 (t, J=8.8 Hz, 2H, NCO$_2$CH$_2$CH$_2$Si(CH$_3$)$_3$) 0.03 (s, 9H, NCO$_2$CH$_2$CH$_2$Si(CH$_3$)$_3$).

$^{13}$C NMR (100 MHz, CDCl$_3$, 20° C.): δ 154.8 (NCO$_2$CH$_3$), 154.3 (NCO$_2$CH$_2$CH$_2$Si(CH$_3$)$_3$), 137.4 (C$_{4a}$), 133.8 (C$_{7a}$), 132.2 (C$_7$), 127.5 (C$_5$), 122.4 (C$_6$), 119.7 (C$_4$), 86.0 (C$_{8a}$), 65.7 (NCO$_2$CH$_2$CH$_2$Si(CH$_3$)$_3$), 60.9 (C$_{3a}$), 53.0 (NCO$_2$CH$_3$), 46.0 (C$_3$), 39.2 (C$_2$), 17.7 (NCO$_2$CH$_2$CH$_2$Si(CH$_3$)$_3$), −1.4 (NCO$_2$CH$_2$CH$_2$Si(CH$_3$)$_3$).

FTIR (thin film) cm$^{-1}$: 2955 (m), 2116 (s), 1716 (s), 1449 (m), 1311 (m).

HRMS (DART) (m/z): calculated for C$_{18}$H$_{25}$N$_5$O$_4$Si [M+H]$^+$: 482.0854, found 482.0870.

$[α]_D^{24}$: −222 (c=0.62, CH$_2$Cl$_2$).

TLC (20% acetone in hexanes), Rf: 0.33 (UV, CAM).

Formation of 7-Amino Group by Azide Reduction

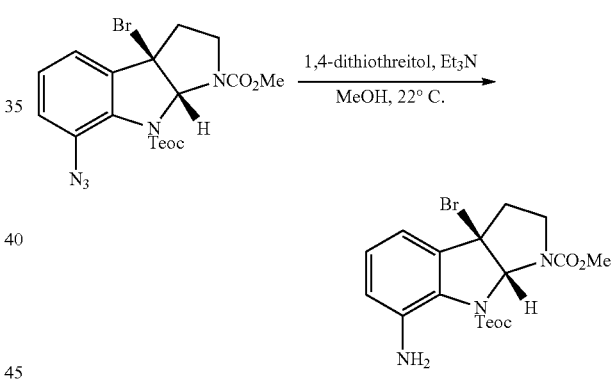

Triethylamine (4.91 mL, 35.2 mmol, 6.30 equiv) was added via syringe to a solution of azide (2.69 g, 5.58 mmol, 1 equiv) and dithiothreitol (4.40 mL, 28.5 mmol, 5.11 equiv) in methanol (56.0 mL). After 15 h, the reaction was diluted with dichloromethane (30 mL) and with a saturated aqueous sodium periodate solution (5 mL). After vigorous stirring for 10 min, the heterogeneous biphasic mixture was washed with saturated aqueous sodium chloride solution (50 mL) then extracted with dichloromethane (3×30 mL). The combined organic extracts were dried over anhydrous sodium sulfate, were filtered, and were concentrated under reduced pressure. The resulting residue was purified by flash column chromatography on silica gel (eluent: 15→25% ethyl acetate in hexanes) to afford cyclotryptamine amine (2.15 g, 84.4%) as a colorless amorphous gum. Structural assignments were made using additional information from gHSQC and gHMBC experiments.

$^1$H NMR (400 MHz, CDCl$_3$, 20° C.): δ 7.03 (app-t, J=7.7 Hz, 1H, C$_5$H), 6.78 (d, J=7.5 Hz, 1H, C$_4$H), 6.67 (d, J=7.9 Hz, 1H, C$_6$H), 6.35 (br-s, 1H, C$_{8a}$H), 4.67 (br-s, 2H, NH$_2$), 4.50-4.28 (m, 2H, NCO$_2$CH$_2$CH$_2$Si(CH$_3$)$_3$), 3.71 (s, 3H, NCO$_2$CH$_3$), 3.64 (br-s, 1H, C$_2$H$_a$), 2.882.75 (m, 2H, C$_2$H$_b$, C$_3$H$_a$), 2.752.62 (m, 1H, C$_3$H$_b$), 1.24-1.06 (m, 2H, NCO$_2$CH$_2$CH$_2$Si(CH$_3$)$_3$), −0.07 (s, 9H, NCO$_2$CH$_2$CH$_2$Si(CH$_3$)$_3$).

$^{13}$C NMR (100 MHz, CDCl$_3$, 20° C.): δ 155.3 (2C, NCO$_2$CH$_3$, (NCO$_2$CH$_2$CH$_2$Si(CH$_3$)$_3$) 138.4 (C$_7$), 135.5 (C$_{4a}$), 128.5 (C$_{7a}$), 127.4 (C$_5$), 119.1 (C$_6$), 112.7 (C$_4$), 84.9 (C$_{8a}$), 65.5 (NCO$_2$CH$_2$CH$_2$Si(CH$_3$)$_3$), 61.9 (C$_{3a}$), 52.8 (NCO$_2$CH$_3$), 46.1 (C$_2$), 39.6 (C$_3$), 17.9 (NCO$_2$CH$_2$CH$_2$Si(CH$_3$)$_3$), −1.4 (NCO$_2$CH$_2$CH$_2$Si(CH$_3$)$_3$).

FTIR (thin film) cm$^{−1}$: 3423 (m), 2955 (s), 1700 (s), 1623 (m).

HRMS (DART) (m/z): calculated for C$_{18}$H$_{27}$BrN$_3$O$_4$Si [M+H]$^+$: 456.0949, found 456.0938.

[α]$_D^{24}$: −322 (c=0.53, CH$_2$Cl$_2$).

TLC (50% ethyl acetate in hexanes), Rf: 0.51 (UV, CAM).

Formation of C7-Sulfonamide and Debromination

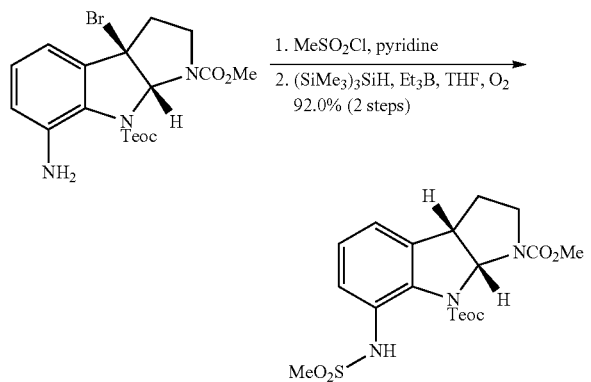

To a solution of cyclotryptamine (2.09 g, 4.58 mmol, 1 equiv) in pyridine (46.0 mL) was added methanesulfonyl chloride (709 µL, 9.16 mmol, 2.00 equiv). After 2 h, the reaction mixture was diluted with dichloromethane (30 mL), washed with saturated aqueous sodium chloride solution (50 mL) then extracted with dichloromethane (3×30 mL). The combined organic extracts were dried over anhydrous sodium sulfate, were filtered, and were concentrated under reduced pressure to afford crude methanesulfonyl cyclotryptamine as a yellow amorphous gum that was used in the next step without further purification.

For characterization purposes, the crude methanesulfonyl cyclotryptamine was purified by flash column chromatography on silica gel (eluent: 15→25% ethyl acetate in hexanes) to afford cyclotryptamine amine as a colorless amorphous gum.

Structural assignments were made using additional information from gCOSY, gHSQC, and gHMBC experiments.

$^1$H NMR (400 MHz, CDCl$_3$, 20° C.): δ 9.09 (s, 1H, NHSO$_2$CH$_3$), 7.61-7.47 (m, 1H, C$_6$H), 7.317.21 (m, 2H, C$_4$H, C$_5$H), 6.34 (s, 1H, C$_{8a}$H), 4.51-4.29 (m, 2H, NCO$_2$CH$_2$CH$_2$Si(CH$_3$)$_3$), 3.66 (app-s, 4H, NCO$_2$CH$_3$, C$_2$H$_a$), 2.91-2.82 (m, 1H, C$_3$H$_a$), 2.80-2.71 (m, 5H, NHSO$_2$CH$_3$, C$_2$H$_b$, C$_3$H$_b$), 1.27-1.09 (m, 2H, NCO$_2$CH$_2$CH$_2$Si(CH$_3$)$_3$) 0.07 (s, 9H, NCO$_2$CH$_2$CH$_2$Si(CH$_3$)$_3$).

$^{13}$C NMR (100 MHz, CDCl$_3$, 20° C.): δ 155.9 (NCO$_2$CH$_2$CH$_2$Si(CH$_3$)$_3$), 154.2 (NCO$_2$CH$_3$), 136.0 (C$_{4a}$), 134.3 (C$_{7a}$), 127.9 (2C, C$_4$ or C$_5$, C$_7$), 126.9 (C$_6$), 120.8 (C$_4$ or C$_5$), 84.9 (C$_{8a}$), 66.9 (NCO$_2$CH$_2$CH$_2$Si(CH$_3$)$_3$), 60.1 (C$_{3a}$), 52.9 (NCO$_2$CH$_3$), 46.1 (C$_2$), 39.2 (NHSO$_2$CH$_3$), 39.0 (C$_3$), 17.9 (NCO$_2$CH$_2$CH$_2$Si(CH$_3$)$_3$), 1.4 (NCO$_2$CH$_2$CH$_2$Si(CH$_3$)$_3$).

FTIR (thin film) cm$^{−1}$: 3175 (w), 2956 (m), 1716 (s), 1688 (s), 1161 (s).

HRMS (ESI) (m/z): calculated for C$_{19}$H$_{28}$BrN$_3$NaO$_6$SSi [M+Na]$^+$: 556.0544, found 556.0550.

[α]$_D^{24}$: −259 (c=0.61, CH$_2$Cl$_2$).

TLC (50% ethyl acetate in hexanes), Rf: 0.38 (UV, CAM).

C3a-Bromide Reduction

Triethylborane (1.0 M in THF, 916 µL, 916 µmol, 0.200 equiv) was added via syringe to a solution of crude methanesulfonyl cyclotryptamine and tris(trimethylsilyl)silane (4.23 mL, 13.7 mmol, 3.00 equiv) in tetrahydrofuran (46.0 mL) at 22° C. under an air atmosphere. After 1 h, the reaction mixture was washed with a saturated aqueous sodium bicarbonate solution (50 mL), then extracted with dichloromethane (3×50 mL). The combined organic extracts were dried over anhydrous sodium sulfate, were filtered, and were concentrated under reduced pressure to yield a colorless semi-solid suspended in a colorless oil. The resulting residue was purified by flash column chromatography on silica gel (eluent: 0→20% acetone in hexanes) to afford the reduced cyclotryptamine (1.92 g, 92.0%) as a colorless amorphous gum over two steps.

Structural assignments were made using additional information from gCOSY, gHSQC, and gHMBC experiments.

$^1$H NMR (400 MHz, CDCl$_3$, 20° C.): δ 9.08 (s, 1H, NHSO$_2$CH$_3$), 7.42 (d, J=8.0 Hz, 1H, C$_6$H), 7.20 (app-t, J=7.8 Hz, 1H, C$_5$H), 7.10 (app-dt, J=1.1, 7.5 Hz, 1H, C$_4$H), 6.32 (d, J=5.7 Hz, 1H, C$_{8a}$H), 4.46-4.27 (m, 2H, NCO$_2$CH$_2$CH$_2$Si(CH$_3$)$_3$), 4.06 (app-br-s, 1H, C$_{3a}$H), 3.65 (app-s, 4H, NCO$_2$CH$_3$, C$_2$H$_a$), 2.79 (app-dd, J=9.6, 18.6 Hz, 1H, C$_2$H$_b$), 2.68 (s, 3H, NHSO$_2$CH$_3$), 2.262.14 (m, 2H, C$_3$H$_2$), 1.23-1.03 (m, 2H, NCO$_2$CH$_2$CH$_2$Si(CH$_3$)$_3$), 0.05 (s, 9H, NCO$_2$CH$_2$CH$_2$Si(CH$_3$)$_3$).

$^{13}$C NMR (100 MHz, CDCl$_3$, 20° C.): δ 155.8 (NCO$_2$CH$_2$CH$_2$Si(CH$_3$)$_3$), 154.8 (NCO$_2$CH$_3$), 135.5 (C$_{4a}$), 135.4 (C$_{7a}$), 127.1 (2C, C$_7$, C$_5$), 125.8 (C$_6$), 121.6 (C$_4$), 77.8 (C$_{8a}$), 66.3 (NCO$_2$CH$_2$CH$_2$Si(CH$_3$)$_3$), 52.6 (NCO$_2$CH$_3$), 46.0 (C$_{3a}$), 45.2 (C$_2$), 38.7 (NHSO$_2$CH$_3$), 28.7 (C$_3$), 17.9 (NCO$_2$CH$_2$CH$_2$Si(CH$_3$)$_3$), −1.5 (NCO$_2$CH$_2$CH$_2$Si(CH$_3$)$_3$).

FTIR (thin film) cm$^{−1}$: 3163 (w), 2955 (m), 1711 (s), 1680 (s), 1160 (s).

HRMS (ESI) (m/z): calculated for C$_{19}$H$_{29}$N$_3$NaO$_6$SSi [M+Na]$^+$: 478.1439, found 478.1430.

[α]$_D^{24}$: −207 (c=0.68, CH$_2$Cl$_2$).

TLC (20% acetone in hexanes), Rf: 0.20 (UV, CAM).

Example 4. Efficient Synthesis of Sulfonylhydrazides

Synthesis of Sulfonamide (+)-10

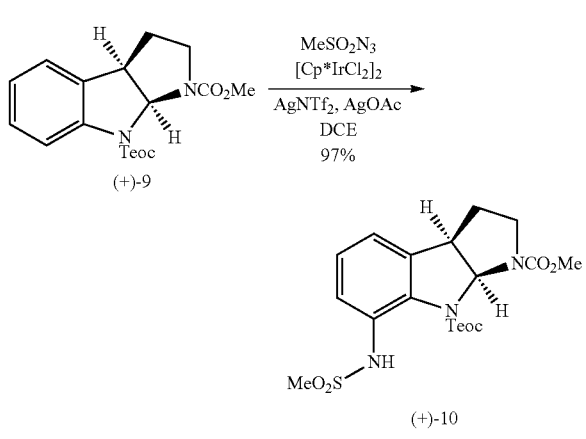

To a suspension of cyclotryptamine (+)-9 (96.6 mg, 266 µmol, 1 equiv), dichloro(pentamethylcyclopentadienyl)iridium (III) dimer ([Cp*IrCl$_2$]$_2$, 17.0 mg, 21.3 µmol, 8.00 mol %), silver bis(trifluoromethanesulfonyl)imide (33.0 mg, 85.1 µmol, 0.320 equiv) and silver acetate (26.7 mg, 160 µmol, 0.600 equiv) in dichloroethane (0.27 mL) was added methanesulfonyl azide (48.3 mg, 399 µmol, 1.50 equiv) (Matano, Y.; Ohkubo, H.; Honsho, Y.; Saito, A.; Seki, S.; Imahori, H. Org. Lett. 2013, 15, 932 (the entirety of which is herein explicitly incorporated by reference)) via syringe. The reaction flask was sealed and the reaction was allowed to stir for 20 h. The reaction mixture was filtered through a pad of Celite and the filter cake was rinsed with ethyl acetate (10 mL). The filtrate was concentrated under reduced pressure. The resulting residue was purified by flash column chromatography on silica gel (eluent: gradient, 20→40% ethyl acetate in hexanes) to afford cyclotryptamine sulfonamide (+)-10 (117 mg, 96.5%) as a pale yellow amorphous gum. Structural assignments were made using additional information from gCOSY, HSQC, and HMBC experiments.

$^1$H NMR (400 MHz, CDCl$_3$, 25° C.): δ 9.08 (s, 1H, NHSO$_2$CH$_3$), 7.42 (d, J=8.0 Hz, 1H, C$_6$H), 7.20 (app-t, J=7.8 Hz, 1H, C$_5$H), 7.10 (app-dt, J=1.1, 7.5 Hz, 1H, C$_4$H), 6.32 (d, J=5.7 Hz, 1H, C$_{8a}$H), 4.46-4.27 (m, 2H, C$_{10}$H$_2$), 4.06 (app-br-s, 1H, C$_{3a}$H), 3.65 (app-s, 4H, NCO$_2$CH$_3$, C$_2$H$_a$), 2.79 (app-dd, J=9.6, 18.6 Hz, 1H, C$_2$H$_b$), 2.68 (s, 3H, NHSO$_2$CH$_3$), 2.26-2.14 (m, 2H, C$_3$H$_2$), 1.23-1.03 (m, 2H, C$_{11}$H$_2$), 0.05 (s, 9H, (C$_{12}$H$_3$)$_3$).

$^{13}$C NMR (100 MHz, CDCl$_3$, 25° C.): δ 155.8 (C$_9$), 154.8 (NCO$_2$CH$_3$), 135.5 (C$_{4a}$), 135.4 (C$_{7a}$), 127.1 (2C, C$_7$, C$_5$), 125.8 (C$_6$), 121.6 (C$_4$), 77.8 (C$_{8a}$), 66.3 (C$_{10}$), 52.6 (NCO$_2$CH$_3$), 46.0 (C$_{3a}$), 45.2 (C$_2$), 38.7 (NHSO$_2$CH$_3$), 28.7 (C$_3$), 17.9 (C$_{11}$), −1.5 (C$_{12}$).

FTIR (thin film) cm$^{-1}$: 3163 (w), 2955 (m), 1711 (s), 1680 (s), 1160 (s).

HRMS (ESI) (m/z): calculated for C$_{19}$H$_{29}$N$_3$NaO$_6$SSi [M+Na]$^+$: 478.1439, found 478.1430.

[α]$_D$$^{24}$: +226 (c=0.61, CH$_2$Cl$_2$).

TLC (20% acetone in hexanes), Rf: 0.20 (UV, CAM).

Synthesis of Sulfonamide (−)-10

To a suspension of cyclotryptamine (−)-9 (278 mg, 767 µmol, 1 equiv), dichloro(pentamethylcyclopentadienyl)iridium (III) dimer ([Cp*IrCl$_2$]$_2$, 48.9 mg, 61.4 µmol, 8.00 mol %), silver bis(trifluoromethanesulfonyl)imide (95.1 mg, 245 µmol, 0.320 equiv) and silver acetate (76.8 mg, 460 µmol, 0.600 equiv) in dichloroethane (0.77 mL) was added methanesulfonyl azide (139 mg, 1.15 mmol, 1.50 equiv) via syringe. The reaction flask was sealed and the reaction was allowed to stir for 20 h. The reaction mixture was filtered through a pad of Celite and the filter cake was rinsed with ethyl acetate (15 mL). The filtrate was concentrated under reduced pressure. The resulting residue was purified by flash column chromatography on silica gel (eluent: gradient, 20→40% ethyl acetate in hexanes) to afford cyclotryptamine sulfonamide (−)-10 (331 mg, 94.7%) as a pale yellow amorphous gum. For full characterization data for cyclotryptamine sulfonamide (−)-10 ([α]$_D$$^{24}$=−207 (c=0.68, CH$_2$Cl$_2$)) see previous procedure in this document.

Synthesis of Sulfonylhydrazide (−)-11

Cyclotryptamine sulfonamide (−)-10 (2.02 g, 4.43 mmol, 1 equiv) was azeotropically dried from anhydrous benzene (3×5 mL) and the residue was dissolved in tetrahydrofuran (44 mL). The solution was cooled to 0° C. and sodium hydride (60% in mineral oil, 230 mg, 5.76 mmol, 1.30 equiv) was added in one portion. The ice-water bath was removed and after 30 min, O-(diphenylphosphinyl)hydroxylamine (1.34 g, 5.76 mmol, 1.30 equiv) was added in one portion. After 1 h, the reaction mixture was diluted with ethyl acetate (30 mL), washed with mixture of saturated aqueous sodium bicarbonate and water (10:1 v/v, 25 mL) and the aqueous layer was extracted with ethyl acetate (3×20 mL). The combined organic extracts were dried over anhydrous sodium sulfate, were filtered, and were concentrated under reduced pressure. The resulting residue was purified by flash column chromatography on silica gel (eluent: 25→50% ethyl acetate in hexanes) to afford hydrazidocyclotryptamine (−)-11 (1.70 g, 81.5%) as an orange amorphous gum.

$^1$H NMR (400 MHz, CDCl$_3$, 25° C.): δ 7.31 (app-p, J=3.7 Hz, 1H, C$_5$H), 7.20-7.14 (m, 2H, C$_4$H, C$_6$H), 6.27 (br-d, J=5.7 Hz, 1H, C$_{8a}$H), 4.50 (br-s, 2H, NH$_2$), 4.29 (t, J=8.9 Hz, 2H, C$_{10}$H$_2$), 4.02 (t, J=6.0 Hz, 1H, C$_{3a}$H), 3.66 (s, 3H, NCO$_2$CH$_3$), 3.55 (br-s, 1H, C$_2$H$_a$), 3.04 (s, 3H, SO$_2$CH$_3$), 2.79 (td, J=6.1, 11.0 Hz, 1H, C$_2$H$_b$), 2.21-2.01 (m, 2H, C$_3$H$_2$), 1.22-1.02 (m, 2H, C$_{11}$H$_2$), 0.03 (s, 9H, (C$_{12}$H$_3$)$_3$).

$^{13}$C NMR (100 MHz, CDCl$_3$, 25° C.): δ 154.9 (C$_9$), 154.6 (NCO$_2$CH$_3$), 140.0 (C$_{7a}$), 136.7 (C$_{4a}$), 133.3 (C$_7$), 126.8 (C$_5$), 123.9 (2C, C$_4$, C$_6$), 78.1 (C$_{8a}$), 65.2 (C$_{10}$), 52.5 (NCO$_2$CH$_3$), 46.1 (br, C$_{3a}$), 44.8 (C$_2$), 37.7 (SO$_2$CH$_3$), 29.3 (C$_3$), 17.9 (C$_{11}$), −1.5 (C$_{12}$).

FTIR (thin film) cm$^{-1}$: 3366 (m), 2954 (m), 1700 (s), 1653 (w), 1559 (w), 1457 (s), 1337 (m).

HRMS (ESI) (m/z): calculated for C$_{19}$H$_{30}$N$_4$NaO$_6$SSi [M+Na]$^+$: 493.1548, found 493.1519.

[α]$_D$$^{24}$: −119 (c=0.49, CH$_2$Cl$_2$).

TLC (50% ethyl acetate in hexanes), Rf: 0.18 (UV, CAM).

Example 5. Diazene Formation Reactions

Diazene Formation with Hydrazidobenzene

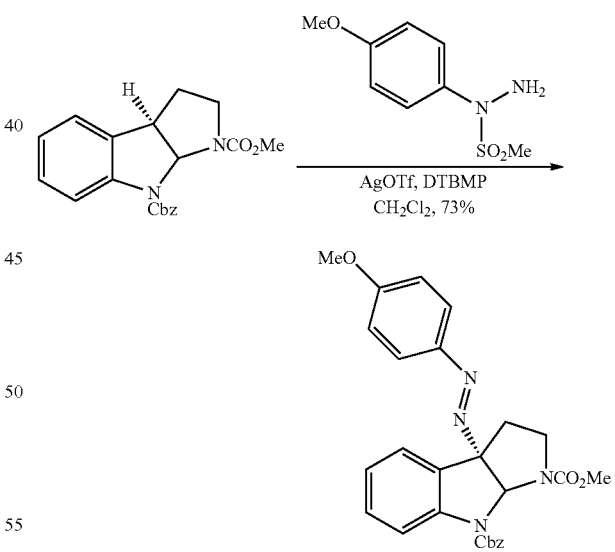

A sample of silver trifluoromethanesulfonate (20.0 mg, 78.0 µmol, 2.00 equiv) was added to a solution of bromocyclotryptamine (16.8 mg, 39.0 µmol, 1 equiv), N-(4-methoxyphenyl)methanesulfonohydrazide (12.8 mg, 59.0 µmol, 1.50 equiv), and 2,6-di-tert-butyl-4-methylpyridine (20.1 mg, 98.0 µmol, 2.50 equiv) in dichloromethane (400 µL) at 22° C. After 1.5 h, the off-white suspension was filtered through a pad of Celite. The filter cake was washed with ethyl acetate (5 mL) and the filtrate was concentrated under reduced pressure. The resulting residue was purified by flash column chromatography on silica gel (eluent: 20%→30% ethyl acetate in hexanes) to afford diazene (13.9 mg, 73.3%) as a bright yellow oil.

Diazene Formation with Hydrazidocyclotryptamine

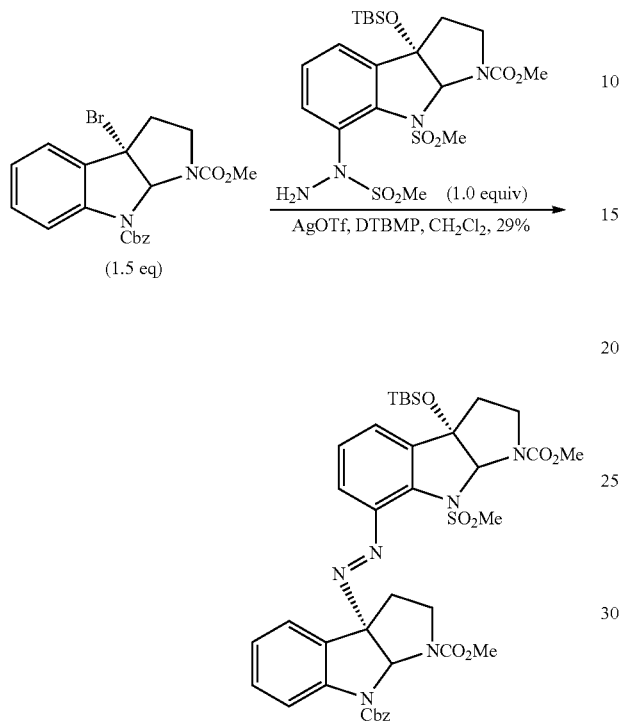

A sample of silver trifluoromethanesulfonate (13.9 mg, 54.0 µmol, 2.00 equiv) was added to a solution of bromocyclotryptamine (15.1 mg, 35.0 µmol, 1.30 equiv), cyclotryptamine methanesulfonohydrazide (14.6 mg, 27.0 µmol, 1 equiv), and 2,6-di-tert-butyl-4-methylpyridine (14.0 mg, 68.0 µmol, 2.50 equiv) in dichloromethane (350 µL) at 22° C. After 1.5 h, the off-white suspension was filtered through a pad of Celite. The filter cake was washed with ethyl acetate (5 mL) and the filtrate was concentrated under reduced pressure. The resulting residue was purified by flash column chromatography on silica gel (eluent: 15%→80% ethyl acetate in hexanes). A fraction of material was then repurified by HPLC to afford cyclotryptamine diazene (6.20 mg, 28.5%) as a bright yellow solid.

As a result of the slow conformational equilibration at ambient temperature, NMR spectra were collected at elevated temperature.

Diazene Formation with Hydrazidocyclotryptamine

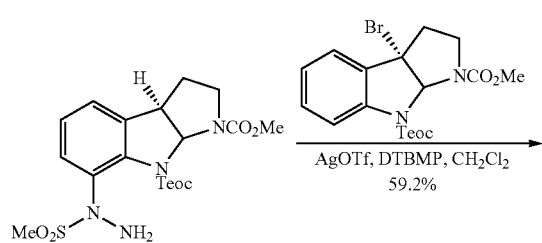

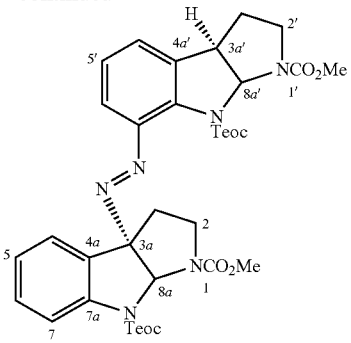

A sample of silver trifluoromethanesulfonate (673 mg, 2.62 mmol, 2.00 equiv) was added to a solution of bromocyclotryptamine (578 mg, 1.31 mmol, 1 equiv), cyclotryptamine methanesulfonohydrazide (802 mg, 1.70 mmol, 1.30 equiv), and 2,6-di-tert-butyl-4-methylpyridine (674 mg, 3.28 mmol, 2.50 equiv) in dichloromethane (13.0 mL) at 22° C. After 1 h, the off-white suspension was filtered through a pad of Celite. The filter cake was washed with ethyl acetate (20 mL) and the filtrate was concentrated under reduced pressure. The resulting residue was purified by flash column chromatography on silica gel (eluent: 25%→35% ethyl acetate in hexanes) to yield the cyclotryptamine dimer (582 mg, 59.2%) as a bright yellow amorphous gum.

$^1$H NMR (400 MHz, CDCl$_3$, 20° C.): δ 7.80 (d, J=8.1 Hz, 1H, C$_7$H), 7.33–7.20 (m, 3H, C$_6$H, C$_4$H, C$_4$'H), 7.17 (d, J=7.7 Hz, 1H, C$_{6'}$H), 7.15–7.08 (m, 1H, C$_{5'}$H), 7.03 (app-t, J=7.5 Hz, 1H, C$_5$H), 6.89 (s, 1H, C$_{8a}$H), 6.41 (br-s, 1H, C$_{8a'}$H), 4.43–4.31 (m, 2H, N$_8$CO$_2$CH$_2$CH$_2$Si(CH$_3$)$_3$), 4.31–4.23 (m, 1H, C$_{3a'}$H), 4.14–3.96 (m, 3H, C$_2$H$_a$, N$_8$CO$_2$CH$_2$CH$_2$Si(CH$_3$)$_3$), 3.89–3.67 (m, 7H, C$_{2'}$H$_a$, N$_1$CO$_2$CH$_3$, N$_{1'}$CO$_2$CH$_3$), 3.10 (td, J=5.2, 11.7 Hz, 1H, C$_{2'}$H$_b$), 2.93 (td, J=6.9, 10.8 Hz, 1H, C$_2$H$_b$), 2.62–2.46 (m, 1H, C$_{3}$H$_a$), 2.37 (dd, J=5.1, 12.6 Hz, 1H, C$_3$H$_b$), 2.28–2.13 (m, 2H, C$_{3'}$H$_2$), 1.15 (dd, J=6.8, 10.8 Hz, 2H, N$_8$CO$_2$CH$_2$CH$_2$Si(CH$_3$)$_3$), 0.96 (br-s, 2H, N$_8$CO$_2$CH$_2$CH$_2$Si(CH$_3$)$_3$), 0.06 (s, 9H, N$_8$CO$_2$CH$_2$CH$_2$Si(CH$_3$)$_3$), −0.02 (s, 9H, N$_8$CO$_2$CH$_2$CH$_2$Si(CH$_3$)$_3$).

$^{13}$C NMR (100 MHz, CDCl$_3$, 20° C.): δ 155.4 (N$_1$CO$_2$CH$_3$ or N$_{1'}$CO$_2$CH$_3$), 155.3 (N$_1$CO$_2$CH$_3$ or N$_{1'}$CO$_2$CH$_3$), 154.9 (N$_8$CO$_2$CH$_2$CH$_2$Si(CH$_3$)$_3$ or N$_8$CO$_2$CH$_2$CH$_2$Si(CH$_3$)$_3$), 153.8 (N$_8$CO$_2$CH$_2$CH$_2$Si(CH$_3$)$_3$ or N$_8$CO$_2$CH$_2$CH$_2$Si(CH$_3$)$_3$), 143.5 (C$_{7a}$), 141.6 (C$_{7'}$), 139.7 (C$_{7a'}$), 135.7 (C$_{4a'}$), 130.0 (C$_6$), 129.2 (C$_{4a}$), 125.7 (C$_{5'}$), 125.4 (C$_4$ or C$_{4'}$), 125.3 (C$_4$ or C$_{4'}$), 123.5 (C$_5$), 117.1 (C$_{6'}$), 116.2 (C$_7$), 88.9 (C$_{3a}$), 79.6 (C$_{8a}$), 79.1 (C$_{8a'}$), 64.8 (C$_{3a'}$), 64.5 (N$_8$CO$_2$CH$_2$CH$_2$Si(CH$_3$)$_3$), 52.8 (N$_1$CO$_2$CH$_3$ or N$_{1'}$CO$_2$CH$_3$), 52.7 (N$_1$CO$_2$CH$_3$ or N$_{1'}$CO$_2$CH$_3$), 46.4 (N$_8$CO$_2$CH$_2$CH$_2$Si(CH$_3$)$_3$), 46.1 (C$_2$), 45.2 (C$_{2'}$), 35.9 (C$_3$), 29.6 (C$_{3'}$), 17.9 (2C, N$_8$CO$_2$CH$_2$CH$_2$Si(CH$_3$)$_3$, N$_8$CO$_2$CH$_2$CH$_2$Si(CH$_3$)$_3$), −1.4 (N$_8$CO$_2$CH$_2$CH$_2$Si(CH$_3$)$_3$ or N$_8$CO$_2$CH$_2$CH$_2$Si(CH$_3$)$_3$), −1.5 (N$_8$CO$_2$CH$_2$CH$_2$Si(CH$_3$)$_3$ or N$_8$CO$_2$CH$_2$CH$_2$Si(CH$_3$)$_3$).

FTIR (thin film) cm$^{-1}$: 2954 (m), 1707 (s), 1602 (w), 1397 (m), 1259 (m).

HRMS (ESI) (m/z): calculated for C$_{36}$H$_{50}$N$_6$NaO$_8$Si$_2$ [M+Na]$^+$: 773.3121, found 773.3115.

[α]$_D^{24}$: −86 (c=0.61, CH$_2$Cl$_2$).

TLC (50% ethyl acetate in hexanes), Rf: 0.32 (UV, CAM).

Example 6. Representative Csp2-Csp3 Bond Formation

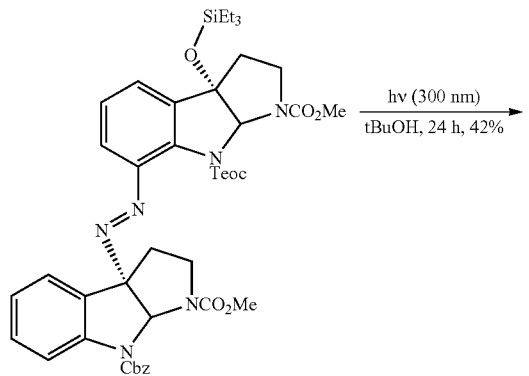

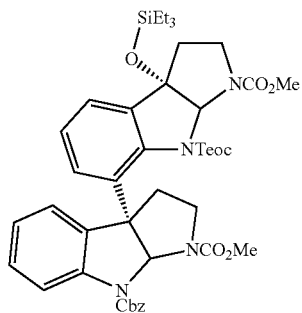

A solution of cyclotryptamine diazene dimer (6.00 mg, 7.00 μmol, 1 equiv) in degassed (N₂ stream, 5 min) tert-butanol (700 μL) was irradiated in a Rayonet photoreactor equipped with 16 radially distributed (r=12.7 cm) 25 W lamps (λ=300 nm) at 25° C. After 24 h, the reaction mixture was concentrated under reduced pressure. The resulting residue was purified by flash column chromatography on silica gel (eluent: 30% ethyl acetate in hexanes) to afford coupled cyclotryptamine dimer (2.50 mg, 42.4%) as an off-white solid.

Example 7. Representative Examples of CH-Amination

In a Diazene-Containing Intermediate

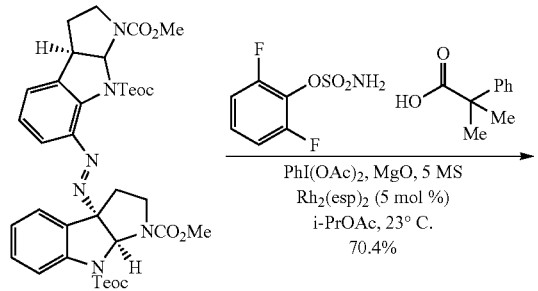

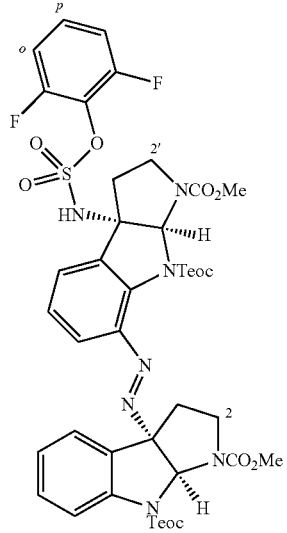

A round bottom flask was charged with 5 Å molecular sieves (13.4 mg, 200 mg/mmol of diazene starting material), magnesium oxide (10.8 mg, 268 μmol, 4.00 equiv) and flame-dried under vacuum for 5 min. The reaction vessel was allowed to cool to 22° C. and back filled with argon. Solid 2,6-difluorophenyl sulfamate (17.8 mg, 87.0 μmol, 1.30 equiv) (J. L. Roizen, D. N. Zalatan and J. Du Bois, *Angew. Chem. Int. Ed.*, 2013, *Early View*, DOI: 10.1002/anie.201304238 (the entirety of which is herein explicitly incorporated by reference)), 2-methyl-2-phenylpropionic acid (5.60 mg, 34.0 μmol, 0.500 equiv), and Rh₂(esp)₂ (0.500 mg, 0.70 μmol, 0.0100 equiv) were added sequentially. A solution of cyclotryptamine diazene dimer (50.0 mg, 67.0 μmol, 1 equiv) in isopropyl acetate (130 μL) was added via syringe at 22° C. and the mixture was allowed to stir. After 5 min, (diacetoxyiodo)benzene (43.2 mg, 134 μmol, 2.00 equiv) was added and the green heterogeneous mixture was agitated by vigorous stirring at 22° C. After 14 h, another portion of Rh₂(esp)₂ (1.00 mg, 1.40 μmol, 0.0200 equiv) was added. After 4 h, the reaction mixture was filtered through a pad of Celite and the filter cake was rinsed with ethyl acetate (5 mL). The filtrate was concentrated under reduced pressure. The resulting residue was purified by flash column chromatography on silica gel (eluent: gradient, 35→50% ethyl acetate in hexanes) to afford cyclotryptamine dimer sulfamate ester (45.2 mg, 70.4%) as a bright yellow amorphous gum. Structural assignments were made using additional information from gCOSY, HSQC, and HMBC experiments.

$^1$H NMR (400 MHz, CDCl₃, 20° C.): δ 7.77 (d, J=8.1 Hz, 1H, C₇H), 7.48 (d J=6.6 Hz, 1H, C₄·H), 7.33-7.27 (m, 2H, C₆H, C₆·H), 7.25-7.13 (m, 3H, C₄H, C₅·H, C$_p$H), 7.01 (app-t, J=7.2 Hz, 1H, C₅H), 6.96 (t, J=8.1 Hz, 2H, C$_m$H), 6.85 (br-s, 1H, C$_{8a}$H), 6.58 (br-s, 1H, C$_{8a'}$H). 6.16 (br-s, 1H, NH), 4.39-4.27 (m, 2H, N₈CO₂CH₂CH₂Si(CH₃)₃ or N₈·CO₂CH₂CH₂Si(CH₃)₃), 4.27-4.19 (m, 1H, N₈CO₂CH$_a$CH₂Si(CH₃)₃ or N₈·CO₂CH$_a$CH₂Si(CH₃)₃), 4.13-3.96 (m, 2H, N₈CO₂CH$_b$CH₂Si(CH₃)₃ or N₈·CO₂CH$_b$CH₂Si(CH₃)₃, C₂H$_a$), 3.83-3.68 (m, 7H, C₂H$_a·$, N₁CO₂CH₃, N₁·CO₂CH₃), 3.07 (td, J=5.2, 11.7 Hz, 1H, C₂H$_b$), 2.90 (br-s, 1H, C₃·H$_a$), 2.81 (br-s, 1H, C₂·H$_b$), 2.63-2.45 (m, 2H, C₃H$_a$, C₃H$_b$), 2.35 (dd, J=5.1, 12.5 Hz, 1H, C₃H$_b$), 1.17-1.07 (m, 2H, N₈CO₂CH₂CH₂Si(CH₃)₃ or $N_{8'}CO_2CH_2CH_2Si(CH_3)_3$), 1.030.80 (m, 2H, $N_8CO_2CH_2CH_2Si(CH_3)_3$ or $N_{8'}CO_2CH_2CH_2Si(CH_3)_3$), 0.05 (s, 9H, $N_8CO_2CH_2CH_2Si(CH_3)_3$ or $N_{8'}CO_2CH_2CH_2Si(CH_3)_3$), −0.03 (s, 9H, $N_8CO_2CH_2CH_2Si(CH_3)_3$ or $N_{8'}CO_2CH_2CH_2Si(CH_3)_3$).

$^{13}C$ NMR (100 MHz, $CDCl_3$, 20° C.): δ 156.0 (dd, J=3.3, 253.7 Hz, $C_o$), 155.4 (2C, $N_1CO_2CH_3$, $N_{1'}CO_2CH_3$), 154.6 ($N_8CO_2CH_2CH_2Si(CH_3)_3$ or $N_{8'}CO_2CH_2CH_2Si(CH_3)_3$), 153.7 ($N_8CO_2CH_2CH_2Si(CH_3)_3$ or $N_{8'}CO_2CH_2CH_2Si(CH_3)_3$), 143.5 ($C_{7a}$), 141.8 ($C_{7'}$), 140.3 ($C_{7a'}$), 133.1 ($C_{4a'}$), 130.0 ($C_6$), 129.0 ($C_{4a}$), 127.8 (t, J=9.2 Hz, $C_p$), 126.9 (t, J=15.6 Hz, $C_i$), 126.2 ($C_5$), 125.5 ($C_4$), 125.4 ($C_{4'}$), 123.5 ($C_5$), 119.7 ($C_{6'}$), 116.3 ($C_7$), 112.7 (dd, J=4.4, 17.7 Hz, $C_m$), 88.9 ($C_{3a}$), 81.6 ($C_{8a}$), 79.7 ($C_{8a'}$), 71.6 ($C_{3a'}$), 65.2 ($N_8CO_2CH_2CH_2Si(CH_3)_3$ or $N_{8'}CO_2CH_2CH_2Si(CH_3)_3$), 64.5 ($N_8CO_2CH_2CH_2Si(CH_3)_3$ or $N_{8'}CO_2CH_2CH_2Si(CH_3)_3$), 52.8 (2C, $N_1CO_2CH_3$, $N_{1'}CO_2CH_3$), 46.1 ($C_2$), 45.0 ($C_{2'}$), 35.6 ($C_3$), 33.4 ($C_{3'}$), 17.9 ($N_8CO_2CH_2CH_2Si(CH_3)_3$ or $N_{8'}CO_2CH_2CH_2Si(CH_3)_3$), 17.7 ($N_8CO_2CH_2CH_2Si(CH_3)_3$ or $N_{8'}CO_2CH_2CH_2Si(CH_3)_3$), −1.4 ($N_8CO_2CH_2CH_2Si(CH_3)_3$ or $N_{8'}CO_2CH_2CH_2Si(CH_3)_3$), −1.5 ($N_8CO_2CH_2CH_2Si(CH_3)_3$ or $N_{8'}CO_2CH_2CH_2Si(CH_3)_3$).

FTIR (thin film) $cm^{-1}$: 3162 (s), 2955 (s), 1717 (s), 1457 (m), 862 (w), 733 (w).

HRMS (ESI) (m/z): calculated for $C_{42}H_{53}F_2N_7NaO_{11}SSi_2$ $[M+Na]^+$: 980.2923, found 980.2917.

$[α]_D^{24}$: 76 (c=0.72, $CH_2Cl_2$).

TLC (50% ethyl acetate in hexanes), Rf: 0.28 (UV, CAM).
In a Dimer with a Csp2-Csp3 Bond in Place

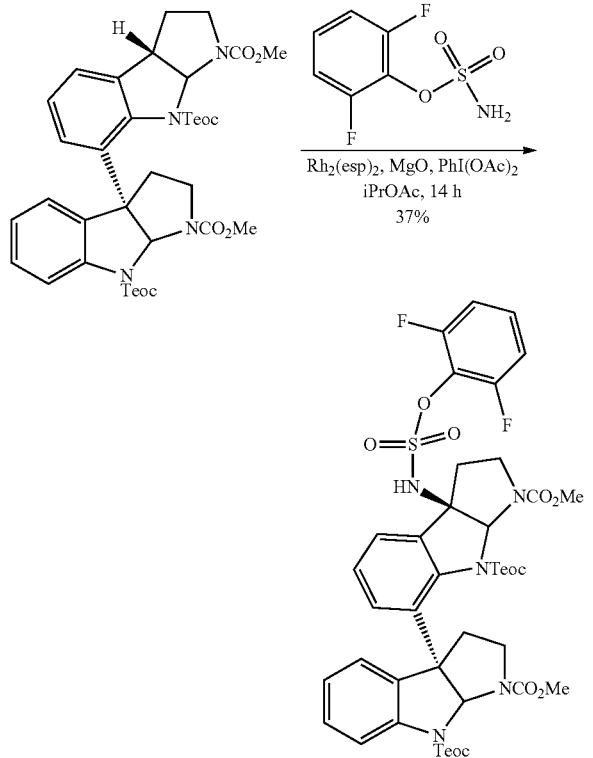

A round bottom flask was charged with 5 Å molecular sieves (39.0 mg, 200 mg/mmol of cyclotryptamine dimer starting material), magnesium oxide (31.4 mg, 780 μmol, 4.00 equiv) and flame-dried under vacuum for 5 min. The reaction vessel was allowed to cool to 22° C. and back filled with argon. Solid 2,6-difluorophenyl sulfamate (59.8 mg, 293 μmol, 1.30 equiv) (J. L. Roizen, D. N. Zalatan and J. Du Bois, *Angew. Chem. Int. Ed.*, 2013, Early View, DOI: 10.1002/anie.201304238 (the entirety of which is herein explicitly incorporated by reference)), 2-methyl-2-phenyl-propionic acid (16.1 mg, 98.0 μmol, 0.500 equiv), and $Rh_2(esp)_2$ (1.50 mg, 2.00 μmol, 0.0100 equiv) were added sequentially. A solution of cyclotryptamine diazene dimer (141 mg, 195 μmol, 1 equiv) in isopropyl acetate (390 μL) was added via syringe at 22° C. and the mixture was allowed to stir. After 5 min, (diacetoxyiodo)benzene (126 mg, 390 μmol, 2.00 equiv) was added and the green heterogeneous mixture was agitated by vigorous stirring at 22° C. After 3 h, another portion of $Rh_2(esp)_2$ (1.50 mg, 2.00 μmol, 0.0100 equiv) was added. After 22 h, the reaction mixture was filtered through a pad of Celite and the filter cake was rinsed with ethyl acetate (5 mL). The filtrate was concentrated under reduced pressure. The resulting residue was purified by flash column chromatography on silica gel (eluent: gradient, 8→20% acetone in hexanes) to afford cyclotryptamine dimer sulfamate ester (66.7 mg, 36.8%) as a bright yellow amorphous gum.

Example 8. Representative Procedure for Silyl Group Deprotection

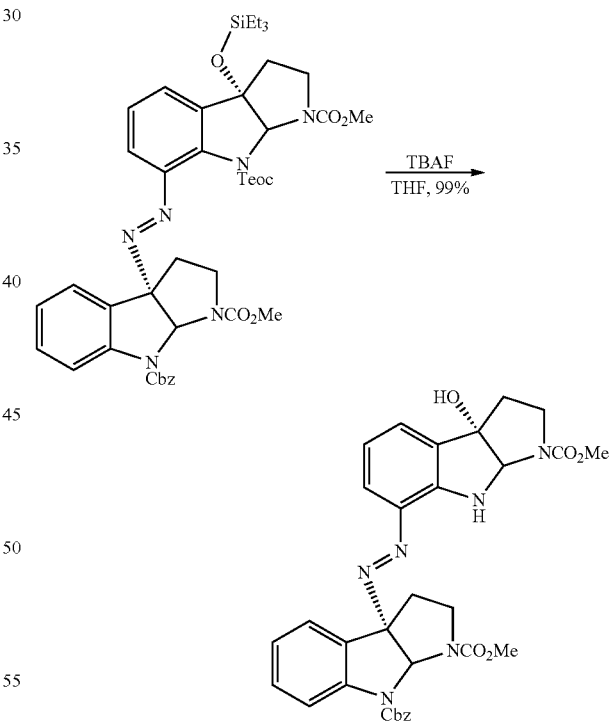

Tetrabutylammonium fluoride (1M in THF, 60.0 μL, 60.0 μmol, 10.0 equiv) was added dropwise to a solution of cyclotryptamine dimer (5.60 mg, 6.00 μmol, 1 equiv) in tetrahydrofuran (100 μL) at 22° C. After 1.5 h, the reaction mixture was concentrated under reduced pressure. The resulting residue was purified by flash column chromatography on silica gel (eluent: 50% ethyl acetate in hexanes) to afford deprotected cyclotryptamine dimer (4.40 mg, >99.9%) as a bright yellow oil.

Example 9: Synthesis of 2,2,2-Trifluoro-N-(4-methoxyphenyl)acetohydrazide (19)

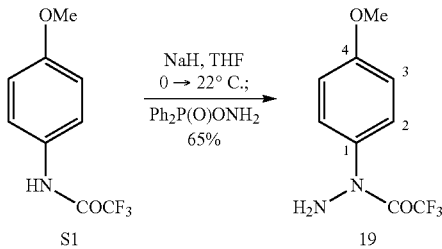

Anilide S1* (140 mg, 0.639 mmol, 1 equiv) was azeotropically dried by concentration from anhydrous benzene (3×2 mL) and the residue was dissolved in tetrahydrofuran (6.4 mL). The resulting solution was cooled to 0° C. and a sample of sodium hydride (60% in mineral oil, 30.7 mg, 0.767 mmol, 1.20 equiv) was added in one portion. The ice-water bath was removed and after 30 min, a sample of O-(diphenylphosphinyl)hydroxylamine (179 mg, 0.767 mmol, 1.20 equiv) was added in one portion. After 1 h, the reaction mixture was diluted with ethyl acetate (10 mL), was washed with a saturated aqueous sodium bicarbonate-water solution (10:1 v/v, 10 mL), and the aqueous layer was extracted with ethyl acetate (3×5 mL). The combined organic extracts were dried over anhydrous sodium sulfate, were filtered, and were concentrated under reduced pressure. The resulting residue was purified by flash column chromatography on silica gel (eluent: 7→20% ethyl acetate in hexanes) to afford hydrazide 19 (96.9 mg, 64.8%) as a tan solid.

$^1$H NMR (400 MHz, CDCl$_3$, 25° C., 1.7:1 mixture of atropisomers, *denotes minor atropisomer): δ 7.32 (d, J=9.0 Hz, 2H, C$_2$H*), 7.23 (d, J=8.6 Hz, 2H, C$_2$H), 6.92 (app-dd, J=6.3, 8.8 Hz, 4H, C$_3$H, C$_3$H*), 4.70 (br-s, 2H, NH$_2$), 4.39 (s, 2H, NH$_2$*), 3.82 (s, 3H, OCH$_3$), 3.80 (s, 3H, OCH$_3$*).

$^{13}$C NMR (125 MHz, CDCl$_3$, 25° C., 1.7:1 mixture of atropisomers, *denotes minor atropisomer): δ 160.3 (C$_4$), 159.0 (C$_4$*), 158.0 (q, J=34.8 Hz, COCF$_3$*), 155.9 (q, J=36.6 Hz, COCF$_3$), 135.0 (C$_1$*), 131.9 (C$_1$), 128.7 (C$_2$), 125.1 (C$_2$*), 117.0 (q, J=286.2 Hz, COCF$_3$*), 116.5 (q, J=286.3 Hz, COCF$_3$), 114.7 (C$_3$*), 114.5 (C$_3$), 55.6 (2C, OCH$_3$, OCH$_3$*).

$^{19}$F NMR (282 MHz, CDCl$_3$, 25° C., 1.5:1 mixture of atropisomers, *denotes minor atropisomer): δ −68.0 (s, COCF$_3$), −70.3 (s, COCF$_3$*).

FTIR (thin film) cm$^{-1}$: 3361 (m), 2966 (w), 2844 (w), 1701 (s), 1608 (m), 1512 (s), 1304 (m).

HRMS (DART) (m/z): calc'd for C$_9$H$_{10}$F$_3$N$_2$O$_2$[M+H]$^+$: 235.0689, found: 235.0688.

TLC (50% ethyl acetate in hexanes), Rf: 0.52 (UV, CAM).

M.p.: 67-69° C. (CH$_2$Cl$_2$).

Example 10: Synthesis of Trifluoroacetohydrazine (±)-23

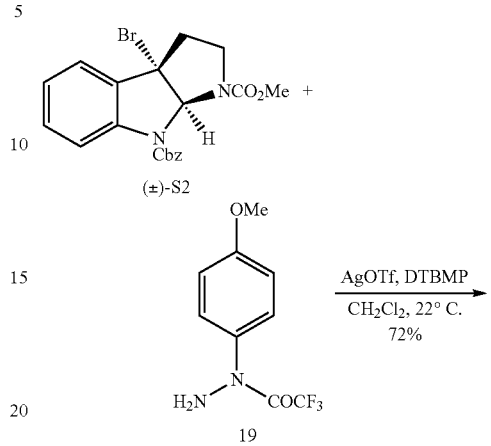

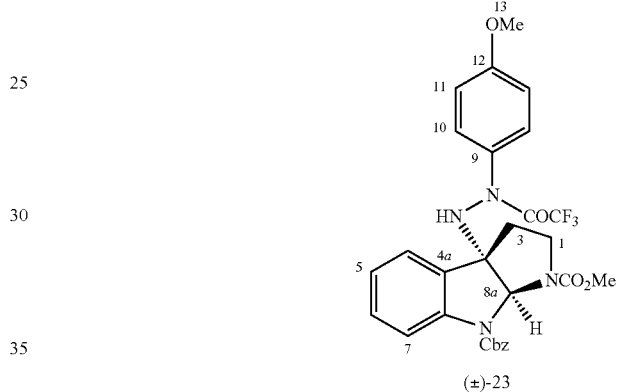

A sample of silver trifluoromethanesulfonate (61.7 mg, 240 μmol, 2.00 equiv) was added to a solution of bromocyclotryptamine (±)-S2 (51.3 mg, 120 μmol, 1 equiv), hydrazide 19 (36.5 mg, 156 μmol, 1.30 equiv), and 2,6-di-tert-butyl-4-methylpyridine (DTBMP, 61.6 mg, 300 μmol, 2.50 equiv) in dichloromethane (1.2 mL) at 22° C. After 1 h, the off-white suspension was diluted with dichloromethane (5 mL), was washed with a mixture of saturated aqueous sodium bicarbonate solution and saturated aqueous sodium thiosulfate solution (1:1 v/v, 10 mL), and the aqueous layer was extracted with dichloromethane (3×5 mL). The combined organic extracts were dried over anhydrous sodium sulfate, were filtered, and were concentrated under reduced pressure. The resulting residue was purified by flash column chromatography on silica gel (eluent: 10%→20% ethyl acetate in hexanes) to yield the trifluoroacetohydrazine (±)-23 (50.8 mg, 72.4%) as a white solid. Structural assignments were made using additional information from gCOSY, gHSQC, and gHMBC experiments.

$^1$H NMR (400 MHz, CDCl$_3$, 25° C., 13.5:1 mixture of atropisomers, *denotes minor atropisomer): δ 7.78 (d, J=8.3 Hz, 1H, C$_7$H), 7.40-7.27 (m, 6H, C$_6$H, Ph$_{Cbz}$-H), 7.22 (d, J=7.6 Hz, 1H, C$_4$H), 7.03 (t, J=7.4 Hz, 1H, C$_5$H), 6.70 (app-s, 4H, C$_{10}$H, C$_{11}$H), 6.41 (s, 1H, NH), 5.78 (s, 1H, C$_{8a}$H), 5.14 (d, J=12.4 Hz, 1H, Ph$_{Cbz}$CH$_a$), 5.00 (d, J=12.3 Hz, 1H, Ph$_{Cbz}$CH$_b$), 3.94-3.84 (m, 1H, C$_2$H$_a$), 3.74 (s, 3H, OCH$_3$*) 3.70 (s, 3H, OCH$_3$), 3.26 (br-s, 3H, NCO$_2$CH$_3$), 2.79 (td, J=5.1, 11.8 Hz, 1H, C$_2$H$_b$), 2.23 (dd, J=5.2, 12.0 Hz, 1H, C$_3$H$_a$), 2.16 (td, J=7.7, 12.1 Hz, 1H, C$_3$H$_b$).

$^{13}$C NMR (125 MHz, CDCl$_3$, 25° C.): δ 160.0 (C$_{12}$), 156.8 (q, J=36.0 Hz, COCF$_3$), 155.2 (NCO$_2$CH$_3$), 153.0 (NC=O$_{Cbz}$), 143.8 (C$_{7a}$), 135.9 (Ph$_{Cbz}$-i-C), 130.7 (C$_9$), 130.4 (C$_{4a}$), 128.6 (2C, C$_{10}$, C$_6$ or Ph$_{Cbz}$), 128.4 (C$_6$ or Ph$_{Cbz}$), 128.3 (C$_6$ or Ph$_{Cbz}$), 128.2 (C$_6$ or Ph$_{Cbz}$), 127.0 (C$_{3a}$), 124.4 (C$_4$), 123.9 (C$_5$), 116.4 (C$_7$), 116.3 (q, J=286 Hz, COCF$_3$), 114.1 (C$_{11}$), 80.0 (C$_{8a}$), 67.6 (Ph$_{Cbz}$CH$_2$), 55.5 (OCH$_3$), 52.5 (NCO$_2$CH$_3$), 44.5 (C$_2$), 36.8 (C$_3$).

$^{19}$F NMR (282 MHz, CDCl$_3$, 25° C., 13.5:1 mixture of atropisomers, *denotes minor atropisomer): δ −67.6 (s, COCF$_3$), −69.3 (s, COCF$_3$*).

FTIR (thin film) cm$^{-1}$: 3359 (s), 2958 (w), 1700 (s), 1606 (w), 1511 (m).

HRMS (ESI) (m/z): calc'd for C$_{29}$H$_{27}$F$_3$N$_4$NaO$_6$ [M+Na]$^+$: 607.1775, found: 607.1792.

TLC (30% ethyl acetate in hexanes), Rf: 0.15 (UV, CAM). M.p.: 168-170° C. (CH$_2$Cl$_2$).

Example 11: Synthesis of Diazine (±)-25

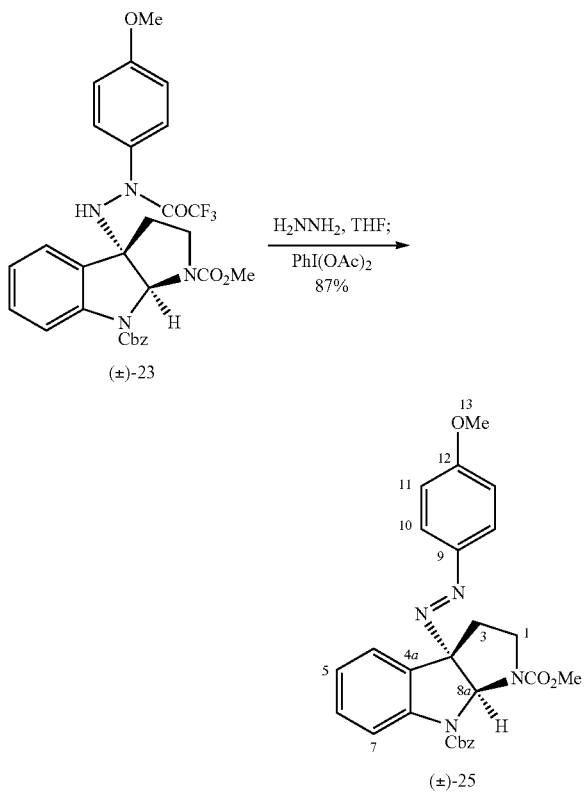

The trifluoroacetohydrazine (±)-23 (36.5 mg, 62.4 μmol, 1 equiv) was dissolved in a solution of hydrazine (1.0 M in tetrahydrofuran, 1.25 mL, 1.25 mmol, 20.0 equiv) at 23° C. After 19 h, the reaction mixture was washed with a saturated aqueous ammonium chloride solution and the aqueous layer was extracted with diethyl ether (3×10 mL). The combined organic extracts were dried over anhydrous sodium sulfate, were filtered, and were concentrated under reduced pressure. The crude hydrazine was dissolved in tetrahydrofuran (0.6 mL) at 23° C. and a sample of (diacetoxyiodo)benzene (40.3 mg, 0.125 mmol, 2.50 equiv) was added in one portion. After 3 h, the reaction mixture was concentrated under reduced pressure, and the resulting residue was purified by flash column chromatography on silica gel (eluent: 10→18% ethyl acetate in hexanes) to afford diazene (±)-25 (26.4 mg, 87.0%) as a bright yellow amorphous gum. Structural assignments were made using additional information from gCOSY, gHSQC, and gHMBC experiments.

$^1$H NMR (400 MHz, CDCl$_3$, 25° C.): δ 7.80 (d, J=8.1 Hz, 1H, C$_7$H), 7.69-7.63 (m, 2H, C$_{10}$H), 7.46 (br-dd, J=1.6, 7.9 Hz, 2H, Ph$_{Cbz}$-o-H), 7.40-7.28 (m, 5H, C$_4$H, C$_6$H, Ph$_{Cbz}$-m-H, Ph$_{Cbz}$-p-H), 7.08 (td, J=1.1, 7.5 Hz, C$_5$H), 6.95-6.89 (m, 2H, C$_{10}$H$_2$), 6.88 (s, 1H, C$_{8a}$H), 5.36 (d, J=12.2 Hz, 1H, Ph$_{Cbz}$CH$_a$), 5.29 (d, J=12.3 Hz, 1H, Ph$_{Cbz}$CH$_b$), 4.06 (dd, J=8.0, 11.2 Hz, 1H, C$_2$H$_a$), 3.85 (s, 3H, OCH$_3$), 3.55 (s, 3H, NCO$_2$CH$_3$), 3.12 (td, J=5.4, 11.8 Hz, C$_2$H$_b$), 2.53 (dd, J=5.3, 12.4 Hz, 1H, C$_3$H$_a$), 2.44 (td, J=7.8, 12.3 Hz, 1H, C$_3$H$_b$).

$^{13}$C NMR (100 MHz, CDCl$_3$, 25° C.): δ 162.3 (C$_{12}$), 155.4 (NCO$_2$CH$_3$), 153.5 (NC=O$_{Cbz}$), 145.8 (C$_9$), 143.2 (C$_{7a}$), 136.3 (Ph$_{Cbz}$-i-C), 130.1 (2C, C$_4$a and C$_4$, C$_6$ or Ph$_{Cbz}$-p-C), 128.7 (C$_4$, C$_6$ or Ph$_{Cbz}$-p-C), 128.4 (Ph$_{Cbz}$-m-C), 128.3 (Ph$_{Cbz}$-o-C), 124.8 (C$_4$, C$_6$ or Ph$_{Cbz}$-p-C), 124.7 (C$_{10}$), 123.9 (C$_5$), 116.6 (C$_7$), 114.1 (C$_{11}$), 88.3 (br-s, C$_{3a}$), 78.9 (C$_{8a}$), 67.7 (Ph$_{Cbz}$CH$_2$), 55.7 (OCH$_3$), 52.7 (NCO$_2$CH$_3$), 45.8 (C$_2$), 35.9 (C$_3$).

FTIR (thin film) cm$^{-1}$: 2949 (m), 2890 (w), 1702 (s), 1601 (s), 1508 (m).

HRMS (DART) (m/z): calc'd for C$_{27}$H$_{27}$N$_4$O$_5$ [M+H]$^+$: 487.1976, found: 487.1963.

TLC (30% ethyl acetate in hexanes), Rf: 0.29 (UV, CAM).

Example 12: Synthesis of N-(4-Methoxyphenyl)methanesulfonohydrazide (20)

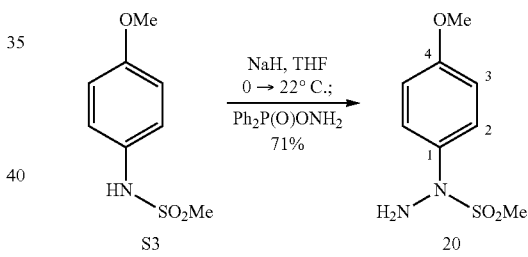

Anilide S3 (50.2 mg, 0.249 mmol, 1 equiv) was azeotropically dried by concentration from anhydrous benzene (3×0.1 mL) and the residue was dissolved in tetrahydrofuran (2.5 mL). The solution was cooled to 0° C. and a sample of sodium hydride (60% in mineral oil, 12.0 mg, 0.299 mmol, 1.20 equiv) was added in one portion. The ice-water bath was removed and after 30 min, a sample of O-(diphenylphosphinyl)hydroxylamine (69.7 mg, 0.299 mmol, 1.20 equiv) was added in one portion. After 1 h, the reaction mixture was diluted with ethyl acetate (3 mL), was washed with saturated aqueous sodium bicarbonate-water solution (10:1 v/v, 5 mL), and the aqueous layer was extracted with ethyl acetate (3×3 mL). The combined organic extracts were dried over anhydrous sodium sulfate, were filtered, and were concentrated under reduced pressure. The resulting residue was purified by flash column chromatography on silica gel (eluent: 25→40% ethyl acetate in hexanes) to afford hydrazine 20 (38.3 mg, 71.1%) as a tan solid.

$^1$H NMR (400 MHz, CDCl$_3$, 25° C.): δ 7.39-7.32 (m, 2H, C$_2$H), 6.94-6.88 (m, 2H, C$_3$H), 4.35 (s, 2H, NH$_2$), 3.81 (s, 3H, OCH$_3$), 3.03 (s, 3H, SO$_2$CH$_3$).

$^{13}$C NMR (100 MHz, CDCl$_3$, 25° C.): δ 159.0 (C$_4$), 134.9 (C$_i$), 126.7 (C$_2$), 114.5 (C$_3$), 55.5 (OCH$_3$), 35.0 (SO$_2$CH$_3$).

FTIR (thin film) cm$^{-1}$: 3425 (s), 2091 (w), 1635 (s), 1508 (m), 1328 (m).

HRMS (DART) (m/z): calc'd for $C_8H_{13}N_2O_3S$ [M+H]$^+$: 217.0641, found: 217.0642.

TLC (50% ethyl acetate in hexanes), Rf: 0.26 (UV, CAM).

M.p.: 116-118° C. (decomp).

Example 13: Synthesis of Diazine (±)-25

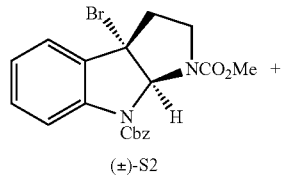

(±)-S2

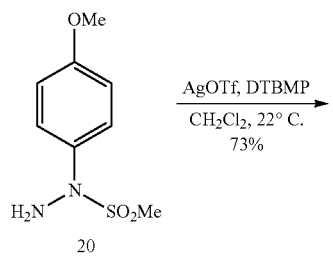

20

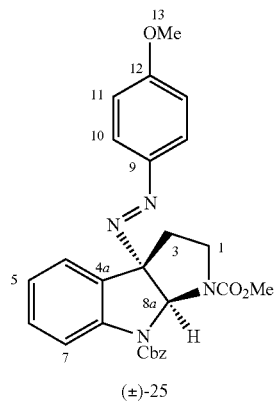

(±)-25

A sample of silver trifluoromethanesulfonate (20.0 mg, 78.0 μmol, 2.00 equiv) was added to a solution of bromocyclotryptamine (±)-S2 (16.8 mg, 39.0 μmol, 1 equiv), hydrazide 20 (12.8 mg, 59.0 μmol, 1.50 equiv), and DTBMP (20.1 mg, 98.0 μmol, 2.50 equiv) in dichloromethane (0.4 mL) at 22° C. After 40 min, the off-white suspension was filtered through a pad of Celite. The filter cake was washed with ethyl acetate (5 mL) and the filtrate was concentrated under reduced pressure. The resulting residue was purified by flash column chromatography on silica gel (eluent: 20%→30% ethyl acetate in hexanes) to yield the diazene (±)-25 (13.9 mg, 73.3%) as a bright yellow amorphous gum. Please see alternative procedure for synthesis of diazene (±)-25 and its full characterization.

Example 14: Synthesis of Tryptamine S5

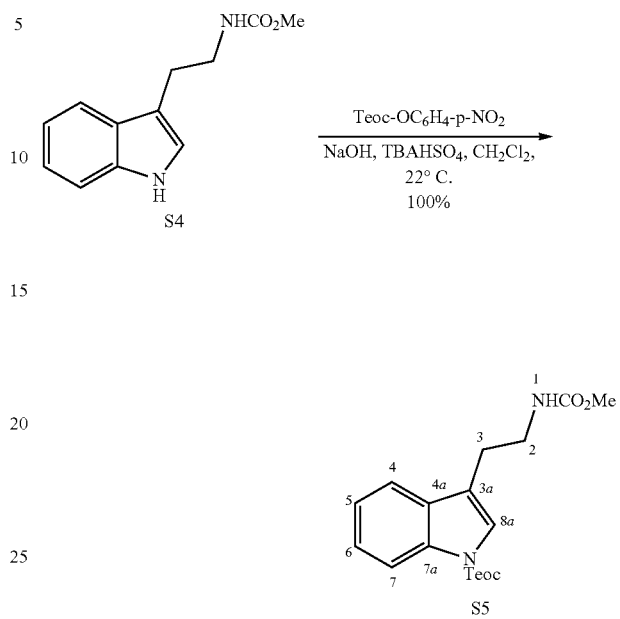

To a solution of 4-nitrophenyl (2-(trimethylsilyl)ethyl) carbonate (7.17 g, 25.3 mmol, 1.50 equiv) (Okoth, R.; Basu, A. *Beilstein J. Org. Chem.* 2013, 9, 608) in dichloromethane (170 mL) at 22° C. under an air atmosphere were sequentially added tryptamine methyl carbamate S4 (3.68 g, 16.9 mmol, 1 equiv), tetra-n-butylammonium hydrogen sulfate (570 mg, 1.69 mmol, 10.0 mol %), and powdered sodium hydroxide (2.02 g, 50.6 mmol, 3.00 equiv). After 13 h, the bright orange suspension was washed with an aqueous solution of sodium hydroxide (1N, 3×50 mL). The organic extract was dried over anhydrous sodium sulfate, was filtered, and was concentrated under reduced pressure. The resulting residue was purified by flash column chromatography on silica gel (eluent: 5%→20% ethyl acetate in hexanes) to afford tryptamine S5 (6.10 g, 99.6%) as white solid. Structural assignments were made using additional information from gCOSY, gHSQC, and gHMBC experiments.

$^1$H NMR (400 MHz, CDCl$_3$, 25° C.): δ 8.18 (d, J=7.5 Hz, 1H, C$_7$H), 7.54 (d, J=7.6 Hz, 1H, C$_4$H), 7.44 (s, 1H, C$_{8a}$H), 7.34 (app-t, J=7.4 Hz, 1H, C$_6$H), 7.25 (app-t, J=7.3 Hz, 1H, C$_5$H), 4.76 (br-s, 1H, NH), 4.58-4.37 (m, 2H, C$_{10}$H$_2$), 3.66 (s, 3H, NHCO$_2$CH$_3$), 3.51 (dd, J=6.1, 12.4 Hz, 2H, C$_2$H$_2$), 2.91 (t, J=6.7 Hz, 2H, C$_3$H$_2$), 1.32-1.14 (m, 2H, C$_{11}$H$_2$), 0.11 (s, 9H, (C$_{12}$H$_3$)$_3$).

$^{13}$C NMR (100 MHz, CDCl$_3$, 25° C.): δ 157.1 (NHCO$_2$CH$_3$), 151.1 (C$_9$), 135.7 (C$_{7a}$), 130.4 (C$_{4a}$), 124.8 (C$_6$), 122.9 (2C, C$_5$, C$_{8a}$) 119.0 (C$_4$), 118.2 (C$_{3a}$), 115.5 (C$_7$), 65.7 (C$_{10}$), 52.2 (NHCO$_2$CH$_3$), 40.6 (C$_2$), 25.7 (C$_3$), 17.9 (C$_{11}$), 1.40 (C$_{12}$).

FTIR (thin film) cm$^{-1}$: 3356 (m), 2955 (s), 1734 (s), 1526 (m), 936 (w).

HRMS (DART) (m/z): calc'd for $C_{18}H_{27}N_2O_4Si$ [M+H]$^+$: 363.1735, found: 363.1758.

TLC (30% ethyl acetate in hexanes), Rf: 0.32 (UV, CAM).

M.p.: 68-70° C. (CH$_2$Cl$_2$).

Example 15: Synthesis of Bromocyclotryptamine (+)-26

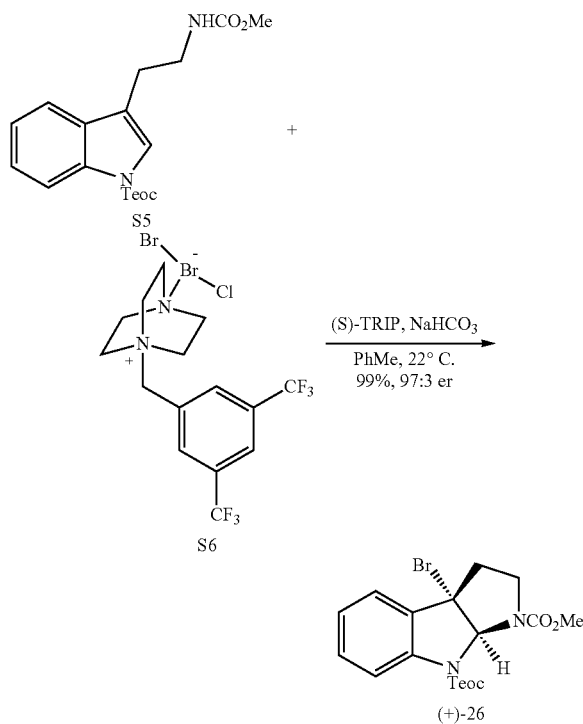

A sample of bromine salt S6 (2.88 g, 5.38 mmol, 1.30 equiv) (Xie, W.; Jiang, G.; Liu, H.; Hu, J.; Pan, X.; Zhang, H.; Wan, X.; Lai, Y.; Ma, D. *Angew. Chem. Int. Ed.* 2013, 52, 12924) was added to a suspension of tryptamine S5 (1.50 g, 4.14 mmol, 1 equiv), (S)-3,3'-Bis(2,4,6-triisopropyl-phenyl)-1,1'-binaphthyl-2,2'-diyl hydrogenphosphate ((S)-TRIP, 309 mg, 410 µmol, 10.0 mol %) (Hoffmann, S.; Seayad, A. M.; List, B. *Angew. Chem. Int. Ed.* 2005, 44, 7424), and sodium hydrogen carbonate (1.39 g, 16.6 mmol, 4.00 equiv) in toluene (83 mL) at 22° C. After stirring for 24 h, the yellow suspension was diluted with a saturated aqueous sodium thiosulfate solution (20 mL) and was stirred vigorously for 10 min. The biphasic mixture was further diluted with deionized water (20 mL) and was then extracted with dichloromethane (3×40 mL). The combined organic extracts were dried over anhydrous sodium sulfate, were filtered, and were concentrated under reduced pressure. The resulting residue was purified by flash column chromatography on silica gel (eluent: 5→15% acetone in hexanes) to afford bromocyclotryptamine (+)-26 (1.81 g, 99.1%, 97:3 er) as a colorless amorphous gum (Further elution with 60% ethyl acetate in hexanes allows for the recovery of the TRIP catalyst). The enantiomeric ratio was determined by chiral HPLC analysis (Chiralpak IA, 5% iPrOH/95% hexanes, 1.0 mL/min, 254 nm, $t_R$ (major)=7.71 min, $t_R$ (minor)=11.2 min). Structural assignments were made using additional information from gCOSY, gHSQC and gHMBC experiments.

$^1$H NMR (400 MHz, CDCl$_3$, 25° C.): δ 7.69 (d, J=8.1 Hz, 1H, C$_7$H), 7.37 (dd, J=0.8, 7.6 Hz, 1H, C$_4$H), 7.30 (td, J=1.3, 7.9 Hz, 1H, C$_6$H), 7.10 (td, J=1.0, 7.6 Hz, 1H, C$_5$H), 6.42 (s, 1H, C$_{8a}$H), 4.45-4.28 (m, 2H, C$_{10}$H$_2$), 3.81-3.74 (m, 1H, C$_2$H$_a$), 3.72 (s, 3H, NHCO$_2$CH$_3$), 2.92-2.80 (m, 2H, C$_2$H$_b$, C$_3$H$_a$), 2.80-2.69 (m, 1H, C$_3$H$_b$), 1.21-1.08 (m, 2H, C$_{11}$H$_2$), 0.06 (s, 9H, (C$_{12}$H$_3$)$_3$).

$^{13}$C NMR (100 MHz, CDCl$_3$, 25° C.): δ 154.7 (NCO$_2$CH$_3$), 153.5 (C$_9$), 141.7 (C$_{7a}$), 132.3 (C$_{4a}$), 130.7 (C$_6$), 124.5 (C$_5$), 123.9 (C$_4$), 117.3 (C$_7$), 84.1 (C$_{8a}$), 64.9 (C$_{10}$), 62.1 (C$_{3a}$), 52.9 (NCO$_2$CH$_3$), 46.3 (C$_2$), 41.3 (C$_3$), 17.8 (C$_{11}$), −1.4 (C$_{12}$).

FTIR (thin film) cm$^{-1}$: 2954 (m), 2896 (w), 1717 (s), 1604 (w), 1402 (m).

HRMS (DART) (m/z): calc'd for C$_{18}$H$_{26}$BrN$_2$O$_4$Si [M+H]$^+$: 441.0840, found: 441.0848.

$[α]_D^{24}$: +183 (c=0.58, CH$_2$Cl$_2$).

TLC (20% acetone in hexanes), Rf: 0.43 (UV, CAM).

Example 16: Synthesis of Bromocyclotryptamine (−)-26

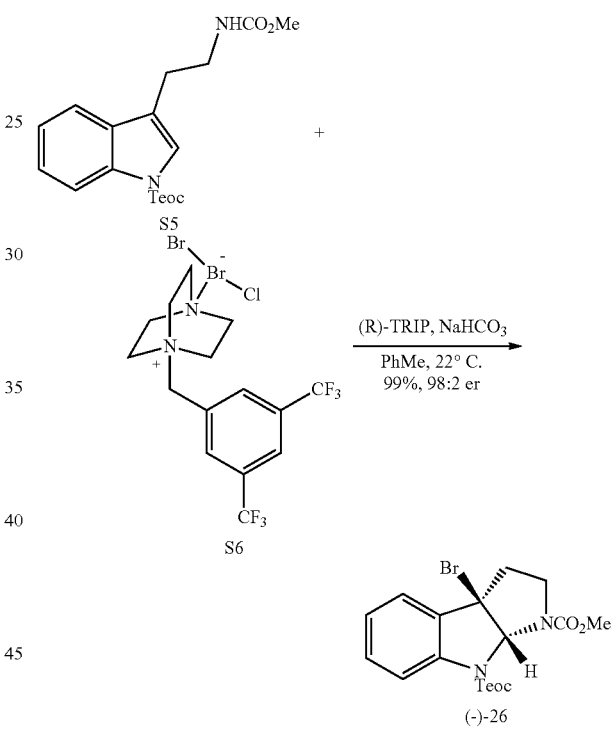

A sample of bromine salt S6 (2.88 g, 5.38 mmol, 1.30 equiv) was added to a suspension of tryptamine S5 (1.50 g, 4.14 mmol, 1 equiv), (R)-TRIP (309 mg, 410 µmol, 10.0 mol %), and sodium hydrogen carbonate (1.39 g, 16.6 mmol, 4.00 equiv) in toluene (83 mL) at 22° C. After stirring for 24 h, the yellow suspension was diluted with a saturated aqueous sodium thiosulfate solution (20 mL) and was stirred vigorously for 10 min. The biphasic mixture was further diluted with deionized water (20 mL) and was then extracted with dichloromethane (3×40 mL). The combined organic extracts were dried over anhydrous sodium sulfate, were filtered, and were concentrated under reduced pressure. The resulting residue was purified by flash column chromatography on silica gel (eluent: 5→10% acetone in hexanes) to afford bromocyclotryptamine (1.80 g, 98.5%, 98:2 er) as a colorless amorphous gum. The enantiomeric ratio was determined by chiral HPLC analysis (Chiralpak IA, 5% iPrOH/ 95% hexanes, 1.0 mL/min, 254 nm, $t_R$ (major)=11.1 min, $t_R$ (minor)=7.63 min). For full characterization data for bromocyclotryptamine (−)-26 ([α]$_D^{24}$=−182 (c=0.63, CH$_2$Cl$_2$)) see previous procedure in this document.

Example 17: Synthesis of Sulfamate Ester (+)-27

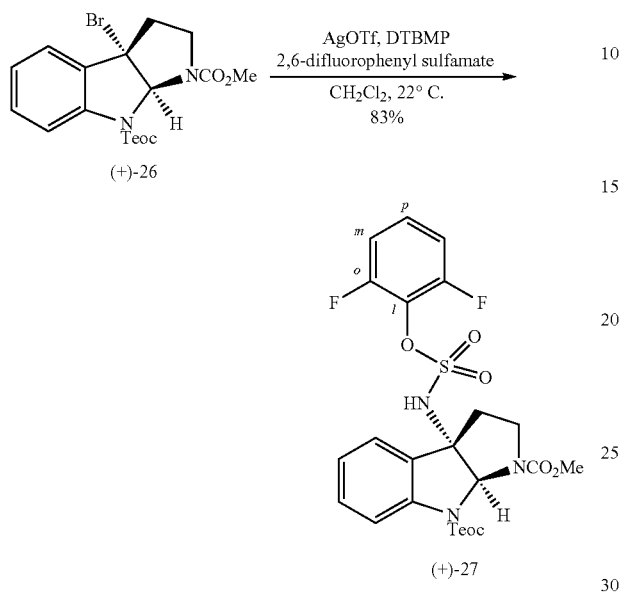

(+)-26

(+)-27

A sample of silver trifluoromethanesulfonate (139 mg, 540 µmol, 2.00 equiv) was added to a solution of bromocyclotryptamine (+)-26 (119 mg, 270 µmol, 1 equiv), 2,6-difluorophenyl sulfamate (82.7 mg, 405 µmol, 1.50 equiv) (Roizen, J. L.; Zalatan, D. L.; Du Bois, J. Angew. Chem. Int. Ed., 2013, 52, 11343), and DTBMP (139 mg, 675 µmol, 2.50 equiv) in dichloromethane (2.7 mL) at 22° C. After 1 h, the off-white suspension was filtered through a pad of Celite. The filter cake was washed with ethyl acetate (5 mL) and the filtrate was concentrated under reduced pressure. The resulting residue was purified by flash column chromatography on silica gel (eluent: 10%→25% ethyl acetate in hexanes) to afford sulfamate ester (+)-27 (128 mg, 83.2%) as a colorless amorphous gum. Structural assignments were made using additional information from gCOSY, gHSQC, and gHMBC experiments.

$^1$H NMR (400 MHz, CDCl$_3$, 25° C.): δ 7.76 (d, J=8.0 Hz, 1H, C$_7$H), 7.43 (d, J=7.5 Hz, 1H, C$_4$H), 7.36 (app-t, J=7.8 Hz, 1H, C$_6$H), 7.25-7.15 (m, 1H, C$_p$H), 7.11 (app-t, J=7.5 Hz, 1H, C$_5$H), 6.98 (t, J=8.1 Hz, 2H, C$_m$H), 6.52 (s, 1H, C$_{8a}$H), 5.77 (br-s, 1H, NH), 4.35-4.20 (m, 2H, C$_{10}$H$_2$), 3.90 (dd, J=7.9, 10.6 Hz, 1H, C$_2$H$_a$), 3.68 (s, 3H, NHCO$_2$CH$_3$), 2.96 (dt, J=7.6, 11.7 Hz, 1H, C$_3$H$_a$), 2.89-2.77 (m, 1H, C$_2$H$_b$), 2.49 (dd, J=4.1, 11.8 Hz, 1H, C$_3$H$_b$), 1.07 (t, J=8.8 Hz, 2H, C$_{11}$H$_2$), 0.03 (s, 9H, (C$_{12}$H$_3$)$_3$).

$^{13}$C NMR (100 MHz, CDCl$_3$, 25° C.): δ 156.1 (dd, J=3.4, 253.7 Hz, C$_o$), 155.1 (NCO$_2$CH$_3$), 153.6 (C$_9$), 143.0 (C$_{7a}$), 131.2 (C$_6$), 129.5 (C$_{4a}$), 127.8 (t, J=9.3 Hz, C$_p$), 126.9 (t, J=15.6 Hz, C$_i$), 124.3 (C$_5$), 123.9 (C$_4$), 117.2 (C$_7$), 112.7 (dd, J=4.6, 17.7 Hz, Cm), 79.8 (C$_{8a}$), 72.0 (C$_{3a}$), 64.8 (C$_{10}$), 52.9 (NCO$_2$CH$_3$), 46.3 (C$_2$), 34.2 (C$_2$), 17.8 (C$_{11}$), −1.5 (C$_{12}$).

$^{19}$F NMR (282 MHz, CDCl$_3$, 25° C.): δ−125.0 (s, C$_6$H$_3$F$_2$).

FTIR (thin film) cm$^{-1}$: 3173 (br-m), 2956 (m), 1683 (s), 1606 (m), 1098 (w).

HRMS (DART) (m/z): calc'd for C$_{24}$H$_{30}$F$_2$N$_3$O$_7$SSi [M+H]$^+$: 570.1536, found: 570.1557.
[α]$_D^{24}$: +56 (c=0.59, CH$_2$Cl$_2$).
TLC (30% ethyl acetate in hexanes), Rf: 0.26 (UV, CAM).

Example 18: Synthesis of Sulfamate Ester (−)-27

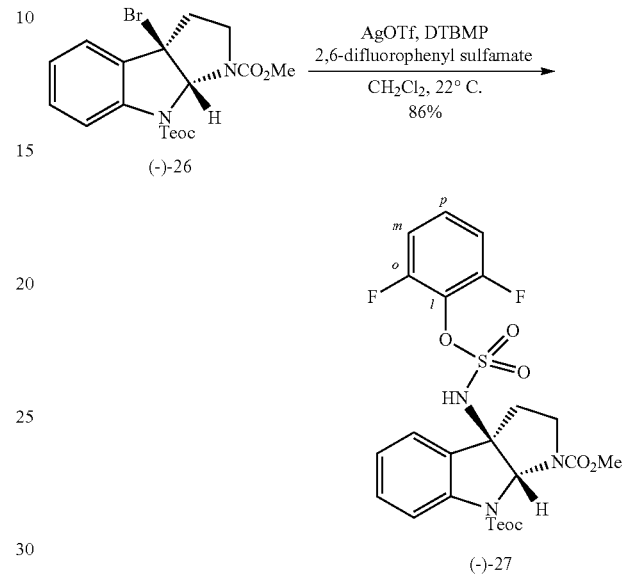

(−)-26

(−)-27

A sample of silver trifluoromethanesulfonate (334 mg, 1.30 mmol, 2.00 equiv) was added to a solution of bromocyclotryptamine (−)-26 (287 mg, 650 µmol, 1 equiv), 2,6-difluorophenyl sulfamate (199 mg, 975 µmol, 1.50 equiv), and DTBMP (334 mg, 1.63 mmol, 2.50 equiv) in dichloromethane (6.5 mL) at 22° C. After 1 h, the off-white suspension was filtered through a pad of Celite. The filter cake was washed with ethyl acetate (15 mL) and the filtrate was concentrated under reduced pressure. The resulting residue was purified by flash column chromatography on silica gel (eluent: 10%→30% ethyl acetate in hexanes) to afford sulfamate ester (−)-27 (320 mg, 86.4%) as a colorless amorphous gum. For full characterization data for sulfamate ester (−)-27 ([α]$_D^{24}$=−55 (c=0.55, CH$_2$Cl$_2$)) see previous procedure in this document.

Example 19: Synthesis of Amine (+)-28

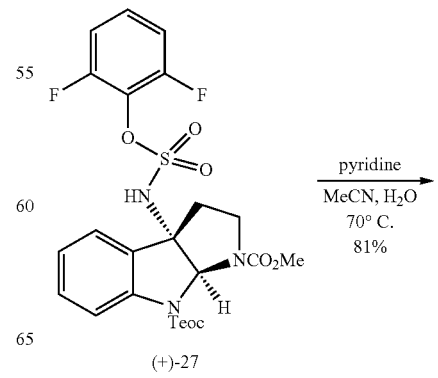

(+)-27

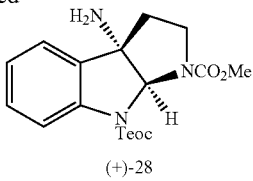

(+)-28

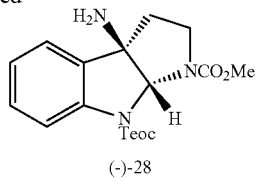

(-)-28

Pyridine (1.63 mL, 20.2 mmol, 20.0 equiv) was added to a solution of sulfamate ester (+)-27 (576 mg, 1.01 mmol, 1 equiv) in a mixture of acetonitrile-water (2:1, 10 mL), via syringe at 22° C. The reaction flask was fitted with a reflux condenser and heated to 70° C. After 23 h, the reaction mixture was allowed to cool to 22° C. The mixture was diluted with dichloromethane (10 mL) and was washed with a saturated aqueous sodium bicarbonate solution (10 mL). The aqueous layer was extracted with dichloromethane (3×5 mL). The combined organic extracts were dried over anhydrous sodium sulfate, were filtered, and were concentrated under reduced pressure. The resulting residue was purified by flash column chromatography on silica gel (eluent: 1→6% methanol in dichloromethane) to afford amine (+)-28 (308 mg, 80.8%) as a colorless oil. Structural assignments were made using additional information from gCOSY, gHSQC, and gHMBC experiments.

$^1$H NMR (400 MHz, CDCl$_3$, 25° C.): δ 7.73 (d, J=8.1 Hz, 1H, C$_7$H), 7.35-7.27 (m, 2H, C$_4$H, C$_6$H), 7.12-7.05 (m, 1H, C$_5$H), 5.91 (s, 1H, C$_{8a}$H), 4.42-4.25 (m, 2H, C$_{10}$H$_2$), 3.91-3.80 (m, 1H, C$_2$H$_a$), 3.72 (s, 3H, NHCO$_2$CH$_3$), 2.90 (td, J=5.5, 11.8 Hz, 1H, C$_2$H$_b$), 2.30 (dd, J=5.4, 12.3 Hz, 1H, C$_3$H$_a$), 2.12 (td, J=8.0, 12.2 Hz, 1H, C$_3$H$_b$), 1.73 (br-s, 2H, NH$_2$), 1.19-1.06 (m, 2H, C$_{11}$H$_2$), 0.06 (s, 9H, (C$_{12}$H$_3$)$_3$).

$^{13}$C NMR (100 MHz, CDCl$_3$, 25° C.): δ 155.4 (NCO$_2$CH$_3$), 154.0 (C$_9$), 142.2 (C$_{7a}$), 134.2 (C$_{4a}$), 129.7 (C$_6$), 124.0 (C$_5$), 123.3 (C$_4$), 116.6 (C$_7$), 83.5 (C$_{8a}$), 69.3 (C$_{3a}$), 64.5 (C$_{10}$), 52.7 (NCO$_2$CH$_3$), 45.8 (C$_2$), 39.0 (C$_3$), 17.9 (C$_{11}$), -1.4 (C$_{12}$).

FTIR (thin film) cm$^{-1}$: 3370 (w), 2954 (m), 1701 (s), 1604 (w), 1405 (m).

HRMS (DART) (m/z): calc'd for C$_{18}$H$_{28}$N$_3$O$_4$Si [M+H]$^+$: 378.1844, found: 378.1860.

[α]$_D^{24}$: +107 (c=0.53, CH$_2$Cl$_2$).

TLC (6% methanol in dichloromethane), Rf: 0.39 (UV, CAM).

Example 20: Synthesis of Amine (-)-28

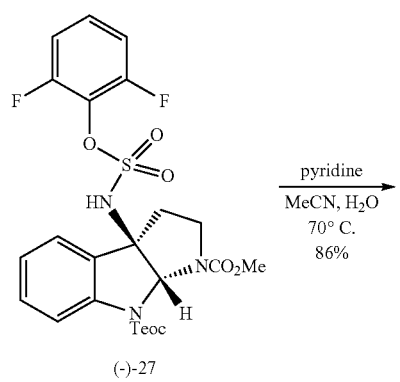

(-)-27

Pyridine (909 µL, 11.2 mmol, 20.0 equiv) was added to a solution of sulfamate ester (-)-27 (320 mg, 562 µmol, 1 equiv) in a mixture of acetonitrile-water (2:1, 5.6 mL), via syringe at 22° C. The reaction flask was fitted with a reflux condenser and heated to 70° C. After 24 h, the reaction mixture was allowed to cool to 22° C. The mixture was diluted with dichloromethane (10 mL) and was washed with a saturated aqueous sodium bicarbonate solution (10 mL). The aqueous layer was extracted with dichloromethane (3×5 mL). The combined organic extracts were dried over anhydrous sodium sulfate, were filtered, and were concentrated under reduced pressure. The resulting residue was purified by flash column chromatography on silica gel (eluent: 1→6% methanol in dichloromethane) to afford the amine (-)-28 (182 mg, 85.8%) as a colorless oil. Structural assignments were made using additional information from gCOSY, HSQC, and HMBC experiments. For full characterization data for amine (-)-28 ([α]$_D^{24}$=-106 (c=0.56, CH$_2$Cl$_2$)) see previous procedure in this document.

Example 21: Synthesis of Cyclotryptamine (+)-29

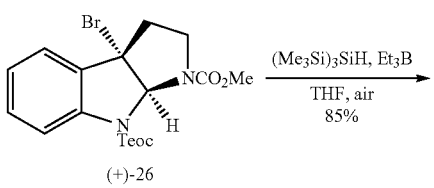

(+)-26

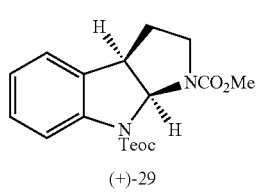

(+)-29

Triethylborane (1.0 M in THF, 210 µL, 210 µmol, 0.10 equiv) was slowly added via syringe to a solution of bromocyclotryptamine (+)-26 (905 mg, 2.05 mmol, 1 equiv) and tris(trimethylsilyl)silane (1.90 mL, 6.15 mmol, 3.00 equiv) in tetrahydrofuran (21 mL) at 22° C. under an air atmosphere. After 3 h, the reaction mixture was washed with a saturated aqueous sodium bicarbonate solution (20 mL), and the aqueous layer was extracted with dichloromethane (3×10 mL). The combined organic extracts were dried over anhydrous sodium sulfate, were filtered, and were concentrated under reduced pressure. The resulting residue was purified by flash column chromatography on silica gel (eluent: 0→8% acetone in hexanes) to afford cyclotryptamine (+)-29 (634 mg, 85.3%) as a colorless amorphous gum. Structural assignments were made using additional information from gCOSY, gHSQC, and gHMBC experiments.

$^1$H NMR (400 MHz, CDCl$_3$, 25° C.): δ 7.69 (d, J=8.0 Hz, 1H, C$_7$H), 7.21 (app-t, J=7.8 Hz, 1H, C$_6$H), 7.15 (d, J=7.4 Hz, 1H, C$_4$H), 7.01 (td, J=0.7, 7.4 Hz, 1H, C$_5$H), 6.42 (d, 1H, C$_{8a}$H), 4.40-4.24 (m, 2H, C$_{10}$H$_2$), 4.00 (t, J=7.3 Hz, 1H, C$_{3a}$H), 3.91-3.81 (m, 1H, C$_2$H$_a$), 3.72 (s, 3H, NHCO$_2$CH$_3$), 2.90 (td, J=5.6, 11.6 Hz, 1H, C$_2$H$_b$), 2.21-2.09 (m, 1H, C$_3$H$_a$), 2.05 (dd, J=5.5, 12.3 Hz, 1H, C$_3$H$_b$), 1.19-1.04 (m, 2H, C$_{11}$H$_2$), 0.05 (s, 9H, (C$_{12}$H$_3$)$_3$).

$^{13}$C NMR (100 MHz, CDCl$_3$, 25° C.): δ 155.3 (NCO$_2$CH$_3$), 153.8 (C$_9$), 142.6 (C$_{7a}$), 131.7 (C$_{4a}$), 128.3 (C$_6$), 124.0 (C$_4$), 123.5 (C$_5$), 116.1 (C$_7$), 76.5 (C$_{8a}$), 64.3 (C$_{10}$), 52.7 (NCO$_2$CH$_3$), 45.4 (br, C$_{3a}$), 45.0 (C$_2$), 31.6 (C$_3$), 17.9 (C$_{11}$), −1.4 (C$_{12}$).

FTIR (thin film) cm$^{-1}$: 2952 (m), 2895 (w), 1699 (s), 1603 (w), 1401 (s), 1305 (m).

HRMS (DART) (m/z): calc'd for C$_{18}$H$_{27}$N$_2$O$_4$Si [M+H]$^+$: 363.1735, found: 363.1740.

[α]$_D^{24}$: +113 (c=0.87, CH$_2$Cl$_2$).

TLC (20% acetone in hexanes), Rf: 0.38 (UV, CAM).

Example 22: Synthesis of Cyclotryptamine (−)-29

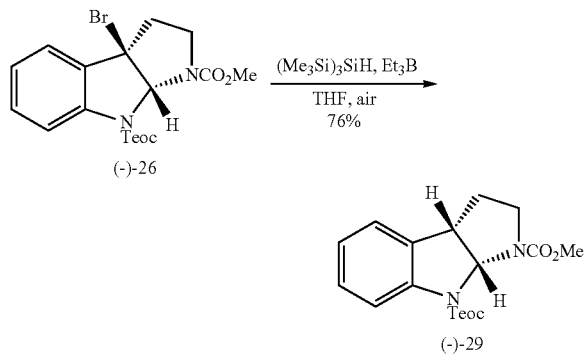

Triethylborane (1.0 M in THF, 320 μL, 320 μmol, 0.10 equiv) was slowly added via syringe to a solution of bromocyclotryptamine (−)-26 (1.39 g, 3.16 mmol, 1 equiv) and tris(trimethylsilyl)silane (2.92 mL, 9.48 mmol, 3.00 equiv) in tetrahydrofuran (32 mL) at 22° C. under an air atmosphere. After 3 h, the reaction mixture was washed with a saturated aqueous sodium bicarbonate solution (30 mL), and the aqueous layer was extracted with dichloromethane (3×20 mL). The combined organic extracts were dried over anhydrous sodium sulfate, were filtered, and were concentrated under reduced pressure. The resulting residue was purified by flash column chromatography on silica gel (eluent: 0→8% acetone in hexanes) to afford cyclotryptamine (−)-29 (866 mg, 75.6%) as a colorless amorphous gum. For full characterization data for cyclotryptamine (−)-29 ([α]$_D^{24}$=−110 (c=0.52, CH$_2$Cl$_2$)) see previous procedure in this document.

Example 23: Synthesis of Cyclotryptamine Sulfonamide (+)-30

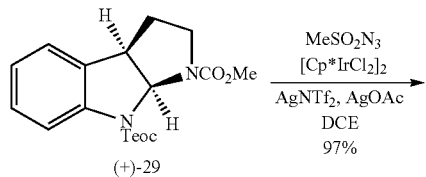

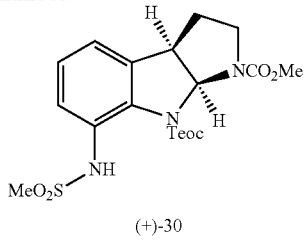

To a suspension of cyclotryptamine (+)-29 (96.6 mg, 266 μmol, 1 equiv), dichloro(pentamethylcyclopentadienyl) iridium (III) dimer ([Cp*IrCl$_2$]$_2$, 17.0 mg, 21.3 μmol, 8.00 mol %), silver bis(trifluoromethanesulfonyl)imide (33.0 mg, 85.1 μmol, 0.320 equiv) and silver acetate (26.7 mg, 160 μmol, 0.600 equiv) in dichloroethane (0.27 mL) was added methanesulfonyl azide (48.3 mg, 399 μmol, 1.50 equiv) (Matano, Y.; Ohkubo, H.; Honsho, Y.; Saito, A.; Seki, S.; Imahori, H. Org. Lett. 2013, 15, 932) via syringe. The reaction flask was sealed with a glass stopper and the reaction was allowed to stir for 20 h. The reaction mixture was filtered through a pad of Celite and the filter cake was rinsed with ethyl acetate (10 mL). The filtrate was concentrated under reduced pressure. The resulting residue was purified by flash column chromatography on silica gel (eluent: 20→40% ethyl acetate in hexanes) to afford cyclotryptamine sulfonamide (+)-30 (117 mg, 96.5%) as a pale yellow amorphous gum. Structural assignments were made using additional information from gCOSY, gHSQC, and gHMBC experiments.

$^1$H NMR (400 MHz, CDCl$_3$, 25° C.): δ 9.08 (s, 1H, NHSO$_2$CH$_3$), 7.42 (d, J=8.0 Hz, 1H, C$_6$H), 7.20 (app-t, J=7.8 Hz, 1H, C$_5$H), 7.10 (app-dt, J=1.1, 7.5 Hz, 1H, C$_4$H), 6.32 (d, J=5.7 Hz, 1H, C$_{8a}$H), 4.46-4.27 (m, 2H, C$_{10}$H$_2$), 4.06 (app-br-s, 1H, C$_{3a}$H), 3.65 (app-s, 4H, NCO$_2$CH$_3$, C$_2$H$_a$), 2.79 (app-dd, J=9.6, 18.6 Hz, 1H, C$_2$H$_b$), 2.68 (s, 3H, NHSO$_2$CH$_3$), 2.26-2.14 (m, 2H, C$_3$H$_2$), 1.23-1.03 (m, 2H, C$_{11}$H$_2$), 0.05 (s, 9H, (C$_{12}$H$_3$)$_3$).

$^{13}$C NMR (100 MHz, CDCl$_3$, 25° C.): δ 155.8 (C$_9$), 154.8 (NCO$_2$CH$_3$), 135.5 (C$_{4a}$), 135.4 (C$_{7a}$), 127.1 (2C, C$_7$, C$_5$), 125.8 (C$_6$), 121.6 (C$_4$), 77.8 (C$_{8a}$), 66.3 (C$_{10}$), 52.6 (NCO$_2$CH$_3$), 46.0 (C$_{3a}$), 45.2 (C$_2$), 38.7 (NHSO$_2$CH$_3$), 28.7 (C$_3$), 17.9 (C$_{11}$), −1.5 (C$_{12}$).

FTIR (thin film) cm$^{-1}$: 3163 (w), 2955 (m), 1711 (s), 1680 (s), 1160 (s).

HRMS (ESI) (m/z): calc'd for C$_{19}$H$_{29}$N$_3$NaO$_6$SSi [M+Na]$^+$: 478.1439, found 478.1430.

[α]$_D^{24}$: +226 (c=0.61, CH$_2$Cl$_2$).

TLC (20% acetone in hexanes), Rf: 0.20 (UV, CAM).

Example 24: Synthesis of Cyclotryptamine Sulfonamide (−)-30

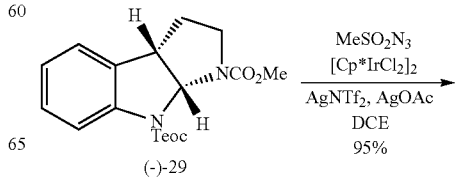

-continued

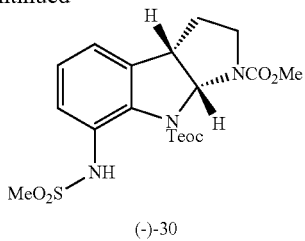

(−)-30

To a suspension of cyclotryptamine (−)-29 (278 mg, 767 µmol, 1 equiv), dichloro(pentamethylcyclopentadienyl)iridium (III) dimer ([Cp*IrCl₂]₂, 48.9 mg, 61.4 µmol, 8.00 mol %), silver bis(trifluoromethanesulfonyl)imide (95.1 mg, 245 µmol, 0.320 equiv) and silver acetate (76.8 mg, 460 µmol, 0.600 equiv) in dichloroethane (0.77 mL) was added methanesulfonyl azide (139 mg, 1.15 mmol, 1.50 equiv) via syringe. The reaction flask was sealed with a glass stopper and the reaction was allowed to stir for 20 h. The reaction mixture was filtered through a pad of Celite and the filter cake was rinsed with ethyl acetate (15 mL). The filtrate was concentrated under reduced pressure. The resulting residue was purified by flash column chromatography on silica gel (eluent: 20→40% ethyl acetate in hexanes) to afford cyclotryptamine sulfonamide (−)-30 (331 mg, 94.7%) as a pale yellow amorphous gum. For full characterization data for cyclotryptamine sulfonamide (−)-30 ($[α]_D^{24}$=−207 (c=0.68, CH₂Cl₂)) see previous procedure in this document.

with ethyl acetate (3×20 mL). The combined organic extracts were dried over anhydrous sodium sulfate, were filtered, and were concentrated under reduced pressure. The resulting residue was purified by flash column chromatography on silica gel (eluent: 25→50% ethyl acetate in hexanes) to afford hydrazidocyclotryptamine (−)-31 (1.70 g, 81.5%) as an orange amorphous gum (this compound decomposes when stored as a solution in chloroform or dichloromethane). Structural assignments were made using additional information from gCOSY, gHSQC, and gHMBC experiments.

¹H NMR (400 MHz, CDCl₃, 25° C.): δ 7.31 (app-p, J=3.7 Hz, 1H, C₅H), 7.20-7.14 (m, 2H, C₄H, C₆H), 6.27 (br-d, J=5.7 Hz, 1H, C₈ₐH), 4.50 (br-s, 2H, NH₂), 4.29 (t, J=8.9 Hz, 2H, C₁₀H₂), 4.02 (t, J=6.0 Hz, 1H, C₃ₐH), 3.66 (s, 3H, NCO₂CH₃), 3.55 (br-s, 1H, C₂Hₐ), 3.04 (s, 3H, SO₂CH₃), 2.79 (td, J=6.1, 11.0 Hz, 1H, C₂H_b), 2.21-2.01 (m, 2H, C₃H₂), 1.22-1.02 (m, 2H, C₁₁H₂), 0.03 (s, 9H, (C₁₂H₃)₃).

¹³C NMR (100 MHz, CDCl₃, 25° C.): δ 154.9 (C₉), 154.6 (NCO₂CH₃), 140.0 (C₇ₐ), 136.7 (C₄ₐ), 133.3 (C₇), 126.8 (C₅), 123.9 (2C, C₄, C₆), 78.1 (C₈ₐ), 65.2 (C₁₀), 52.5 (NCO₂CH₃), 46.1 (br, C₃ₐ), 44.8 (C₂), 37.7 (SO₂CH₃), 29.3 (C₃), 17.9 (C₁₁), −1.5 (C₁₂).

FTIR (thin film) cm⁻¹: 3366 (m), 2954 (m), 1700 (s), 1653 (w), 1559 (w), 1457 (s), 1337 (m).

HRMS (ESI) (m/z): calc'd for C₁₉H₃₀N₄NaO₆SSi [M+Na]⁺: 493.1548, found 493.1519.

$[α]_D^{24}$: −119 (c=0.49, CH₂Cl₂).

TLC (50% ethyl acetate in hexanes), Rf: 0.18 (UV, CAM).

Example 25: Synthesis of Hydrazidocyclotryptamine (−)-31

Example 26: Synthesis of Hydrazidocyclotryptamine (+)-31

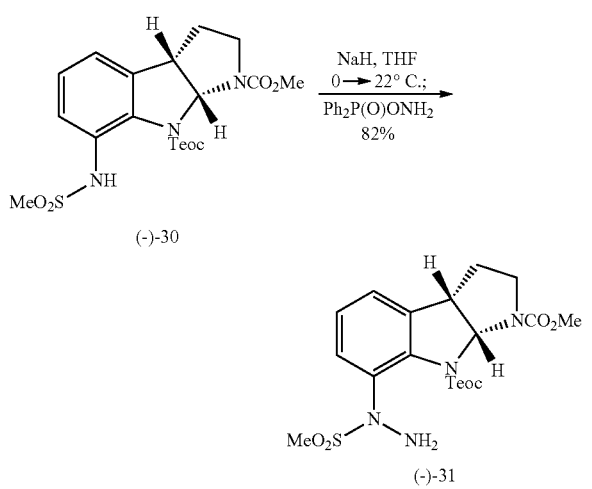

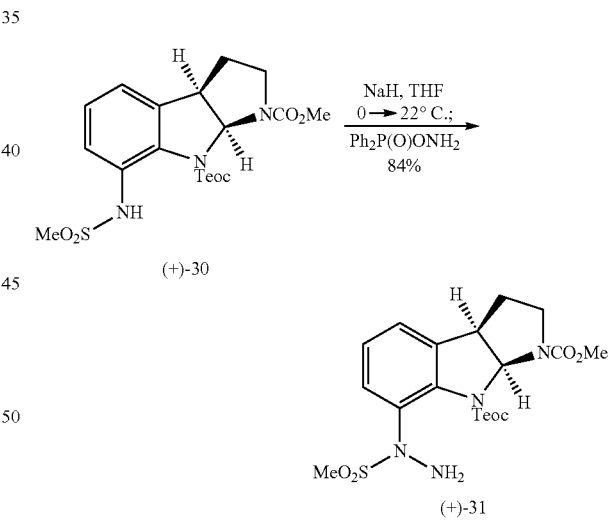

Cyclotryptamine sulfonamide (−)-30 (2.02 g, 4.43 mmol, 1 equiv) was azeotropically dried by concentration from anhydrous benzene (3×5 mL) and the residue was dissolved in tetrahydrofuran (44 mL). The solution was cooled to 0° C. and a sample of sodium hydride (60% in mineral oil, 230 mg, 5.76 mmol, 1.30 equiv) was added in one portion. The ice-water bath was removed and after 30 min, a sample of O-(diphenylphosphinyl)hydroxylamine (1.34 g, 5.76 mmol, 1.30 equiv) was added in one portion. After 1 h, the reaction mixture was diluted with ethyl acetate (30 mL), was washed with a mixture of saturated aqueous sodium bicarbonate and water (10:1 v/v, 25 mL), and the aqueous layer was extracted Cyclotryptamine sulfonamide (+)-30 (106 mg, 233 µmol, 1 equiv) was azeotropically dried by concentration from anhydrous benzene (3×1 mL) and the residue was dissolved in tetrahydrofuran (2.3 mL). The solution was cooled to 0° C. and a sample of sodium hydride (60% in mineral oil, 12.1 mg, 303 µmol, 1.30 equiv) was added in one portion. The ice-water bath was removed and after 30 min, a sample of O-(diphenylphosphinyl)hydroxylamine (70.7 mg, 303 µmol, 1.30 equiv) was added in one portion. After 1 h, the reaction mixture was diluted with ethyl acetate (2 mL), washed with mixture of saturated aqueous sodium bicarbonate and water (10:1 v/v, 5 mL) and the aqueous layer was extracted with ethyl acetate (3×3 mL). The combined organic extracts were dried over anhydrous sodium sulfate, were filtered, and were concentrated under reduced pressure. The resulting residue was purified by flash column chromatography on silica gel (eluent: 25→50% ethyl acetate in hexanes) to afford hydrazidocyclotryptamine (+)-31 (91.8 mg, 83.7%) as an orange amorphous gum. For full characterization data for hydrazidocyclotryptamine (+)-31 ($[\alpha]_D^{24}$=+132 (c=0.50, $CH_2Cl_2$)) see previous procedure in this document.

Example 27: Synthesis of Diazene Dimer (+)-32

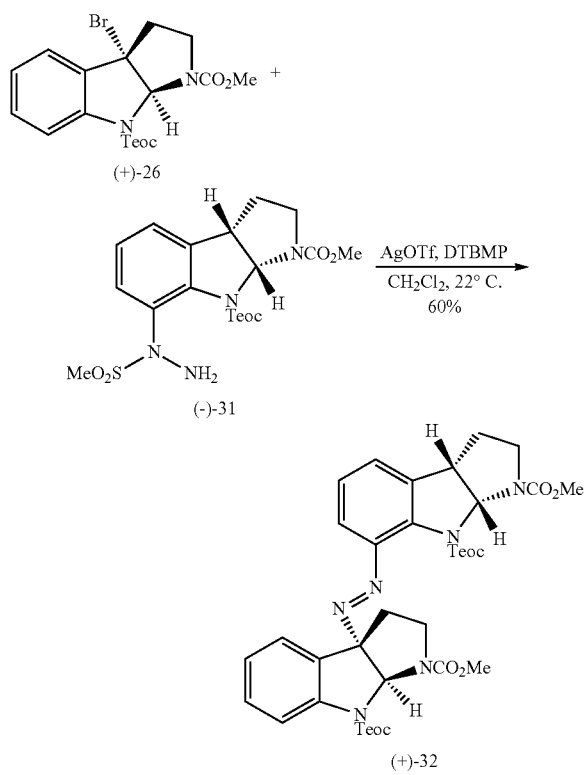

A sample of silver trifluoromethanesulfonate (827 mg, 3.22 mmol, 2.00 equiv) was added to a solution of bromocyclotryptamine (+)-26 (711 mg, 1.61 mmol, 1 equiv), hydrazidocyclotryptamine (−)-31 (983 mg, 2.09 mmol, 1.30 equiv), and DTBMP (828 mg, 4.03 mmol, 2.50 equiv) in dichloromethane (16 mL) at 22° C. After 1 h, the off-white suspension was filtered through a pad of Celite. The filter cake was washed with ethyl acetate (25 mL) and the filtrate was concentrated under reduced pressure. The resulting residue was purified by flash column chromatography on silica gel (eluent: 20%→35% ethyl acetate in hexanes) to yield the diazene dimer (+)-32 (725 mg, 60.0%) as a bright yellow amorphous gum. Structural assignments were made using additional information from gCOSY, gHSQC, and gHMBC experiments.

$^1$H NMR (400 MHz, $CDCl_3$, 25° C.): δ 7.81 (d, J=8.1 Hz, 1H, $C_7H$), 7.47 (d, J=7.4 Hz, 1H, $C_4H$), 7.30 (app-td, J=1.3, 7.9 Hz, 1H, $C_6H$), 7.25-7.19 (m, 2H, $C_{4'}H$, $C_{6'}H$) 7.16-7.10 (m, 1H, $C_{5'}H$), 7.07 (app-t, J=7.3 Hz, 1H, $C_5H$), 6.87 (br-s, 1H, $C_{8a}H$), 6.37 (br-s, 1H, $C_{8a'}H$), 4.32 (ddd, J=1.7, 5.4, 7.7 Hz, 2H, $C_{10}H_2$ or $C_{10'}H_2$), 4.12-4.03 (m, 4H, $C_2H_a$, $C_{3a}H$, $C_{10}H_2$ or $C_{10'}H_2$), 3.79 (br-s, 3H, $N_1CO_2CH_3$ or $N_1'CO_2CH_3$), 3.75 (app-s, 4H, $C_2H_a$, $N1CO_2CH_3$ or $N_1·CO_2CH_3$), 3.09 (td, J=5.3, 11.7 Hz, 1H, $C_2H_b$), 2.94 (td, J=6.8, 10.9 Hz, 1H, $C_2·H_b$), 2.46 (dd, J=11.8, 19.8 Hz, 1H, $C_3H_a$), 2.35 (dd, J=4.8, 12.2 Hz, 1H, $C_3H_b$), 2.30-2.13 (m, 2H, $C_3·H_2$), 1.13 (dd, J=6.9, 10.6 Hz, 2H, $C_{11}H_2$ or $C_{11'}H_2$), 0.86 (br-s, 2H, $C_{11}H_2$ or $C_{11'}H_2$), 0.04 (s, 9H, $(C_{12}H_3)_3$ or $(C_{12'}H_3)_3$), −0.05 (s, 9H, $(C_{12}H_3)_3$ or $(C_{12'}H_3)_3$).

$^{13}$C NMR (100 MHz, $CDCl_3$, 25° C.): δ 155.3 (2C, $N_1CO_2CH_3$, $N_1·CO_2CH_3$), 154.6 ($C_9$ or $C_{9'}$), 153.6 ($C_9$ or $C_{9'}$), 143.3 ($C_{7a}$), 141.5 ($C_{7'}$), 139.5 ($C_{7a'}$), 135.7 ($C_{4a'}$), 129.9 ($C_6$), 129.5 ($C_{4a}$), 125.8 ($C_4$), 125.6 ($C_{5'}$), 125.3 ($C_{4'}$), 123.5 ($C_5$), 117.2 ($C_{6'}$), 115.9 ($C_7$), 88.8 ($C_{3a}$), 79.0 (2C, $C_{8a}$, $C_{8a'}$), 64.6 ($C_{10}$ or $C_{10'}$), 64.3 ($C_{10}$ or $C_{10'}$), 52.8 ($N_1CO_2CH_3$ or $N_1·CO_2CH_3$), 52.6 ($N_1CO_2CH_3$ or $N_1·CO_2CH_3$), 46.4 ($C_{3a'}$), 45.8 ($C_2$), 45.2 ($C_{2'}$), 36.7 ($C_3$), 29.4 ($C_{3'}$), 17.9 ($C_{11}$ or $C_{11'}$), 17.7 ($C_{11}$ or $C_{11'}$), −1.5 (2C, $C_{12}$, $C_{12'}$).

FTIR (thin film) $cm^{-1}$: 2955 (m), 1701 (s), 1603 (w), 1448 (m), 1396 (m).

HRMS (ESI) (m/z): calc'd for $C_{36}H_{50}N_6NaO_8Si_2$ [M+Na]$^+$: 773.3121, found 773.3104.

$[\alpha]_D^{24}$: +361 (c=0.61, $CH_2Cl_2$).

TLC (50% ethyl acetate in hexanes), Rf: 0.33 (UV, CAM).

Example 28: Synthesis of Diazene Dimer (−)-33

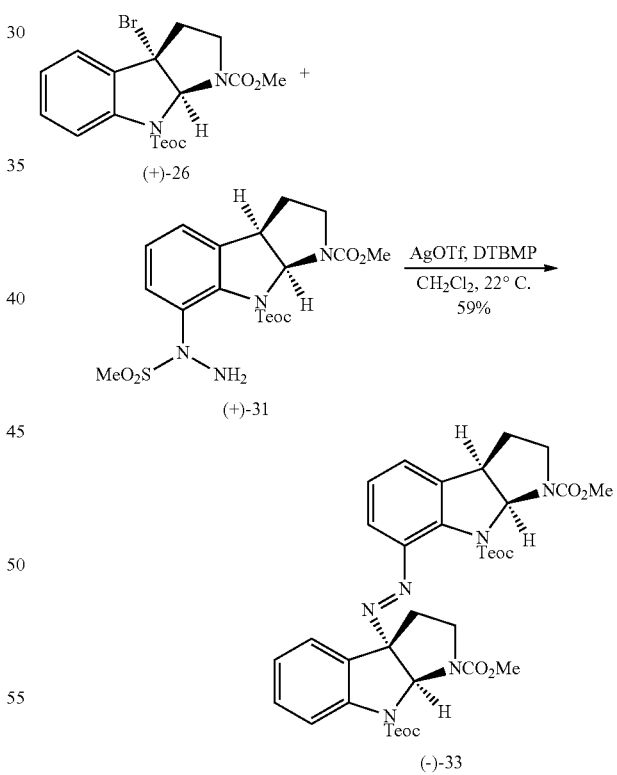

A sample of silver trifluoromethanesulfonate (673 mg, 2.62 mmol, 2.00 equiv) was added to a solution of bromocyclotryptamine (+)-26 (578 mg, 1.31 mmol, 1 equiv), hydrazidocyclotryptamine (+)-31 (802 mg, 1.70 mmol, 1.30 equiv), and DTBMP (674 mg, 3.28 mmol, 2.50 equiv) in dichloromethane (13 mL) at 22° C. After 1 h, the off-white suspension was filtered through a pad of Celite. The filter cake was washed with ethyl acetate (20 mL) and the filtrate was concentrated under reduced pressure. The resulting residue was purified by flash column chromatography on silica gel (eluent: 25%→35% ethyl acetate in hexanes) to yield the diazene dimer (−)-33 (582 mg, 59.2%) as a bright yellow amorphous gum. Structural assignments were made using additional information from gCOSY, gHSQC, and gHMBC experiments.

$^1$H NMR (400 MHz, CDCl$_3$, 25° C.): δ 7.80 (d, J=8.1 Hz, 1H, C$_7$H), 7.33-7.20 (m, 3H, C$_6$H, C$_4$H, C$_{4'}$H), 7.17 (d, J=7.7 Hz, 1H, C$_{6'}$H), 7.15-7.08 (m, 1H, C$_{5'}$H), 7.03 (app-t, J=7.5 Hz, 1H, C$_5$H), 6.89 (s, 1H, C$_{8a}$H), 6.41 (br-s, 1H, C$_{8a'}$H), 4.43-4.31 (m, 2H, C$_{10}$H$_2$ or C$_{10'}$H$_2$), 4.31-4.23 (m, 1H, C$_{10}$H$_a$ or C$_{10'}$H$_a$), 4.14-3.96 (m, 3H, C$_2$H$_a$, C$_{3a}$H, C$_{10}$H$_b$ or C$_{10'}$H$_b$), 3.89-3.67 (m, 7H, C$_{2'}$H$_a$, N$_1$CO$_2$CH$_3$, N$_{1'}$CO$_2$CH$_3$), 3.10 (td, J=5.2, 11.7 Hz, 1H, C$_2$H$_b$), 2.93 (td, J=6.9, 10.8 Hz, 1H, C$_{2'}$H$_b$), 2.62-2.46 (m, 1H, C$_3$H$_a$), 2.37 (dd, J=5.1, 12.6 Hz, 1H, C$_3$H$_b$), 2.28-2.13 (m, 2H, C$_{3'}$H$_2$), 1.15 (dd, J=6.8, 10.8 Hz, 2H, C$_{11}$H$_2$ or C$_{11'}$H$_2$), 0.96 (br-s, 2H, C$_{11}$H$_2$ or C$_{11'}$H$_2$), 0.06 (s, 9H, (C$_{12}$H$_3$)$_3$ or (C$_{12'}$H$_3$)$_3$), −0.02 (s, 9H, (C$_{12}$H$_3$)$_3$ or (C$_{12'}$H$_3$)$_3$).

$^{13}$C NMR (100 MHz, CDCl$_3$, 25° C.): δ 155.4 (N$_1$CO$_2$CH$_3$ or N$_{1'}$CO$_2$CH$_3$), 155.3 (N$_1$CO$_2$CH$_3$ or N$_{1'}$CO$_2$CH$_3$), 154.9 (C$_9$ or C$_{9'}$), 153.8 (C$_9$ or C$_{9'}$), 143.5 (C$_{7a}$), 141.6 (C$_{7'}$), 139.7 (C$_{7a'}$), 135.7 (C$_{4a'}$), 130.0 (C$_6$), 129.2 (C$_{4a}$), 125.7 (C$_{5'}$), 125.4 (C$_4$ or C$_{4'}$), 125.3 (C$_4$ or C$_{4'}$), 123.5 (C$_5$), 117.1 (C$_{6'}$), 116.2 (C$_7$), 88.9 (C$_{3a}$), 79.6 (C$_{8a}$), 79.1 (C$_{8a'}$), 64.8 (C$_{10}$ or C$_{10'}$), 64.5 (C$_{10}$ or C$_{10'}$), 52.8 (N$_1$CO$_2$CH$_3$ or N$_{1'}$CO$_2$CH$_3$), 52.7 (N$_1$CO$_2$CH$_3$ or N$_{1'}$CO$_2$CH$_3$), 46.4 (C$_{3a'}$), 46.1 (C$_2$), 45.2 (C$_{2'}$), 35.9 (C$_3$), 29.6 (C$_{3'}$), 17.9 (2C, C$_{11}$, C$_{11'}$), −1.4 (C$_{12}$ or C$_{12'}$), −1.5 (C$_{12}$ or C$_{12'}$).

FTIR (thin film) cm$^{-1}$: 2954 (m), 1707 (s), 1603 (w), 1397 (m), 1259 (m).

HRMS (ESI) (m/z): calc'd for C$_{36}$H$_{50}$N$_6$NaO$_8$Si$_2$ [M+Na]$^+$: 773.3121, found 773.3115.

[α]$_D^{24}$: −86 (c=0.61, CH$_2$Cl$_2$).

TLC (50% ethyl acetate in hexanes), Rf: 0.32 (UV, CAM).

Example 29: Synthesis of Diazene Dimer Sulfamate (+)-34

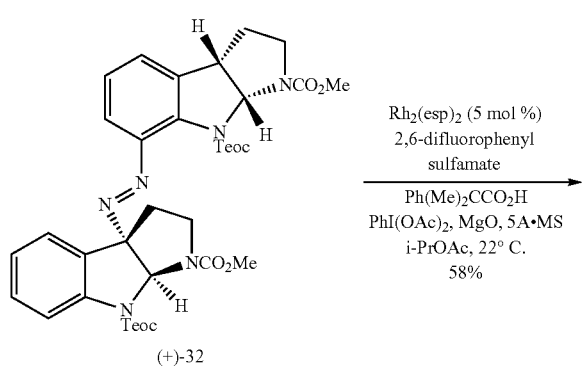

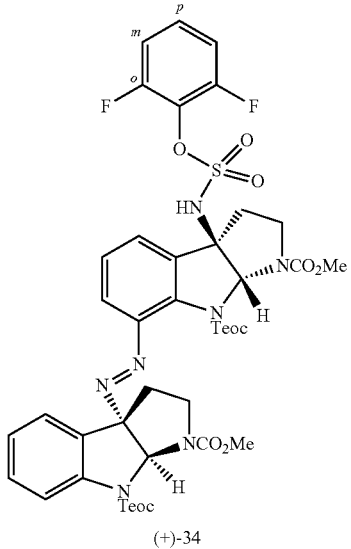

A round-bottom flask equipped with a stir bar was charged with crushed 5 Å molecular sieves (133 mg, 200 mg/mmol of (+)-32) and magnesium oxide (107 mg, 2.66 mmol, 4.00 equiv). The flask and its contents were flame-dried under reduced pressure for 5 min. The reaction vessel was allowed to cool to 22° C. and was then back filled with argon. Solid 2,6-difluorophenyl sulfamate (177 mg, 866 μmol, 1.30 equiv), 2-methyl-2-phenylpropionic acid (54.7 mg, 333 μmol, 0.500 equiv), and Rh$_2$(esp)$_2$ (25.0 mg, 33.0 μmol, 5.00 mol %) were added sequentially. A solution of diazene dimer (+)-32 (500 mg, 666 μmol, 1 equiv) in isopropyl acetate (1.33 mL) was added via syringe at 22° C. The resulting mixture was allowed to stir for 5 min. A sample of (diacetoxyiodo)benzene (428 mg, 1.33 mmol, 2.00 equiv) was then added and the green suspension was allowed to stir vigorously at 22° C. After 22 h, the reaction mixture was filtered through a pad of Celite and the filter cake was rinsed with ethyl acetate (5 mL). The filtrate was concentrated under reduced pressure. The resulting residue was purified by flash column chromatography on silica gel (eluent: 10→25% acetone in hexanes) to afford diazene dimer sulfamate (+)-34 (371 mg, 58.1%) as a bright yellow amorphous gum. Structural assignments were made using additional information from gCOSY, gHSQC, and gHMBC experiments.

$^1$H NMR (400 MHz, CDCl$_3$, 25° C.): δ 7.80 (d, J=8.1 Hz, 1H, C$_7$H), 7.53-7.42 (m, 2H, C$_4$H, C$_{4'}$H), 7.38 (d, J=7.8 Hz, 1H, C$_{6'}$H), 7.35-7.28 (m, 1H, C$_6$H), 7.25-7.14 (m, 2H, C$_5$H, C$_p$H), 7.06 (app-t, J=7.4 Hz, 1H, C$_5$H), 6.98 (t, J=8.2 Hz, 2H, C$_m$H), 6.83 (s, 1H, C$_{8a}$H), 6.56 (br-s, 1H, C$_{8a'}$H), 5.74 (br-s, 1H, NH), 4.39-4.23 (m, 2H, C$_{10}$H$_2$ or C$_{10'}$H$_2$), 4.13-3.99 (m, 2H, C$_2$H$_a$, C$_{10}$H$_a$ or C$_{10'}$H$_a$), 3.89-3.80 (m, 1H, C$_{2'}$H$_a$), 3.77 (s, 3H, N$_1$CO$_2$CH$_3$ or N$_{1'}$CO$_2$CH$_3$), 3.73 (app-s, 4H, C$_{10}$H$_b$ or C$_{10'}$H$_b$, N$_1$CO$_2$CH$_3$ or N$_{1'}$CO$_2$CH$_3$), 3.08 (td, J=5.0, 11.6 Hz, 1H, C$_2$H$_b$), 2.91 (br-d, J=19.3 Hz, 2H, C$_{2'}$H$_b$, C$_3$H$_a$) 2.58-2.41 (m, 2H, C$_3$H$_b$, C$_{3'}$H$_a$), 2.35 (dd, J=4.2, 11.9 Hz, 1H, C$_{3'}$H$_b$), 1.13 (dd, J=6.7, 10.7 Hz, 2H, C$_{11}$H$_2$ or C$_{11'}$H$_2$), 0.84 (br-s, 2H, C$_{11}$H$_2$ or C$_{11'}$H$_2$), 0.03 (s, 9H, (C$_{12}$H$_3$)$_3$ or (C$_{12'}$H$_3$)$_3$), −0.02 (s, 9H, (C$_{12}$H$_3$)$_3$ or (C$_{12'}$H$_3$)$_3$).

$^{13}$C NMR (100 MHz, CDCl$_3$, 25° C.): δ 156.0 (dd, J=3.3, 253.8 Hz, C$_o$), 155.3 (2C, N$_1$CO$_2$CH$_3$, N$_{1'}$CO$_2$CH$_3$), 154.2 (C$_9$ or C$_{9'}$), 153.6 (C$_9$ or C$_{9'}$), 143.3 (C$_{7a}$), 141.7 (C$_{7'}$), 140.0

($C_{7a'}$), 133.1 ($C_{4a'}$), 129.9 ($C_6$), 129.4 ($C_{4a}$), 127.7 (t, J=9.1 Hz, $C_p$), 126.8 (t, J=15.7 Hz, $C_j$), 126.0 ($C_{5'}$), 125.7 ($C_4$), 125.6 ($C_{4'}$), 123.5 ($C_5$), 119.8 ($C_{6'}$), 115.9 ($C_7$), 112.6 (d, J=22.0 Hz, Cm), 89.0 ($C_{3a}$), 81.6 ($C_{8a'}$), 78.9 ($C_{8a}$), 71.5 ($C_{3a'}$), 65.0 ($C_{10}$ or $C_{10'}$), 64.4 ($C_{10}$ or $C_{10'}$), 52.8 ($N_1CO_2CH_3$ or $N_1CO_2CH_3$), 52.7 ($N_1CO_2CH_3$ or $N_1CO_2CH_3$), 45.8 ($C_2$), 44.9 ($C_{2'}$), 36.4 ($C_3$), 33.6 ($C_{3'}$), 17.8 ($C_{11}$ or $C_{11'}$), 17.5 ($C_{11}$ or $C_{11'}$), −1.5 ($C_{12}$ or $C_{12'}$), −1.6 ($C_{12}$ or $C_{12'}$).

$^{19}F$ NMR (282 MHz, $CDCl_3$, 25° C.): δ−124.4 (s, $C_6H_3F_2$).

FTIR (thin film) cm$^{-1}$: 3171 (br-m), 2955 (s), 1717 (s), 1606 (m), 1302 (w).

HRMS (ESI) (m/z): calc'd for $C_{42}H_{53}F_2N_7NaO_{11}SSi_2$ [M+Na]$^+$: 980.2923, found 980.2904.

$[α]_D^{24}$: +282 (c=0.77, $CH_2Cl_2$).

TLC (20% acetone in hexanes), Rf: 0.10 (UV, CAM).

Example 30: Synthesis of Diazene Dimer Mixed Sulfamide (+)-35

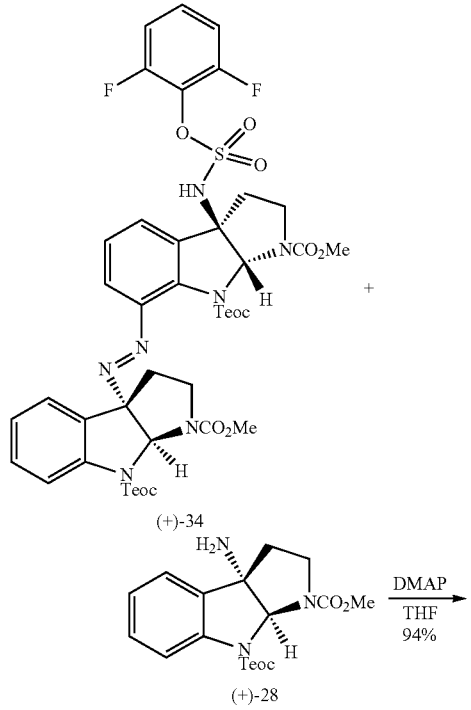

A sample of 4-(dimethylamino)pyridine (98.6 mg, 807 μmol, 2.20 equiv) was added to a solution of diazene dimer sulfamate (+)-34 (352 mg, 367 μmol, 1 equiv) and amine (+)-28 (153 mg, 404 μmol, 1.10 equiv) in tetrahydrofuran (3.7 mL) at 22° C. After 24 h, the bright yellow solution was concentrated under reduced pressure. The resulting residue was purified by flash column chromatography on silica gel (eluent: 15%→70% ethyl acetate in hexanes) to afford diazene dimer mixed sulfamide (+)-35 (416 mg, 94.0%) as a bright yellow amorphous gum. As a result of the slow conformational equilibration at ambient temperature, NMR spectra were collected at elevated temperature.

$^1H$ NMR (400 MHz, $C_6D_6$, 70° C.): δ 8.17 (d, J=8.1 Hz, 1H), 7.96 (d, J=8.0 Hz, 1H), 7.54 (d, J=7.4 Hz, 1H), 7.37 (d, J=7.9 Hz, 1H), 7.24-7.18 (m, 2H), 7.15-7.10 (m, 3H), 7.03-6.95 (m, 2H), 6.90 (app-t, J=7.3 Hz, 1H), 6.76 (s, 1H), 6.68 (s, 1H), 5.47 (s, 1H), 5.26 (s, 1H), 4.48-4.30 (m, 5H), 4.14 (td, J=6.2, 10.7 Hz, 1H), 4.01-3.91 (m, 1H), 3.66 (app-s, 5H), 3.61 (s, 3H), 3.52 (s, 3H), 2.96 (td, J=4.9, 11.5 Hz, 1H), 2.65-2.54 (m, 2H), 2.43 (app-dd, J=11.9, 20.4 Hz, 1H), 2.19 (dd, J=4.4, 12.2 Hz, 1H), 2.12-1.90 (m, 4H), 1.20-1.00 (m, 6H), 0.00 (s, 9H), −0.03 (app-s, 18H).

$^{13}C$ NMR (100 MHz, $C_6D_6$, 70° C.): δ 155.7, 155.3, 155.2, 155.0, 154.3, 153.8, 144.4, 144.0, 142.6, 141.0, 134.5, 130.9, 130.4, 130.3, 130.2, 126.2, 125.8, 125.6, 124.7, 123.9, 123.6, 119.6, 117.5, 116.6, 89.9, 82.3, 80.2, 79.6, 71.4 (2C), 65.3, 64.8, 64.2, 52.4 (3C), 46.0, 45.1, 44.7, 37.2, 37.1, 36.7, 18.2 (2C), 18.1, −1.5 (3C).

FTIR (thin film) cm$^{-1}$: 3233 (m), 2955 (s), 1716 (s), 1604 (m), 1318 (w).

HRMS (ESI) (m/z): calc'd for $C_{54}H_{76}N_{10}NaO_{14}SSi_3$ [M+Na]$^+$: 1227.4463, found: 1227.4460.

$[α]_D^{24}$: +264 (c=0.67, $CH_2Cl_2$).

TLC (60% ethyl acetate in hexanes), Rf: 0.25 (UV, CAM).

Example 31: Synthesis of Bis-Diazene Trimer (+)-36

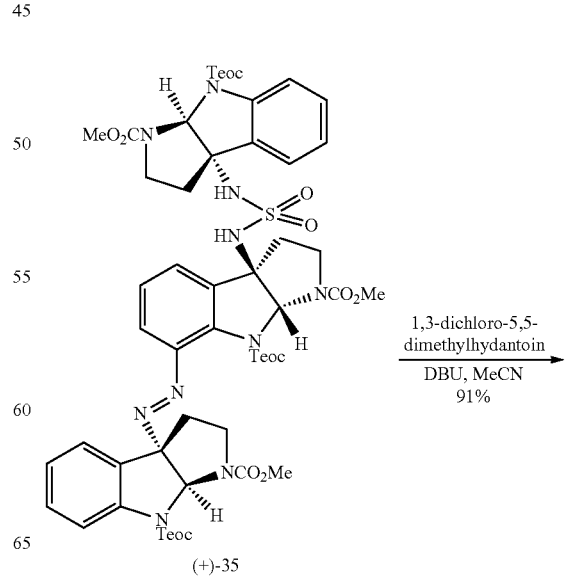

189

-continued

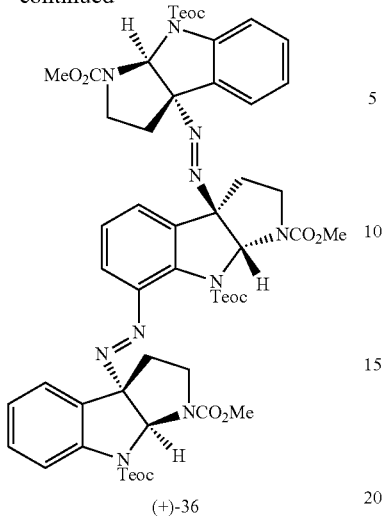

(+)-36

To a solution of diazene dimer mixed sulfamide (+)-35 (302 mg, 251 μmol, 1 equiv) in acetonitrile (12.6 mL) at 22° C. was added via syringe 1,8-diazabicyclo[5.4.0]undec-7-ene (DBU, 113 μL, 753 μmol, 3.00 equiv) followed immediately by 1,3-dichloro-5,5-dimethylhydantoin (124 mg, 628 μmol, 2.50 equiv) in a single portion. After 1 h, the mixture was diluted with dichloromethane (10 mL) and was washed with a saturated aqueous potassium carbonate-water solution (1:1, 10 mL). The aqueous layer was extracted with dichloromethane (3×10 mL). The combined organic extracts were dried over anhydrous sodium sulfate, were filtered, and were concentrated under reduced pressure. The resulting residue was purified by flash column chromatography on silica gel (eluent: 25→50% ethyl acetate in hexanes) to afford bis-diazene trimer (+)-36 (260 mg, 90.9%) as a bright yellow amorphous gum. As a result of the slow conformational equilibration at ambient temperature, NMR spectra were collected at elevated temperature.

$^1$H NMR (400 MHz, CD$_3$CN, 50° C.): δ 7.77 (d, J=8.1 Hz, 1H), 7.70 (d, J=8.1 Hz, 1H), 7.48 (d, J=7.1 Hz, 1H), 7.40-7.35 (m, 1H), 7.35-7.27 (m, 2H), 7.27-7.21 (m, 2H), 7.15-7.07 (m, 2H), 7.02 (app-td, J=0.8, 7.5 Hz, 1H), 6.73 (s, 1H), 6.46 (s, 1H), 6.37 (s, 1H), 4.37-4.21 (m, 4H), 4.11-3.97 (m, 2H), 3.93-3.80 (m, 2H), 3.80-3.74 (m, 1H), 3.70 (app-s, 6H), 3.65 (s, 3H), 3.08-2.87 (m, 3H), 2.57 (dd, J=5.3, 12.5 Hz, 1H), 2.53-2.38 (m, 3H), 2.36-2.18 (m, 2H), 1.16-1.02 (m, 4H), 0.91-0.73 (m, 2H), 0.07 (s, 9H), 0.05 (s, 9H), −0.01 (s, 9H).

$^{13}$C NMR (100 MHz, CD$_3$CN, 50° C.): δ 156.2, 156.1 (2C), 155.3, 154.5, 154.4, 144.6 (2C), 143.3, 140.9, 134.9, 131.2, 131.1, 131.0, 130.2, 127.6, 127.1, 126.8, 126.0, 124.7, 124.6, 120.3, 117.3, 116.9, 90.0, 89.7, 89.4, 81.8, 79.7, 79.6, 65.7, 65.2 (2C), 53.4, 53.3 (2C), 46.9, 46.7 (2C), 37.3, 36.1, 33.6, 18.7 (2C), 18.6, −1.1, −1.2 (2C).

FTIR (thin film) cm$^{-1}$: 2954 (m), 2896 (m), 1713 (s), 1603 (w), 1447 (m).

HRMS (ESI) (m/z): calc'd for C$_{54}$H$_{74}$N$_{10}$NaO$_{12}$Si$_3$ [M+Na]$^+$: 1161.4688, found: 1161.4704.

[α]$_D^{24}$: +297 (c=0.43, CH$_2$Cl$_2$).

TLC (50% ethyl acetate in hexanes), Rf: 0.43 (UV, CAM).

190

Example 32: Synthesis of Mono-Diazene Trimer (+)-37

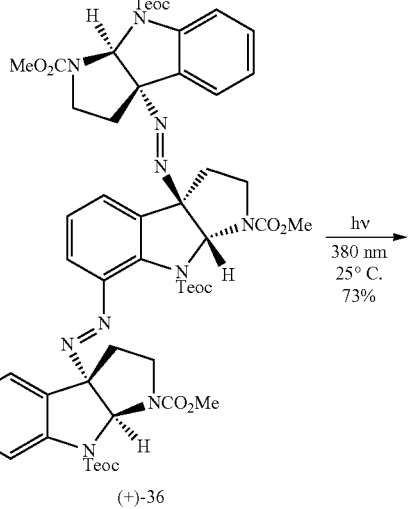

A solution of bis-diazene trimer (+)-36 (397 mg, 348 μmol, 1 equiv) in dichloromethane (30 mL) was concentrated under reduced pressure in a 1 L round-bottom flask to provide a thin film of diazene coating the flask. The flask was backfilled with argon and irradiated in a Rayonet photoreactor equipped with 16 radially distributed (r=12.7 cm) 25 W lamps (λ=380 nm) at 25° C. After 15 h, the lamps were turned off and the resulting residue was purified by flash column chromatography on silica gel (eluent: 20→60% ethyl acetate in hexanes) to afford mono-diazene trimer (+)-37 (282 mg, 72.9%) as a bright yellow amorphous gum. As a result of the slow conformational equilibration at ambient temperature, NMR spectra were collected at elevated temperature.

$^1$H NMR (400 MHz, CD$_3$CN, 60° C.): δ 7.75 (d, J=8.1 Hz, 1H), 7.65 (d, J=8.1 Hz, 1H), 7.46 (d, J=7.5 Hz, 1H), 7.32 (app-ddd, J=1.3, 7.9, 8.8 Hz, 1H), 7.28-7.14 (m, 4H), 7.09 (app-td, J=0.9, 7.5 Hz, 1H), 6.77 (app-t, J=7.5 Hz, 1H), 6.66 (s, 1H), 6.40 (br-d, J=6.6 Hz, 1H), 6.22 (s, 1H), 6.06 (s, 1H), 4.40-4.26 (m, 3H), 4.26-4.15 (m, 1H), 3.98 (ddd, J=2.6, 6.0, 11.2 Hz, 1H), 3.88-3.72 (m, 3H), 3.68 (app-d, J=1.9 Hz, 9H), 3.63-3.51 (m, 1H), 3.06-2.93 (m, 1H), 2.83-2.67 (m, 2H), 2.50-2.40 (m, 2H), 2.40-2.28 (m, 2H), 2.28-2.16 (m, 2H), 1.20-1.01 (m, 4H), 0.96-0.80 (m, 2H), 0.09 (s, 9H), 0.07 (s, 9H), 0.05 (s, 9H).

$^{13}$C NMR (100 MHz, CD$_3$CN, 60° C.): δ 156.3, 155.9, 155.8, 154.6, 154.3, 154.2, 144.7, 144.5, 143.2, 140.7, 137.3, 132.2, 131.3, 131.1, 130.4, 127.0, 126.8, 125.3, 124.8, 124.7, 119.7, 117.3, 117.0, 90.1, 81.7, 79.9, 79.8, 65.8, 65.4, 65.2, 62.7, 61.8, 53.4 (2C), 53.3, 46.9 (2C), 46.5, 37.6, 35.2, 34.3, 18.9, 18.8, 18.5, −1.1 (3C). All expected $^{13}$C signals were observed in the product of the next step of the synthesis, trimer (+)-25. One of the 48 carbon resonances for intermediate (+)-24 is obscured (likely a second aromatic resonance at 126.8 ppm.

FTIR (thin film) cm$^{-1}$: 2954 (m), 1717 (s), 1602 (w), 1448 (m), 1251 (m).

HRMS (ESI) (m/z): calc'd for C$_{54}$H$_{74}$N$_8$NaO$_{12}$Si$_3$ [M+Na]$^+$: 1133.4626, found: 1133.4646.

[α]$_D^{24}$: +370 (c=0.57, CH$_2$Cl$_2$).

TLC (70% ethyl acetate in hexanes), Rf: 0.35 (UV, CAM).

Example 33: Synthesis of Cyclotryptamine Trimer (+)-38

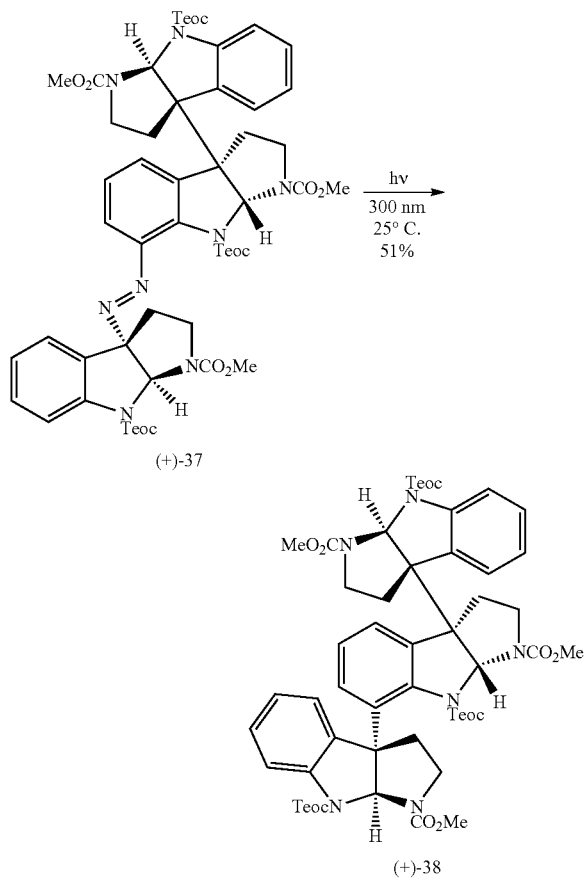

A solution of mono-diazene trimer (+)-37 (52.9 mg, 47.6 µmol, 1 equiv) in dichloromethane (3 mL) was concentrated under reduced pressure in a 500-mL round-bottom flask to provide a thin film of diazene coating the flask. The flask was back filled with argon and irradiated in a Rayonet photoreactor equipped with 16 radially distributed (r=12.7 cm) 25 W lamps (λ=300 nm) at 25° C. After 30 h, the lamps were turned off and the resulting residue was purified by flash column chromatography on silica gel (eluent: 18→35% ethyl acetate in hexanes) to afford cyclotryptamine trimer (+)-38 (26.2 mg, 50.8%) as an off-white solid. As a result of the slow conformational equilibration at ambient temperature, NMR spectra were collected at elevated temperature.

$^1$H NMR (400 MHz, CD$_3$CN, 60° C.): δ 7.66 (d, J=8.0 Hz, 1H), 7.62 (d, J=8.1 Hz, 1H), 7.33-7.26 (m, 2H), 7.23-7.18 (m, 1H), 7.18-7.10 (m, 2H), 7.10-6.99 (app-br-s, 1H), 6.82 (app-t, J=7.7 Hz, 1H), 6.73 (app-t, J=7.8 Hz, 1H), 6.38 (s, 1H), 6.31 (br-s, 1H), 6.25 (s, 1H), 5.78 (s, 1H), 4.41-4.33 (m, 1H), 4.33-4.17 (m, 3H), 3.97 (app-t, J=9.9 Hz, 1H), 3.80 (dd, J=7.5, 11.1, 1H), 3.73-3.65 (m, 1H), 3.69 (s, 3H), 3.67 (s, 3H), 3.61 (s, 3H), 3.46-3.35 (m, 1H), 2.97-2.89 (m, 1H), 2.78-2.65 (m, 3H), 2.36-2.28 (m, 1H), 2.27-2.04 (m, 5H), 1.16-1.02 (m, 4H), 0.85-0.75 (m, 1H), 0.75-0.65 (m, 1H), 0.09 (s, 9H), 0.06 (s, 9H), 0.05 (s, 9H).

$^{13}$C NMR (100 MHz, CD$_3$CN, 60° C.): δ 156.4, 156.0, 155.6, 154.8, 154.7, 154.3, 144.3, 144.0, 142.5, 138.2, 136.6, 136.2, 132.3, 130.9, 130.2, 128.7, 127.6, 126.4, 125.5, 124.9, 124.1, 124.0, 117.1, 115.9, 86.2, 80.4, 80.1, 65.5, 65.4, 64.8, 62.2, 61.7, 61.2, 53.4 (2C), 53.1, 46.9, 46.2, 46.1, 35.7, 35.0 (2C), 19.0 (2C), 18.5, −1.1 (3C).

FTIR (thin film) cm$^{-1}$: 2954 (m), 2897 (w), 1716 (s), 1601 (w), 1400 (s).

HRMS (ESI) (m/z): calc'd for C$_{54}$H$_{74}$N$_6$NaO$_{12}$Si$_3$ [M+Na]$^+$: 1105.4565, found: 1105.4566.

[α]$_D^{24}$: +129 (c=0.50, CH$_2$Cl$_2$).

TLC (60% ethyl acetate in hexanes), Rf: 0.26 (UV, CAM).

Example 34: Synthesis of Cyclotryptamine Trimer (+)-S9

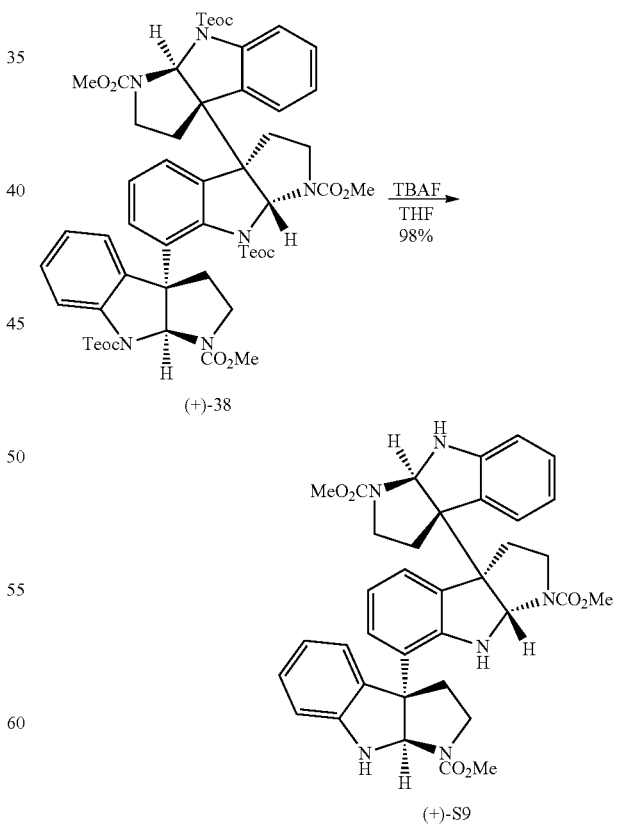

Tetrabutylammonium fluoride (1.0 M in tetrahydrofuran, 570 µL, 570 µmol, 15.0 equiv) was added to cyclotryptamine trimer (+)-38 (41.2 mg, 38.0 µmol, 1 equiv) at 22° C. under an atmosphere of argon. After 1 h, the reaction mixture was diluted with ethyl acetate (5 mL) and washed with a saturated aqueous sodium carbonate solution (5 mL). The aqueous layer was extracted with dichloromethane (3×3 mL). The combined organic extracts were dried over anhydrous sodium sulfate, were filtered, and were concentrated under reduced pressure. The resulting yellow-green residue was purified by flash column chromatography on silica gel (20→40% acetone in hexanes) to yield cyclotryptamine trimer (+)-S9 (24.3 mg, 98.3%) as a pale yellow solid.

$^1$H NMR (400 MHz, CD$_3$CN, 25° C.): δ 7.31-7.05 (m, 1.5H), 7.05-6.93 (m, 2H), 6.90-6.78 (m, 1.5H), 6.78-6.57 (m, 4H), 6.57-6.31 (m, 2H), 6.10-5.64 (m, 1.5H), 5.57-5.31 (m, 2H), 5.28-5.04 (m, 2H), 4.98 (app-s, 0.5H), 3.78-3.59 (m, 9H), 3.59-3.37 (m, 4H), 3.02-2.89 (m, 1H), 2.89-2.71 (m, 1H), 2.66-2.44 (m, 3H), 2.44-2.19 (m, 3H). The reported integrals for intermediate (+)-26 are an approximation due to presence of multiple conformers and significant atropisomerism.

$^{13}$C NMR (125 MHz, CD$_3$CN, 25° C.): δ 155.8, 155.3, 155.1, 115.0, 154.7, 154.6, 151.3 (br), 149.4, 149.1, 131.8, 131.6, 130.4, 130.3, 129.9, 129.6, 129.5, 129.4, 129.3, 129.1, 129.0, 127.0, 126.9 (2C), 125.0, 124.2, 124.1, 123.9, 123.5 (br), 120.8, 120.7, 120.5, 120.4, 118.8, 118.7, 111.2, 110.9, 110.8, 110.5, 109.8 (2C), 109.6, 79.6, 79.5, 78.9, 78.8, 78.7, 78.6, 78.5, 77.9, 77.7, 77.1, 77.0, 76.9, 63.3, 63.2, 62.6, 62.5, 62.2, 62.1, 61.4, 61.3, 60.7, 60.6, 59.7, 59.6, 52.9 (2C), 52.7, 52.6, 64.3, 46.1, 46.0, 45.9, 45.6, 37.1 (2C), 37.0, 36.8, 36.6, 34.5, 34.1 (2C), 33.9, 33.1, 32.8 (2C).

FTIR (thin film) cm$^{-1}$: 3346 (br-m), 2956 (w), 1699 (s), 1456 (s), 1320 (w).

HRMS (ESI) (m/z): calc'd for C$_{36}$H$_{39}$N$_6$O$_6$ [M+H]$^+$: 651.2926, found: 651.2922.

[α]$_D^{24}$: +111 (c=0.52, CH$_2$Cl$_2$).

TLC (70% ethyl acetate in hexanes), Rf: 0.20 (UV, CAM).

M.p.: 138-140° C. (CH$_2$Cl$_2$).

Example 35: Synthesis of (−)-Hodgkinsine B (3)

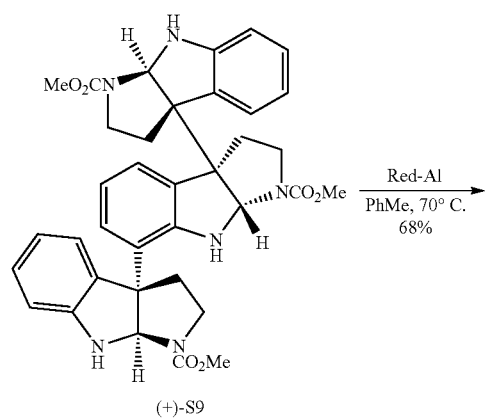

(+)-S9

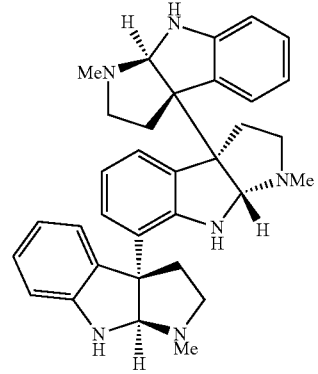

(−)-hodgkinsine B (3)

Cyclotryptamine trimer (+)-S9 (47.3 mg, 72.7 µmol, 1 equiv) was azeotropically dried by concentration from anhydrous benzene (3×1 mL) and the residue was dissolved in toluene (3.6 mL). A solution of sodium bis(2-methoxyethoxy)aluminum hydride in toluene (Red-Al, 70% wt, 273 µL, 945 µmol, 13.5 equiv) was added via syringe at 22° C. The reaction flask was fitted with a reflux condenser and was immersed in a pre-heated 70° C. oil bath. After 1 h, the reaction mixture was allowed to cool to 22° C. and excess reducing reagent was quenched by the addition of a saturated aqueous sodium sulfate solution (100 µL). The resulting heterogeneous mixture was stirred for 10 min and then solid anhydrous sodium sulfate was added. The mixture was filtered through a plug of Celite and the filter cake was rinsed with dichloromethane (5 mL). The filtrate was concentrated under reduced pressure and the resulting residue was purified by flash column chromatography on silica gel (eluent: 3.6% methanol, 0.4% ammonium hydroxide→9.0% methanol, 1.0% ammonium hydroxide in chloroform) to afford (−)-hodgkinsine B (3, 25.8 mg, 68.4%) as an off-white solid. As a result of the slow conformational equilibration at ambient temperature, NMR spectra were collected at −30° C.

$^1$H NMR (400 MHz, CDCl$_3$, −30° C., 1.5:1 mixture of atropisomers, *denotes minor atropisomer): δ 7.36 (d, J=7.5 Hz, 0.8H), 7.26-7.16 (m, 1.6H), 7.14-7.05 (m, 2H), 7.02-6.93 (m, 1H), 6.86-6.73 (m, 1.6H), 6.63 (app-d, J=7.8 Hz, 0.6H), 6.60 (app-d, J=9.0 Hz, 0.4H*), 6.56 (app-d, J=7.8 Hz, 0.4H*), 6.48 (d, J=7.7 Hz, 0.6H), 6.39 (t, J=7.5 Hz, 0.4H*), 6.13 (t, J=7.6 Hz, 0.6H), 5.82 (br-d, J=7.6 Hz, 0.4H*), 5.63 (d, J=7.4 Hz, 0.6H), 5.09-5.04 (m, 1.6H), 4.89 (br-s, 0.4H), 4.41 (d, J=3.7 Hz, 0.6H), 4.32 (br-s, 0.4H), 4.24 (br-s, 0.4H), 4.13 (app br-d, J=16.5 Hz, 1H), 3.84 (br-d, J=3.8 Hz), 2.95 (t, J=7.5 Hz, 0.6H), 2.91-2.62 (m, 3H), 2.61-2.21 (m, 13.2H), 2.46 (app-s), 2.42 (app-s), 2.34 (app-s), 2.32 (app-s) 2.19-2.01 (m, 3.2H), 1.93 (dd, J=5.0, 12.1 Hz, 0.6H), 1.87-1.80 (m, 0.4H*).

$^{13}$C NMR (100 MHz, CDCl$_3$, −30° C.): δ 152.0, 151.0, 150.9, 150.2, 149.5, 133.0, 132.1, 131.8, 131.6, 131.5, 128.2, 127.9, 127.7, 126.6, 125.3, 125.0, 124.7, 124.2, 122.5, 122.0, 121.8, 118.5, 118.2, 118.0, 115.6, 114.8, 109.2, 109.0, 108.9, 107.8, 85.8, 85.4, 83.2, 82.7, 81.8, 63.2, 62.8, 62.7, 60.4, 60.3, 52.5, 52.3 (2C), 52.0, 51.8, 39.7, 38.7, 37.8, 37.6, 36.3, 35.7, 35.4, 35.3, 35.2. Due to atropisomerism, more than the expected 33 $^{13}$C NMR signals were observed.

FTIR (thin film) cm$^{-1}$: 3383 (br-s), 2933 (m), 2793 (w), 1653 (m), 1605 (s), 1487 (s), 1351 (w).

HRMS (DART) (m/z): calc'd for C$_{33}$H$_{39}$N$_6$[M+H]$^+$: 519.3231, found: 519.3230.

$[\alpha]_D^{24}$: −88 (c=0.21, $CH_2Cl_2$). Literature value: $[\alpha]_D^{27}$=−77.0 (c 1, $CHCl_3$) and: $[\alpha]_D^{27}$=−55.0 (c 0.8, $CHCl_3$, 83% ee), see J. J. Kodanko, L. E. Overman *Angew. Chem. Int. Ed.* 2003, 42, 2528. Literature value: $[\alpha]_D^{25}$=−69.5 (c 1, $CHCl_3$), see R. H. Snell, R. L. Woodward, M. C. Willis *Angew. Chem. Int. Ed.* 2011, 50, 9116.

TLC (9% methanol, 1% ammonium hydroxide in chloroform), Rf: 0.22 (UV, CAM).

M.p.: 156-158° C. ($CH_2Cl_2$).

TABLE S1

Comparison of $^1H$ NMR data for (—)-hodgkinsine B (3) with literature data from Kodanko, J. J.; Overman, L. E. *Angew. Chem. Int. Ed.* 2003, 42, 2528 ($CDCl_3$)

| Overman's Report (—)-hodgkinsine B (3) $^1H$ NMR, 500 MHz $CDCl_3$, −30° C. | This Work (—)-hodgkinsine B (3) $^1H$ NMR, 400 MHz $CDCl_3$, −30° C. |
|---|---|
| 7.37 (d, J = 7.8 Hz, 3H) | 7.36 (d, J = 7.5 Hz, 0.8H) |
| 7.23-7.16 (m, 8H) | 7.26-7.16 (m, 1.6H) |
| 7.13-7.06 (m, 10H) | 7.14-7.05 (m, 2H) |
| 6.99-6.95 (m, 6H) | 7.02-6.93 (m, 1H) |
| 6.83-6.78 (m, 8H) | 6.86-6.73 (m, 1.6H) |
| 6.64-6.55 (m, 9H) | 6.63 (app-d, J = 7.8 Hz, 0.6H) |
| — | 6.60 (app-d, J = 9.0 Hz, 0.4H*) |
| — | 6.56 (app-d, J = 7.8 Hz, 0.4H*) |
| 6.48 (d, J = 7.8 Hz, 3H) | 6.48 (d, J = 7.7 Hz, 0.6H) |
| 6.39 (t, J = 7.4 Hz, 2H) | 6.39 (t, J = 7.5 Hz, 0.4H*) |
| 6.13 (t, J = 7.6 Hz, 3H) | 6.13 (t, J = 7.6 Hz, 0.6H) |
| 5.84 (d, J = 7.4 Hz, 3H) | 5.82 (br-d, J = 7.6 Hz, 0.4H*) |
| 5.63 (d, J = 7.5 Hz, 3H) | 5.63 (d, J = 7.4 Hz, 0.6H) |
| 5.06-5.02 (m, 8H) | 5.09-5.04 (m, 1.6H) |
| 4.91 (br-s, 2H) | 4.89 (br-s, 0.4H) |
| 4.40 (d, J = 3.5 Hz, 3H) | 4.41 (d, J = 3.7 Hz, 0.6H) |
| 4.28 (s, 2H) | 4.32 (br-s, 0.4H) |
| 4.17-4.09 (m, 7H) | 4.24 (br-s, 0.4H) |
| — | 4.13 (app br-d, J = 16.5 Hz, NH, 1H) assignment of these resonances was supported by key HSQC correlations |
| 3.83 (s, 3H) | 3.84 (br-d, J = 3.8 Hz, NH, 0.6H) |
| 2.96 (t, J = 7.9 Hz, 3H) | 2.95 (t, J = 7.5 Hz, 0.6H) |
| 2.87-2.70 (m, 14H) | 2.91-2.62 (m, 3H) |
| 2.58-2.32 (m, 64H) | 2.61-2.21 (m, 13.2H) |
| — | 2.46 (app-s) |
| — | 2.42 (app-s) |
| — | 2.34 (app-s) |
| — | 2.32 (app-s) |
| 2.15-2.04 (m, 22H) | 2.19-2.01 (m, 3.2H) |
| 1.96-1.93 (m, 3H) | 1.93 (dd, J = 5.0, 12.1 Hz, 0.6H) |
| 1.84 (br-s, 2H) | 1.87-1.80 (m, 0.4H*) |
| 1.25-1.23 (m, 3H) | No signal observed 1.25-1.23 ppm in pure samples of (—)-hodgkinsine (3). |

*denotes the minor isomer

TABLE S2

Comparison of $^{13}C$ NMR data for (—)-hodgkinsine B (3) with literature data from Kodanko, J. J.; Overman, L. E. *Angew. Chem. Int. Ed.* 2003, 42, 2528 ($CDCl_3$)

| Overman's Report (—)-hodgkinsine B (3) $^{13}C$ NMR, 125 MHz $CDCl_3$, −30° C. | This Work (—)-hodgkinsine B (3) $^{13}C$ NMR, 100 MHz $CDCl_3$, −30° C. | Chemical Shift Difference $\Delta\delta = \delta$ (this work) − $\delta$ (Overman's Report) |
|---|---|---|
| 152.3 | 152.0 | −0.3 |
| 151.4 | 151.0 | −0.4 |
| 151.2 | 150.9 | −0.3 |
| 150.7 | 150.2 | −0.5 |
| 149.9 | 149.5 | −0.4 |
| 137.8 | — | No signal observed even with excellent signal-to-noise ratio. |
| 133.5 | 133.0 | −0.5 |
| 132.6 | 132.1 | −0.5 |
| 132.5 | 131.8 | −0.7 |
| 132.2 | 131.8 | −0.6 |
| 132.1 | 131.6 | −0.5 |
| 131.9 | 131.5 | −0.4 |
| 130.2 | — | No signal observed even with excellent signal-to-noise ratio. |
| 128.5 | 128.2 | −0.3 |
| 128.3 | 127.9 | −0.4 it is suspected that this signal corresponded to two resonances. |
| 128.3 | — | |
| 128.0 | 127.7 | −0.3 |
| 127.0 | 126.6 | −0.3 |
| 125.5 | 125.3 | −0.3 |
| 125.3 | 125.0 | −0.3 |
| 125.1 | 124.7 | −0.4 |
| 124.6 | 124.2 | −0.4 |
| 122.9 | 122.5 | −0.4 |
| 122.4 | 122.0 | −0.4 |
| — | 121.8 | −0.3 An unreported peak was observed at 122.1 ppm in the 13C spectrum of (—)-hodgkinsine B in Kodanko, J. J.; Overman, L. E. Angew. Chem. Int. Ed. 2003, 42, 2528 consistent with this observed data. |
| 118.9 | 118.5 | −0.4 |
| 118.6 | 118.2 | −0.4 |
| 118.3 | 118.0 | −0.3 |
| 115.8 | 115.6 | −0.2 |
| 115.2 | 114.8 | −0.4 |
| 109.5 | 109.2 | −0.3 |
| 109.3 | 108.9 | −0.4 |
| 108.1 | 107.8 | −0.3 |
| 86.2 | 85.8 | −0.4 |
| 85.8 | 85.4 | −0.4 |
| 83.6 | 83.2 | −0.4 |
| 83.1 | 82.7 | −0.4 |
| 82.2 | 81.8 | −0.4 |
| 63.7 | 63.2 | −0.5 |
| 63.6 | 63.2 | −0.4 |
| 63.3 | 62.8 | −0.5 |
| 63.0 | 62.7 | −0.3 |
| 60.8 | 60.4 | −0.4 |
| 60.7 | 60.3 | −0.4 |
| 58.9 | — | No signal observed even with excellent signal-to-noise ratio. |
| 52.9 | 52.5 | −0.4 |
| 52.7 | 52.3 | −0.4 |
| 52.6 | 52.3 | −0.3 |
| 52.4 | 52.0 | −0.4 |
| 52.1 | 51.8 | −0.3 |
| 40.0 | 39.7 | −0.3 |
| 39.2 | 38.7 | −0.5 |
| 38.2 | 37.8 | −0.4 |
| 38.0 | 37.6 | −0.4 |
| 36.6 | 36.3 | −0.3 |
| 36.1 | 35.7 | −0.4 |
| 35.8 | 35.4 | −0.4 |
| 35.7 | 35.3 | −0.4 |
| 35.6 | 35.2 | −0.4 |
| 21.6 | — | No signals observed at 21.6 and 18.9 ppm, which has an excellent signal-to-noise ratio. Notably, trimeric |
| 18.9 | — | |

TABLE S2-continued

Comparison of $^{13}$C NMR data for (—)-hodgkinsine B (3) with literature data from Kodanko, J. J.; Overman, L. E. Angew. Chem. Int. Ed. 2003, 42, 2528 (CDCl$_3$)

| Overman's Report (—)-hodgkinsine B (3) $^{13}$C NMR, 125 MHz CDCl$_3$, −30° C. | This Work (—)-hodgkinsine B (3) $^{13}$C NMR, 100 MHz CDCl$_3$, −30° C. | Chemical Shift Difference Δδ = δ (this work) − δ (Overman's Report) |
|---|---|---|
| | | cyclotryptamines do not have $^{13}$C signals below 30 ppm, see J. J. Kodanko; S. Hiebert; E. A. Peterson; L. Sung; L. E. Overman; V. de Moura Linck; G. C. Goerck; T. A. Amador; M. B. Leal; E. Elisabetsky J. Org. Chem. 2007, 72, 7909. |

Example 36: Synthesis of Diazene Dimer Sulfamate (−)-39

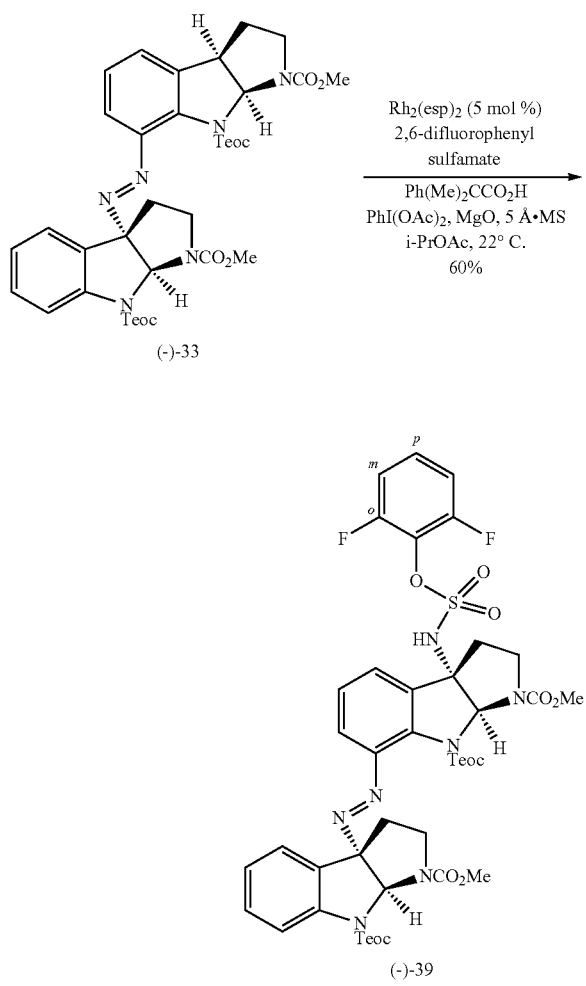

A round-bottom flask equipped with a stir bar was charged with crushed 5 Å molecular sieves (202 mg, 200 mg/mmol of (−)-33) and magnesium oxide (163 mg, 4.04 mmol, 4.00 equiv). The flask and its contents were flame-dried under vacuum for 5 min. The reaction vessel was allowed to cool to 22° C. and was then backfilled with argon. Solid 2,6-difluorophenyl sulfamate (267 mg, 1.31 mmol, 1.30 equiv), 2-methyl-2-phenylpropionic acid (83.7 mg, 510 μmol, 0.500 equiv), and Rh$_2$(esp)$_2$ (38.7 mg, 51.0 μmol, 5.00 mol %) were added sequentially. A solution of diazene dimer (−)-33 (757 mg, 1.01 mmol, 1 equiv) in isopropyl acetate (2.0 mL) was added via syringe at 22° C. and the mixture was allowed to stir for 5 min. A sample of (diacetoxyiodo)benzene (651 mg, 2.02 mmol, 2.00 equiv) was then added and the green suspension was allowed to stir vigorously at 22° C. After 14 h, the reaction mixture was filtered through a pad of Celite and the filter cake was rinsed with ethyl acetate (7 mL). The filtrate was concentrated under reduced pressure and the resulting residue was purified by flash column chromatography on silica gel (eluent: 5→20% acetone in hexanes) to afford diazene dimer sulfamate (−)-39 (578 mg, 59.7%) as a bright yellow amorphous gum. Structural assignments were made using additional information from gCOSY, gHSQC, and gHMBC experiments.

$^1$H NMR (400 MHz, CDCl$_3$, 25° C.): δ 7.77 (d, J=8.1 Hz, 1H, C$_7$H), 7.48 (d J=6.6 Hz, 1H, C$_4$·H), 7.33-7.27 (m, 2H, C$_6$H, C$_6$·H), 7.25-7.13 (m, 3H, C$_4$H, C$_5$·H, C$_p$H), 7.01 (app-t, J=7.2 Hz, 1H, C$_5$H), 6.96 (t, J=8.1 Hz, 2H, C$_m$H), 6.85 (br-s, 1H, C$_{8a}$H), 6.58 (br-s, 1H, C$_{8a'}$H). 6.16 (br-s, 1H, NH), 4.39-4.27 (m, 2H, C$_{10}$H$_2$ or C$_{10'}$H$_2$), 4.27-4.19 (m, 1H, C$_{10}$H$_a$ or C$_{10'}$H$_a$), 4.13-3.96 (m, 2H, C$_{10}$H$_b$ or C$_{10'}$H$_b$, C$_2$H$_a$), 3.83-3.72 (m, 1H, C$_{2'}$H$_a$), 3.72 (app-s, 6H, N$_1$CO$_2$CH$_3$, N$_{1'}$CO$_2$CH$_3$), 3.07 (td, J=5.2, 11.7 Hz, 1H, C$_{2'}$H$_b$), 2.90 (br-s, 1H, C$_3$H$_a$), 2.81 (br-s, 1H, C$_{2'}$H$_b$), 2.63-2.45 (m, 2H, C$_3$H$_a$, C$_3$·H$_b$), 2.35 (dd, J=5.1, 12.5 Hz, 1H, C$_3$H$_b$), 1.17-1.07 (m, 2H, C$_{11}$H$_2$ or C$_{11'}$H$_2$), 1.03-0.80 (m, 2H, C$_{11}$H$_2$ or C$_{11'}$H$_2$), 0.05 (s, 9H, (C$_{12}$H$_3$)$_3$ or (C$_{12'}$H$_3$)$_3$), −0.03 (s, 9H, (C$_{12}$H$_3$)$_3$ or (C$_{12'}$H$_3$)$_3$).

$^{13}$C NMR (100 MHz, CDCl$_3$, 25° C.): δ 156.0 (dd, J=3.3, 253.7 Hz, C$_o$), 155.4 (2C, N$_1$CO$_2$CH$_3$, N$_{1'}$CO$_2$CH$_3$), 154.6 (C$_9$ or C$_{9'}$), 153.7 (C$_9$ or C$_{9'}$), 143.5 (C$_{7a}$), 141.8 (C$_{7'}$), 140.3 (C$_{7a'}$), 133.1 (C$_{4a'}$), 130.0 (C$_6$), 129.0 (C$_{4a}$), 127.8 (t, J=9.2 Hz, C$_p$), 126.9 (t, J=15.6 Hz, C$_i$), 126.2 (C$_{5'}$), 125.5 (C$_4$), 125.4 (C$_{4'}$), 123.5 (C$_5$), 119.7 (C$_{6'}$), 116.3 (C$_7$), 112.7 (dd, J=4.4, 17.7 Hz, Cm), 88.9 (C$_{3a}$), 81.6 (C$_{8a'}$), 79.7 (C$_{8a}$), 71.6 (C$_{3a'}$), 65.2 (C$_{10}$ or C$_{10'}$), 64.5 (C$_{10}$ or C$_{10'}$), 52.8 (2C, N$_1$CO$_2$CH$_3$, N$_{1'}$CO$_2$CH$_3$), 46.1 (C$_2$), 45.0 (C$_{2'}$), 35.6 (C$_3$), 33.4 (C$_{3'}$), 17.9 (C$_{11}$ or C$_{11'}$), 17.7 (C$_{11}$ or C$_{11'}$), −1.4 (C$_{12}$ or C$_{12'}$), −1.5 (C$_{12}$ or C$_{12'}$).

$^{19}$F NMR (282 MHz, CDCl$_3$, 25° C.): δ−125.0 (s, C$_6$H$_3$F$_2$).

FTIR (thin film) cm$^{-1}$: 3162 (s), 2955 (s), 1717 (s), 1457 (m), 862 (w), 733 (w).

HRMS (ESI) (m/z): calc'd for C$_{42}$H$_{53}$F$_2$N$_7$NaO$_{11}$SSi$_2$ [M+Na]$^+$: 980.2923, found 980.2917.

[α]$_D^{24}$: −76 (c=0.72, CH$_2$Cl$_2$).

TLC (50% ethyl acetate in hexanes), Rf: 0.28 (UV, CAM).

Example 37: Synthesis of Diazene Dimer Mixed Sulfamide (−)-40

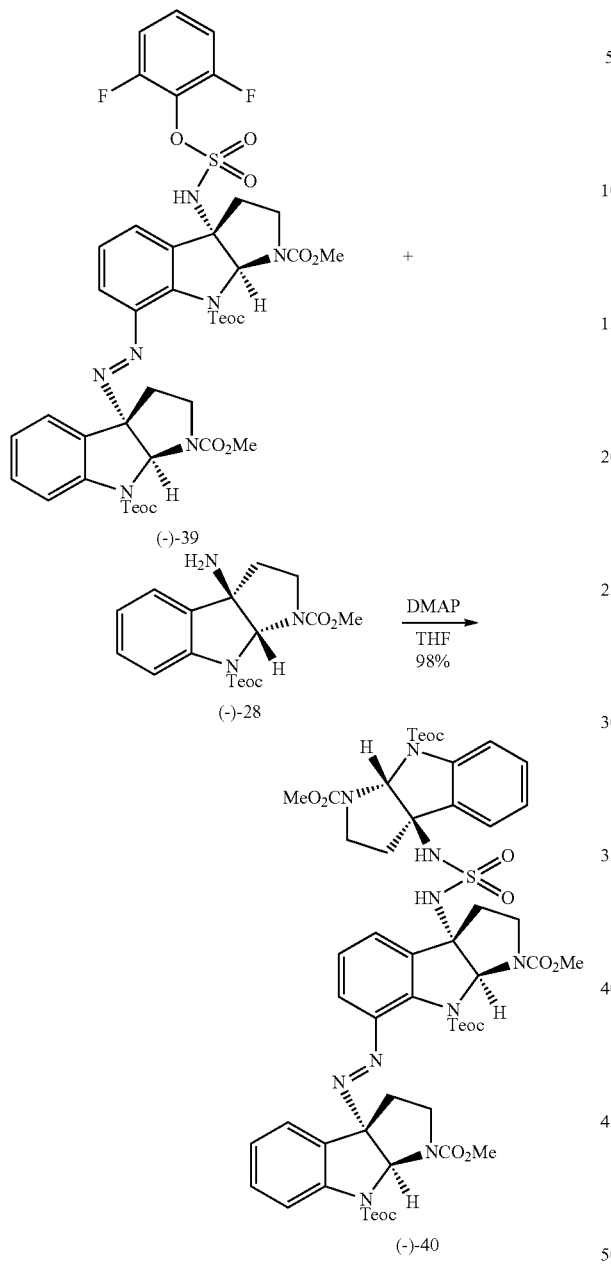

A sample of 4-(dimethylamino)pyridine (109 mg, 891 μmol, 2.20 equiv) was added to a solution of diazene dimer sulfamate (−)-39 (388 mg, 405 μmol, 1 equiv) and amine (−)-28 (168 mg, 446 μmol, 1.10 equiv) in tetrahydrofuran (4.10 mL) at 22° C. After 24 h, the bright yellow solution was concentrated under reduced pressure. The resulting residue was purified by flash column chromatography on silica gel (eluent: 20%→70% ethyl acetate in hexanes) to afford diazene dimer mixed sulfamide (−)-40 (480 mg, 98.3%) as a bright yellow amorphous gum. As a result of the slow conformational equilibration at ambient temperature, NMR spectra were collected at elevated temperature.

$^1$H NMR (400 MHz, C$_6$D$_6$, 70° C.): δ 8.18 (d, J=8.0 Hz, 1H), 7.98 (d, J=8.1 Hz, 1H), 7.31 (dd, J=1.1, 8.0 Hz, 1H), 7.20 (s, 1H), 7.19-7.12 (m, 5H), 6.96 (app-t, J=7.7 Hz, 1H), 6.91 (td, J=0.9, 7.5 Hz, 1H), 6.86 (td, J=0.9, 7.5 Hz, 1H), 6.81 (s, 1H), 6.69 (s, 1H), 5.38 (br-s, 1H), 5.25 (br-s, 1H), 4.49 (td, J=6.2, 10.9 Hz, 1H), 4.45-4.32 (m, 4H), 4.23 (td, J=6.4, 10.8 Hz, 1H), 3.98 (dd, J=7.9, 11.2 Hz, 1H), 3.70-3.60 (m, 5H), 3.58 (s, 3H), 3.53 (s, 3H), 2.98 (td, J=5.3, 11.7 Hz, 1H), 2.66-2.45 (m, 3H), 2.19 (dd, J=5.2, 12.5 Hz, 1H), 2.11-1.90 (m, 4H), 1.19-0.98 (m, 6H), −0.01 (app-d, J=2.9 Hz, 18H), −0.03 (s, 9H).

$^{13}$C NMR (100 MHz, C$_6$D$_6$, 70° C.): δ 156.0, 155.3, 155.2, 154.9, 154.4, 153.9, 144.6, 144.1, 142.8, 141.1, 134.6, 130.9, 130.5, 130.3, 130.0, 126.1, 125.8, 125.3, 124.6, 123.9, 123.6, 119.4, 117.6, 116.8, 89.9, 82.2, 80.2 (2C), 71.4, 71.3, 65.5, 64.8, 64.3, 52.4 (3C), 46.1, 45.0, 44.7, 37.2, 36.7, 36.2, 18.2 (2C), 18.1, −1.5 (3C).

FTIR (thin film) cm$^{-1}$: 3228 (m), 2955 (m), 2896 (w), 1715 (s), 1402 (m).

HRMS (ESI) (m/z): calc'd for C$_{54}$H$_{76}$N$_{10}$NaO$_{14}$SSi$_3$ [M+Na]$^+$: 1227.4463, found: 1227.4462.

[α]$_D^{24}$: −83 (c=0.64, CH$_2$Cl$_2$).

TLC (60% ethyl acetate in hexanes), Rf: 0.28 (UV, CAM).

Example 38: Synthesis of Bis-Diazene Trimer (−)-41

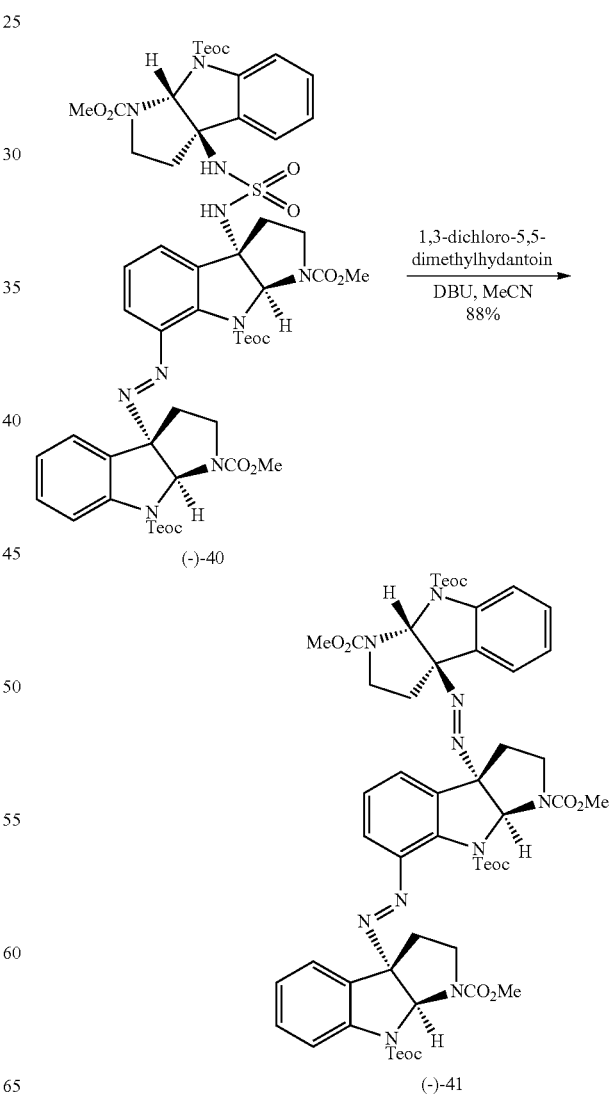

To a solution of diazene dimer mixed sulfamide (−)-40 (480 mg, 398 μmol, 1 equiv) in acetonitrile (20.0 mL) at 22° C. was added via syringe 1,8-diazabicyclo[5.4.0]undec-7-ene (DBU, 178 μL, 1.19 mmol, 3.00 equiv) followed immediately by 1,3-dichloro-5,5-dimethylhydantoin (196 mg, 995 μmol, 2.50 equiv) in a single portion. After 1 h, the mixture was diluted with dichloromethane (20 mL) and was washed with a saturated aqueous potassium carbonate-water solution (1:1, 30 mL). The aqueous layer was extracted with dichloromethane (3×30 mL). The combined organic extracts were dried over anhydrous sodium sulfate, were filtered, and were concentrated under reduced pressure. The resulting residue was purified by flash column chromatography on silica gel (eluent: 20→50% ethyl acetate in hexanes) to afford bis-diazene trimer (−)-41 (397 mg, 87.5%) as a bright yellow amorphous gum. As a result of the slow conformational equilibration at ambient temperature, NMR spectra were collected at elevated temperature.

$^1$H NMR (400 MHz, CD$_3$CN, 50° C.): δ 7.77 (d, J=8.0 Hz, 1H), 7.70 (d, J=8.0 Hz, 1H), 7.42-7.19 (m, 6H), 7.12 (app-t, J=6.4 Hz, 1H), 7.08 (app-t, J=7.5 Hz, 1H), 7.02 (app-t, J=7.4 Hz, 1H), 6.73 (s, 1H), 6.46 (s, 1H), 6.39 (s, 1H), 4.38-4.20 (m, 4H), 4.20-4.08 (m, 1H), 4.01 (br-dd, J=7.4, 10.3 Hz, 1H), 3.93-3.76 (m, 3H), 3.69 (app-s, 6H), 3.65 (s, 3H), 3.08-2.89 (m, 2H), 2.57 (dd, J=5.1, 12.5 Hz, 1H), 2.53-2.38 (m, 3H), 2.37-2.20 (m, 2H), 1.17-1.03 (m, 4H), 0.90-0.67 (m, 2H), 0.07 (app-s, 18H), −0.03 (s, 9H).

$^{13}$C NMR (100 MHz, CD$_3$CN, 50° C.): δ 156.2, 156.0 (2C), 155.3, 154.4, 154.3, 144.6, 144.5, 143.1, 141.3, 134.8, 131.2, 131.1, 130.6, 130.1, 127.7, 127.1, 126.6, 125.9, 124.6, 124.5, 119.8, 117.2, 117.0, 90.2, 89.6, 89.3, 81.8, 79.7, 79.6, 65.7, 65.2, 65.1, 53.3 (2C), 53.2, 46.9, 46.6 (2C), 36.9, 36.0, 33.6, 18.6 (3C), −1.2 (2C), −1.3.

FTIR (thin film) cm$^{-1}$: 2954 (m), 2896 (w), 1713 (s), 1603 (w), 1401 (m), 1252 (w).

HRMS (ESI) (m/z): calc'd for C$_{54}$H$_{74}$N$_{10}$NaO$_{12}$Si$_3$ [M+Na]$^+$: 1161.4688, found: 1161.4673.

[α]$_D^{24}$: −86 (c=0.61, CH$_2$Cl$_2$).

TLC (50% ethyl acetate in hexanes), Rf: 0.23 (UV, CAM).

Example 39: Synthesis of Mono-Diazene Trimer (−)-S7

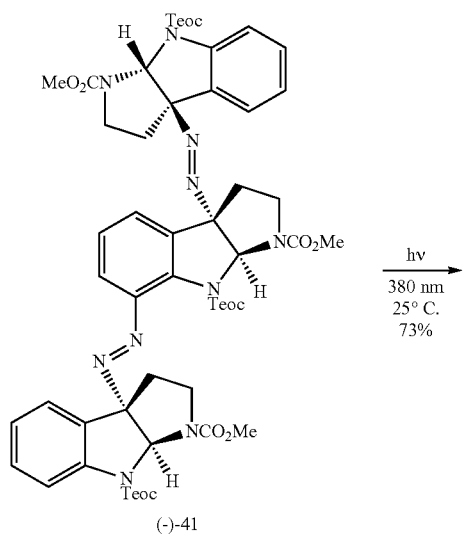

(−)-41

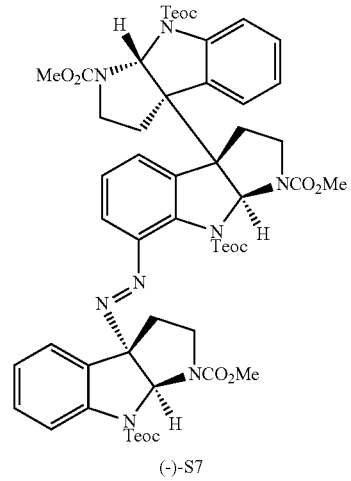

(−)-S7

A solution of bis-diazene trimer (−)-41 (397 mg, 348 μmol, 1 equiv) in dichloromethane (30 mL) was concentrated under reduced pressure in a 1 L round-bottom flask to provide a thin film of diazene coating the flask. The flask was backfilled with argon and irradiated in a Rayonet photoreactor equipped with 16 radially distributed (r=12.7 cm) 25 W lamps (λ=380 nm) at 25° C. After 15 h, the lamps were turned off and the resulting residue was purified by flash column chromatography on silica gel (eluent: 20→60% ethyl acetate in hexanes) to afford mono-diazene trimer (−)-S7 (282 mg, 72.9%) as a bright yellow amorphous gum. As a result of the slow conformational equilibration at ambient temperature, NMR spectra were collected at elevated temperature.

$^1$H NMR (400 MHz, CD$_3$CN, 60° C.): δ 7.75 (d, J=8.0 Hz, 1H), 7.66 (d, J=8.0 Hz, 1H, 7.38-7.27 (m, 2H), 7.27-7.15 (m, 4H), 7.06 (app-t, J=7.5 Hz, 1H), 6.77 (app-t, J=7.8 Hz, 1H), 6.69 (s, 1H), 6.41 (br-d, J=5.8 Hz, 1H), 6.23 (s, 1H), 6.08 (s, 1H), 4.39-4.28 (m, 3H), 4.21 (td, J=7.0, 10.5 Hz, 1H), 3.99 (dd, J=7.8, 11.1 Hz, 1H), 3.94-3.85 (m, 1H), 3.82 (dd, J=7.7, 11.0 Hz, 1H), 3.75 (dd, J=7.9, 10.9 Hz, 1H), 3.72-3.62 (m, 10H), 3.01 (td, J=5.6, 11.6 Hz, 1H), 2.75 (app-dtd, J=5.5, 11.5, 14.1 Hz, 2H), 2.47 (td, J=7.8, 12.1 Hz, 1H), 2.35 (app-ddd, J=7.0, 12.2, 13.5 Hz, 3H), 2.28-2.16 (m, 2H), 1.18-1.04 (m, 4H), 0.94-0.81 (m, 2H), 0.10 (s, 9H), 0.07 (s, 9H), 0.06 (s, 9H).

$^{13}$C NMR (100 MHz, CD$_3$CN, 60° C.): δ 156.4, 155.9, 155.8, 154.6, 154.4, 154.3, 144.8, 144.5, 143.0, 141.2, 137.3, 132.2, 131.1, 130.8, 130.4, 127.0, 126.9 (2C), 125.3, 124.8, 124.6, 119.2, 117.3, 117.1, 90.2, 81.7, 80.3, 79.9, 65.8, 65.4, 65.3, 62.7, 61.8, 53.4 (2C), 53.3, 47.1, 46.9, 46.5, 37.2, 36.2, 34.2, 18.9, 18.8, 18.6, −1.1 (3C).

FTIR (thin film) cm$^{-1}$: 2954 (m), 2896 (w), 1717 (s), 1448 (m), 1400 (m).

HRMS (ESI) (m/z): calc'd for C$_{54}$H$_{74}$N$_8$NaO$_{12}$Si$_3$ [M+Na]$^+$: 1133.4626, found: 1133.4601.

[α]$_D^{24}$: −162 (c=0.54, CH$_2$Cl$_2$).

TLC (50% ethyl acetate in hexanes), Rf: 0.19 (UV, CAM).

Example 40: Synthesis of Cyclotryptamine Trimer (−)-42

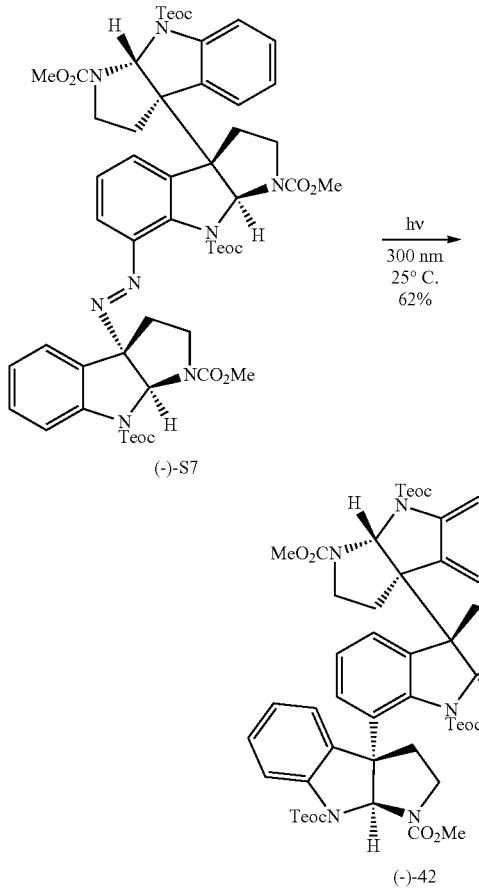

A solution of mono-diazene trimer (−)-S7 (141 mg, 127 μmol, 1 equiv) in dichloromethane (15 mL) was concentrated under reduced pressure in a 2 L round-bottom flask to provide a thin film of diazene coating the flask. The flask was back filled with argon and irradiated in a Rayonet photoreactor equipped with 16 radially distributed (r=12.7 cm) 25 W lamps (λ=300 nm) at 25° C. After 15 h, the lamps were turned off and the resulting residue was purified by flash column chromatography on silica gel (eluent: 30→40% ethyl acetate in hexanes) to afford cyclotryptamine trimer (−)-42 (84.9 mg, 61.7%) as an off-white solid. As a result of the slow conformational equilibration at ambient temperature, NMR spectra were collected at elevated temperature.

$^1$H NMR (400 MHz, CD$_3$CN, 60° C.): δ 7.74 (d, J=8.0 Hz, 1H), 7.70 (d, J=8.1 Hz, 1H), 7.29 (app-dd, J=7.2, 14.2 Hz, 2H), 7.22 (app-t, J=7.8 Hz, 1H), 7.13-7.00 (m, 2H), 6.91 (d, J=7.5 Hz, 1H), 6.78 (d, J=7.5 Hz, 1H), 6.69 (s, 1H), 6.48 (d, J=7.9 Hz, 1H), 6.40 (br-d, J=5.8 Hz, 1H), 6.36 (s, 1H), 6.04 (s, 1H), 4.50-4.34 (m, 2H), 4.33-4.22 (m, 2H), 3.94 (td, J=6.0, 11.4 Hz, 1H), 3.80 (dd, J=7.4, 11.1 Hz, 1H), 3.76-3.59 (m, 3H), 3.69 (s, 3H), 3.67 (s, 3H), 3.62 (s, 3H), 2.95 (td, J=8.3, 11.8 Hz, 1H), 2.79-2.36 (m, 3H), 2.35-2.15 (m, 3H), 2.09 (td, J=8.5, 11.9 Hz, 1H), 1.98-1.91 (m, 1H), 1.25-1.06 (m, 4H), 1.04-0.81 (m, 2H), 0.12 (s, 9H), 0.08 (s, 9H), 0.06 (s, 9H).

$^{13}$C NMR (100 MHz, CD$_3$CN, 60° C.): δ 156.2, 156.0, 155.8, 155.0 (2C), 154.4, 144.5, 144.4, 142.7, 139.5, 138.2, 134.8, 133.0, 132.3, 130.4, 129.8, 127.4, 125.5, 125.4, 125.3, 125.0, 124.3, 117.6, 117.2, 83.0, 80.7, 80.2, 66.1, 65.4, 65.0, 61.7 (2C), 61.5, 53.4, 53.2, 53.1, 46.9 (2C), 46.1, 35.7, 34.3, 33.4, 19.0 (2C), 18.7, −1.0 (2C), −1.1.

FTIR (thin film) cm$^{-1}$: 2954 (m), 2896 (w), 1716 (s), 1447 (w), 1400 (m).

HRMS (ESI) (m/z): calc'd for C$_{54}$H$_{74}$N$_6$NaO$_{12}$Si$_3$ [M+Na]$^+$: 1105.4565, found: 1105.4539.

[α]$_D^{24}$: −35 (c=0.57, CH$_2$Cl$_2$)

TLC (50% ethyl acetate in hexanes), Rf: 0.28 (UV, CAM).

M.p.: 108-110° C. (CH$_2$Cl$_2$).

Example 41: Synthesis of Cyclotryptamine Trimer (+)-S8

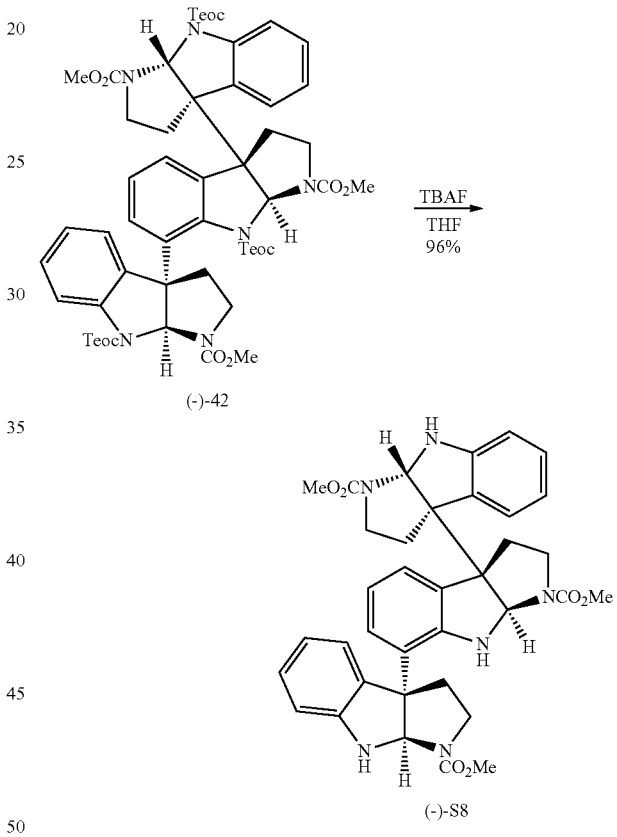

Tetrabutylammonium fluoride (1M in tetrahydrofuran, 1.80 mL, 1.80 mmol, 15.0 equiv) was added to cyclotryptamine trimer (−)-42 (130 mg, 120 μmol) at 22° C. under an atmosphere of argon. After 1 h, the reaction mixture was diluted with ethyl acetate (2 mL) and washed with a saturated aqueous sodium carbonate solution (3×3 mL). The aqueous layer was extracted with dichloromethane (3×3 mL). The combined organic extracts were dried over anhydrous sodium sulfate, were filtered, and were concentrated under reduced pressure. The resulting yellow-green residue was purified by flash column chromatography on silica gel (eluent: 20→40% acetone in hexanes) to yield cyclotryptamine trimer (+)-S8 (75.1 mg, 96.2%) as a pale yellow solid.

$^1$H NMR (400 MHz, DMSO-d$_6$, 90° C.): δ 7.11 (d, J=7.7 Hz, 1H), 7.00 (app-td, J=0.9, 7.6 Hz, 1H), 6.95 (d, J=7.3 Hz, 1H), 6.86 (app-t, J=7.5 Hz, 1H), 6.77 (d, J=6.9 Hz, 1H), 6.70-6.59 (m, 3H), 6.42 (d, J=7.8 Hz, 1H), 6.27 (app-t, J=7.3 Hz, 1H), 6.22-6.13 (m, 2H), 5.89 (s, 1H), 5.54 (s, 1H), 5.30 (s, 1H), 5.27 (s, 1H), 5.17 (s, 1H), 3.75-3.68 (m, 4H), 3.65 (s, 3H), 3.63 (s, 3H), 3.61-3.54 (m, 2H), 3.01-2.92 (m, 1H), 2.88 (td, J=7.4, 10.3 Hz, 1H), 2.78 (td, J=6.1, 10.9 Hz, 1H), 2.62-2.52 (m, 1H), 2.42 (br-ddd, J=2.0, 6.7, 8.0 Hz, 1H), 2.33-2.20 (m, 3H), 2.07 (dd, J=5.9, 12.5 Hz, 1H). Acquisition of NMR spectra in DMSO-d6 at 90° C. resulted in simplification of the spectra by convergence of the signals for some of the atropisomers. However, gradual sample decomposition with heating during extended acquisition time was observed as previously noted, see: S. M. Canham; B. D. Hafensteiner; A. D. Lebsack; T. L. May-Dracka; S. Nam; B. A. Stearns; L. E. Overman Tetrahedron 2015, 71, 6424. Acquisition of NMR spectra at low temperature (−80° C. to 0° C.) did not yield more informative NMR spectra.

$^1$H NMR (400 MHz, $CD_3CN$, 25° C.): δ 7.25-7.10 (m, 1H), 7.03 (br-t, J=8.2 Hz, 1H), 6.99-6.90 (m, 1H), 6.90-6.81 (m, 1H), 6.81-6.71 (m, 2H), 6.71-6.57 (m, 2H), 6.48-6.31 (m, 1H), 6.30-6.00 (m, 2H), 5.99-5.70 (m, 1H), 5.63-5.37 (m, 1H), 5.32-5.23 (m, 1H), 5.23-5.11 (m, 2H), 5.11-5.00 (m, 1H), 3.77 (app-d, J=8.0 Hz, 2H), 3.74-3.49 (m, 10H), 2.99-2.80 (m, 2H), 2.80-2.66 (m, 1H), 2.65-2.37 (m, 2H), 2.37-2.22 (m, 3H), 2.17-2.02 (m, 1H).

$^{13}$C NMR (100 MHz, $CD_3CN$, 25° C.): δ 155.9, 155.8, 155.7, 155.3, 155.1, 154.9, 151.0, 150.8, 150.8, 149.4, 149.0, 148.9, 148.8, 131.1, 131.0, 130.7, 130.6, 129.6 (2C), 129.4, 129.3, 129.2, 129.1, 127.2, 127.1, 126.9, 124.9, 124.7, 123.7, 123.6, 121.0, 120.6, 120.5, 119.3, 119.2, 118.7, 110.6, 110.3, 109.6, 109.5, 109.4, 109.3, 80.5, 80.3, 79.9, 79.6, 78.5, 78.0, 77.7, 77.3, 63.3, 62.5, 62.3, 62.2, 61.4, 60.7, 59.6, 52.9, 52.8, 52.7, 46.3, 46.2, 46.0, 45.9, 45.8, 37.1, 36.9, 36.6, 34.5, 34.2, 33.3, 33.2. More than the expected 36 $^{13}$C resonances were observed due to presence of multiple atropisomers. All observed resonances are listed.

FTIR (thin film) $cm^{-1}$: 3335 (br-m), 2955 (m), 1700 (s), 1608 (m), 1457 (s).

HRMS (ESI) (m/z): calc'd for $C_{36}H_{39}N_6O_6$ [M+H]$^+$: 651.2926, found: 651.2916.

$[α]_D^{24}$: +187 (c=0.54, $CH_2Cl_2$).

TLC (70% ethyl acetate in hexanes), Rf: 0.10 (UV, CAM).

M.p.: 153-155° C. ($CH_2Cl_2$).

Example 42: Synthesis of (−)-Hodgkinsine (4)

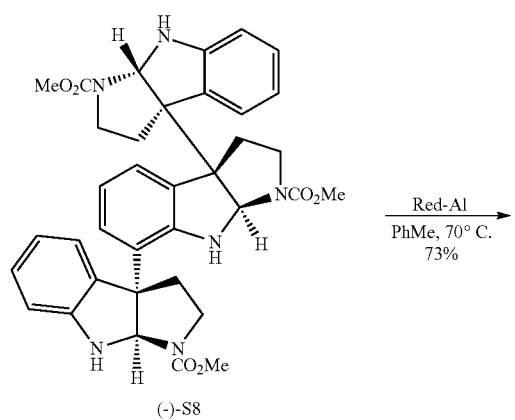

(−)-S8

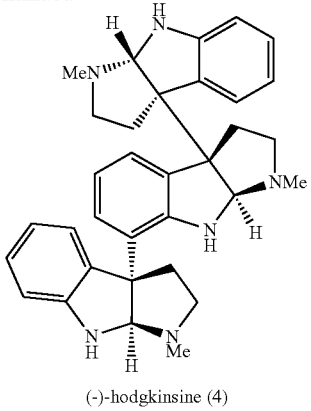

(−)-hodgkinsine (4)

Cyclotryptamine trimer (+)-S8 (49.9 mg, 76.7 μmol, 1 equiv) was azeotropically dried from anhydrous benzene (3×1 mL) and the residue was dissolved in toluene (3.8 mL). A solution of sodium bis(2-methoxyethoxy)aluminum hydride in toluene (Red-Al, 70% wt, 300 □L, 1.04 mmol, 13.5 equiv) was added via syringe at 22° C. The reaction flask was fitted with a reflux condenser and was immerse in a pre-heated 70° C. oil bath. After 1 h, the reaction mixture was allowed to cool to 22° C., and the excess reducing reagent was quenched by the addition of a saturated aqueous sodium sulfate solution (100 μL). The resulting heterogeneous mixture was stirred for 5 min and then solid anhydrous sodium sulfate was added. The mixture was filtered through a plug of Celite and the filter cake was rinsed with ethyl acetate (15 mL). The filtrate was concentrated under reduced pressure and the resulting residue was purified by flash column chromatography on silica gel (eluent: 3.6% methanol, 0.4% ammonium hydroxide→7.2% methanol, 0.5% ammonium hydroxide in chloroform) to afford (−)-hodgkinsine (4), 28.9 mg, 72.6%) as a white solid. As a result of the slow conformational equilibration at ambient temperature, NMR spectra were collected at −30° C.

$^1$H NMR (400 MHz, $CDCl_3$, −30° C.): δ 7.36 (d, J=7.5 Hz, 1H), 7.22 (app-d, J=7.2 Hz, 2H), 7.18 (d, J=7.4 Hz, 1H), 7.14-7.03 (m, 4H), 6.96 (d, J=7.8 Hz, 1H), 6.89 (t, J=7.6 Hz, 1H), 6.85-6.75 (m, 3H), 6.74-6.58 (m, 3H), 6.50 (d, J=7.8 Hz, 1H), 6.44 (d, J=7.8 Hz, 1H), 6.17 (app-dt, J=15.1, 7.5 Hz, 2H), 5.54 (d, J=7.4 Hz, 1H), 5.42 (br-d, J=6.1 Hz, 1H), 5.07 (br-s, 2H), 4.94 (d, J=3.9 Hz, 1H), 4.50 (s, 1H), 4.27 (br-s, 2H), 4.10 (s, 1H), 4.04 (d, J=4.0 Hz, 1H), 3.74 (d, J=3.7 Hz, 1H), 3.13-2.96 (m, 4H), 2.95-2.80 (m, 4H), 2.63-2.24 (m, 28H), 2.14-1.96 (m, 4H), 1.93-1.80 (m, 2H).

$^{13}$C NMR (100 MHz, $CDCl_3$, −30° C.): δ 152.2, 151.1, 150.9, 150.8, 149.5, 132.7, 132.3, 132.2, 131.7, 131.6, 128.3, 127.9, 127.6, 126.7, 126.6, 126.2, 125.2, 124.3, 124.1, 122.5, 122.1, 118.6, 118.4, 118.2, 117.5, 116.9, 115.3, 109.2, 109.1, 108.5, 108.3, 87.1, 86.7, 82.8, 82.4, 82.2, 82.0, 63.6, 63.3, 63.0, 62.9, 60.4, 60.2, 52.5, 52.2, 51.9, 38.7, 38.3, 38.0, 36.9, 36.1, 35.6, 35.3 (2C), 34.9.

FTIR (thin film) $cm^{-1}$: 3379 (br-m), 2936 (s), 1605 (m), 1486 (s), 1350 (w).

HRMS (DART) (m/z): calc'd for $C_{33}H_{39}N_6$ [M+H]$^+$: 519.3231, found: 519.3254.

$[α]_D^{24}$: −39 (c=0.38, $CHCl_3$). Literature value: $[α]_D^{24}$=−33.6 (c 1, $CHCl_3$), see L. Verotta, T. Pilati, M. Tatò, E. Elisabetsky, T. A. Amador, D. S. Nunes J. Nat. Prod. 1998, 61, 392.

TLC (9% methanol, 1% ammonium hydroxide in chloroform), Rf: 0.10 (UV, CAM).

M.p.: 124-126° C. ($CH_2Cl_2$). Literature value: 128° C., see L. Verotta, T. Pilati, M. Tatò, E. Elisabetsky, T. A. Amador, D. S. Nunes J. Nat. Prod. 1998, 61, 392.

TABLE S3

Comparison of $^1$H NMR data for (—)-hodgkinsine (4) with literature data from Verotta, L.; Pilati, T.; Tatò, M.; Elisabetsky, E.; Amador, T. A.; Nunes, D. S. *J. Nat. Prod*. 1998, 61, 392.

| Assignment | Verotta's Isolation Report (—)-hodgkinsine (4) $^1$H NMR, 600 MHz CDCl$_3$, −30° C. | This Work (—)-hodgkinsine (4) $^1$H NMR, 400 MHz CDCl$_3$, −30° C. |
|---|---|---|
| C4" | 7.37* (d, J = 7.9 Hz, 1H) | 7.36 (d, J = 7.5 Hz, 1H) |
| C4' | 7.23 (d, J = 7.7 Hz, 1H) | 7.22 (app-d, J = 7.2 Hz, 2H) |
| C4 | 7.22 (d, J = 7.8 Hz, 1H) | — |
| C4 | 7.17* (d, J = 7.8 Hz, 1H) | 7.18 (d, J = 7.4 Hz, 1H) |
| C6' | 7.13 (d, J = 7.9 Hz, 1H) | 7.14-7.03 (m, 4H) |
| C6" | 7.11* (t, J = 7.3 Hz, 1H) | — |
| C6 | 7.10 (t, J = 7.3 Hz, 1H) | — |
| C6 | 7.08* (t, J = 7.3 Hz, 1H) | — |
| C6' | 6.98* (d, J = 7.9 Hz, 1H) | 6.96 (d, J = 7.8 Hz, 1H) |
| C6" | 6.89 (t, J = 7.3 Hz, 1H) | 6.89 (t, J = 7.6 Hz, 1H) |
| C5 | 6.84 (t, J = 7.2 Hz, 1H) | 6.85-6.75 (m, 3H) |
| C5" | 6.81* (t, J = 7.3 Hz, 1H) | — |
| C5 | 6.79* (t, J = 7.2 Hz, 1H) | — |
| C5' | 6.70 (t, J = 7.4 Hz, 1H) | 6.74-6.58 (m, 3H) |
| C7 | 6.65 (d, J = 7.7 Hz, 1H) | — |
| C7 | 6.62* (d, J = 7.7 Hz, 1H) | — |
| C7" | 6.51 (d, J = 7.9 Hz, 1H) | 6.50 (d, J = 7.8 Hz, 1H) |
| C7" | 6.46* (d, J = 7.9 Hz, 1H) | 6.44 (d, J = 7.8 Hz, 1H) |
| C5" | 6.20 (t, J = 7.3 Hz, 1H) | 6.17 (app-dt, J = 15.1, 7.5 Hz, 2H) |
| C5' | 6.16* (t, J = 7.4 Hz, 1H) | — |
| C4' | 5.57* (d, J = 7.7 Hz, 1H) | 5.54 (d, J = 7.4 Hz, 1H) |
| C4" | 5.44 (d, J = 7.9 Hz, 1H) | 5.42 (br-d, J = 6.1 Hz, 1H) |
| C8a' | 5.08 (br-s, J = 6.7 Hz, 1H) | 5.07 (br-s, 2H) |
| C8a" | 5.08* (br-s, 1H) | — |
| C8a" | 5.08 (br-s, 1H) | — |
| C8a | 4.97 (br-s, J = 4.8 Hz, 1H) | 4.94 (d, J = 3.9 Hz, 1H) |
| C8a | 4.52* (br-s, J = 6.5 Hz, 1H) | 4.50 (s, 1H) |
| N—H | 4.25 (br-s, J = 5.0 Hz, 1H) | 4.27 (br-s, 2H) |
| C8a' | 4.23* (br-s, J = 6.7 Hz, 1H) | — |
| N—H | 4.20 (br-s, 1H) | — |
| N—H | 4.15* (br-s, 1H) | 4.10 (s, 1H) |
| N—H | 4.12 (br-s, J = 6.5 Hz, 1H) | — |
| N—H | 4.04* (br-s, J = 5.7 Hz, 1H) | 4.04 (d, J = 4.0 Hz, 1H) |
| N—H | 3.72* (br-s, J = 5.0 Hz, 1H) | 3.74 (d, J = 3.7 Hz, 1H) |
| C3"β | 3.04 (dd, J = 12.6 Hz, 1H) | 3.13-2.96 (m, 4H) |
| C3"β | 3.01* (dd, J = 11.0 Hz, 1H) | — |
| C2"β | 3.01* (m, 1H) | — |
| C2'β | 2.92* (m, 1H) | 2.95-2.80 (m, 4H) |
| C2"β | 2.89 (m, 1H) | — |
| C2β | 2.86 (m, 1H) | — |
| C2β | 2.86* (m, 1H) | — |
| C2'β | 2.86 (m, 1H) | — |
| C3'β | 2.59* (m, J = 11.4 Hz, 1H) | 2.63-2.24 (m, 28H) |
| C2"α | 2.56* (m, 1H) | — |
| C3'β | 2.53 (m, J = 12.6 Hz, 1H) | — |
| C2"α | 2.51 (m, 1H) | — |
| N—CH$_3$ | 2.46* (s, 3H) | — |
| N—CH$_3$ | 2.45 (s, 3H) | — |
| C3β | 2.44* (m, 1H) | — |
| C3β | 2.43 (m, 1H) | — |
| N—CH$_3$ | 2.42 (s, 3H) | — |
| N—CH$_3$ | 2.38 (s, 3H) | — |
| C2α | 2.37 (m, 1H) | — |
| C2α | 2.36* (m, 1H) | — |
| C2'α | 2.36 (m, 1H) | — |
| C2'α | 2.32* (m, 1H) | — |
| N—CH$_3$ | 2.31* (s, 3H) | — |
| N—CH$_3$ | 2.20* (s, 3H) | — |
| C3α | 2.13 (m, 1H) | 2.14-1.96 (m, 4H) |
| C3α | 2.11* (m, 1H) | — |
| C3'α | 2.07* (dd, J = 12.6, 5.5 Hz, 1H) | — |
| C3'α | 2.01 (dd, J = 12.6, 5.5 Hz, 1H) | — |
| C3"α | 1.91* (dd, J = 12.6, 5.5 Hz, 1H) | 1.93-1.80 (m, 2H) |
| C3"α | 1.87 (dd, J = 12.6, 5.5 Hz, 1H) | — |

*denotes minor conformer

TABLE S4

Comparison of $^{13}$C NMR data for (—)-hodgkinsine (4) with literature data from Verotta, L.; Pilati, T.; Tatò, M.; Elisabetsky, E.; Amador, T. A.; Nunes, D. S. *J. Nat. Prod.* 1998, 61, 392.

| Assignment | Verotta's Isolation Report (—)-hodgkinsine (4) $^{13}$C NMR, 200 MHz CDCl$_3$, −30° C. | This Work (—)-hodgkinsine (4) $^{13}$C NMR, 125 MHz CDCl$_3$, −30° C. | Chemical Shift Difference Δδ = δ (this work) − δ (Verotta Report) |
|---|---|---|---|
| C7a" | 152.1* | 152.2 | 0.1 |
| C7a" | 151.1 | 151.1 | 0 |
| C7a' | 150.8 | 150.9 | 0.1 |
| C7a | 150.8 | 150.8 | 0 |
| C7a | 150.8* | — | N/A |
| C7a' | 149.5* | 149.5 | 0 |
| C4a" | 132.7* | 132.7 | 0 |
| C4a' | 132.3 | 132.3 | 0 |
| C4a' | 132.3* | 132.2 | −0.1 |
| C4a" | 131.7 | 131.7 | 0 |
| C4a | 131.7 | 131.6 | −0.1 |
| C4a | 131.6* | — | N/A |
| C6 | 127.9 | 128.3 | 0.4 |
| C6" | 127.9* | 127.9 | 0 |
| C6 | 127.8* | — | N/A |
| C6" | 127.4 | 127.6 | 0.2 |
| C4 | 126.4 | 126.7 | 0.3 |
| C4 | 126.3* | 126.6 | 0.3 |
| C6' | 126.0 | 126.2 | 0.2 |
| C6' | 125.0* | 125.2 | 0.2 |
| C4" | 124.2 | 124.3 | 0.1 |
| C4" | 124.0* | 124.1 | 0.1 |
| C4' | 122.4* | 122.5 | 0.1 |
| C4' | 121.9 | 122.1 | 0.2 |
| C5 | 118.5 | 118.6 | 0.1 |
| C5 | 118.2* | 118.4 | 0.2 |
| C5" | 118.2* | 118.2 | 0 |
| C5" | 117.5 | 117.5 | 0 |
| C5' | 116.8 | 116.9 | 0.1 |
| C5' | 115.3* | 115.3 | 0 |
| C7 | 109.0* | 109.2 | 0.2 |
| C7 | 109.0 | 109.1 | 0.1 |
| C7" | 108.4* | 108.5 | 0.1 |
| C7" | 108.1 | 108.3 | 0.2 |
| C8a | 87.0* | 87.1 | 0.1 |
| C8a | 86.4 | 86.7 | 0.3 |
| C8a' | 82.6* | 82.8 | 0.2 |
| C8a" | 82.3* | 82.4 | 0.1 |
| C8a" | 82.3 | 82.2 | −0.1 |
| C8a' | 81.7 | 82.0 | 0.3 |
| C3a | 63.0* | 63.6 | 0.6 |
| C3a' | 63.0 | 63.3 | 0.3 |
| C3a' | 62.9* | 63.0 | 0.1 |
| C3a | 62.8 | 62.9 | 0.1 |
| C3a" | 60.3* | 60.4 | 0.1 |
| C3a" | 60.0 | 60.2 | 0.2 |
| C2" | 52.2* | 52.5 | 0.3 |
| C2 | 51.9* | 52.2 | 0.3 |
| C2" | 51.9 | 51.9 | 0 |
| C2' | 51.9 | — | N/A |
| C2' | 51.7* | — | N/A |
| C3" | 38.4* | 38.7 | 0.3 |
| C3" | 38.0 | 38.3 | 0.3 |
| C3 | 37.6 | 38.0 | 0.4 |
| C3' | 37.6* | — | N/A |
| C3' | 36.7 | 36.9 | 0.2 |
| C3 | 35.7* | 36.1 | 0.4 |
| N—CH$_3$ | 35.2 | 35.6 | 0.4 |
| N—CH$_3$ | 35.1 | 35.3 | 0.2 |
| N—CH$_3$ | 35.0 | 35.3 | 0.3 |
| N—CH$_3$ | 34.9 | 34.9 | 0 |

TABLE S4-continued

Comparison of $^{13}C$ NMR data for (—)-hodgkinsine (4) with literature data from Verotta, L.; Pilati, T.; Tatò, M.; Elisabetsky, E.; Amador, T. A.; Nunes, D. S. *J. Nat. Prod.* 1998, 61, 392.

| Assignment | Verotta's Isolation Report (—)-hodgkinsine (4) $^{13}C$ NMR, 200 MHz CDCl$_3$, −30° C. | This Work (—)-hodgkinsine (4) $^{13}C$ NMR, 125 MHz CDCl$_3$, −30° C. | Chemical Shift Difference Δδ = δ (this work) − δ (Verotta Report) |
|---|---|---|---|
| N—CH$_3$ | 34.9* | — | N/A |
| N—CH$_3$ | 34.9* | — | N/A |
| C2 | 5.17 This resonance was likely a typographical error as all C2 resonances are observed near 52 ppm in these systems. | — | N/A |
| C7' | nd | — | N/A |
| C7' | nd | — | N/A |

*denotes minor conformer

Example 43: Synthesis of (−)-Calycosidine (5)

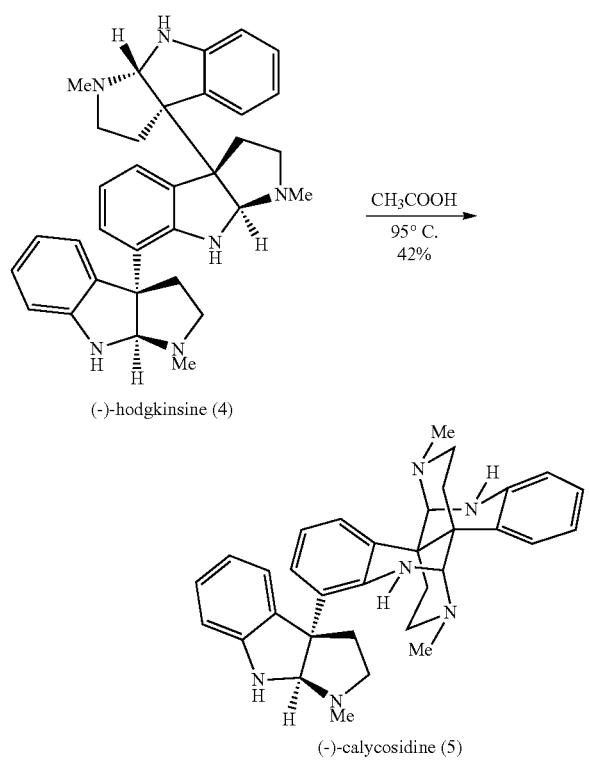

(−)-hodgkinsine (4)

CH$_3$COOH
95° C.
42%

(−)-calycosidine (5)

A solution of (−)-hodgkinsine (4, 10.5 mg, 20.2 μmol, 1 equiv) in aqueous acetic acid (0.1 M, 1 mL) contained in a pressure tube was sparged with argon for 5 min. The pressure tube was sealed and was immersed in a pre-heated 95° C. oil bath. After 36 h, the mixture was allowed to cool to 22° C. and was partitioned between dichloromethane (3 mL) and an aqueous sodium hydroxide solution (1 N, 2 mL). The layers were separated, and the aqueous layer was extracted with dichloromethane (2×3 mL). The combined organic layers were washed with a saturated aqueous sodium bicarbonate solution (5 mL), were dried over anhydrous sodium sulfate, were filtered, and were concentrated under reduced pressure. The resulting residue was purified by flash column chromatography on alumina (eluent: 100% ethyl acetate→10% methanol in dichloromethane) followed by flash column chromatography on silica (eluent: 2.7% methanol, 0.3% ammonium hydroxide→5.4% methanol, 0.6% ammonium hydroxide in chloroform) to afford (−)-calycosidine (5, 4.4 mg, 42%) as a tan amorphous gum.

$^1$H NMR (400 MHz, CDCl$_3$, 25° C.): δ 7.25 (d, J=7.0 Hz, 1H), 7.20 (d, J=7.1 Hz, 1H), 7.11-7.06 (m, 2H), 7.03 (td, J=1.4, 7.6 Hz, 1H), 6.87-6.79 (m, 2H), 6.77-6.67 (m, 3H), 6.56 (dd, J=1.2, 8.0 Hz, 1H), 5.57 (s, 1H), 4.83 (d, J=3.8 Hz, 1H, NH), 4.30 (s, 1H), 4.20 (d, J=3.4 Hz, 1H), 3.14-2.78 (m, 1H, NH), 2.67-2.57 (m, 1H), 2.50-2.38 (m, 1H), 2.34 (s, 3H), 2.31-2.28 (m, 1H), 2.27 (s, 3H), 2.24-2.20 (m, 1H), 2.23 (s, 3H), 2.20-2.08 (m, 3H), 1.98-1.74 (m, 3H), 1.32-1.20 (m, 1H), 1.03 (dd, J=3.1, 11.6 Hz, 1H).

$^{13}$C NMR (125 MHz, CDCl$_3$, 25° C.): δ 148.1, 147.3, 144.5, 133.4, 128.8, 128.2, 126.9 (2C), 124.8, 124.5, 123.7, 120.2, 120.0, 119.8, 117.6, 117.4, 112.2, 110.4, 88.3, 74.6, 71.0, 59.9, 47.8, 46.2 (2C), 43.2, 42.2, 38.3, 38.2, 36.4 (2C), 33.4, 33.1.

FTIR (thin film) cm$^{-1}$: 2924 (s), 2853 (m), 1653 (w), 1607 (s), 1487 (s), 1374 (w), 1265 (m).

HRMS (DART) (m/z): calc'd for C$_{33}$H$_{39}$N$_6$[M+H]$^+$: 519.3231, found: 519.3249.

$[α]_D^{24}$: −7 (c=0.11, CHCl$_3$). Literature value: $[α]_D$=−18 (c 1, CHCl$_3$), see F. Libot, N. Kunesch, J. Poisson *Heterocycles* 1988, 27, 2381. Literature value: $[α]_D$=−18 (c 1, CHCl$_3$), see F. Libot, C. Miet, N. Kunesch, J. Poisson *J. Nat. Prod.* 1987, 50, 468.

TLC (Al$_2$O$_3$, 1% methanol in dichloromethane), Rf: 0.33 (UV, CAM).

TABLE S5

Comparison of $^1$H NMR data for (—)-calycosidine (5) with literature data from F. Libot, N. Kunesch, J. Poisson *Heterocycles* 1988, 27, 2381/ F. Libot, C. Miet, N. Kunesch, J. Poisson *J. Nat. Prod.* 1987, 50, 468.

| Kunesch's Isolation Report (—)-calycosidine (5) $^1$H NMR, 400 MHz CDCl$_3$ | This Work (—)-calycosidine (5) $^1$H NMR, 400 MHz CDCl$_3$, 25° C. |
|---|---|
| 7.25 (d, J = 9 Hz, 1H) | 7.25 (d, J = 7.0 Hz, 1H) |
| 7.20 (d, J = 9 Hz, 1H) | 7.20 (d, J = 7.1 Hz, 1H) |
| 7.09 (d, J = 9 Hz, 1H) | 7.11-7.06 (m, 2H) |
| 7.08 (t, J = 9 Hz, 1H) | |
| 7.03 (t, J = 9 Hz, 1H) | 7.03 (td, J = 1.4, 7.6 Hz, 1H) |
| 6.84 (t, J = 9 Hz, 1H) | 6.87-6.79 (m, 2H) |
| 6.82 (t, J = 9 Hz, 1H) | |
| 6.74 (t, J = 9 Hz, 1H) | 6.77-6.67 (m, 3H) |
| 6.73 (t, J = 9 Hz, 1H) | |
| 6.70 (d, J = 9 Hz, 1H) | |
| 6.58 (d, J = 9 Hz, 1H) | 6.56 (dd, J = 1.2, 8.0 Hz, 1H) |

TABLE S5-continued

Comparison of $^1$H NMR data for (—)-calycosidine (5) with literature data from F. Libot, N. Kunesch, J. Poisson *Heterocycles* 1988, 27, 2381/ F. Libot, C. Miet, N. Kunesch, J. Poisson *J. Nat. Prod.* 1987, 50, 468.

| Kunesch's Isolation Report (—)-calycosidine (5) $^1$H NMR, 400 MHz CDCl$_3$ | This Work (—)-calycosidine (5) $^1$H NMR, 400 MHz CDCl$_3$, 25° C. |
|---|---|
| 5.57 (s, 1H) | 5.57 (s, 1H) |
| — | 4.83 (d, J = 3.8 Hz, 1H, NH) supported by HSQC correlations |
| 4.36 (s, 1H) | 4.30 (s, 1H) |
| 4.17 (s, 1H) | 4.20 (d, J = 3.4 Hz, 1H) |
| — | 3.14-2.78 (m, 1H, NH) supported by HSQC correlations |
| 2.63 (m, 2H) | 2.67-2.57 (m, 1H) |
| 2.45 (m, 2H) | 2.50-2.38 (m, 1H) |
| 2.33 (s, 3H) | 2.34 (s, 3H) |
| 2.25 (s, 3H) | 2.31-2.28 (m, 1H) |
| — | 2.27 (s, 3H) |
| 2.23 (s, 3H) | 2.24-2.20 (m, 1H) |
| — | 2.23 (s, 3H) |
| 2.17 (s, 3H) | 2.20-2.08 (m, 3H) |
| 1.88 (m, 3H) | 1.98-1.74 (m, 3H) |
| 1.25 (dd, J = 3, 12 Hz, 1H) | 1.32-1.20 (m, 1H) |
| 1.03 (dd, J = 3, 12 Hz, 1H) | 1.03 (dd, J = 3.1, 11.6 Hz, 1H) |

TABLE S6

Comparison of $^{13}$C NMR data for (—)-calycosidine (5) with literature data from F. Libot, N. Kunesch, J. Poisson *Heterocycles* 1988, 27, 2381/ F. Libot, C. Miet, N. Kunesch, J. Poisson *J. Nat. Prod.* 1987, 50, 468.

| Assignment | Kunesch's Isolation Report (—)-calycosidine (5) $^{13}$C NMR, 100 MHz CDCl$_3$ | This Work (—)-calycosidine (5) $^{13}$C NMR, 100 MHz CDCl$_3$, 25° C. | Chemical Shift Difference $\Delta\delta = \delta$ (this work) − $\delta$ (Kunesch Report) |
|---|---|---|---|
| C7a/C7a'/C7a" | 148.1 | 148.1 | 0 |
| C7a/C7a'/C7a" | 147.3 | 147.3 | 0 |
| C7a/C7a'/C7a" | 144.5 | 144.5 | 0 |
| C4a/C4a'/C4a" | 133.3 | 133.4 | 0.1 |
| C4a/C4a'/C4a" | 128.7 | 128.8 | 0.1 |
| — | 128.1 | 128.2 | 0.1 |
| — | 126.8 | 126.9 | 0.1 |
| — | — | 126.9 | N/A The reported data only lists 31 of the 33 theoretical 13C signals. |
| C4a/C4a'/C4a" | 124.7 | 124.8 | 0.1 |
| — | 124.4 | 124.5 | 0.1 |
| — | 123.6 | 123.7 | 0.1 |
| — | 120.1 | 120.2 | 0.1 |
| — | 119.9 | 120.0 | 0.1 |
| — | 118.9 | 119.8 | 0.9 |
| — | 117.5 | 117.6 | 0.1 |
| — | 117.4 | 117.4 | 0 |
| C7/C7'/C7" | 112.2 | 112.2 | 0 |
| C7/C7'/C7" | 110.4 | 110.4 | 0 |
| C8a/C8a'/C8a" | 88.2 | 88.3 | 0.1 |
| C8a/C8a'/C8a" | 74.5 | 74.6 | 0.1 |
| C8a/C8a'/C8a" | 70.9 | 71.0 | 0.1 |
| C3a/C3a'/C3a" | 58.9 | 59.9 | 0.1 |
| C2/C2'/C2" | 47.7 The signal at 47.7 was omitted in the list of $^{13}$C resonances provided for (—)-calycosidine in the reference; however, it is in the assignment table of the same report. | 47.8 | 0.1 |
| C2/C2'/C2" | 46.2 | 46.2 | 0 |
| — | 46.1 | 46.2 | 0.1 |
| N1—CH$_3$/N1'—CH$_3$/N1"—CH$_3$ | 43.2 | 43.2 | 0 |
| N1—CH$_3$/N1'—CH$_3$/N1"—CH$_3$ | 42.1 | 42.2 | 0.1 |
| C3/C3'/C3" | 38.2 | 38.3 | 0.1 |
| C3/C3'/C3" | 38.1 | 38.2 | 0.1 |
| — | 37.5 | 36.4 | −1.1 |
| N1—CH$_3$/N1'—CH$_3$/N1"—CH$_3$ | 36.4 | 36.4 | 0 |
| C3a/C3a'/C3a" | 33.4 | 33.4 | 0 |
| C3a/C3a'/C3a" | 33.1 | 33.1 | 0 |

Example 44: Synthesis of Diazene Dimer Amine (−)-43

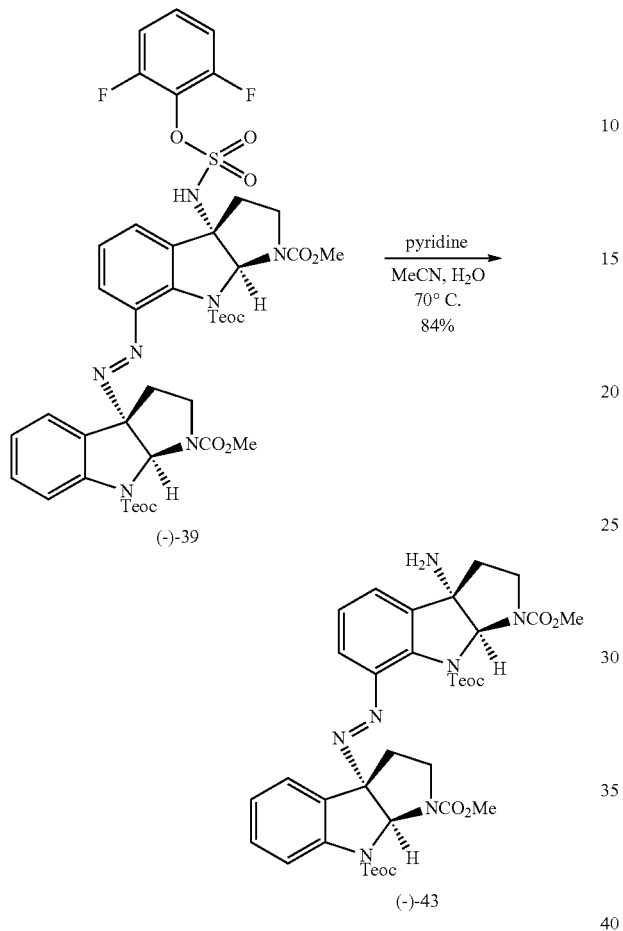

Pyridine (645 µL, 7.98 mmol, 20.0 equiv) was added to a solution of diazene dimer sulfamate (−)-39 (382 mg, 399 µmol, 1 equiv) in a mixture of acetonitrile-water (2:1, 4 mL) via syringe at 22° C. The reaction flask was fitted with a reflux condenser and was immersed in a pre-heated 70° C. oil bath. After 24 h, the reaction mixture was allowed to cool to 22° C. The mixture was diluted with dichloromethane (50 mL) and was washed with a saturated aqueous sodium bicarbonate solution (50 mL). The aqueous layer was extracted with dichloromethane (3×5 mL). The combined organic extracts were dried over anhydrous sodium sulfate, were filtered, and were concentrated under reduced pressure. The resulting residue was purified by flash column chromatography on silica gel (eluent: 1→6% methanol in dichloromethane) to afford the diazene dimer amine (−)-43 (257 mg, 84.1%) as a bright yellow oil. Structural assignments were made using additional information from gCOSY, gHSQC, and gHMBC experiments.

$^1$H NMR (400 MHz, CDCl$_3$, 25° C.): δ 7.80 (d, J=8.1 Hz, 1H, C$_7$H), 7.37 (app-dd, J=1.3, 7.3 Hz, 1H, C$_4$H), 7.33-7.27 (m, 1H, C$_6$H), 7.27-7.22 (m, 2H, C$_4$H, C$_6$H), 7.20-7.14 (m, 1H, C$_5$H), 7.02 (app-td, J=0.8, 7.5 Hz, 1H, C$_5$H), 6.89 (s, 1H, C$_{8a}$H), 5.90 (br-s, 1H, C$_{8a'}$H), 4.43-4.23 (m, 3H, C$_{10}$H$_2$ or C$_{10'}$H$_2$, C$_{10}$H$_a$ or C$_{10'}$H$_a$), 4.16-3.98 (m, 2H, C$_2$H$_a$, C$_{10}$H$_a$ or C$_{10'}$H$_a$), 3.81-3.73 (m, 1H, C$_2$H$_a$), 3.75 (app-s, 6H, N$_1$CO$_2$CH$_3$, N$_1$CO$_2$CH$_3$), 3.11 (td, J=5.3, 11.8 Hz, 1H, C$_2$H$_b$), 2.89 (td, J=5.4, 11.6 Hz, 1H, C$_2$H$_b$), 2.56 (td, J=8.0, 12.3 Hz, 1H, C$_3$H$_a$), 2.39 (dd, J=2.6, 5.0 Hz, 1H, C$_3$H$_a$), 2.36 (dd, J=2.9, 5.0 Hz, 1H, C$_3$H$_b$), 2.21 (td, J=8.2, 12.2 Hz, 1H, C$_3$H$_b$), 1.70 (br-s, 2H, NH$_2$), 1.15 (dd, J=7.0, 10.6 Hz, 2H, C$_{11}$H$_2$ or C$_{11'}$H$_2$), 0.97 (br-s, 2H, C$_{11}$H$_2$ or C$_{11'}$H$_2$), 0.06 (s, 9H, (C$_{12}$H$_3$)$_3$ or (C$_{12'}$H$_3$)$_3$), 0.00 (s, 9H, (C$_{12}$H$_3$)$_3$ or (C$_{12'}$H$_3$)$_3$).

$^{13}$C NMR (100 MHz, CDCl$_3$, 25° C.): δ 155.4 (2C, N$_1$CO$_2$CH$_3$, N$_1$CO$_2$CH$_3$), 155.0 (C$_9$ or C$_{9'}$), 153.8 (C$_9$ or C$_{9'}$), 143.5 (C$_{7a}$), 141.8 (C$_{7'}$), 139.3 (C$_{7a'}$), 137.6 (C$_{4a'}$), 130.0 (C$_6$), 129.1 (C$_{4a}$), 126.1 (C$_{5'}$), 125.4 (C$_4$), 124.8 (C$_{4'}$), 123.5 (C$_5$), 118.5 (C$_{6'}$), 116.2 (C$_7$), 89.0 (C$_{3a}$), 85.5 (C$_{8a'}$), 79.6 (C$_{8a}$), 69.6 (C$_{3a'}$), 64.9 (C$_{10}$ or C$_{10'}$), 64.5 (C$_{10}$ or C$_{10'}$), 52.8 (N$_1$CO$_2$CH$_3$ or N$_1$CO$_2$CH$_3$), 52.7 (N$_1$CO$_2$CH$_3$ or N$_1$CO$_2$CH$_3$), 46.1 (C$_2$), 45.7 (C$_{2'}$), 36.9 (br, C$_3$), 35.8 (C$_3$), 17.9 (C$_{11}$ or C$_{11'}$), 17.8 (C$_{11}$ or C$_{11'}$), −1.4 (2C, C$_{12}$, C$_{12'}$).

FTIR (thin film) cm$^{-1}$: 3378 (w), 2954 (m), 1706 (s), 1603 (w), 1252 (m).

HRMS (ESI) (m/z): calc'd for C$_{36}$H$_{51}$N$_7$NaO$_8$Si$_2$ [M+Na]$^+$: 788.3230, found 788.3219.

[α]$_D^{24}$: −104 (c=0.69, CH$_2$Cl$_2$).

TLC (6% methanol in dichloromethane), Rf: 0.45 (UV, CAM).

Example 45: Synthesis of Diazene Dimer Mixed Sulfamide (+)-S10

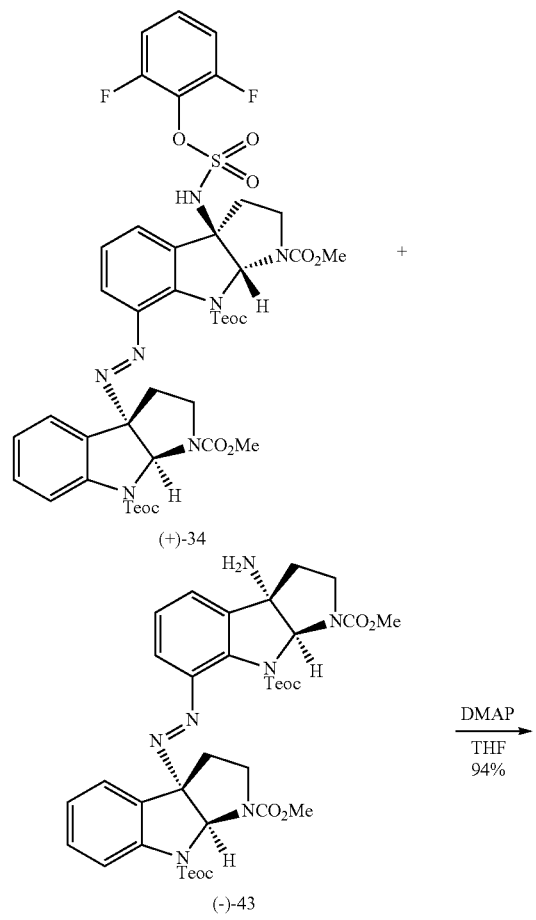

-continued

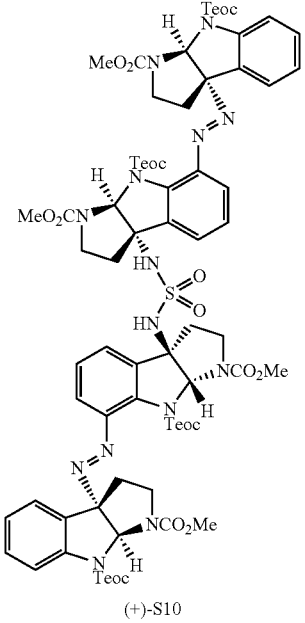

(+)-S10

A sample of 4-(dimethylamino)pyridine (137 mg, 1.12 mmol, 2.20 equiv) was added to a solution of diazene dimer sulfamate (+)-34 (490 mg, 511 µmol, 1 equiv) and diazene amine (−)-43 (430 mg, 562 µmol, 1.10 equiv) in tetrahydrofuran (5.10 mL) at 22° C. After 7 h, the bright yellow solution was concentrated under reduced pressure. The resulting residue was purified by flash column chromatography on silica gel (eluent: 30%→75% ethyl acetate in hexanes) to afford diazene dimer mixed sulfamide (+)-S10 (766 mg, 94.0%) as a bright yellow amorphous gum. As a result of the slow conformational equilibration at ambient temperature, NMR spectra were collected at elevated temperature.

$^1$H NMR (400 MHz, $C_6D_6$, 70° C.): δ 8.19 (d, J=8.1 Hz, 2H), 7.53 (d, J=7.4 Hz, 1H), 7.36 (d, J=8.0 Hz, 1H), 7.30 (d, J=8.0 Hz, 1H), 7.22-7.14 (m, 6H), 7.05 (d, J=7.3 Hz, 1H), 6.99 (td, J=7.5, 0.7 Hz, 1H), 6.93 (t, J=7.8 Hz, 1H), 6.87 (td, J=7.5, 5.6 Hz, 2H), 6.83 (s, 1H), 6.80 (s, 1H), 5.62 (br-s, 1H), 5.42 (br-s, 1H), 4.53-4.35 (m, 6H), 4.19 (app-dtd, J=17.3, 10.9, 6.4 Hz, 2H), 4.00-3.90 (m, 2H), 3.68 (s, 3H), 3.65 (s, 3H), 3.62 (s, 3H), 3.59 (s, 3H), 3.55-3.40 (m, 2H), 2.96 (td, J=11.7, 5.3 Hz, 2H), 2.58-2.44 (m, 2H), 2.39 (ddd, J=15.5, 9.9, 6.1 Hz, 2H), 2.19 (ddd, J=12.3, 4.9, 2.4 Hz, 2H), 1.86 (dd, J=12.0, 4.9 Hz, 1H), 1.77 (dd, J=12.0, 5.1 Hz, 1H), 1.65 (td, J=11.9, 8.1 Hz, 1H), 1.54 (td, J=11.9, 8.5 Hz, 1H), 1.24-0.94 (m, 8), 0.00 (s, 9H), −0.01 (s, 9H), −0.02 (s, 9H), −0.04 (s, 9H).

$^{13}$C NMR (100 MHz, $C_6D_6$, 70° C.): δ 156.4, 156.2, 155.3 (2C), 154.9, 154.8 (2C), 153.7, 144.5, 144.4, 142.7, 142.6, 141.0, 140.8, 135.0, 134.8, 130.3, 130.2 (2C), 130.0, 126.2, 126.0 (2C), 125.8 (2C), 125.2, 123.6, 123.5, 119.5, 119.2, 116.8, 116.6, 89.9, 89.8, 81.8, 81.6, 79.8, 79.5, 71.1, 70.9, 65.7, 65.5, 64.4, 64.2, 52.4 (4C), 46.0 (2C), 44.6 (2C), 37.1, 36.7 (2C), 36.4, 18.2 (2C), 18.0, 17.9, −1.5 (4C).

FTIR (thin film) cm$^{-1}$: 3228 (w), 2954 (m), 1701 (s), 1457 (m), 838 (m).

HRMS (ESI) (m/z): calc'd for $C_{72}H_{100}N_{14}NaO_{18}SSi_4$ [M+Na]$^+$: 1615.6030, found: 1615.6162.

[α]$_D^{24}$: +130 (c=0.59, $CH_2Cl_2$).

TLC (70% ethyl acetate in hexanes), Rf: 0.21 (UV, CAM).

Example 46: Synthesis of Tris-Diazene Tetramer (+)-44

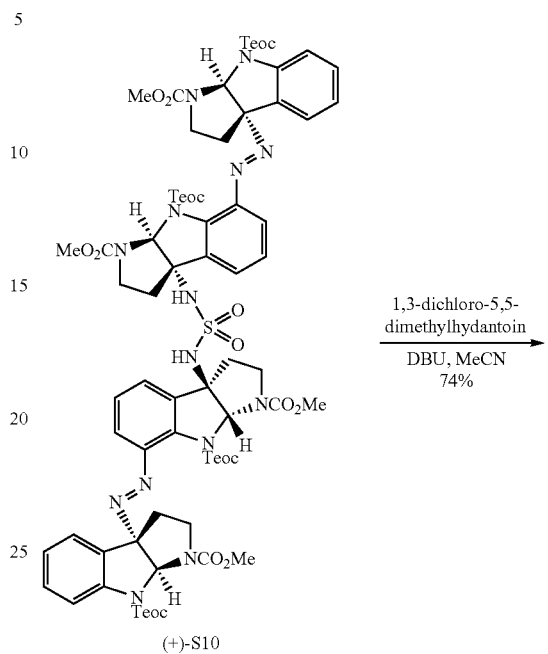

To a solution of diazene dimer mixed sulfamide (+)-S10 (766 mg, 481 µmol, 1 equiv) in acetonitrile (24.1 mL) at 22° C. was added via syringe 1,8-diazabicyclo[5.4.0]undec-7-ene (DBU, 215 µL, 1.44 mmol, 3.00 equiv) followed immediately by 1,3-dichloro-5,5-dimethylhydantoin (236 mg, 1.20 mmol, 2.50 equiv) in a single portion. After 1 h, the mixture was diluted with dichloromethane (10 mL) and was washed with a saturated aqueous potassium carbonate-water solution (1:1, 30 mL). The aqueous layer was extracted with dichloromethane (3×30 mL) and the combined organic extracts were dried over anhydrous sodium sulfate, were filtered, and were concentrated under reduced pressure. The resulting residue was purified by flash column chromatography on silica gel (eluent: 35→60% ethyl acetate in hexanes) to afford tris-diazene tetramer (+)-44 (541 mg, 73.6%) as a bright yellow amorphous gum. As a result of the slow conformational equilibration at ambient temperature, NMR spectra were collected at elevated temperature.

$^1$H NMR (400 MHz, CD$_3$CN, 50° C.): δ 7.77 (d, J=8.1 Hz, 2H), 7.48 (d, J=8.9 Hz, 1H), 7.38-7.18 (m, 9H), 7.09 (app-dtd, J=1.0, 7.5, 11.6 Hz, 2H), 6.74 (app-s, 2H), 6.32 (app-d, J=1.7 Hz, 1H), 6.30 (app-d, J=2.2 Hz, 1H), 4.40-4.26 (m, 4H), 4.19-3.94 (m, 4H), 3.89-3.73 (m, 4H), 3.70 (s, 6H), 3.69 (s, 3H), 3.68 (s, 3H), 3.08-2.98 (m, 2H), 2.93 (td, J=5.6, 11.4 Hz, 2H), 2.56-2.35 (m, 8H), 1.18-1.07 (m, 4H), 0.92-0.69 (m, 4H), 0.07 (s, 9H), 0.05 (s, 9H), 0.01 (s, 9H), −0.01 (s, 9H).

$^{13}$C NMR (100 MHz, CD$_3$CN, 50° C.): δ 156.3, 156.2, 156.0 (2C), 155.3, 155.2, 154.5 (2C), 144.7, 144.6, 143.4, 143.2, 141.4, 141.0, 134.7 (2C), 131.1 (3C), 130.7, 127.7, 127.6, 127.1 (2C), 126.8, 126.7, 124.6 (2C), 120.3, 119.9, 117.1, 116.9, 90.3, 90.1, 89.5 (2C), 81.8, 81.7, 79.8, 79.7, 65.8, 65.7, 65.2 (2C), 53.4 (2C), 53.3 (2C), 47.0, 46.9, 46.7 (2C), 37.4, 37.1, 33.7 (2C), 18.7 (4C), −1.1 (4C).

FTIR (thin film) cm$^{-1}$: 2954 (m), 2896 (w), 1717 (s), 1448 (w), 1395 (m).

HRMS (ESI) (m/z): calc'd for C$_{72}$H$_{98}$N$_{14}$NaO$_{16}$SSi$_4$ [M+Na]: 1549.6255, found: 1549.6665.

[α]$_D^{24}$: +145 (c=0.62, CH$_2$Cl$_2$).

TLC (60% ethyl acetate in hexanes), Rf: 0.33 (UV, CAM).

Example 47: Synthesis of Bis-Diazene Tetramer (+)-45

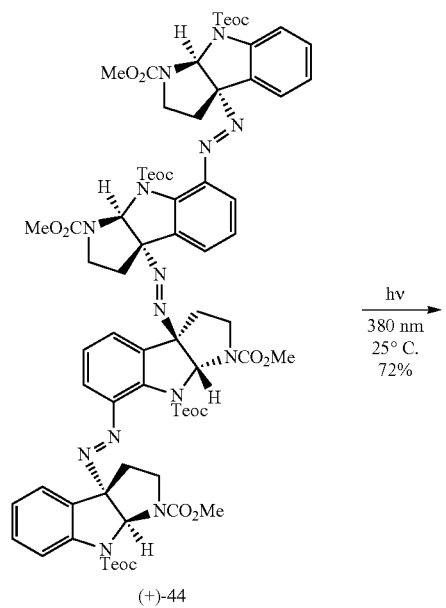

(+)-44

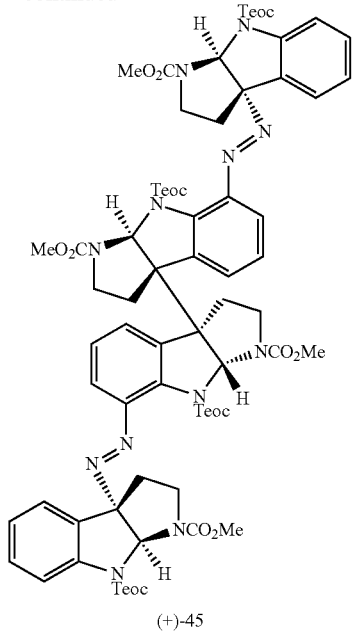

(+)-45

A solution of tris-diazene tetramer (+)-44 (541 mg, 354 μmol, 1 equiv) in dichloromethane (30 mL) was concentrated under reduced pressure in a 2 L round-bottom flask to provide a thin film of diazene coating the flask. The flask was back filled with argon and irradiated in a Rayonet photoreactor equipped with 16 radially distributed (r=12.7 cm) 25 W lamps (λ=380 nm) at 25° C. After 24 h, the lamps were turned off and the resulting residue was purified by flash column chromatography on silica gel (eluent: 30→70% ethyl acetate in hexanes) to afford bis-diazene tetramer (+)-45 (384 mg, 72.3%) as a bright yellow amorphous gum. As a result of the slow conformational equilibration at ambient temperature, NMR spectra were collected at elevated temperature.

$^1$H NMR (400 MHz, CD$_3$CN, 70° C.): δ 7.78 (app-t, J=7.2 Hz, 2H), 7.49 (app-t, J=6.8 Hz, 1H), 7.37-7.26 (m, 3H), 7.21-7.14 (m, 2H), 7.14-7.01 (m, 4H), 6.94 (br-s, 2H), 6.75 (dd, J=6.5, 10.7 Hz, 2H), 6.22 (app-br-s, 2H), 4.41-4.26 (m, 4H), 4.13-3.93 (m, 4H), 3.93-3.78 (m, 2H), 3.78-3.65 (m, 14H), 3.09-2.94 (m, 2H), 2.80-2.66 (m, 2H), 2.57-2.34 (m, 4H), 2.26 (app-br-s, 4H), 1.20-1.06 (m, 4H), 1.01-0.79 (m, 4H), 0.13-0.01 (m, 36H).

$^{13}$C NMR (100 MHz, CD$_3$CN, 70° C.): δ 156.5, 156.4, 155.9, 155.8, 154.9 (2C), 154.8 (2C), 145.0, 144.9, 143.4, 143.3, 141.3, 140.8, 136.9 (2C), 131.4, 131.3, 131.2, 131.0, 127.4, 127.3, 127.0 (2C), 126.9 (2C), 124.8, 124.7, 119.8, 119.4, 117.2 (2C), 90.4 (2C), 82.0, 81.9, 80.5, 80.0, 66.2 (2C), 65.4, 65.3, 62.3 (2C), 53.5 (2C), 53.5 (2C), 47.2, 47.1, 46.7 (2C), 37.8, 37.6, 34.7, 34.6, 19.1 (3C), 19.0, −0.8 (2C), −0.9 (2C).

FTIR (thin film) cm$^{-1}$: 2954 (m), 2896 (w), 1717 (s), 1457 (m), 1251 (w).

HRMS (ESI) (m/z): calc'd for C$_{72}$H$_{98}$N$_{12}$NaO$_{16}$Si$_4$ [M+Na]$^+$: 1521.6193, found: 1521.6283.

[α]$_D^{24}$: +155 (c=0.55, CH$_2$Cl$_2$).

TLC (50% ethyl acetate in hexanes), Rf: 0.13 (UV, CAM).

Example 48: Synthesis of Tetramer (+)-46

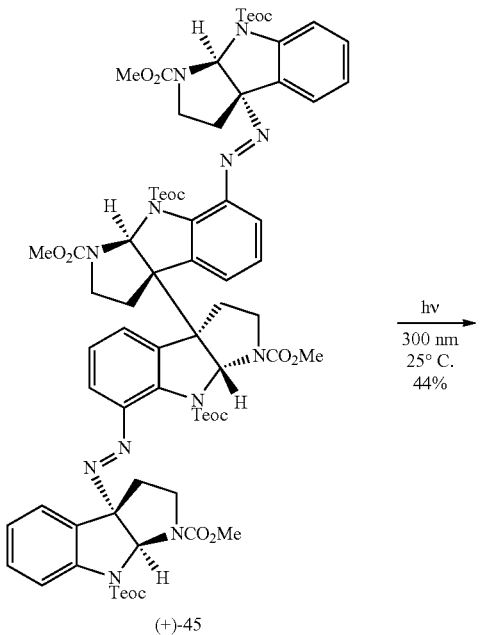

A solution of bis-diazene tetramer (+)-45 (62.2 mg, 41.5 µmol, 1 equiv) in dichloromethane (5 mL) was concentrated under reduced pressure in a 500-mL round-bottom flask to provide a thin film of diazene coating the flask. The flask was backfilled with argon and irradiated in a Rayonet photoreactor equipped with 16 radially distributed (r=12.7 cm) 25 W lamps (λ=300 nm) at 25° C. After 18 h, the lamps were turned off and the resulting residue was purified by flash column chromatography on silica gel (eluent: 6→12% acetone in hexanes) to afford tetramer (+)-46 (26.2 mg, 43.7%) as a bright yellow amorphous gum. As a result of the slow conformational equilibration at ambient temperature, NMR spectra were collected at elevated temperature.

$^1$H NMR (400 MHz, CD$_3$CN, 70° C.): δ 7.75 (app-d, J=8.1 Hz, 2H), 7.30 (t, J=7.8 Hz, 1H), 7.20 (app-br t, J=7.8 Hz, 4H), 7.11-6.99 (m, 4H), 6.97-6.86 (m, 2H), 6.78 (s, 1H), 6.50 (d, J=7.9 Hz, 1H), 6.44 (s, 1H), 6.33 (s, 1H), 6.27 (s, 1H), 4.43-4.34 (m, 1H), 4.34-4.24 (m, 3H), 4.20 (br-td, J=5.3, 11.4 Hz, 1H), 4.08-3.89 (m, 4H), 3.84-3.75 (m, 1H), 3.73-3.63 (m, 1H), 3.69 (app-s, 6H), 3.66 (s, 3H), 3.64 (s, 3H), 3.60 (br-dd, J=8.5, 10.3 Hz, 1H), 3.53 (br-dd, J=8.3, 10.2 Hz, 1H), 3.06 (dt, J=8.0, 11.7 Hz, 1H), 2.98 (dt, J=6.8, 11.0 Hz, 1H), 2.87-2.74 (m, 2H), 2.69-2.54 (m, 2H), 2.25 (br-dd, J=5.4, 12.5 Hz, 1H), 2.07-1.99 (m, 2H), 1.91-1.78 (m, 2H), 1.15-0.98 (m, 6H), 0.98-0.86 (m, 2H), 0.08 (app-d, J=2.7 Hz, 18H), 0.06 (s, 9H), 0.02 (s, 9H).

$^{13}$C NMR (100 MHz, CD$_3$CN, 70° C.): δ 156.5, 156.3, 156.0, 155.9 (2C), 155.7, 155.1, 154.8, 144.5, 144.2, 142.7, 142.3, 139.4, 138.4, 138.2, 137.0, 136.4, 135.2, 133.1, 131.2, 129.9, 129.1, 128.3, 127.9, 126.6, 125.6, 125.4, 124.3 (2C), 124.1, 117.8, 116.2, 86.5, 83.0, 81.2, 81.1, 66.5, 66.2, 65.2, 65.0, 61.8, 61.5, 61.1, 60.9, 53.5, 53.4, 53.3 (2C), 47.1, 46.5, 46.4 (2C), 35.0, 34.3 (2C), 33.9, 19.4, 19.3, 19.1, 19.0, −0.9, −1.0 (3C).

FTIR (thin film) cm$^{-1}$: 2954 (m), 2896 (w), 1717 (s), 1396 (m), 1043 (w).

HRMS (ESI) (m/z): calc'd for C$_{72}$H$_{98}$N$_8$NaO$_{16}$Si$_4$ [M+Na]$^+$: 1465.6070, found: 1465.6112.

[α]$_D^{24}$: +95 (c=0.28, CH$_2$Cl$_2$).

TLC (50% ethyl acetate in hexanes), Rf: 0.31 (UV, CAM).

M.p.: 127-129° C. (CH$_2$Cl$_2$).

Example 49: Synthesis of Tetramer (+)-S11

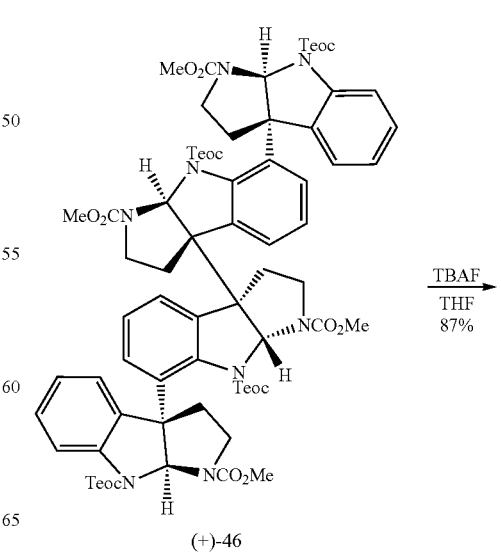

Example 50: Synthesis of (−)-Quadrigemine C (7)

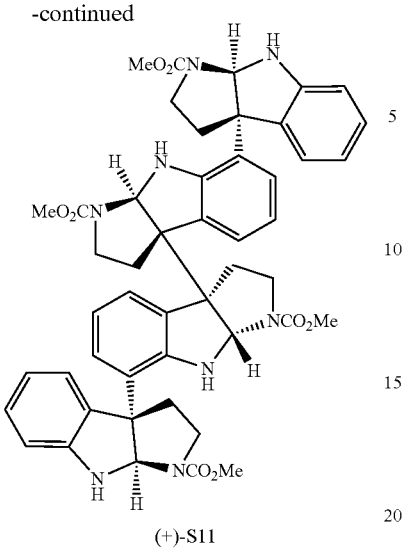

(+)-S11

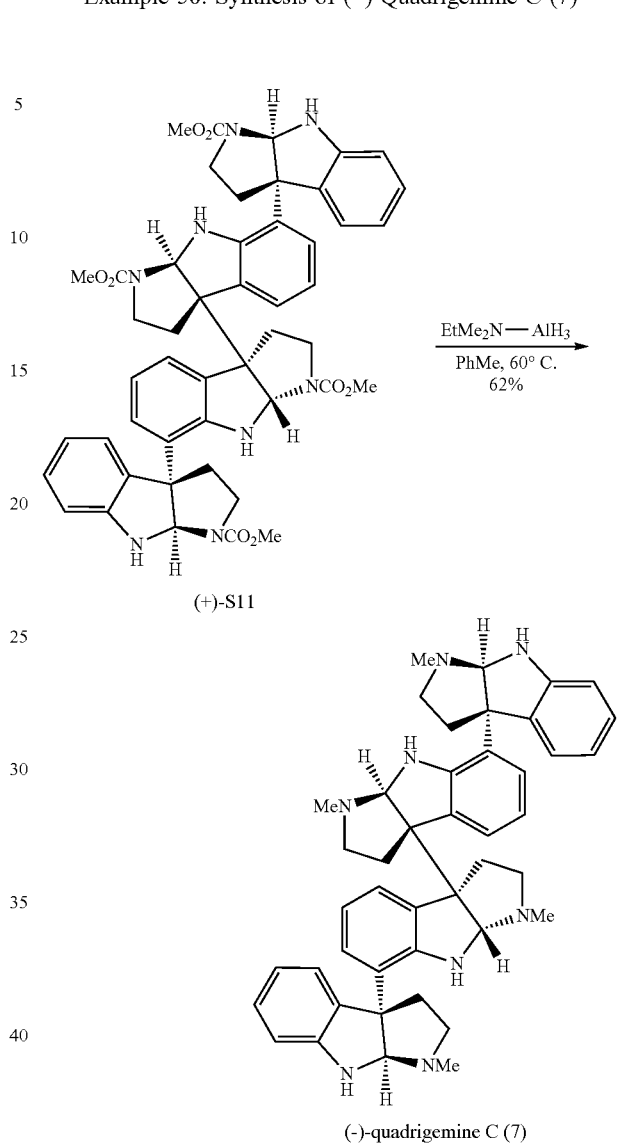

Tetrabutylammonium fluoride (1.0 M in tetrahydrofuran, 1.30 mL, 1.30 mmol, 20.0 equiv) was added to tetramer (+)-46 (94.0 mg, 65.1 µmol, 1 equiv) at 22° C. under an atmosphere of argon. After 1 h, the reaction mixture was diluted with ethyl acetate (2 mL) and washed with a saturated aqueous sodium carbonate solution (3×3 mL). The aqueous layer was extracted with dichloromethane (3×3 mL). The combined organic extracts were dried over anhydrous sodium sulfate, were filtered, and were concentrated under reduced pressure. The resulting yellow-green residue was purified by flash column chromatography on silica gel (eluent: 20→35% acetone in hexanes) to yield tetramer (+)-S11 (49.0 mg, 86.8%) as a pale yellow solid.

$^1$H NMR (400 MHz, CD$_3$CN, 25° C.): δ 7.30-6.96 (m, 5.5H), 6.96-6.73 (m, 2.5H), 6.73-6.47 (m, 5H), 6.38 (s, 1H), 6.23-5.74 (m, 2H), 5.74-5.38 (m, 2.5H), 5.31-5.05 (m, 2H), 5.05-4.87 (m, 1H), 4.76 (app-d, J=22.2 Hz, 0.5H), 3.88-3.54 (m, 13H), 3.54-3.40 (m, 3H), 3.40-3.27 (m, 1H), 3.03-2.88 (m, 2H), 2.88-2.78 (m, 1H), 2.78-2.42 (m, 5H), 2.37-2.26 (m, 1H), 2.17-2.11 (m, 2H). The reported integrals for intermediate (+)-S11 are an approximation due to presence of multiple conformers and significant atropisomerism $^{13}$C NMR (100 MHz, CD$_3$CN, 25° C.): δ 155.8, 155.3, 155.1, 154.9, 154.7 (2C), 149.2, 148.9, 148.8, 131.1, 129.7, 129.1, 129.0, 126.8, 126.7, 126.3, 125.2, 124.6, 124.1, 124.0, 123.9, 123.5, 123.4, 123.2, 123.1, 121.3, 121.2, 120.6 (2C), 120.3, 119.6, 110.7, 110.5, 80.2, 79.7, 79.4, 79.3, 78.7, 77.9, 77.7, 77.3, 76.3, 76.1, 62.3, 62.2, 61.4, 61.2, 60.7, 60.6, 59.6, 59.5, 53.2, 52.9 (2C), 52.8, 52.6, 46.4, 46.2, 46.1, 46.0, 45.8, 45.6, 37.2, 36.5, 33.7, 32.2, 29.7. Due to atropisomerism, more than the expected 48 13C NMR signals were observed.

FTIR (thin film) cm$^{-1}$: 3325 (m), 2955 (m), 2879 (w), 1700 (s), 1599 (w), 1457 (m).

HRMS (ESI) (m/z): calc'd for C$_{48}$H$_{50}$N$_8$NaO$_8$ [M+Na]$^+$: 889.3644, found: 889.3668.

[α]$_D^{24}$: +290 (c=0.58, CH$_2$Cl$_2$).

TLC (80% ethyl acetate in hexanes), Rf: 0.20 (UV, CAM).

M.p.: 165° C. (decomp.).

Tetramer (+)-S11 (53.5 mg, 61.7 µmol, 1 equiv) was azeotropically dried by concentration from anhydrous benzene (3×1 mL) and the residue was dissolved in toluene (0.9 mL). A solution of alane N,N-dimethylethylamine complex in toluene (0.5 M, 2.22 mL, 1.11 mmol, 18.0 equiv) was added via syringe at 22° C. The reaction flask was then sealed and immersed in a pre-heated 60° C. oil bath. After 1 h, the reaction mixture was allowed to cool to 22° C. and excess reducing reagent was quenched by the addition of a saturated aqueous sodium sulfate solution (200 µL). The resulting heterogeneous mixture was stirred for 10 min and then solid anhydrous sodium sulfate was added. The mixture was filtered through a plug of Celite and the filter cake was rinsed with ethyl acetate (10 mL). The filtrate was concentrated under reduced pressure. The resulting residue was purified by flash column chromatography on silica gel (eluent: 3.6% methanol, 0.4% ammonium hydroxide→5.4% methanol, 0.6% ammonium hydroxide in chloroform) to afford (−)-quadrigemine C (7, 26.2 mg, 61.5%) as an off-white solid. As a result of the slow conformational equilibration at ambient temperature, NMR spectra were collected at −32° C.

¹H NMR (400 MHz, CDCl₃, −32° C., 2.2:1 mixture of atropisomers, *denotes minor atropisomer): δ 7.26-7.03 (m, 5H), 6.96-6.89 (m, 1H), 6.89-6.75 (m, 2.3H), 6.70-6.52 (m, 3H), 6.20 (t, J=7.6 Hz, 0.7H), 6.02 (t, J=7.5 Hz, 0.3H*), 5.71 (d, J=7.2 Hz, 0.7H), 5.56-5.27 (m, 1H), 5.16-4.74 (m, 2.5H), 4.55-4.02 (m, 3.5H), 3.14-2.66 (m, 6H), 2.66-1.69 (m), 2.49 (s), 2.44 (s), 2.41 (s), 2.38 (s), 2.33 (s), 2.27 (s). The reported integrals for (−)-quadrigemine C (7) are an approximation due to presence of multiple conformers and significant atropisomerism.

¹³C NMR (100 MHz, CDCl₃, −32° C.): δ 151.0, 150.8, 150.4, 149.4, 149.1, 132.0, 131.8, 131.7, 127.9, 127.0, 126.8, 126.2, 125.9, 125.2, 124.5, 123.2, 122.5, 122.3, 122.0, 121.5, 118.5, 116.2, 115.3, 109.3, 109.0, 87.0, 86.5, 85.4, 81.9, 77.5, 77.4, 77.2, 76.8, 63.0, 62.7, 62.6, 62.4, 60.6, 60.3, 60.2, 52.6, 52.5, 52.4, 52.3, 51.8, 39.6, 39.1, 38.1, 37.0, 36.0, 35.4, 35.2 (2C).

FTIR (thin film) cm⁻¹: 2934 (m), 2793 (m), 1670 (s), 1606 (s), 1487 (s), 1352 (m), 1248 (s). Due to atropisomerism, more than the expected 44 ¹³C NMR signals were observed.

HRMS (ESI) (m/z): calc'd for $C_{44}H_{51}N_8$ [M+H]⁺: 691.4231, found: 691.4236.

$[\alpha]_D^{24}$: −81 (c=0.51, CHCl₃). Literature value: $[\alpha]_D$=−69 (c 1, CHCl₃), see F. Libot, C. Miet, N. Kunesch, J. Poisson *J. Nat. Prod.* 1987, 50, 468. Literature value: $[\alpha]_D^{20}$=−64 (c 1, CHCl₃), see L. Verotta, T. Pilati, M. Tatò, E. Elisabetsky, T. A. Amador, D. S. Nunes *J. Nat. Prod.* 1998, 61, 392.

TLC (9% methanol, 1% ammonium hydroxide in chloroform), Rf: 0.24 (UV, CAM).

M.p.: 150-152° C. (CH₂Cl₂).

TABLE S7

Comparison of ¹H NMR data for (—)-quadrigemine C (7) with literature data from Libot, F.; Miet, C.; Kunesch, N.; Poisson, J.; *J. Nat. Prod.* 1987, 50, 468.

| Poisson's Isolation Report (—)-quadrigemine C (7) ¹H NMR CDCl₃ | This Work (—)-quadrigemine C (7) ¹H NMR, 400 MHz CDCl₃, −30° C. |
|---|---|
| 7.15-6.63 (m) | 7.26-7.03 (m, 5H) |
| — | 6.96-6.89 (m, 1H) |
| — | 6.89-6.75 (m, 2.3H) |
| — | 6.70-6.52 (m, 3H) |
| — | 6.20 (t, J = 7.6 Hz, 0.7H) |
| — | 6.02* (t, J = 7.5 Hz, 0.3H) |
| 5.67 (m) | 5.71 (d, J = 7.2 Hz, 0.7H) |
| 5.07 (m) | 5.56-5.27 (m, 1H) |
| 4.65 (m) | 5.16-4.74 (m, 2.5H) |
| 4.23 (m) | 4.55-4.02 (m, 3.5H) |
| — | 3.14-2.66 (6H) |
| — | 2.66-1.69 (m) |
| 2.50 (m, 12H) | 2.49 (s) |
| — | 2.44 (s) |
| — | 2.41 (s) |
| — | 2.38 (s) |
| — | 2.33 (s) |
| — | 2.27 (s) |

*denotes minor conformer

TABLE S8

Comparison of ¹³C NMR data for (—)-quadrigemine C (7) with literature data from Libot, F.; Miet, C.; Kunesch, N.; Poisson, J.; *J. Nat. Prod.* 1987, 50, 468.

| Poisson's Isolation Report (—)-quadrigemine C (7) ¹³C NMR, 20 MHz CDCl₃ | This Work (—)-quadrigemine C (7) ¹³C NMR, 125 MHz CDCl₃, −30° C. | Chemical Shift Difference Δδ = δ (this work) − δ (Poisson Report) |
|---|---|---|
| — | 151.0 | N/A |
| — | 150.8 | N/A |
| 150.6 | 150.4 | −0.2 |
| — | 149.4 | N/A |
| — | 149.1 | N/A |
| 132.2 | 132.0 | −0.2 |
| — | 131.8 | N/A |
| — | 131.7 | N/A |
| 127.6 | 127.9 | 0.3 |
| — | 127.0 | N/A |
| — | 126.8 | N/A |
| 126.2 | 126.2 | 0 |
| 125.7 | 125.9 | 0.2 |
| 124.8 | 125.2 | 0.4 |
| 124.0 | 124.5 | 0.5 |
| 123.6 | 123.2 | −0.4 |
| — | 122.5 | N/A |
| — | 122.3 | N/A |
| 122.2 | 122.0 | −0.2 |
| — | 121.5 | N/A |
| 118.5 | 118.5 | 0 |
| 117.0 | | N/A |
| 116.1 | 116.2 | −0.1 |
| 115.6 | 115.3 | −0.3 |
| — | 109.3 | N/A |
| 108.7 | 109.0 | 0.3 |
| — | 87.0 | N/A |
| 86.7 | 86.5 | −0.2 |
| 85.8 | 85.4 | −0.4 |
| 82.3 | 81.9 | −0.4 |
| — | 77.5 | N/A |
| — | 77.4 | N/A |
| — | 77.2 | N/A |
| — | 76.8 | N/A |
| — | 63.0 | N/A |
| — | 62.7 | N/A |
| 62.6 | 62.6 | 0 |
| — | 62.4 | N/A |
| 60.6 | 60.6 | 0 |
| — | 60.3 | N/A |
| — | 60.2 | N/A |
| 53.2 | 52.6 | −0.6 |
| — | 52.5 | N/A |
| — | 52.4 | N/A |
| — | 52.3 | N/A |
| — | 51.8 | N/A |
| — | 39.6 | N/A |
| — | 39.1 | N/A |
| — | 38.1 | N/A |
| — | 37.0 | N/A |
| 36.3 | 36.0 | −0.3 |
| — | 35.4 | N/A |
| 35.2 | 35.2(3C) | 0 |

Example 51: Synthesis of (−)-Psycholeine (8)

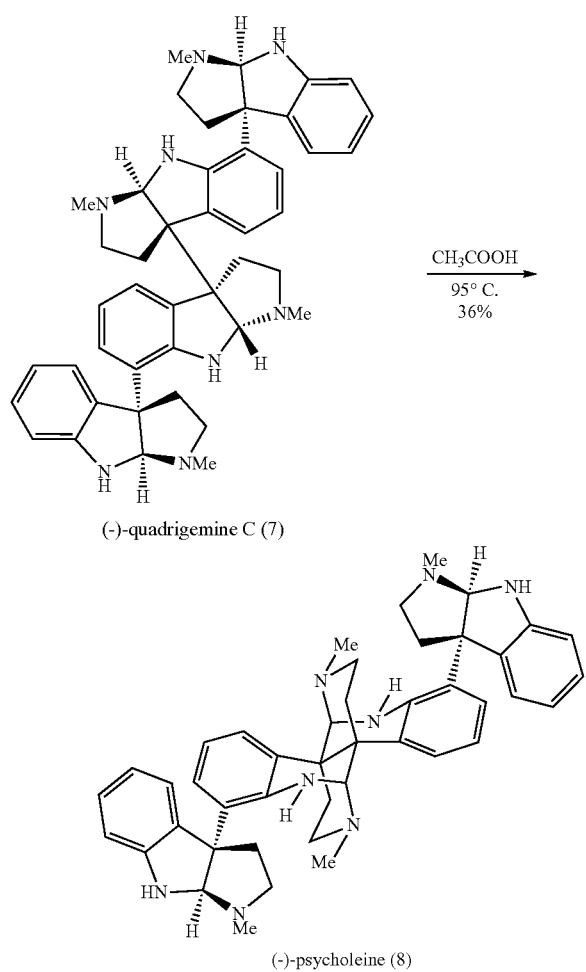

(−)-quadrigemine C (7)

CH₃COOH
95° C.
36%

(−)-psycholeine (8)

A solution of (−)-quadrigemine C (7, 9.8 mg, 14.2 μmol, 1 equiv) in aqueous acetic acid (0.1 M, 700 μL) contained in a pressure tube was sparged with argon for 5 min. The pressure tube was sealed and was immersed in a pre-heated 95° C. oil bath. After 36 h, the mixture was allowed to cool to 22° C. and partitioned between dichloromethane (3 mL) and aqueous solution of sodium hydroxide (1 N, 3 mL). The layers were separated, and the aqueous layer was extracted with dichloromethane (2×10 mL). The combined organic layers were washed with a saturated aqueous sodium bicarbonate solution (5 mL), were dried over anhydrous sodium sulfate, were filtered, and were concentrated under reduced pressure. The resulting residue was purified by flash column chromatography on silica gel (eluent: 1→3% methanol in dichloromethane saturated with ammonium hydroxide) to afford (−)-psycholeine (8, 3.5 mg, 36%) as a tan solid.

$^1$H NMR (400 MHz, CDCl$_3$, 25° C.): δ 7.28-7.23 (m, 2H), 7.20 (d, J=7.2 Hz, 1H), 7.09-7.03 (m, 2H), 6.97 (app-td, J=1.1, 7.8 Hz, 1H), 6.91 (d, J=7.6 Hz, 1H), 6.86 (d, J=7.6 Hz, 1H), 6.81 (t, J=7.3 Hz, 1H), 6.73 (app-td, J=1.8, 7.5 Hz, 2H), 6.69-6.64 (m, 2H), 6.57 (d, J=7.8 Hz, 1H), 5.94 (s, 1H), 5.56 (s, 1H), 4.46 (s, 1H), 4.22 (s, 1H), 2.75-2.58 (m, 4H), 2.55-2.16 (m, 9H), 2.39 (s, 3H), 2.38 (s, 3H), 2.36 (s, 3H), 2.14 (s, 3H), 2.03-1.97 (m, 1H), 1.90-1.74 (m, 4H), 1.12 (app-d, J=11.1 Hz, 1H), 1.05 (app-d, J=12.4 Hz, 1H).

$^{13}$C NMR (100 MHz, CDCl$_3$, 25° C.): δ 149.4, 148.1, 147.3, 146.7, 133.4, 133.3, 128.7 (2C), 128.2, 127.7, 124.9, 124.8, 123.7, 123.2, 120.2 (3C), 120.1, 119.9, 119.6, 117.6, 117.3, 110.4, 109.8, 88.0, 87.6, 74.2, 72.1, 60.9, 59.9, 48.6, 47.7, 46.6, 46.0, 43.9, 43.0, 38.6, 38.1, 37.8, 37.6, 36.5, 36.3, 32.9, 32.5.

FTIR (thin film) cm$^{-1}$: 2920 (m), 1653 (w), 1609 (s), 1489 (s), 1312 (w), 1267 (m).

HRMS (DART) (m/z): calc'd for C$_{44}$H$_{51}$N$_8$ [M+H]$^+$: 691.4231, found: 691.4223.

[α]$_D^{24}$: −155 (c=0.14, EtOH). Literature value: [α]$_D^{20}$=−150 (c 0.4, EtOH), see Guéritte-Voegelein, F.; Sévenet, T.; Pusset, J.; Adeline, M.-T.; Gillet, B.; Beloeil, J.-C.; Guénard, D.; Potier, P. J. Nat. Prod. 1992, 55, 923. Literature value: [α]$_D^{28}$=−150 (c 0.1, EtOH), see Lebsack, A. D.; Link, J. T.; Overman, L. E.; Stearns, B. A. J. Am. Chem. Soc. 2002, 124, 9008.

TLC (10% methanol in ammonia-saturated dichloromethane), Rf: 0.27 (UV, CAM).

M.p.: 220° C. (decomp.).

TABLE S9

Comparison of $^1$H NMR data for (—)-psycholeine (8) with literature data from Guéritte-Voegelein, F.; Sévenet, T.; Pusset, J.; Adeline, M.-T.; Gillet, B.; Beloeil, J.-C.; Guénard, D.; Potier, P. J. Nat. Prod. 1992, 55, 923 and Lebsack, A. D. Ph.D. Dissertation, University of California, Irvine, 2002 (original publication, see Lebsack, A. D.; Link, J. T.; Overman, L. E.; Stearns, B. A. J. Am. Chem. Soc. 2002, 124, 9008) (CDCl$_3$)

| Sevenet's Isolation Report ((—)-psycholeine (8)) $^{13}$C NMR, 400 MHz CDCl$_3$/CD$_3$OD | Lebsack's Ph.D. Dissertation (—)-psycholeine (8) $^1$H NMR, 500 MHz CDCl$_3$, "rt" | This Work (—)-psycholeine (8) $^1$H NMR, 400 MHz CDCl$_3$, 25° C. |
|---|---|---|
| — | 7.27-7.23 (m, 2H) | 7.28-7.23 (m, 2H) |
| — | 7.20 (d, J = 6.8 Hz, 1H) | 7.20 (d, J = 7.2 Hz, 1H) |
| — | 7.08-7.02 (m, 2H) | 7.09-7.03 (m, 2H) |
| — | 6.96 (app-t, J = 7.0 Hz, 1H) | 6.97 (app-td, J = 1.1, 7.8 Hz, 1H) |
| — | 6.91 (d, J = 7.6 Hz, 1H) | 6.91 (d, J = 7.6 Hz, 1H) |
| — | 6.85 (d, J = 7.5 Hz, 1H) | 6.86 (d, J = 7.6 Hz, 1H) |
| — | 6.80 (t, J = 7.0 Hz, 1H) | 6.81 (t, J = 7.3 Hz, 1H) |
| — | 6.73 (app-dt, J = 1.8, 7.4 Hz, 2H) | 6.73 (app-dt, J = 1.8, 7.5 Hz, 2H) |
| — | 6.68-6.65 (m, 2H) | 6.69-6.64 (m, 2H) |
| — | 6.56 (d, J = 7.7 Hz, 1H) | 6.57 (s, 1H) |
| 5.95 (s) | 5.93 (s, 1H) | 5.94 (s, 1H) |
| 5.57 (s) | 5.56 (s, 1H) | 5.56 (s, 1H) |
| 4.46 (s) | 4.46 (s, 1H) | 4.46 (s, 1H) |
| 4.21 (s) | 4.22 (s, 1H) | 4.22 (s, 1H) |

TABLE S9-continued

Comparison of $^1$H NMR data for (—)-psycholeine (8) with literature data from Guéritte-Voegelein, F.; Sévenet, T.; Pusset, J.; Adeline, M.-T.; Gillet, B.; Beloeil, J.-C.; Guénard, D.; Potier, P. *J. Nat. Prod.* 1992, 55, 923 and Lebsack, A. D. Ph.D. Dissertation, University of California, Irvine, 2002 (original publication, see Lebsack, A. D.; Link, J. T.; Overman, L. E.; Stearns, B. A. *J. Am. Chem. Soc.* 2002, 124, 9008) (CDCl$_3$)

| Sevenet's Isolation Report ((—)-psycholeine (8)) $^{13}$C NMR, 400 MHz CDCl$_3$/CD$_3$OD | Lebsack's Ph.D. Dissertation (—)-psycholeine (8) $^1$H NMR, 500 MHz CDCl$_3$, "rt" | This Work (—)-psycholeine (8) $^1$H NMR, 400 MHz CDCl$_3$, 25° C. |
|---|---|---|
| 2.66 (m) | 2.70-2.58 (m, 4H) | 2.75-2.58 (m, 4H) |
| 2.66 (m) | — | |
| 2.45 (m) | 2.46-2.14 (m, 21H) | 2.55-2.16 (m, 9H)) |
| 2.40 (s) | — | 2.39 (s, 3H) |
| 2.40 (s) | — | 2.38 (s, 3H) |
| 2.33 (s) | — | 2.36 (s, 3H) |
| 2.16 (s) | — | 2.14 (s, 3H) |
| 2.20 (m) | 2.20-1.98 (m, 1H) | 2.03-1.97 (m, 1H) |
| 2.20 (m) | — | — |
| 1.94 (m) | 1.91-1.78 (m, 4H) | 1.90-1.74 (m, 4H) |
| 1.80 (m) | — | — |
| 1.77 (m) | — | |
| 1.74 (m) | — | — |
| 1.12 (d, J = 12 Hz) | 1.13 (app-dd, J = 9.8 Hz, 1H) | 1.12 (app-d, J = 11.1 Hz, 1H) |
| 1.04 (d, J = 12 Hz) | 1.06 (app-dd, J = 13.7 Hz, 1H) | 1.05app-d, J = 12.4 Hz, 1H) |

TABLE S10

Comparison of $^{13}$C NMR data for (—)-psycholeine (8) with literature data from Guéritte-Voegelein, F.; Sévenet, T.; Pusset, J.; Adeline, M.-T.; Gillet, B.; Beloeil, J.-C.; Guénard, D.; Potier, P. *J. Nat. Prod.* 1992, 55, 923 and Lebsack, A. D. Ph.D. Dissertation, University of California, Irvine, 2002 (original publication, see Lebsack, A. D.; Link, J. T.; Overman, L. E.; Stearns, B. A. *J. Am. Chem. Soc.* 2002, 124, 9008) (CDCl$_3$)

| Sevenet's Isolation Report ((—)-psycholeine (8)) $^{13}$C NMR, 100 MHz CDCl$_3$/CD$_3$OD | Lebsack's Ph.D. Dissertation (—)-psycholeine (8) $^{13}$C NMR, 125 MHz CDCl$_3$, "rt" | This Work (—)-psycholeine (8) $^{13}$C NMR, 100 MHz CDCl$_3$, 25° C. | Chemical Shift Difference $\Delta\delta = \delta$ (this work) − $\delta$ (Lebsack's Dissertation) |
|---|---|---|---|
| — | 149.5 | 149.4 | −0.1 |
| — | 148.3 | 148.1 | −0.2 |
| — | 147.4 | 147.3 | −0.1 |
| — | 146.8 | 146.7 | −0.1 |
| 133.80 | 133.6 | 133.4 | −0.2 |
| 132.40 | 133.5 | 133.3 | −0.3 |
| 129.00 | 128.9 | 128.7 | −0.2 |
| — | — | 128.7 | N/A The previously reported $^{13}$C data for (—)-psycholeine (8) lists 41 of the 44 theoretical signals, whereas herein detection of all the expected resonances was possible. |
| — | 128.2 | 128.2 | 0 |
| — | 127.8 | 127.7 | −0.1 |
| — | 124.9 | 124.9 | 0 |
| — | 124.8 | 124.8 | 0 |
| — | 123.7 | 123.7 | 0 |
| — | 123.3 | 123.2 | −0.1 |
| — | 120.3 | 120.2 | −0.1 |
| — | 120.2 | 120.2 | 0 |
| — | — | 120.2 | N/A The previously reported $^{13}$C data for (—)-psycholeine (8) lists 41 of the 44 theoretical signals, whereas herein detection of all the expected resonances was possible. |
| — | — | 120.1 | N/A The previously reported $^{13}$C data for (—)-psycholeine (8) lists 41 of the 44 theoretical signals, whereas herein detection of all the expected resonances was possible. |
| — | 119.9 | 119.9 | 0 |

TABLE S10-continued

Comparison of $^{13}$C NMR data for (—)-psycholeine (8) with literature data from Guéritte-Voegelein, F.; Sévenet, T.; Pusset, J.; Adeline, M.-T.; Gillet, B.; Beloeil, J.-C.; Guénard, D.; Potier, P. *J. Nat. Prod.* 1992, 55, 923 and Lebsack, A. D. Ph.D. Dissertation, University of California, Irvine, 2002 (original publication, see Lebsack, A. D.; Link, J. T.; Overman, L. E.; Stearns, B. A. *J. Am. Chem. Soc.* 2002, 124, 9008) (CDCl$_3$)

| Sevenet's Isolation Report ((—)-psycholeine (8)) $^{13}$C NMR, 100 MHz CDCl$_3$/CD$_3$OD | Lebsack's Ph.D. Dissertation (—)-psycholeine (8) $^{13}$C NMR, 125 MHz CDCl$_3$, "rt" | This Work (—)-psycholeine (8) $^{13}$C NMR, 100 MHz CDCl$_3$, 25° C. | Chemical Shift Difference $\Delta\delta = \delta$ (this work) – $\delta$ (Lebsack's Dissertation) |
|---|---|---|---|
| — | 119.6 | 119.6 | 0 |
| — | 117.7 | 117.6 | −0.1 |
| — | 117.4 | 117.3 | −0.1 |
| — | 110.4 | 110.4 | 0 |
| — | 109.9 | 109.8 | −0.1 |
| 88.51 | 88.1 | 88.0 | −0.1 |
| 87.50 | 87.7 | 87.6 | −0.1 |
| 74.00 | 74.4 | 74.2 | −0.2 |
| 72.00 | 72.2 | 72.1 | −0.1 |
| 60.65 | 61.1 | 60.9 | −0.2 |
| 59.56 | 61.0 | 59.9 | −0.1 |
| 48.05 | 48.8 | 48.6 | −0.2 |
| 47.17 | 47.9 | 47.7 | −0.2 |
| 46.30 | 46.7 | 46.6 | −0.1 |
| 45.85 | 46.1 | 46.0 | −0.1 |
| 43.69 | 43.9 | 43.9 | 0 |
| 42.61 | 43.1 | 43.0 | −0.1 |
| — | 38.9 | 38.6 | −0.3 |
| 38.05 | 38.6 | 38.1 | −0.5 |
| — | 37.9 | 37.8 | −0.1 |
| 37.50 (2C) | 37.7 | 37.6 | −0.1 |
| 36.08 | 36.8 | 36.5 | −0.3 |
| 35.60 | 36.7 | 36.3 | −0.4 |
| 32.80 | 33.0 | 32.9 | −0.1 |
| 32.40 | 32.6 | 32.5 | −0.1 |

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

We claim:

1. A method of preparing a compound of Formula (II'):

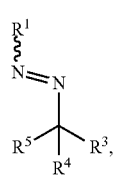

Formula (II')

or a salt, tautomer, or stereoisomer thereof, comprising reacting a compound of Formula (III'), or a salt, tautomer, or stereoisomer thereof, and a compound of Formula (IV'), or a salt, tautomer, or stereoisomer thereof:

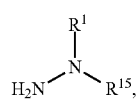

Formula (III')

-continued

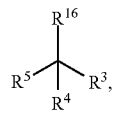

Formula (IV')

wherein:

R$^1$ is alkenyl, aryl, or heteroaryl;

zero, one, two, or three of (i) R$^3$ and R$^4$, (ii) R$^3$ and R$^5$, and (iii) R$^4$ and R$^5$ taken together with the carbon atoms to which they are attached independently form a substituted or unsubstituted, 5-14 membered ring, and the remaining R$^3$, R$^4$, and/or R$^5$ are independently absent, alkyl, aryl, heteroaryl, carbocyclyl, or heterocyclyl, provided that each of R$^4$ and R$^5$ is not absent;

each instance of R$^{11}$ and R$^{12}$ is independently selected from H, C$_1$-C$_{12}$ alkyl, C$_2$-C$_{12}$ alkenyl, C$_2$-C$_{12}$ alkynyl, aryl, heteroaryl, carbocyclyl, or heterocyclyl, wherein R$^{11}$ and R$^{12}$ taken together with the carbon atoms to which they are attached form an aryl, heteroaryl, carbocyclic, or heterocyclic ring;

each instance of R$^{13}$ and R$^{14}$ is independently selected from C$_1$-C$_{12}$ alkyl, C$_2$-C$_{12}$ alkenyl, C$_2$-C$_{12}$ alkynyl, aryl, heteroaryl, carbocyclyl, heterocyclyl, —OR$^{11}$, —(CH$_2$)$_r$SiMe$_3$, or —(CH$_2$)$_r$R$^{11}$;

each instance of R$^{15}$ is independently —S(=O)$_p$R$^{13}$, —S(=O)$_2$NR$^{11}$R$^{12}$, —C(=O)R$^{13}$, —C(=O)R$^{20}$, —C(=O)O(CH$_2$)$_r$R$^{20}$, —C(=O)CF$_3$, —C(=O)OR$^{20}$, —P(=O)R$^{13}$R$^{14}$, or, —P(=O)NR$^{11}$R$^{12}$;

each instance of R$^{16}$ is independently I, Br, Cl, —OH, —OSO$_2$CF$_3$, —OS(O)$_2$R$^{13}$, —OP(=O)R$^{13}$R$^{14}$, —OC(=NR$^{11}$)R$^{12}$, —OC(=NR$^{11}$)CCl$_3$, —OR$^{11}$, or —N$_2$$^+$X$^-$, wherein X$^-$ is halogen;

each instance of R$^{20}$ is independently —Si(alkyl)$_3$, —Si(alkyl)$_2$aryl, or Si(aryl)$_2$alkyl;

each instance of p is independently 1 or 2; and each instance of r is independently an integer from 1 to 4.

2. The method of claim 1, wherein a compound of Formula (II'), or a salt, tautomer, or stereoisomer thereof, is of the formula:

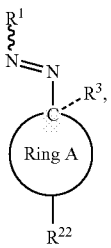

Formula (II'-A)

or a salt, tautomer, or stereoisomer thereof, and a compound of Formula (IV'), or a salt, tautomer, or stereoisomer thereof, is of the formula:

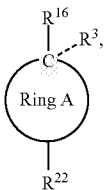

Formula (IV'-A)

or a salt, tautomer, or stereoisomer thereof, wherein:

Ring A is a substituted or unsubstituted, 5-14 membered ring;

----- is a single bond or absent;

R$^3$ is absent, alkyl, aryl, heteroaryl, carbocyclyl, or heterocyclyl, or R$^3$ is fused to Ring A to additionally form a substituted or unsubstituted, 5-14 membered ring;

R$^{22}$ is absent, hydrogen, alkyl, aryl, heteroaryl, carbocyclyl, heterocyclyl, —N=N-aryl, —N=N-heteroaryl, —N=N-carbocyclyl, or —N=N-heterocyclyl.

3. The method of claim 2, wherein a compound of Formula (IV'-A), or a salt, tautomer, or stereoisomer thereof, is of the formula:

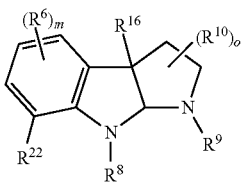

Formula (IV'-B) or a salt, tautomer, or stereoisomer thereof, wherein:

each instance of R$^6$ is independently halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, C$_1$-C$_{12}$ alkyl, C$_2$-C$_{12}$ alkenyl, C$_2$-C$_{12}$ alkynyl, aryl, heteroaryl, carbocyclyl, or heterocyclyl, or two R$^6$ groups taken together with the carbon atoms to which they are attached form an aryl, heteroaryl, carbocyclic, or heterocyclic ring;

each instance of R$^8$ and R$^9$ is independently H, C$_1$-C$_{12}$ alkyl, C$_2$-C$_{12}$ alkenyl, C$_2$-C$_{12}$ alkynyl, —C(=O)R$^{11}$, —C(=O)OR$^{11}$, —C(=O)NR$^{11}$R$^{12}$, —SR$^{11}$, —S(=O)$_p$R$^{13}$, —S(=O)$_2$NR$^{11}$R$^{12}$, —C(=O)O(CH$_2$)$_o$R$^{11}$, aryl, heteroaryl, carbocyclyl, heterocyclyl, —C(=O)OCH$_2$CH$_2$Si(CH$_3$)$_3$, or nitrogen protecting group;

each instance of R$^{10}$ is independently selected from H, C$_1$-C$_{12}$ alkyl; C$_2$-C$_{12}$ alkenyl, C$_2$-C$_{12}$ alkynyl, —C(=O)R$^{11}$, —C(=O)OR$^{11}$, —C(=O)NR$^{11}$R$^{12}$, —S(=O)$_p$R$^{13}$, —OH, —OR$^{11}$, —OC(=O)R$^{11}$, —NR$^{11}$R$^{12}$, aryl, heteroaryl, carbocyclyl, or heterocyclyl, or two R$^{10}$ groups taken together with the carbon atoms to which they are attached form an aryl, heteroaryl, carbocyclic, or heterocyclic ring;

each instance of o is independently an integer from 0 to 4; and each instance of m is an integer from 0 to 3.

4. The method of claim 1, wherein the compound of Formula (III'), or a salt, tautomer, or stereoisomer thereof, is of the formula:

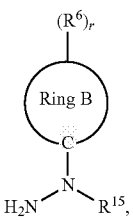

or a salt, tautomer, or stereoisomer thereof, wherein:

Ring B is a substituted or unsubstituted, 5-14 membered ring;

each instance of R$^6$ is independently halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, C$_1$-C$_{12}$ alkyl, C$_2$-C$_{12}$ alkenyl, C$_2$-C$_{12}$ alkynyl, aryl, heteroaryl, carbocyclyl, or heterocyclyl, or two R$^6$ groups taken together with the carbon atoms to which they are attached form an aryl, heteroaryl, carbocyclic, or heterocyclic ring; and r is an integer from 0 to 5.

5. The method of claim 4, wherein the compound of Formula (III'), or a salt, tautomer, or stereoisomer thereof, is of the formula:

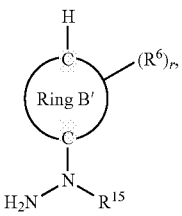

or a salt, tautomer, or stereoisomer thereof, wherein Ring B' is a substituted or unsubstituted, 5-14 membered ring comprising two or more carbon atoms in the ring system.

6. The method of claim 1, wherein the compound of Formula (III'), or a salt, tautomer, or stereoisomer thereof, is of the formula:

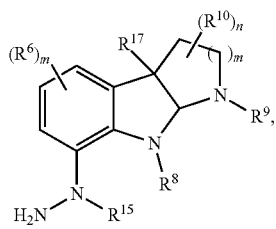

Formula (III'-C)

or a salt, tautomer, or stereoisomer thereof, wherein:
each instance of $R^6$ is independently halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, $C_1$-$C_{12}$ alkyl, $C_2$-$C_{12}$ alkenyl, $C_2$-$C_{12}$ alkynyl, aryl, heteroaryl, carbocyclyl, or heterocyclyl, or two $R^6$ groups taken together with the carbon atoms to which they are attached form an aryl, heteroaryl, carbocyclic, or heterocyclic ring;
each instance of $R^8$ and $R^9$ is independently H, $C_1$-$C_{12}$ alkyl, $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —SR$^{11}$, —S(=O)$_p$R$^{13}$, —S(=O)$_2$NR$^{11}$R$^{12}$, —C(=O)O(CH$_2$)$_o$R$^{11}$, aryl, heteroaryl, carbocyclyl, heterocyclyl, —C(=O)OCH$_2$CH$_2$Si(CH$_3$)$_3$, or nitrogen protecting group;
each instance of $R^{10}$ is independently H, $C_1$-$C_{12}$ alkyl; $C_2$-$C_{12}$ alkenyl, $C_2$-$C_{12}$ alkynyl, —C(=O)R$^{11}$, —C(=O)OR$^{11}$, —C(=O)NR$^{11}$R$^{12}$, —S(=O)$_p$R$^{13}$, —OH, —OR$^{11}$, —OC(=O)R$^{11}$, —NR$^{11}$R$^{12}$, aryl, heteroaryl, carbocyclyl, or heterocyclyl, or two $R^{10}$ groups taken together with the carbon atoms to which they are attached form an aryl, heteroaryl, carbocyclic, or heterocyclic ring;
$R^{17}$ is H, —OH, —OR$^{11}$, —NR$^{11}$R$^{12}$, aryl, heteroaryl, carbocyclyl, heterocyclyl,

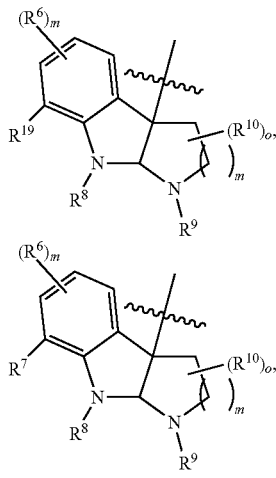

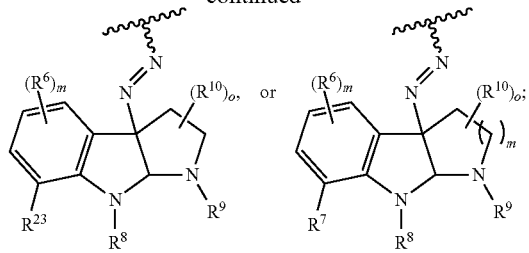

$R^{19}$ is selected from H, alkyl, alkenyl, aryl, heteroaryl, carbocyclyl, heterocyclyl, and

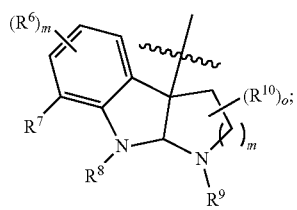

$R^7$ is H, —N$_3$, —N(R$^{15}$)NH$_2$, —NHR$^{15}$, hydrogen, alkyl, aryl, heteroaryl, carbocyclyl, heterocyclyl, —N=N-aryl, —N=N-heteroaryl, —N=N-carbocyclyl, or —N=N-heterocyclyl;
$R^{23}$ is absent, hydrogen, alkyl, aryl, heteroaryl, carbocyclyl, heterocyclyl, —N=N-aryl, —N=N-heteroaryl, —N=N-carbocyclyl, or —N=N-heterocyclyl;
m is an integer from 0 to 3; and
n and o are each independently an integer from 0 to 4.

7. The method of claim 1 further comprising reacting a compound of Formula (II'):

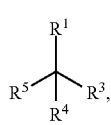

Formula (II')

or a salt, tautomer, or stereoisomer thereof, by extruding one or more equivalents of dinitrogen.

8. The method of claim 7, wherein the product of reacting a compound of Formula (II'), or a salt, tautomer, or stereoisomer thereof, is a compound of Formula (I'):

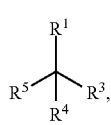

Formula (I')

or a salt, tautomer, or stereoisomer thereof.

9. The method of claim 8, wherein the compound of Formula (I'), or a salt, tautomer, or stereoisomer thereof, is of the formula:

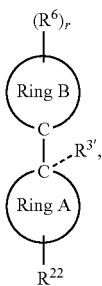

or a salt, tautomer, or stereoisomer thereof, wherein:
R$^{22}$ is absent, hydrogen, alkyl, aryl, heteroaryl, carbocyclyl, heterocyclyl, —N=N-aryl, —N=N-heteroaryl, —N=N-carbocyclyl, or —N=N-heterocyclyl;
Ring A is a substituted or unsubstituted, 5-14 membered ring;
---- is a single bond or absent;
R$^3$ is absent, alkyl, aryl, heteroaryl, carbocyclyl, or heterocyclyl, or R$^3$ is fused to Ring A to additionally form a substituted or unsubstituted, 5-14 membered ring;
Ring B is a substituted or unsubstituted, 5-14 membered ring;
each instance of R$^6$ is independently halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, C$_1$-C$_{12}$ alkyl, C$_2$-C$_{12}$ alkenyl, C$_2$-C$_{12}$ alkynyl, aryl, heteroaryl, carbocyclyl, or heterocyclyl, or two R$^6$ groups taken together with the carbon atoms to which they are attached form an aryl, heteroaryl, carbocyclic, or heterocyclic ring; and
r is an integer from 0 to 5.

10. The method of claim 9, wherein the compound of Formula (I'), or a salt, tautomer, or stereoisomer thereof, is:

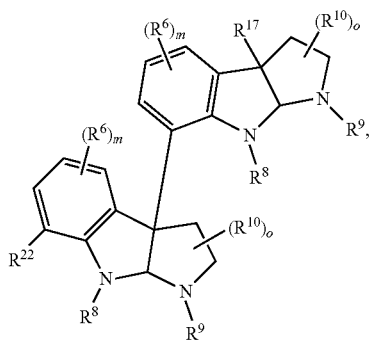

or a salt, tautomer, or stereoisomer thereof, wherein:
each instance of R$^6$ is independently halogen, —OH, —OR$^{11}$, —OC(=O)R$^{11}$, —NR$^{11}$R$^{12}$, —S(=O)$_p$R$^{13}$, —C(=O)R$^{11}$, —C(=O)OR$^{11}$, —C(=O)NR$^{11}$NR$^{12}$, C$_1$-C$_{12}$ alkyl, C$_2$-C$_{12}$ alkenyl, C$_2$-C$_{12}$ alkynyl, aryl, heteroaryl, carbocyclyl, or heterocyclyl, or two R$^6$ groups taken together with the carbon atoms to which they are attached form an aryl, heteroaryl, carbocyclic, or heterocyclic ring;
each instance of R$^8$ and R$^9$ is independently H, C$_1$-C$_{12}$ alkyl, C$_2$-C$_{12}$ alkenyl, C$_2$-C$_{12}$ alkynyl, —C(=O)R$^{11}$, —C(=O)OR$^{11}$, —C(=O)NR$^{11}$R$^{12}$, —SR$^{11}$, —S(=O)$_p$R$^{13}$, —S(=O)$_2$NR$^{11}$R$^{12}$, —C(=O)O(CH$_2$)$_o$R$^{11}$, aryl, heteroaryl, carbocyclyl, heterocyclyl, —C(=O)OCH$_2$CH$_2$Si(CH$_3$)$_3$, or nitrogen protecting group;
each instance of R$^{10}$ is independently selected from H, C$_1$-C$_{12}$ alkyl; C$_2$-C$_{12}$ alkenyl, C$_2$-C$_{12}$ alkynyl, —C(=O)R$^{11}$, —C(=O)OR$^{11}$, —C(=O)NR$^{11}$R$^{12}$, —S(=O)$_p$R$^{13}$, —OH, —OR$^{11}$, —OC(=O)R$^{11}$, —NR$^{11}$R$^{12}$, aryl, heteroaryl, carbocyclyl, or heterocyclyl, or two R$^{10}$ groups taken together with the carbon atoms to which they are attached form an aryl, heteroaryl, carbocyclic, or heterocyclic ring;
each instance of o is independently an integer from 0 to 4;
each instance of m is an integer from 0 to 3;
each instance of R$^{22}$ is independently absent, hydrogen, alkyl, aryl, heteroaryl, carbocyclyl, heterocyclyl, —N=N-aryl, —N=N-heteroaryl, —N=N-carbocyclyl, or —N=N-heterocyclyl;
R$^{17}$ is H, —OH, —OR$^{11}$, —NR$^{11}$R$^{12}$, aryl, heteroaryl, carbocyclyl, heterocyclyl,

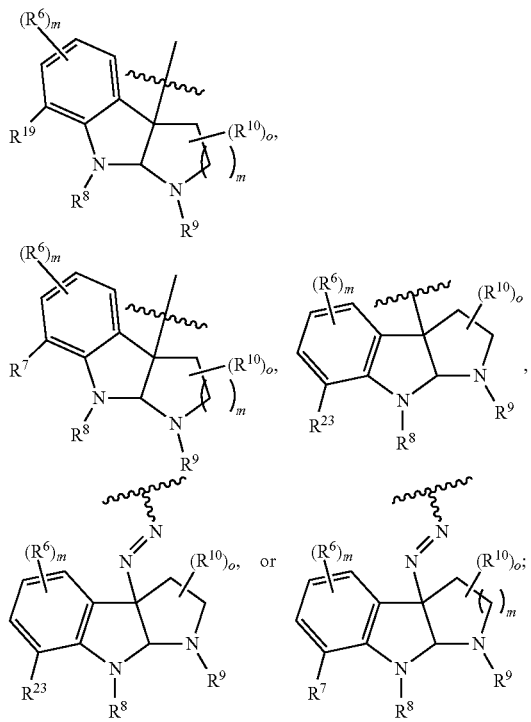

R$^{19}$ is selected from H, alkyl, alkenyl, aryl, heteroaryl, carbocyclyl, heterocyclyl, and

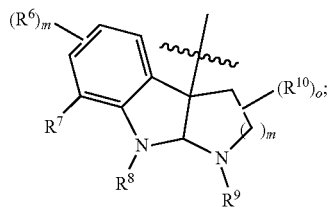

R$^7$ is H, —N$_3$, —N(R$^{15}$)NH$_2$, —NHR$^{15}$, hydrogen, alkyl, aryl, heteroaryl, carbocyclyl, heterocyclyl, —N═N-aryl, —N═N-heteroaryl, —N═N-carbocyclyl, or —N═N-heterocyclyl; and
R[23] is absent, hydrogen, alkyl, aryl, heteroaryl, carbocyclyl, heterocyclyl, —N═N-aryl, —N═N-heteroaryl, —N═N-carbocyclyl, or —N═N-heterocyclyl.
11. The method of claim 7, wherein the product of reacting a compound of Formula (II'), or a salt, tautomer, or stereoisomer thereof, is of the formula:
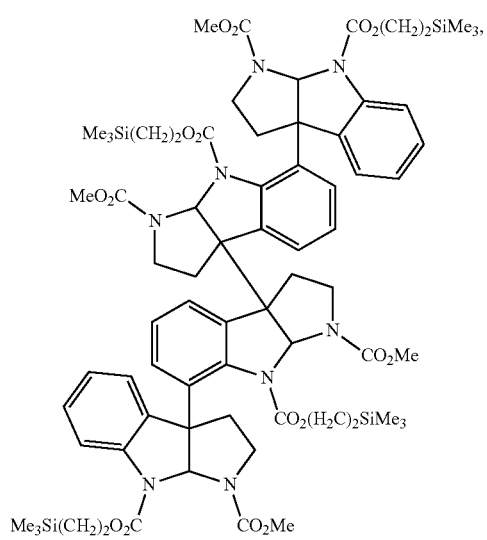
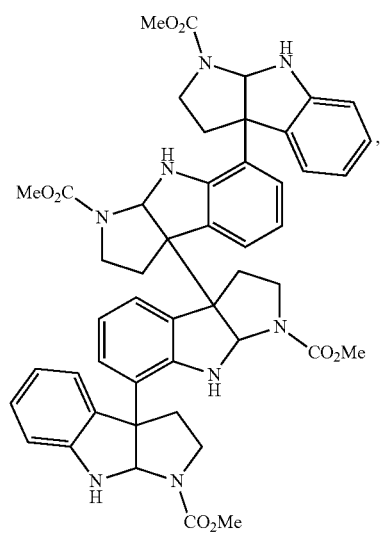
-continued
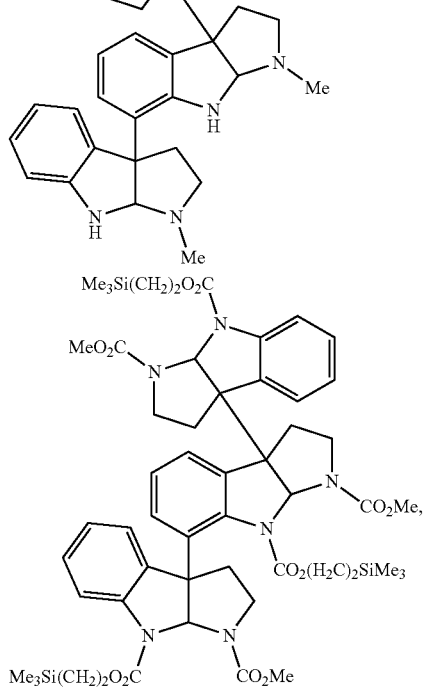
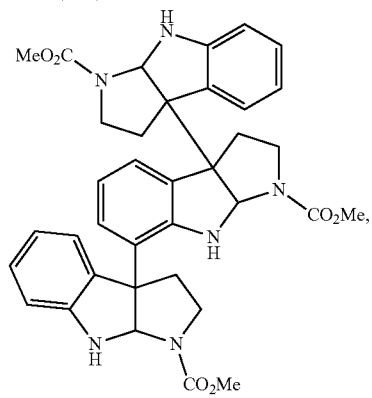
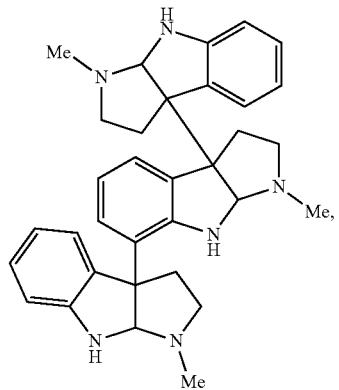

-continued

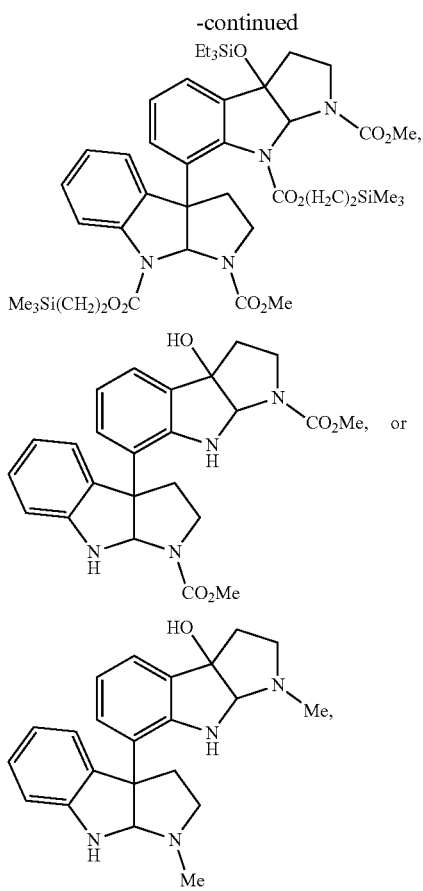

or a salt, tautomer, or stereoisomer thereof.

12. The method of claim 2, wherein:

Ring A is a substituted or unsubstituted, 5-14 membered ring, saturated, unsaturated, or aromatic, carbocyclic ring or a substituted or unsubstituted, 5-14 membered, saturated, unsaturated, or aromatic, heterocyclic ring;

$R^3$ is absent, alkyl, aryl, heteroaryl, carbocyclyl, or heterocyclyl, or $R^3$ is fused to Ring A to additionally form a substituted or unsubstituted, 5-14 membered, saturated, unsaturated, or aromatic, carbocyclic ring or a substituted or unsubstituted, 5-14 membered, saturated, unsaturated, or aromatic, heterocyclic ring.

13. The method of claim 3, wherein:

R22

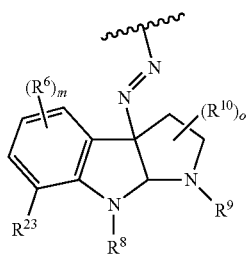

or

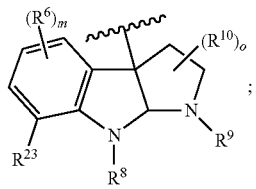

and $R^{23}$ is absent, hydrogen, alkyl, aryl, heteroaryl, carbocyclyl, heterocyclyl, —N═N-aryl, —N═N-heteroaryl, —N═N-carbocyclyl, or —N═N-heterocyclyl.

14. The method of claim 4, wherein the compound of Formula (III') or a salt, tautomer, or stereoisomer thereof, is of the formula:

Formula (III'-A)

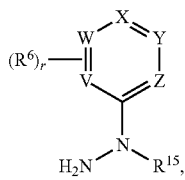

or a salt, tautomer, or stereoisomer thereof, wherein V, W, X, Y, and Z are each independently —CH or N.

15. The method of claim 4, wherein the compound of Formula (III'), or a salt, tautomer, or stereoisomer thereof, is of the formula:

Formula (III'-B)

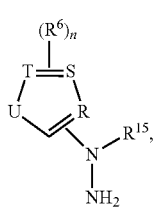

or a salt, tautomer, or stereoisomer thereof, wherein R, S, and T are each independently —CH or N; and U is O, S, or $NR^{11}$, wherein $R^{11}$ is independently H, $C_1$-$C_{12}$ alkyl, $C_2$-$C_{12}$ alkenyl, $C_2$-$C_{12}$ alkynyl, aryl, heteroaryl, carbocyclyl, or heterocyclyl; and n is an integer from 0 to 4.

16. The method of claims 7, wherein the reaction by extruding one or more equivalents of dinitrogen is a radical recombination reaction.

17. The method of claim 16, wherein the reaction by extruding one or more equivalents of dinitrogen is carried out by irradiation.

18. The method of claim 1, wherein the reaction of a compound of Formula (III'), or a salt, tautomer, or stereoisomer thereof, and a compound of Formula (IV'), or a salt, tautomer, or stereoisomer thereof, comprises an electrophilic activation of a compound of Formula (IV'), or a salt, tautomer, or stereoisomer thereof.

19. The method of claim 18, wherein the electrophilic activation comprises reaction of the compound of Formula (IV'), or a salt, tautomer, or stereoisomer thereof, with a silver (I) salt, and a base.

20. The method of claim 19, wherein the compound of Formula (III'), or a salt, tautomer, or stereoisomer thereof, is resistant to oxidation by the silver (I) salt.

* * * * *

UNITED STATES PATENT AND TRADEMARK OFFICE
CERTIFICATE OF CORRECTION

PATENT NO. : 10,640,508 B2
APPLICATION NO. : 16/161036
DATED : May 5, 2020
INVENTOR(S) : Mohammad Movassaghi et al.

Page 1 of 1

It is certified that error appears in the above-identified patent and that said Letters Patent is hereby corrected as shown below:

In the Claims

In Claim 9, at Column 237, Lines 1 to 12:

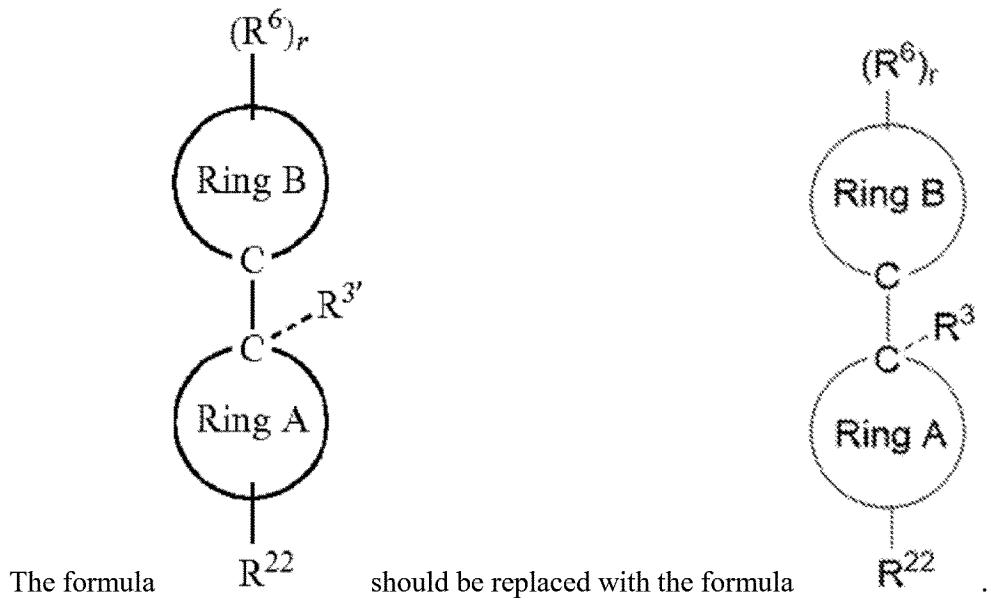

The formula [left structure] should be replaced with the formula [right structure].

Signed and Sealed this
Twentieth Day of October, 2020

Andrei Iancu
*Director of the United States Patent and Trademark Office*